(12) United States Patent
Hashimoto et al.

(10) Patent No.: US 7,112,600 B1
(45) Date of Patent: Sep. 26, 2006

(54) FUSED-RING COMPOUNDS AND USE THEREOF AS DRUGS

(75) Inventors: Hiromasa Hashimoto, Takatsuki (JP); Kenji Mizutani, Takatsuki (JP); Atsuhito Yoshida, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 645 days.

(21) Appl. No.: 10/180,558

(22) Filed: Jun. 26, 2002

Related U.S. Application Data

(63) Continuation-in-part of application No. 09/939,374, filed on Aug. 24, 2001, which is a continuation-in-part of application No. PCT/JP00/09181, filed on Dec. 22, 2000.

(30) Foreign Application Priority Data

| Dec. 27, 1999 | (JP) | ............. | 11/369008 |
| Dec. 25, 2000 | (JP) | ............. | 2000/391904 |
| Jun. 20, 2001 | (JP) | ............. | 2001/193786 |
| Nov. 16, 2001 | (JP) | ............. | 2001/351537 |

(51) Int. Cl.
| A01N 43/50 | (2006.01) |
| C07D 235/04 | (2006.01) |
| C07D 401/00 | (2006.01) |
| C07D 405/14 | (2006.01) |
| A81K 31/418 | (2006.01) |

(52) U.S. Cl. .............. 514/394; 548/305.1; 548/304.1; 548/253; 548/181; 514/234.5; 514/381; 514/254; 514/378; 514/338; 514/365

(58) Field of Classification Search ............. 514/394, 514/338, 234.5, 365, 378, 254; 548/305.1, 548/304.7, 253, 181, 309.4, 306.1, 307.1, 548/247, 159, 236, 261, 315.4; 546/273.4, 546/199; 540/588, 575; 544/333, 146, 211, 544/321, 370, 139, 357, 364
See application file for complete search history.

(56) References Cited

U.S. PATENT DOCUMENTS

| 3,644,382 | A | 2/1972 | Clemence et al. |
| 3,778,504 | A | 12/1973 | Clemence et al. |
| 4,250,317 | A | 2/1981 | Meyer et al. |
| 4,360,679 | A | 11/1982 | Meyer et al. |
| 5,280,030 | A | 1/1994 | Jegham et al. |
| 5,563,143 | A | 10/1996 | Cohan et al. |
| 5,633,388 | A | 5/1997 | Diana et al. |
| 5,814,651 | A | 9/1998 | Duplantier et al. |
| 5,998,398 | A | 12/1999 | Daluge et al. |
| 6,166,219 | A | 12/2000 | Yamasaki et al. |
| 6,211,177 | B1 | 4/2001 | Sperl et al. |
| 6,448,281 | B1 * | 9/2002 | Beaulieu et al. ............. 514/394 |
| 6,770,666 | B1 | 8/2004 | Hashimoto et al. |
| 2003/0050320 | A1 | 3/2003 | Hashimoto et al. |
| 2004/0082635 | A1 | 4/2004 | Hashimoto et al. |
| 2004/0097438 | A1 | 5/2004 | Hashimoto et al. |

FOREIGN PATENT DOCUMENTS

| EP | 0 010 063 A2 | 4/1980 |
| EP | 0 507 650 | 10/1992 |
| EP | 0 694 535 A1 | 1/1996 |
| JP | 03 031264 | 2/1991 |
| JP | 06-025182 | 2/1994 |
| JP | 06-025182 A | 2/1994 |
| WO | WO 96/07646 | 3/1996 |
| WO | WO 96/35713 | 11/1996 |
| WO | WO 97/25316 | 7/1997 |
| WO | WO 97/41884 | 11/1997 |
| WO | WO 97/46237 | 12/1997 |
| WO | WO 98/05327 | 2/1998 |
| WO | WO 98/37072 | 8/1998 |
| WO | WO 98/50029 | 11/1998 |
| WO | WO 98/50030 | 11/1998 |
| WO | WO 98/50031 | 11/1998 |
| WO | WO 99/24060 | 5/1999 |
| WO | WO 99/51619 | 10/1999 |
| WO | WO 01/21634 A1 | 3/2001 |
| WO | WO 01/47883 A1 | 7/2001 |
| WO | WO 02/04425 A2 | 1/2002 |

OTHER PUBLICATIONS

U.S. Appl. No. 60/216,084, filed Jul. 6, 2000, Beaulieu.

Haskell et al., "Neuraminidase Inhibition and Viral Chemotherapy," *Journal of Medicinal Chemistry*, 13(4), 697–704 (1970).

Behrens et al., "Identification and properties of the RNA-dependent RNA polymerase of hepatitis C virus," *The EMBO Journal*, 15(1), 12–22 (1996).

(Continued)

*Primary Examiner*—James O. Wilson
*Assistant Examiner*—Paul V. Ward
(74) *Attorney, Agent, or Firm*—Leydig, Voit & Mayer, Ltd.

(57) ABSTRACT

The present invention provides a fused ring compound of the following formula [I]

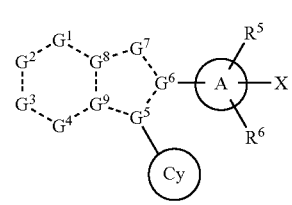

wherein each symbol is as defined in the specification, a pharmaceutically acceptable salt thereof, and a therapeutic agent for hepatitis C, which contains this compound. The compound of the present invention shows an anti-hepatitis C virus (HCV) action based on the HCV polymerase inhibitory activity, and is useful as a therapeutic agent or prophylactic agent for hepatitis C.

20 Claims, No Drawings

OTHER PUBLICATIONS

Minami et al., "Skin Disorders in Hepatitis C Virus Antibody Positive Patients," *The Japanese Journal of Dermatology*, 111(7), 1075–1081 (2001).

Kataev et al., "Preparation and immunomodulating effect of (1–thietanyl–3)benzimidazoles," *Khimiko–Farmatsevticheskii Zhurnal*, 30(7), 22–24 (1996).

Khaliullin et al., "Synthesis of biologically active derivatives of xanthine and benzimidazole," *Chemical Abstracts Service*, Columbus, Ohio, Database Accession No. 129:493337 (1997).

Orjales et al., "New 2–Piperazinylbenzimidazole Derivatives as 5–$HT_3$ Antagonists. Synthesis and Pharmacological Evaluation," *J. Med. Chem.*, 40(4), 586–593 (1997).

Kataev et al., "Synthesis and Immunostimulation Activity of 1–(Thietan–3–yl) Benzimidazoles," *Pharmaceutical Chemistry Journal*, 30(7), 448–450 (1996).

Hori et al., "Design and Syntheses of a Series of Novel Serotonin$_3$ Antagonists," *Chem. Pharm. Bull.*, 41 (10), 1832–1841 (1993).

* cited by examiner

FUSED-RING COMPOUNDS AND USE THEREOF AS DRUGS

This is a continuation in part of U.S. patent application Ser. No. 09/939,374 filed on Aug. 24, 2001, which is a continuation in part of PCT/JP00/09181 filed on Dec. 22, 2000.

TECHNICAL FIELD

The present invention relates to a novel fused ring compound and a pharmaceutically acceptable salt thereof useful as a therapeutic agent for hepatitis C, and to an intermediate compound for the synthesis thereof. The present invention also relates to a novel use of a certain fused ring compound or a pharmaceutically acceptable salt thereof as a therapeutic agent for hepatitis C. More particularly, the present invention relates to a therapeutic agent for hepatitis C, which contains a novel fused ring compound or a pharmaceutically acceptable salt thereof, which is effective for the prophylaxis or treatment of hepatitis C and which shows anti-hepatitis C virus (HCV) activity, particularly anti-HCV activity based on an RNA-dependent RNA polymerase inhibitory activity.

BACKGROUND ART

In 1989, a main causative virus of non-A non-B post-transfusion hepatitis was found and named hepatitis C virus (HCV). Since then, several types of hepatitis viruses have been found besides type A, type B and type C, wherein hepatitis caused by HCV is called hepatitis C.

The patients infected with HCV are considered to involve several percent of the world population, and the infection with HCV characteristically becomes chronic.

HCV is an envelope RNA virus, wherein the genome is a single strand plus-strand RNA, and belongs to the genus Hepacivirus of Flavivirus (from The International Committee on Taxonomy of Viruses, International Union of Microbiological Societies). Of the same hepatitis viruses, for example, hepatitis B virus (HBV), which is a DNA virus, is eliminated by the immune system and the infection with this virus ends in an acute infection except for neonates and infants having yet immature immunological competence. In contrast, HCV somehow avoids the immune system of the host due to an unknown mechanism. Once infected with this virus, even an adult having a mature immune system frequently develops persistent infection.

When chronic hepatitis is associated with the persistent infection with HCV, it advances to cirrhosis or hepatic cancer in a high rate. Enucleation of tumor by operation does not help much, because the patient often develops recurrent hepatic cancer due to the sequela inflammation in non-cancerous parts. In addition, there is a report on the involvement of HCV infection in dermatosis such as chronic urticaria, lichen planus, cryoglobulinemic purpura and the like (The Japanese Journal of Dermatology, 111(7), 1075–81, 2001).

Thus, an effective therapeutic method of hepatitis C is desired. Apart from the symptomatic therapy to suppress inflammation with an anti-inflammatory agent, the development of a therapeutic agent that reduces HCV to a low level free from inflammation and that eradicates HCV has been strongly demanded.

At present, a treatment with interferon is the only effective method known for the eradication of HCV. However, interferon can eradicate the virus only in about one-third of the patient population. For the rest of the patients, it has no effect or provides only a temporary effect. Therefore, an anti-HCV drug to be used in the place of or concurrently with interferon is awaited in great expectation.

In recent years, Ribavirin (1-β-D-ribofuranosyl-1H-1,2,4-triazole-3-carboxamide) has become commercially available as a therapeutic agent for hepatitis C, which is to be used concurrently with interferon. It enhances the efficacy of interferon but only to a low efficacy rate, and a different novel therapeutic agent for hepatitis C is desired.

Also, an attempt has been made to potentiate the immunocompetence of the patient with an interferon agonist, an interleukin-12 agonist and the like, thereby to eradicate the virus, but an effective pharmaceutical agent has not been found yet.

In addition, the inhibition of HCV growth, wherein HCV-specific protein is targeted, has been drawing attention these days.

The gene of HCV encodes a protein such as serine protease, RNA helicase, RNA-dependent RNA polymerase and the like. These proteins function as a specific protein essential for the growth of HCV.

One of the specific proteins, RNA-dependent RNA polymerase (hereinafter to be also briefly referred to as an HCV polymerase), is an enzyme essential for the growth of the virus. The gene replication of HCV having a plus-strand RNA gene is considered to involve synthesis of a complementary minus-strand RNA by the use of the plus-strand RNA as a template, and, using the obtained minus-strand RNA as a template, amplifying the plus-strand RNA. The portion called NS5B of a protein precursor, that HCV codes for, has been found to show an RNA-dependent RNA polymerase activity (EMBO J., 15, 12–22, 1996), and is considered to play a central role in the HCV gene replication.

Therefore, an HCV polymerase inhibitor can be a target in the development of an anti-HCV drug, and the development thereof is eagerly awaited. However, an effective HCV polymerase inhibitor has not been developed yet, like in other attempts to develop an anti-HCV drug based on other action mechanisms. As the situation stands, no pharmaceutical agent can treat hepatitis C satisfactorily.

The following discloses known compounds relatively similar to the compound of the present invention.

The therapeutic agents for hepatitis C, which have a benzimidazole skeleton, are known from JP-A-2001-247550 (WO01/47883, EP1162196A1) and WO02/04425.

These publications disclose the following β-ketoamide compounds J etc. and K etc., respectively, as anti-HIV agents having an integrase inhibitory activity:

compound J

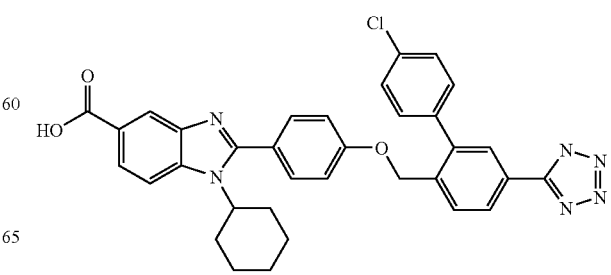

-continued compound K

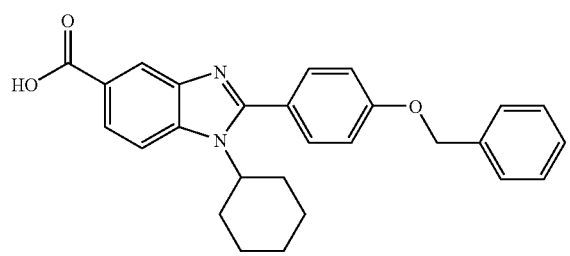

Note that the earliest publication dates of these publications are Jul. 5, 2001 (WO01/47883) and Jan. 17, 2002 (WO02/04425), and the priority date of the present application is Jun. 26, 2001, antedating these publication dates.

In addition, a known therapeutic agent for hepatitis C having a benzimidazole skeleton is also disclosed in WO97/36866, Japanese Patent Application under PCT laid-open under kohyo No. 2000-511899 (EP906097) and WO99/51619.

WO97/36866 discloses the following compound D and the like, and HCV helicase inhibitory activity of the compounds.

Japanese Patent Application under PCT laid-open under kohyo No. 2000-511899 (EP906097) discloses the following compound E and the like, and WO99/51619 discloses the following compound F and the like, in both of which a possibility of these compounds being effective as an HCV inhibitor is mentioned.

However, these publications do not include the compound disclosed in the present specification, or a disclosure suggestive thereof.

A known anti-hepatitis virus agent having a benzimidazole skeleton is disclosed in Japanese Patent Application under PCT laid-open under kohyo No. 2000-503017 (WO97/25316) and Japanese Patent Application under PCT laid-open under kohyo No. 10-505092 (WO96/7646).

WO97/25316 discloses the following compound A and the like, wherein the use thereof is for a treatment of viral infection. The target virus is a DNA virus such as hepatitis B virus and the like. However, this publication does not include the compound disclosed in the present specification or a description regarding or suggestive of HCV.

Japanese Patent Application under PCT laid-open under kohyo No. 10-505092 discloses the following compound B and the like, wherein the use thereof is for a treatment of viral infection. The target virus is a DNA virus such as herpesvirus and hepatitis B virus. However, this publication does not include the compound disclosed in the present specification or a description regarding or suggestive of HCV.

compound A

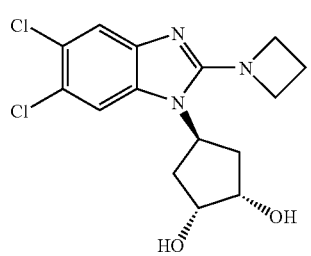

compound D

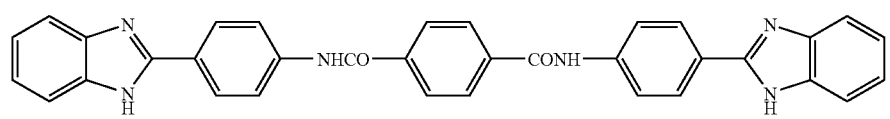

compound E

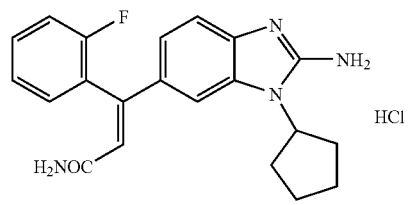

compound F

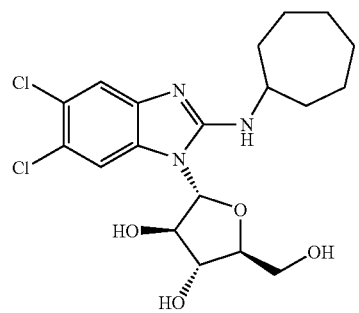

-continued

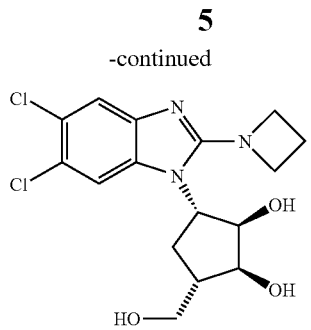
compound B

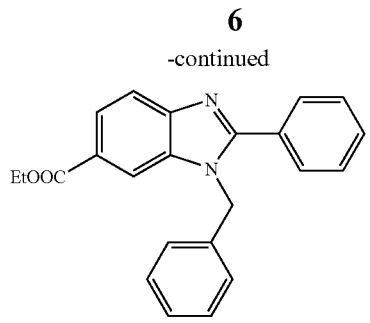
compound G

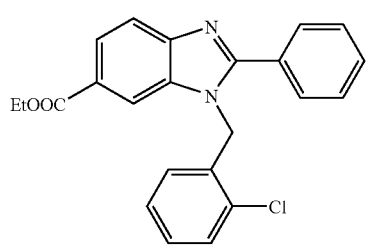
compound H

The benzimidazole derivatives having an antiviral activity have been disclosed in JP-A-3-31264, U.S. Pat. No. 3,644,382 and U.S. Pat. No. 3,778,504. In addition, WO98/37072 discloses, as a production inhibitor of tumor necrosis factor (TNF) and cyclic AMP, a benzimidazole derivative for the use as an anti-human immunodeficiency virus (HIV) agent and an anti-inflammation agent. WO98/05327 discloses, as a reverse transcriptase inhibitor, a benzimidazole derivative for the use as an anti-HIV agent. J. Med. Chem. (13(4), 697–704, 1970) discloses, as a neuraminidase inhibitor, a benzimidazole derivative for the use as an anti-influenza virus agent.

However, none of these publications includes the compound of the present invention or a description regarding or suggestive of an anti-HCV effect.

Known benzimidazole derivatives having a pharmaceutical use other than as an antiviral agent are disclosed in JP-A-8-501318 (U.S. Pat. No. 5,814,651) and JP-A-8-134073 (U.S. Pat. No. 5,563,143). These publications disclose the following compound C and the like as a catechol diether compound, and the use thereof as an anti-inflammation agent. However, neither of the publications includes the compound of the present invention, and as the action mechanism, the former discloses phosphodiesterase IV and the latter discloses TNF. These publications do not include a description regarding or suggestive of an anti-HCV effect.

Japanese Patent Application under PCT laid-open under kohyo No. 2000-159749 (EP882718) discloses the following compound G and the like, and the use thereof for the treatment of bronchitis, glomerulonephritis and the like. However, this publication does not include the compound of the present invention, but discloses only a phosphodiesterase IV inhibitory and hypoglycemic action. This publication does not include a description regarding or suggestive of an anti-HCV effect.

U.S. Pat. No. 6,211,177 discloses the following compound H and the like with their use as antitumor agents. However, this publication does not encompass the compound of the present invention, and does not disclose or suggest an anti-HCV effect.

compound C

WO98/50029, WO98/50030 and WO98/50031 disclose benzimidazole derivatives as an antitumor agent having a protein isoprenyl transferase action. While this publication discloses a wide scope of the claims, at least it does not include a compound analogous to the compound of the present invention or a description regarding or suggestive of an anti-HCV effect.

JP-A-8-109169 (EP694535) discloses the application of a tachykinin receptor antagonist to treat an inflammatory disease, and WO96/35713 discloses the application thereof as a growth hormone release promoter to treat a growth hormone-related disease such as osteoporosis and the like. However, none of these publications includes a description regarding or suggestive of an anti-HCV effect.

WO2001/21634 discloses the following compound I in a chemical library. However, this publication does not encompass the compound of the present invention. While it discloses an antimicrobial activity of certain compounds, this publication does not teach or suggest an anti-HCV effect.

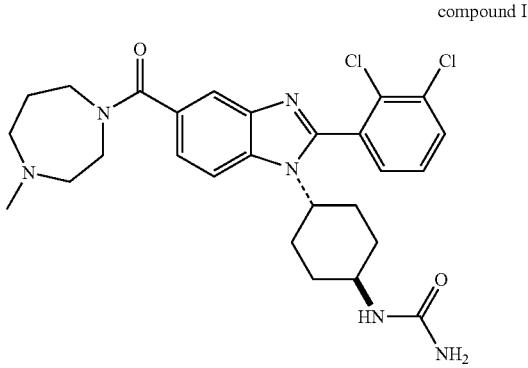
compound I

JP-A-53-14735 discloses a benzimidazole derivative as a brightener besides its pharmaceutical use, but this publication does not include the compound of the present invention.

SUMMARY OF THE INVENTION

Based on the findings from the preceding studies, it has been elucidated that a pharmaceutical agent having an anti-HCV activity is effective for the prophylaxis and treatment of hepatitis C, and particularly an anti-HCV agent having an inhibitory activity on RNA-dependent RNA polymerase of HCV can be a prophylactic and therapeutic agent effective against hepatitis C and a prophylactic and therapeutic agent for the disease caused by hepatitis C.

Accordingly, the present invention provides a pharmaceutical agent having an anti-HCV activity, particularly a pharmaceutical agent having an RNA-dependent RNA polymerase inhibitory activity.

The present inventors have made an in-depth study of compounds having an anti-HCV activity, particularly RNA-dependent RNA polymerase inhibitory activity, and completed the present invention.

Thus, the present invention provides the following (1) to (88).

(1) A therapeutic agent for hepatitis C, which comprises a fused ring compound of the following formula [I] or a pharmaceutically acceptable salt thereof as an active ingredient:

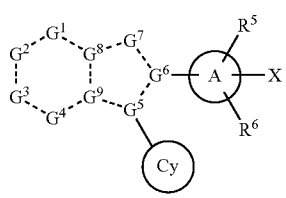

[I]

wherein a broken line is a single bond or a double bond,
$G^1$ is C(—$R^1$) or a nitrogen atom,
$G_2$ is C(—$R^2$) or a nitrogen atom,
$G^3$ is C(—$R^3$) or a nitrogen atom,
$G^4$ is C(—$R^4$) or a nitrogen atom,
$G^5$, $G^6$, $G^8$ and $G^9$ are each independently a carbon atom or a nitrogen atom,
$G^7$ is C(—$R^7$), an oxygen atom, a sulfur atom, or a nitrogen atom optionally substituted by $R^8$,
wherein $R^1$, $R^2$, $R^3$ and $R^4$ are each independently, (1) hydrogen atom,
(2) $C_{1-6}$ alkanoyl,
(3) carboxyl,
(4) cyano,
(5) nitro,
(6) $C_{1-6}$ alkyl optionally substituted by 1 to 3 substituent(s) selected from the following group A, group A; halogen atom, hydroxyl group, carboxyl, amino, $C_{1-6}$ alkoxy, $C_{1-6}$ alkoxy $C_{1-6}$ alkoxy, $C_{1-6}$ alkoxycarbonyl and $C_{1-6}$ alkylamino,
(7) —COO$R^{a1}$
   wherein $R^{a1}$ is optionally substituted $C_{1-6}$ alkyl (as defined above), $C_{6-14}$ aryl $C_{1-6}$ alkyl optionally substituted by 1 to 5 substituent(s) selected from the following group B or glucuronic acid residue, group B; halogen atom, cyano, nitro, $C_{16}$ alkyl, halogenated $C_{1-6}$ alkyl, $C_{1-6}$ alkanoyl, —(CH$_2$)$_r$—COOR$^{b1}$, —(CH$_2$)$_r$—CONR$^{b1}$R$^{b2}$, —(CH$_2$)$_r$—NR$^{b1}$R$^{b2}$, —(CH$_2$)$_r$—NR$^{b1}$—COR$^{b2}$, —(CH$_2$)$_r$—NHSO$_2$R$^{b1}$, —(CH$_2$)$_r$—OR$_{b1}$, —(CH$_2$)$_r$—SR$^{b1}$, —(CH$_2$)$_r$—SO$_2$R$^{b1}$ and —(CH$_2$)$_r$—SO$_2$NR$^{b1}$R$^{b2}$
   wherein $R^{b1}$ and $R^{b2}$ are each independently hydrogen atom or $C_{1-6}$ alkyl and r is 0 or an integer of 1 to 6, (8) —CONR$^{a2}$R$^{a3}$
   wherein $R^{a2}$ and $R^{a3}$ are each independently hydrogen atom, $C_{1-6}$ alkoxy or optionally substituted $C_{1-6}$ alkyl (as defined above),
(9) —C(=NR$^{a4}$)NH$_2$
   wherein $R^{a4}$ is hydrogen atom or hydroxyl group,
(10) —NHR$^{a5}$
   wherein $R^{a5}$ is hydrogen atom, $C_{1-6}$ alkanoyl or $C_{1-6}$ alkylsulfonyl,
(11) —OR$^{a6}$ wherein $R^{1-6}$ is hydrogen atom or optionally substituted $C_{1-6}$ alkyl (as defined above),
(12) —SO$_2$R$^{a7}$
   wherein $R^{a7}$ is hydroxyl group, amino, $C_{1-6}$ alkyl or $C_{1-6}$ alkylamino,
(13) —P(=O)(OR$^{a31}$)$_2$
   wherein $R^{a31}$ is hydrogen atom, optionally substituted $C_{1-6}$ alkyl (as defined above) or $C_{6-14}$ aryl $C_{1-6}$ alkyl optionally substituted by 1 to 5 substituent(s) selected from the above group B or

(14) heterocyclic group having 1 to 4 heteroatom(s) selected from an oxygen atom, a nitrogen atom and a sulfur atom, and $R^7$ and $R^8$ are each hydrogen atom or optionally substituted $C_{1-6}$ alkyl (as defined above),
ring Cy is
(1) $C_{3-8}$ cycloalkyl optionally substituted by 1 to 5 substituent(s) selected from the following group C, group C; hydroxyl group, halogen atom, $C_{1-6}$ alkyl and $C_{1-6}$ alkoxy,
(2) $C_{3-8}$ cycloalkenyl optionally substituted by 1 to 5 substituent(s) selected from the above group C, or

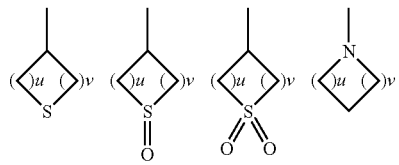

(3)

wherein u and v are each independently an integer of 1 to 3,
ring A
(1) $C_{6-14}$ aryl,
(2) $C_{3-8}$ cycloalky,
(3) $C_{3-8}$ cycloalkenyl or
(4) heterocyclic group having 1 to 4 heteroatom(s) selected from an oxygen atom, a nitrogen atom and a sulfur atom,
$R^5$ and $R^6$ are each independently
(1) hydrogen atom,
(2) halogen atom,
(3) optionally substituted $C_{1-6}$ alkyl (as defined above) or
(4) —OR$^{a8}$ wherein $R^{a8}$ is hydrogen atom, $C_{1-6}$ alkyl or $C_{6-14}$ aryl $C_{1-6}$ alkyl, and
is
(1) hydrogen atom,
(2) halogen atom,
(3) cyano,
(4) nitro,
(5) amino, $C_{1-6}$ alkanoylamino,
(6) $C_{1-6}$ alkylsulfonyl, (7) optionally substituted $C_{1-6}$ alkyl (as defined above),
(8) $C_{2-6}$ alkenyl optionally substitutd by 1 to 3 substituent(s) selected from the above group A,
(9) —COOR$^{a9}$
   wherein R$^{a9}$ is hydrogen atom or $C_{1-6}$ alkyl,
(10) —CONH—(CH$_2$)$_1$—R$^{a10}$
   wherein R$^{a10}$ is optionally substituted $C_{1-6}$ alkyl (as defined above), $C_{1-6}$ alkoxycarbonyl or $C_{1-6}$ alkanoylamino and 1 is 0 or an integer of 1 to 6,
(11) —OR$^{a11}$
   wherein R$^{a11}$ is hydrogen atom or optionally substituted $C_{1-6}$ alkyl (as defined above)
or

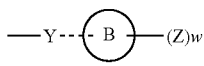 (12)

wherein
   ring B is
   (1') $C_{6-14}$ aryl,
   (2') $C_{3-8}$ cycloalkyl or
   (3') heterocyclic group (as defined above),
   each Z is independently
   (1') a group selected from the following group D,
   (2') $C_{6-14}$ aryl optionally substituted by 1 to 5 substituent(s) selected from the following group D,
   (3') $C_{3-8}$ cycloalkyl optionally substituted by 1 to 5 substituent(s) selected from the following group D,
   (4') $C_{6-14}$ aryl $C_{1-6}$ alkyl optionally substituted by 1 to 5 substituent(s) selected from the following group D,
   (5') heterocyclic group optionally substituted by 1 to 5 substituent(s) selected from the following group D,
   wherein the heterocyclic group has 1 to 4 heteroatom(s) selected from an oxygen atom, a nitrogen atom and a sulfur atom, or
   (6') heterocycle $C_{1-6}$ alkyl optionally substituted by 1 to 5 substituent(s) selected from the following group D,
   wherein the heterocycle $C_{1-6}$ alkyl is $C_{1-6}$ alkyl substituted by heterocyclic group optionally substituted by 1 to 5 substituent(s) selected from the group D, as defined above,
group D:
   (a) hydrogen atom,
   (b) halogen atom,
   (c) cyano,
   (d) nitro,
   (e) optionally substituted $C_{1-6}$ alkyl (as defined above),
   (f) —(CH$_2$)$_t$—COR$^{a18}$, (hereinafter each t means independently 0 or an integer of 1 to 6),
   wherein R$^{a18}$ is
      (1") optionally substituted $C_{1-6}$ alkyl (as defined above),
      (2") $C_{6-14}$ aryl optionally substituted by 1 to 5 substituent(s) selected from the above group B or
      (3") heterocyclic group optionally substituted by 1 to 5 substituent(s) selected from the above group B wherein the heterocyclic group has 1 to 4 heteroatom(s) selected from an oxygen atom, a nitrogen atom and a sulfur atom,
   (g) —(CH$_2$)$_t$—COOR$^{a19}$
      wherein R$^{a19}$ is hydrogen atom, optionally substituted $C_{1-6}$ alkyl (as defined above) or $C_{6-14}$ aryl $C_{1-6}$ alkyl optionally substituted by 1 to 5 substituent(s) selected from the above group B,
   (h) —(CH$_2$)$_t$—CONR$^{a27}$R$^{a28}$
      wherein R$^{a27}$ and R$^{a28}$ are each independently,
      (1") hydrogen atom,
      (2") optionally substituted $C_{1-6}$ alkyl (as defined above),
      (3") $C_{6-14}$ aryl optionally substituted by 1 to 5 substituent(s) selected from the above group B,
      (4") $C_{6-14}$ aryl $C_{1-6}$ alkyl optionally substituted by 1 to 5 substituent(s) selected from the above group B,
      (5") heterocyclic group optionally substituted by 1 to 5 substituent(s) selected from the above group B,
      (6") heterocycle $C_{1-6}$ alkyl optionally substituted by 1 to 5 substituent(s) selected from the above group B,
      wherein the heterocycle $C_{1-6}$ alkyl is $C_{1-6}$ alkyl substituted by heterocyclic group optionally substituted by 1 to 5 substituent(s) selected from the above group B, as defined above,
      (7") $C_{3-8}$ cycloalkyl optionally substituted by 1 to 5 substituent(s) selected from the above group B,
      (8") $C_{3-8}$ cycloalkyl $C_{1-6}$ alkyl optionally substituted by 1 to 5 substituent(s) selected from the above group B,
      (9") hydroxyl group or
      (10") $C_{1-6}$ alkoxy,
   (i) —(CH$_2$)$_t$—C(=NR$^{a33}$)NH$_2$
      wherein R$^{a33}$ is hydrogen atom, $C_{1-6}$ alkyl, hydroxyl group or $C_{1-6}$ alkoxy,
   (j) —(CH$_2$)$_t$—OR$^{a20}$
      wherein R$^{a20}$ is
      (1") hydrogen atom,
      (2") optionally substituted $C_{1-6}$ alkyl (as defined above),
      (3") optionally substituted $C_{2-6}$ alkenyl (as defined above),
      (4") $C_{2-6}$ alkynyl optionally substituted by 1 to 3 substituent(s) selected from the above group A,
      (5") $C_{6-14}$ aryl optionally substituted by 1 to 5 substituent(s) selected from the above group B,
      (6") $C_{6-14}$ aryl $C_{1-6}$ alkyl optionally substituted by 1 to 5 substituent(s) selected from the above group B,
      (7") heterocyclic group optionally substituted by 1 to 5 substituent(s) selected from the above group B,
      (8") heterocycle $C_{1-6}$ alkyl optionally substituted by 1 to 5 substituent(s) selected from the above group B,
      (9") $C_{3-8}$ cycloalkyl optionally substituted by 1 to 5 substituent(s) selected from the above group B, or
      (10") $C_{3-8}$ cycloalkyl $C_{1-6}$ alkyl optionally substituted by 1 to 5 substituent(s) selected from the above group B,
   (k) —(CH$_2$)$_t$—O—(CH$_2$)$_p$—COR$^{a21}$
      wherein R$^{a21}$ is amino, $C_{1-6}$ alkylamino or heterocyclic group optionally substituted by 1 to 5 substituent(s) selected from the above group B, and p is 0 or an integer of 1 to 6, (l) —(CH$_2$)$_t$—NR$^{a22}$R$^{a23}$
  wherein R$^{a22}$ and R$^{a23}$ are each independently
  (1") hydrogen atom,
  (2") optionally substituted C$_{1-6}$ alkyl (as defined above),
  (3") C$_{6-14}$ aryl optionally substituted by 1 to 5 substituent(s) selected from the above group B,
  (4") C$_{6-14}$ aryl C$_{1-6}$ alkyl optionally substituted by 1 to 5 substituent(s) selected from the above group B,
  (5") heterocycle C$_{1-6}$ alkyl optionally substituted by 1 to 5 substituent(s) selected from the above group B or
  (6") heterocyclic group optionally substituted by 1 to 5 substituent(s) selected from the above group B,
(m) —(CH$_2$)$_t$—NR$^{a29}$CO—R$^{a24}$
  wherein R$^{a29}$ is hydrogen atom, C$_{1-6}$ alkyl or C$_{1-6}$ alkanoyl, and R$^{a24}$ is
  (1") amino,
  (2") C$_{1-6}$ alkylamino,
  (3") optionally substituted C$_{1-6}$ alkyl (as defined above),
  (4") C$_{6-14}$ aryl optionally substituted by 1 to 5 substituent(s) selected from the above group B,
  (5") heterocyclic group optionally substituted by 1 to 5 substituent(s) selected from the above group B or
  (6") heterocycle C$_{1-6}$ alkyl optionally substituted by 1 to 5 substituent(s) selected from the above group B,
(n) —(CH$_2$)$_t$—NR$^{a29}$SO$_2$—R$^{a25}$
  wherein R$^{a29}$ is as defined above, and R$^{a25}$ is hydrogen atom, optionally substituted C$_{1-6}$ alkyl (as defined above), C$_{6-14}$ aryl optionally substituted by 1 to 5 substituent(s) selected from the above group B or heterocyclic group optionally substituted by 1 to 5 substituent(s) selected from the above group B,
(o) —(CH$_2$)$_t$—S(O)$_q$—R$^{a25}$
  wherein R$^{a25}$ is as defined above, and q is 0, 1 or 2,
(p) —(CH$_2$)$_t$—SO$_2$—NHR$^{a26}$
  wherein R$^{a26}$ is hydrogen atom, optionally substituted C$_{1-6}$ alkyl (as defined above), C$_{6-14}$ aryl optionally substituted by 1 to 5 substituent(s) selected from the above group B or heterocyclic group optionally substituted by 1 to 5 substituent(s) selected from the above group B,
and
(q) heterocyclic group having 1 to 4 heteroatom(s) selected from an oxygen atom, a nitrogen atom and a sulfur atom, and
w is an integer of 1 to 3, and
Y is
  (1') a single bond,
  (2') C$_{1-6}$ alkylene,
  (3') C$_{2-6}$ alkenylene,
  (4') —(CH$_2$)$_m$—O—(CH$_2$)$_n$—,
    (hereinafter m and n are each independently 0 or an integer of 1 to 6),
  (5') —CO—,
  (6') —CO$_2$—(CH$_2$)$_n$—,
  (7') —CONH—(CH$_2$)$_n$—NH—,
  (8') —NHCO$_2$—,
  (9') —NHCONH—,
  (10') —O—(CH$_2$)$_n$—CO—,
  (11') —O—(CH$_2$)$_n$—O—,
  (12') —SO$_2$—,
  (13') —(CH$_2$)$_m$—NR$^{a12}$—(CH$_2$)$_n$—
    wherein R$^{a12}$ is
    (1") hydrogen atom,
    (2") optionally substituted C$_{1-6}$ alkyl (as defined above),
    (3") C$_{6-14}$ aryl C$_{1-6}$ alkyl optionally substituted by 1 to 5 substituent(s) selected from the above group B,
    (4") C$_{6-14}$ aryl optionally substituted by 1 to 5 substituent(s) selected from the above group B,
    (5") —COR$^{b5}$
      wherein R$^{b5}$ is hydrogen atom, optionally substituted C$_{1-6}$ alkyl (as defined above), C$_{6-14}$ aryl optionally substituted by 1 to 5 substituent(s) selected from the above group B or C$_{6-14}$ aryl C$_{1-6}$ alkyl optionally substituted by 1 to 5 substituent(s) selected from the above group B,
    (6") —COOR$^{b5}$ (R$^{b5}$ is as defined above) or
    (7") —SO$_2$R$^{b5}$ (R$^{b5}$ is as defined above),
  (14') —NR$^{a12}$CO—(R$^{a12}$ is as defined above),
  (15') —CONR$^{a13}$—(CH$_2$)$_n$—
    wherein R$^{a13}$ is hydrogen atom, optionally substituted C$_{1-6}$ alkyl (as defined above) or C$_{6-14}$ aryl C$_{1-6}$ alkyl optionally substituted by 1 to 5 substituent(s) selected from the above group B,
  (16') —CONH—CHR$^{a14}$—
    wherein R$^{a14}$ is C$_{6-14}$ aryl optionally substituted by 1 to 5 substituent(s) selected from the above group B,
  (17') —O—(CH$_2$)$_m$—CR$^{a15}$R$^{a16}$—(CH$_2$)$_n$—
    wherein R$^{a15}$ and R$^{a16}$ are each independently
    (1") hydrogen atom,
    (2") carboxyl,
    (3") C$_{1-6}$ alkyl,
    (4") —OR$^{b6}$
    wherein R$^{b7}$ is C$_{1-6}$ alkyl or C$_{6-14}$ aryl C$_{1-6}$ alkyl,
    (5") —NHR$^{b7}$
    wherein R$^{b7}$ is hydrogen atom, C$_{1-6}$ alkyl, C$_{1-6}$ alkanoyl or C$_{6-14}$ aryl C$_{1-6}$ alkyloxycarbonyl, or R$^{a15}$ is optionally
    (6")

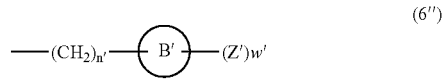

wherein n', ring B', Z' and w' are the same as the above-mentioned n, ring B, Z and w, respectively, and may be the same as or different from the respective counterparts,
  (18') —(CH$_2$)$_n$—NR$^{a12}$—CHR$^{a15}$—(R$^{a12}$ and R$^{a15}$ are each as defined above),
  (19') —NR$^{a17}$SO$_2$—
    wherein R$^{a17}$ is hydrogen atom or C$_{1-6}$ alkyl,
  (20') —S(O)$_e$—(CH$_2$)$_m$—CR$^{a15}$R$^{a16}$—(CH$_2$)$_n$— (e is 0, 1 or 2, R$^{a15}$ and R$^{a16}$ are each as defined above), or
  (21') —(CH$_2$)$_m$—CR$^{a15}$R$^{a16}$—(CH$_2$)$_n$—(R$^{a15}$ and R$^{a16}$ are each as defined above).
(2) The therapeutic agent of (1) above, wherein 1 to 4 of the G$^1$, G$^2$, G$^3$, G$^4$, G$^5$, G$^6$, G$^7$, G$^8$ and G$^9$ is (are) a nitrogen atom.
(3) The therapeutic agent of (2) above, wherein G$^2$ is C(—R$^2$) and G$^6$ is a carbon atom.

(4) The therapeutic agent of (2) or (3) above, wherein $G^5$ is a nitrogen atom.
(5) The therapeutic agent of (1) above, wherein, in formula [I], the moiety
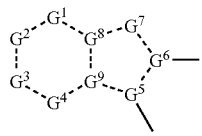
is a fused ring selected from
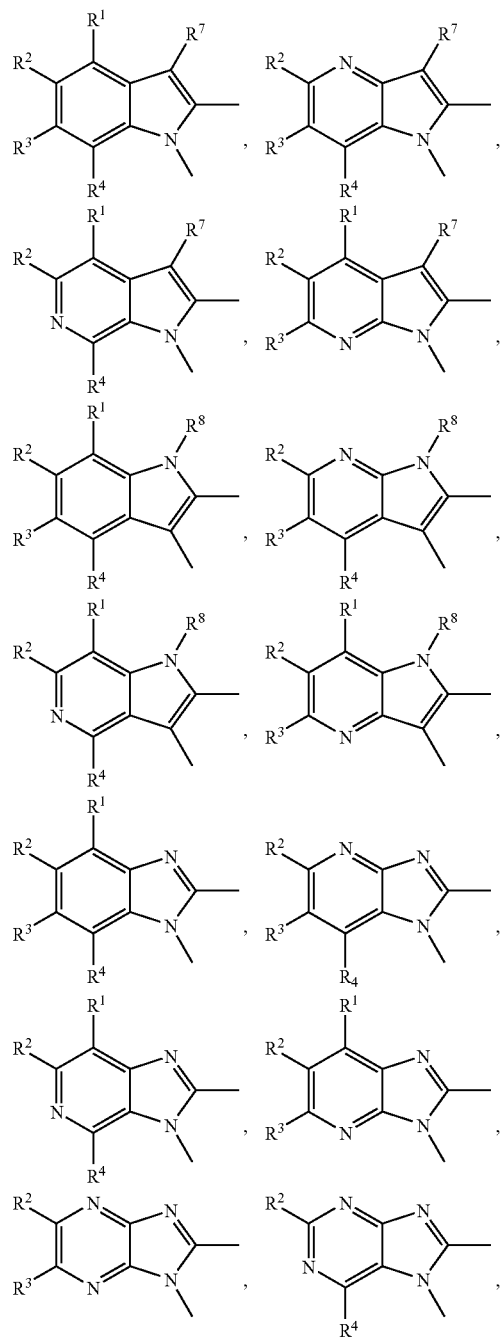
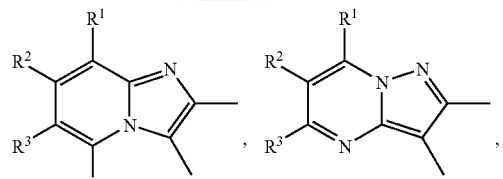
-continued
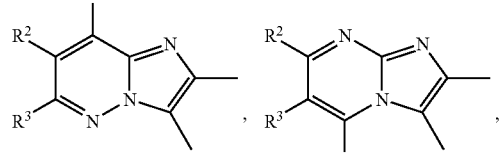
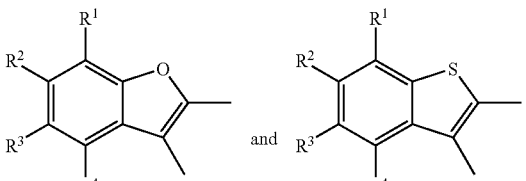
(6) The therapeutic agent of (5) above, wherein, in formula [I], the moiety
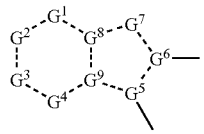
is a fused ring selected from
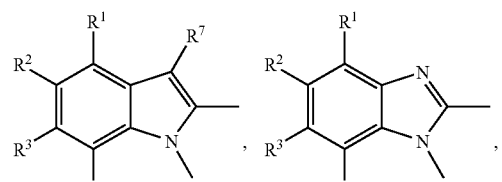
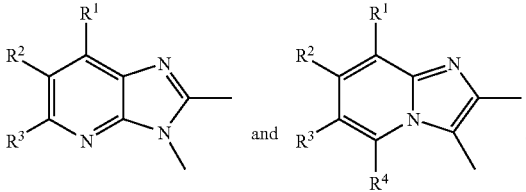
(7) The therapeutic agent of (6) above, which comprises a fused ring compound of the following formula [I-1]
[I-1]
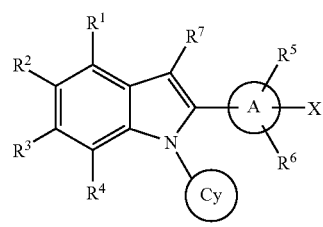

wherein each symbol is as defined in (1), or a pharmaceutically acceptable salt thereof as an active ingredient.

(8) The therapeutic agent of (6) above, which comprises a fused ring compound of the following formula [I-2]

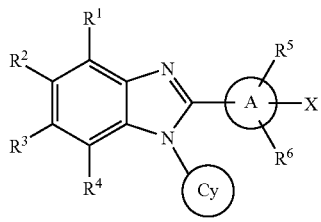
[I-2]

wherein each symbol is as defined in (1), or a pharmaceutically acceptable salt thereof as an active ingredient.

(9) The therapeutic agent of (6) above, which comprises a fused ring compound of the following formula [I-3]

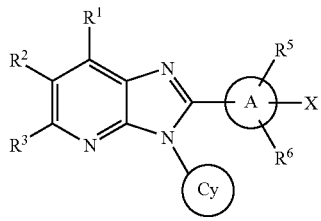
[I-3]

wherein each symbol is as defined in (1),
or a pharmaceutically acceptable salt thereof as an active ingredient.

(10) The therapeutic agent of (6) above, which comprises a fused ring compound of the following formula [I-4]

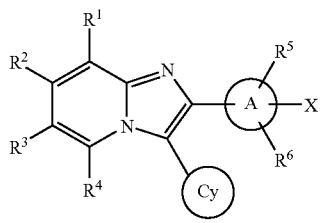
[I-4]

wherein each symbol is as defined in (1),
or a pharmaceutically acceptable salt thereof as an active ingredient.

(11) The therapeutic agent of any of (1) to (10) above, wherein at least one of $R^1$, $R^2$, $R^3$ and $R^4$ is carboxyl, —COOR$^{a1}$, CONR$^{a2}$R$^{a3}$, —SO$_2$R$^{a7}$ (wherein R$^{a1}$, R$^{a2}$, R$^{a3}$ and R$^{a7}$ are as defined in (1)),

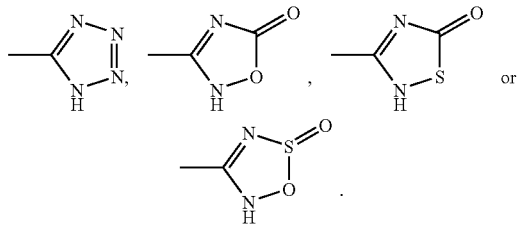

(12) The therapeutic agent of (11) above, wherein at least one of $R^1$, $R^2$, $R^3$ and $R^4$ is carboxyl, —COOR$^{a1}$, —CONR$^{a2}$R$^{a3}$ or —SO$_2$R$^{a7}$ wherein R$^{a1}$, R$^{a2}$, R$^{a3}$ and R$^{a7}$ are as defined in (1).

(13) The therapeutic agent of any of (1) to (10) above, wherein at least one of $R^1$, $R^2$, $R^3$ and $R^4$ is —COOR$^{a1}$ wherein R$^{a1}$ is glucuronic acid residue.

(14) The therapeutic agent of any of (1) to (10) above, wherein at least one of $R^1$, $R^2$, $R^3$ and $R^4$ is heterocyclic group having 1 to 4 heteroatom(s) selected from an oxygen atom, a nitrogen atom and a sulfur atom.

(15) The therapeutic agent of any of (1) to (14) above, wherein the ring Cy is cyclopentyl, cyclohexyl, cycloheptyl, tetrahydrothiopyranyl or piperidino.

(16) The therapeutic agent of any of (1) to (14) above, wherein the ring Cy is

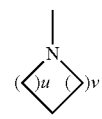

wherein each symbol is as defined in (1).

(17) The therapeutic agent of any of (1) to (16) above, wherein the ring A is $C_{6-14}$ aryl.

(18) The therapeutic agent of any of (1) to (17) above, wherein at least one substituent optionally substituted by group A is a substituent substituted by $C_{1-6}$ alkoxy $C_{1-6}$ alkoxy.

(19) The therapeutic agent of any of (1) to (18) above, wherein the Y is —(CH$_2$)$_m$—CR$^{a15}$R$^{a16}$—(CH$_2$)$_n$— wherein each symbol is as defined in (1).

(20) The therapeutic agent of any of (1) to (19) above, wherein at least one group represented by Z is heterocycle $C_{1-6}$ alkyl optionally substituted by 1 to 5 substituent(s) selected from the group D.

(21) The therapeutic agent of any of (1) to (19) above, wherein at least one group represented by Z is a heterocyclic group optionally substituted by 1 to 5 substituent(s) selected from the group D, wherein said heterocyclic group is selected from the following groups:

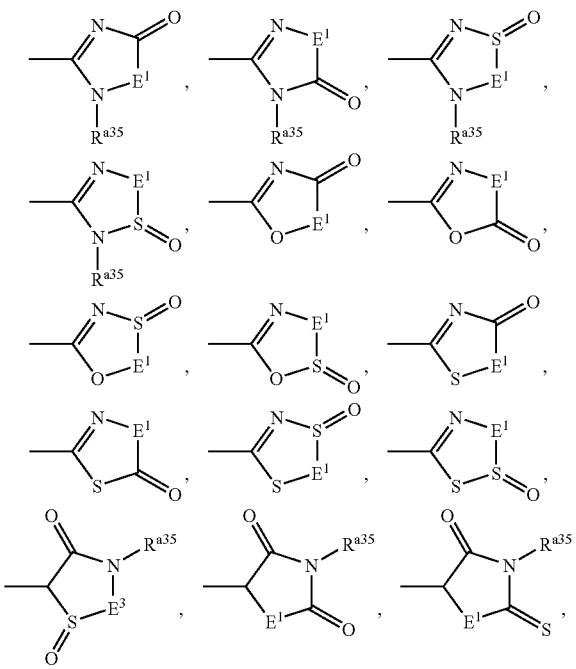

17

-continued

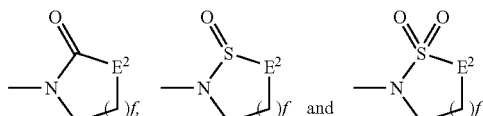

wherein E¹ is an oxygen atom, a sulfur atom or N(—R$^{a35}$), E² is an oxygen atom, CH₂ or N(—R$^{a35}$), E³ is an oxygen atom or a sulfur atom, wherein each R$^{a35}$ is independently hydrogen atom or C$_{1-6}$ alkyl, f is an integer of 1 to 3, and h and h' are the same or different and each is an integer of 1 to 3.

(22) The therapeutic agent of (21) above, wherein at least one group represented by Z is heterocyclic group optionally substituted by 1 to 5 substituent(s) selected from the group D wherein said heterocyclic group is selected from the following groups:

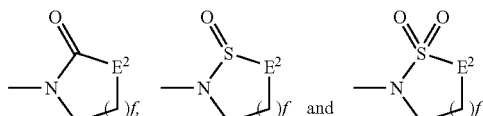

wherein each symbol is as defined in (21).

(23) The therapeutic agent of any of (1) to (19) above, wherein at least one group represented by group D is —(CH₂)$_t$—CONR$^{a27}$R$^{a28}$ wherein each symbol is as defined in (1), and at least one of R$^{a27}$ and R$^{a28}$ is C$_{1-6}$ alkoxy.

(24) The therapeutic agent of any of (1) to (19) above, wherein at least one group represented by group D is —(CH₂)$_t$—C(=NR$^{a33}$)NH₂ wherein each symbol is as defined in (1), and R$^{a33}$ is hydroxyl group or C$_{1-6}$ alkoxy.

(25) The therapeutic agent of any of (1) to (19) above, wherein at least one group represented by group D is —(CH₂)$_t$—O—(CH₂)$_p$—COR$^{a21}$, wherein each symbol is as defined in (1), and R$^{a21}$ is amino.

(26) The therapeutic agent of any of (1) to (19) above, wherein at least one group represented by group D is —(CH₂)$_t$—NR$^{a29}$CO—R$^{a24}$ wherein each symbol is as defined in (1), and R$^{a24}$ is amino or C$_{1-6}$ alkylamino.

(27) The therapeutic agent of any of (1) to (19) above, wherein at least one group represented by group D is —(CH₂)$_t$—NR$^{a22}$R$^{a23}$ wherein each symbol is as defined in (1), and at lease one of R$^{a22}$ and R$^{a23}$ is heterocyclic group optionally substituted by 1 to 5 substituent(s) selected from the group B.

(28) The therapeutic agent of any of (1) to (19) above, wherein at least one group represented by group D is heterocyclic group having 1 to 4 heteroatom(s) selected from an oxygen atom, a nitrogen atom and a sulfur atom.

18

(29) A fused ring compound of the following formula [II]

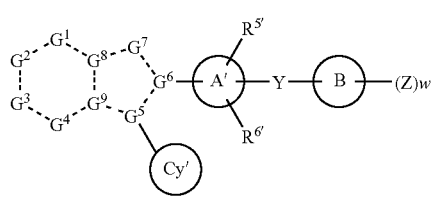

[II]

wherein
the moiety

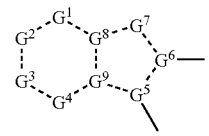

is a fused ring selected from

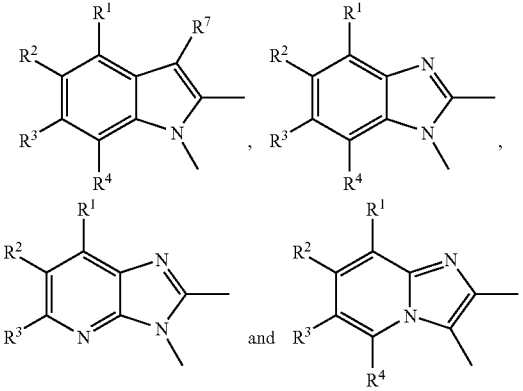

wherein R¹, R², R³ and R⁴ are each independently,
(1) hydrogen atom,
(2) C$_{1-6}$ alkanoyl,
(3) carboxyl,
(4) cyano,
(5) nitro,
(6) C$_{1-6}$ alkyl optionally substituted by 1 to 3 substituent(s) selected from the following group A, group A; halogen atom, hydroxyl group, carboxyl, amino, C$_{1-6}$ alkoxy, C$_{1-6}$ alkoxy C$_{1-6}$ alkoxy, C$_{1-6}$ alkoxycarbonyl and C$_{1-6}$ alkylamino,
(7) —COOR$^{a1}$
  wherein R$^{a1}$ is optionally substituted C$_{1-6}$ alkyl (as defined above), C$_{6-14}$ aryl C$_{1-6}$ alkyl optionally substituted by 1 to 5 substituent(s) selected from the following group B or glucuronic acid residue, group B; halogen atom, cyano, nitro, C$_{1-6}$ alkyl, halogenated C$_{1-6}$ alkyl, C$_{1-6}$ alkanoyl, —(CH₂)$_r$—COOR$^{b1}$, —(CH₂)$_r$—CONR$^{b1}$R$^{b2}$, —(CH₂)$_r$—NR$^{b1}$R$^{b2}$, —(CH₂)$_r$—NR$^{b1}$—COR$^{b2}$, —(CH₂)$_r$—NHSO₂R$^{b1}$, —(CH₂)$_r$—OR$^{b1}$, —(CH₂)$_r$—SR$^{b1}$, —(CH₂)$_r$—SO₂R$^{b1}$ and —(CH₂)$_r$—SO₂NR$^{b1}$R$^{b2}$ wherein R$^{b1}$ and R$^{b2}$ are each independently hydrogen atom or C$_{1-6}$ alkyl and r is 0 or an integer of 1 to 6,
(8) —CONR$^{a2}$R$^{a3}$
  wherein R$^{a2}$ and R$^{a3}$ are each independently hydrogen atom, C$_{1-6}$ alkoxy or optionally substituted C$_{1-6}$ alkyl (as defined above), (9) —C(=NR$^{a4}$)NH$_2$
wherein R$^{a4}$ is hydrogen atom or hydroxyl group,
(10) —NHR$_{a5}$
wherein R$^{a5}$ is hydrogen atom, C$_{1-6}$ alkanoyl or C$_{1-6}$ alkylsulfonyl,
(11) —OR$^{a6}$
wherein R$^{a6}$ is hydrogen atom or optionally substituted C$_{1-6}$ alkyl (as defined above),
(12) —SO$_2$R$^{a7}$
wherein R$^{a7}$ is hydroxyl group, amino, C$_{1-6}$ alkyl or C$_{1-6}$ alkylamino,
(13) —P(=O)(OR$^{a31}$)$_2$
wherein R$^{a31}$ is hydrogen atom, optionally substituted C$_{1-6}$ alkyl (as defined above) or C$_{6-14}$ aryl C$_{1-6}$ alkyl optionally substituted by 1 to 5 substituent(s) selected from the above group B,
or
(14) heterocyclic group having 1 to 4 heteroatom(s) selected from an oxygen atom, a nitrogen atom and a sulfur atom, and
R$^7$ is hydrogen atom or optionally substitute C$_{1-6}$ alkyl (as defined above),
ring Cy' is
(1) C$_{3-8}$ cycloalkyl optionally substituted by 1 to 5 substituent(s) selected from the following group C, group C; hydroxyl group, halogen atom, C$_{1-6}$ alkyl and C$_{1-6}$ alkoxy, or
(2)

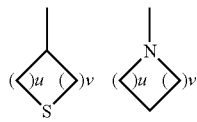

wherein u and v are each independently an integer of 1 to 3,
ring A'0 is a group selected from a group consisting of phenyl, pyridyl, pyrazinyl, pyrimidinyl, pyridazinyl, cyclohexyl, cyclohexenyl, furyl and thienyl,
R$^5$ and R$^{6'}$ are each independently
(1) hydrogen atom,
(2) halogen atom,
(3) optionally substituted C$_{1-6}$ alkyl (as defined above) or
(4) hydroxyl group
ring B is
(1) C$_{6-14}$ aryl,
(2) C$_{3-8}$ cycloalkyl or
(3) heterocyclic group having 1 to 4 heteroatom(s) selected from an oxygen atom, a nitrogen atom and a sulfur atom,
each Z is independently
(1) a group selected from the following group D,
(2) C$_{6-14}$ aryl optionally substituted by 1 to 5 substituent(s) selected from the following group D,
(3) C$_{3-8}$ cycloalkyl optionally substituted by 1 to 5 substituent(s) selected from the following group D,
(4) C$_{6-14}$ aryl C$_{1-6}$ alkyl optionally substituted by 1 to 5 substituent(s) selected from the following group D,
(5) heterocyclic group optionally substituted by 1 to 5 substituent(s) selected from the following group D wherein the heterocyclic group has 1 to 4 heteroatom(s) selected from an oxygen atom, a nitrogen atom and a sulfur atom, or
(6) heterocycle C$_{1-6}$ alkyl optionally substituted by 1 to 5 substituent(s) selected from the following group D wherein the heterocycle C$_{1-6}$ alkyl is C$_{1-6}$ alkyl substituted by heterocyclic group optionally substituted by 1 to 5 substituent(s) selected from the group D, as defined above, group D:
(a) hydrogen atom,
(b) halogen atom,
(c) cyano,
(d) nitro,
(e) optionally substituted C$_{1-6}$ alkyl (as defined above),
(f) —(CH$_2$)$_t$—COR$^{a10}$, (hereinafter each t means independently 0 or an integer of 1 to 6),
wherein R$^{a18}$ is
(1') optionally substituted C$_{1-6}$ alkyl (as defined above),
(2') C$_{6-14}$ aryl optionally substituted by 1 to 5 substituent(s) selected from the above group B or
(3') heterocyclic group optionally substituted by 1 to 5 substituent(s) selected from the above group B wherein the heterocyclic group has 1 to 4 heteroatom(s) selected from an oxygen atom, a nitrogen atom and a sulfur atom,
(g) —(CH$_2$)$_t$—COOR$^{a19}$
wherein R$^{a19}$ is hydrogen atom, optionally substituted C$_{1-6}$ alkyl (as defined above) or C$_{6-14}$ aryl C$_{1-6}$ alkyl optionally substituted by 1 to 5 substituent(s) selected from the above group B,
(h) —(CH$_2$)$_t$—CONR$^{a27}$R$^{a28}$
wherein R$^{a27}$ and R$^{a28}$ are each independently,
(1') hydrogen atom,
(2') optionally substituted C$_{1-6}$ alkyl (as defined above),
(3') C$_{6-14}$ aryl optionally substituted by 1 to 5 substituent(s) selected from the above group B,
(4') C$_{6-14}$ aryl C$_{1-6}$ alkyl optionally substituted by 1 to 5 substituent(s) selected from the above group B,
(5') heterocyclic group optionally substituted by 1 to 5 substituent(s) selected from the above group B,
(6') heterocycle C$_{1-6}$ alkyl optionally substituted by 1 to 5 substituent(s) selected from the above group B,
wherein the heterocycle C$_{1-6}$ alkyl is C$_{1-6}$ alkyl substituted by heterocyclic group optionally substituted by 1 to 5 substituent(s) selected from the above group B, as defined above,
(7') C$_{3-8}$ cycloalkyl optionally substituted by 1 to 5 substituent(s) selected from the above group B,
(8') C$_{3-8}$ cycloalkyl C$_{1-6}$ alkyl optionally substituted by 1 to 5 substituent(s) selected from the above group B,
(9') hydroxyl group or
(10') C$_{1-6}$ alkoxy,
(i) —(CH$_2$)$_t$—C(=NR$^{a33}$)NH$_2$
wherein R$^{a33}$ is hydrogen atom, C$_{1-6}$ alkyl, hydroxyl group or C$_{1-6}$ alkoxy,
(j) —(CH$_2$)$_t$—OR$^{a20}$
wherein R$^{a20}$ is
(1') hydrogen atom,
(2') optionally substituted C$_{1-6}$ alkyl (as defined above),
(3') optionally substituted C$_{2-6}$ alkenyl (as defined above),
(4') C$_{2-6}$ alkynyl optionally substituted by 1 to 3 substituent(s) selected from the above group A,
(5') C$_{6-14}$ aryl optionally substituted by 1 to 5 substituent(s) selected from the above group B, (6') $C_{6-14}$ aryl $C_{1-6}$ alkyl optionally substituted by 1 to 5 substituent(s) selected from the above group B, (7') heterocyclic group optionally substituted by 1 to 5 substituent(s) selected from the above group B, (8') heterocycle $C_{1-6}$ alkyl optionally substituted by 1 to 5 substituent(s) selected from the above group B, (9') $C_{3-8}$ cycloalkyl optionally substituted by 1 to 5 substituent(s) selected from the above group B, or (10') $C_{3-8}$ cycloalkyl $C_{1-6}$ alkyl optionally substituted by 1 to 5 substituent(s) selected from the above group B, (k) —$(CH_2)_t$—O—$(CH_2)_p$—$COR^{a21}$ wherein $R^{a21}$ is amino, $C_{1-6}$ alkylamino or heterocyclic group optionally substituted by 1 to 5 substituent(s) selected from the above group B, and p is 0 or an integer of 1 to 6, (l) —$(CH_2)_t$—$NR^{a22}R^{a23}$ wherein $R^{a22}$ and $R^{a23}$ are each independently (1') hydrogen atom, (2') optionally substituted $C_{1-6}$ alkyl (as defined above), (3') $C_{6-14}$ aryl optionally substituted by 1 to 5 substituent(s) selected from the above group B, (4') $C_{6-14}$ aryl $C_{1-6}$ alkyl optionally substituted by 1 to 5 substituent(s) selected from the above group B, (5') heterocycle $C_{1-6}$ alkyl optionally substituted by 1 to 5 substituent(s) selected from the above group B or (6') heterocyclic group optionally substituted by 1 to 5 substituent(s) selected from the above group B, (m) —$(CH_2)_t$—$NR^{a29}CO$—$R^{a24}$ wherein $R^{a29}$ is hydrogen atom, $C_{1-6}$ alkyl or $C_{1-6}$ alkanoyl, and $R^{a24}$ is (1') amino, (2') $C_{1-6}$ alkylamino, (3') optionally substituted $C_{1-6}$ alkyl (as defined above), (4') $C_{6-14}$ aryl optionally substituted by 1 to 5 substituent(s) selected from the above group B, (5') heterocyclic group optionally substituted by 1 to 5 substituent(s) selected from the above group B, or (6') heterocycle $C_{1-6}$ alkyl optionally substituted by 1 to 5 substituent(s) selected from the above group B, (n) —$(CH_2)_5$—$NR^{a29}SO_2$—$R^{a25}$ wherein $R^{a29}$ is as defined above, and $R^{a25}$ is hydrogen atom, optionally substituted $C_{1-6}$ alkyl (as defined above), $C_{6-14}$ aryl optionally substituted by 1 to 5 substituent(s) selected from the above group B or heterocyclic group optionally substituted by 1 to 5 substituent(s) selected from the above group B, (o) —$(CH_2)_t$—$S(O)_q$—$R^{a25}$ wherein $R^{a25}$ is as defined above, and q is 0, 1 or 2, (p) —$(CH_2)_t$—$SO_2$—$NHR^{a26}$ wherein $R^{a26}$ is hydrogen atom, optionally substituted $C_{1-6}$ alkyl (as defined above), $C_{6-14}$ aryl optionally substituted by 1 to 5 substituent(s) selected from the above group B or heterocyclic group optionally substituted by 1 to 5 substituent(s) selected from the above group B, and (q) heterocyclic group having 1 to 4 heteroatom(s) selected from an oxygen atom, a nitrogen atom and a sulfur atom, is an integer of 1 to 3, and y is (1) a single bond, (2) $C_{1-6}$ alkylene, (3) $C_{2-6}$ alkenylene, (4) —$(CH_2)_m$—O—$(CH_2)_n$—, (hereinafter m and n are each independently 0 or an integer of 1 to 6), (5) —CO—, (6) —$CO_2$—$(CH_2)_n$—, (7) —CONH—$(CH_2)_n$—NH—, (8) —$NHCO_2$—, (9) —NHCONH—,

(10) —O—$(CH_2)_n$—CO—,

(11) —O—$(CH_2)_n$—O—,

(12) —$SO_2$—,

(13) —$(CH_2)_m$—$NR^{a12}$—$(CH_2)_n$— wherein $R^{a12}$ is (1') hydrogen atom, (2') optionally substituted $C_{1-6}$ alkyl (as defined above), (3') $C_{6-14}$ aryl $C_{1-6}$ alkyl optionally substituted by 1 to 5 substituent(s) selected from the above group B, (4') $C_{6-14}$ aryl optionally substituted by 1 to 5 substituent(s) selected from the above group B, (5') —$COR^{b5}$ wherein $R^{b5}$ is hydrogen atom, optionally substituted $C_{1-6}$ alkyl (as defined above), $C_{6-14}$ aryl optionally substituted by 1 to 5 substituent(s) selected from the above group B or $C_{6-14}$ aryl $C_{1-6}$ alkyl optionally substituted by 1 to 5 substituent(s) selected from the above group B, (6') —$COOR^{b5}$ ($R^{b5}$ is as defined above) or (7') —$SO_2R^{b5}$ ($R^{b5}$ is as defined above),

(14) —$NR^{a12}CO$— ($R^{a12}$ is as defined above),

(15) —$CONR^{a13}$—$(CH_2)_n$— wherein $R^{a13}$ is hydrogen atom, optionally substituted $C_{1-6}$ alkyl (as defined above) or $C_{6-14}$ aryl $C_{1-6}$ alkyl optionally substituted by 1 to 5 substituent(s) selected from the above group B,

(16) —CONH—$CHR^{a14}$— wherein $R^{a14}$ is $C_{6-14}$ aryl optionally substituted by 1 to 5 substituent(s) selected from the above group B,

(17) —O—$(CH_2)_m$—$CR^{a15}R^{a16}$—$(CH_2)_n$— wherein $R^{a15}$ and $R^{a16}$ are each independently (1') hydrogen atom, (2') carboxyl, (3') $C_{1-6}$ alkyl, (4') —$OR^{b6}$ wherein $R^{b6}$ is $C_{1-6}$ alkyl or $C_{6-14}$ aryl $C_{1-6}$ alkyl, or (5') —$NHR^{b7}$ wherein $R^{b7}$ is hydrogen atom, $C_{1-6}$ alkyl, $C_{1-6}$ alkanoyl or $C_{6-14}$ aryl $C_{1-6}$ alkyloxycarbonyl, or $R^{a15}$ is optionally (6')

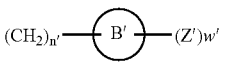

wherein n', ring B', Z' and w' are the same as the above-mentioned n, ring B, Z and w, respectively, and may be the same as or different from the respective counterparts,

(18) —$(CH_2)_n$—$NR^{a12}$—$CHR^{a15}$— ($R^{a12}$ and $R^{a15}$ are each as defined above),

(19) —NR$^{a17}$SO$_2$—
   wherein R$^{a17}$ is hydrogen atom or C$_{1-6}$ alkyl,
(20) —S(O)$_e$—(CH$_2$)$_m$—CR$^{a15}$R$^{a16}$—(CH$_2$)$_n$— (e is 0, 1 or 2, R$^{a15}$ and R$^{a16}$ are each as defined above), or
(21) —(CH$_2$)$_m$—CR$^{a15}$R$^{a16}$—(CH$_2$)$_n$— (R$^{a15}$ and R$^{a16}$ are each as defined above), or a pharmaceutically acceptable salt thereof.

(30) The fused ring compound of (29) above, which is represented by the following formula [II-1]

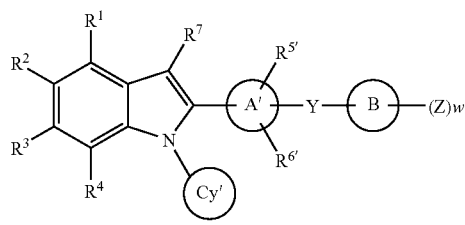

[II-1]

wherein each symbol is as defined in (29), or a pharmaceutically acceptable salt thereof.

(31) The fused ring compound of (29) above, which is represented by the following formula [II-2]

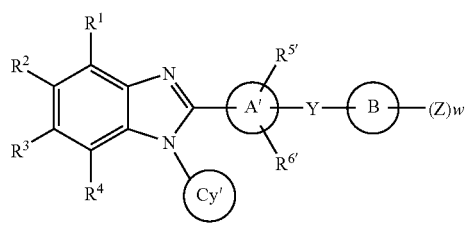

[II-2]

wherein each symbol is as defined in (29), or a pharmaceutically acceptable salt thereof.

(32) The fused ring compound of (29) above, which is represented by the following formula [II-3]

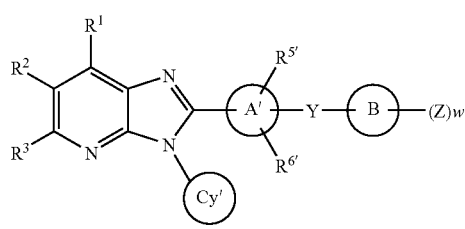

[II-3]

wherein each symbol is as defined in (29), or a pharmaceutically acceptable salt thereof.

(33) The fused ring compound of (29) above, which is represented by the following formula [II-4]

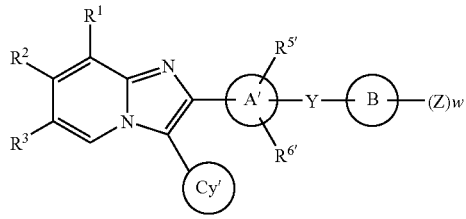

[II-4]

wherein each symbol is as defined in (29), or a pharmaceutically acceptable salt thereof.

(34) The fused ring compound of any of (29) to (33) above, wherein at least one of R$^1$, R$^2$, R$^3$ and R$^4$ is carboxyl, —COOR$^{a1}$, —CONR$^{a2}$R$^{a3}$, —SO$_2$R$^{a7}$ (wherein R$^{a1}$, R$^{a2}$, R$^{a3}$ and R$^{a7}$ are as defined in (29)),

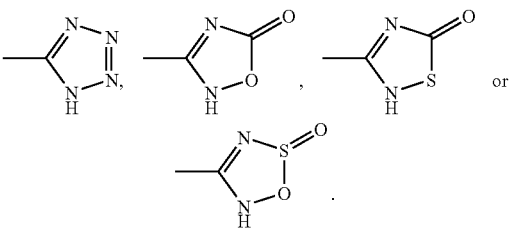

or a pharmaceutically acceptable salt thereof.

(35) The fused ring compound of (34) above, wherein at least one of R$^1$, R$^2$, R$^3$ and R$^4$ is carboxyl, —COOR$^{a1}$ or —SO$_2$R$^{a7}$ wherein R$^{a1}$ and R$^{a7}$ are as defined in (29), or a pharmaceutically acceptable salt thereof.

(36) The fused ring compound of (35) above, wherein at least one of R$^1$, R$^2$, R$^3$ and R$^4$ is carboxyl or —COOR$^{a1}$ wherein R$^{a1}$ is as defined in (29), or a pharmaceutically acceptable salt thereof.

(37) The fused ring compound of (36) above, wherein R$^2$ is carboxyl and R$^1$, R$^3$ and R$^4$ are hydrogen atoms, or a pharmaceutically acceptable salt thereof.

(38) The fused ring compound of any of (29) to (33) above, wherein at least one of R$^1$, R$^2$, R$^3$ and R$^4$ is —COOR$^{a1}$ wherein R$^{a1}$ is glucuronic acid residue, or a pharmaceutically acceptable salt thereof.

(39) The fused ring compound of any of (29) to (33) above, wherein at least one of R$^1$, R$^2$, R$^3$ and R$^4$ is heterocyclic group having 1 to 4 heteroatom(s) selected from an oxygen atom, a nitrogen atom and a sulfur atom, or a pharmaceutically acceptable salt thereof.

(40) The fused ring compound of any of (29) to (33) above, wherein the ring Cy' is cyclopentyl, cyclohexyl, cycloheptyl or tetrahydrothiopyranyl, or a pharmaceutically acceptable salt thereof.

(41) The fused ring compound of (40) above, wherein the ring Cy' is cyclopentyl, cyclohexyl or cycloheptyl, or a pharmaceutically acceptable salt thereof.

(42) The fused ring compound of any of (29) to (39) above, wherein the ring Cy' is

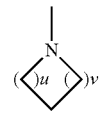

wherein each symbol is as defined in (29), or a pharmaceutically acceptable salt thereof.

(43) The fused ring compound of any of (29) to (42) above, wherein the ring A' is phenyl, pyridyl, pyrazinyl, pyrimidinyl or pyridazinyl, or a pharmaceutically acceptable salt thereof.

(44) The fused ring compound of (43) above, wherein the ring A' is phenyl or pyridyl, or a pharmaceutically acceptable salt thereof.

(45) The fused ring compound of (44) above, wherein the ring A' is phenyl, or a pharmaceutically acceptable salt thereof.

(46) The fused ring compound of any of (29) to (45) above, wherein at least one substituent optionaly substituted by group A is a substituent substituted by $C_{1-6}$ alkoxy $C_{1-6}$ alkoxy, or a pharmaceutically acceptable salt thereof.

(47) The fused ring compound of any of (29) to (46) above, wherein the Y is $-(CH_2)_m-O-(CH_2)_n-$, $-NHCO_2-$, $-CONH-CHR^{a14}-$, $-(CH_2)_m-NR^{a12}-(CH_2)_n$, $-CONR^{a13}-(CH_2)_n-$, $-O-(CH_2)_m-CR^{a15}R^{126}-(CH_2)_n-$ or $-(CH_2)_n-NR^{a12}-CHR^{a15}-$ (wherein each symbol is as defined in (29)), or a pharmaceutically acceptable salt thereof.

(48) The fused ring compound of (47) above, wherein the Y is $-(CH_2)_m-O-(CH_2)_n-$ or $-O-(CH_2)_m-CR^{a15}R^{a16}-(CH_2)_n-$ (wherein each symbol is as defined in (29)), or a pharmaceutically acceptable salt thereof.

(49) The fused ring compound of (48) above, wherein the Y is $-(CH_2)_m-O-(CH_2)_n-$ wherein each symbol is as defined in (29), or a pharmaceutically acceptable salt thereof.

(50) The fused ring compound of any of (29) to (46) above, wherein the Y is $-(CH_2)_mCR^{a15}R^{a16}-(CH_2)_n-$ (wherein each symbol is as defined in (29)), or a pharmaceutically acceptable salt thereof.

(51) The fused ring compound of any of (29) to (50) above, wherein the $R^2$ is carboxyl, $R^1$, $R^3$ and $R^4$ are hydrogen atoms, the ring Cy' is cyclopentyl, cyclohexyl or cycloheptyl, and the ring A' is phenyl, or a pharmaceutically acceptable salt thereof.

(52) The fused ring compound of any of (29) to (51) above, wherein at least one group represented by Z is heterocycle $C_{1-6}$ alkyl optionally substituted by 1 to 5 substituent(s) selected from the group D, or a pharmaceutically acceptable salt thereof.

(53) The fused ring compound of any of (29) to (51) above, wherein at least one group represented by Z is heterocyclic group optionally substituted by 1 to 5 substituent(s) selected from the group D, wherein said heterocyclic group is selected from the following groups:

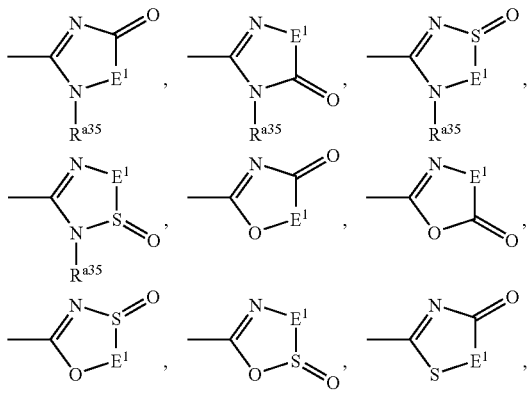

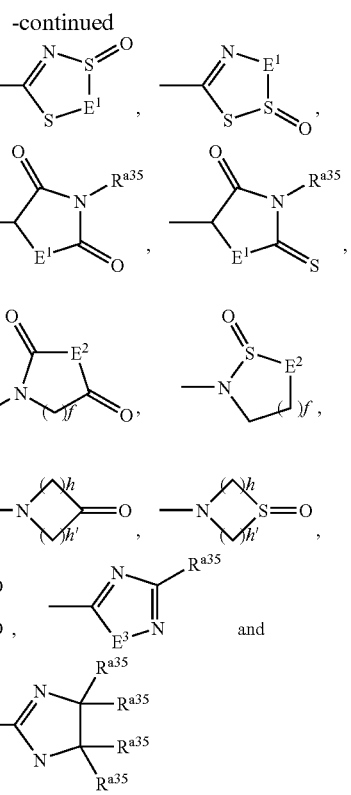

wherein $E^1$ is an oxygen atom, a sulfur atom or $N(-R^{a35})$, $E^2$ is an oxygen atom, $CH_2$ or $N(-R^{a35})$, $E^3$ is an oxygen atom or a sulfur atom, wherein each $R^{a35}$ is independently hydrogen atom or $C_{1-6}$ alkyl, f is an integer of 1 to 3, and h and h' are the same or different and each is an integer of 1 to 3, or a pharmaceutically acceptable salt thereof.

(54) The fused ring compound of (53) above, wherein at least one group represented by Z is heterocyclic group optionally substituted by 1 to 5 substituent(s) selected from the group D, wherein said heterocyclic group is selected from the following groups:

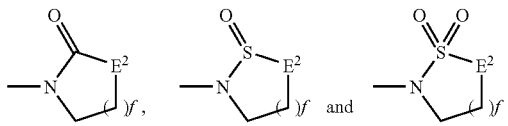

wherein each symbol is as defined in (53), or a pharmaceutically acceptable salt thereof.

(55) The fused ring compound of any of (29) to (51) above, wherein at least one group represented by group D is $-(CH_2)_t-CONR^{a27}R^{a28}$ wherein each symbol is as defined in (29), and at least one of $R^{a27}$ and $R^{a28}$ is $C_{1-6}$ alkoxy, or a pharmaceutically acceptable salt thereof.

(56) The fused ring compound of any of (29) to (51) above, wherein at least one group represented by group D is $-(CH_2)_t-C(=NR^{a33})NH_2$ wherein each symbol is as defined in (29), and $R^{a33}$ is hydroxyl group or $C_{1-6}$ alkoxy, or a pharmaceutically acceptable salt thereof.

The fused ring compound of any of (29) to (51) above, wherein at least one group represented by group D is $-(CH_2)_t-O-(CH_2)_p-COR^{a21}$ wherein each symbol is as defined in (29), and $R^{a21}$ is amino, or a pharmaceutically acceptable salt thereof.

The fused ring compound of any of (29) to (51) above, wherein at least one group represented by group D is —(CH$_2$)$_r$—NR$^{a29}$CO—R$^{a24}$ wherein each symbol is as defined in (29), and R$^{a24}$ is amino or C$_{1-6}$ alkylamino, or a pharmaceutically acceptable salt thereof.

The fused ring compound of any of (29) to (51) above, wherein at least one group represented by group D is —(CH$_2$)$_r$—NR$^{a22}$R$^{a23}$ wherein each symbol is as defined in (29), and at least one of R$^{a22}$ and R$^{a23}$ is heterocyclic group optionally substituted by 1 to 5 substituent(s) selected from the group B, or a pharmaceutically acceptable salt thereof.

The fused ring compound of any of (29) to (51) above, wherein at least one group represented by group D is heterocyclic group having 1 to 4 heteroatom(s) selected from an oxygen atom, a nitrogen atom and a sulfur atom, or a pharmaceutically acceptable salt thereof.

The fused ring compound of the formula [I] or a pharmaceutically acceptable salt thereof, which is selected from the group consisting of ethyl 2-[4-(3-bromophenoxy)phenyl]-1-cyclohexylbenzimidazole-5-carboxylate (Example 1), 2-[4-(3-bromophenoxy)phenyl]-1-cyclohexylbenzimidazole-5-carboxylic acid (Example 2), ethyl 1-cyclohexyl-2-(4-hydroxyphenyl)benzimidazole-5-carboxylate (Example 3), ethyl 2-[4-(2-bromo-5-chlorobenzyloxy)phenyl]-1-cyclohexylbenzimidazole-5-carboxylate (Example 4), ethyl 2-{4-[2-(4-chlorophenyl)-5-chlorobenzyloxy]phenyl}-1-cyclohexylbenzimidazole-5-carboxylate (Example 5), 2-{4-[2-(4-chlorophenyl)-5-chlorobenzyloxy]phenyl}-1-cyclohexylbenzimidazole-5-carboxylic acid (Example 6), ethyl 2-[4-(2-bromo-5-methoxybenzyloxy)phenyl]-1-cyclohexylbenzimidazole-5-carboxylate (Example 7), ethyl 2-{4-[2-(4-chlorophenyl)-5-methoxybenzyloxy]phenyl}-1-cyclohexylbenzimidazole-5-carboxylate (Example 8), 2-{4-[2-(4-chlorophenyl)-5-methoxybenzyloxy]phenyl}-1-cyclohexylbenzimidazole-5-carboxylic acid (Example 9), ethyl 1-cyclohexyl-2-{4-[(E)-2-phenylvinyl]phenyl}benzimidazole-5-carboxylate (Example 10), 1-cyclohexyl-2-{4-[(E)-2-phenylvinyl]phenyl}benzimidazole-5-carboxylic acid (Example 11), 2-(4-benzyloxyphenyl)-1-cyclopentylbenzimidazole-5-carboxylic acid (Example 12), 2-(4-benzyloxyphenyl)-1-cyclopentylbenzimidazole-5-carboxamide (Example 13), 2-(4-benzyloxyphenyl)-5-cyano-1-cyclopentylbenzimidazole (Example 14), 2-(4-benzyloxyphenyl)-1-cyclopentylbenzimidazole-5-carboxamide oxime (Example 15), ethyl 1-cyclohexyl-2-{4-[{4-(4-fluorophenyl)-2-methyl-5-thiazolyl}methoxy]phenyl}benzimidazole-5-carboxylate (Example 16), 1-cyclohexyl-2-{4-[{4-(4-fluorophenyl)-2-methyl-5-thiazolyl}-methoxy]phenyl}benzimidazole-5-carboxylic acid (Example 17), ethyl 1-cyclohexyl-2-(2-fluoro-4-hydroxyphenyl)benzimidazole-5-carboxylate (Example 18), ethyl 2-{4-[bis(3-fluorophenyl)methoxy]-2-fluorophenyl}-1-cyclohexylbenzimidazole-5-carboxylate (Example 19), 2-{4-[bis(3-fluorophenyl)methoxy]-2-fluorophenyl}-1-cyclohexylbenzimidazole-5-carboxylic acid (Example 20), ethyl 1-cyclopentyl-2-(4-nitrophenyl)benzimidazole-5-carboxylate (Example 21), ethyl 2-(4-aminophenyl)-1-cyclopentylbenzimidazole-5-carboxylate (Example 22), ethyl 2-(4-benzoylaminophenyl)-1-cyclopentylbenzimidazole-5-carboxylate (Example 23), 2-(4-benzoylaminophenyl)-1-cyclopentylbenzimidazole-5-carboxylic acid (Example 24), ethyl 2-{4-[3-(3-chlorophenyl)phenoxy]phenyl}-1-cyclohexylbenzimidazole-5-carboxylate (Example 25), 2-{4-[3-(3-chlorophenyl)phenoxy]phenyl}-1-cyclohexylbenzimidazole-5-carboxylic acid (Example 26), ethyl 2-[4-(3-acetoxyphenyloxy)phenyl]-1-cyclohexylbenzimidazole-5-carboxylate (Example 27), ethyl 1-cyclohexyl-2-[4-(3-hydroxyphenyloxy)phenyl]-benzimidazole-5-carboxylate (Example 28), ethyl 1-cyclohexyl-2-{4-[3-(4-pyridylmethoxy)phenyloxy]phenyl}-benzimidazole-5-carboxylate (Example 29), 1-cyclohexyl-2-{4-[3-(4-pyridylmethoxy)phenyloxy]phenyl}-benzimidazole-5-carboxylic acid (Example 30), 2-(4-benzyloxyphenyl)-1-cyclopentylbenzimidazole (Example 31), ethyl 2-(4-benzyloxyphenyl)-1-cyclopentylbenzimidazole-5-carboxylate (Example 32), 2-(4-benzyloxyphenyl)-1-cyclopentyl-N,N-dimethylbenzimidazole-5-carboxamide (Example 33), 2-(4-benzyloxyphenyl)-1-cyclopentyl-N-methoxy-N-methylbenzimidazole-5-carboxamide (Example 34), 2-(4-benzyloxyphenyl)-1-cyclopentyl-5-(1-hydroxy-1-methylethyl)benzimidazole (Example 35), 5-acetyl-2-(4-benzyloxyphenyl)-1-cyclopentylbenzimidazole (Example 36), 2-(4-benzyloxyphenyl)-1-cyclopentyl-N-(2-dimethylaminoethyl)-benzimidazole-5-carboxamide dihydrochloride (Example 37), 2-(4-benzyloxyphenyl)-1-cyclopentyl-5-nitrobenzimidazole (Example 38), 5-amino-2-(4-benzyloxyphenyl)-1-cyclopentylbenzimidazole hydrochloride (Example 39), 5-acetylamino-2-(4-benzyloxyphenyl)-1-cyclopentylbenzimidazole (Example 40), 2-(4-benzyloxyphenyl)-1-cyclopentyl-5-methanesulfonyl-aminobenzimidazole (Example 41), 5-sulfamoyl-2-(4-benzyloxyphenyl)-1-cyclopentylbenzimidazole (Example 42), 2-[4-(4-tert-butylbenzyloxy)phenyl]-1-cyclopentylbenzimidazole-5-carboxylic acid (Example 43), 2-[4-(4-carboxybenzyloxy)phenyl]-1-cyclopentylbenzimidazole-5-carboxylic acid (Example 44), 2-[4-(4-chlorobenzyloxy)phenyl]-1-cyclopentylbenzimidazole-5-carboxylic acid (Example 45), 2-{4-[(2-chloro-5-thienyl)methoxy]phenyl}-1-cyclopentylbenzimidazole-5-carboxylic acid (Example 46), 1-cyclopentyl-2-[4-(4-trifluoromethylbenzyloxy)phenyl]-benzimidazole-5-carboxylic acid (Example 47), 1-cyclopentyl-2-[4-(4-methoxybenzyloxy)phenyl]benzimidazole-5-carboxylic acid (Example 48), 1-cyclopentyl-2-[4-(4-pyridylmethoxy)phenyl]benzimidazole-5-carboxylic acid hydrochloride (Example 49), 1-cyclopentyl-2-[4-(4-methylbenzyloxy)phenyl]benzimidazole-5-carboxylic acid (Example 50), 1-cyclopentyl-2-{4-[(3,5-dimethyl-4-isoxazolyl)methoxy]phenyl}-benzimidazole-5-carboxylic acid (Example 51), 1-cyclopentyl-2-(4-hydroxyphenyl)benzimidazole-5-carboxylic acid (Example 52),

[2-(4-benzyloxyphenyl)-1-cyclopentylbenzimidazol-5-yl]-carbonylaminoacetic acid (Example 53), 2-[4-(2-chlorobenzyloxy)phenyl]-1-cyclopentylbenzimidazole-5-carboxylic acid (Example 54),
2-[4-(3-chlorobenzyloxy)phenyl]-1-cyclopentylbenzimidazole-5-carboxylic acid (Example 55),
2-(4-benzyloxyphenyl)-3-cyclopentylbenzimidazole-5-carboxylic acid (Example 56),
2-[4-(benzenesulfonylamino)phenyl]-1-cyclopentylbenzimidazole-5-carboxylic acid (Example 57),
1-cyclopentyl-2-[4-(3,5-dichlorophenylcarbonylamino)phenyl]-benzimidazole-5-carboxylic acid (Example 58),
2-{4-[(4-chlorophenyl)carbonylamino]phenyl}-1-cyclopentylbenzimidazole-5-carboxylic acid (Example 59),
2-{4-[(4-tert-butylphenyl)carbonylamino]phenyl}-1-cyclopentylbenzimidazole-5-carboxylic acid (Example 60),
2-{4-[(4-benzyloxyphenyl)carbonylamino]phenyl}-1-cyclopentylbenzimidazole-5-carboxylic acid (Example 61),
trans-4-[2-(4-benzyloxyphenyl)-5-carboxybenzimidazol-1-yl]cyclohexan-1-ol (Example 62),
trans-1-[2-(4-benzyloxyphenyl)-5-carboxybenzimidazol-1-yl]-4-methoxycyclohexane (Example 63),
2-(4-benzyloxyphenyl)-5-carboxymethyl-1-cyclopentylbenzimidazole (Example 64),
2-[1-benzyloxycarbonyl-4-piperidyl]-1-cyclopentylbenzimidazole-5-carboxylic acid (Example 65),
2-[(4-cyclohexylphenyl)carbonylamino]-1-cyclopentylbenzimidazole-5-carboxylic acid (Example 66),
1-cyclopentyl-2-[4-(3,5-dichlorobenzyloxy)phenyl]benzimidazole-5-carboxylic acid (Example 67),
1-cyclopentyl-2-[4-(3,4-dichlorobenzyloxy)phenyl]benzimidazole-5-carboxylic acid (Example 68),
1-cyclopentyl-2-[4-(phenylcarbamoylamino)phenyl]benzimidazole-5-carboxylic acid (Example 69),
1-cyclopentyl-2-[4-(diphenylmethoxy)phenyl]benzimidazole-5-carboxylic acid (Example 70),
1-cyclopentyl-2-(4-phenethyloxyphenyl)benzimidazole-5-carboxylic acid (Example 71),
trans-1-[2-(4-benzyloxyphenyl)-5-carboxybenzimidazol-1-yl]-4-tert-butylcyclohexane (Example 72),
2-(4-benzyloxyphenyl)-5-carboxymethoxy-1-cyclopentylbenzimidazole (Example 73),
2-(4-benzylaminophenyl)-1-cyclopentylbenzimidazole-5-carboxylic acid (Example 74),
2-[4-(N-benzenesulfonyl-N-methylamino)phenyl]-1-cyclopentylbenzimidazole-5-carboxylic acid (Example 75),
2-[4-(N-benzyl-N-methylamino)phenyl]-1-cyclopentylbenzimidazole-5-carboxylic acid (Example 76),
1-cyclohexyl-2-(4-phenethylphenyl)benzimidazole-5-carboxylic acid (Example 77),
2-(1-benzyl-4-piperidyl)-1-cyclopentylbenzimidazole-5-carboxylic acid (Example 78),
2-(1-benzoyl-4-piperidyl)-1-cyclopentylbenzimidazole-5-carboxylic acid (Example 79),
1-cyclopentyl-2-[1-(p-toluenesulfonyl)-4-piperidyl]-benzimidazole-5-carboxylic acid (Example 80),
1-cyclohexyl-2-[4-(3,5-dichlorobenzyloxy)phenyl]benzimidazole-5-carboxylic acid (Example 81),
1-cyclohexyl-2-[4-(diphenylmethoxy)phenyl]benzimidazole-5-carboxylic acid (Example 82),
1-cyclohexyl-2-[4-(3,5-di-tert-butylbenzyloxy)phenyl]-benzimidazole-5-carboxylic acid (Example 83),
2-(4-benzyloxyphenyl)-1-(4-methylcyclohexyl)benzimidazole-5-carboxylic acid (Example 84),
1-cyclohexyl-2-{4-[2-(2-naphthyl)ethoxy]phenyl}benzimidazole-5-carboxylic acid (Example 85),
1-cyclohexyl-2-[4-(1-naphthyl)methoxyphenyl]benzimidazole-5-carboxylic acid (Example 86),
1-cyclohexyl-2-[4-(dibenzylamino)phenyl]benzimidazole-5-carboxylic acid (Example 87),
2-[4-(2-biphenylylmethoxy)phenyl]-1-cyclohexylbenzimidazole-5-carboxylic acid (Example 88),
2-(4-benzyloxyphenyl)-1-cyclohexylbenzimidazole-5-carboxylic acid (Example 89),
1-cyclohexyl-2-[4-(dibenzylmethoxy)phenyl]benzimidazole-5-carboxylic acid (Example 90),
2-(4-benzoylmethoxyphenyl)-1-cyclohexylbenzimidazole-5-carboxylic acid (Example 91),
2-(4-benzyl-1-piperazinyl)-1-cyclohexylbenzimidazole-5-carboxylic acid dihydrochloride (Example 92),
1-cyclohexyl-2-[4-(3,3-diphenylpropyloxy)phenyl]benzimidazole-5-carboxylic acid (Example 93),
2-[4-(3-chloro-6-phenylbenzyloxy)phenyl]-1-cyclohexylbenzimidazole-5-carboxylic acid (Example 94),
2-(4-benzyloxypiperidino)-1-cyclohexylbenzimidazole-5-carboxylic acid (Example 95),
1-cyclohexyl-2-{4-[2-(phenoxy)ethoxy]phenyl}benzimidazole-5-carboxylic acid (Example 96),
1-cyclohexyl-2-[4-(3-phenylpropyloxy)phenyl]benzimidazole-5-carboxylic acid (Example 97),
1-cyclohexyl-2-[4-(5-phenylpentyloxy)phenyl]benzimidazole-5-carboxylic acid (Example 98),
2-(3-benzyloxy-5-isoxazolyl)-1-cyclohexylbenzimidazole-5-carboxylic acid (Example 99),
2-(2-benzyloxy-5-pyridyl)-1-cyclohexylbenzimidazole-5-carboxylic acid (Example 100),
1-cyclohexyl-2-{4-[2-(3,4,5-trimethoxyphenyl)ethoxy]phenyl}-benzimidazole-5-carboxylic acid (Example 101),
2-(4-benzyloxyphenyl)-1-(4,4-dimethylcyclohexyl)benzimidazole-5-carboxylic acid (Example 102),
1-cyclohexyl-2-{4-[2-(1-naphthyl)ethoxy]phenyl}benzimidazole-5-carboxylic acid (Example 103),
2-[4-(2-benzyloxyphenoxy)phenyl]-1-cyclohexylbenzimidazole-5-carboxylic acid (Example 104),
2-[4-(3-benzyloxyphenoxy)phenyl]-1-cyclohexylbenzimidazole-5-carboxylic acid (Example 105),
1-cyclohexyl-2-[4-(2-hydroxyphenoxy)phenyl]benzimidazole-5-carboxylic acid (Example 106),
1-cyclohexyl-2-[4-(3-hydroxyphenoxy)phenyl]benzimidazole-5-carboxylic acid (Example 107),
1-cyclohexyl-2-[4-(2-methoxyphenoxy)phenyl]benzimidazole-5-carboxylic acid (Example 108),
1-cyclohexyl-2-[4-(3-methoxyphenoxy)phenyl]benzimidazole-5-carboxylic acid (Example 109),
1-cyclohexyl-2-[4-(2-propoxyphenoxy)phenyl]benzimidazole-5-carboxylic acid (Example 110),
1-cyclohexyl-2-[4-(3-propoxyphenoxy)phenyl]benzimidazole-5-carboxylic acid (Example 111),
1-cyclohexyl-2-{4-[2-(3-methyl-2-butenyloxy)phenoxy]phenyl}-benzimidazole-5-carboxylic acid (Example 112),
1-cyclohexyl-2-{4-[3-(3-methyl-2-butenyloxy)phenoxy]phenyl}-benzimidazole-5-carboxylic acid (Example 113),
1-cyclohexyl-2-[4-(2-isopentyloxyphenoxy)phenyl]benzimidazole-5-carboxylic acid (Example 114), 1-cyclohexyl-2-[4-(3-isopentyloxyphenoxy)phenyl] benzimidazole-5-carboxylic acid (Example 115), 1-cyclohexyl-2-{4-[2-(10,11-dihydro-5H-dibenzo[b,f] azepin-5-yl)ethoxy]phenyl}benzimidazole-5-carboxylic acid (Example 116), 1-cyclohexyl-2-{4-[2-(4-trifluoromethylphenyl) benzyloxy]-phenyl}benzimidazole-5-carboxylic acid (Example 117), 2-{4-[bis(4-chlorophenyl)methoxy]phenyl}-1-cyclohexylbenzimidazole-5-carboxylic acid (Example 118), 1-cyclohexyl-2-{4-[2-(4-methoxyphenyl)ethoxy]phenyl}-benzimidazole-5-carboxylic acid (Example 119), 1-cyclohexyl-2-{4-[2-(2-methoxyphenyl)ethoxy]phenyl}-benzimidazole-5-carboxylic acid (Example 120), 1-cyclohexyl-2-{4-[2-(3-methoxyphenyl)ethoxy]phenyl}-benzimidazole-5-carboxylic acid (Example 121), 2-(4-benzyloxyphenyl)-1-cycloheptylbenzimidazole-5-carboxylic acid (Example 122), 1-cyclohexyl-2-[4-(2-phenethyloxyphenoxy)phenyl] benzimidazole-5-carboxylic acid (Example 123), 1-cyclohexyl-2-[4-(3-phenethyloxyphenoxy)phenyl] benzimidazole-5-carboxylic acid (Example 124), 1-cyclohexyl-2-[4-(2,2-diphenylethoxy)phenyl] benzimidazole-5-carboxylic acid (Example 125), 2-(4-benzyloxyphenyl)-1-(3-cyclohexenyl)benzimidazole-5-carboxylic acid (Example 126), cis-1-[2-(4-benzyloxyphenyl)-5-carboxybenzimidazol-1-yl]-4-fluorocyclohexane (Example 127), 1-cyclohexyl-2-[4-(2-phenoxyphenoxy)phenyl] benzimidazole-5-carboxylic acid (Example 128), 1-cyclohexyl-2-[4-(3-phenoxyphenoxy)phenyl] benzimidazole-5-carboxylic acid (Example 129), 2-{4-[(2R)-2-benzyloxycarbonylamino-2-phenylethoxy] phenyl}-1-cyclohexylbenzimidazole-5-carboxylic acid (Example 130), 1-cyclohexyl-2-{2-fluoro-4-[2-(4-trifluoromethylphenyl)-benzyloxy]phenyl}benzimidazole-5-carboxylic acid (Example 131), 2-[4-(4-benzyloxyphenoxy)phenyl]-1-cyclohexylbenzimidazole-5-carboxylic acid (Example 132), 2-{4-[bis(4-methylphenyl)methoxy]phenyl}-1-cyclohexylbenzimidazole-5-carboxylic acid (Example 133), 2-{4-[bis(4-fluorophenyl)methoxy]phenyl}-1-cyclohexylbenzimidazole-5-carboxylic acid (Example 134), 1-cyclohexyl-6-methoxy-2-[4-(3-phenylpropoxy)phenyl]-benzimidazole-5-carboxylic acid (Example 135), 1-cyclohexyl-6-hydroxy-2-[4-(3-phenylpropoxy)phenyl]-benzimidazole-5-carboxylic acid (Example 136), 1-cyclohexyl-6-methyl-2-[4-(3-phenylpropoxy)phenyl]-benzimidazole-5-carboxylic acid (Example 137), 2-{4-[2-(2-benzyloxyphenyl)ethoxy]phenyl}-1-cyclohexylbenzimidazole-5-carboxylic acid (Example 138), 2-{4-[2-(3-benzyloxyphenyl)ethoxy]phenyl}-1-cyclohexylbenzimidazole-5-carboxylic acid (Example 139), 2-[4-(2-carboxymethyloxyphenoxy)phenyl]-1-cyclohexylbenzimidazole-5-carboxylic acid (Example 140), 2-[4-(3-carboxymethyloxyphenoxy)phenyl]-1-cyclohexylbenzimidazole-5-carboxylic acid (Example 141), 2-{4-[3-chloro-6-(4-methylphenyl)benzyloxy]phenyl}-1-cyclohexylbenzimidazole-5-carboxylic acid (Example 142), 2-{4-[3-chloro-6-(4-methoxyphenyl)benzyloxy]phenyl}-1-cyclohexylbenzimidazole-5-carboxylic acid (Example 143), 1-cyclohexyl-2-{2-methyl-4-[2-(4-trifluoromethylphenyl)-benzyloxy]phenyl}benzimidazole-5-carboxylic acid (Example 144), 2-{4-[2-(4-tert-butylphenyl)-5-chlorobenzyloxy]phenyl}-1-cyclohexylbenzimidazole-5-carboxylic acid (Example 145), 2-{4-(3-chloro-6-phenylbenzyloxy)-2-fluorophenyl}-1-cyclohexylbenzimidazole-5-carboxylic acid (Example 146), 2-{4-[3-chloro-6-(3,5-dichlorophenyl)benzyloxy]phenyl}-1-cyclohexylbenzimidazole-5-carboxylic acid (Example 147), 2-{4-[bis(4-fluorophenyl)methoxy]-2-fluorophenyl}-1-cyclohexylbenzimidazole-5-carboxylic acid (Example 148), 2-{4-(4-benzyloxyphenoxy)-2-chlorophenyl}-1-cyclohexylbenzimidazole-5-carboxylic acid (Example 149), 2-{4-(4-benzyloxyphenoxy)-2-trifluoromethylphenyl}-1-cyclohexylbenzimidazole-5-carboxylic acid (Example 150), 2-{4-[3-chloro-6-(2-trifluoromethylphenyl)benzyloxy] phenyl}-1-cyclohexylbenzimidazole-5-carboxylic acid (Example 151), 2-{4-[(2R)-2-amino-2-phenylethoxy]phenyl}-1-cyclohexylbenzimidazole-5-carboxylic acid (Example 152), 2-[4-(2-biphenylyloxy)phenyl]-1-cyclohexylbenzimidazole-5-carboxylic acid (Example 153), 2-[4-(3-biphenylyloxy)phenyl]-1-cyclohexylbenzimidazole-5-carboxylic acid (Example 154), 2-{4-[2-{(1-tert-butoxycarbonyl-4-piperidyl) methoxy}phenoxy]-phenyl}-1-cyclohexylbenzimidazole-5-carboxylic acid (Example 155), 2-{4-[3-{(1-tert-butoxycarbonyl-4-piperidyl) methoxy}phenoxy]-phenyl}-1-cyclohexylbenzimidazole-5-carboxylic acid (Example 156), 2-{4-[3-chloro-6-(3,4,5-trimethoxyphenyl)benzyloxy] phenyl}-1-cyclohexylbenzimidazole-5-carboxylic acid (Example 157), 2-{4-[2-(2-biphenylyl)ethoxy]phenyl}-1-cyclohexylbenzimidazole-5-carboxylic acid (Example 158), 2-[4-(2-biphenylylmethoxy)phenyl]-1-cyclohexylbenzimidazole-5-carboxylic acid (Example 159), 1-cyclohexyl-2-{4-[2-(4-piperidylmethoxy)phenoxy] phenyl}-benzimidazole-5-carboxylic acid hydrochloride (Example 160), 1-cyclohexyl-2-{4-[3-(4-piperidylmethoxy)phenoxy] phenyl}-benzimidazole-5-carboxylic acid hydrochloride (Example 161), 2-{4-[(2R)-2-acetylamino-2-phenylethoxy]phenyl}-1-cyclohexylbenzimidazole-5-carboxylic acid (Example 162), 1-cyclohexyl-2-{4-[3-(4-methyl-3-pentenyloxy)phenoxy] phenyl}-benzimidazole-5-carboxylic acid (Example 163), 1-cyclohexyl-2-{4-[3-(3-methyl-3-butenyloxy)phenoxy] phenyl}-benzimidazole-5-carboxylic acid (Example 164), 2-{4-[{(2S)-1-benzyl-2-pyrrolidinyl}methoxy]phenyl}-1-cyclohexyl-benzimidazole-5-carboxylic acid hydrochloride (Example 165), 2-{4-[3-chloro-6-(4-methylthiophenyl)benzyloxy]phenyl}-1-cyclohexylbenzimidazole-5-carboxylic acid (Example 166), 2-{4-[3-chloro-6-(4-methanesulfonylphenyl)benzyloxy]phenyl}-1-cyclohexylbenzimidazole-5-carboxylic acid (Example 167), 2-{4-[3-chloro-6-(2-thienyl)benzyloxy]phenyl}-1-cyclohexylbenzimidazole-5-carboxylic acid (Example 168), 2-{4-[3-chloro-6-(3-chlorophenyl)benzyloxy]phenyl}-1-cyclohexylbenzimidazole-5-carboxylic acid (Example 169), 2-{4-[3-chloro-6-(3-pyridyl)benzyloxy]phenyl}-1-cyclohexylbenzimidazole-5-carboxylic acid (Example 170), 2-{4-[3-chloro-6-(4-fluorophenyl)benzyloxy]phenyl}-1-cyclohexylbenzimidazole-5-carboxylic acid (Example 171), 2-[4-(4-benzyloxyphenoxy)-3-fluorophenyl]-1-cyclohexylbenzimidazole-5-carboxylic acid (Example 172), 2-[4-(2-bromo-5-chlorobenzyloxy)phenyl]-1-cyclohexylbenzimidazole-5-carboxylic acid (Example 173), 2-{4-[3-chloro-6-(4-chlorophenyl)benzyloxy]-2-fluorophenyl}-1-cyclohexylbenzimidazole-5-carboxylic acid (Example 174), 2-{4-[2-{(1-acetyl-4-piperidyl)methoxy}phenoxy]phenyl}-1-cyclohexylbenzimidazole-5-carboxylic acid (Example 175), 2-{4-[3-{(1-acetyl-4-piperidyl)methoxy}phenoxy]phenyl}-1-cyclohexylbenzimidazole-5-carboxylic acid (Example 176), 1-cyclohexyl-2-{4-[3-(2-propynyloxy)phenoxy]phenyl}benzimidazole-5-carboxylic acid (Example 177), 1-cyclohexyl-2-{4-[3-(3-pyridylmethoxy)phenoxy]phenyl}-benzimidazole-5-carboxylic acid (Example 178), 2-(4-benzyloxy-2-methoxyphenyl)-1-cyclohexylbenzimidazole-5-carboxylic acid (Example 179), 2-[4-(2-bromo-5-methoxybenzyloxy)phenyl]-1-cyclohexylbenzimidazole-5-carboxylic acid (Example 180), 2-[4-(carboxydiphenylmethoxy)phenyl]-1-cyclohexylbenzimidazole-5-carboxylic acid (Example 181), 2-{4-[2-(4-chlorophenyl)-5-nitrobenzyloxy]phenyl}-1-cyclohexylbenzimidazole-5-carboxylic acid (Example 182), 2-{4-[3-acetylamino-6-(4-chlorophenyl)benzyloxy]phenyl}-1-cyclohexylbenzimidazole-5-carboxylic acid (Example 183), 2-{4-[2-(4-carboxyphenyl)-5-chlorobenzyloxy]phenyl}-1-cyclohexylbenzimidazole-5-carboxylic acid (Example 184), 2-{4-[{(2S)-1-benzyloxycarbonyl-2-pyrrolidinyl}methoxy]phenyl}-1-cyclohexylbenzimidazole-5-carboxylic acid (Example 185), 2-{2-chloro-4-[2-(4-trifluoromethylphenyl)benzyloxy]phenyl}-1-cyclohexylbenzimidazole-5-carboxylic acid (Example 186), 1-cyclohexyl-2-{4-[3-(2-pyridylmethoxy)phenoxy]phenyl}-benzimidazole-5-carboxylic acid (Example 187), 2-{4-[2-(4-chlorophenyl)-5-fluorobenzyloxy]phenyl}-1-cyclohexylbenzimidazole-5-carboxylic acid (Example 188), 2-{4-[3-carboxy-6-(4-chlorophenyl)benzyloxy]phenyl}-1-cyclohexylbenzimidazole-5-carboxylic acid (Example 189), 2-{4-[3-carbamoyl-6-(4-chlorophenyl)benzyloxy]phenyl}-1-cyclohexylbenzimidazole-5-carboxylic acid (Example 190), 1-cyclohexyl-2-{4-[2-(dimethylcarbamoylmethoxy)phenoxy]-phenyl}benzimidazole-5-carboxylic acid (Example 191), 1-cyclohexyl-2-{4-[2-(piperidinocarbonylmethoxy)phenoxy]-phenyl}benzimidazole-5-carboxylic acid (Example 192), 2-{4-[{(2S)-1-benzenesulfonyl-2-pyrrolidinyl}methoxy]phenyl}-1-cyclohexylbenzimidazole-5-carboxylic acid (Example 193), 2-{4-[{(2S)-1-benzoyl-2-pyrrolidinyl}methoxy]phenyl}-1-cyclohexylbenzimidazole-5-carboxylic acid (Example 194), 2-{4-[2-(4-carbamoylphenyl)-5-chlorobenzyloxy]phenyl}-1-cyclohexylbenzimidazole-5-carboxylic acid (Example 195), 1-cyclohexyl-2-{4-[3-(dimethylcarbamoylmethoxy)phenoxy]-phenyl}benzimidazole-5-carboxylic acid (Example 196), 1-cyclohexyl-2-{4-[3-(piperidinocarbonylmethoxy)phenoxy]-phenyl}benzimidazole-5-carboxylic acid (Example 197), 1-cyclohexyl-2-{4-[3-{(1-methanesulfonyl-4-piperidyl)methoxy}-phenoxy]phenyl}benzimidazole-5-carboxylic acid (Example 198), 1-cyclohexyl-2-{4-[{2-methyl-5-(4-chlorophenyl)-4-oxazolyl}-methoxy]phenyl}benzimidazole-5-carboxylic acid (Example 199), 2-{4-[3-(3-chlorobenzyloxy)phenoxy]phenyl}-1-cyclohexylbenzimidazole-5-carboxylic acid (Example 200), 2-{4-[3-(4-chlorobenzyloxy)phenoxy]phenyl}-1-cyclohexylbenzimidazole-5-carboxylic acid (Example 201), 1-cyclohexyl-2-{4-[3-(4-fluorobenzyloxy)phenoxy]phenyl}-benzimidazole-5-carboxylic acid (Example 202), 1-cyclohexyl-2-{4-[{(2S)-1-(4-nitrophenyl)-2-pyrrolidinyl}-methoxy]phenyl}benzimidazole-5-carboxylic acid (Example 203), 1-cyclohexyl-2-{4-[{(2S)-1-phenyl-2-pyrrolidinyl}methoxy]-phenyl}benzimidazole-5-carboxylic acid hydrochloride (Example 204), 2-{4-[{(2S)-1-(4-acetylaminophenyl)-2-pyrrolidinyl}methoxy]-phenyl}-1-cyclohexylbenzimidazole-5-carboxylic acid (Example 205), 2-{4-[{5-(4-chlorophenyl)-2-methyl-4-thiazolyl}methoxy]phenyl}-1-cyclohexylbenzimidazole-5-carboxylic acid (Example 206), 2-{4-[bis(3-fluorophenyl)methoxy]phenyl}-1-cyclohexylbenzimidazole-5-carboxylic acid (Example 207), 1-cyclohexyl-2-{4-[2-(4-chlorophenyl)-3-nitrobenzyloxy]phenyl}-benzimidazole-5-carboxylic acid (Example 208), 1-cyclohexyl-2-{4-[3-(4-tetrahydropyranyloxy)phenoxy]phenyl}-benzimidazole-5-carboxylic acid (Example 209), 1-cyclohexyl-2-{4-[3-(4-trifluoromethylbenzyloxy)phenoxy]phenyl}-benzimidazole-5-carboxylic acid (Example 210), 1-cyclohexyl-2-{4-[3-{(1-methyl-4-piperidyl)methoxy}phenoxy]-phenyl}benzimidazole-5-carboxylic acid (Example 211), 2-{4-[3-(4-tert-butylbenzyloxy)phenoxy]phenyl}-1-cyclohexylbenzimidazole-5-carboxylic acid (Example 212), 2-{4-[3-(2-chlorobenzyloxy)phenoxy]phenyl}-1-cyclohexylbenzimidazole-5-carboxylic acid (Example 213), 1-cyclohexyl-2-{4-[3-(3-pyridyl)phenoxy]phenyl}benzimidazole-5-carboxylic acid (Example 214), 2-{4-[3-(4-chlorophenyl)phenoxy]phenyl}-1-cyclohexylbenzimidazole-5-carboxylic acid (Example 215), 1-cyclohexyl-2-{4-[3-(4-methoxyphenyl)phenoxy]phenyl}-benzimidazole-5-carboxylic acid (Example 216), 1-cyclohexyl-2-{4-[{4-(4-methanesulfonylphenyl)-2-methyl-5-thiazolyl}methoxy]phenyl}benzimidazole-5-carboxylic acid (Example 217), 2-{4-[{4-(4-chlorophenyl)-2-methyl-5-thiazolyl}methoxy]phenyl}-1-cyclohexylbenzimidazole-5-carboxylic acid (Example 218), 2-{4-[1-(4-chlorobenzyl)-3-piperidyloxy]phenyl}-1-cyclohexylbenzimidazole-5-carboxylic acid (Example 219), 1-cyclohexyl-2-{4-[3-{(2-methyl-4-thiazolyl)methoxy}phenoxy]-phenyl}benzimidazole-5-carboxylic acid (Example 220), 1-cyclohexyl-2-{4-[3-{(2,4-dimethyl-5-thiazolyl)methoxy}phenoxy]-phenyl}benzimidazole-5-carboxylic acid (Example 221), 1-cyclohexyl-2-{4-[3-(3,5-dichlorophenyl)phenoxy]phenyl}-benzimidazole-5-carboxylic acid (Example 222), 2-{4-[1-(4-chlorobenzyl)-4-piperidyloxy]phenyl}-1-cyclohexylbenzimidazole-5-carboxylic acid (Example 223), 2-{4-[3-(4-chlorobenzyloxy)piperidino]phenyl}-1-cyclohexylbenzimidazole-5-carboxylic acid (Example 224), 2-{4-[4-carbamoyl-2-(4-chlorophenyl)benzyloxy]phenyl}-1-cyclohexylbenzimidazole-5-carboxylic acid (Example 225), 2-{4-[4-(4-chlorobenzyloxy)piperidino]phenyl}-1-cyclohexylbenzimidazole-5-carboxylic acid (Example 226), 2-{4-[3-{(2-chloro-4-pyridyl)methoxy}phenoxy]phenyl}-1-cyclohexylbenzimidazole-5-carboxylic acid (Example 227), 2-{4-[{(2S)-1-(4-dimethylcarbamoylphenyl)-2-pyrrolidinyl}-methoxy]phenyl}-1-cyclohexylbenzimidazole-5-carboxylic acid (Example 228), 2-{4-[2-(4-chlorophenyl)-5-ethoxycarbonylbenzyloxy]phenyl}-1-cyclohexylbenzimidazole-5-carboxylic acid (Example 229), 1-cyclohexyl-2-[4-(3-trifluoromethylphenoxy)phenyl]-benzimidazole-5-carboxylic acid (Example 230), 1-cyclohexyl-2-{4-[{4-(4-dimethylcarbamoylphenyl)-2-methyl-5-thiazolyl}methoxy]phenyl}benzimidazole-5-carboxylic acid (Example 231), 2-{4-[2-(4-chlorophenyl)-5-dimethylcarbamoylbenzyloxy]phenyl}-1-cyclohexylbenzimidazole-5-carboxylic acid (Example 232), 2-{4-[{4-(4-chlorophenyl)-2-methyl-5-pyrimidinyl}methoxy]phenyl}-1-cyclohexylbenzimidazole-5-carboxylic acid hydrochloride (Example 233), 2-{4-[{2-(4-chlorophenyl)-3-pyridyl}methoxy]phenyl}-1-cyclohexylbenzimidazole-5-carboxylic acid dihydrochloride (Example 234), 2-{4-[{3-(4-chlorophenyl)-2-pyridyl}methoxy]phenyl}-1-cyclohexylbenzimidazole-5-carboxylic acid (Example 235), 2-{4-[2-(3-chlorophenyl)-4-methylamino-1,3,5-triazin-6-yloxy]phenyl}-1-cyclohexylbenzimidazole-5-carboxylic acid trifluoroacetate (Example 236), 2-{4-[2-(4-chlorophenyl)-4-(5-tetrazolyl)benzyloxy]phenyl}-1-cyclohexylbenzimidazole-5-carboxylic acid (Example 237), 2-[4-(4-benzyloxy-6-pyrimidinyloxy)phenyl]-1-cyclohexylbenzimidazole-5-carboxylic acid (Example 238), 1-cyclohexyl-2-{4-[4-(4-pyridylmethoxy)-6-pyrimidinyloxy]phenyl}-benzimidazole-5-carboxylic acid (Example 239), 2-{4-[4-(3-chlorophenyl)-6-pyrimidinyloxy]phenyl}-1-cyclohexylbenzimidazole-5-carboxylic acid (Example 240), methyl 2-{4-[2-(4-chlorophenyl)-5-methoxybenzyloxy]phenyl}-1-cyclohexylbenzimidazole-5-carboxylate (Example 241), 2-{4-[2-(4-chlorophenyl)-5-methoxybenzyloxy]phenyl}-1-cyclohexyl-benzimidazole-5-carboxylic acid hydrochloride (Example 242), ethyl 2-{4-[3-(4-chlorophenyl)pyridin-2-ylmethoxy]phenyl}-1-cyclohexylbenzimidazole-5-carboxylate (Example 243), methyl 2-[4-(2-bromo-5-tert-butoxycarbonylbenzyloxy)phenyl]-1-cyclohexylbenzimidazole-5-carboxylate (Example 244), methyl 2-{4-[5-tert-butoxycarbonyl-2-(4-chlorophenyl)benzyloxy]-phenyl}-1-cyclohexylbenzimidazole-5-carboxylate (Example 245), methyl 2-{4-[5-carboxy-2-(4-chlorophenyl)benzyloxy]phenyl}-1-cyclohexylbenzimidazole-5-carboxylate hydrochloride (Example 246), methyl 2-{4-[2-(4-chlorophenyl)-5-methylcarbamoylbenzyloxy]-phenyl}-1-cyclohexylbenzimidazole-5-carboxylate (Example 247), 2-{4-[2-(4-chlorophenyl)-5-methylcarbamoylbenzyloxy]phenyl}-1-cyclohexylbenzimidazole-5-carboxylic acid hydrochloride (Example 248), 2-{4-[3-(tert-butylsulfamoyl)-6-(4-chlorophenyl)benzyloxy]-phenyl}-1-cyclohexylbenzimidazole-5-carboxylic acid (Example 249), 2-{4-[2-(4-chlorophenyl)-5-sulfamoylbenzyloxy]phenyl}-1-cyclohexylbenzimidazole-5-carboxylic acid trifluoroacetate (Example 250), 2-(4-benzyloxycyclohexyl)-1-cyclohexylbenzimidazole-5-carboxylic acid hydrochloride (Example 251), 2-[2-(2-biphenylyloxymethyl)-5-thienyl]-1-cyclohexylbenzimidazole-5-carboxylic acid (Example 252), 2-[2-(2-biphenylyloxymethyl)-5-furyl]-1-cyclohexylbenzimidazole-5-carboxylic acid (Example 253), 1-cyclohexyl-2-{4-[{4-(4-fluorophenyl)-2-hydroxymethyl-5-thiazolyl}methoxy]phenyl}benzimidazole-5-carboxylic acid (Example 254), 1-cyclohexyl-2-{4-[{4-(4-carboxyphenyl)-2-methyl-5-thiazolyl}-methoxy]phenyl}benzimidazole-5-carboxylic acid hydrochloride (Example 255), 1-cyclohexyl-2-{2-fluoro-4-[4-fluoro-2-(3-fluorobenzoyl)-benzyloxy]phenyl}benzimidazole-5-carboxylic acid (Example 256), 2-{4-[2-(4-chlorophenyl)-5-methoxybenzyloxy]phenyl}-1-cyclohexylbenzimidazole-5-sulfonic acid (Example 257), 2-{4-[2-(4-chlorophenyl)-5-methoxybenzyloxy]phenyl}-3-cyclohexylbenzimidazole-4-carboxylic acid (Example 258), 1-cyclohexyl-2-{4-[3-dimethylcarbamoyl-5-(4-pyridylmethoxy)-phenoxy]phenyl}benzimidazole-5-carboxylic acid dihydrochloride (Example 259), 1-cyclohexyl-2-{4-[3-carboxy-5-(4-pyridylmethoxy)phenoxy]-phenyl}benzimidazole-5-carboxylic acid dihydrochloride (Example 260), 2-{4-[2-(4-chlorophenyl)-5-methoxybenzyloxy]phenyl}-1-cyclohexylbenzimidazole-4-carboxylic acid (Example 261), 2-{4-[3-carbamoyl-6-(4-chlorophenyl)benzyloxy]phenyl}-1-cyclohexylbenzimidazole-5-carboxylic acid hydrochloride (Example 262), 2-{4-[{2-(4-carboxyphenyl)-3-pyridyl}methoxy]phenyl}-1-cyclohexylbenzimidazole-5-carboxylic acid (Example 263), 2-{4-[2-(4-chlorophenyl)-5-methoxybenzyloxy]phenyl}-1-(4-tetrahydrothiopyranyl)benzimidazole-5-carboxylic acid (Example 264), 2-{4-[2-(4-chlorophenyl)-5-dimethylcarbamoylbenzyloxy]phenyl}-1-cyclohexylbenzimidazole-5-carboxylic acid hydrochloride (Example 265), 1-cyclohexyl-2-{4-[3-dimethylcarbamoyl-6-(4-trifluoromethylphenyl)benzyloxy]phenyl}benzimidazole-5-carboxylic acid hydrochloride (Example 266), 1-cyclohexyl-2-{4-[3-dimethylcarbamoyl-6-(4-methylthiophenyl)-benzyloxy]phenyl}benzimidazole-5-carboxylic acid hydrochloride (Example 267), 2-{4-[2-(4-chlorophenyl)-5-methylcarbamoylbenzyloxy]-2-fluorophenyl}-1-cyclohexylbenzimidazole-5-carboxylic acid hydrochloride (Example 268), 2-{4-[2-(4-chlorophenyl)-5-dimethylcarbamoylbenzyloxy]-2-fluorophenyl}-1-cyclohexylbenzimidazole-5-carboxylic acid hydrochloride (Example 269), 2-{4-[3-carbamoyl-6-(4-chlorophenyl)benzyloxy]-2-fluorophenyl}-1-cyclohexylbenzimidazole-5-carboxylic acid hydrochloride (Example 270), 2-{4-[3-dimethylcarbamoyl-6-(4-methanesulfonylphenyl)benzyloxy]-phenyl}-1-cyclohexylbenzimidazole-5-carboxylic acid hydrochloride (Example 271), 2-{4-[3-dimethylcarbamoyl-6-(3-pyridyl)benzyloxy]phenyl}-1-cyclohexylbenzimidazole-5-carboxylic acid dihydrochloride (Example 272), 2-{4-[3-dimethylcarbamoyl-6-(4-dimethylcarbamoylphenyl)-benzyloxy]phenyl}-1-cyclohexylbenzimidazole-5-carboxylic acid (Example 273), 2-{4-[2-(4-chlorophenyl)-5-methoxybenzyloxy]phenyl}-1-(1-oxo-4-tetrahydrothiopyranyl)benzimidazole-5-carboxylic acid (Example 274), 2-{4-[2-(4-chlorophenyl)-5-methoxybenzyloxy]phenyl}-1-(1,1-dioxo-4-tetrahydrothiopyranyl)benzimidazole-5-carboxylic acid (Example 275), 2-{4-[2-(4-chlorophenyl)-5-methoxybenzyloxy]-2-fluorophenyl}-1-(4-tetrahydrothiopyranyl)benzimidazole-5-carboxylic acid (Example 276), 2-{4-[2-(4-chlorophenyl)-5-methoxybenzyloxy]-2-fluorophenyl}-1-(1-oxo-4-tetrahydrothiopyranyl)benzimidazole-5-carboxylic acid (Example 277), 2-{4-[2-(4-chlorophenyl)-5-methoxybenzyloxy]-2-fluorophenyl}-1-(1,1-dioxo-4-tetrahydrothiopyranyl)benzimidazole-5-carboxylic acid (Example 278), 2-{4-[2-(4-chlorophenyl)-5-dimethylsulfamoylbenzyloxy]phenyl}-1-cyclohexylbenzimidazole-5-carboxylic acid hydrochloride (Example 279), 2-{4-[2-(4-chlorophenyl)-5-methanesulfonylbenzyloxy]phenyl}-1-cyclohexylbenzimidazole-5-carboxylic acid hydrochloride (Example 280), methyl 2-{4-[5-carboxy-2-(4-chlorophenyl)benzyloxy]-2-fluorophenyl}-1-cyclohexylbenzimidazole-5-carboxylate hydrochloride (Example 281), 2-{4-[2-(4-chlorophenyl)-5-dimethylaminobenzyloxy]phenyl}-1-cyclohexylbenzimidazole-5-carboxylic acid dihydrochloride (Example 282), 2-{4-[2-(4-chlorophenyl)-5-methanesulfonylaminobenzyloxy]phenyl}-1-cyclohexylbenzimidazole-5-carboxylic acid hydrochloride (Example 283), 2-{4-[2-(4-chlorophenyl)-5-diethylcarbamoylbenzyloxy]-2-fluorophenyl}-1-cyclohexylbenzimidazole-5-carboxylic acid hydrochloride (Example 284), 2-{4-[2-(4-chlorophenyl)-5-isopropylcarbamoylbenzyloxy]-2-fluorophenyl}-1-cyclohexylbenzimidazole-5-carboxylic acid hydrochloride (Example 285), 2-{4-[2-(4-chlorophenyl)-5-piperidinocarbonylbenzyloxy]-2-fluorophenyl}-1-cyclohexylbenzimidazole-5-carboxylic acid hydrochloride (Example 286), 2-{4-[2-(4-chlorophenyl)-5-(1-pyrrolidinyl)carbonylbenzyloxy]-2-fluorophenyl}-1-cyclohexylbenzimidazole-5-carboxylic acid hydrochloride (Example 287), 2-{4-[2-(4-chlorophenyl)-5-(2-hydroxyethyl)carbamoylbenzyloxy]-2-fluorophenyl}-1-cyclohexylbenzimidazole-5-carboxylic acid hydrochloride (Example 288), 2-{4-[2-(4-chlorophenyl)-5-(4-hydroxypiperidino)-carbonylbenzyloxy]-2-fluorophenyl}-1-cyclohexylbenzimidazole-5-carboxylic acid hydrochloride (Example 289), 2-{4-[2-(4-chlorophenyl)-5-morpholinocarbonylbenzyloxy]-2-fluorophenyl}-1-cyclohexylbenzimidazole-5-carboxylic acid hydrochloride (Example 290), 2-{4-[2-(4-chlorophenyl)-5-thiomorpholinocarbonylbenzyloxy]-2-fluorophenyl}-1-cyclohexylbenzimidazole-5-carboxylic acid hydrochloride (Example 291), 2-{4-[3-(carboxymethylcarbamoyl)-6-(4-chlorophenyl)benzyloxy]-2-fluorophenyl}-1-cyclohexylbenzimidazole-5-carboxylic acid hydrochloride (Example 292), 2-{4-[2-{4-(2-carboxyethyl)phenyl}-5-chlorobenzyloxy]phenyl}-1-cyclohexylbenzimidazole-5-carboxylic acid (Example 293), 2-{4-[3-chloro-6-(4-hydroxymethylphenyl)benzyloxy]phenyl}-1-cyclohexylbenzimidazole-5-carboxylic acid hydrochloride (Example 294), 2-{4-[3-chloro-6-(4-methoxymethylphenyl)benzyloxy]phenyl}-1-cyclohexylbenzimidazole-5-carboxylic acid hydrochloride (Example 295), 2-{4-[2-(3-carboxyphenyl)-5-chlorobenzyloxy]phenyl}-1-cyclohexylbenzimidazole-5-carboxylic acid (Example 296), 2-{4-[2-(4-chlorophenyl)-5-methylthiobenzyloxy]phenyl}-1-cyclohexylbenzimidazole-5-carboxylic acid (Example 297), 2-{4-[2-(4-chlorophenyl)-5-methylsulfinylbenzyloxy]phenyl}-1-cyclohexylbenzimidazole-5-carboxylic acid (Example 298), 2-{4-[2-(4-chlorophenyl)-5-cyanobenzyloxy]phenyl}-1-cyclohexyl-benzimidazole-5-carboxylic acid hydrochloride (Example 299), 2-{4-[bis(3-pyridyl)methoxy]-2-fluorophenyl}-1-cyclohexylbenzimidazole-5-carboxylic acid (Example 300), 2-{4-[bis(4-dimethylcarbamoylphenyl)methoxy]-2-fluorophenyl}-1-cyclohexylbenzimidazole-5-carboxylic acid (Example 301), sodium 2-{4-[2-thienyl-3-thienylmethoxy]-2-fluorophenyl}-1-cyclohexylbenzimidazole-5-carboxylate (Example 302), methyl 2-{4-[2-(4-chlorophenyl)-5-(dimethylcarbamoyl)benzyloxy]-2-fluorophenyl}-1-cyclohexylbenzimidazole-5-carboxylate (Example 303), sodium 2-{4-[2-(4-chlorophenyl)-5-(dimethylcarbamoyl)benzyloxy]-2-fluorophenyl}-1-cyclohexylbenzimidazole-5-carboxylate (Example 304), 2-{4-[5-carboxy-2-(4-chlorophenyl)benzyloxy]-2-fluorophenyl}-1-cyclohexylbenzimidazole-5-carboxylic acid (Example 305), 2-{4-[2-(4-carboxyphenyl)-5-methoxybenzyloxy]phenyl}-1-cyclohexylbenzimidazole-5-carboxylic acid (Example 306), 2-{4-[2-(4-carbamoylphenyl)-5-(dimethylcarbamoyl)benzyloxy]-phenyl}-1-cyclohexylbenzimidazole-5-carboxylic acid (Example 307), 2-{4-[5-amino-2-(4-chlorophenyl)benzyloxy]phenyl}-1-cyclohexylbenzimidazole-5-carboxylic acid (Example 308), 2-{4-[5-(4-chlorophenyl)-2-methoxybenzylsulfinyl]phenyl}-1-cyclohexylbenzimidazole-5-carboxylic acid hydrochloride (Example 309), 2-{4-[5-(4-chlorophenyl)-2-methoxybenzylsulfonyl]phenyl}-1-cyclohexylbenzimidazole-5-carboxylic acid hydrochloride (Example 310), 2-{4-[2-(4-chlorophenyl)-5-methoxybenzylthio]phenyl}-1-cyclohexylbenzimidazole-5-carboxylic acid hydrochloride (Example 311), 2-{4-[bis(4-carboxyphenyl)methoxy]-2-fluorophenyl}-1-cyclohexylbenzimidazole-5-carboxylic acid (Example 312), 2-[4-(phenyl-3-pyridylmethoxy)-2-fluorophenyl]-1-cyclohexylbenzimidazole-5-carboxylic acid (Example 313), methyl 2-{4-[2-(4-chlorophenyl)-5-(methylcarbamoyl)benzyloxy]-2-fluorophenyl}-1-cyclohexylbenzimidazole-5-carboxylate (Example 314), 2-{4-[5-chloro-2-(4-pyridyl)benzyloxy]-2-fluorophenyl}-1-cyclohexylbenzimidazole-5-carboxylic acid hydrochloride (Example 315), 2-{4-[2-(4-chlorophenyl)-5-(benzylcarbamoyl)benzyloxy]-2-fluorophenyl}-1-cyclohexylbenzimidazole-5-carboxylic acid hydrochloride (Example 316), 2-{4-[2-(4-chlorophenyl)-5-(cyclohexylmethylcarbamoyl)benzyloxy]-2-fluorophenyl}-1-cyclohexylbenzimidazole-5-carboxylic acid hydrochloride (Example 317), 2-{4-[2-(4-chlorophenyl)-5-(4-pyridylmethylcarbamoyl)benzyloxy]-2-fluorophenyl}-1-cyclohexylbenzimidazole-5-carboxylic acid dihydrochloride (Example 318), 2-{4-[2-(4-chlorophenyl)-5-(N-benzyl-N-methylcarbamoyl)-benzyloxy]-2-fluorophenyl}-1-cyclohexylbenzimidazole-5-carboxylic acid hydrochloride (Example 319), 2-{4-[5-dimethylaminocarbonyl-2-(4-pyridyl)benzyloxy]phenyl}-1-cyclohexylbenzimidazole-5-carboxylic acid dihydrochloride (Example 320), 2-{4-[2-(4-chlorophenyl)-5-(4-methylpiperazin-1-ylcarbonyl)benzyloxy]phenyl}-1-cyclohexylbenzimidazole-5-carboxylic acid dihydrochloride (Example 321), 2-{4-[2-(4-chlorophenyl)-5-{N-(3-pyridylmethyl)carbamoyl}-benzyloxy]phenyl}-1-cyclohexylbenzimidazole-5-carboxylic acid dihydrochloride (Example 322), 2-{4-[2-(4-chlorophenyl)-5-{N-(2-pyridylmethyl)carbamoyl}-benzyloxy]phenyl}-1-cyclohexylbenzimidazole-5-carboxylic acid dihydrochloride (Example 323), 2-{4-[2-(4-chlorophenyl)-5-(cyclohexylcarbamoyl)benzyloxy]-phenyl}-1-cyclohexylbenzimidazole-5-carboxylic acid hydrochloride (Example 324), 2-{4-[2-(4-chlorophenyl)-5-(2-pyridin-4-ylethylcarbamoyl)-benzyloxy]phenyl}-1-cyclohexylbenzimidazole-5-carboxylic acid dihydrochloride (Example 325), 2-{4-[(4-fluorophenyl){4-(dimethylaminocarbonyl)phenyl}methoxy]-2-fluorophenyl}-1-cyclohexylbenzimidazole-5-carboxylic acid (Example 326), 2-{4-[(4-fluorophenyl)(4-carboxyphenyl)methoxy]-2-fluorophenyl}-1-cyclohexylbenzimidazole-5-carboxylic acid (Example 327), 2-{4-[2-(4-chlorophenyl)-5-(4-oxopiperidinocarbonyl)-benzyloxy]phenyl}-1-cyclohexylbenzimidazole-5-carboxylic acid hydrochloride (Example 328), 2-{4-[2-(4-chlorophenyl)-5-hydroxybenzyloxy]phenyl}-1-cyclohexylbenzimidazole-5-carboxylic acid hydrochloride (Example 329), 2-{4-[2-(4-chlorophenyl)-5-(isopropylcarbamoyl)benzyloxy]phenyl}-1-cyclohexylbenzimidazole-5-carboxylic acid hydrochloride (Example 330), 2-{4-[2-(4-chlorophenyl)-5-(N-isopropyl-N-methylcarbamoyl)-benzyloxy]phenyl}-1-cyclohexylbenzimidazole-5-carboxylic acid hydrochloride (Example 331), 2-{4-[2-(4-chlorophenyl)-5-(phenylcarbamoyl)benzyloxy]phenyl}-1-cyclohexylbenzimidazole-5-carboxylic acid hydrochloride (Example 332), 2-{4-[2-(4-chlorophenyl)-5-(4-methoxypiperidinocarbonyl)-benzyloxy]phenyl}-1-cyclohexylbenzimidazole-5-carboxylic acid hydrochloride (Example 333), 2-{4-[2-(4-chlorophenyl)-5-(3-hydroxypropyloxy)benzyloxy]phenyl}-1-cyclohexylbenzimidazole-5-carboxylic acid (Example 334), 2-{4-[2-(4-chlorophenyl)-5-(2-hydroxyethoxy)benzyloxy]phenyl}-1-cyclohexylbenzimidazole-5-carboxylic acid hydrochloride (Example 335), methyl 2-[4-(2-bromo-5-nitrobenzyloxy)-2-fluorophenyl]-1-cyclohexylbenzimidazole-5-carboxylate (Example 336), methyl 2-[4-{2-(4-chlorophenyl)-5-nitrobenzyloxy}-2-fluorophenyl]-1-cyclohexylbenzimidazole-5-carboxylate (Example 337), methyl 2-[4-{5-amino-2-(4-chlorophenyl)benzyloxy}-2-fluorophenyl]-1-cyclohexylbenzimidazole-5-carboxylate (Example 338), methyl 2-[4-{2-(4-chlorophenyl)-5-(2-oxopyrrolidin-1-yl)benzyloxy}-2-fluorophenyl]-1-cyclohexylbenzimidazole-5-carboxylate (Example 339), 2-[4-{2-(4-chlorophenyl)-5-(2-oxopyrrolidin-1-yl)benzyloxy}-2-fluorophenyl]-1-cyclohexylbenzimidazole-5-carboxylic acid hydrochloride (Example 340), 2-{4-[2-(4-chlorophenyl)-5-(4-methylpiperidin-1-ylcarbonyl)benzyloxy]phenyl}-1-cyclohexylbenzimidazole-5-carboxylic acid hydrochloride (Example 341), 2-{4-[5-acetyl-2-(4-chlorophenyl)benzyloxy]phenyl}-1-cyclohexylbenzimidazole-5-carboxylic acid hydrochloride (Example 342), 2-{4-[2-(4-chlorophenyl)-5-{(4-hydroxypiperidin-1-ylcarbonyl)-methoxy}benzyloxy]phenyl}-1-cyclohexylbenzimidazole-5-carboxylic acid (Example 343), 2-{4-[2-(4-chlorophenyl)-5-(2-methoxyethoxy)benzyloxy]phenyl}-1-cyclohexylbenzimidazole-5-carboxylic acid hydrochloride (Example 344), 2-{4-[2-(4-chlorophenyl)-5-{2-(2-methoxyethoxy)ethoxy}-benzyloxy]phenyl}-1-cyclohexylbenzimidazole-5-carboxylic acid hydrochloride (Example 345), 2-{4-[2-(4-chlorophenyl)-5-(isobutylcarbonyl)benzyloxy]phenyl}-1-cyclohexylbenzimidazole-5-carboxylic acid (Example 346), 2-{4-[2-(4-chlorophenyl)-5-(2-methylthiazol-4-yl)benzyloxy]-phenyl}-1-cyclohexylbenzimidazole-5-carboxylic acid (Example 347), 2-{4-[2-(4-chlorophenyl)-5-(3,4-dihydroxypiperidin-1-ylcarbonyl)benzyloxy]phenyl}-1-cyclohexylbenzimidazole-5-carboxylic acid hydrochloride (Example 348), 2-{4-[2-(4-chlorophenyl)-5-(3-methyl-1,2,4-oxadiazol-5-yl)benzyloxy]phenyl}-1-cyclohexylbenzimidazole-5-carboxylic acid hydrochloride (Example 349), 2-{4-[2-(4-chlorophenyl)-4-(isopropylcarbamoyl)benzyloxy]phenyl}-1-cyclohexylbenzimidazole-5-carboxylic acid hydrochloride (Example 350), 2-{4-[2-(4-chlorophenyl)-4-(piperidinocarbonyl)benzyloxy]phenyl}-1-cyclohexylbenzimidazole-5-carboxylic acid (Example 351), 2-{4-[2-(4-chlorophenyl)-5-{(1-hydroxy-2-methylpropan-2-yl)carbamoyl]benzyloxy]phenyl}-1-cyclohexylbenzimidazole-5-carboxylic acid hydrochloride (Example 352), 2-{4-[2-(4-chlorophenyl)-5-(4,4-dimethyl-2-oxazolin-2-yl)}benzyloxy]phenyl}-1-cyclohexylbenzimidazole-5-carboxylic acid dihydrochloride (Example 353), 2-{4-[2-(4-chlorophenyl)-4-(4-hydroxypiperidin-1-ylcarbonyl)benzyloxy]phenyl}-1-cyclohexylbenzimidazole-5-carboxylic acid hydrochloride (Example 354), 2-{4-[2-(4-chlorophenyl)-4-{(2-hydroxyethyl)carbamoyl}-benzyloxy]phenyl}-1-cyclohexylbenzimidazole-5-carboxylic acid hydrochloride (Example 355), 2-{4-[2-(4-chlorophenyl)-4-{(4-pyridylmethyl)carbamoyl}-benzyloxy]phenyl}-1-cyclohexylbenzimidazole-5-carboxylic acid (Example 356), 2-{4-[2-(4-chlorophenyl)-4-(dimethylcarbamoyl)benzyloxy]phenyl}-1-cyclohexylbenzimidazole-5-carboxylic acid hydrochloride (Example 357), 2-{4-[5-(2-aminothiazol-4-yl)-2-(4-chlorophenyl)benzyloxy]-phenyl}-1-cyclohexylbenzimidazole-5-carboxylic acid dihydrochloride (Example 358), 2-{4-[2-(4-chlorophenyl)-5-(4-hydroxypiperidin-1-ylsulfonyl)benzyloxy]phenyl}-1-cyclohexylbenzimidazole-5-carboxylic acid hydrochloride (Example 359), 2-{4-[5-(dimethylcarbamoyl)-2-(4-fluorophenyl)benzyloxy]phenyl}-1-cyclohexylbenzimidazole-5-carboxylic acid hydrochloride (Example 360), 2-{4-[5-(dimethylcarbamoyl)-2-(3-fluorophenyl)benzyloxy]phenyl}-1-cyclohexylbenzimidazole-5-carboxylic acid hydrochloride (Example 361), 2-{4-[2-(5-chlorothiophen-2-yl)-5-(dimethylcarbamoyl)benzyloxy]-phenyl}-1-cyclohexylbenzimidazole-5-carboxylic acid hydrochloride (Example 362), 2-{4-[2-bromo-5-(5-methyloxazol-2-yl)benzyloxy]phenyl}-1-cyclohexylbenzimidazole-5-carboxylic acid hydrochloride (Example 363), 2-{4-[2-bromo-5-(5-methylthiazol-2-yl)benzyloxy]phenyl}-1-cyclohexylbenzimidazole-5-carboxylic acid hydrochloride (Example 364), 2-{4-[2-(4-chlorophenyl)-5-(5-methyloxazol-2-yl)benzyloxy]-phenyl}-1-cyclohexylbenzimidazole-5-carboxylic acid hydrochloride (Example 365), 2-{4-[2-(4-chlorophenyl)-5-(5-methylthiazol-2-yl)benzyloxy]-phenyl}-1-cyclohexylbenzimidazole-5-carboxylic acid hydrochloride (Example 366), 2-{4-[2-(4-chlorophenyl)-5-tetrazol-5-ylbenzyloxy]phenyl}-1-cyclohexylbenzimidazole-5-carboxylic acid hydrochloride (Example 367), 2-{4-[5-chloro-2-(4-cyanophenyl)benzyloxy]phenyl}-1-cyclohexylbenzimidazole-5-carboxylic acid hydrochloride (Example 368), 2-{4-[5-chloro-2-(4-tetrazol-5-ylphenyl)benzyloxy]phenyl}-1-cyclohexylbenzimidazole-5-carboxylic acid hydrochloride (Example 369), 2-{4-[2-(4-chlorophenyl)-5-{2-(4-hydroxypiperidin-1-yl)ethoxy}benzyloxy]phenyl}-1-cyclohexylbenzimidazole-5-carboxylic acid hydrochloride (Example 370), 2-{4-[2-(4-chlorophenyl)-5-(2-oxopiperidin-1-yl)benzyloxy]-2-fluorophenyl}-1-cyclohexylbenzimidazole-5-carboxylic acid hydrochloride (Example 371), 2-{4-[3-(4-chlorophenyl)-5-(dimethylcarbamoyl)benzyloxy]-2-fluorophenyl}-1-cyclohexylbenzimidazole-5-carboxylic acid hydrochloride (Example 372), 2-{4-[2-(4-chlorophenyl)-5-(N-hydroxyamidino)benzyloxy]-2-fluorophenyl}-1-cyclohexylbenzimidazole-5-carboxylic acid dihydrochloride (Example 373), 2-{4-[2-(4-chlorophenyl)-5-(2,5-dihydro-5-oxo-4H-1,2,4-oxadiazol-3-yl)benzyloxy]-2-fluorophenyl}-1-cyclohexylbenzimidazole-5-carboxylic acid hydrochloride (Example 374), 2-{4-[2-(4-chlorophenyl)-5-(2-oxo-3H-1,2,3,5-oxathiadiazol-4-yl)benzyloxy]-2-fluorophenyl}-1-cyclohexylbenzimidazole-5-carboxylic acid hydrochloride (Example 375), 2-{4-[2-(4-chlorophenyl)-5-(2,5-dihydro-5-oxo-4H-1,2,4-thiadiazol-3-yl)benzyloxy]-2-fluorophenyl}-1-cyclohexylbenzimidazole-5-carboxylic acid hydrochloride (Example 376), 2-{4-[2-(4-chlorophenyl)-5-(cyclopropylcarbamoyl)benzyloxy]-2-fluorophenyl}-1-cyclohexylbenzimidazole-5-carboxylic acid hydrochloride (Example 377), 2-{4-[2-(4-chlorophenyl)-5-(cyclobutylcarbamoyl)benzyloxy]-2-fluorophenyl}-1-cyclohexylbenzimidazole-5-carboxylic acid hydrochloride (Example 378), 2-{4-[2-(4-chlorophenyl)-5-(tert-butylcarbamoyl)benzyloxy]-2-fluorophenyl}-1-cyclohexylbenzimidazole-5-carboxylic acid hydrochloride (Example 379), 2-{4-[2-(4-chlorophenyl)-5-(isobutylcarbamoyl)benzyloxy]-2-fluorophenyl}-1-cyclohexylbenzimidazole-5-carboxylic acid hydrochloride (Example 380), 2-{4-[2-(4-chlorophenyl)-5-{(1-hydroxypropan-2-yl)carbamoyl}-benzyloxy]-2-fluorophenyl}-1-cyclohexylbenzimidazole-5-carboxylic acid hydrochloride (Example 381), 2-{4-[2-(4-chlorophenyl)-5-(methoxycarbamoyl)benzyloxy]-2-fluorophenyl}-1-cyclohexylbenzimidazole-5-carboxylic acid hydrochloride (Example 382), 2-{4-[2-(4-chlorophenyl)-5-{(2,3-dihydroxypropyl)carbamoyl}-benzyloxy]-2-fluorophenyl}-1-cyclohexylbenzimidazole-5-carboxylic acid hydrochloride (Example 383), 2-{4-[2-(4-chlorophenyl)-5-(N-ethyl-N-methylcarbamoyl)benzyloxy]-2-fluorophenyl}-1-cyclohexylbenzimidazole-5-carboxylic acid hydrochloride (Example 384), 2-{4-[2-(4-chlorophenyl)-5-(N-methyl-N-propylcarbamoyl)-benzyloxy]-2-fluorophenyl}-1-cyclohexylbenzimidazole-5-carboxylic acid hydrochloride (Example 385), 2-{4-[2-(4-chlorophenyl)-5-(N-isopropyl-N-methylcarbamoyl)-benzyloxy]-2-fluorophenyl}-1-cyclohexylbenzimidazole-5-carboxylic acid hydrochloride (Example 386), 2-{4-[2-(4-chlorophenyl)-5-(2,6-dimethylpiperidin-1-ylcarbonyl)-benzyloxy]-2-fluorophenyl}-1-cyclohexylbenzimidazole-5-carboxylic acid hydrochloride (Example 387), 2-{4-[5-(butylcarbamoyl)-2-(4-chlorophenyl)benzyloxy]-2-fluorophenyl}-1-cyclohexylbenzimidazole-5-carboxylic acid hydrochloride (Example 388), 2-{4-[2-(4-chlorophenyl)-5-(propylcarbamoyl)benzyloxy]-2-fluorophenyl}-1-cyclohexylbenzimidazole-5-carboxylic acid hydrochloride (Example 389), 2-{4-[2-(4-chlorophenyl)-5-(ethylcarbamoyl)benzyloxy]-2-fluorophenyl}-1-cyclohexylbenzimidazole-5-carboxylic acid hydrochloride (Example 390), 2-{4-[2-(4-chlorophenyl)-5-{(dimethylcarbamoyl)amino}benzyloxy]-2-fluorophenyl}-1-cyclohexylbenzimidazole-5-carboxylic acid hydrochloride (Example 391), 2-{4-[2-(4-chlorophenyl)-5-{(morpholinocarbonyl)amino}benzyloxy]-2-fluorophenyl}-1-cyclohexylbenzimidazole-5-carboxylic acid hydrochloride (Example 392), 2-{4-[2-(4-chlorophenyl)-5-ureidobenzyloxy]-2-fluorophenyl}-1-cyclohexylbenzimidazole-5-carboxylic acid hydrochloride (Example 393), 2-{4-[2-(4-chlorophenyl)-5-{(ethylcarbamoyl)amino}benzyloxy]-2-fluorophenyl}-1-cyclohexylbenzimidazole-5-carboxylic acid hydrochloride (Example 394), 2-{4-[2-(4-chlorophenyl)-5-{(isopropylcarbamoyl)amino}benzyloxy]-2-fluorophenyl}-1-cyclohexylbenzimidazole-5-carboxylic acid hydrochloride (Example 395), 2-{4-[2-(3,4-difluorophenyl)-5-(isopropylcarbamoyl)benzyloxy]-2-fluorophenyl}-1-cyclohexylbenzimidazole-5-carboxylic acid (Example 396), 2-{4-[2-(2,4-difluorophenyl)-5-(isopropylcarbamoyl)benzyloxy]-2-fluorophenyl}-1-cyclohexylbenzimidazole-5-carboxylic acid hydrochloride (Example 397), 2-{4-[2-(3,5-dichlorophenyl)-5-(isopropylcarbamoyl)benzyloxy]-2-fluorophenyl}-1-cyclohexylbenzimidazole-5-carboxylic acid hydrochloride (Example 398), 2-{4-[2-(3-chloro-4-fluorophenyl)-5-(isopropylcarbamoyl)-benzyloxy]-2-fluorophenyl}-1-cyclohexylbenzimidazole-5-carboxylic acid hydrochloride (Example 399), 2-{4-[2-(3,4-dichlorophenyl)-5-(isopropylcarbamoyl)benzyloxy]-2-fluorophenyl}-1-cyclohexylbenzimidazole-5-carboxylic acid hydrochloride (Example 400), 2-{4-[2-(4-chloro-2-fluorophenyl)-5-(isopropylcarbamoyl)-benzyloxy]-2-fluorophenyl}-1-cyclohexylbenzimidazole-5-carboxylic acid hydrochloride (Example 401), 2-{4-[2-(4-chloro-2-fluorophenyl)-5-(pyrrolidin-1-ylcarbonyl)-benzyloxy]-2-fluorophenyl}-1-cyclohexylbenzimidazole-5-carboxylic acid hydrochloride (Example 402), 2-{4-[2-(4-chloro-3-fluorophenyl)-5-(pyrrolidin-1-ylcarbonyl)-benzyloxy]-2-fluorophenyl}-1-cyclohexylbenzimidazole-5-carboxylic acid hydrochloride (Example 403), 2-{4-[2-(4-chloro-3-fluorophenyl)-5-(isopropylcarbamoyl)-benzyloxy]-2-fluorophenyl}-1-cyclohexylbenzimidazole-5-carboxylic acid hydrochloride (Example 404), 2-{4-[2-{4-(methylthio)phenyl}-5-(2-oxopyrrolidin-1-yl)benzyloxy]-2-fluorophenyl}-1-cyclohexylbenzimidazole-5-carboxylic acid hydrochloride (Example 405), 2-{4-[2-{4-(methylthio)phenyl}-5-(isopropylcarbamoyl)benzyloxy]-2-fluorophenyl}-1-cyclohexylbenzimidazole-5-carboxylic acid hydrochloride (Example 406), 2-{4-[4-chloro-2-(4-chlorophenyl)-5-(1,1-dioxoisothiazolidin-2-yl)benzyloxy]-2-fluorophenyl}-1-cyclohexylbenzimidazole-5-carboxylic acid hydrochloride (Example 407), 2-{4-[4-chloro-2-(4-chlorophenyl)-5-(2-oxopyrrolidin-1-yl)benzyloxy]-2-fluorophenyl}-1-cyclohexylbenzimidazole-5-carboxylic acid hydrochloride (Example 408), 2-{4-[2-(4-chlorophenyl)-5-(isopropylaminosulfonyl)benzyloxy]-2-fluorophenyl}-1-cyclohexylbenzimidazole-5-carboxylic acid hydrochloride (Example 409), 2-{4-[2-(4-chlorophenyl)-5-(dimethylcarbamoyl)benzyloxy]-2-fluorophenyl}-1-cyclopentylbenzimidazole-5-carboxylic acid hydrochloride (Example 410), 2-{4-[2-(4-chlorophenyl)-5-(4-hydroxypiperidin-1-ylcarbonyl)-benzyloxy]-2-fluorophenyl}-1-cyclopentylbenzimidazole-5-carboxylic acid hydrochloride (Example 411), 2-{4-[2-(4-chlorophenyl)-5-(isopropylcarbamoyl)benzyloxy]-2-fluorophenyl}-1-cyclopentylbenzimidazole-5-carboxylic acid hydrochloride (Example 412), 2-{4-[2-(4-chlorophenyl)-5-(isopropylcarbamoyl)benzyloxy]phenyl}-1-cyclopentylbenzimidazole-5-carboxylic acid hydrochloride (Example 413), 2-{4-[2-(4-chlorophenyl)-5-(dimethylcarbamoyl)benzyloxy]phenyl}-1-cyclopentylbenzimidazole-5-carboxylic acid hydrochloride (Example 414), 2-{4-[2-(4-chlorophenyl)-5-(4-hydroxypiperidin-1-ylcarbonyl)benzyloxy]phenyl}-1-cyclopentylbenzimidazole-5-carboxylic acid hydrochloride (Example 415), 2-{4-[2-(4-chlorophenyl)-5-(isopropylcarbamoyl)benzyloxy]phenyl}-1-(tetrahydrothiopyran-4-yl)benzimidazole-5-carboxylic acid hydrochloride (Example 416), 2-{4-[2-(4-chlorophenyl)-5-(pyrrolidin-1-ylcarbonyl)benzyloxy]-phenyl}-1-(tetrahydrothiopyran-4-yl)benzimidazole-5-carboxylic acid hydrochloride (Example 417), 2-{4-[2-(4-chlorophenyl)-5-(isopropylcarbamoyl)benzyloxy]-2-fluorophenyl}-1-(tetrahydrothiopyran-4-yl)benzimidazole-5-carboxylic acid hydrochloride (Example 418), 2-{4-[2-(4-chlorophenyl)-5-(2-oxopyrrolidin-1-yl)benzyloxy]-2-fluorophenyl}-1-(tetrahydrothiopyran-4-yl)benzimidazole-5-carboxylic acid hydrochloride (Example 419), 2-{4-[2-(4-chlorophenyl)-5-(isopropylcarbamoyl)benzyloxy]-2-fluorophenyl}-1-piperidinobenzimidazole-5-carboxylic acid hydrochloride (Example 420), 2-{4-[2-(4-chlorophenyl)-5-(pyrrolidin-1-ylcarbonyl)benzyloxy]-2-fluorophenyl}-1-piperidinobenzimidazole-5-carboxylic acid (Example 421), 2-{4-[2-(4-chlorophenyl)-5-(2-imidazolin-2-yl)benzyloxy]-2-fluorophenyl}-1-cyclohexylbenzimidazole-5-carboxylic acid dihydrochloride (Example 422), 2-{4-[2-(4-chlorophenyl)-5-(2-oxooxazolidin-3-yl)benzyloxy]-2-fluorophenyl}-1-cyclohexylbenzimidazole-5-carboxylic acid hydrochloride (Example 423), 2-{4-[2-(4-chlorophenyl)-5-(2-oxoimidazolidin-1-yl)benzyloxy]-2-fluorophenyl}-1-cyclohexylbenzimidazole-5-carboxylic acid hydrochloride (Example 424), 2-{4-[2-(4-chlorophenyl)-5-(2-oxazolin-2-ylamino)benzyloxy]-2-fluorophenyl}-1-cyclohexylbenzimidazole-5-carboxylic acid dihydrochloride (Example 425), 2-{4-[{2-[{(dimethylcarbamoyl)methoxy}methyl]-4-(4-fluorophenyl)thiazol-5-yl}methoxy]phenyl}-1-cyclohexylbenzimidazole-5-carboxylic acid hydrochloride (Example 426), 2-{4-[{4-(4-fluorophenyl)-2-(4-hydroxypiperidin-1-ylmethyl)thiazol-5-yl}methoxy]phenyl}-1-cyclohexylbenzimidazole-5-carboxylic acid dihydrochloride (Example 427), 2-{4-[{4-(4-fluorophenyl)-2-[(carbamoylmethoxy)methyl]thiazol-5-yl}methoxy]phenyl}-1-cyclohexylbenzimidazole-5-carboxylic acid hydrochloride (Example 428), 2-{4-[{4-(4-fluorophenyl)-2-(methylcarbamoyl)thiazol-5-yl}methoxy]-2-fluorophenyl}-1-cyclohexylbenzimidazole-5-carboxylic acid hydrochloride (Example 429), 2-{4-[{4-(4-fluorophenyl)-2-{(2-hydroxyethyl)carbamoyl}thiazol-5-yl}methoxy]-2-fluorophenyl}-1-cyclohexylbenzimidazole-5-carboxylic acid hydrochloride (Example 430), 2-{4-[{2-(4-fluorophenyl)-5-(dimethylcarbamoyl)thiophen-3-yl}methoxy]-2-fluorophenyl}-1-cyclohexylbenzimidazole-5-carboxylic acid hydrochloride (Example 431), 2-{4-[{2-(4-fluorophenyl)-5-(isopropylcarbamoyl)thiophen-3-yl}methoxy]-2-fluorophenyl}-1-cyclohexylbenzimidazole-5-carboxylic acid hydrochloride (Example 432), 2-{4-[{2-(4-fluorophenyl)-5-(4-hydroxypiperidin-1-ylcarbonyl)thiophen-3-yl}methoxy]-2-fluorophenyl}-1-cyclohexylbenzimidazole-5-carboxylic acid hydrochloride (Example 433), 2-{4-[2-(4-chlorophenyl)-5-(dimethylcarbamoyl)benzyloxy]-2-fluorophenyl}-1-cyclohexyl-5-tetrazol-5-ylbenzimidazole (Example 434), 2-{4-[2-(4-carboxyphenyl)-5-chlorobenzyloxy]-2-fluorophenyl}-1-cyclohexyl-5-tetrazol-5-ylbenzimidazole hydrochloride (Example 435), 2-{4-[2-(4-chlorophenyl)-5-(isopropylcarbamoyl)benzyloxy]-2-fluorophenyl}-1-cyclohexyl-5-(2,5-dihydro-5-oxo-4H-1,2,4-oxadiazol-3-yl)benzimidazole hydrochloride (Example 436), 2-{4-[5-carboxy-2-(4-chlorophenyl)benzyloxy]-2-fluorophenyl}-5-cyano-1-cyclohexylbenzimidazole (Example 437), 2-{4-[2-(4-chlorophenyl)-5-(dimethylcarbamoyl)benzyloxy]-2-fluorophenyl}-5-cyano-1-cyclohexylbenzimidazole (Example 438), 2-{4-[{N-(4-dimethylcarbamoyl)-N-(4-fluorophenyl)amino}-methyl]phenyl}-1-cyclohexylbenzimidazole-5-carboxylic acid (Example 439), 2-{5-[bis(3-fluorophenyl)methyl]-2-fluoro-4-hydroxyphenyl}-1-cyclohexylbenzimidazole-5-carboxylic acid (Example 440), 2-{3-[bis(3-fluorophenyl)methyl]-2-fluoro-4-hydroxyphenyl}-1-cyclohexylbenzimidazole-5-carboxylic acid (Example 441), 2-{4-[(3-dimethylcarbamoylphenyl)(4-fluorophenyl)methoxy]-2-fluorophenyl}-1-cyclohexylbenzimidazole-5-carboxylic acid hydrochloride (Example 442), 2-{4-[{3-(4-hydroxypiperidyl-1-ylcarbonyl)phenyl}(4-fluorophenyl)methoxy]-2-fluorophenyl}-1-cyclohexylbenzimidazole-5-carboxylic acid hydrochloride (Example 443), 1-{[2-{4-([4-(4-fluorophenyl)-2-methylthiazol-5-yl]methoxy)phenyl}-1-cyclohexylbenzimidazol-5-yl]carbonyl}-β-D-glucuronic acid (Example 444), {[2-{4-[bis(3-fluorophenyl)methoxy]-2-fluorophenyl}-1-cyclohexylbenzimidazol-5-yl]carbonyl}-β-D-glucuronic acid (Example 445), 2-{4-[2-(4-chlorophenyl)-5-(1,1-dioxoisothiazolidin-2-yl)benzyloxy]-2-fluorophenyl}-1-cyclohexylbenzimidazole-5-carboxylic acid hydrochloride (Example 446), 3-([4-(5-aminosulfonyl-1-cyclohexylbenzimidazol-2-yl)-3-fluorophenoxy]methyl)-4-(4-chlorophenyl)-N-isopropylbenzamide (Example 447), 2-[4-{2-(4-chlorophenyl)-6-(isopropylaminocarbonyl)benzyloxy}-2-fluorophenyl]-1-cyclohexylbenzimidazole-5-carboxylic acid hydrochloride (Example 448), 2-[4-(2-(4-chlorophenyl)-4-fluoro-5-(1,1-dioxoisothiazolidin-2-yl)benzyloxy}-2-fluorophenyl]-1-cyclohexylbenzimidazole-5-carboxylic acid hydrochloride (Example 449), 2-[4-{2-(4-chlorophenyl)-5-(isopropylaminocarbonyl)benzyloxy}-2-fluorophenyl]-1-cyclohexyl-4-methoxybenzimidazole-5-carboxylic acid hydrochloride (Example 450), 2-[4-{2-(4-chlorophenyl)-5-(N-isopropylcarbonyl-N-methylamino)benzyloxy}-2-fluorophenyl]-1-cyclohexylbenzimidazole-5-carboxylic acid hydrochloride (Example 451), 2-[4-{2-(4-chlorophenyl)-5-(isopropylcarbonylamino)benzyloxy}-2-fluorophenyl]-1-cyclohexylbenzimidazole-5-carboxylic acid hydrochloride (Example 452), 2-[3-{[4-(4-fluorophenyl)-2-methylthiazol-5-yl]methyl}-4-hydroxyphenyl]-1-cyclohexylbenzimidazole-5-carboxylic acid (Example 453), 2-[4-{2-(4-chlorophenyl)-4-fluoro-5-(2-oxopyrrolidin-1-yl)benzyloxy}-2-fluorophenyl]-1-cyclohexylbenzimidazole-5-carboxylic acid hydrochloride (Example 454), 2-[4-{2-(4-chlorophenyl)-5-(methylsulfonylamino)benzyloxy}-2-fluorophenyl]-1- cyclohexylbenzimidazole-5-carboxylic acid hydrochloride (Example 455),
2-[4-{2-(4-chlorophenyl)-5-[N-methyl-N-(methylsulfonyl) amino]benzyloxy}-2-fluorophenyl]-1-cyclohexylbenzimidazole-5-carboxylic acid hydrochloride (Example 456),
2-[4-{[3-(4-chlorophenyl)-6-(2-oxopyrrolidin-1-yl)pyridin-2-yl]methyloxy}-2-fluorophenyl]-1-cyclohexylbenzimidazole-5-carboxylic acid hydrochloride (Example 457),
2-[4-{2-(4-chlorophenyl)-5-(acetylamino)benzyloxy}-2-fluorophenyl]-1-cyclohexylbenzimidazole-5-carboxylic acid hydrochloride (Example 458),
2-[4-{2-(4-chlorophenyl)-5-(N-acetyl-N-ethylamino) benzyloxy}-2-fluorophenyl]-1-cyclohexylbenzimidazole-5-carboxylic acid hydrochloride (Example 459),
2-[4-{2-(4-chlorophenyl)-5-(N-acetyl-N-propylainiro) benzyloxy}-2-fluorophenyl]-1-cyclohexylbenzimidazole-5-carboxylic acid hydrochloride (Example 460),
2-[4-{2-(4-chlorophenyl)-5-[N-ethyl-N-(methylsulfonyl) amino]-benzyloxy}-2-fluorophenyl]-1-cyclohexylbenzimidazole-5-carboxylic acid hydrochloride (Example 461),
2-[4-{2-(4-chlorophenyl)-5-[N-(methylsulfonyl)-N-propylamino]benzyloxy}-2-fluorophenyl]-1-cyclohexylbenzimidazole-5-carboxylic acid hydrochloride (Example 462),
2-[4-{2-(4-chlorophenyl)-5-(N-acetyl-N-methylamino) benzyloxy}-2-fluorophenyl]-1-cyclohexylbenzimidazole-5-carboxylic acid hydrochloride (Example 463),
2-[4-{2-(4-chlorophenyl)-5-[N-(ethylsulfonyl)-N-methylamino]-benzyloxy}-2-fluorophenyl]-1-cyclohexylbenzimidazole-5-carboxylic acid hydrochloride (Example 464),
2-[4-{2-(4-chlorophenyl)-5-[N-ethyl-N-(ethylsulfonyl) amino]-benzyloxy}-2-fluorophenyl]-1-cyclohexylbenzimidazole-5-carboxylic acid hydrochloride (Example 465),
2-[4-{2-(4-chlorophenyl)-5-[N-(ethylcarbonyl)-N-methylamino]-benzyloxy}-2-fluorophenyl]-1-cyclohexylbenzimidazole-5-carboxylic acid hydrochloride (Example 466),
2-[4-{2-(4-chlorophenyl)-5-[N-ethyl-N-(ethylcarborlyl) amino]-benzyloxy}-2-fluorophenyl]-1-cyclohexylbenzimidazole-5-carboxylic acid hydrochloride (Example 467),
2-[4-{2-(4-chlorophenyl)-5-methoxybenzyloxy}-2-fluorophenyl]-1-cyclohexylbenzimidazole-5-carboxylic acid (Example 468),
2-[4-{2-(4-chlorophenyl)-5-(N-acetyl-N-isopropylamino)-benzyloxy}-2-fluorophenyl]-1-cyclohexylbenzimidazole-5-carboxylic acid hydrochloride (Example 469),
{[2-{4-[2-(4-chlorophenyl)-5-(2-oxopyrrolidin-1-yl) benzyloxy]-2-fluorophenyl}-1-cyclohexylbenzoimidazol-5-yl]carbonyl-β-D-glucuronic acid (Example 470),
methyl 2-{4-[2-(4-chlorophenyl)-5-methoxybenzyloxy] phenyl}-1-cyclohexyl-1H-indole-5-carboxylate (Example 501),
2-{4-[2-(4-chlorophenyl)-5-methoxybenzyloxy]phenyl}-1-cyclohexyl-1H-indole-5-carboxylic acid (Example 502),
2-(4-benzyloxyphenyl)-1-cyclopentyl-1H-indole-5-carboxylic acid (Example 503),
ethyl 2-(4-benzyloxyphenyl)-3-cyclohexylimidazo[1,2-a] pyridine-7-carboxylate (Example 601),
2-(4-benzyloxyphenyl)-3-cyclohexylimidazo[1,2-a] pyridine-7-carboxylic acid (Example 602),
2-{4-[2-(4-chlorophenyl)-5-methoxybenzyloxy]phenyl}-3-cyclohexyl-3H-imidazo[4,5-b]pyridine-6-carboxylic acid (Example 701),
2-{4-[2-(4-chlorophenyl)-5-(isopropylcarbamoyl) benzyloxy]phenyl}-3-cyclohexyl-3H-dimidazo[4,5-b] pyridine-6-carboxylic acid hydrochloride (Example 702), and
2-{4-[2-(4-chlorophenyl)-5-(pyrrolidin-1-ylcarbonyl) benzyloxy]-phenyl}-3-cyclohexyl-3H-imidazo[4,5-b] pyridine-6-carboxylic acid hydrochloride (Example 703).

The fused ring compound of the formula [I] or a pharmaceutically acceptable salt thereof, which is selected from the group consisting of
2-{4-[2-(4-chlorophenyl)-5-(4-oxopiperidinocarbonyl)-benzyloxy]phenyl}-1-cyclohexylbenzimidazole-5-carboxylic acid hydrochloride (Example 328),
2-{4-[2-(4-chlorophenyl)-5-hydroxybenzyloxy]phenyl}-1-cyclohexylbenzimidazole-5-carboxylic acid hydrochloride (Example 329),
2-{4-[2-(4-chlorophenyl)-5-(isopropylcarbamoyl) benzyloxy]phenyl}-1-cyclohexylbenzimidazole-5-carboxylic acid hydrochloride (Example 330),
2-{4-[2-(4-chlorophenyl)-5-(N-isopropyl-N-methylcarbamoyl)-benzyloxy]phenyl}-1-cyclohexylbenzimidazole-5-carboxylic acid hydrochloride (Example 331),
2-{4-[2-(4-chlorophenyl)-5-(phenylcarbamoyl)benzyloxy] phenyl}-1-cyclohexylbenzimidazole-5-carboxylic acid hydrochloride (Example 332),
2-{4-[2-(4-chlorophenyl)-5-(4-methoxypiperidinocarbonyl)-benzyloxy]phenyl}-1-cyclohexylbenzimidazole-5-carboxylic acid hydrochloride (Example 333),
2-{4-[2-(4-chlorophenyl)-5-(3-hydroxypropyloxy) benzyloxy]phenyl}-1-cyclohexylbenzimidazole-5-carboxylic acid (Example 334),
2-{4-[2-(4-chlorophenyl)-5-(2-hydroxyethoxy)benzyloxy] phenyl}-1-cyclohexylbenzimidazole-5-carboxylic acid hydrochloride (Example 335),
methyl 2-[4-(2-bromo-5-nitrobenzyloxy)-2-fluorophenyl]-1-cyclohexylbenzimidazole-5-carboxylate (Example 336),
methyl 2-[4-{2-(4-chlorophenyl)-5-nitrobenzyloxy}-2-fluorophenyl]-1-cyclohexylbenzimidazole-5-carboxylate (Example 337),
methyl 2-[4-{5-amino-2-(4-chlorophenyl)benzyloxy}-2-fluorophenyl]-1-cyclohexylbenzimidazole-5-carboxylate (Example 338),
methyl 2-[4-{2-(4-chlorophenyl)-5-(2-oxopyrrolidin-1-yl) benzyloxy}-2-fluorophenyl]-1-cyclohexylbenzimidazole-5-carboxylate (Example 339),
2-[4-{2-(4-chlorophenyl)-5-(2-oxopyrrolidin-1-yl) benzyloxy}-2-fluorophenyl]-1-cyclohexylbenzimidazole-5-carboxylic acid hydrochloride (Example 340),
2-{4-[2-(4-chlorophenyl)-5-(4-methylpiperidin-1-ylcarbonyl)benzyloxy]phenyl}-1-cyclohexylbenzimidazole-5-carboxylic acid hydrochloride (Example 341),
2-{4-[5-acetyl-2-(4-chlorophenyl)benzyloxy]phenyl}-1-cyclohexylbenzimidazole-5-carboxylic acid hydrochloride (Example 342),
2-{4-[2-(4-chlorophenyl)-5-{(4-hydroxypiperidin-1-ylcarbonyl)-methoxy}benzyloxy]phenyl}-1-cyclohexylbenzimidazole-5-carboxylic acid (Example 343), 2-{4-[2-(4-chlorophenyl)-5-(2-methoxyethoxy)benzyloxy] phenyl}-1-cyclohexylbenzimidazole-5-carboxylic acid hydrochloride (Example 344), 2-{4-[2-(4-chlorophenyl)-5-{2-(2-methoxyethoxy)ethoxy}-benzyloxy]phenyl}-1-cyclohexylbenzimidazole-5-carboxylic acid hydrochloride (Example 345), 2-{4-[2-(4-chlorophenyl)-5-(isobutylcarbonyl)benzyloxy] phenyl}-1-cyclohexylbenzimidazole-5-carboxylic acid (Example 346), 2-{4-[2-(4-chlorophenyl)-5-(2-methylthiazol-4-yl) benzyloxy]-phenyl}-1-cyclohexylbenzimidazole-5-carboxylic acid (Example 347), 2-{4-[2-(4-chlorophenyl)-5-(3,4-dihydroxypiperidin-1-ylcarbonyl)benzyloxy]phenyl}-1-cyclohexylbenzimidazole-5-carboxylic acid hydrochloride (Example 348), 2-{4-[2-(4-chlorophenyl)-5-(3-methyl-1,2,4-oxadiazol-5-yl)benzyloxy]phenyl}-1-cyclohexylbenzimidazole-5-carboxylic acid hydrochloride (Example 349), 2-{4-[2-(4-chlorophenyl)-4-(isopropylcarbamoyl) benzyloxy]phenyl}-1-cyclohexylbenzimidazole-5-carboxylic acid hydrochloride (Example 350), 2-{4-[2-(4-chlorophenyl)-4-(piperidinocarbonyl) benzyloxy]phenyl}-1-cyclohexylbenzimidazole-5-carboxylic acid hydrochloride (Example 351), 2-{4-[2-(4-chlorophenyl)-5-{(1-hydroxy-2-methylpropan-2-yl)carbamoyl}benzyloxy]phenyl}-1-cyclohexylbenzimidazole-5-carboxylic acid hydrochloride (Example 352), 2-{4-[2-(4-chlorophenyl)-5-(4,4-dimethyl-2-oxazolin-2-yl)}benzyloxy]phenyl}-1-cyclohexylbenzimidazole-5-carboxylic acid dihydrochloride (Example 353), 2-{4-[2-(4-chlorophenyl)-4-(4-hydroxypiperidin-1-ylcarbonyl)benzyloxy]phenyl}-1-cyclohexylbenzimidazole-5-carboxylic acid hydrochloride (Example 354), 2-{4-[2-(4-chlorophenyl)-4-{(2-hydroxyethyl)carbamoyl}-benzyloxy]phenyl}-1-cyclohexylbenzimidazole-5-carboxylic acid hydrochloride (Example 355), 2-{4-[2-(4-chlorophenyl)-4-{(4-pyridylmethyl)carbamoyl}-benzyloxy]phenyl}-1-cyclohexylbenzimidazole-5-carboxylic acid (Example 356), 2-{4-[2-(4-chlorophenyl)-4-(dimethylcarbamoyl) benzyloxy]phenyl}-1-cyclohexylbenzimidazole-5-carboxylic acid hydrochloride (Example 357), 2-{4-[5-(2-aminothiazol-4-yl)-2-(4-chlorophenyl) benzyloxy]-phenyl}-1-cyclohexylbenzimidazole-5-carboxylic acid dihydrochloride (Example 358), 2-{4-[2-(4-chlorophenyl)-5-(4-hydroxypiperidin-1-ylsulfonyl)benzyloxy]phenyl}-1-cyclohexylbenzimidazole-5-carboxylic acid hydrochloride (Example 359), 2-{4-[5-(dimethylcarbamoyl)-2-(4-fluorophenyl) benzyloxy]phenyl}-1-cyclohexylbenzimidazole-5-carboxylic acid hydrochloride (Example 360), 2-{4-[5-(dimethylcarbamoyl)-2-(3-fluorophenyl) benzyloxy]phenyl}-1-cyclohexylbenzimidazole-5-carboxylic acid hydrochloride (Example 361), 2-{4-[2-(5-chlorothiophen-2-yl)-5-(dimethylcarbamoyl) benzyloxy]-phenyl}-1-cyclohexylbenzimidazole-5-carboxylic acid hydrochloride (Example 362), 2-{4-[2-bromo-5-(5-methyloxazol-2-yl)benzyloxy] phenyl}-1-cyclohexylbenzimidazole-5-carboxylic acid hydrochloride (Example 363), 2-{4-[2-bromo-5-(5-methylthiazol-2-yl)benzyloxy] phenyl}-1-cyclohexylbenzimidazole-5-carboxylic acid hydrochloride (Example 364), 2-{4-[2-(4-chlorophenyl)-5-(5-methyloxazol-2-yl) benzyloxy]-phenyl}-1-cyclohexylbenzimidazole-5-carboxylic acid hydrochloride (Example 365), 2-{4-[2-(4-chlorophenyl)-5-(5-methylthiazol-2-yl) benzyloxy]-phenyl}-1-cyclohexylbenzimidazole-5-carboxylic acid hydrochloride (Example 366), 2-{4-[2-(4-chlorophenyl)-5-tetrazol-5-ylbenzyloxy] phenyl}-1-cyclohexylbenzimidazole-5-carboxylic acid hydrochloride (Example 367), 2-{4-[5-chloro-2-(4-cyanophenyl)benzyloxyphenyl]-1-cyclohexylbenzimidazole-5-carboxylic acid hydrochloride (Example 368), 2-{4-[5-chloro-2-(4-tetrazol-5-ylphenyl)benzyloxy] phenyl}-1-cyclohexylbenzimidazole-5-carboxylic acid hydrochloride (Example 369), 2-{4-[2-(4-chlorophenyl)-5-{2-(4-hydroxypiperidin-1-yl) ethoxy}benzyloxy]phenyl}-1-cyclohexylbenzimidazole-5-carboxylic acid hydrochloride (Example 370), 2-{4-[2-(4-chlorophenyl)-5-(2-oxopiperidin-1-yl) benzyloxy]-2-fluorophenyl}-1-cyclohexylbenzimidazole-5-carboxylic acid hydrochloride (Example 371), 2-{4-[3-(4-chlorophenyl)-5-(dimethylcarbamoyl) benzyloxy]-2-fluorophenyl}-1-cyclohexylbenzimidazole-5-carboxylic acid hydrochloride (Example 372), 2-{4-[2-(4-chlorophenyl)-5-(N-hydroxyamidino) benzyloxy]-2-fluorophenyl}-1-cyclohexylbenzimidazole-5-carboxylic acid dihydrochloride (Example 373), 2-{4-[2-(4-chlorophenyl)-5-(2,5-dihydro-5-oxo-4H-1,2,4-oxadiazol-3-yl)benzyloxy]-2-fluorophenyl}-1-cyclohexylbenzimidazole-5-carboxylic acid hydrochloride (Example 374), 2-{4-[2-(4-chlorophenyl)-5-(2-oxo-3H-1,2,3,5-oxathiadiazol-4-yl) benzyloxy]-2-fluorophenyl}-1-cyclohexylbenzimidazole-5-carboxylic acid hydrochloride (Example 375), 2-{4-[2-(4-chlorophenyl)-5-(2,5-dihydro-5-oxo-4H-1,2,4-thiadiazol-3-yl)benzyloxy]-2-fluorophenyl}-1-cyclohexylbenzimidazole-5-carboxylic acid hydrochloride (Example 376), 2-{4-[2-(4-chlorophenyl)-5-(cyclopropylcarbamoyl) benzyloxy]-2-fluorophenyl}-1-cyclohexylbenzimidazole-5-carboxylic acid hydrochloride (Example 377), 2-{4-[2-(4-chlorophenyl)-5-(cyclobutylcarbamoyl) benzyloxy]-2-fluorophenyl}-1-cyclohexylbenzimidazole-5-carboxylic acid hydrochloride (Example 378), 2-{4-[2-(4-chlorophenyl)-5-(tert-butylcarbamoyl) benzyloxy]-2-fluorophenyl}-1-cyclohexylbenzimidazole-5-carboxylic acid hydrochloride (Example 379), 2-{4-[2-(4-chlorophenyl)-5-(isobutylcarbamoyl) benzyloxy]-2-fluorophenyl}-1-cyclohexylbenzimidazole-5-carboxylic acid hydrochloride (Example 380), 2-{4-[2-(4-chlorophenyl)-5-{(1-hydroxypropan-2-yl) carbamoyl}-benzyloxy]-2-fluorophenyl}-1-cyclohexylbenzimidazole-5-carboxylic acid hydrochloride (Example 381), 2-{4-[2-(4-chlorophenyl)-5-(methoxycarbamoyl) benzyloxy]-2-fluorophenyl}-1-cyclohexylbenzimidazole-5-carboxylic acid hydrochloride (Example 382), 2-{4-[2-(4-chlorophenyl)-5-{(2,3-dihydroxypropyl) carbamoyl}-benzyloxy]-2-fluorophenyl}-1- cyclohexylbenzimidazole-5-carboxylic acid hydrochloride (Example 383),
2-{4-[2-(4-chlorophenyl)-5-(N-ethyl-N-methylcarbamoyl)benzyloxy]-2-fluorophenyl}-1-cyclohexylbenzimidazole-5-carboxylic acid hydrochloride (Example 384),
2-{4-[2-(4-chlorophenyl)-5-(N-methyl-N-propylcarbamoyl)-benzyloxy]-2-fluorophenyl}-1-cyclohexylbenzimidazole-5-carboxylic acid hydrochloride (Example 385),
2-{4-[2-(4-chlorophenyl)-5-(N-isopropyl-N-methylcarbamoyl)-benzyloxy]-2-fluorophenyl}-1-cyclohexylbenzimidazole-5-carboxylic acid hydrochloride (Example 386),
2-{4-[2-(4-chlorophenyl)-5-(2,6-dimethylpiperidin-1-ylcarbonyl)-benzyloxy]-2-fluorophenyl}-1-cyclohexylbenzimidazole-5-carboxylic acid hydrochloride (Example 387),
2-{4-[5-(butylcarbamoyl)-2-(4-chlorophenyl)benzyloxy]-2-fluorophenyl}-1-cyclohexylbenzimidazole-5-carboxylic acid hydrochloride (Example 388),
2-{4-[2-(4-chlorophenyl)-5-(propylcarbamoyl)benzyloxy]-2-fluorophenyl}-1-cyclohexylbenzimidazole-5-carboxylic acid hydrochloride (Example 389),
2-{4-[2-(4-chlorophenyl)-5-(ethylcarbamoyl)benzyloxy]-2-fluorophenyl}-1-cyclohexylbenzimidazole-5-carboxylic acid hydrochloride (Example 390),
2-{4-[2-(4-chlorophenyl)-5-{(dimethylcarbamoyl)amino}benzyloxy]-2-fluorophenyl}-1-cyclohexylbenzimidazole-5-carboxylic acid hydrochloride (Example 391),
2-{4-[2-(4-chlorophenyl)-5-{(morpholinocarbonyl)amino}benzyloxy]-2-fluorophenyl}-1-cyclohexylbenzimidazole-5-carboxylic acid hydrochloride (Example 392),
2-{4-[2-(4-chlorophenyl)-5-ureidobenzyloxy]-2-fluorophenyl}-1-cyclohexylbenzimidazole-5-carboxylic acid hydrochloride (Example 393),
2-{4-[2-(4-chlorophenyl)-5-{(ethylcarbamoyl)amino}benzyloxy]-2-fluorophenyl}-1-cyclohexylbenzimidazole-5-carboxylic acid hydrochloride (Example 394),
2-{4-[2-(4-chlorophenyl)-5-{(isopropylcarbamoyl)amino}benzyloxy]-2-fluorophenyl}-1-cyclohexylbenzimidazole-5-carboxylic acid hydrochloride (Example 395),
2-{4-[2-(3,4-difluorophenyl)-5-(isopropylcarbamoyl)benzyloxy]-2-fluorophenyl}-1-cyclohexylbenzimidazole-5-carboxylic acid (Example 396),
2-{4-[2-(2,4-difluorophenyl)-5-(isopropylcarbamoyl)benzyloxy]-2-fluorophenyl}-1-cyclohexylbenzimidazole-5-carboxylic acid hydrochloride (Example 397),
2-{4-[2-(3,5-dichlorophenyl)-5-(isopropylcarbamoyl)benzyloxy]-2-fluorophenyl}-1-cyclohexylbenzimidazole-5-carboxylic acid hydrochloride (Example 398),
2-{4-[2-(3-chloro-4-fluorophenyl)-5-(isopropylcarbamoyl)-benzyloxy]-2-fluorophenyl}-1-cyclohexylbenzimidazole-5-carboxylic acid hydrochloride (Example 399),
2-{4-[2-(3,4-dichlorophenyl)-5-(isopropylcarbamoyl)benzyloxy]-2-fluorophenyl}-1-cyclohexylbenzimidazole-5-carboxylic acid hydrochloride (Example 400),
2-{4-[2-(4-chloro-2-fluorophenyl)-5-(isopropylcarbamoyl)-benzyloxy]-2-fluorophenyl}-1-cyclohexylbenzimidazole-5-carboxylic acid hydrochloride (Example 401),
2-{4-[2-(4-chloro-2-fluorophenyl)-5-(pyrrolidin-1-ylcarbonyl)-benzyloxy]-2-fluorophenyl}-1-cyclohexylbenzimidazole-5-carboxylic acid hydrochloride (Example 402),
2-{4-[2-(4-chloro-3-fluorophenyl)-5-(pyrrolldin-1-ylcarbonyl)-benzyloxy]-2-fluorophenyl}-1-cyclohexylbenzimidazole-5-carboxylic acid hydrochloride (Example 403),
2-{4-[2-(4-chloro-3-fluorophenyl)-5-(isopropylcarbamoyl)-benzyloxy]-2-fluorophenyl}-1-cyclohexylbenzimidazole-5-carboxylic acid hydrochloride (Example 404),
2-{4-[2-{4-(methylthio)phenyl}-5-(2-oxopyrrolidin-1-yl)benzyloxy]-2-fluorophenyl}-1-cyclohexylbenzimidazole-5-carboxylic acid hydrochloride (Example 405),
2-{4-[2-{4-(methylthio)phenyl}-5-(isopropylcarbamoyl)benzyloxy]-2-fluorophenyl}-1-cyclohexylbenzimidazole-5-carboxylic acid hydrochloride (Example 406),
2-{4-[4-chloro-2-(4-chlorophenyl)-5-(1,1-dioxoisothiazolidin-2-yl)benzyloxy]-2-fluorophenyl}-1-cyclohexylbenzimidazole-5-carboxylic acid hydrochloride (Example 407),
2-{4-[4-chloro-2-(4-chlorophenyl)-5-(2-oxopyrrolidin-1-yl)benzyloxy]-2-fluorophenyl}-1-cyclohexylbenzimidazole-5-carboxylic acid hydrochloride (Example 408),
2-{4-[2-(4-chlorophenyl)-5-(isopropylaminosulfonyl)benzyloxy]-2-fluorophenyl}-1-cyclohexylbenzimidazole-5-carboxylic acid hydrochloride (Example 409),
2-{4-[2-(4-chlorophenyl)-5-(dimethylcarbamoyl)benzyloxy]-2-fluorophenyl}-1-cyclopentylbenzimidazole-5-carboxylic acid hydrochloride (Example 410),
2-{4-[2-(4-chlorophenyl)-5-(4-hydroxypiperidin-1-ylcarbonyl)-benzyloxy]-2-fluorophenyl}-1-cyclopentylbenzimidazole-5-carboxylic acid hydrochloride (Example 411),
2-{4-[2-(4-chlorophenyl)-5-(isopropylcarbamoyl)benzyloxy]-2-fluorophenyl}-1-cyclopentylbenzimidazole-5-carboxylic acid hydrochloride (Example 412),
2-{4-[2-(4-chlorophenyl)-5-(isopropylcarbamoyl)benzyloxy]phenyl}-1-cyclopentylbenzimidazole-5-carboxylic acid hydrochloride (Example 413),
2-{4-[2-(4-chlorophenyl)-5-(dimethylcarbamoyl)benzyloxy]phenyl}-1-cyclopentylbenzimidazole-5-carboxylic acid hydrochloride (Example 414),
2-{4-[2-(4-chlorophenyl)-5-(4-hydroxypiperidin-1-ylcarbonyl)benzyloxy]phenyl}-1-cyclopentylbenzimidazole-5-carboxylic acid hydrochloride (Example 415),
2-{4-[2-(4-chlorophenyl)-5-(isopropylcarbamoyl)benzyloxy]phenyl}-1-(tetrahydrothiopyran-4-yl)benzimidazole-5-carboxylic acid hydrochloride (Example 416),
2-{4-[2-(4-chlorophenyl)-5-(pyrrolidin-1-ylcarbonyl)benzyloxy]-phenyl}-1-(tetrahydrothiopyran-4-yl)benzimidazole-5-carboxylic acid hydrochloride (Example 417),
2-{4-[2-(4-chlorophenyl)-5-(isopropylcarbamoyl)benzyloxy]-2-fluorophenyl}-1-(tetrahydrothiopyran-4-yl)benzimidazole-5-carboxylic acid hydrochloride (Example 418), 2-{4-[2-(4-chlorophenyl)-5-(2-oxopyrrolidin-1-yl) benzyloxy]-2-fluorophenyl}-1-(tetrahydrothiopyran-4-yl)benzimidazole-5-carboxylic acid hydrochloride (Example 419), 2-{4-[2-(4-chlorophenyl)-5-(isopropylcarbamoyl) benzyloxy]-2-fluorophenyl}-1-piperidinobenzimidazole-5-carboxylic acid hydrochloride (Example 420), 2-{4-[2-(4-chlorophenyl)-5-(pyrrolidin-1-ylcarbonyl) benzyloxy]-2-fluorophenyl}-1-piperidinobenzimidazole-5-carboxylic acid (Example 421), 2-{4-[2-(4-chlorophenyl)-5-(2-imidazolin-2-yl)benzyloxy]-2-fluorophenyl}-1-cyclohexylbenzimidazole-5-carboxylic acid dihydrochloride (Example 422), 2-{4-[2-(4-chlorophenyl)-5-(2-oxooxazolidin-3-yl) benzyloxy]-2-fluorophenyl}-1-cyclohexylbenzimidazole-5-carboxylic acid hydrochloride (Example 423), 2-{4-[2-(4-chlorophenyl)-5-(2-oxoimidazolidin-1-yl) benzyloxy]-2-fluorophenyl}-1-cyclohexylbenzimidazole-5-carboxylic acid hydrochloride (Example 424), 2-{4-[2-(4-chlorophenyl)-5-(2-oxazolin-2-ylamino) benzyloxy]-2-fluorophenyl}-1-cyclohexylbenzimidazole-5-carboxylic acid dihydrochloride (Example 425), 2-{4-[{2-[{(dimethylcarbamoyl)methoxy}methyl]-4-(4-fluorophenyl)thiazol-5-yl}methoxy]phenyl}-1-cyclohexylbenzimidazole-5-carboxylic acid hydrochloride (Example 426), 2-{4-[{4-(4-fluorophenyl)-2-(4-hydroxypiperidin-1-ylmethyl)thiazol-5-yl}methoxy]phenyl}-1-cyclohexylbenzimidazole-5-carboxylic acid dihydrochloride (Example 427), 2-{4-[{4-(4-fluorophenyl)-2-[(carbamoylmethoxy)methyl] thiazol-5-yl}methoxy]phenyl}-1-cyclohexylbenzimidazole-5-carboxylic acid hydrochloride (Example 428), 2-{4-[{4-(4-fluorophenyl)-2-(methylcarbamoyl)thiazol-5-yl}methoxy]-2-fluorophenyl}-1-cyclohexylbenzimidazole-5-carboxylic acid hydrochloride (Example 429), 2-{4-[{4-(4-fluorophenyl)-2-{(2-hydroxyethyl) carbamoyl}thiazol-5-yl}methoxy]-2-fluorophenyl}-1-cyclohexylbenzimidazole-5-carboxylic acid hydrochloride (Example 430), 2-{4-[{2-(4-fluorophenyl)-5-(dimethylcarbamoyl)thiophen-3-yl}methoxy]-2-fluorophenyl}-1-cyclohexylbenzimidazole-5-carboxylic acid hydrochloride (Example 431), 2-{4-[{2-(4-fluorophenyl)-5-(isopropylcarbamoyl) thiophen-3-yl}methoxy]-2-fluorophenyl}-1-cyclohexylbenzimidazole-5-carboxylic acid hydrochloride (Example 432), 2-{4-[{2-(4-fluorophenyl)-5-(4-hydroxypiperidin-1-ylcarbonyl)thiophen-3-yl}methoxy]-2-fluorophenyl}-1-cyclohexylbenzimidazole-5-carboxylic acid hydrochloride (Example 433), 2-{4-[2-(4-chlorophenyl)-5-(dimethylcarbamoyl) benzyloxy]-2-fluorophenyl}-1-cyclohexyl-5-tetrazol-5-ylbenzimidazole (Example 434), 2-{4-[2-(4-carboxyphenyl)-5-chlorobenzyloxy]-2-fluorophenyl}-1-cyclohexyl-5-tetrazol-5-ylbenzimidazole hydrochloride (Example 435), 2-{4-[2-(4-chlorophenyl)-5-(isopropylcarbamoyl) benzyloxy]-2-fluorophenyl}-1-cyclohexyl-5-(2,5-dihydro-5-oxo-4H-1,2,4-oxadiazol-3-yl)benzimidazole hydrochloride (Example 436), 2-{4-[5-carboxy-2-(4-chlorophenyl)benzyloxy]-2-fluorophenyl}-5-cyano-1-cyclohexylbenzimidazole (Example 437), 2-{4-[2-(4-chlorophenyl)-5-(dimethylcarbamoyl) benzyloxy]-2-fluorophenyl}-5-cyano-1-cyclohexylbenzimidazole (Example 438), 2-{4-[{N-(4-dimethylcarbamoyl)-N-(4-fluorophenyl) amino}-methyl]phenyl}-1-cyclohexylbenzimidazole-5-carboxylic acid (Example 439), 2-{5-[bis(3-fluorophenyl)methyl]-2-fluoro-4-hydroxyphenyl}-1-cyclohexylbenzimidazole-5-carboxylic acid (Example 440), 2-{3-[bis(3-fluorophenyl)methyl]-2-fluoro-4-hydroxyphenyl}-1-cyclohexylbenzimidazole-5-carboxylic acid (Example 441), 2-{4-[(3-dimethylcarbamoylphenyl) (4-fluorophenyl) methoxy]-2-fluorophenyl}-1-cyclohexylbenzimidazole-5-carboxylic acid hydrochloride (Example 442), 2-{4-[{3-(4-hydroxypiperidyl-1-ylcarbonyl)phenyl}(4-fluorophenyl)methoxy]-2-fluorophenyl}-1-cyclohexylbenzimidazole-5-carboxylic acid hydrochloride (Example 443), 1-{[2-{4-([4-(4-fluorophenyl)-2-methylthiazol-5-yl] methoxy)phenyl}-1-cyclohexylbenzimidazol-5-yl] carbonyl}-β-D-glucuronic acid (Example 444), {[2-{4-[bis(3-fluorophenyl)methoxy]-2-fluorophenyl}-1-cyclohexylbenzimidazol-5-yl]carbonyl}-β-D-glucuronic acid (Example 445), 2-{4-[2-(4-chlorophenyl)-5-(1,1-dioxoisothiazolidin-2-yl) benzyloxy]-2-fluorophenyl}-1-cyclohexylbenzimidazole-5-carboxylic acid hydrochloride (Example 446), 3-{[4-(5-aminosulfonyl-1-cyclohexylbenzimidazol-2-yl)-3-fluorophenoxy]methyl}-4-(4-chlorophenyl)-N-isopropylbenzamide (Example 447), 2-[4-{2-(4-chlorophenyl)-6-(isopropylaminocarbonyl) benzyloxy}-2-fluorophenyl]-1-cyclohexylbenzimidazole-5-carboxylic acid hydrochloride (Example 448), 2-[4-{2-(4-chlorophenyl)-4-fluoro-5-(1,1-dioxoisothiazolidin-2-yl)benzyloxy}-2-fluorophenyl]-1-cyclohexylbenzimidazole-5-carboxylic acid hydrochloride (Example 449), 2-[4-{2-(4-chlorophenyl)-5-(isopropylaminocarbonyl) benzyloxy}-2-fluorophenyl]-1-cyclohexyl-4-methoxybenzimidazole-5-carboxylic acid hydrochloride (Example 450), 2-[4-{2-(4-chlorophenyl)-5-(N-isopropylcarbonyl-N-methylamino)benzyloxy}-2-fluorophenyl]-1-cyclohexylbenzimidazole-5-carboxylic acid hydrochloride (Example 451), 2-[4-{2-(4-chlorophenyl)-5-(isopropylcarbonylamino) benzyloxy}-2-fluorophenyl]-1-cyclohexylbenzimidazole-5-carboxylic acid hydrochloride (Example 452), 2-{3-{[4-(4-fluorophenyl)-2-methylthiazol-5-yl]methyl}-4-hydroxyphenyl]-1-cyclohexylbenzimidazole-5-carboxylic acid (Example 453), 2-[4-{2-(4-chlorophenyl)-4-fluoro-5-(2-oxopyrrolidin-1-yl) benzyloxy}-2-fluorophenyl]-1-cyclohexylbenzimidazole-5-carboxylic acid hydrochloride (Example 454), 2-[4-{2-(4-chlorophenyl)-5-(methylsulfonylamino) benzyloxy}-2-fluorophenyl]-1-cyclohexylbenzimidazole-5-carboxylic acid hydrochloride (Example 455), 2-[4-(2-{4-chlorophenyl)-5-[N-methyl-N-(methylsulfonyl) amino]benzyloxy}-2-fluorophenyl]-1- cyclohexylbenzimidazole-5-carboxylic acid hydrochloride (Example 456),
2-[4-{[3-(4-chlorophenyl)-6-(2-oxopyrrolidin-1-yl)pyridin-2-yl]methyloxy}-2-fluorophenyl]-1-cyclohexylbenzimidazole-5-carboxylic acid hydrochloride (Example 457),
2-[4-{2-(4-chlorophenyl)-5-(acetylamino)benzyloxy}-2-fluorophenyl]-1-cyclohexylbenzimidazole-5-carboxylic acid hydrochloride (Example 458),
2-[4-{2-(4-chlorophenyl)-5-(N-acetyl-N-ethylamino)benzyloxy}-2-fluorophenyl]-1-cyclohexylbenzimidazole-5-carboxylic acid hydrochloride (Example 459),
2-[4-{2-(4-chlorophenyl)-5-(N-acetyl-N-propylamino)benzyloxy}-2-fluorophenyl]-1-cyclohexylbenzimidazole-5-carboxylic acid hydrochloride (Example 460),
2-[4-{2-(4-chlorophenyl)-5-[N-ethyl-N-(methylsulfonyl)amino]-benzyloxy}-2-fluorophenyl]-1-cyclohexylbenzimidazole-5-carboxylic acid hydrochloride (Example 461),
2-[4-{2-(4-chlorophenyl)-5-[N-(methylsulfonyl)-N-propylamino]benzyloxy}-2-fluorophenyl]-1-cyclohexylbenzimidazole-5-carboxylic acid hydrochloride (Example 462),
2-[4-{2-(4-chlorophenyl)-5-(N-acetyl-N-methylamino)benzyloxy}-2-fluorophenyl]-1-cyclohexylbenzimidazole-5-carboxylic acid hydrochloride (Example 463),
2-[4-{2-(4-chlorophenyl)-5-[N-(ethylsulfonyl)-N-methylamino]-benzyloxy}-2-fluorophenyl]-1-cyclohexylbenzimidazole-5-carboxylic acid hydrochloride (Example 464),
2-[4-{2-(4-chlorophenyl)-5-[N-ethyl-N-(ethylsulfonyl)amino]-benzyloxy}-2-fluorophenyl]-1-cyclohexylbenzimidazole-5-carboxylic acid hydrochloride (Example 465),
2-[4-{2-(4-chlorophenyl)-5-[N-(ethylcarbonyl)-N-methylamino]-benzyloxy}-2-fluorophenyl]-1-cyclohexylbenzimidazole-5-carboxylic acid hydrochloride (Example 466),
2-[4-{2-(4-chlorophenyl)-5-[N-ethyl-N-(ethylcarbonyl)amino]-benzyloxy}-2-fluorophenyl]-1-cyclohexylbenzimidazole-5-carboxylic acid hydrochloride (Example 467),
2-[4-{2-(4-chlorophenyl)-5-methoxybenzyloxy}-2-fluorophenyl]-1-cyclohexylbenzimidazole-5-carboxylic acid (Example 468),
2-[4-{2-(4-chlorophenyl)-5-(N-acetyl-N-isopropylamino)-benzyloxy}-2-fluorophenyl]-1-cyclohexylbenzimidazole-5-carboxylic acid hydrochloride (Example 469),
{[2-{4-[2-(4-chlorophenyl)-5-(2-oxopyrrolidin-1-yl)benzyloxy]-2-fluorophenyl}-1-cyclohexylbenzoimidazol-5-yl]carbonyl-β-D-glucuronic acid (Example 470),
2-{4-[2-(4-chlorophenyl)-5-(isopropylcarbamoyl)benzyloxy]phenyl}-3-cyclohexyl-3H-dimidazo[4,5-b]pyridine-6-carboxylic acid hydrochloride (Example 702), and
2-{4-[2-(4-chlorophenyl)-5-(pyrrolidin-1-ylcarbonyl)benzyloxy]-phenyl}-3-cyclohexyl-3H-imidazo[4,5-b]pyridine-6-carboxylic acid hydrochloride (Example 703).

A pharmaceutical composition comprising a fused ring compound of any of (29) to (62) above, or a pharmaceutically acceptable salt thereof, and a pharmaceutically acceptable carrier.

A hepatitis C virus polymerase inhibitor comprising a fused ring compound of any of (1) to (28) and (29) to (62) above, or a pharmaceutically acceptable salt thereof, and a pharmaceutically acceptable carrier.

An anti-hepatitis C virus agent comprising a fused ring compound of any of (1) to (28) and (29) to (62) above, or a pharmaceutically acceptable salt thereof, and a pharmaceutically acceptable carrier.

A therapeutic agent for hepatitis C comprising a fused ring compound of any of (29) to (62) above, or a pharmaceutically acceptable salt thereof, and a pharmaceutically acceptable carrier.

An anti-hepatitis C virus agent comprising (a) the anti-hepatitis C virus agent of (65) above and (b) at least one agent selected from the group consisting of a different antiviral agent, an antiinflammatory agent and an immunostimulant.

An anti-hepatitis C virus agent comprising (a) the anti-hepatitis C virus agent of (65) above and (b) interferon.

A therapeutic agent for hepatitis C comprising (a) the hepatitis C virus polymerase inhibitor of (64) above and (b) at least one agent selected from the group consisting of a different antiviral agent, an antiinflammatory agent and an immunostimulant.

A therapeutic agent for hepatitis C comprising (a) the hepatitis C virus polymerase inhibitor of (64) above and (b) interferon.

A benzimidazole compound of the folllowing formula [III]

[III]

wherein $R^{a36}$ is hydrogen atom or carboxyl-protecting group, $R^{a37}$ is cyclopentyl or cyclohexyl, and $R^{a38}$ is hydrogen atom or fluorine atom, or a salt thereof.

A thiazole compound selected from the group consisting of 4-(4-fluorophenyl)-5-hydroxymethyl-2-methylthiazole and 4-(4-fluorophenyl)-5-chloromethyl-2-methylthiazole, or a pharmaceutically acceptable salt thereof.

A biphenyl compound selected from the group consisting of 1-(4'-chloro-2-hydroxymethyl-biphenyl-4-yl)-2-pyrrolidinone and 1-(4'-chloro-2-chloromethyl-biphenyl-4-yl)-2-pyrrolidinone, or a pharmaceutically acceptable salt thereof.

A pharmaceutical composition comprising (a) a fused ring compound of the formula [I] of (1) above or a pharmaceutically acceptable salt thereof and (b) at least one agent selected from the group consisting of an antiviral agent other than the compound of (1) above, an antiinflammatory agent and an immunostimulant.

A pharmaceutical composition comprising (a) a fused ring compound of the formula [I] of (1) above or a pharmaceutically acceptable salt thereof and (b) interferon.

A method for treating hepatitis C, which comprises administering an effective amount of a fused ring compound of the formula [I] of (1) above or a pharmaceutically acceptable salt thereof.

The method of (76) above, further comprising administering an effective amount of at least one agent selected from the group consisting of an antiviral agent other than the compound of claim 1, an antiinflammatory agent and an immunostimulant.

The method of (76) above, further comprising administering an effective amount of interferon.

A method for inhibiting hepatitis C virus polymerase, which comprises administering an effective amount of a fused ring compound of the formula [I] of (1) above or a pharmaceutically acceptable salt thereof.

The method of (79) above, further comprising administering an effective amount of at least one agent selected from the group consisting of an antiviral agent other than the compound of (1) above, an antiinflammatory agent and an immunostimulant.

The method of (79) above, further comprising administering an effective amount of interferon.

Use of a fused ring compound of the formula [I] of (1) above or a pharmaceutically acceptable salt thereof for the production of a pharmaceutical agent for treating hepatitis C.

Use of a fused ring compound of the formula [I] of (1) above or a pharmaceutically acceptable salt thereof for the production of a hepatitis C virus polymerase inhibitor.

A pharmaceutical composition for the treatment of hepatitis C, which comprises a fused ring compound of the formula [I] of (1) above or a pharmaceutically acceptable salt thereof, and a pharmaceutically acceptable carrier.

A pharmaceutical composition for inhibiting hepatitis C virus polymerase, which comprises a fused ring compound of the formula [I] of (1) above or a pharmaceutically acceptable salt thereof, and a pharmaceutically acceptable carrier.

A commercial package comprising a pharmaceutical composition of (84) above and a written matter associated therewith, the written matter stating that the pharmaceutical composition can or should be used for treating hepatitis C.

A commercial package comprising a pharmaceutical composition of (85) above and a written matter associated therewith, the written matter stating that the pharmaceutical composition can or should be used for inhibiting hepatitis C virus polymerase.

1-Cyclohexyl-2-(3-furanyl)-1H-benzimidazole-5-carboxylic acid (Example 471).

DETAILED DESCRIPTION OF THE INVENTION

The definitions of respective substituents and moieties used in the present specification are as follows.

The halogen atom is a fluorine atom, chlorine atom, is bromine atom or iodine atom, preferably fluorine atom, chlorine atom or bromine atom.

Particularly preferably, the halogen atom is fluorine atom at $R^5$, $R^{5'}$, $R^6$, $R^{6'}$, group A and group C, and fluorine atom or chlorine atom at X, Z, Z', group B and group D.

The $C_{1-6}$ alkyl is straight chain or branched chain alkyl having 1 to 6 carbon atoms, and is exemplified by methyl, ethyl, propyl, isopropyl, butyl, isobutyl, sec-butyl, tert-butyl, pentyl, isopentyl, tert-pentyl, hexyl and the like.

Preferably, it is straight chain or branched chain alkyl having 1 to 4 carbon atoms, and is particularly preferably methyl at $R^{a7}$, $R^{a8}$, $R^{a9}$, $R^{a15}$, $R^{a16}$, $R^{a17}$, $R^{a33}$, $R^{a35}$, $R^{b6}$ and $R^{b7}$ and methyl or tert-butyl at $R^{b1}$, $R^{b2}$, group B and group C, and methyl, ethyl, propyl or isopropyl at $R^{a29}$.

The halogenated $C_{1-6}$ alkyl is the above-defined $C_{1-6}$ alkyl except that it is substituted by the above-defined halogen atom. Preferably, it is halogenated alkyl wherein the alkyl moiety thereof is straight chain or branched chain alkyl having 1 to 4 carbon atoms. Examples thereof include fluoromethyl, difluoromethyl, trifluoromethyl, bromomethyl, chloromethyl, 1,2-dichloromethyl, 2,2-dichloromethyl, 2,2,2-trifluoroethyl and the like.

The halogenated $C_{1-6}$ alkyl is particularly preferably trifluoromethyl at group B.

The $C_{1-6}$ alkylene is straight chain alkylene having 1 to 6 carbon atoms, and is exemplified by methylene, ethylene, trimethylene, tetramethylene, pentamethylene or hexamethylene.

The $C_{1-6}$ alkylene is preferably methylene or ethylene at Y.

The $C_{2-6}$ alkenylene is straight chain alkenylene having 2 to 6 carbon atoms, and is exemplified by vinylene, propenylene, 1-butenylene, 1,3-butadienylene and the like.

The $C_{2-6}$ alkenylene is preferably vinylene at Y.

The $C_{1-6}$ alkoxy is alkyloxy wherein the alkyl moiety thereof is the above-defined $C_{1-6}$ alkyl. Preferably, it is alkoxy wherein the alkyl moiety thereof is straight chain or branched chain alkyl having 1 to 4 carbon atoms. Examples thereof include methoxy, ethoxy, propoxy, isopropyloxy, butoxy, isobutyloxy, tert-butyloxy, pentyloxy, hexyloxy and the like.

The $C_{1-6}$ alkoxy is particularly preferably methoxy at $R^{a2}$, $R^{a3}$, $R^{a27}$, $R^{a28}$, $R^{a33}$, group A and group C.

The $C_{1-6}$ alkoxy $C_{1-6}$ alkoxy is that wherein $C_{1-6}$ alkoxy in the above definition is substituted by $C_{1-6}$ alkoxy defined above and is preferably that wherein the alkyl moiety thereof is straight chain or branched chain alkyl having 1 to 4 carbon atoms. Specific examples include methoxymethyl, ethoxymethyl, methoxyethoxy, methoxypropoxy, isopropyloxyethoxy and the like.

The group A is particularly preferably methoxyethoxy.

The $C_{1-6}$ alkanoyl is alkylcarbonyl wherein the alkyl moiety thereof is the above-defined $C_{1-6}$ alkyl. Preferably, it is alkanoyl wherein the alkyl moiety thereof is straight chain or branched chain alkyl having 1 to 4 carbon atoms. Examples thereof include acetyl, propionyl, butyryl, isobutyryl, pivaloyl and the like.

The $C_{1-6}$ alkanoyl is particularly preferably acetyl at $R^1$, $R^2$, $R^3$, $R^4$, $R^{a5}$, $R^{a29}$, $R^{b7}$ and group B.

The $C_{1-6}$ alkoxycarbonyl is alkyloxycarbonyl wherein the alkoxy moiety thereof is the above-defined $C_{1-6}$ alkoxy. Preferably, it is alkoxycarbonyl wherein the alkyl moiety thereof is straight chain or branched chain alkyl having 1 to 4 carbon atoms. Examples thereof include methoxycarbonyl, ethoxycarbonyl, propoxycarbonyl, isopropyloxycarbonyl, butoxycarbonyl, isobutyloxycarbonyl, tert-butyloxycarbonyl, pentyloxycarbonyl, hexyloxycarbonyl and the like.

The $C_{1-6}$ alkoxycarbonyl is particularly preferably methoxycarbonyl or ethoxycarbonyl at $R^{a10}$ and group A.

The $C_{1-6}$ alkylamino is alkylamino or dialkylamino wherein the alkyl moiety thereof is the above-defined $C_{1-6}$ alkyl. Preferably, it is alkylamino or dialkylamino wherein the alkyl moiety thereof is straight chain or branched chain alkyl having 1 to 4 carbon atoms. Examples thereof include methylamino, ethylamino, propylamino, isopropylamino, butylamino, isobutylamino, tert-butylamino, pentylamino, hexylamino, dimethylamino, diethylamino, methylethylamino, N-isopropyl-N-isobutylamino and the like.

The $C_{1-6}$ alkylamino is particularly preferably methylamino at $R^{a7}$, and particularly preferably dimethylamino at $R^{a21}$ and group A, and particularly preferably dimethylamino, ethylamino or isopropylamino at $R^{a24}$.

The $C_{1-6}$ alkanoylamino is alkylcarbonylamino wherein the alkanoyl moiety thereof is the above-defined $C_{1-6}$ alkanoyl. Preferably, it is alkylcarbonylamino wherein the alkyl moiety thereof is straight chain or branched chain alkyl having 1 to 4 carbon atoms. Examples thereof include acetylamino, propionylamino, butyrylamino, isobutyrylamino, pivaloylamino and the like.

The $C_{1-6}$ alkanoylamino is particularly preferably acetylamino at X and $R^{a10}$.

The $C_{1-6}$ alkylsulfonyl is alkylsulfonyl wherein the alkyl moiety thereof is the above-defined $C_{1-6}$ alkyl. Preferably, it is alkylsulfonyl wherein the alkyl moiety thereof is straight chain or branched chain alkyl having 1 to 4 carbon atoms. Examples thereof include methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl and the like.

The $C_{1-6}$ alkylsulfonyl is particularly preferably methylsulfonyl at X and $R^{a5}$.

The $C_{6-14}$ aryl is aromatic hydrocarbon having 6 to 14 carbon atoms. Examples thereof include phenyl, naphthyl, anthryl, indenyl, azulenyl, fluorenyl, phenanthryl and the like.

The $C_{6-14}$ aryl is preferably phenyl or naphthyl, particularly preferably phenyl at the ring A, ring A', ring B and ring B'.

The $C_{3-8}$ cycloalkyl is saturated cycloalkyl having 3 to 8, preferably 5 to 7, carbon atoms. Examples thereof include cyclopropyl, cyclobutyl, cyclopentyl, cyclohexyl, cycloheptyl and cyclooctyl.

The $C_{3-8}$ cycloalkyl is particularly preferably cyclohexyl at the ring A, ring A', ring B and ring B'.

The $C_{3-8}$ cycloalkenyl is cycloalkenyl having 3 to 8, preferably 5 to 7, carbon atoms and has at least 1, preferably 1 or 2, double bond(s). Examples thereof include cyclopropenyl, cyclobutenyl, cyclopentenyl, cyclopentadienyl, cyclohexenyl, 2,4-cyclohexadien-1-yl, 2,5-cyclohexadien-1-yl, cycloheptenyl and cyclooctenyl and the like, but do not include aryl (e.g., phenyl) or completely saturated cycloalkyl.

The $C_{3-8}$ cycloalkenyl is preferably cyclohexenyl at the ring A and ring A'.

The heterocyclic group has, as an atom constituting the ring, 1 to 4 heteroatom(s) selected from an oxygen atom, a nitrogen atom and a sulfur atom, besides a carbon atom, and includes saturated ring and unsaturated ring, monocyclic ring and fused ring having the number of ring atom constituting the ring of 3 to 14.

The heterocyclic group as a moriocyclic ring includes, for example, pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isoxazolyl, thiazolyl, isothiazolyl, thiadiazolyl, pyrrolinyl, pyrrolidinyl, imidazolidinyl, piperidyl, piperazinyl, morpholinyl, thiomorpholinyl, tetrahydropyranyl and the like.

The heterocyclic group includes the groups of the following formulas.

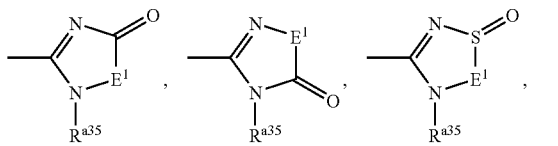

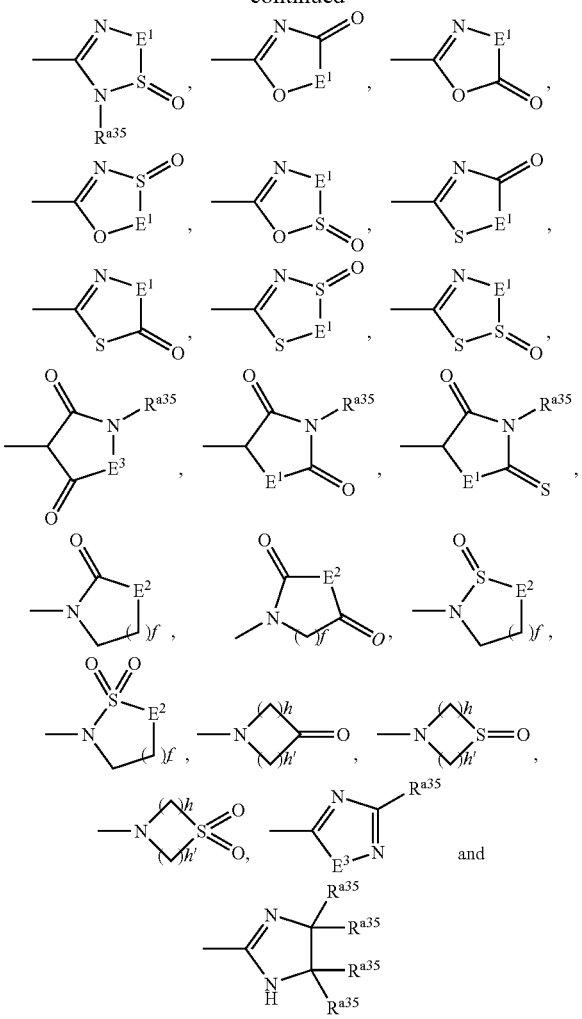

wherein $E^1$ is an oxygen atom, a sulfur atom or N(—$R^{a35}$), $E^2$ is an oxygen atom, $CH_2$ or N(—$R^{a35}$), $E^3$ is an oxygen atom or a sulfur atom, wherein $R^{a35}$ is independently hydrogen atom or $C_{1-6}$ alkyl, f is an integer of 1 to 3, and h and h' are the same or different and each is an integer of 1 to 3.

Specific examples of the heterocyclic group include

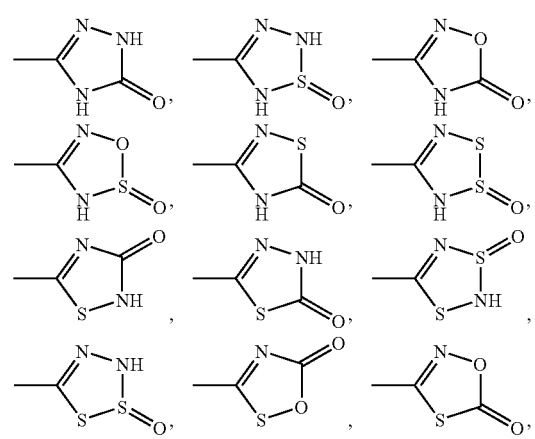

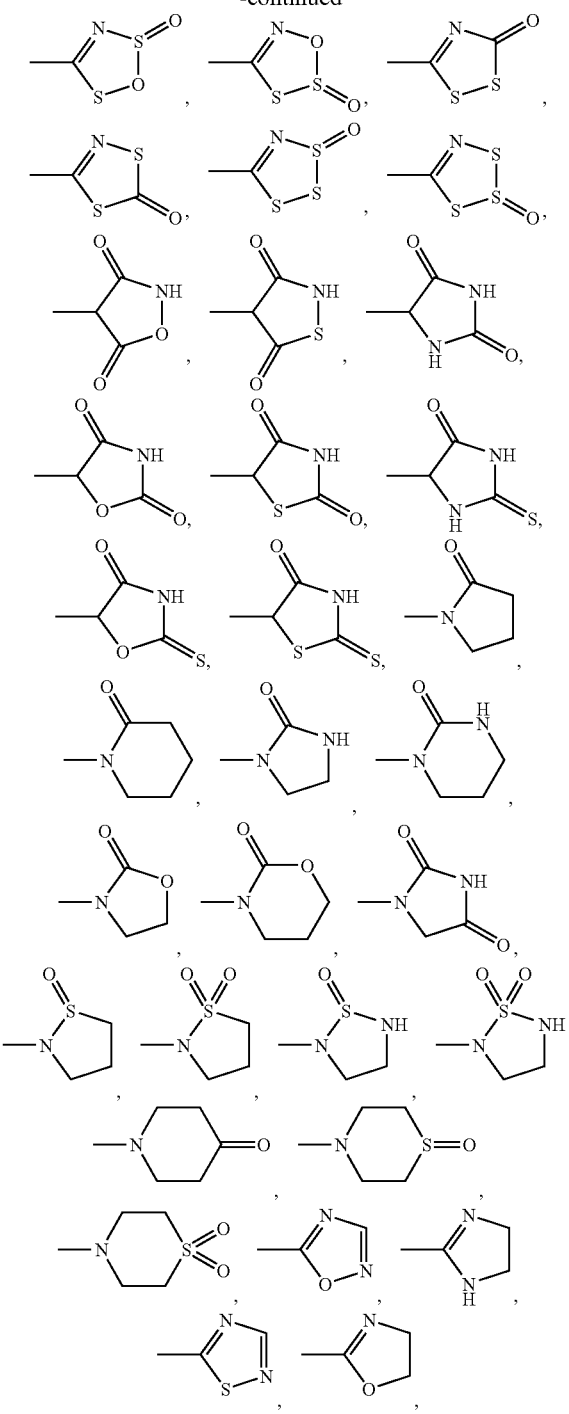

and the like.

Examples of the heterocyclic group as a fused ring include quinolyl, isoquinolyl, quinazolinyl, quinoxalyl, phthalazinyl, cinnolinyl, naphthyridinyl, 5,6,7,8-tetrahydroquinolyl, indolyl, benzimidazolyl, 2,3-dihydrobenzimidazolyl, 2,3-dihydro-2-oxobenzimidazolyl, indolinyl, benzofuranyl, benzothienyl, benzoxazolyl, benzothiazolyl and the like.

Preferably, it is a heterocyclic group which is a 5-membered or a 6-membered monocyclic group. Examples thereof include pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isoxazolyl, thiazolyl, isothiazolyl, thiadiazolyl, pyrrolidinyl, piperidyl, piperazinyl

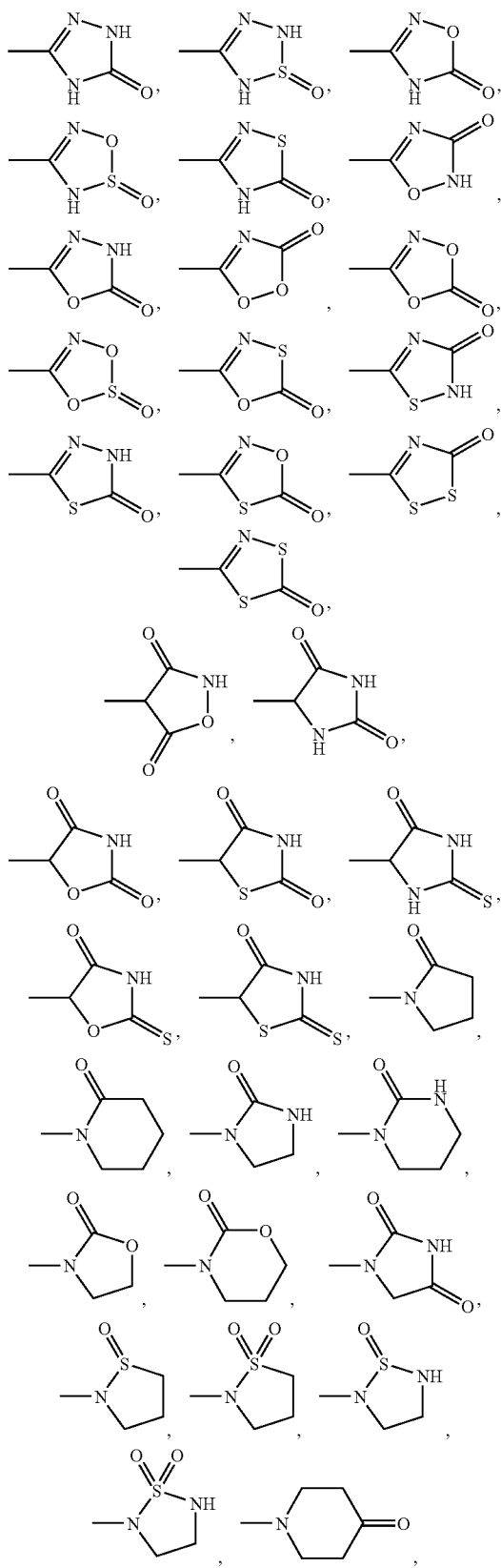

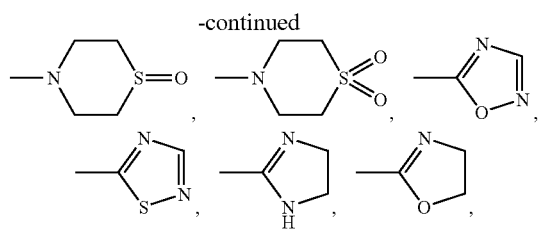

and the like.

At $R^1$, $R^2$, $R^3$, $R^4$, Z and group D, tetrazolyl and 5-oxo-$\Delta^2$-1,2,4-oxadiazolin-3-yl are particularly preferable.

The heterocyclic group is preferably pyridyl, pyrazinyl, pyrimidinyl or pyridazinyl which is an aromatic group, and particularly preferably pyridyl at the ring A and ring A'.

The heterocyclic group is particularly preferably pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isoxazolyl, thiazolyl, isothiazolyl or thiadiazolyl, which is an aromatic group, at the ring B and ring B'. More preferably it is pyridyl or thiazolyl, most preferably thiazolyl.

The $C_{6-14}$ aryl $C_{1-6}$ alkyl is arylalkyl wherein the alkyl moiety thereof is the above-defined $C_{1-6}$ alkyl and the aryl moiety is the above-defined $C_{6-14}$ aryl. Preferably, it is arylalkyl wherein the alkyl moiety thereof is straight chain alkyl having 1 to 4 carbon atoms and the aryl moiety is phenyl. Examples thereof include benzyl, phenethyl, 3-phenylpropyl, 2-phenylpropyl, 4-phenylbutyl and the like.

The $C_{6-14}$ aryl $C_{1-6}$ alkyl is particularly preferably benzyl at $R^{a8}$ and $R^{b6}$.

The glucuronic acid residue is glucuronic acid less any hydroxyl group, preferably β-D-glucuronic acid substituted at 1-position.

The $C_{6-14}$ aryl $C_{1-6}$ alkyloxycarbonyl is arylalkyloxycarbonyl wherein the $C_{6-14}$ aryl $C_{1-6}$ alkyl moiety thereof is the above-defined $C_{6-14}$ aryl $C_{1-6}$ alkyl. Preferably, it is arylalkyloxycarbonyl wherein the alkyl moiety thereof is straight chain alkyl having 1 to 4 carbon atoms and the aryl moiety is phenyl. Examples thereof include benzyloxycarbonyl, phenethyloxycarbonyl, 3-phenylpropyloxycarbonyl, 2-phenylpropyloxycarbonyl, 4-phenylbutyloxycarbonyl and the like.

The $C_{6-14}$ aryl $C_{1-6}$ alkyloxycarbonyl is particularly preferably benzyloxycarbonyl at $R^{b7}$.

The optionally substituted $C_{1-6}$ alkyl is the above-defined $C_{1-6}$ alkyl, preferably that wherein straight chain or branched chain alkyl having 1 to 4 carbon atoms is optionally substituted with 1 to 3 substituent(s), and includes unsubstituted alkyl. The substituent(s) is(are) selected from the above-defined halogen atom, hydroxyl group, carboxyl, amino, the above-defined $C_{1-6}$ alkoxy, the above-defined $C_{1-6}$ alkoxy $C_{1-6}$ alkoxy, the above-defined $C_{1-6}$ alkoxycarbonyl and the above-defined $C_{1-6}$ alkylamino. Examples of optionally substituted $C_{1-6}$ alkyl include methyl, ethyl, propyl, isopropyl, butyl, isobutyl, sec-butyl, tert-butyl, pentyl, isopentyl, tert-pentyl, neopentyl, 1-ethylpropyl, hexyl, trifluoromethyl, hydroxymethyl, 2-hydroxyethyl, 3-hydroxypropyl, 4-hydroxybutyl, 1-hydroxy-1-methylethyl, 1-hydroxypropan-2-yl, 1,3-dihydroxypropan-2-yl, 1-hydroxy-2-methylpropan-2-yl, carboxylmethyl, 2-carboxylethyl, methoxymethyl, methoxyethyl, methoxyethoxymethyl, ethoxycarbonylmethyl, 2-ethoxycarbonylethyl, 2-dimethylaminoethyl and the like.

Preferably, the optionally substituted $C_{1-6}$ alkyl is methyl, 1-hydroxy-1-methylethyl, carboxylmethyl or 2-dimethylaminoethyl at $R^1$, $R^2$, $R^3$ and $R^4$, methyl or trifluoromethyl at $R^5$, $R^{5'}$, $R^6$ and $R^{6'}$, methyl at $R^7$, $R^8$, $R^{a31}$ and $R^{b5}$, methyl, ethyl or isopropyl at $R^{a24}$, methyl or isopropyl at $R^{a18}$, methyl or ethyl at $R^{a1}$, $R^{a19}$ and $R^{a25}$, methyl, carboxylmethyl or 2-dimethylaminoethyl at $R^{a2}$ and $R^{a3}$, methyl or carboxylmethyl at $R^{a6}$, methyl, ethyl, isopropyl, butyl or trifluoromethyl at X, methyl, ethyl, isopropyl, butyl, isobutyl, tert-butyl, isopentyl, neopentyl, 1-ethylpropyl or carboxylmethyl at $R^{a10}$, methyl, ethyl, propyl, isopropyl, butyl, isobutyl, trifluoromethyl, 2-hydroxyethyl or carboxylmethyl at $R^{a11}$, methyl or 4-hydroxybutyl at $R^{a12}$, methyl, ethyl, isopropyl, butyl, 2-hydroxyethyl, 4-hydroxybutyl, ethoxycarbonylmethyl, 2-(ethoxycarbonyl)ethyl or 2-dimethylaminoethyl at $R^{a13}$, methyl, propyl, butyl, isopentyl, trifluoromethyl, hydroxymethyl, 2-hydroxyethyl, 3-hydroxypropyl, methoxyethyl, methoxyethoxyethyl or carboxymethyl at $R^{a20}$, methyl or ethyl at $R^{a22}$ and $R^{a23}$, methyl isopropyl or tert-butyl at $R^{a26}$, methyl, ethyl, propyl, isopropyl, butyl, tert-butyl, isobutyl, 2-hydroxyethyl, 1-hydroxypropan-2-yl, 1-hydroxy-2-methylpropan-2-yl or carboxylmethyl at $R^{a27}$ and $R^{a28}$, and methyl, ethyl, propyl, isopropyl, tert-butyl, trifluoromethyl, hydroxymethyl, 2-hydroxyethyl, 2-carboxylethyl, methoxymethyl or ethoxycarbonylmethyl at Z, Z' and group D.

It is particularly preferably, trifluoromethyl at $R^5$, $R^{5'}$, $R^6$ and $R^{6'}$, methyl or tert-butyl at $R^{a26}$, methyl, tert-butyl, trifluoromethyl or hydroxymethyl at Z, Z' and group D, and methyl at other substituents.

The optionally substituted $C_{2-6}$ alkenyl is that wherein straight chain or branched chain alkenyl having 2 to 6 carbon atoms is optionally substituted by 1 to 3 substituent(s), and includes unsubstituted alkenyl. The substituent(s) is(are) selected from the above-defined halogen atom, hydroxyl group, carboxyl, amino, the above-defined $C_{1-6}$ alkoxy, the above-defined $C_{1-6}$ alkoxy $C_{1-6}$ alkoxy, the above-defined $C_{1-6}$ alkoxycarbonyl and the above-defined $C_{1-6}$ alkylamino. Examples of optionally substituted $C_{2-6}$ alkenyl include vinyl, allyl, 1-propenyl, isopropenyl, 1-butenyl, 2-butenyl, 1,3-butadienyl, 2-isopentenyl, 3-isohexenyl, 4-methyl-3-pentenyl, 2-carboxylethenyl and the like.

The optionally substituted $C_{2-6}$ alkenyl is preferably 2-carboxylethenyl at X, and preferably 2-isopentenyl, 3-isohexenyl or 4-methyl-3-pentenyl at $R^{a20}$.

The optionally substituted $C_{2-6}$ alkynyl is that wherein straight chain or branched chain alkynyl having 2 to 6 carbon atoms is optionally substituted by 1 to 3 substituent(s), and includes unsubstituted alkynyl. The substituent(s) is(are) selected from the above-defined halogen atom, hydroxyl group, carboxyl, amino, the above-defined $C_{1-6}$ alkoxy, the above-defined $C_{1-6}$ alkoxycarbonyl and the above-defined $C_{1-6}$ alkylamino. Examples thereof include ethynyl, 1-propynyl, 2-propynyl, 3-butynyl and the like.

The optionally substituted $C_{2-6}$ alkynyl is preferably 2-propynyl at $R^{a20}$.

The $C_{6-14}$ aryl optionally substituted by 1 to 5 substituent(s) selected from group B is that wherein the above-defined $C_{6-14}$ aryl is optionally substituted by 1 to 5 substituent(s), and includes unsubstituted aryl. The substituent(s) is(are) selected from the above-defined halogen atom, cyano, nitro, the above-defined $C_{1-6}$ alkyl, the above-defined halogenated $C_{1-6}$ alkyl, the above-defined $C_{1-6}$ alkanoyl, —$(CH_2)_r$—$COOR^{b1}$, —$(CH_2)_r$—$CONR^{b1}R^{b2}$, —$(CH_2)_r$—$NR^{b1}R^{b2}$, —$(CH_2)^r$—$NR^{b1}COR^{b2}$, —$(CH_2)_r$—$NHSO_2R^{b1}$, —$(CH_2)_r$—$OR^{b1}$, —$(CH_2)_r$—$SR^{b1}$, —$(CH_2)_r$—$SO_2R^{b1}$ and —$(CH_2)_r$—

$SO_2NR^{b1}R^{b2}$ (wherein $R^{b1}$ and $R^{b2}$ are each independently hydrogen atom or the above-defined $C_{1-6}$ alkyl and r is 0 or an integer of 1 to 6).

Examples thereof include phenyl, naphthyl, anthryl, indenyl, azulenyl, fluorenyl, phenanthryl, 3-fluorophenyl, 4-fluorophenyl, 3-chlorophenyl, 4-chlorophenyl, 2,4-dichlorophenyl, 3,5-dichlorophenyl, pentafluorophenyl, 4-methylphenyl, 4-tert-butylphenyl, 2-trifluoromethyiphenyl, 4-trifluoromethylphenyl, 4-nitrophenyl, 4-cyanophenyl, 4-acetylphenyl, 4-carboxyphenyl, 4-carbamoylphenyl, 4-aminophenyl, 4-dimethylaminophenyl, 4-acetylaminophenyl, 4-(methylsulfonylamino)phenyl, 4-methoxyphenyl, 3,4,5-trimethoxyphenyl, 4-methylthiophenyl, 4-methylsulfonylphenyl, 4-aminosulfonylphenyl, 3-nitro-4-methoxyphenyl and 4-nitro-3-methoxyphenyl.

The aryl moiety is preferably phenyl, the group B here is preferably the above-defined halogen atom, nitro, the above-defined $C_{1-6}$ alkyl, the above-defined halogenated $C_{1-6}$ alkyl or $—(CH_2)_r—OR^{b1}$. Examples of group B include fluorine atom, chlorine atom, nitro, methyl, tert-butyl, trifluoromethyl and methoxy. Particularly preferably, it is fluorine atom or chlorine atom.

With regard to "$C_{6-14}$ aryl optionally substituted by 1 to 5 substituent(s) selected from group B", it is preferably phenyl, 4-tert-butylphenyl, 4-fluorophenyl, 3-chlorophenyl, 4-chlorophenyl, 4-methoxyphenyl or 4-trifluoromethylphenyl at $R^{a12}$, $R^{a27}$ and $R^{a28}$, phenyl at $R^{a14}$, $R^{a22}$, $R^{a23}$, $R^{a26}$ and $R^{b5}$, phenyl or 3-fluorophenyl at $R^{a18}$, phenyl or 2,4-dichlorophenyl at $R^{a20}$, phenyl, 4-chlorophenyl, 4-trifluoromethylphenyl, 3,5-dichlorophenyl, 3-nitro-4-methoxyphenyl or 4-nitro-3-methoxyphenyl at $R^{a24}$, and phenyl or 4-methylphenyl at $R^{a25}$.

It is particularly preferably phenyl at other substituents.

The $C_{6-14}$ aryl optionally substituted by 1 to 5 substituent(s) selected from group D is that wherein the above-defined $C_{6-14}$ aryl is optionally substituted by 1 to 5 substituent(s), and includes unsubstituted aryl. The substituent(s) is(are) selected from the above-mentioned group D (substituents shown under (a) to (q)).

Examples of group D here include fluorine atom, chlorine atom, bromine atom, nitro, cyano, methyl, ethyl, propyl, isopropyl, tert-butyl, trifluoromethyl, hydroxymethyl, 2-hydroxyethyl, methoxymethyl, 2-carboxyethyl, methoxycarbonylmethyl, ethoxycarbonylmethyl, acetyl, carboxyl, methoxycarbonyl, ethoxycarbonyl, carbamoyl, methylaminocarbonyl, isopropylaminocarbonyl, dimethylaminocarbonyl, diethylaminocarbonyl, (2-hydroxyethyl)aminocarbonyl, (carboxylmethyl)aminocarbonyl, hydroxyl group, methoxy, ethoxy, propyloxy, isopropyloxy, isopentyloxy, 2-isopentenyloxy, 3-isohexenyloxy, 4-methyl-3-pentenyloxy, 2-propynyloxy, hydroxymethyloxy, carboxylmethyloxy, (dimethylaminocarbonyl)methyloxy, amino, methylamino, dimethylamino, diethylamino, acetylamino, methylsulfonylamino, methylthio, methylsulfonyl, methylsulfinyl, aminosulfonyl, methylaminosulfonyl, dimethylaminosulfonyl and tetrazolyl.

Examples of $C_{6-14}$ aryl optionally substituted by 1 to 5 substituent(s) selected from group D include phenyl, naphthyl, anthryl, indenyl, azulenyl, fluorenyl, phenanthryl, 3-fluorophenyl, 4-fluorophenyl, 3-chlorophenyl, 4-chlorophenyl, 2,4-dichlorophenyl, 3,5-dichlorophenyl, 4-bromophenyl, 4-nitrophenyl, pentafluorophenyl, 4-methylphenyl, 4-tert-butylphenyl, 2-trifluoromethylphenyl, 4-trifluoromethylphenyl, 4-(hydroxymethyl)phenyl, 4-(methoxymethyl)phenyl, 4-(2-carboxylethyl)phenyl, 3-carboxylphenyl, 4-carboxylphenyl, 4-methoxyphenyl, 3,4,5-trimethoxyphenyl, 4-carbamoylphenyl, 4-methylthiophenyl, 4-(dimethylaminocarbonyl)phenyl, 4-methylsulfonylphenyl, 4-acetylaminophenyl, 4-cyanophenyl, 4-acetylphenyl, 4-aminophenyl, 4-dimethylaminophenyl, 4-(methylsulfonylamino)phenyl, 4-methylsulfinylphenyl, 4-aminosulfonylphenyl and 3-nitro-4-methoxyphenyl, 4-nitro-3-methoxyphenyl and 4-tetrazol-5-ylphenyl.

At Z and Z', the aryl moiety is preferably phenyl.

The group D here is preferably the above-defined halogen atom, nitro, the above-defined optionally substituted $C_{1-6}$ alkyl, $—(CH_2)_r—COOR^{a19}$, $—(CH_2)_r—CONR^{a27}R^{a28}$, $—(CH_2)_r—OR^{a20}$, $—(CH_2)_r—NR^{a29}CO—R^{a24}$, $—(CH_2)_r—S(O)_q—R^{a25}$ or $—(CH_2)_r—SO_2—NHR^{a26}$.

Particularly preferably, it is the above-defined halogen atom, the above-defined optionally substituted $C_{1-6}$ alkyl, $—(CH_2)_r—COOR^{a19}$, $—(CH_2)_r—CONR^{a27}R^{a28}$, $—(CH_2)_r—OR^{a20}$ or $—(CH_2)_r—S(O)_q—R^{a25}$, which is specifically fluorine atom, chlorine atom, bromine atom, nitro, methyl, tert-butyl, carboxyl, trifluoromethyl, hydroxymethyl, methoxymethyl, 2-carboxylethyl, methoxy, carbamoyl, methylthio, dimethylaminocarbonyl, methylsulfonyl or acetylamino. More preferably, it is fluorine atom, chlorine atom, methyl, tert-butyl, carboxyl, methoxy, carbamoyl, methylthio, dimethylaminocarbonyl, methylsulfonyl or acetylamino, most preferably fluorine atom or chlorine atom.

Examples of $C_{6-14}$ aryl optionally substituted by 1 to 5 substituent(s) selected from group D preferably include phenyl, 3-fluorophenyl, 4-fluorophenyl, 3-chlorophenyl, 4-chlorophenyl, 3,5-dichlorophenyl, 4-bromophenyl, 4-nitrophenyl, 4-methylphenyl, 4-tert-butylphenyl, 2-trifluoromethylphenyl, 4-trifluoromethylphenyl, 4-(hydroxymethyl)phenyl, 4-(methoxymethyl)phenyl, 4-(2-carboxylethyl)phenyl, 3-carboxyphenyl, 4-carboxylphenyl, 4-methoxyphenyl, 3,4,5-trimethoxyphenyl, 4-carbamoylphenyl, 4-methylthiophenyl, 4-(dimethylaminocarbonyl)phenyl, 4-methylsulfonylphenyl, 4-acetylaminophenyl, 4-methylsulfinylphenyl, 4-aminosulfonylphenyl, 4-cyanophenyl and 4-tetrazolylphenyl, particularly preferably 4-chlorophenyl.

The heterocyclic group optionally substituted by 1 to 5 substituent(s) selected from group B is that wherein the above-defined heterocyclic group is optionally substituted by 1 to 5 slbstituent(s), and includes unsubstituted heterocyclic group. The substituent(s) is(are) selected from the above-defined halogen atom, cyano, nitro, the above-defined $C_{1-6}$ alkyl, the above-defined halogenated $C_{1-6}$ alkyl, the above-defined $C_{1-6}$ alkanoyl, $—(CH_2)_r—COOR^{b1}$, $—(CH_2)_r—CONR^{b1}R^{b2}$, $—(CH_2)_r—NR^{b1}R^{b2}$, $—(CH_2)_r—NR^{b1}—COR^{b2}$, $—(CH_2)_r—NHSO_2R^{b1}$, $—(CH_2)_r—OR^{b1}$, $—(CH_2)_r—SR^{b1}$, $—(CH_2)_r—SO_2R^{b1}$ and $—(CH_2)_r—SO_2NR^{b1}R^{b2}$ wherein $R^{b1}$ and $R^{b2}$ are each independently hydrogen atom or the above-defined $C_{1-6}$ alkyl and r is 0 or an integer of 1 to 6.

Examples thereof include 2-pyridyl, 3-pyridyl, 4-pyridyl, 3-fluoropyridin-4-yl, 3-chloropyridin-4-yl, 4-chloropyridin-3-yl, pyrazinyl, pyrimidinyl, pyridazinyl, 1,3,5-triazinyl, pyrrolyl, pyrazolyl, imidazolyl, 1,2,4-triazolyl, tetrazolyl, 2-thienyl, 3-thienyl, furyl, oxazolyl, 2-methyloxazol-4-yl, isoxazolyl, thiazolyl, 2-methylthiazol-4-yl, 2,5-dimethylthiazol-4-yl, 2,4-dimethylthiazol-5-yl, isothiazolyl, thiadiazolyl, pyrrolinyl, pyrrolidinyl, 3-hydroxypyrrolidinyl, imidazolidinyl, azetidinyl, piperidyl, 3-hydroxypiperidino, 4-hydroxypiperidino, 3,4-dihydroxypiperidino, 4-methoxypiperidino, 4-carboxypiperidino, 4-(hydroxymethyl)piperidino, 2-oxopiperidino, 4-oxopiperidino, 2,2,6,6-tetramethylpiperidino, 2,2,6,6-tetramethyl-4-hydroxypiperidino, N-methylpiperidin-4-yl, N-(tert-butoxycarbonyl)piperidin-4-yl, N-acetylpiperidin-4-yl, N-methylsulfonylpiperidin-4-yl, piperazinyl, 4-methylpiperazinyl, 4-methylsulfonylpiperazinyl, morpholinyl, thiomorpholinyl, 1-oxothiomorpholin-4-yl, 1,1-dioxothiomorpholin-4-yl, tetrahydropyranyl, quinolyl, isoquinolyl, quinazolinyl, quinoxalyl, phthalazinyl, cinnolinyl, naphthyridinyl, 5,6,7,8-tetrahydroquinolyl, indolyl, benzimidazolyl, indolinyl, benzofuranyl, benzothienyl, benzoxazolyl, benzothiazolyl,

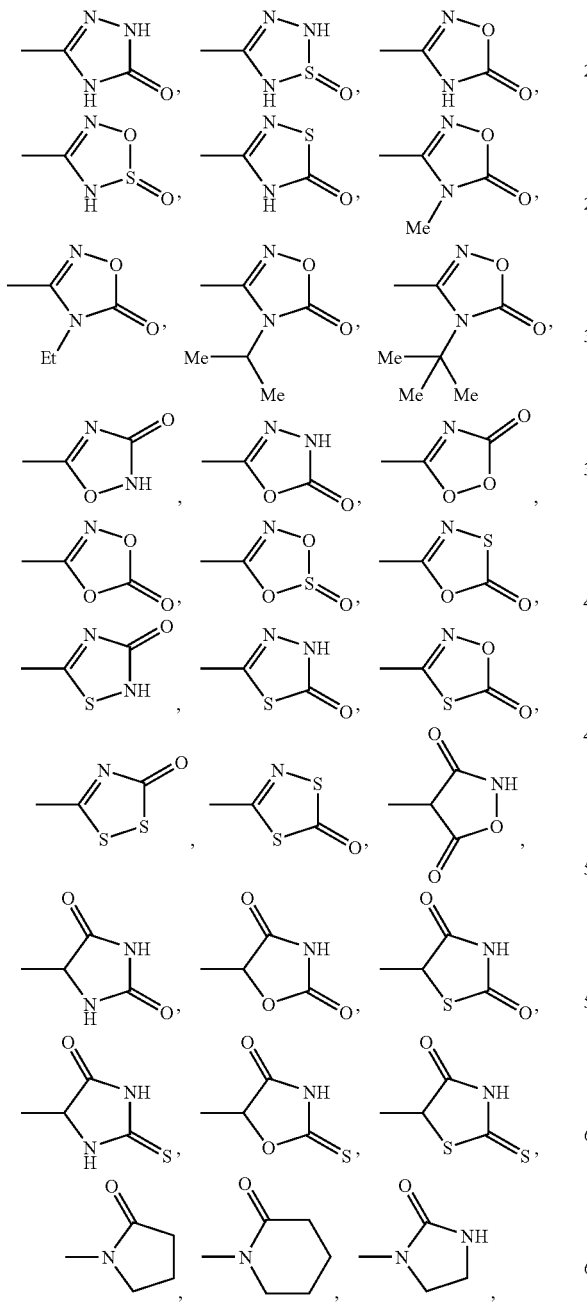

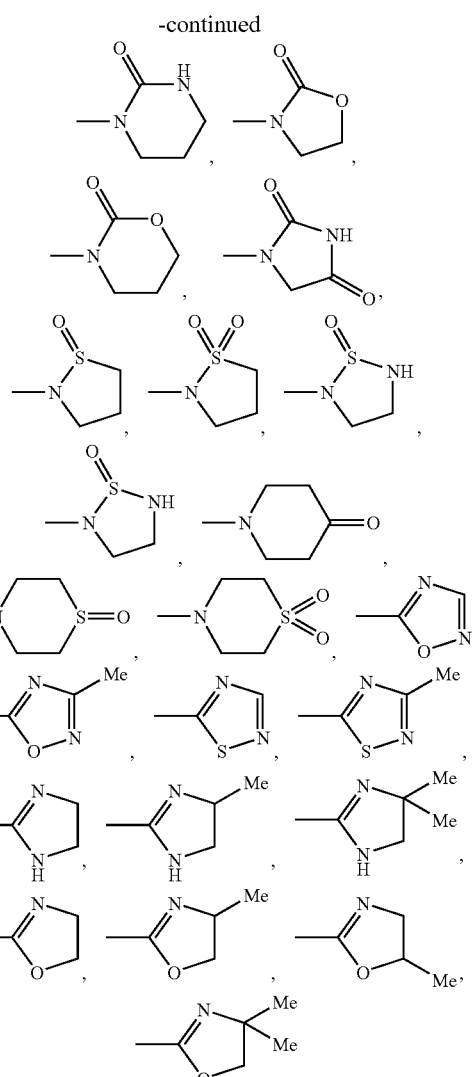

and the like.

The heterocyclic moiety is preferably a heterocyclic group which is a 5-membered or a 6-membered monocyclic group. Examples thereof include pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isoxazolyl, thiazolyl, isothiazolyl, thiadiazolyl, pyrrolidinyl, piperidyl, piperazinyl, morpholinyl, thiomorpholinyl and tetrahydropyranyl, and the group B here is preferably the above-defined halogen atom, the above-defined $C_{1-6}$ alkyl, the above-defined halogenated $C_{1-6}$ alkyl, the above-defined $C_{1-6}$ alkanoyl, —$(CH_2)_r$—$COOR^{b1}$, —$(CH_2)_r$—$CONR^{b1}R^{b2}$ or —$(CH_2)_r$—$OR^{b1}$.

Examples of heterocyclic group optionally substituted by 1 to 5 substituent(s) selected from group B preferably include piperidino, 4-methylpiperidino, 2,6-dimethylpiperidino, 4-hydroxypiperidino, 1-piperazinyl, 1-(methylsulfonyl)piperidin-4-yl, 1-pyrrolidinyl, morpholino, 4-thiomorpholinyl, tetrahydropyranyl, pyridyl, thiazolyl,

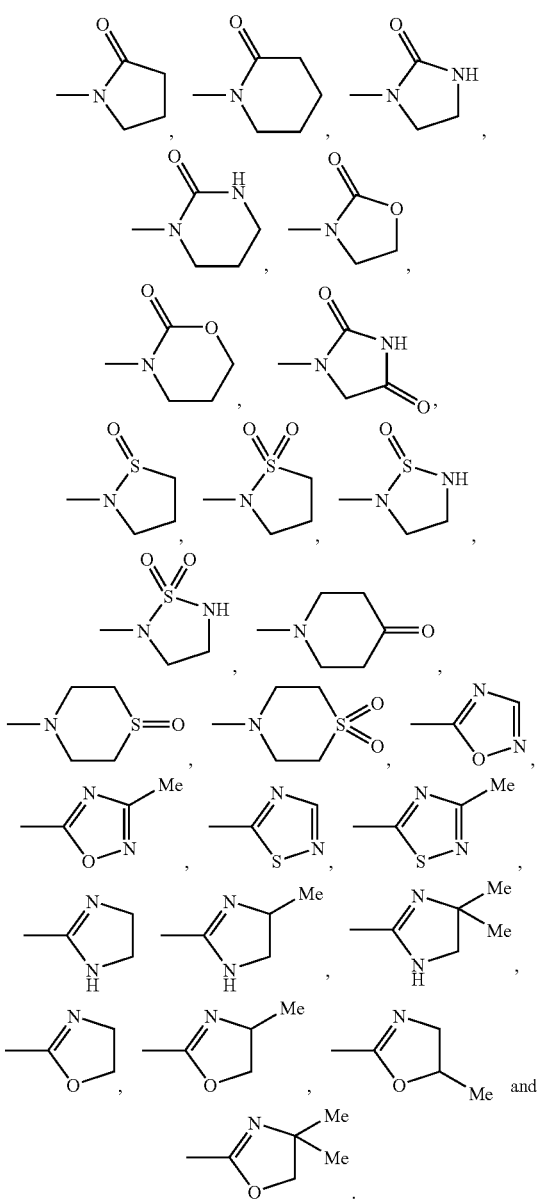

Particularly preferably, it is piperidino, 4-methylpiperidino, 2,6-dimethylpiperidino, 4-hydroxypiperidino, 1-piperazinyl, 1-pyrrolidinyl, morpholino or 4-thioiorpholinyl at $R^{a18}$, tetrahydropyranyl or 4-hydroxypiperidino at $R^{a20}$, piperidino, 4-hydroxypiperidino or 3,4-dihydroxypiperidino at $R^{a21}$, pyridyl or morpholino at $R^{a24}$, pyridyl or 4-hydroxypiperidino at $R^{a25}$, pyridyl or thiazolyl at $R^{a26}$ and at $R^{a27}$ and $R^{a28}$, it is 1-(methylsulfonyl)piperidin-4-yl, 3-hydroxypyrrolidinyl, 3-hydroxypiperidino, 4-hydroxypiperidino, 3,4-dihydroxypiperidino, 4-methoxypiperidino, 4-carboxypiperidino, 4-(hydroxymethyl)piperidino, 2-oxopiperidino, 4-oxopiperidino, 2,2,6,6-tetramethylpiperidino, 2,2,6,6-tetramethyl-4-hydroxypiperidino, 4-methylsulfonylpiperazinyl, 1-oxothiomorpholin-4-yl or 1,1-dioxothiomorpholin-4-yl, and 2-oxazolin-2-yl at $R^{a22}$ and $R^{a23}$.

The heterocyclic group optionally substituted by 1 to 5 substituent(s) selected from group D is that wherein the above-defined heterocyclic group is optionally substituted by 1 to 5 substituent(s), and includes unsubstituted heterocyclic group. The substituent(s) is(are) selected from the substituent(s) of the above-mentioned group D (substituents shown under (a) to (q)).

Examples of the group D here include the substituent(s) exemplified for $C_{6-14}$ aryl optionally substituted by 1 to 5 substituent(s) selected from group D.

Examples of heterocyclic group optionally substituted by 1 to 5 substituent(s) selected from group D include 2-pyridyl, 3-pyridyl, 4-pyridyl, 3-fluoropyridin-4-yl, 3-chloropyridin-4-yl, 4-chloropyridin-3-yl, pyrazinyl, pyrimidinyl, pyridazinyl, 1,3,5-triazinyl, pyrrolyl, pyrazolyl, imidazolyl, 1,2,4-triazolyl, tetrazolyl, 2-thienyl, 3-thienyl, furyl, oxazolyl, 2-methyloxazol-4-yl, isoxazolyl, thiazolyl, 2-methylthiazol-4-yl, 2,5-dimethylthiazol-4-yl, 2,4-dimethylthiazol-5-yl, isothiazolyl, thiadiazolyl, pyrrolinyl, pyrrolidinyl, imidazolidinyl, piperidyl, N-methylpiperidin-4-yl, N-(tert-butoxycarbonyl)piperidin-4-yl, N-acetylpiperidin-4-yl, N-methylsulfonylpiperidin-4-yl, piperazinyl, morpholinyl, thiomorpholinyl, tetrahydropyranyl, quinolyl, isoquinolyl, quinazolinyl, quinoxalyl, phthalazinyl, cinnolinyl, naphthyridinyl, 5,6,7,8-tetrahydroquinolyl, indolinyl, benzimidazolyl, indolinyl, benzofuranyl, benzothienyl, benzoxazolyl, benzothiazolyl

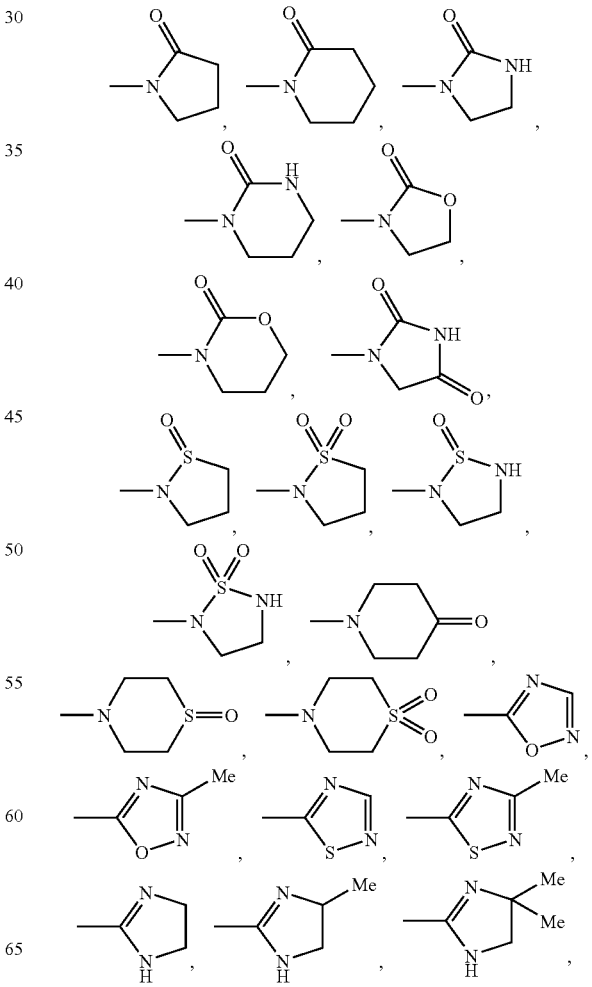

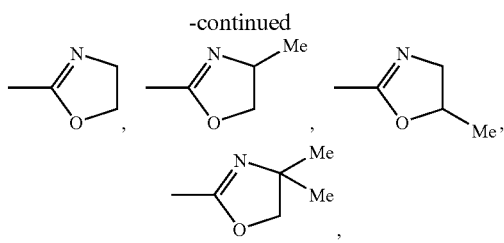

and the like.

In addition, the heterocyclic group may be substituted at the 3-, 4-, 5- or 6-position of 2-pyridyl, at the 2-, 4-, 5- or 6-position of 3-pyridyl, at the 2-, 3-, 5- or 6-position of 4-pyridinyl, at the 3-, 4- or 5-position of 2-thienyl, or at the 2-, 4- or 5-position of 3-thienyl, by fluorine atom, chlorine atom, bromine atom, nitro, methyl, tert-butyl, carboxyl, trifluoromethyl, hydroxymethyl, methoxymethyl, 2-carboxylethyl, methoxy, carbamoyl, methylthio, dimethylaminocarbonyl, methylsulfonyl, amino or acetylamino.

At Z and Z', the heterocyclic moiety is preferably a heterocyclic group which is a 5-membered or 6-membered monocyclic group. Examples thereof include pyridyl, pyrazinyl, pyrimidinyl, is pyridazinyl, 1,3,5-triazinyl, pyrrolyl, 2-oxopyrrolidinyl, 2-oxopiperidyl, pyrazolyl, imidazolyl, 2-imidazolinyl, 2-oxoimidazolidinyl, 1,2,4-triazolyl, tetrazolyl, thienyl, furyl, oxazolyl, isoxazolyl, 2-oxazolinyl, thiazolyl, isothiazolyl, 1,1-dioxoisothiazolidinyl, thiadiazolyl, pyrrolidinyl, piperidyl, piperazinyl, morpholinyl, thiomorpholinyl, tetrahydropyranyl, $\Delta^2$-1,2,4-oxadiazolyl, 5-oxo-$\Delta^2$-1,2,4-oxadiazolyl, 5-oxo-$\Delta^2$-1,2,4-thiadiazolinyl and 2-oxo-3H-1,2,3,5-oxathiadiazolinyl. The group D here is preferably the above-defined halogen atom, nitro, the above-defined optionally substituted $C_{1-6}$ alkyl, —$(CH_2)_r$—$COOR^{a19}$, —$(CH_2)_r$—$CONR^{a27}R^{a28}$, —$(CH_2)_r$—$OR^{a20}$, —$(CH_2)_r$—$NR^{a29}CO$—$R^{a24}$, —$(CH_2)_r$—$S(O)_q$—$R^{a25}$ or —$(CH_2)_r$—$SO_2$—$NHR^{a26}$.

Examples of heterocyclic group optionally substituted by 1 to 5 substituent(s) selected from group D preferably include piperidino, 4-hydroxypiperidino, 2-oxopiperidin-1-yl, 1-piperazinyl, 1-pyrrolidinyl, 2-oxopyrrolidin-1-yl, morpholino, 4-thiomorpholinyl, 4-tetrahydropyranyl, 3-pyridyl, 2-pyrimidinyl, 2-imidazolin-2-yl, 2-oxoimidazolidin-1-yl, 2-oxooxazolidin-1-yl, 5-tetrazolyl, 2-thiazolyl, 4-thiazolyl, 5-thiazolyl, 2-methylthiazol-4-yl, 5-methylthiazol-2-yl, 2-aminothiazol-4-yl, 3-methyl-1,2,4-oxadiazol-5-yl, 1,1-dioxoisothiazolidin-2-yl, 4,4-dimethyl-$\Delta 2$-oxazolin-2-yl, 2-thienyl, 5-chlorothiophen-2-yl, 5-methyloxazol-2-yl, 5-oxo-$\Delta^2$-1,2,4-oxadiazolin-3-yl, 5-oxo-$\Delta^2$-1,2,4-thiadiazolin-3-yl and 2-oxo-3H-1,2,3,5-oxathiazolin-4-yl.

Particularly preferably, it is pyridyl, pyrimidinyl, tetrazolyl, thienyl, piperidyl, 2-oxopiperidin-1-yl, 2-oxopyrrolidin-1-yl, 2-imidazolin-2-yl, 2-oxoimidazolidin-1-yl, 2-oxooxazolidin-1-yl, 2-methylthiazol-4-yl, 5-methylthiazol-2-yl, 2-aminothiazol-4-yl, 3-methyl-1,2,4-oxadiazol-5-yl, 1,1-dioxoisothiazolidin-2-yl, 4,4-dimethyl-$\Delta^2$-oxazolin-2-yl, 5-chlorothiophen-2-yl, 5-methyloxazol-2-yl, 5-oxo-$\Delta^2$-1,2,4-oxadiazolin-3-yl, 5-oxo-$\Delta^2$-1,2,4-thiadiazolin-3-yl or 2-oxo-3H-1,2,3,5-oxathiadiazolin-4-yl, more preferably 2-oxopiperidin-1-yl, 2-oxopyrrolidin-1-yl, 2-oxoimidazolidin-1-yl, 2-oxooxazolidin-1-yl or 1,1-dioxoisothiazolidin-2-yl, most preferably 2-oxopyrrolidin-1-yl.

The $C_{3-8}$ cycloalkyl optionally substituted by 1 to 5 substituent(s) selected from group C is that wherein the above-defined $C_{3-8}$ cycloalkyl is optionally substituted by the 1 to 5 substituent(s) selected from hydroxyl group, the above-defined halogen atom, the above-defined $C_{1-6}$ alkyl and the above-defined $C_{1-6}$ alkoxy, which may be unsubstituted. Examples thereof include cyclopropyl, cyclobutyl, cyclopentyl, cyclohexyl, cycloheptyl, 4-fluorocyclohexyl, 2-methylcyclopentyl, 3-methylcyclohexyl, 4-methylcyclohexyl, 4,4-dimethylcyclohexyl, 3,5-dimethylcyciohexyl, 4-tert-butylcyclohexyl, 4-hydroxycyclohexyl, 4-methoxycyclohexyl and 2,3,4,5,6-pentafluorocyclohexyl.

The cycloalkyl moiety is preferably cyclopentyl or cyclohexyl, particularly preferably cyclohexyl.

At the ring Cy and ring Cy', the $C_{3-8}$ cycloalkyl optionally substituted by 1 to 5 substituent(s) selected from group C is preferably cyclopentyl, cyclohexyl, 4-fluorocyclohexyl, 4-methylcyclohexyl, 4,4-dimethylcyclohexyl, 4-tert-butylcyclohexyl, 4-hydroxycyclohexyl or 4-methoxycyclohexyl, more preferably cyclopentyl or cyclohexyl, particularly preferably cyclohexyl.

The $C_{3-8}$ cycloalkyl optionally substituted by 1 to 5 substituent(s) selected from the above group B is that wherein the above-defined $C_{3-8}$ cycloalkyl is optionally substituted by 1 to 5 substituent(s), and includes unsubstituted cycloalkyl. The substituents are selected from the above group B.

Specific examples thereof include cyclopropyl, cyclobutyl, cyclopentyl, cyclohexyl, cycloheptyl, 4-fluorocyclohexyl, 2-methylcyclopentyl, 3-methylcyclohexyl, 4-methylcyclohexyl, 4,4-dimethylcyclohexyl, 3,5-dimethylcyclohexyl, 4-tert-butylcyclohexyl, 4-hydroxycyclohexyl, 4-methoxycyclohexyl and 2,3,4,5,6-pentafluorocyclohexyl.

Also exemplified are those wherein cyclopentyl or cyclohexyl is substituted by fluorine atom, chlorine atom, bromine atom, nitro, methyl, tert-butyl, carboxyl, trifluoromethyl, hydroxymethyl, methoxymethyl, 2-carboxylethyl, methoxy, carbamoyl, methylthio, dimethylaminocarbonyl, methylsulfonyl or acetylamino.

At cycloalkyl moiety, it is preferably cyclopropyl, cyclobutyl, cyclopentyl or cyclohexyl. As the $C_{3-8}$ cycloalkyl optionally substituted by 1 to 5 substituent(s) selected from the above group B, it is particularly preferably cyclopropyl, cyclobutyl, cyclohexyl or 4-hydroxycyclohexyl at $R^{a27}$ and $R^{a28}$.

The $C_{3-8}$ cycloalkyl optionally substituted by 1 to 5 substituent(s) selected from group D is that wherein the above-defined $C_{3-8}$ cycloalkyl is optionally substituted by 1 to 5 substituent(s), and includes unsubstituted cycloalkyl. The substituent(s) is(are) selected from the substituent(s) of the above-mentioned group D (substituents shown under (a) to (q)).

The group D here includes the substituents recited with regard to $C_{6-14}$ aryl optionally substituted by 1 to 5 substituent(s) selected from group D.

Examples thereof include cyclopropyl, cyclobutyl, cyclopentyl, cyclohexyl, cycloheptyl, 4-fluorocyclohexyl, 2-methylcyclopentyl, 3-methylcyclohexyl, 4-methylcyclohexyl, 4,4-dimethylcyclohexyl, 3,5-dimethylcyclohexyl, 4-tert-butylcyclohexyl, 4-hydroxycyclohexyl, 4-methoxycyclohexyl and 2,3,4,5,6-pentafluorocyclohexyl.

The group D may be, for example, cyclopentyl or cyclohexyl substituted by fluorine atom, chlorine atom, bromine atom, nitro, methyl, tert-butyl, carboxyl, trifluoromethyl, hydroxymethyl, methoxymethyl, 2-carboxylethyl, methoxy, carbamoyl, methylthio, dimethylaminocarbonyl, methylsulfonyl or acetylamino.

The cycloalkyl moiety is preferably cyclopentyl or cyclohexyl, and at Z and Z', it is particularly preferably cyclohexyl.

The optionally substituted $C_{3-8}$ cycloalkenyl is that wherein the above-defined $C_{3-8}$ cycloalkenyl is optionally substituted by substituent(s) selected from hydroxyl group, the above-defined halogen atom, the above-defined $C_{1-6}$ alkyl and the above-defined $C_{1-6}$ alkoxy, which may be unsubstituted. Examples thereof include cyclopropenyl, cyclobutenyl, cyclopentenyl, cyclopentadienyl, cyclohexenyl, 4-fluoro-2-cyclohexenyl, 4-methyl-2-cyclohexenyl, 4-methyl-3-cyclohexenyl, 2,4-cyclohexadien-1-yl, 2,5-cyclohexadien-1-yl, cycloheptenyl and cyclooctenyl and the like, but do not include aryl (e.g., phenyl) or completely saturated cycloalkyl.

The optionally substituted $C_{3-8}$ cycloalkenyl is particularly preferably cyclohexenyl at the ring Cy.

The $C_{6-14}$ aryl $C_{1-6}$ alkyl optionally substituted by 1 to 5 substituent(s) selected from group B is that wherein the above-defined $C_{6-14}$ aryl $C_{1-6}$ alkyl is optionally substituted by 1 to 5 substituent(s), and includes unsubstituted arylalkyl. The substituent(s) is(are) selected from the above-mentioned group B.

Examples thereof include benzyl, 1-naphthylmethyl, 2-naphthylmethyl, phenethyl, 3-phenylpropyl, 2-phenylpropyl, 3-fluorobenzyl, 4-fluorobenzyl, 3-chlorobenzyl, 4-chlorobenzyl, 2,4-dichlorobenzyl, 3,5-dichlorobenzyl, pentafluorobenzyl, 4-methylbenzyl, 4-tert-butylbenzyl, 2-trifluoromethylbenzyl, 4-trifluoromethylbenzyl, 4-nitrobenzyl, 4-cyanobenzyl, 4-acetylbenzyl, 4-carboxylbenzyl, 4-carbamoylbenzyl, 4-aminobenzyl, 4-dimethylaminobenzyl, 4-acetylaminobenzyl, 4-(methylsulfonylamino)benzyl, 4-methoxybenzyl, 3,4,5-trimethoxybenzyl, 4-methylthiobenzyl, 4-methylsulfonylbenzyl, 4-aminosulfonylbenzyl, 3-nitro-4-methoxybenzyl and 4-nitro-3-methoxybenzyl.

The $C_{6-14}$ aryl $C_{1-6}$ alkyl moiety is preferably benzyl or phenethyl, particularly preferably benzyl. The group B is preferably the above-defined halogen atom, nitro, the above-defined $C_{1-6}$ alkyl, the above-defined halogenated $C_{1-6}$ alkyl or $-(CH_2)_r-OR^{b1}$. Examples thereof include fluorine atom, chlorine atom, nitro, methyl, tert-butyl, trifluoromethyl, methoxy or trifluoromethyloxy, particularly preferably fluorine atom or chlorine atom.

The specific $C_{6-14}$ aryl $C_{1-6}$ alkyl optionally substituted by 1 to 5 substituent(s) selected from group B at $R^{a12}$ and $R^{a13}$ is preferably benzyl, phenethyl, 3-chlorobenzyl, 4-chlorobenzyl, 4-tert-butylbenzyl or 3-trifluoromethylbenzyl, it is preferably benzyl at $R^{a1}$, $R^{a19}$, $R^{a27}$, $R^{a28}$, $R^{a3l}$ and $R^{b5}$, it is preferably benzyl, phenethyl, 4-fluorobenzyl, 2-chlorobenzyl, 3-chlorobenzyl, 4-chlorobenzyl, 4-tert-butylbenzyl or 4-trifluoromethylbenzyl at $R^{a20}$, and 4-chlorobenzyl, 3,5-dichlorobenzyl or 4-trifluoromethylbenzyl at $R^{a22}$ and $R^{a23}$.

It is particularly preferably benzyl at other substituents.

The $C_{6-14}$ aryl $C_{1-6}$ alkyl optionally substituted by 1 to 5 substituent(s) selected from group D is that wherein the above-defined $C_{6-14}$ aryl $C_{1-6}$ alkyl is optionally substituted by 1 to 5 substituent(s), and includes unsubstituted aryl. The substituent(s) is(are) selected from the substituent(s) of the above-mentioned group D (substituents shown under (a) to (q)).

Examples of group D include fluorine atom, chlorine atom, bromine atom, nitro, cyano, methyl, ethyl, propyl, isopropyl, tert-butyl, trifluoromethyl, hydroxymethyl, 2-hydroxyethyl, methoxymethyl, 2-carboxyethyl, methoxycarbonylmethyl, ethoxycarbonylmethyl, acetyl, carboxyl, methoxycarbonyl, ethoxycarbonyl, carbamoyl, methylaminocarbonyl, isopropylaminocarbonyl, dimethylaminocarbonyl, diethylaminocarbonyl, (2-hydroxyethyl)aminocarbonyl, (carboxylmethyl)aminocarbonyl, hydroxyl group, methoxy, ethoxy, isopropyloxy, hydroxymethyloxy, carboxylmethyloxy, (dimethylaminocarbonyl)methyloxy, amino, methylamino, dimethylamino, diethylamino, acetylamino, methylsulfonylamino, methylthio, methylsulfonyl, methylsulfinyl, aminosulfonyl, methylaminosulfonyl and dimethylaminosulfonyl.

Examples of $C_{6-14}$ aryl $C_{1-6}$ alkyl optionally substituted by 1 to 5 substituent(s) selected from group D include benzyl, 1-naphthylmethyl, 2-naphthylmethyl, phenethyl, 3-phenylpropyl, 2-phenylpropyl, 3-fluorobenzyl, 4-fluorobenzyl, 3-chlorobenzyl, 4-chlorobenzyl, 2,4-dichlorobenzyl, 3,5-dichlorobenzyl, 4-bromobenzyl, 4-nitrobenzyl, pentafluorobenzyl, 4-methylbenzyl, 4-tert-butylbenzyl, 2-trifluoromethylbenzyl, 4-trifluoromethylbenzyl, 4-(hydroxymethyl)benzyl, 4-(methoxymethyl)benzyl, 4-(2-carboxylethyl)benzyl, 3-carboxylbenzyl, 4-carboxylbenzyl, 4-methoxybenzyl, 3,4,5-trimethoxybenzyl, 4-carbamoylbenzyl, 4-methylthiobenzyl, 4-(dimethylaminocarbonyl)benzyl, 4-methylsulfonylbenzyl, 4-(acetylamino)benzyl, 4-cyanobenzyl, 4-acetylbenzyl, 4-aminobenzyl, 4-dimethylaminobenzyl, 4-(methylsulfonylamino)benzyl, 4-methylsulfinylbenzyl, 4-aminosulfonylbenzyl, (3-nitro-4-methoxyphenyl)methyl and (4-nitro-3-methoxyphenyl)methyl.

At Z and Z', the $C_{6-14}$ aryl $C_{1-6}$ alkyl moiety is preferably benzyl or phenethyl, and the group D here is preferably the above-defined halogen atom, nitro, the above-defined optionally substituted $C_{1-6}$ alkyl, $-(CH_2)_t-COOR^{a19}$, $-(CH_2)_t-CONR^{a27}R^{a28}$, $-(CH_2)_t-OR^{a20}$, $-(CH_2)_t-NR^{a29}CO-R^{a24}$, $-(CH_2)_t-S(O)_q-R^{a25}$ or $-(CH_2)_t-SO_2-NHR^{a26}$.

The $C_{6-14}$ aryl $C_{1-6}$ alkyl optionally substituted by 1 to 5 substituent(s) selected from group D is preferably benzyl, 3-fluorobenzyl, 4-fluorobenzyl, 3-chlorobenzyl, 4-chlorobenzyl, 3,5-dichlorobenzyl, 4-bromobenzyl, 4-nitrobenzyl, 4-methylbenzyl, 4-tert-butylbenzyl, 2-trifluoromethylbenzyl, 4-trifluoromethylbenzyl, 4-(hydroxymethyl)benzyl, 4-(methoxymethyl)benzyl, 4-(2-carboxylethyl)benzyl, 3-carboxylbenzyl, 4-carboxylbenzyl, 4-methoxybenzyl, 3,4,5-trimethoxybenzyl, 4-carbamoylbenzyl, 4-methylthiobenzyl, 4-(dimethylaminocarbonyl)benzyl, 4-methylsulfonylbenzyl, 4-acetylaminobenzyl, 4-methylsulfinylbenzyl or 4-aminosulfonylbenzyl.

It is particularly preferably the above-defined halogen atom, the above-defined optionally substituted $C_{1-6}$ alkyl, $-(CH_2)_t-COOR^{a19}$, $-(CH_2)_t-CONR^{a27}R^{a28}$, $-(CH_2)_5-OR^{a20}$ or $-(CH_2)_t-S(O)_q-R^{a25}$. Examples thereof include fluorine atom, chlorine atom, bromine atom, nitro, methyl, tert-butyl, carboxyl, trifluoromethyl, hydroxymethyl, methoxymethyl, 2-carboxylethyl, methoxy, carbamoyl, methylthio, dimethylaminocarbonyl, methylsulfonyl and acetylamino. It is more preferably fluorine atom, chlorine atom, methyl, tert-butyl, carboxyl, methoxy, carbamoyl, methylthio, dimethylaminocarbonyl or methylsulfonyl, most preferably fluorine atom or chlorine atom.

The heterocycle $C_{1-6}$ alkyl optionally substituted by 1 to 5 substituent(s) selected from group B is that wherein the above-defined heterocycle $C_{1-6}$ alkyl is optionally substituted by 1 to 5 substituent(s), and includes unsubstituted heterocycle $C_{1-6}$ alkyl. The substituent(s) is(are) selected from the above-mentioned group B.

Examples thereof include 2-pyridylmethyl, 3-pyridylmethyl, 2-chloropyridin-4-ylmethyl, 4-pyridylmethyl, pyrrolylmethyl, imidazolylmethyl, 2-thienylmethyl, 3-thienylmethyl, 2-furylmethyl, 2-oxazolylmethyl, 5-isothiazolylmethyl, 2-methyloxazol-4-ylmethyl, 2-thiazolylmethyl, 4-thiazolylmethyl, 5-thiazolylmethyl, 2-methylthiazol-4-ylmethyl, 2-methlythiazol-5-ylmethyl, 2,5-dimethylthiazol-4-ylmethyl, 4-methylthiazol-2-ylmethyl, 2,4-dimethylthiazol-5-ylmethyl, 2-isothiazolylmethyl, 2-pyrrolinylmethyl, pyrrolidinylmethyl, piperidylmethyl, 4-piperidylmethyl, 1-methylpiperidin-4-ylmethyl, 4-hydroxypiperidinomethyl, 3-hydroxypyrrolidinylmethyl, 2-(4-hydroxypiperidino) ethyl, 1-(tert-butoxycarbonyl)piperidin-4-ylmethyl, 1-acetylpiperidin-4-ylmethyl, 1-methylsulfonylpiperidin-4-ylmethyl, piperazinylmethyl, morpholinomethyl, thiomorpholinylmethyl, 1-tetrahydropyranylmethyl, 2-quinolylmethyl, 1-isoquinolylmethyl and the like.

The heterocyclic moiety is preferably a heterocyclic group which is a 5-membered or 6-membered monocyclic group. Examples thereof include pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isoxazolyl, thiazolyl, isothiazolyl, thiadiazolyl, pyrrolidinyl, piperidyl, piperazinyl, morpholinyl, thiomorpholinyl and tetrahydropyranyl, and the alkyl moiety thereof is preferably straight chain alkyl having 1 to 4 carbon atoms. The group B here is preferably the above-defined halogen atom, the above-defined $C_{1-6}$ alkyl, the above-defined halogenated $C_{1-6}$ alkyl, the above-defined $C_{1-6}$ alkanoyl, $-(CH_2)_r-COOR^{b1}$, $-(CH_2)_r-CONR^{b1}R_{b2}$ or $-(CH_2)_r-OR^{b1}$.

Examples of heterocycle $C_{1-6}$ alkyl optionally substituted by 1 to 5 substituent(s) selected from group B preferably include 2-pyridylmethyl, 3-pyridylmethyl, 2-chloropyridin-4-ylmethyl, 4-pyridylmethyl, piperidin-4-ylmethyl, 1-methylpiperidin-4-ylmethyl, 2-(4-hydroxypiperidino) ethyl, 1-acetylpiperidin-4-ylmethyl, 1-(tert-butoxycarbonyl) piperidin-4-ylmethyl, 1-(methylsulfonyl)-piperidin-4-ylmethyl, 2-thiazolylmethyl, 4-thiazolylmethyl, 2-methylthiazolin-4-ylmethyl, 2,4-dimethylthiazolin-5-ylmethyl and 4-methylthiazol-2-ylmethyl. Particularly preferably, it is 2-pyridylmethyl, 3-pyridylmethyl, 2-chloropyridin-4-ylmethyl, 4-pyridylmethyl, piperidin-4-ylmethyl, 1-methylpiperidin-4-ylmethyl, 2-(4-hydroxypiperidino)ethyl, 1-acetylpiperidin-4-ylmethyl, 1-(tert-butoxycarbonyl)piperidin-4-ylmethyl, 1-(methylsulfonyl)piperidin-4-ylmethyl, 2-methylthiazolin-4-ylmethyl, 2,4-dimethylthiazolin-5-ylmethyl or 4-methylthiazol-2-ylmethyl at $R^{a20}$, 2-pyridylmethyl at $R^{a22}$ and $R^{a23}$, and 4-pyridylmethyl or 4-methylthiazol-2-ylmethyl at $R^{a27}$ and $R^{a28}$.

The heterocycle $C_{1-6}$ alkyl optionally substituted by 1 to 5 substituent(s) selected from group D is that wherein the above-defined heterocycle $C_{1-6}$ alkyl is optionally substituted by 1 to 5 substituent(s), and includes unsubstituted heterocycle $C_{1-6}$ alkyl. The substituent(s) is(are) selected from the above-mentioned group D (substituents shown under (a) to (q)).

Examples of group D here include fluorine atom, chlorine atom, bromine atom, nitro, cyano, methyl, ethyl, propyl, isopropyl, tert-butyl, trifluoromethyl, hydroxymethyl, 2-hydroxyethyl, methoxymethyl, 2-carboxylethyl, methoxycarbonylmethyl, ethoxycarbonylmethyl, acetyl, carboxyl, methoxycarbonyl, ethoxycarbonyl, carbamoyl, methylaminocarbonyl, isopropylaminocarbonyl, dimethylaminocarbonyl, diethylaminocarbonyl, (2-hydroxyethyl)aminocarbonyl, (carboxylmethyl) aminocarbonyl, hydroxyl group, methoxy, ethoxy, isopropyloxy, hydroxymethyloxy, carboxylmethyloxy, (dimethylaminocarbonyl)methyloxy, amino, methylamino, dimethylamino, diethylamino, acetylamino, methylsulfonylamino, methyltiio, methylsulfonyl, methylsulfinyl, aminosulfonyl, methylaminosulfonyl and dimethylaminosulfonyl.

Examples of heterocycle $C_{1-6}$ alkyl optionally substituted by 1 to 5 substituent(s) selected from group D include 2-pyridylmethyl, 3-pyridylmethyl, 2-chloropyridin-4-ylmethyl, 4-pyridylmethyl, pyrrolylmethyl, imidazolylmethyl, 2-thienylmethyl, 3-thienylmethyl, 2-furylmethyl, 2-oxazolylmethyl, 5-isothiazolylmethyl, 2-methyloxazol-4-ylmethyl, 2-thiazolylmethyl, 4-thiazolylmethyl, 5-thiazolylmethyl, 2-methylthiazol-4-ylmethyl, 2-methylthiazol-5-ylmethyl, 2,5-dimethylthiazol-4-ylmethyl, 4-methylthiazol-2-ylmethyl, 2,4-dimethylthiazol-5-ylmethyl, 2-isothiazolylmethyl, 2-pyrrolinylmethyl, pyrrolidinylmethyl, piperidylmethyl, 4-piperidylmethyl, 1-methylpiperidin-4-ylmethyl, 4-hydroxypiperidinomethyl, 2-(4-hydroxypiperidino)ethyl, 1-(tert-butoxycarbonyl)piperidin-4-ylmethyl, 1-acetylpiperidin-4-ylmethyl, 1-methylsulfonylpiperidin-4-ylmethyl, piperazinylmethyl, morpholinomethyl, thiomorpholinylmethyl, 1-tetrahydropyranylmethyl, 2-quinolylmethyl, 1-isoquinolylmethyl, and the like.

Preferable heterocyclic moiety at Z and Z' is heterocylic group which is 5-membered or 6-membered monocyclic group. Examples of the heterocyclic moiety include pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isooxazolyl, thiazolyl, isothiazolyl, thiadiazolyl, pyrrolidinyl, piperidyl, piperazinyl, morpholinyl, thiomorpholinyl and tetrahydropyranyl, and the alkyl moiety is preferably straight chain alkyl having 1 to 4 carbon atoms, particularly methyl (i.e., methylene).

Preferable group D is the above-defined halogen atom, nitro, the above-defined optionally substituted $C_{1-6}$ alkyl, $(CH_2)_t$—COOR$^{a19}$, —$(CH_2)_t$—CONR$^{a27}$R$^{a28}$, —$(CH_2)_t$—$(CH_2)_t$OR$^{a20}$, —$(CH_2)_t$—NR$^{a29}$CO—R$^{a24}$, —$(CH_2)_t$—S(O)$_a$—R$^{a25}$ or —$(CH_2)_t$—SO$_2$—NHR$^{a26}$.

Preferable examples of heterocycle $C_{1-6}$ alkyl optionally substituted by 1 to 5 substituent(s) selected from group D include 2-pyridylmethyl, 3-pyridylmethyl, 2-chloropyridin-4-ylmethyl, 4-pyridylmethyl, piperidin-4-ylmethyl, 1-methylpiperidin-4-ylmethyl, 4-hydroxypiperidinomethyl, 2-(4-hydroxypiperidino)ethyl, 1-acetylpiperidin-4-ylmethyl, 1-(tert-butoxycarbonyl)piperidin-4-ylmethyl, 1-(methylsulfonyl)piperidin-4-ylmethyl, 2-thiazolylmethyl, 4-thiazolylmethyl, 2-methylthiazolin-4-ylmethyl, 2,4-dimethylthiazolin-5-ylmethyl and 4-methylthiazol-2-ylmethyl.

Particularly preferred is 4-hydroxypiperidinomethyl.

The $C_{3-8}$ cycloalkyl $C_{1-6}$ alkyl optionally substituted by 1 to 5 substituent(s) selected from the above group B is that wherein the above-defined $C_{3-8}$ cycloalkyl $C_{1-6}$ alkyl is optionally substituted by 1 to 5 substituent(s), and includes unsubstituted cycloalkylalkyl. The substituents are selected from the above group B.

Specific examples thereof include cyclopropylmethyl, cyclobutylmethyl, cyclopentylmethyl, cyclohexylmethyl, 2-(cyclopentyl)ethyl, 2-(cyclohexyl)ethyl, cycloheptylmethyl, 4-fluorocyclohexylmethyl, 2-methylcyclopentylmethyl, 3-methylcyclohexylmethyl, 4-methylcyclohexylmethyl, 4,4-dimethylcyclohexylmethyl, 3,5-dimethylcyclohexylmethyl, 4-tert-butylcyclohexylmethyl, 4-hydroxycyclohexylmethyl, 4-methoxycyclohexylmethyl and 2,3,4,5,6-pentafluorocyclohexylmethyl.

Also exemplified are those wherein cyclopentylmethyl or cyclohexylmethyl is substituted by fluorine atom, chlorine atom, bromine atom, nito, methyl, tert-butyl, carboxyl, trifluoromethyl, hydroxymethyl, methoxymethyl, 2-carboxylethyl, methoxy, carbamoyl, methylthio, dimethylaminocarbonyl, methylsulfonyl or acetylamino.

At cycloalkyl moiety, it is preferably cyclopentylmethyl or cyclohexylmethyl, and at $R^{a20}$, $R^{a27}$ and $R^{a28}$, it is particularly preferably cyclohexylmethyl.

The carboxyl-protecting group only needs to be suitable for reaction conditions, and is capable of protecting and deprotecting and may be, for example, methyl; substituted methyl group such as methoxymethyl, methylthiomethyl, 2-tetrahydropyranyl, methoxyethoxymethyl, benzyloxymethyl, phenacyl, diacylmethyl, phthalimidomethyl etc.; ethyl; substituted ethyl group such as 2,2,2-trichloroethyl, 2-chloroethyl, 2-(trimethylsilyl)ethyl, 2-methylthioethyl, 2-(p-toluenesulfonyl)ethyl, t-butyl etc.; benzyl; substituted benzyl group such as diphenylmethyl, triphenylmethyl, p-nitrobenzyl, 4-picolyl, p-methoxybenzyl, 2-(9,10-dioxo)anthrylmethyl etc.; silyl group such as trimethylsilyl, t-butyldimethylsilyl, phenyldimethylsilyl etc.; and the like.

Preferred are industrially effective protecting groups and specifically preferred as $R^{a36}$ are methyl and ethyl.

In formula [I], X is preferably

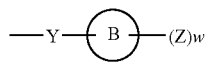

wherein each symbol is as defined above.

$G^1$, $G^2$, $G^3$ and $G^4$ are each preferably (C—$R^1$), (C—$R^2$), (C—$R^3$) and (C—$R^4$), $G^5$ is preferably a nitrogen atom, and $G^6$, $G^8$ and $G^9$ are preferably a carbon atom. $G^7$ is preferably C(—$R^7$) or unsubstituted nitrogen atom, wherein $R^7$ is preferably hydrogen atom.

A preferable combination is $G^2$ of (C—$R^2$) and $G^6$ of a carbon atom, particularly preferably $G^2$ of (C—$R^2$), $G^6$ of a carbon atom and $G^5$ of a nitrogen atom, most preferably $G^2$ of (C—$R^2$), $G^6$ of a carbon atom, $G^5$ of a nitrogen atom and $G^7$ of unsubstituted nitrogen atom.

In formulas [I] and [II], 1 to 4 of $G^1$ to $G^9$ in the moiety

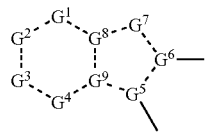

is(are) preferably a nitrogen atom, specifically preferably

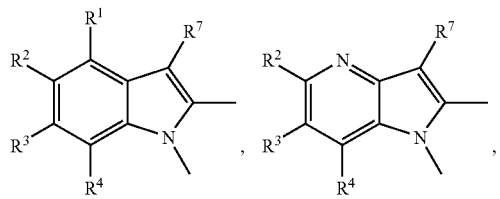

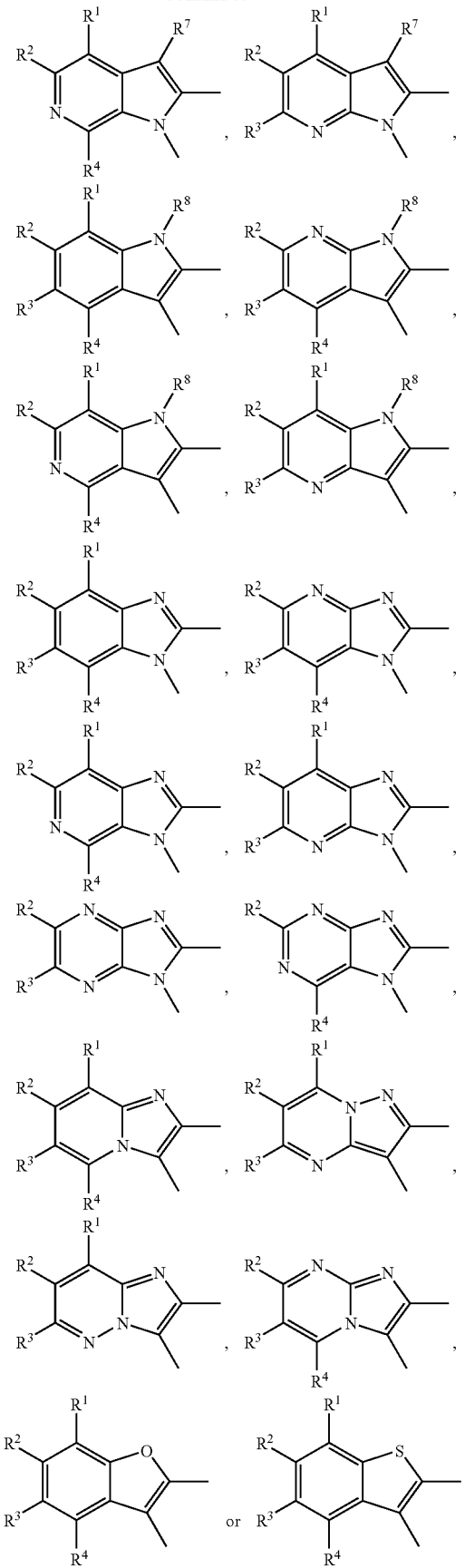

particularly preferably

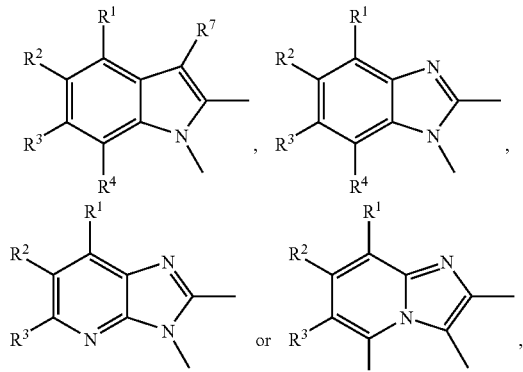

more preferably

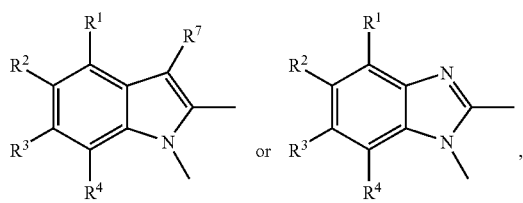

most preferably

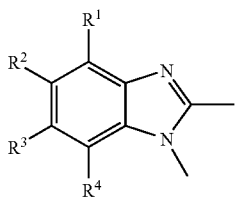

It is also a preferable embodiment wherein the moiety is aromatic ring.

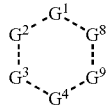

$R^1$ and $R^3$ are preferably hydrogen atom or —$OR^{a6}$ ($R^{a6}$ is as defined above), particularly preferably hydrogen atom. $R^2$ is preferably carboxyl, —$COOR^{a1}$, —$CONR^{a2}R^{a3}$, —$SO_2R^{a7}$ (each symbol is as defined above) or heterocyclic group having 1 to 4 heteroatom(s) selected from an oxygen atom, a nitrogen atom and a sulfur atom, particularly preferably carboxyl, —$COOR^{a1}$ or —$SO_2R^{a7}$, more preferably carboxyl or —$COOR^{a1}$, most preferably carboxyl. $R^4$ is preferably hydrogen atom.

$R^{a1}$ is preferably optionally substituted $C_{1-6}$ alkyl.

When $R^2$ is carboxyl or —$COOR^{a1}$, at least one of $R^1$, $R^3$ and $R^4$ is preferably hydroxyl group, halogen atom (particularly fluorine atom, chlorine atom) or —$OR^{a6}$ (wherein $R^{a6}$ is preferably hydrogen atom or methyl).

The ring Cy and ring Cy' are preferably cyclopentyl, cyclohexyl, cycloheptyl, tetrahydrothiopyranyl or piperidino, particularly preferably cyclopentyl, cyclohexyl or cycloheptyl, more preferably cyclohexyl.

The ring A and ring A' are preferably phenyl, pyridyl, pyrazinyl, pyrimidinyl, pyridazinyl, cyclohexyl, cyclohexenyl, furyl or thienyl, particularly preferably phenyl, pyridyl, pyrazinyl, pyrimidinyl or pyridazinyl, more preferably phenyl or pyridyl, and most preferably phenyl.

The ring B and ring B' are preferably $C_{1-6}$ aryl or heterocyclic group, specifically preferably, phenyl, pyridyl, pyrazinyl, pyrimidinyl, pyridazinyl, 1,3,5-triazinyl, pyrrolyl, pyrazolyl, imidazolyl, 1,2,4-triazolyl, tetrazolyl, thienyl, furyl, oxazolyl, isoxazolyl, thiazolyl, isothiazolyl or thiadiazolyl, particularly preferably phenyl, pyridyl, pyrimidinyl, 1,3,5-triazinyl or thiazolyl, more preferably, phenyl, pyridyl or thiazolyl, and most preferably phenyl or thiazolyl.

With regard to $R^5$ and $R^6$, one of them is preferably hydrogen atom and the other is halogen atom, particularly fluorine atom. Alternatively, the both are preferably hydrogen atoms. When ring A is phenyl, $R^5$ and $R^6$ preferably are present at an ortho position from $G^6$. The same applies to $R^5'$ and $R^{6'}$.

Y is preferably —$(CH_2)_m$—O—$(CH_2)_n$—, —$NHCO_2$—, —$CONH$—$CHR^{a14}$—, —$(CH_2)_m$—$NR^{a12}$—$(CH_2)_n$—, —$CONR^{a13}$—$(CH_2)_n$—, —O—$(CH_2)_m$—$CR^{a15}R^{a16}$—$(CH_2)_n$— or —$(CH_2)_n$—$NR^{a12}$—$CHR^{a15}$— (each symbol is as defined above), more preferably, —$(CH_2)_m$—O—$(CH_2)_n$— or —O—$(CH_2)_m$—$CR^{a15}R^{a16}$—$(CH_2)_n$—, most preferably —$(CH_2)_m$—O—$(CH_2)_n$—.

The l, m and n are preferably 0 or an integer of 1 to 4, particularly preferably 0, 1 or 2, at Y. In —$(CH_2)_m$—O—$(CH_2)_n$—, m=n=0 or m=0 and n=1 is more preferable, most preferably m=0 and n=1. In —O—$(CH_2)_m$—$CR^{a15}R^{a16}$—$(CH_2)_n$—, m=n=0, m=0 and n=1, m=1 and n=0 or m=1 and n=1 is more preferable, most preferably m=0 and n=1.

When Y is —O—$(CH_2)_m$—$CR^{a15}R^{a16}$—$(CH_2)_n$—, $R^{a16}$ is preferably hydrogen atom, $R^{a15}$ is preferably

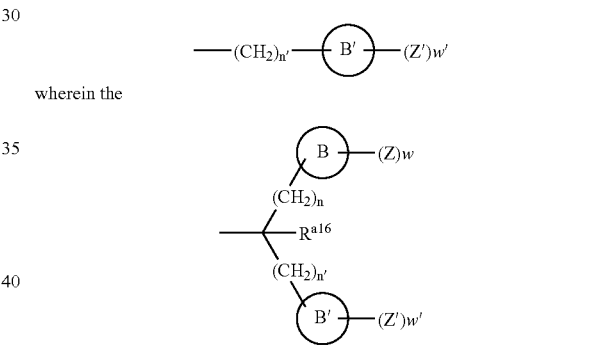

wherein the moiety is preferably symmetric. The preferable mode of n, ring B, Z and w and the preferable mode of n', ring B', Z' and w' are the same.

When ring A is phenyl, X or Y is preferably present at the para-position relative to $G^6$. When ring B and ring B' are phenyl, Z is preferably present at the ortho or meta-position relative to Y. It is preferable that the 3-position on phenyl have one substituent or the 2-position and the 5-position on phenyl each have one substituent.

When ring B is bonded to Y as pyridin-2-yl, Z is preferably substituted at the 3-position and 6-position of pyridyl; when it is bonded to Y as pyridin-3-yl, Z is preferably substituted at the 2-position and 5-position of pyridyl; and when it is bonded to Y as pyridin-4-yl, Z is preferably substituted at the 2-position and 5-position of pyridyl.

When ring B is thiazolyl, Y is preferably substituted at the 5-position, and Z is preferably substituted at the 2-position, the 4-position or the 2-position and the 4-position. Similarly, when ring B' is thiazolyl, $(CH_2)_n$ is also preferably substituted at the 5-position, and Z' is preferably substituted at the 2-position, the 4-position or the 2-position and the 4-position.

Z and Z' are preferably group D, "$C_{6-14}$ aryl optionally substituted by 1 to 5 substituent(s) selected from group D"

or "heterocyclic group optionally substituted by 1 to 5 substituent(s) selected from group D", particularly preferably group D or "$C_{6-14}$ aryl optionally substituted by 1 to 5 substituent(s) selected from group D".

More preferably, they are the above-defined halogen atom, nitro, the above-defined optionally substituted $C_{1-6}$ alkyl, —$(CH_2)_t$—$COOR^{a19}$, —$(CH_2)_t$—$CONR^{a27}R^{a28}$, —$(CH_2)_t$—$OR^{a20}$, —$(CH_2)_t$—$NR^{a29}CO$—$R^{a24}$, —$(CH_2)_t$—$S(O)_q$—$R^{a25}$ or —$(CH_2)_t$—$SO_2$—$NHR^{a26}$, or $C_{6-14}$ aryl or heterocyclic group optionally substituted by these.

With regard to Z and Z', the preferable mode of group D that directly substitutes each ring B and ring B' and the preferable mode of group D that substitutes $C_{6-14}$ aryl, $C_{3-8}$ cycloalkyl, $C_{6-14}$ aryl $C_{1-6}$ alkyl or heterocyclic group are the same, wherein they may be the same with or different from each other.

Specific examples of the substituent preferably include fluorine atom, chlorine atom, bromine atom, nitro, cyano, methyl, ethyl, propyl, isopropyl, tert-butyl, trifluoromethyl, hydroxymethyl, 2-hydroxyethyl, methoxymethyl, 2-carboxylethyl, methoxycarbonylmethyl, ethoxycarbonylmethyl, carbamoylmethoxymethyl, (dimethylaminocarbonyl)methoxymethyl, acetyl, isovaleryl, carboxyl, methoxycarbonyl, ethoxycarbonyl, carbamoyl, methylaminocarbonyl, hydroxyaminocarbonyl, ethylaminocarbonyl, propylaminocarbonyl, isopropylaminocarbonyl, butylaminocarbonyl, isobutylaminocarbonyl, tert-butylaminocarbonyl, (4-hydroxybutyl)aminocarbonyl, (1-hydroxypropan-2-yl)aminocarbonyl, (2,3-dihydroxypropyl)aminocarbonyl, (1,3-dihydroxypropan-2-yl)aminocarbonyl, methoxyaminocarbonyl, {2-[2-(methoxy)ethoxy]ethyl}aminocarbonyl, N-ethyl-N-methylaminocarbonyl, N-methyl-N-propylaminocarbonyl, N-isopropyl-N-methylaminocarbonyl, dimethylaminocarbonyl, diethylaminocarbonyl, (2-hydroxyethyl)aminocarbonyl, (2-hydroxy-2-methylpropan-2-yl)aminocarbonyl, (carboxylmethyl)aminocarbonyl, hydroxyl group, methoxy, ethoxy, propyloxy, isopropyloxy, butyloxy, isopentyloxy, 2-isopentenyloxy, 3-isohexenyloxy, 4-methyl-3-pentenyloxy, 2-propynyloxy, trifluoromethyloxy, hydroxymethyloxy, carboxylmethyloxy, (dimethylaminocarbonyl)methyloxy, amino, methylamino, dimethylamino, diethylamino, acetylamino, N-acetyl-N-methylamino, N-acetyl-N-ethylamino, N-acetyl-N-propylamino, N-acetyl-N-isopropylamino, N-ethylcarbonyl-N-methylamino, N-ethyl-N-(ethylcarbonyl)amino, ureido, isopropylcarbonylamino, isobutylcarbonylamino, tert-butylcarbonylamino, (ethylamino)carbonylamino, (isopropylamino)carbonylamino, (dimethylamino) carbonylamino, (4-hydroxypiperidino)carbonylamino, [(4-hydroxypiperidino)methyl]carbonylamino, [(3-hydroxypyrrolidinyl)methyl]carbonylamino, methylsulfonylamino, isopropylsulfonylamino, N-(methylsulfonyl)-N-methylamino, N-(ethylsulfonyl)-N-methylamino, N-(isopropylsulfonyl)-N-methylamino, N-(methylsulfonyl)-N-ethylamino, N-(methylsulfonyl)-N-propylamino, N-(ethylsulfonyl)-N-ethylamino, methylthio, methylsulfonyl, isopropylsulfonyl, isobutylsulfonyl, methylsulfinyl, isopropylsulfinyl, aminosulfonyl, methylaminosulfonyl, dimethylaminosulfonyl, isopropylaminosulfonyl, tert-butylaminosulfonyl, hydroxyamidino, phenyl, 3-fluorophenyl, 4-fluorophenyl, 3-chlorophenyl, 4-chlorophenyl, 2,4-difluorophenyl, 3,4-difluorophenyl, 3,4-dichlorophenyl, 3,5-dichlorophenyl, 4-chloro-3-fluorophenyl, 4-chloro-2-fluorophenyl, 4-bromophenyl, 4-nitrophenyl, 4-cyanophenyl, 4-methylphenyl, 4-ethylphenyl, 4-propylphenyl, 4-isopropylphenyl, 4-tert-butylphenyl, 2-trifluoromethylphenyl, 4-trifluoromethylphenyl, 4-(hydroxymethyl)phenyl, 4-(2-hydroxyethyl)phenyl, 4-(methoxymethyl)phenyl, 4-(2-carboxylethyl)phenyl, 4-(methoxycarbonylmethyl)phenyl, 4-(ethoxycarbonylmethyl)phenyl, 4-acetylphenyl, 3-carboxylphenyl, 4-carboxylphenyl, 4-(methoxycarbonyl)phenyl, 4-(ethoxycarbonyl)phenyl, 4-carbamoylphenyl, 4-(methylaminocarbonyl)phenyl, 4-(isopropylaminocarbonyl)phenyl, 4-(dimethylaminocarbonyl)phenyl, 4-(diethylaminocarbonyl)phenyl, 4-[(2-hydroxyethyl)aminocarbonyl]phenyl, 4-[(carboxylmethyl)aminocarbonyl]phenyl, 4-hydroxyphenyl, 4-methoxyphenyl, 3,4,5-trimethoxyphenyl, 4-ethoxyphenyl, 4-propyloxyphenyl, 4-isopropyloxyphenyl, 4-butyloxyphenyl, 4-isopentyloxyphenyl, 4-(2-isopentenyloxy)phenyl, 4-(3-isohexenyloxy)phenyl, 4-(4-methyl-3-pentenyloxy)phenyl, 4-(2-propynyloxy)phenyl, 4-(trifluoromethyloxy)phenyl, 4-(hydroxymethyloxy)phenyl, 4-(carboxylmethyloxy)phenyl, 4-[(dimethylaminocarbonyl)methyloxy]phenyl, 4-aminophenyl, 4-(methylamino)phenyl, 4-(dimethylaminophenyl), 4-(diethylamino)phenyl, 4-(acetylamino)phenyl, N-acetyl-N-methylamino, 4-(N-acetyl-N-methylamino)phenyl, 4-(N-acetyl-N-ethylamino)phenyl, 4-(N-acetyl-N-propylamino)phenyl, 4-(N-acetyl-N-isopropylamino)phenyl, 4-(N-ethylcarbonyl-N-methylamino)phenyl, 4-[N-ethyl-N-(ethylcarbonyl)amino]phenyl, 4-(methylsulfonylamino)phenyl, 4-(methylthio)phenyl, 4-(methylsulfonyl)phenyl, 4-(methylsulfinyl)phenyl, 4-(aminosulfonyl)phenyl, 4-(methylaminosulfonyl)phenyl, 4-(dimethylaminosulfonyl)phenyl, 4-(tert-butylaminosulfonyl)phenyl, tetrazol-5-ylphenyl, cyclohexyl, benzyl, 4-chlorobenzyl, phenethyl, benzyloxy, 4-fluorobenzyloxy, 2-chlorobenzyloxy, 3-chlorobenzyloxy, 4-chlorobenzyloxy, 4-tert-butylbenzyloxy, 4-trifluoromethylbenzyloxy, phenethyloxy, 2-thienyl, 2-thiazolyl, 2-pyridyl, 3-pyridyl, 4-pyridyl, 6-fluoropyridin-3-yl, 5-fluoropyridin-2-yl, 6-chloropyridin-3-yl, 6-methylpyridin-3-yl, 2-pyrimidinyl, 5-tetrazolyl, piperidino, 2-oxopiperidin-1-yl, 2-oxopyrrolidin-1-yl, 2-imidazolin-2-yl, 2-oxoimidazolidin-1-yl, 2-oxooxazolidin-1-yl, 2-methylthiazol-4-yl, 5-methylthiazol-2-yl, 2-aminothiazol-4-yl, 3-methyl-1,2,4-oxadiazol-5-yl, 1,1-dioxoisothiazolidin-2-yl, 4,4-dimethyl-$\Delta^2$-oxazolin-2-yl, 5-chlorothiophen-2-yl, 5-methyloxazol-2-yl, 5-oxo-$\Delta^2$-1,2,4-oxadiazolin-3-yl, 5-oxo-$\Delta^2$-1,2,4-thiadiazolin-3-yl, 2-oxo-3H-1,2,3,5-oxathiadiazolin-4-yl, 4-hydroxypiperidinomethyl, piperidinocarbonyl, 4-hydroxypiperidinocarbonyl, 3,4-dihydroxypiperidinocarbonyl, 1-piperazinylcarbonyl, 1-pyrrolidinylcarbonyl, morpholinocarbonyl, 4-thiomorpholinylcarbonyl, phenoxy, 2,4-dichlorophenoxy, tetrahydropyranyloxy, 2-pyridylmethyloxy, 3-pyridylmethyloxy, 2-chloropyridin-4-ylmethyloxy, 4-pyridylmethyloxy, 2-piperidylmethyloxy, 3-piperidylmethyloxy, 4-piperidylmethyloxy, 1-methylpiperidin-4-ylmethyloxy, 1-acetylpiperidin-4-ylmethyloxy, 1-(tert-butoxycarbonyl)piperidin-4-ylmethyloxy, 1-(methylsulfonyl)piperidin-4-ylmethyloxy, 2-methylthiazolin-4-yloxy, 2,4-dimethylthiazolin-5-yloxy, dimethylaminocarbonylmethyloxy, piperidinocarbonylmethyloxy, 4-hydroxypiperidinocarbonylmethyloxy, 2-methylthiazol-4-yl, (2-methylthiazol-4-yl)methyloxy, (2,4-dimethylthiazol- 5-yl)methyloxy, benzoyl, 3-fluorobenzoyl, 4-chlorobenzylamino, 3,5-dichlorobenzylamino, 4-trifluoromethylbenzylamino, 2-pyridylmethylamino, benzoylamino, 4-chlorobenzoylamino, 4-trifluoromethylbenzoylamino, 3,5-dichlorobenzoylamino, 3-nitro-4-methoxybenzoylamino, 4-nitro-3-methoxybenzoylamino, 3-pyridylcarbonylamino, 4-morpholinocarbonylamino, 2-oxazolinylamino, 4-hydroxypiperidinosulfonyl, methylphenylsulfonylamino, 2-thiazolylaminosulfonyl, 2-pyridylaminosulfonyl, benzylaminocarbonyl, N-benzyl-N-methylaminocarbonyl, (4-pyridylmethyl)aminocarbonyl or (cyclohexylmethyl) aminocarbonyl, 2-hydroxyethyloxy, 3-hydroxypropyloxy, 2-methoxyethoxy, 2-(2-methoxyethoxy)ethoxy, azetidinylcarbonyl, 3-hydroxypyrrolidinylcarbonyl, 3-hydroxypiperidinocarbonyl, 4-hydroxypiperidinocarbonyl, 3,4-dihydroxypiperidinocarbonyl, 4-methoxypiperidinocarbonyl, 4-carboxypiperidinocarbonyl, 4-(hydroxymethyl) piperidinocarbonyl, 2-oxopiperidinocarbonyl, 4-oxopiperidinocarbonyl, 2,6-dimethylpiperidinocarbonyl, 2,2,6,6-tetramethylpiperidinocarbonyl, 2,2,6,6-tetramethyl-4-hydroxypiperidinocarbonyl, 1-oxothiomorpholin-4-ylcarbonyl, 1,1-dioxothiomorpholin-4-ylcarbonyl, 1-(methylsulfonyl)piperidin-4-ylaminocarbonyl, 4-methylsulfonylpiperazinylcarbonyl, 4-methylpiperazinylcarbonyl, N,N-bis(2-hydroxyethyl) aminocarbonyl, phenylaminocarbonyl, cyclopropylaminocarbonyl, cyclobutylaminocarbonyl, cyclohexylaminocarbonyl, 4-hydroxycyclohexylaminocarbonyl, 4-methylthiazol-2-ylmethylaminocarbonyl, 2-(4-hydroxypiperidino)ethyloxy, 2-pyridylmethylaminocarbonyl, 3-pyridylmethylaminocarbonyl, N-methyl-N-(4-pyridylmethyl)aminocarbonyl, cyclohexylmethyloxy, 4-hydroxypiperidinocarbonylmethyloxy and 4-methylthiazol-2-ylmethyloxy.

Particularly preferable examples of the substituent include fluorine atom, chlorine atom, bromine atom, nitro, cyano, methyl, hydroxymethyl, carboxyl, carbamoyl, methylaminocarbonyl, isopropylaminocarbonyl, dimethylaminocarbonyl, diethylaminocarbonyl, (2-hydroxylethyl)aminocarbonyl, (carboxymethyl) aminocarbonyl, methoxy, 2-isopentenyloxy, 2-propynyloxy, methylthio, methylamino, dimethylamino, acetylamino, N-acetyl-N-methylamino, N-acetyl-N-ethylamino, N-acetyl-N-propylamino, N-acetyl-N-isopropylamino, N-ethylcarbonyl-N-methylamino, N-ethyl-N-(ethylcarbonyl)amino, methylsulfonylamino, methylsulfonyl, aminosulfonyl, dimethylaminosulfonyl, tert-butylaminosulfonyl, phenyl, 3-fluorophenyl, 4-fluorophenyl, 3-chlorophenyl, 4-chlorophenyl, 3,5-dichlorophenyl, 4-nitrophenyl, 4-methylphenyl, 4-tert-butylphenyl, 4-trifluoromethylphenyl, 4-(methoxymethyl) phenyl, 4-(2-hydroxylethyl)phenyl, 3-carboxylphenyl, 4-carboxylphenyl, 4-methoxyphenyl, 4-carbamoylphenyl, 4-methylthiophenyl, 4-(dimethylaminocarbonyl)phenyl, 4-methylsulfonylphenyl, benzyl, phenethyl, benzyloxy, 4-fluorobenzyloxy, 4-chlorobenzyloxy, 2-thiazolyl, 3-pyridyl, 4-pyridyl, 4-pyridylmethyloxy, 2-piperidylmethyloxy, 3-piperidylmethyloxy, 4-piperidylmethyloxy, 1-methylpiperidin-4-ylmethyloxy, 1-acetylpiperidin-4-ylmethyloxy, 2-chloropiperidin-4-ylmethyloxy, 1-(methylsulfonyl)piperidin-4-ylmethyloxy, 2-methylthiazol-4-yl, (2-methylthiazol-4-yl)methyloxy, (2,4-dimethylthiazol-5-yl)methyloxy, 5-tetrazolyl, 3-fluorobenzoyl, piperidinocarbonyl, 4-hydroxylpiperidinocarbonyl, 1-pyrrolidinylcarbonyl, morpholinocarbonyl, 4-thiomorpholinylcarbonyl, benzylaminocarbonyl, N-benzyl-N-methylaminocarbonyl, (4-pyridylmethyl)aminocarbonyl and (cyclohexylmethyl) aminocarbonyl.

Most preferable substituents are fluorine atom, chlorine atom, methyl, hydroxymethyl, carboxyl, carbamoyl, methylaminocarbonyl, dimethylaminocarbonyl, methoxy, methylamino, acetylamino, aminosulfonyl, dimethylaminosulfonyl, tert-butylaminosulfonyl, phenyl, 3-fluorophenyl, 4-fluorophenyl, 3-chlorophenyl, 4-chlorophenyl, 3,5-dichlorophenyl, 4-methylphenyl, 4-tert-butylphenyl, 4-trifluoromethylphenyl, 4-carboxylphenyl, 4-methoxyphenyl, 4-carbamoylphenyl, 4-methylthiophenyl, 4-(dimethylaminocarbonyl)phenyl, 4-methylsulfonylphenyl and 2-oxopyrrolidin-1-yl.

The w is preferably 1 or 2, r and t are preferably 0, 1 or 2, particularly preferably 0 or 1, more preferably 0, p is preferably 1, and q is preferably 0 or 2.

In formula [I], when X is

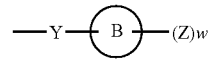

wherein each symbol is as defined above and w is 2 or above, one of Z is preferably $C_{6-14}$ aryl optionally substituted by 1 to 5 substituent(s) selected from group D or heterocyclic group optionally substituted by 1 to 5 substituent(s) selected from group D, particularly preferably $C_{6-14}$ aryl optionally substituted by 1 to 5 substituent(s) selected from group D.

When ring B is phenyl, w is 2 and phenyl is bonded to Y at the 1-position, one of the most preferable embodiments is that wherein Z is bonded to the 2-position and 5-position of phenyl, Z at the 2-position is "$C_{6-14}$ aryl optionally substituted by 1 to 5 substituent(s) selected from group D" and Z at the 5-position is "heterocyclic group optionally substituted by 1 to 5 substituent(s) selected from group D".

The pharmaceutically acceptable salt may be any as long as it forms a non-toxic salt with a compound of the above-mentioned formula [I] or [II]. Such salt can be obtained by reacting the compound with an inorganic acid, such as hydrochloric acid, sulfuric acid, phosphoric acid, hydrobromic acid and the like, or an organic acid, such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid, meglumine acid and the like, or an inorganic base, such as sodium hydroxide, potassium hydroxide, calcium hydroxide, magnesium hydroxide, ammonium hydroxide and the like, or an organic base, such as methylamine, diethylamine, triethylamine, triethanolamine, ethylenediamine, tris(hydroxymethyl) methylamine, guanidine, choline, cinchonine and the like, with an amino acid, such as lysine, arginine, alanine and the like. The present invention encompasses water-retaining product, hydrate and solvate of each compound.

The compounds of the above-mentioned formula [I] or [II] have various isomers. For example, E compound and Z compound are present as geometric isomers, and when the compound has an asymmetric carbon, an enantiomer and a diastereomer are present due to the asymmetric carbon. A tautomer may be also present. The present invention encompasses all of these isomers and mixtures thereof.

The present invention also encompasses prodrug and metabolite of each compound.

A prodrug means a derivative of the compound of the present invention, which is capable of chemical or metabolic decomposition, which shows inherent efficacy by reverting to the original compound after administration to a body, and which includes salts and complexes without a covalent bond.

When the inventive compound is used as a pharmaceutical preparation, the inventive compound is generally admixed with pharmaceutically acceptable carriers, excipients, diluents, binders, disintegrators, stabilizers, preservatives, buffers, emulsifiers, aromatics, coloring agents, sweeteners, thickeners, correctives, solubilizers, and other additives such as water, vegetable oil, alcohol such as ethanol, benzyl alcohol and the like, polyethylene glycol, glycerol triacetate, gelatin, lactose, carbohydrate such as starch and the like, magnesium stearate, talc, lanolin, petrolatum and the like, and prepared into a dosage form of tablets, pills, powders, granules, suppositories, injections, eye drops, liquids, capsules, troches, aerosols, elixirs, suspensions, emulsions, syrups and the like, which can be administered systemically or topically and orally or parenterally.

While the dose varies depending on the age, body weight, general condition, treatment effect, administration route and the like, it is from 0.1 mg to 1 g for an adult per dose, which is given one to several times a day.

The prophylaxis of hepatitis C means, for example, administration of a pharmaceutical agent to an individual found to carry an HCV by a test and the like but without a symptom of hepatitis C, or to an individual who shows an improved disease state of hepatitis after a treatment of hepatitis C, but who still carries an HCV and is associated with a risk of recurrence of hepatitis.

The therapeutic agent for hepatitis C of the present invention is expected to provide a synergestic effect when concurrently used with other antiviral agents, antiinflammatory agents or immunostimulants.

The medicaments with the prospect of synergestic effect include, for example, interferon-α, interferon-β, interferon-γ, interleukin-2, interleukin-8, interleukin-10, interleukin-12, TNFα, recombinant or modified products thereof, agonists, antibodies, vaccines, ribozymes, antisense nucleotides and the like.

As evidenced in the combination therapy of anti-HIV agents, which is also called a cocktail therapy, the combined use of various anti-virus agents againt viruses showing frequent genetic mutations is expected to show effect for suppressing emergence and increase of drug tolerant viruses. For example, 2 or 3 agents from HCV-IRES inhibitors, HCV-NS3 protease inhibitors, HCV-NS2NS3 protease inhibitors, HCV-NS5A inhibitors and HCV polymerase inhibitor may be used in combination. Specifically, the combined use with Ribavirin(R), interferon-α (IFN-α, Roferon(R), Intron A(R), Sumiferon(R), MultiFeron(R), Infergen(R), Omniferon(R), Pegasys(R), PEG-Intron A(R)), interferon-β (Frone(R), Rebif(R), AvoneX(R), IFNβMOCHIDA(R)), interferon-ω, 1-β-L-ribofuranosyl-1H-1,2,4-triazole-3-carboxamide, 16α-bromo-3β-hydroxy-5α-androstan-17-one, 1H-imidazole-4-ethanamide dihydrochloride, HCV ribozyme Heptazyme(R), polyclonal antibody Civacir(R), lactoferrin GPX-400, (1S,2R,8R,8aR)-1,2,8-trihydroxyoctahydroindolizidinium chloride, HCV vaccine (MTH-68/B, Innivax C(R), Engerix B(R)), antisense oligonucleotide ISIS-14803, HCV-RNA transcriptase inhibitor VP-50406, tetrachlorodecaoxide (high concentration Oxoferin(R)), tetrahydrofuran-3-yl (S)-N-3-[3-(3-methoxy-4-oxazol-5-ylphenyl)ureido]benzylcarbamate, 4-amino-2-ethoxymethyl-α,α-dimethyl-1H-imidazo[4,5-c]quinoline-1-ethanol, interleukin-2 (Proleukin(R)), thymosin α1 and the like is exemplified, wherein (R) shows product names.

Furthermore, the combined use with the compounds disclosed in JP-A-08-268890, JP-A-10-101591, JP-A-07-069899, WO99/61613 and the like as HCV IRES inhibitors; the compounds disclosed in WO98/22496, WO99/07733, WO99/07734, WO00/09543, WO00/09558, WO01/59929, WO98/17679, EP932617, WO99/50230, WO00/74768, WO97/43310, U.S. Pat. No. 5,990,276, WO01/58929, WO01/77113, WO02/8198, WO02/8187, WO02/8244, WO02/8256, WO01/07407, WO01/40262, WO01/64678, WO98/46630, JP-A-11-292840, JP-A-10-298151, JP-A-11-127861, JP-A-2001-103993, WO98/46597, WO99/64442, WO00/31129, WO01/32961, WO93/15730, U.S. Pat. No. 7,832,236, WO00/200400, WO02/8251, WO01/16379, WO02/7761 and the like as HCV protease inhibitors; the compounds disclosed in WO97/36554, U.S. Pat. No. 5,830,905, ,WO97/36866, U.S. Pat. No. 5,633,388, WO01/07027, WO00/24725 and the like as HCV helicase inhibitors; the compounds disclosed in WO00/10573, WO00/13708, WO00/18231, WO00/06529, WO02/06246, WO01/32153, WO01/60315, WO01/77091, WO02/04425, WO02/20497, WO00/04141 and the like as HCV polymerase inhibitors; the compounds disclosed in WO01/58877, JP-A-11-180981, WO01/12214 and the like as interferon agonists or enhancers; and the like is also exemplified.

Inasmuch as HCV is known to be a virus associated with many genetic mutations, a compound effective for many genotypes is one of the preferable modes. If a compound ensures high blood concentration when administered as a pharmaceutical agent to an animal infected with HCV, it is also one of the preferable modes. From these aspects, a compound having high inhibitory activity on both HCV type 1a and type 1b and high blood concentration, such as 2-{4-[2-(4-chlorophenyl)-5-(2-oxopyrrolidin-1-yl)benzyloxy]-2-fluorophenyl}-1-cyclohexylbenzimidazole-5-carboxylic acid hydrochloride, is particularly preferable.

The fused ring compound of the formula [I] or [II] of the present invention can be administered to mammals inclusive of human for the purpose of prevention or treatment of hepatitis C or inhibition of hepatitis C virus polymerase. The fused ring compound of the present invention can be also administered to mammals inclusive of human along with at least one pharmaceutical agent (hereinafter combination drug) selected from an antiviral agent other than the compound of the formula [I], an antiinflammatory agent and an immunostimulant for the purpose of prevention or treatment of hepatitis C or inhibition of hepatitis C virus polymerase. In the case of combined administration, the compound of the present invention can be administered simultaneously with the combination drug or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The administration route may be the same or different.

In the case of a combined administration, the compound of the present invention can be administered once a day or several times a day in a single dose of 0.1 mg to 1 g, or may be administered in a smaller dose. The combination drug can be administered in a dose generally used for the prevention or treatment of hepatitis C or in a smaller dose.

Examples of other antiviral agent include interferons (interferon α, interferon β, interferon γ etc.), Ribavirin (1-β-D-ribofuranosyl-1H-1,2,4-triazole-3-carboxamide) and the like.

Examples of the production method of the compound to be used for the practice of the present invention are given in the following. However, the production method of the compound of the present invention is not limited to these examples.

Even if no directly corresponding disclosure is found in the following Production Methods, the steps may be modified for efficient production of the compound, such as introduction of a protecting group into a functional group with deprotection in a subsequent step, and changing the order of Production Methods and steps.

The treatment after reaction in each step may be conventional ones, for which typical methods, such as isolation and purification, crystallization, recrystallization, silica gel chromatography, preparative HPLC and the like, can be appropriately selected and combined.

Production Method 1

In this Production Method, a benzimidazole compound is formed from a nitrobenzene compound.

Production Method 1-1

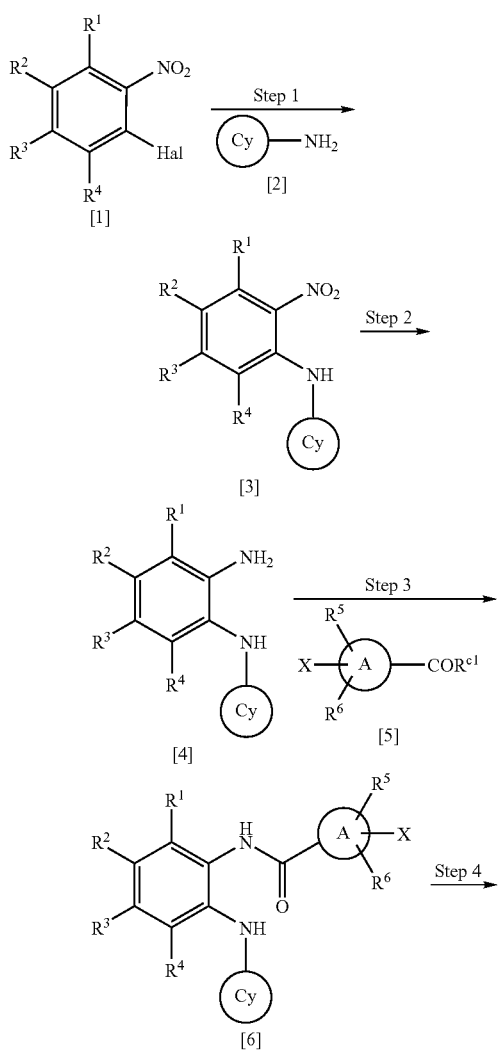

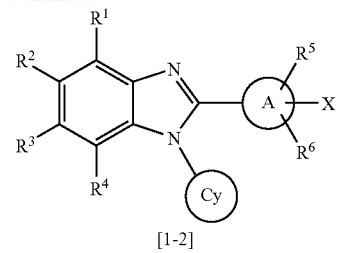

wherein Hal is halogen atom, such as chlorine atom, bromine atom and the like, $R^{el}$ is halogen atom, such as chlorine atom, bromine atom and the like, or hydroxyl group, and other symbols are as defined above.

Step 1

A compound [1] obtained by a conventional method or a commercially available compound [1] is reacted with amine compound [2] in a solvent such as N,N-dimethylformamide (DMF), acetonitrile, tetrahydrofuran (THF), toluene and the like in the presence or absence of a base such as potassium carbonate, triethylamine, potassium t-butoxide and the like at room temperature or with heating to give compound [3].

Step 2

The compound [3] is hydrogenated in a solvent such as methanol, ethanol, THF, ethyl acetate, acetic acid, water and the like in the presence of a catalyst such as palladium carbon, palladium hydroxide, platinum oxide, Raney nickel and the like at room temperature or with heating to give compound [4]. In addition, compound [3] is reduced with a reducing agent such as zinc, iron, tin(II) chloride, sodium sulfite and the like, or reacted with hydrazine in the presence of iron(III) chloride to give compound [4]. The compound [4] can be also obtained by reacting compound [3] with sodium hydrosulfite under alkaline conditions.

Step 3

The compound [4] is condensed with carboxylic acid compound [5] in a solvent such as DMF, acetonitrile, THF, chloroform, ethyl acetate, methylene chloride, toluene and the like using a condensing agent such as dicyclohexylcarbodiimide, 1-ethyl-3-(3-dimethylaminopropyl)carbodiimide hydrochloride, diphenylphosphoryl azide and the like and, where necessary, adding N-hydroxysuccinimide, 1-hydroxybenzotriazole and the like to give amide compound [6]. Alternatively, amide compound [6] can be obtained from compound [5] as follows. The carboxylic acid compound [5] is converted to an acid halide derived with thionyl chloride, oxalyl chloride and the like, or an active ester (e.g., mixed acid anhydride derived with ethyl chlorocarbonate and the like), which is then reacted in the presence of a base, such as triethylamine, potassium carbonate, pyridine and the like, or in an amine solvent, such as pyridine and the like, to give amide compound [6].

Step 4

The compound [6] is heated in a solvent such as ethanol, methanol, toluene, DMF, chloroform and the like or without a solvent in the presence of an acid such as acetic acid, formic acid, hydrochloric acid, dilute sulfuric acid, phosphoric acid, polyphosphoric acid, p-toluenesulfonic acid and the like, a halogenating agent such as zinc chloride, phosphorus oxychloride, thionyl chloride and the like or acid anhydride such as acetic anhydride and the like, to allow cyclization to give compound [I-2].

Production Method 1-2

This Production Method is an alternative method for producing compound [I-2].

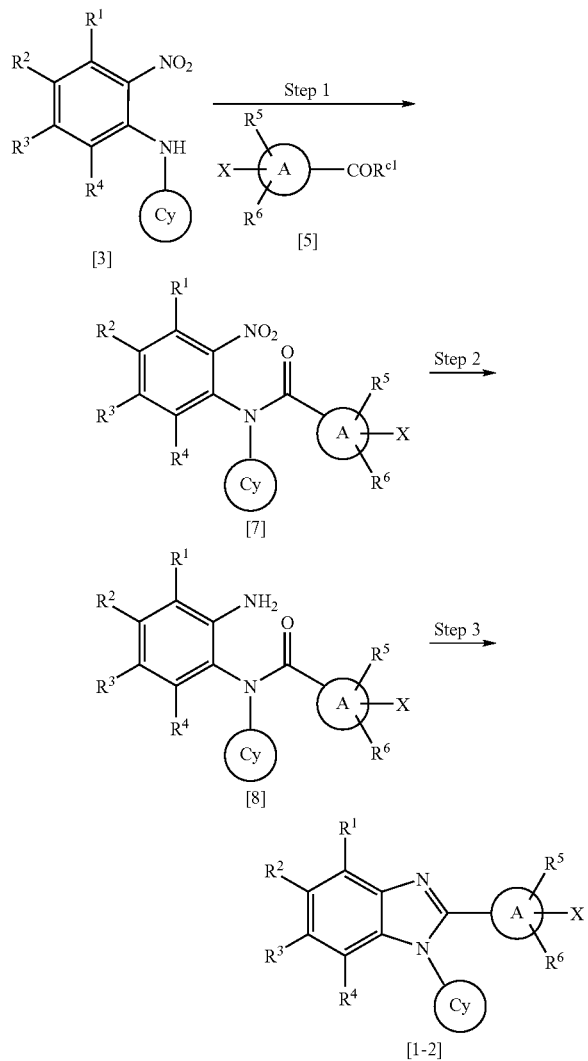

wherein each symbol is as defined above.

Step 1

The compound [3] obtained in the same manner as in Step 1 of Production Method 1-1 is subjected to amide condensation with compound [5] in the same manner as in Step 3 of Production Method 1-1 to give compound [7].

Step 2

The compound [7] is reduced in the same manner as in Step 2 of Production Method 1-1 to give compound [8].

Step 3

The compound [8] is subjected to cyclization in the same manner as in Step 4 of Production Method 1-1 to give compound [I-2].

Production Method 1-3

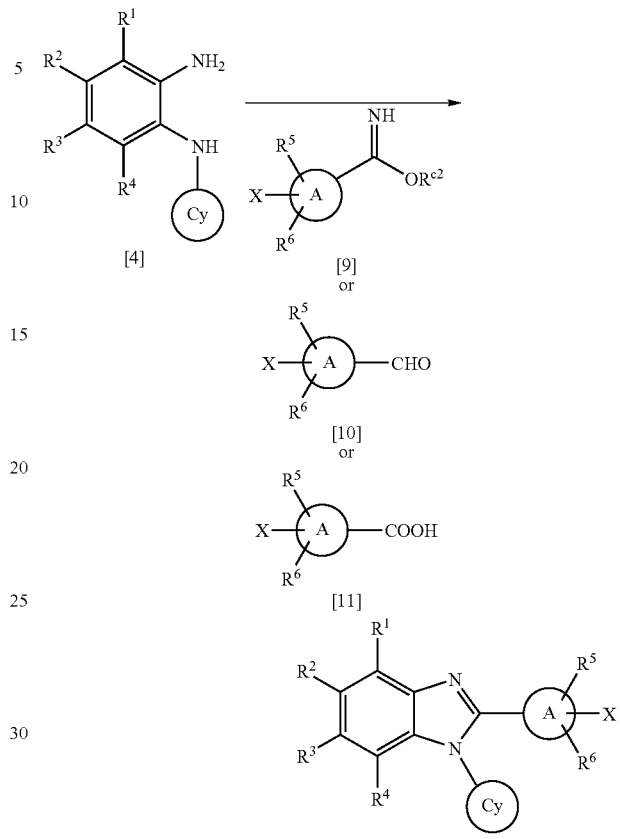

wherein $R^{c2}$ is alkyl such as methyl, ethyl and the like, and other symbols are as defined above.

The compound [4] is reacted with imidate compound [9] in a solvent such as methanol, ethanol, acetic acid, DMF, THF, chloroform and the like at room temperature or with heating to give compound [I-2].

In addition, compound [4] may be reacted with aldehyde compound [10] in a solvent such as acetic acid, formic acid, acetonitrile, DMF, nitrobenzene, toluene and the like in the presence or absence of an oxidizing agent such as benzofuroxan, manganese dioxide, 2,3-dichloro-5,6-dicyano-p-benzoquinone, iodine, potassium ferricyanide and the like with heating to give compound [I-2].

Alternatively, compound [4] and carboxylic acid compound [11] may be heated to allow reaction in the presence of polyphosphoric acid, phosphoric acid, phosphorus oxychloride, hydrochloric acid and the like to give compound [I-2].

Production Method 2

In this Production Method, conversion of the substituents ($R^1$, $R^2$, $R^3$, $R^4$) on the benzene ring of benzimidazole is shown. While a method of converting $R^2$ when $R^1$, $R^3$ and $R^4$ are hydrogen atoms is shown, this Production Method is applicable irrespective of the position of substitution.

Production Method 2-1
Conversion of carboxylic acid ester moiety to amide

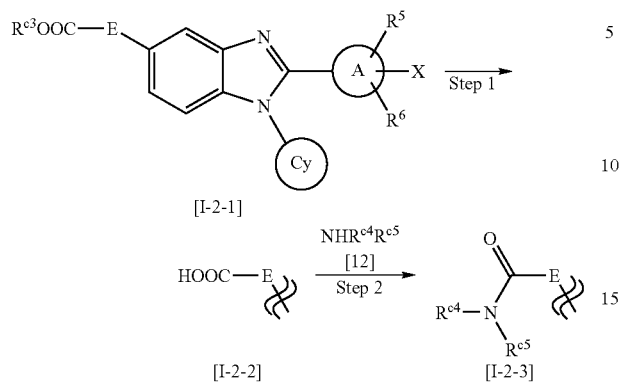

wherein E is a single bond, $-(CH_2)_s-$, $-O-(CH_2)_s-$ or $-NH-(CH_2)_s-$ (wherein s is an integer of 1 to 6), $R^{c3}$, $R^{c4}$ and $R^{c5}$ are $C_{1-6}$ alkyl, and other symbols are as defined above.

Step 1

The compound [I-2-1] obtained in the same manner as in the above-mentioned Production Method is subjected to hydrolysis in a solvent such as methanol, ethanol, THF, dioxane and the like, or in a mixed solvent of these solvents and water under basic conditions with sodium hydroxide, potassium hydroxide, potassium carbonate, lithium hydroxide and the like or under acidic conditions with hydrochloric acid, sulfuric acid and the like to give compound [I-2-2].

Step 2

The compound [I-2-2] is reacted with compound [12] in the same manner as in Step 3 of Production Method 1-1 to give compound [I-2-3].

Production Method 2-2
Conversion of cyano group to substituted amidino group

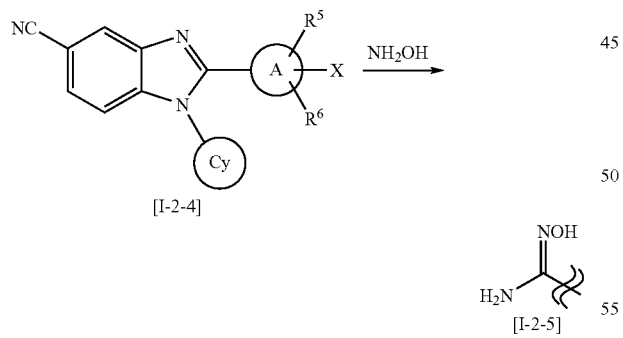

wherein each symbol is as defined above.

The compound [I-2-4] obtained in the same manner as in the above-mentioned Production Method is reacted with hydroxylamine in a solvent such as water, methanol, ethanol, THF, DMF and the like to give compound [I-2-5]. When a salt of hydroxylamine such as hydrochloride and the like is used, the reaction is carried out in the presence of a base such as sodium hydrogencarbonate, sodium hydroxide, triethylamine and the like.

Production Method 2-3
Conversion of sulfonic acid ester moiety to sulfonic acid

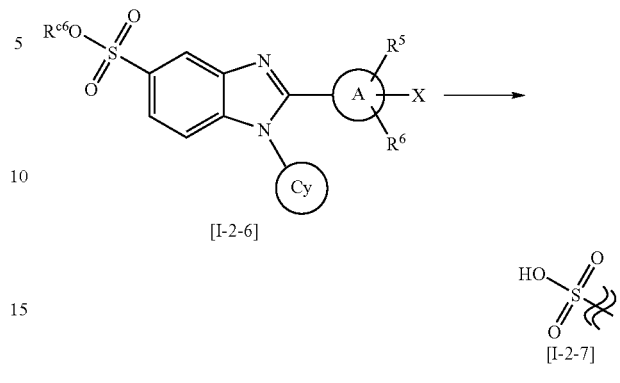

wherein $R^{c6}$ is $C_{1-6}$ alkyl, and other symbols are as defined above.

The compound [I-2-6] obtained in the same manner as in the above-mentioned Production Method is reacted with iodide salt such as sodium iodide, lithium iodide and the like, bromide salt such as sodium bromide, trimethylammonium bromide and the like, amine such as pyridine, trimethylamine, triazole and the like, phosphine such as triphenylphosphine and the like in a solvent such as DMF, dimethyl sulfoxide (DMSO), acetonitrile, methanol, ethanol, water and the like with heating to give compound [I-2-7].

Production Method 3

This Production Method relates to convertion of the substituent(s) on phenyl group at the 2-position of benzimidazole. This Production Method can be used even when phenyl is a different ring.

Production Method 3-1
Conversion of hydroxyl group to ether

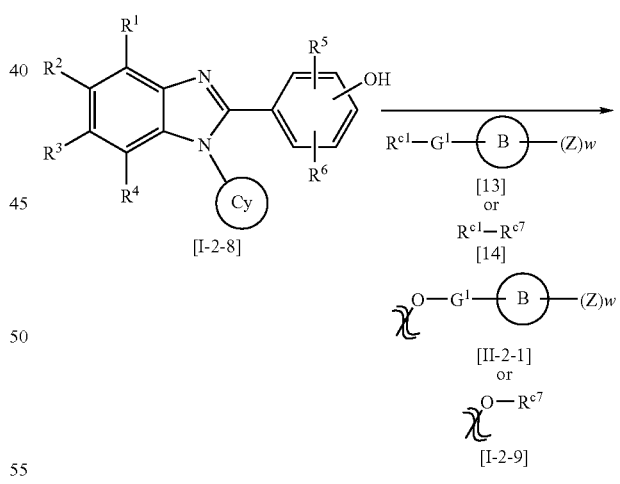

wherein $R^{c7}$ is optionally substituted alkyl corresponding to $R^{a11}$, $G^1$ is a single bond, $*-(CH_2)_n-$, $*-(CH_2)_n-O-$, $*-(CH_2)_n-CO-$ or $*-(CH_2)_m-CR^{a15}R^{a16}$ $)-(CH_2)_n-$, wherein $*$ show the side to be bonded to $R^{c1}$, and other symbols are as defined above.

When $R^{c1}$ of compound [13] is halogen atom, compound [I-2-8] obtained in the same manner as in the above-mentioned Production Method is reacted with compound [13] in a solvent such as DMF, DMSO, acetonitrile, ethanol, THF and the like in the presence of a base such as sodium hydride, sodium hydroxide, potassium hydroxide, potassium carbonate, sodium ethoxide, potassium t-butoxide and the like at room temperature or with heating to give compound [II-2-1].

When $R^{c1}$ of compound [13] is hydroxyl group, the hydroxyl group of compound [13] is converted to halogen atom with thionyl chloride, phosphorus tribromide, carbon tetrabromide-triphenylphosphine and the like and reacted with compound [I-2-8] by the aforementioned method to give compound [II-2-1]. In this case, compound [I-2-8] may be subjected to Mitsunobu reaction with compound [13] in a solvent such as DMF, acetonitrile, THF and the like using triphenylphosphine-diethyl azodicarboxylate and the like to give compound [II-2-1].

The compound [I-2-9] can be obtained in the same manner from compound [I-2-8] and compound [14].

Production Method 3-2

Conversion of nitro to substituted amino group

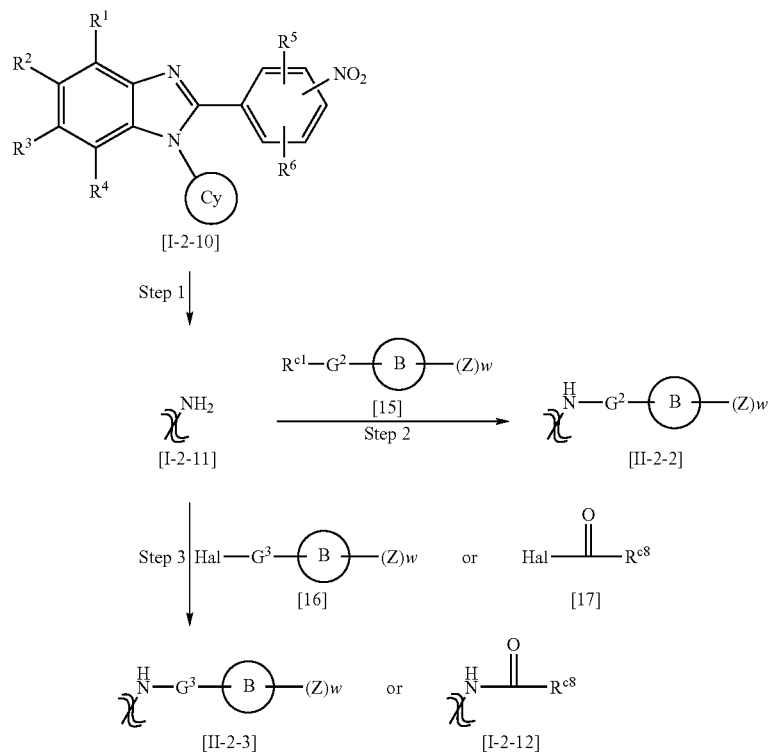

wherein $R^{c8}$ is $C_{1-6}$ alkyl, $G^2$ is *—$(CH_2)_n$— or *—$CHR^{a15}$, $G^3$ is —CO—, *—$CO_2$—, *—CONH— or —$SO_2$—, and other symbols are as defined above.

Step 1

The nitro compound [I-2-10] obtained in the same manner as in the above-mentioned Production Method is reacted in the same manner as in Step 2 of Production Method 1-1 to give compound [I-2-11].

Step 2

The compound [I-2-11] is alkylated with compound [15] in the same manner as in Production Method 3-1 to give compound [II-2-2].

Step 3

When $G^3$ of compound [16] is —CO—, —$CO_2$— or —CONH—, compound [I-2-11] is acylated with compound [16] in the same manner as in Step 3 of Production Method 1-1 to give compound [II-2-3].

When $G^3$ of compound [16] is —$SO_2$—, sulfonylation is conducted using sulfonyl halide instead of acid halide used in Step 3 of Production Method 1-1 to give compound [II-2-3].

The compound [I-2-11] is acylated with compound [17] in the same manner as above to give compound [I-2-12].

This Production Method is applied in the same manner as above to give disubstituted compounds (tertiary amine) of compound [II-2-2], compound [II-2-3] and compound [I-2-12].

Production Method 3-3

Conversion of carboxylic acid ester moiety to amide

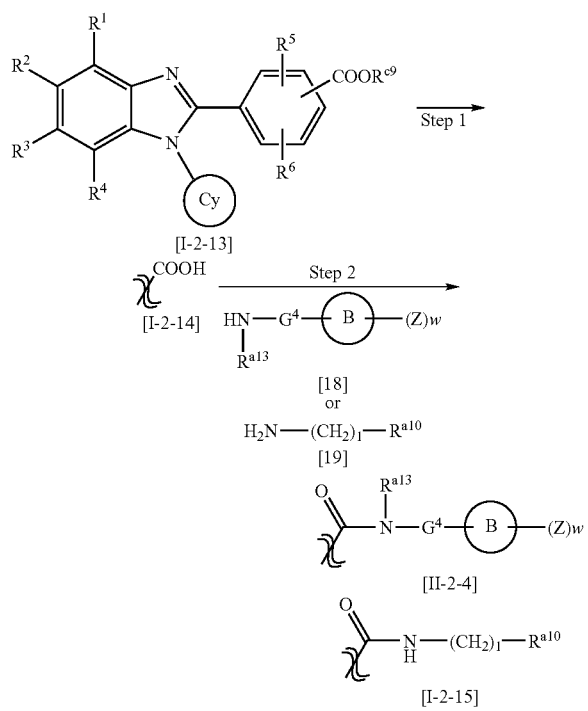

wherein $R^{c9}$ is $C_{1-6}$ alkyl, $G^4$ is #—$(CH_2)_n$—, #—$(CH_2)_n$—NH— or #—$CHR^{a14}$— wherein # shows the side that is bounded to amine and other symbols are as defined above.

Step 1

The compound [I-2-13] obtained in the same manner as in the above-mentioned Production Method is reacted in the same manner as in Step 1 of Production Method 2-1 to give compound [I-2-14].

Step 2

The compound [I-2-14] is reacted with compound [18] in the same manner as in Step 2 of Production Method 2-1 to give compound [II-2-4].

The compound [I-2-15] is obtained from compound [I-2-14] and compound [19] in the same manner as above.

Production Method 4

In this Production Method, additional substituent(s) is(are) introduced into ring B on phenyl group that substitutes the 2-position of benzimidazole. This Production Method is applicable even when phenyl is a different ring.

Production Method 4-1

Direct bonding of ring Z″ to ring B

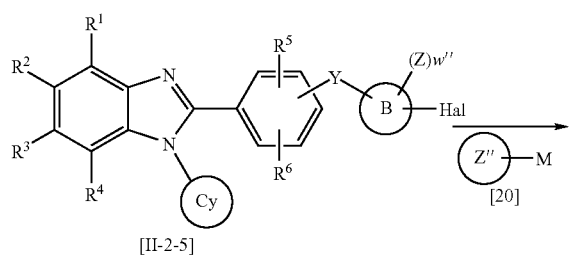

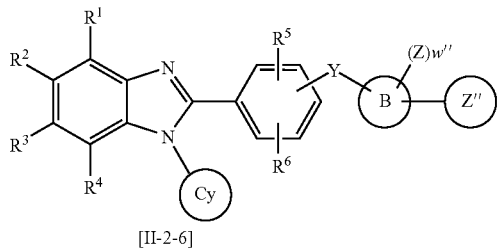

wherein ring Z″-M is aryl metal compound, ring Z″ moiety is optionally substituted $C_{6-14}$ aryl or optionally substituted heterocyclic group corresponding to substituent Z, and the metal moiety contains boron, zinc, tin, magnesium and the like, such as phenylboronic acid, w″ is 0, 1 or 2, and other symbols are as defined above.

The compound [II-2-5] obtained in the same manner as in the above-mentioned Production Method is reacted with aryl metal compound [20] in a solvent such as DMF, acetonitrile, 1,2-dimethoxyethane, THF, toluene, water and the like in the presence of a palladium catalyst such as tetrakis (triphenylphosphine)palladium, bis(triphenylphosphine) palladium(II) dichloride, palladium acetate-triphenylphosphine and the like, a nickel catalyst such as nickel chloride, [1,3-bis(diphenylphosphino)propane]nickel (II) chloride and the like, and a base such as potassium carbonate, potassium hydrogencarbonate, sodium hydrogencarbonate, potassium phosphate, triethylamine and the like at room temperature or with heating, to give compound [II-2-6].

Production Method 4-2

Conversion of hydroxyl group to ether

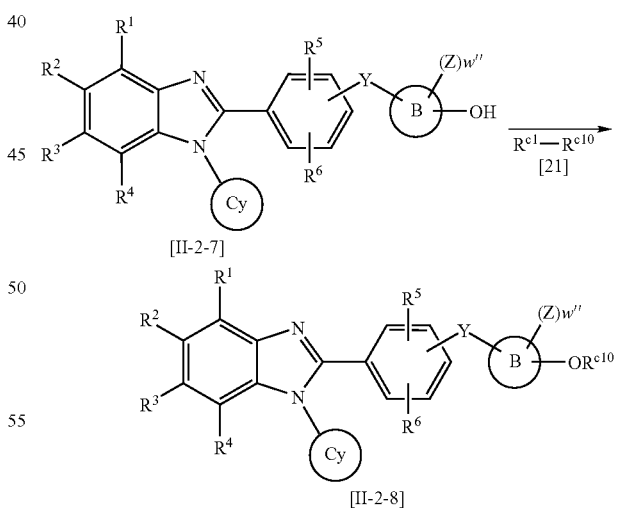

wherein $R^{c10}$ is —$R^{a20}$ or —$(CH_2)_p$—$COR^{a21}$ corresponding to substituent Z, and other symbols are as defined above.

The compound [II-2-7] obtained in the same manner as in the above-mentioned Production Method is reacted with compound [21] in the same manner as in Production Method 3-1 to give compound [II-2-8].

Production Method 4-3
Synthesis in advance of ring B part such as compound [13] in Production Method 3-1

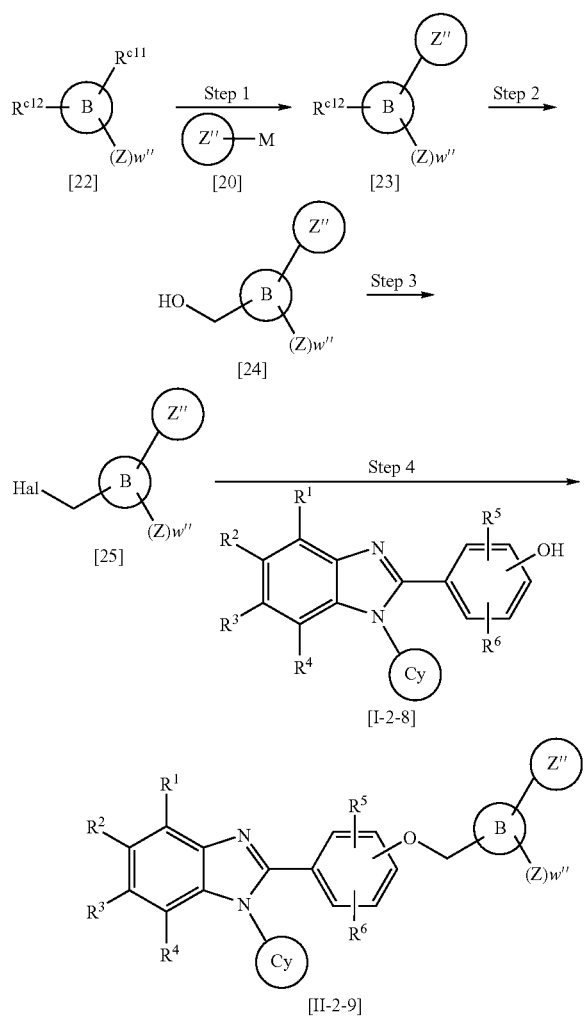

wherein $R^{c11}$ is leaving group such as chlorine atom, bromine atom, iodine atom, trifluoromethanesulfonyloxy and the like, $R^{c12}$ is formyl, carboxyl or carboxylic acid ester such as methoxycarbonyl, ethoxycarbonyl, tert-butoxycarbonyl and the like, and other symbols are as defined above.
Step 1
Commercially available compound [22] or compound [22] obtained by a conventional method is reacted with aryl metal compound [20] in the same manner as in Production Method 4-1 to give compound [23].
Step 2
The compound [23] obtained in the same manner as in the above-mentioned Production Method is reduced according to a conventional method to give compound [24].

For example, compound [23] is reacted with in a solvent such as methanol, ethanol, THF and the like in the presence of a reducing agent such as lithium aluminum hydride, sodium borohydride and the like under cooling to heating to give compound [24].
Step 3
The compound [24] obtained in the same manner as in the above-mentioned Production Method is reacted in a solvent such as 1,4-dioxane, diethyl ether, THF, dichloromethane, chloroform, toluene and the like with a halogenating agent, such as phosphorus pentachloride, phosphorus tribromide, thionyl chloride and the like, to give compound [25]. For an accerelated reaction, the reaction may be carried out in the presence of a tertiary amine such as DMF, pyridine and the like, or under heating.
Step 4
The compound [24] or [25] obtained in the same manner as in the above-mentioned Production Method is reacted with compound [I-2-8] in the same manner as in Production Method 3-1 to give compound [II-2-9].
Production Method 4-4

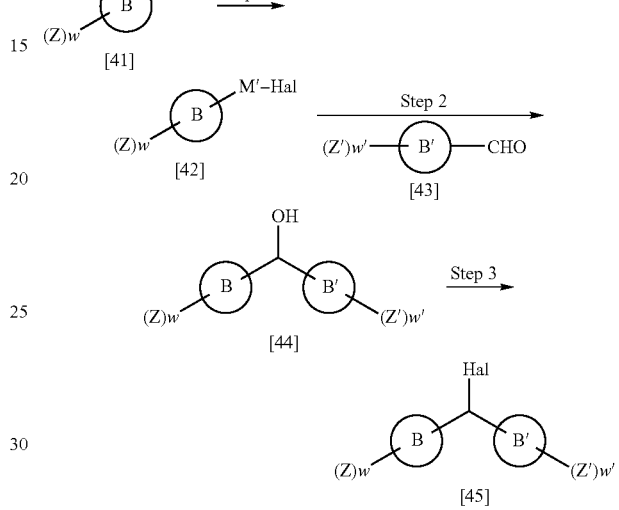

wherein M' is a metal such as magnesium, lithium, zinc and the like, and other symbols are as defined above.
Step 1
Commercially available compound [41] or compound [41] obtained by a conventional method is converted to aryl metal reagent by a conventional method to give compound [42].

For example, when M' is magnesium, magnesium is reacted with compound [41] in a solvent such as THF, diethyl ether, benzene, toluene and the like, preferably THF, from cooling to heating preferably at −100° C. to 100° C. to give compound [42].
Step 2
The compound [42] obtained in the same manner as in the above-mentioned Production Method is reacted with compound [43] to give compound [44].

The compound [42] is reacted in a solvent such as diethyl ether, benzene, toluene, THF and the like, preferably THF, from cooling to room temperature, preferably at −100° C. to 30° C. to give compound [44].
Step 3
The compound [44] obtained in the same manner as in the above-mentioned Production Method is halogenated in the same manner as in Step 3 of Production Method 4-3 to give compound [45].

The compound [44] is reacted with thionyl chloride and pyridine preferably in toluene solvent to give compound [45].

When compound [45] is symmetric, namely, when the ring B-(Z)w moiety and the ring B'-(Z')w' moiety are the same, compound [42] is reacted with formate such as methyl formate, ethyl formate and the like, preferably ethyl formate, in a solvent such as diethyl ether, benzene, toluene, THF and the like, preferably THF, from cooling to room temperature, preferably at −100° C. to 30° C., to give compound [45].

Production Method 4-5

Method including steps to introduce a protecting group into a functional group

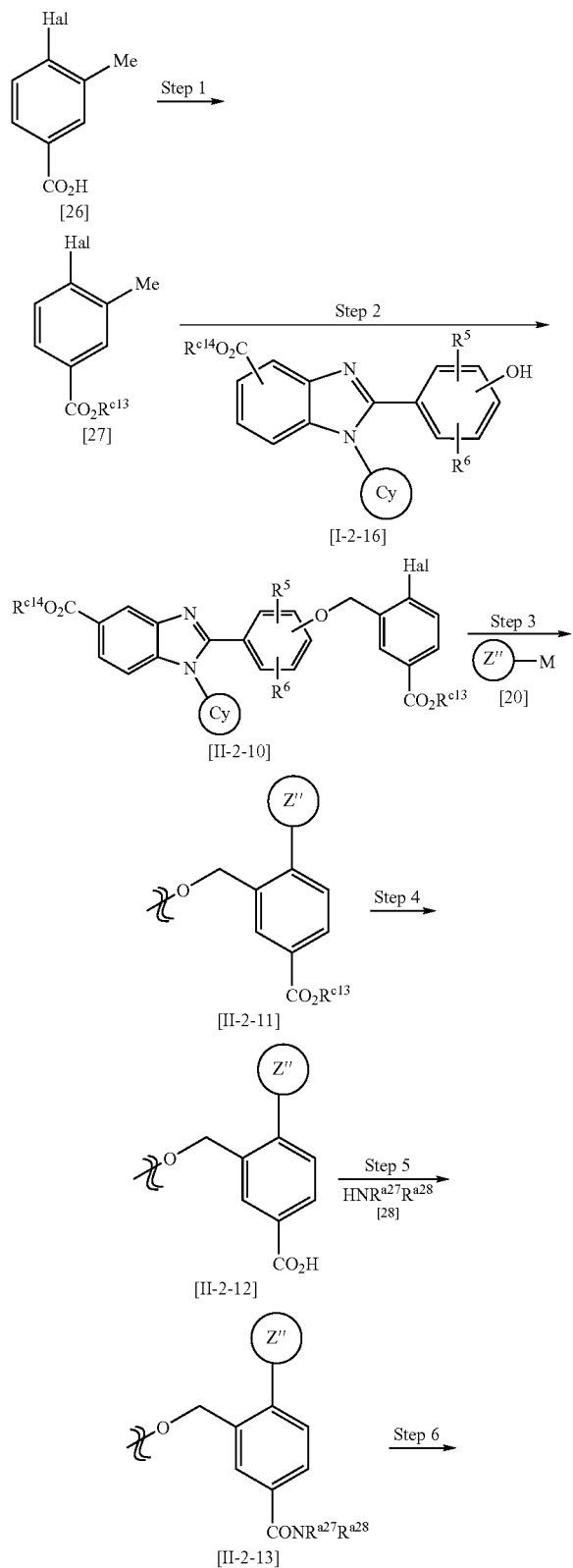
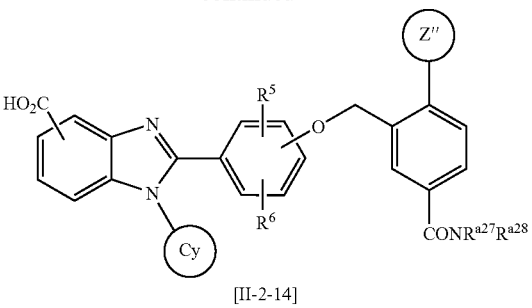

wherein $R^{c13}$ is carboxylic acid protecting group such as tert-butyl and the like, $R^{c14}$ is carboxylic acid protecting group such as methyl and the like and other symbols are as defined above.

Step 1

Commercially available compound [26] or compound [26] obtained by a conventional method is protected by a conventional method to give compound [27].

For example, when $R^{c13}$ is tert-butyl, compound [26] is converted to acid halide with thionyl chloride, oxalyl chloride and the like in a solvent such as THF, chloroform, dichloromethane, toluene and the like, and reacted with potassium tert-butoxide to give compound [27].

As used herein, $R^{c13}$ may be a different protecting group as long as it is not removed during the Step 2 or Step 3 but removed in Step 4 without affecting —$CO_2R^{c14}$.

Step 2

The methyl group of compound [27] obtained in the same manner as in the above-mentioned Production Method is converted to bromomethyl with N-bromosuccinimide and N,N'-azobisisobutyronitrile and reacted with compound [I-2-16] in the same manner as in Production Method 3-1 to give compound [II-2-10].

Step 3

The compound [II-2-10] obtained in the same manner as in the above-mentioned Production Method is reacted with aryl metal compound [20] in the same manner as in Production Method 4-1 to give compound [II-2-11].

Step 4

The $R^{c13}$ of the compound [II-2-11] obtained in the same manner as in the above-mentioned Production Method is removed by a conventional method to give compound [II-2-12].

The protecting group of carboxylic acid can be removed by a conventional deprotection method according to the protecting group. In this Step, the conditions free from reaction of $R^{c14}$ are preferable. For example, when $R^{c13}$ is tert-butyl, compound [II-2-11] is treated with trifluoroacetic acid in a solvent such as dichloromethane, chloroform and the like to give compound [II-2-12].

Step 5

The compound [II-2-12] obtained in the same manner as in the above-mentioned Production Method is subjected to amide condensation with compound [28] in the same manner as in Step 3 of Production-Method 1-1 to give compound [II-2-13].

Step 6

The compound [II-2-13] obtained in the same manner as in the above-mentioned Production Method is deprotected in the same manner as in Step 1 of Production Method 2-1 to give compound [II-2-14].

As used herein, $R^{c14}$ is preferably a protecting group that does not react during the Step 1 through Step 5 but removed in this Step.

For example, when $R^{c14}$ is methyl, compound [II-2-13] is reacted in an alcohol solvent such as methanol, ethanol, n-propanol, isopropanol and the like or a mixed solvent of alcohol solvent and water in the presence of a base such as potassium carbonate, sodium carbonate, lithium hydroxide, sodium hydroxide, potassium hydroxide and the like from cooling to heating for deprotection, followed by acidifying the reaction solution to give compound [II-2-14].

Production Method 4-6

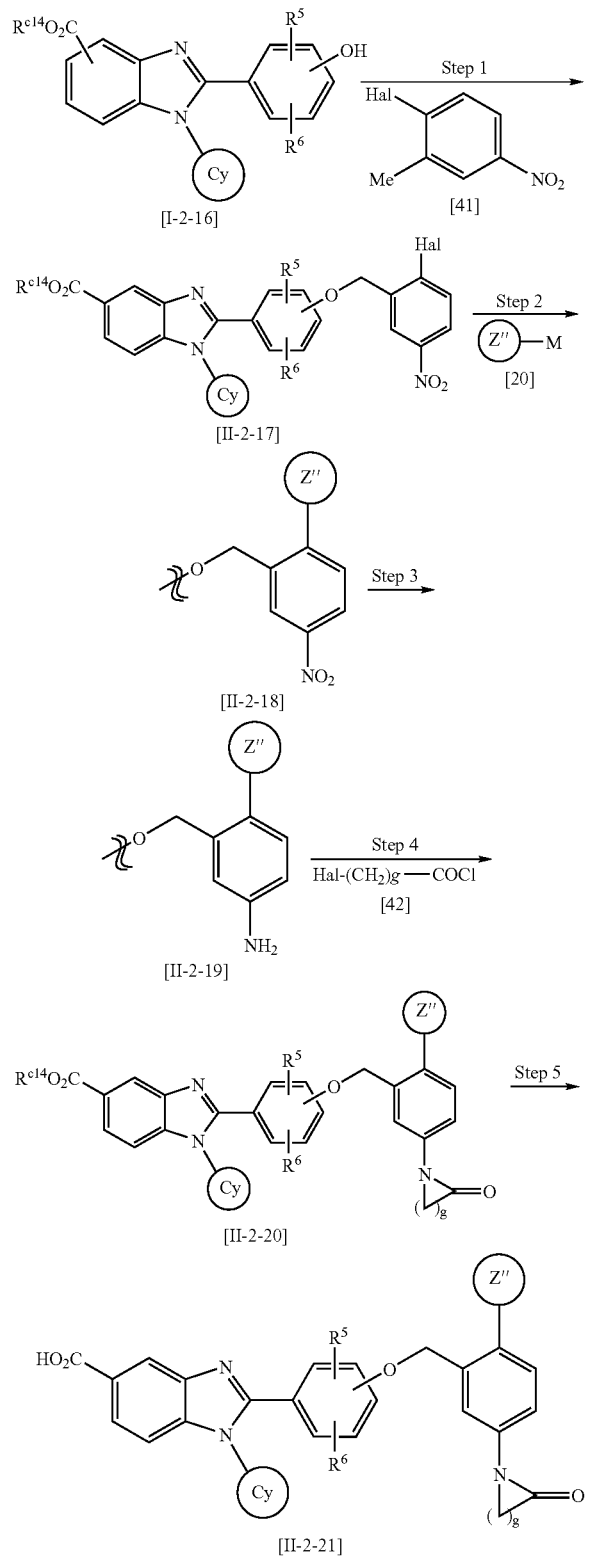

wherein g is an integer of 1 to 5, and other sumbols are as defined above.

Step 1

The compound [I-2-16] obtained by the above-mentioned Production Method is reacted with toluene derivative [41] in the same manner as in Step 2 of Production Method 4-5 to give compound [II-2-17].

Step 2

The compound [II-2-17] obtained by the above-mentioned Production Method is reacted with aryl metal compound [20] in the same manner as in Production Method 4-1 to give compound [II-2-18].

Step 3

The compound [II-2-18] obtained by the above-mentioned Production Method is reduced in the same manner as in Step 2 of Production Method 1-1 to give compound [II-2-19].

Step 4

The compound [II-2-19] obtained by the above-mentioned Production Method is amide condensed with compound [42] in the same manner as in Step 3 of Production Method 1-1 and subjected to cyclization in the same manner as in Step 1 of Production Method 1-1 to give compound [II-2-20].

Step 5

The compound [II-2-20] obtained by the above-mentioned Production Method is hydrolyzed in the same manner as in Step 1 of Production Method 2-1 to give compound [II-2-21].

Production Method 4-7

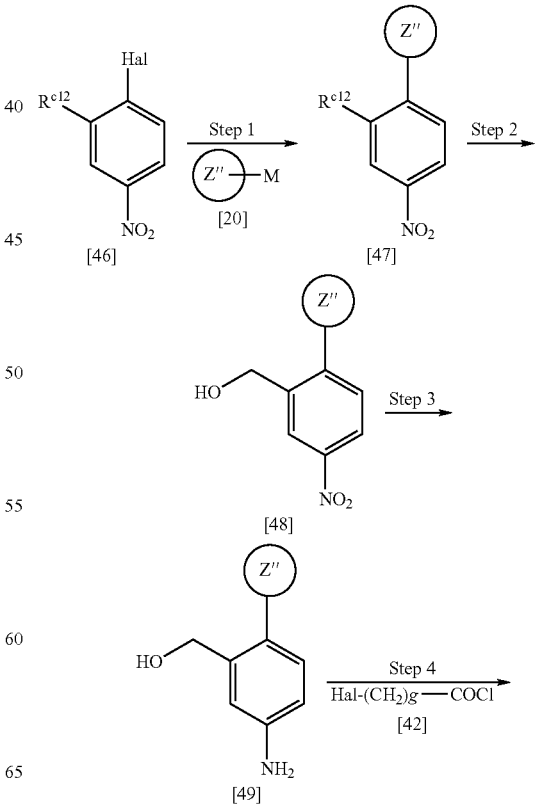

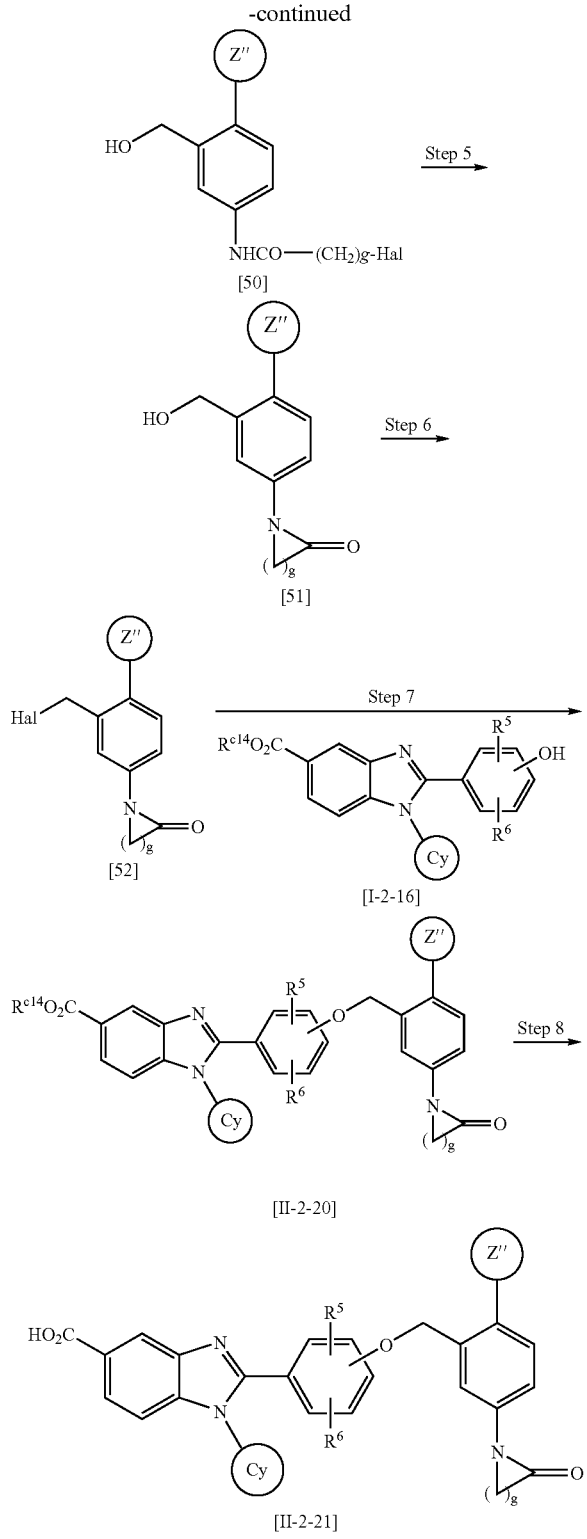

wherein each symbol is as defined above.

Step 1

Commercially available product or compound [46] obtained by a conventional method is reacted with compound [20] in the same manner as in Production Method 4-1 to give compound [47].

Step 2

The compound [47] obtained in the same manner as in the above-mentioned Production Method is reduced in the same manner as in the above-mentioned Production Method 4-3 Step 2 to give compound [48].

Step 3

The compound [48] obtained in the same manner as in the above-mentioned Production Method is reduced in the same manner as in the above-mentioned Production Method 1-1 Step 2 to give compound [49].

Step 4

The compound [49] obtained in the same manner as in the above-mentioned Production Method is reacted with compound [42] in a solvent such as DMF, acetonitrile, THF, chloroform, ethyl acetate, methylene chloride and toluene to give compound [50]. To enhance the reaction selectivity for amino group, acetic acid and sodium acetate may be added in an equivalent amount ratio.

Step 5

The compound [50] obtained in the same manner as in the above-mentioned Production Method is subjected to cyclization reaction in the same manner as in the above-mentioned Production Method 1-1 Step 1 to give compound [51].

Step 6

The compound [51] obtained in the same manner as in the above-mentioned Production Method is halogenated in the same manner as in the above-mentioned Production Method 4-3 Step 3 to give compound [52].

Step 7

The compound [52] obtained in the same manner as in the above-mentioned Production Method is reacted in the same manner as in the above-mentioned Production Method 3-1 with compound [I-2-16] obtained in the same manner as in the above-mentioned Production Method to give compound [II-2-20].

Step 8

The compound [II-2-20] obtained in the same manner as in the above-mentioned Production Method is hydrolyzed in the same manner as in the above-mentioned Production Method 2-1 Step 1 to give compound [II-2-21].

Production Method 5

Formation of indole ring

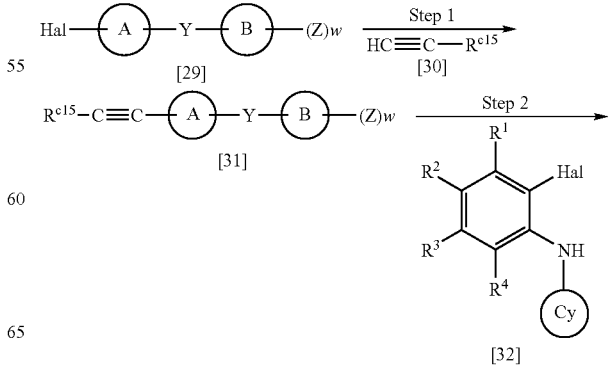

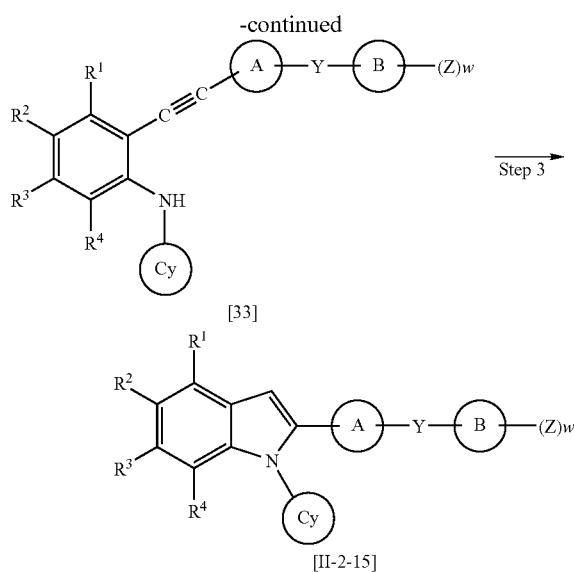

[33]

[II-2-15]

wherein $R^{c15}$ is protecting group such as trimethylsilyl, tert-butyldimethylsilyl, tert-butyldiphenylsilyl and the like, and other symbols are as defined above.

Step 1

The compound [29] obtained in the same manner as in the above-mentioned Production Method or conventional method is reacted with compound [30] in a solvent such as DMF, acetonitrile, 1,2-dimethoxyethane, THF, toluene, water and the like using a palladium catalyst such as tetrakis(triphenylphosphine)palladium, bis(triphenylphosphine)palladium(II) dichloride, palladium acetate-triphenylphosphine and the like, a copper catalyst such as copper(I) iodide and the like or a mixture thereof, and in the presence of a base such as potassium carbonate, potassium hydrogencarbonate, sodium hydrogencarbonate, potassium phosphate, triethylamine and the like to give compound [31].

Step 2

The compound [31] obtained in the same manner as in the above-mentioned Production Method is reacted in an alcohol solvent such as methanol, ethanol and the like or a mixed solvent of an alcohol solvent and a solvent such as DMF, acetonitrile, THF, chloroform, dichloromethane, ethyl acetate, methylene chloride, toluene and the like in the presence of a base such as potassium carbonate, sodium carbonate, lithium hydroxide, sodium hydroxide, potassium hydroxide, lithium hydride, sodium hydride, potassium hydride and the like at room temperature or with heating for deprotection, and reacted with compound [32] obtained in the same manner as in Step 1 of Production Method 1-1 in the same manner as in Step 1 of Production Method 5 to give compound [33].

Step 3

The compound [33] obtained in the same manner as in the above-mentioned Production Method was subjected to cyclization in a solvent such as DMF, acetonitrile, THF, chloroform, dichloromethane, ethyl acetate, methylene chloride, toluene and the like in the presence of a copper catalyst such as copper(I) iodide and the like or a palladium catalyst such as palladium(II) chloride and the like at room temperature or with heating to give compound [II-2-15].

Production Method 6
Formation of imidazo[1,2-a]pyridine ring

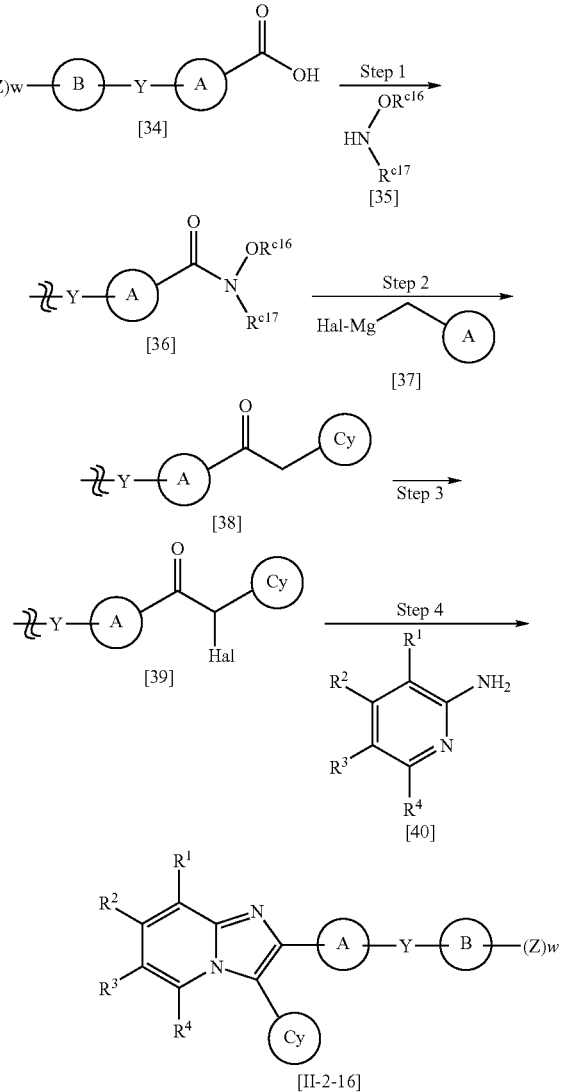

[II-2-16]

wherein $R^{c16}$ and $R^{c17}$ are each independently alkyl, such as methyl, ethyl and the like, and other symbols are as defined above.

Step 1

The compound [34] obtained by the above-mentioned Production Method or a conventional method is subjected to amide condensation with compound [35] in the same manner as in Step 3 of Production Method 1-1 to give compound [36].

Step 2

The compound [36] obtained by the above-mentioned Production Method is reacted with Grignard reagent [37] obtained by a conventional method to give compound [38].

Alternatively, an acid halide of compound [34] may be used instead of compound [36].

Step 3

The compound [38] obtained by the above-mentioned Production Method is subjected to halogenation by a conventional method to give compound [39].

For example, when Hal is a bromine atom, compound [38] is reacted with bromine under cooling or at room temperature in a solvent such as DMF, acetonitrile, THF, chloroform, dichloromethane, ethyl acetate, toluene and the like to give compound [39].

Alternatively, a halogenating agent such as hypohalite (e.g., hypochlorite and the like), N-bromosuccinimide and the like may be used instead of bromine for halogenation.

Step 4

The compound [39] obtained by the above-mentioned Production Method is subjected to cyclization with compound [40] obtained by a conventional or known method (JP-A-8-48651) in the presence of a base such as potassium carbonate, sodium carbonate, lithium hydroxide, sodium hydroxide, potassium hydroxide, lithium hydride, sodium hydride, potassium hydride and the like in a solvent or without a solvent at room temperature or with heating to give compound [II-2-16].

In the compounds of the formulas [I] and [II], a desired heterocyclic group can be formed according to a method similar to the methods disclosed in known publications. Examples of such heterocyclic group and reference publications are recited in the following.

5-oxo-$\Delta^2$-1,2,4-oxadiazol-3-yl (or 2,5-dihydro-5-oxo-4H-1,2,4-oxadiazol-3-yl), 5-oxo-$\Delta^2$-1,2,4-thiadiazolin-3-yl (or 2,5-dihydro-5-oxo-4H-1,2,4-thiadiazol-3-yl), 2-oxo-$\Delta^3$-1,2,3,5-oxathiadiazolin-4-yl (or 2-oxo-$\Delta^3$-1,2,4-oxathiadiazol-4-yl): Journal of Medicinal Chemistry, 39(26), 5228–35, 1996, 5-oxo-$\Delta^2$-1,2,4-triazolin-3-yl: J Org Chem, 61(24), 8397–8401, 1996, 1-oxo-$\Delta^3$-1,2,3,5-thiatriazolin-4-yl: Liebigs Ann Chem, 1376, 1980, 3-oxo-$\Delta^4$-1,2,4-oxadiazolin-5-yl: EP145095, 5-oxo-$\Delta^2$-1,3,4-oxadiazolin-2-yl: J Org Chem, 20, 412, 1955, 5-oxo-$\Delta^3$-1,2,4-dioxazolin-3-yl: J Prakt Chem, 314, 145, 1972, 3-oxo-$\Delta^4$-1,2,4-thiadiazolin-5-yl: JP-A-61-275271, 5-oxo-$\Delta^3$-1,2,4-dithiazolin-3-yl: J Org Chem, 61(19), 6639–6645, 1996, 2-oxo-$\Delta^4$-1,3,4-dioxazolin-5-yl: J Org Chem, 39, 2472, 1974, 2-oxo-$\Delta^4$-1,3,4-oxathiazolin-5-yl: J Med Chem, 35(20), 3691–98, 1992, 5-oxo-$\Delta^2$-1,3,4-thiadiazolin-2-yl: J Prakt Chem, 332(1), 55, 1990, 5-oxo-$\Delta^2$-1,4,2-oxathiazolin-3-yl: J Org Chem, 31, 2417, 1966, 2-oxo-$\Delta^4$-1,3,4-dithiazolin-5-yl: Tetrahedron Lett, 23, 5453, 1982, 2-oxo-$\Delta^4$-1,3,2,4-dioxathiazolin-5-yl: Tetrahedron Lett, 319, 1968, 3,5-dioxoisooxazolidin-4-yl: Helv Chim Acta, 1973, 48, 1965, 2,5-dioxoimidazolidin-4-yl: Heterocycles, 43(1), 49–52, 1996, 5-oxo-2-thioxoimidazolidin-4-yl: Heterocycles, 5, 391, 1983, 2,4-dioxooxazolidin-5-yl: J Am Chem Soc, 73, 4752, 1951,
4-oxo-2-thioxooxazolidin-5-yl: Chem Ber, 91, 300, 1958,
2,4-dioxothiazolidin-5-yl: JP-A-57-123175,
4-oxo-2-thioxothiazolidin-5-yl: Chem Pharm Bull, 30, 3563, 1982, The Production Methods shown in the above-mentioned Production Methods 2 to 4 can be used for the synthesis of compounds other than benzimidazole of the formulas [I] and [II], such as compounds [II-2-15] and [II-2-16].

The compounds of the formulas [I], [II] and [III], 4-(4-fluorophenyl)-5-hydroxymethyl-2-methylthiazole and 4-(4-fluorophenyl)-5-chloromethyl-2-methylthiazole and production methods thereof of the present invention are explained in detail in the following by way of Examples. It is needless to say that the present invention is not limited by these Examples.

Example 1

Production of ethyl 2-[4-(3-bromophenoxy)phenyl]-1-cyclohexylbenzimidazole-5-carboxylate Step 1: Production of ethyl 4-chloro-3-nitrobenzoate 4-Chloro-3-nitrobenzoic acid (300 g) was dissolved in ethyl alcohol (1500 ml) and concentrated sulfuric acid (100 ml) was added with ice-cooling. The mixture was refluxed under heating for 7 hr. The reaction mixture was poured into ice-cold water and the precipitated crystals were collected by filtration to give the title compound (332 g, yield 97%).

$^1$H-NMR (300 MHz, CDCl$_3$): 8.50 (1H, d, J=2.1 Hz), 8.16(1H, dd, J=8.4, 2.1 Hz), 7.63(1H, d, J=8.4 Hz), 4.43(2H, q, J=7.5 Hz), 1.42(3H, t, J=7.5 Hz)

Step 2: Production of ethyl 4-cyclohexylamino-3-nitrobenzoate

Ethyl 4-chloro-3-nitrobenzoate (330 g) obtained in the previous step was dissolved in acetonitrile (1500 ml), and cyclohexylamine (220 g) and triethylamine (195 g) were added. The mixture was refluxed under heating overnight. The reaction mixture was poured into ice-cold water and the precipitated crystals were collected by filtration to give the title compound (400 g, yield 94%).

$^1$H-NMR (300 MHz, CDCl$_3$): 8.87(1H, d, J=2.1 Hz), 8.35–8.46(1H, m), 8.02(1H, dd, J=9.1, 2.1 Hz), 6.87(1H, d, J=9.1 Hz), 4.35(2H, q, J=7.1 Hz), 3.65–3.50(1H, m), 2.14–1.29(10H, m), 1.38(3H, t, J=7.1 Hz)

Step 3: Production of ethyl 3-amino-4-cyclohexylaminobenzoate

Ethyl 4-cyclohexylamino-3-nitrobenzoate (400 g) obtained in the previous step was dissolved in ethyl acetate (1500 ml) and ethyl alcohol (500 ml), and 7.5% palladium carbon (50% wet, 40 g) was added. The mixture was hydrogenated for 7 hr at atmospheric pressure. The catalyst was filtered off and the filtrate was concentrated under reduced pressure. Diisopropyl ether was added to the residue and the precipitated crystals were collected by filtration to give the title compound (289 g, yield 80%).

$^1$H-NMR (300 MHz, CDCl$_3$): 7.57(1H, dd, J=8.4, 1.9 Hz), 7.41(1H, d, J=1.9 Hz), 6.59(1H, d, J=8.4 Hz), 4.30(2H, q, J=7.1 Hz), 3.40–3.30(1H, m), 2.18–2.02(2H, m), 1.88–1.15(8H, m), 1.35(3H, t, J=7.1 Hz)

Step 4: Production of ethyl 3-[4-(3-bromophenoxy)benzoyl]amino-4-cyclohexylaminobenzoate 4-(3-Bromophenoxy)benzoic acid (74 g) was dissolved in chloroform (500 ml), and oxalyl chloride (33 ml) and dimethylformamide (catalytic amount) were added. The mixture was stirred for 4 hr at room temperature. The reaction mixture was concentrated under reduced pressure and dissolved in dichloromethane (150 ml). The resulting solution was added dropwise to a solution of ethyl 3-amino-4-cyclohexylaminobenzoate (66 g) obtained in the previous step in dichloromethane (500 ml) and triethylamine (71 ml), and the mixture was stirred for 1 hr at room temperature. The reaction mixture was poured into water and extracted with dichloromethane. The organic layer was washed with saturated brine, dried over anhydrous magnesium sulfate, and concentrated under reduced pressure. Diethyl ether was added to the residue for crystallization and the crystals were collected by filtration to give the title compound (129 g, yield 95%).

$^1$H-NMR (300 MHz, CDCl$_3$): 8.00–7.78(4H, m), 7.66 (1H, brs), 7.37–7.18(3H, m), 7.13–6.59(3H, m), 6.72(1H, d, J=8.7 Hz), 4.50(1H, brs), 4.29(2H, q, J=7.2 Hz), 3.36(1H, m), 2.12–1.96(2H, m), 1, 83–1.56(3H, m), 1.47–1.12(5H, m), 1.37(3H, t, J=7.2 Hz)

Step 5: Production of ethyl 2-[4-(3-bromophenoxy)phenyl]-1-cyclohexylbenzimidazole-5-carboxylate Ethyl 3-[4-(3-bromophenoxy)benzoyl]amino-4-cyclohexylaminobenzoate (129 g) obtained in the previous step was suspended in acetic acid (600 ml) and the resulting suspension was refluxed under heating for 3 hr. The reaction mixture was concentrated under reduced pressure. Water was added to the residue and the precipitated crystals were collected by filtration to give the title compound (124 g, yield 99%).

$^1$H-NMR (300 MHz, CDCl$_3$): 8.51(1H, d, J=1.5 Hz), 8.00(1H, dd, J=8.4, 1.5 Hz), 7.67(1H, d, J=8.4 Hz), 7.63(2H, d, J=8.7 Hz), 7.35–7.21(3H, m), 7.17(2H, d, J=8.7 Hz), 7.14(1H, m), 4.42(2H, q, J=7.2 Hz), 4.38(1H, m), 2.43–2.22 (2H, m), 2.07–1.87(4H, m), 1.80(1H, m), 1.42(3H, t, J=7.2 Hz), 1.40–1.27(3H, m)

Example 2

Production of 2-[4-(3-bromophenoxy)phenyl]-1-cyclohexylbenzimidazole-5-carboxylic acid Ethyl 2-[4-(3-bromophenoxy)phenyl]-1-cyclohexylbenzimidazole-5-carboxylate (1.0 g) obtained in Example 1 was dissolved in tetrahydrofuran (10 ml) and ethyl alcohol (10 ml), and 4N sodium hydroxide (10 ml) was added. The mixture was refluxed under heating for 1 hr. The reaction mixture was concentrated under reduced pressure and water was added to the residue. The mixture was acidified with 6N hydrochloric acid and the precipitated crystals were collected by filtration to give the title compound (0.9 g, yield 96%).
melting point: 255–256° C.
FAB-Ms: 491(MH+)

$^1$H-NMR (300 MHz, DMSO-d$_6$): (12.75(1H, brs), 8.24 (1H, s), 7.96(1H, d, J=8.7 Hz), 7.86(1H, d, J=8.7 Hz), 7.71(2H, d, J=8.6 Hz), 7.47–7.34(3H, m), 7.24(2H, d, J=8.6 Hz), 7.20(1H, m), 4.31(1H, m), 2.38–2.18(2H, m), 2.02–1.79(4H, m), 1.65(1H, m), 1.44–1.20(3H, m)

Example 3

Production of ethyl 1-cyclohexyl-2-(4-hydroxyphenyl) benzimidazole-5-carboxylate Ethyl 3-amino-4-cyclohexylaminobenzoate (130 g) obtained in Example 1, Step 3, and methyl 4-hydroxybenzimidate hydrochloride (139 g) were added to methyl alcohol (1500 ml), and the mixture was refluxed under heating for 4 hr. The reaction mixture was allowed to cool and the precipitated crystals were collected by filtration to give the title compound (131 g, yield 72%).

$^1$H-NMR (300 MHz, CDCl$_3$): 10.02(1H, brs), 8.21(1H, d, J=1.4 Hz), 7.93(1H, d, J=8.6 Hz), 7.83(1H, dd, J=8.6, 1.4 Hz), 7.48(2H, d, J=8.6 Hz), 6.95(2H, d, J=8.6 Hz), 4.39–4.25(1H, m), 4.33(1H, q, J=7.0 Hz), 2.35–2.18(2H, m), 1.98–1.79(4H, m), 1.70–1.60(1H, m), 1.46–1.19(3H, m), 1.35(3H, t, J=7.0 Hz)

Example 4

Production of ethyl 2-[4-(2-bromo-5-chlorobenzyloxy) phenyl]-1-cyclohexylbenzimidazole-5-carboxylate 2-Bromo-5-chlorobenzyl bromide prepared from 2-bromo-5-chlorotoluene (50 g), N-bromosuccinimide and N,N'-azobisisobutyronitrile, and ethyl 1-cyclohexyl-2-(4-hydroxyphenyl)benzimidazole-5-carboxylate (50 g) obtained in Example 3 were suspended in dimethylformamide (300 ml). Potassium carbonate (38 g) was added and the mixture was stirred for 1 hr at 80° C. with heating. The reaction mixture was allowed to cool and then added to a mixed solvent of water-ethyl acetate. The precipitated crystals were collected by filtration to give the title compound (50 g, yield 64%).

$^1$H-NMR (300 MHz, CDCl$_3$): 8.50(1H, d, J=1.4 Hz), 7.97(1H, dd, J=8.6, 1.4 Hz), 7.70–7.57(5H, m), 7.20(1H, dd, J=8.4, 2.5 Hz), 7.14(2H, d, J=8.7 Hz), 5.17(2H, s), 4.46–4.30 (1H, m), 4.41(2H, q, J=7.1 Hz), 2.40–2.20(2H, m), 2.02–1.21(8H, m), 1.42(3H, t, J=7.1 Hz)

Example 5

Production of ethyl 2-{4-[2-(4-chlorophenyl)-5-chlorobenzyloxy]-phenyl}-1-cyclohexylbenzimidazole-5-carboxylate Ethyl 2-[4-(2-bromo-5-chlorobenzyloxy)phenyl]-1-cyclohexylbenzimidazole-5-carboxylate (49 g) obtained in Example 4, 4-chlorophenylboronic acid (18 g) and tetrakis (triphenylphosphine)palladium (10 g) were suspended in 1,2-dimethoxyethane (600 ml). Saturated aqueous sodium hydrogencarbonate solution (300 ml) was added and the mixture was refluxed under heating for 2 hr. Chloroform was added to the reaction mixture. The organic layer was washed successively with saturated aqueous sodium hydrogencarbonate solution, water and saturated brine, dried over anhydrous magnesium sulfate, and concentrated under reduced pressure. The residue was purified by silica gel flash chromatography (developing solvent, chloroform:ethyl acetate= 97:3). Ethyl acetate and diisopropyl ether were added to the resulting oil for crystallization and the resulting crystals were collected by filtration to give the title compound (44 g, yield 85%).

$^1$H-NMR (300 MHz, CDCl$_3$): 8.49(1H, d, J=1.4 Hz), 7.97(1H, dd, J=8.6, 1.6 Hz), 7.70–7.60(2H, m), 7.55(2H, d, J=8.7 Hz), 4.95(2H, s), 4.48–4.28(1H, m), 4.40(2H, m), 2.02–1.20(8H, m), 1.41(3H, t, J=7.1 Hz)

Example 6

Production of 2-{4-[2-(4-chlorophenyl)-5-chlorobenzyloxy] phenyl}-1-cyclohexylbenzimidazole-5-carboxylic acid Ethyl 2-{4-[2-(4-chlorophenyl)-5-chlorobenzyloxy] phenyl}-1-cyclohexylbenzimidazole-5-carboxylate (43 g) obtained in Example 5 was treated in the same manner as in Example 2 to give the title compound (33 g, yield 76%).
melting point: 243–244° C.
FAB-Ms: 571(MH+)

$^1$H-NMR (300MHz, DMSO-d$_6$): 8.32(1H, s), 8.28 (1H, d, J=8.9Hz), 8.05(1H, d, J=8.8Hz), 7.76–7.72(3H, m), 7.58–7.46(5H, m), 7.40(1H, d, J=8.3Hz), 7.24(2H, d, J=8.9Hz), 5.11(2H, s), 4.36(1H, m), 2.40–2.15(2H, m), 2.15–1.95(2H, m), 1.95–1.75(2H, m), 1.75–1.55(1H, m), 1.55–1.15(3H, m)

Example 7

Production of ethyl 2-[4-(2-bromo-5-methoxybenzyloxy)phenyl]-1-cyclohexylbenzimidazole-5-carboxylate Ethyl 1-cyclohexyl-2-(4-hydroxyphenyl)benzimidazole-5-carboxylate obtained in Example 3 and 2-bromo-5-methoxybenzyl bromide were treated in the same manner as in Example 4 to give the title compound (59 g).

Example 8

Production of ethyl 2-{4-[2-(4-chlorophenyl)-5-methoxybenzyloxy]-phenyl}-1-cyclohexylbenzimidazole-5-carboxylate Ethyl 2-[4-(2-bromo-5-methoxybenzyloxy)phenyl]-1-cyclohexylbenzimidazole-5-carboxylate obtained in Example 7 was treated in the same manner as in Example 5 to give the title compound (48 g, yield 77%).

$^1$H-NMR (300MHz, CDCl$_3$): 8.49(1H, d, J=1.4Hz), 7.97 (1H, dd, J=8.6, 1.4Hz), 7.64(1H, d, J=8.6Hz), 7.54(2H, d, J=8.7Hz), 7.37(2H, d, J=8.6Hz), 7.31(2H, d, J=8.6Hz), 7.25(1H, d, J=8.4Hz), 7.19(1H, d, J=2.7Hz), 7.00(2H, d, J=8.7Hz), 6.97(1H, dd, J=8.4, 2.7Hz), 4.98(2H, s), 4.41(2H, q, J=7.1Hz), 4.42–4.29(1H, m), 3.88(3H, s), 2.40–2.20(2H, m), 2.01–1.88(4H, m), 1.83–1.73(1H, m), 1.42(3H, t, J=7.1Hz), 1.41–1.25(3H, m)

Example 9

Production of 2-{4-[2-(4-chlorophenyl)-5-methoxybenzyloxy]phenyl}-1-cyclohexylbenzimidazole-5-carboxylic acid Ethyl 2-{4-[2-(4-chlorophenyl)-5-methoxybenzyloxy]phenyl}-1-cyclohexylbenzimidazole-5-carboxylate (52 g) obtained in Example 8 was treated in the same manner as in Example 2 to give the title compound (44 g, yield 89%).

melting point: 248–249° C.

FAB-Ms: 568(MH+)

$^1$H-NMR (300MHz, DMSO-d$_6$): 8.20(1H, s), 7.88(1H, d, J=8.7Hz), 7.85(1H, d, J=8.7Hz), 7.57(d, 2H, J=8.6Hz), 7.46(2H, d, J=8.6Hz), 7.44(2H, d, J=8.6Hz), 7.29(1H, d, J=8.5Hz), 7.24(1H, d, J=2.6Hz), 7.11(2H, d, J=8.6Hz), 7.06 (1H, dd, J=8.5, 2.6Hz), 5.04(2H, s), 4.26(1H, m), 3.83(3H, s), 2.38–2.29(2H, m)

Example 10

Production of ethyl 1-cyclohexyl-2-{4-[(E)-2-phenylvinyl]phenyl}-benzimidazole-5-carboxylate Ethyl 3-amino-4-cyclohexylaminobenzoate (500 mg) obtained in Example 1, Step 3, was dissolved in methyl alcohol (6 ml) and trans-4-stilbenecarbaldehyde (397 mg) was added under ice-cooling. The mixture was stirred overnight at room temperature. The reaction mixture was ice-cooled and benzofuroxan (259 mg) dissolved in acetonitrile (2 ml) was added. The mixture was stirred for 7 hr at 50° C. The reaction mixture was ice-cooled. After 1N sodium hydroxide was added, ethyl acetate was added and the mixture was extracted. The organic layer was washed with water and saturated brine, dried over anhydrous magnesium sulfate, and concentrated under reduced pressure. The residue was purified by silica gel flash chromatography (developing solvent, n-hexane:ethyl acetate=4:1) to give the title compound (540 mg, yield 63%).

$^1$H-NMR (300MHz, DMSO-d$_6$): 8.28(1H, d, J=1.4Hz), 8.01(1H, d, J=8.7Hz), 7.90–7.80(3H, m), 7.75–7.65(4H, m), 7.50–7.25(5H, m), 4.35(2H, q, J=7.0Hz), 4.31(1H, m), 2.40–2.20(2H, m), 2.00–1.80(4H, m), 1.63(1H, m), 1.40–1.20(3H, m), 1.36(3H, t, J=7.0Hz)

Example 11

Production of 1-cyclohexyl-2-{4-[(E)-2-phenylvinyl]phenyl}-benzimidazole-5-carboxylic acid Ethyl 1-cyclohexyl-2-{4-[(E)-2-phenylvinyl]phenyl}-benzimidazole-5-carboxylate (127 mg) obtained in Example 10 was treated in the same manner as in Example 2 to give the title compound (116 mg, yield 97%).

melting point: not lower than 300° C.

FAB-Ms: 423(MH+) $^1$H-NMR (300MHz, DMSO-d$_6$): 8.25(1H, s), 7.96–7.29(13H, m), 4.33(1H, brt), 2.41–2.23 (2H, m), 2.03–1.78(4H, m), 1.71–1.59(1H, m), 1.49–1.20 (3H, m)

Example 12

Production of 2-(4-benzyloxyphenyl)-1-cyclopentylbenzimidazole-5-carboxylic acid In the same manner as in Examples 1 and 2, the title compound (700 mg) was obtained.

FAB-Ms: 413(MH+)

$^1$H-NMR (300MHz, CDCl$_3$): 8.60(1H, s), 8.04(1H, d, J=9.0Hz), 7.63(2H, d, J=8.4Hz), 7.51–7.32(6H, m), 7.14 (2H, d, J=9.0Hz), 5.16(2H, s), 5.03–4.89(1H, m), 2.41–1.63 (8H, m)

Example 13

Production of 2-(4-benzyloxyphenyl)-1-cyclopentylbenzimidazole-5-carboxamide 2-(4-Benzyloxyphenyl)-1-cyclopentylbenzimidazole-5-carboxylic acid (700 mg) obtained in Example 12 was dissolved in dimethylformamide (10 ml), and ammonium chloride (108 mg), 1-ethyl-3-(3-dimethylaminopropyl) carbodiimide hydrochloride (390 mg), 1-hydroxybenzotriazole (275 mg) and triethylamine (0.3 ml) were added. The mixture was stirred overnight at room temperature. Water was added to the reaction mixture and the mixture was extracted with ethyl acetate. The organic layer was washed successively with saturated aqueous sodium hydrogencarbonate, water and saturated brine, dried over anhydrous magnesium sulfate, and concentrated under reduced pressure. Ethyl acetate and diisopropyl ether were added to the residue for crystallization and the crystals were collected by filtration to give the title compound (571 mg, yield 81%).

melting point: 232–233° C.

FAB-Ms: 412(MH+)

$^1$H-NMR (300MHz, CDCl$_3$): 8.23(1H, d, =1.5Hz), 7.86 (1H, dd, J=8.5, 1.5Hz), 7.65–7.30(8H, m), 7.13(2H, d, J=8.8Hz), 5.16(2H, s), 4.93(1H, quint, J=8.8Hz), 2.40–1.60 (8H, m)

Example 14

Production of 2-(4-benzyloxyphenyl)-5-cyano-1-cyclopentylbenzimidazole

In the same manner as in Example 1, the title compound (400 mg) was obtained.

FAB-Ms: 394(MH+)

$^1$H-NMR (300MHz, CDCl$_3$): 8.11(1H, s), 7.68–7.30(9H, m), 7.13(2H, s), 5.16(2H, s), 4.94(1H, quint, J=8.9Hz), 2.35–1.60(8H, m)

Example 15

Production of 2-(4-benzyloxyphenyl)-1-cyclopentylbenzimidazole-5-carboxamide oxime 2-(4-Benzyloxyphenyl)-5-cyano-1-cyclopentylbenzimidazole (400 mg) obtained in Example 14 was suspended in ethyl alcohol (3 ml) and water (1.5 ml), and hydroxylamine hydrochloride (141 mg) and sodium hydrogencarbonate (170 mg) were added. The mixture was refluxed under heating overnight. The reaction mixture was allowed to cool and the precipitated crystals were collected by filtration to give the title compound (312 mg, yield 71%).

melting point: 225–226° C.

FAB-Ms: 456(MH+)

¹H-NMR (300MHz, DMSO-d₆): 8.20(1H, s), 7.50–7.31 (9H, m), 7.12(2H, d, J=8.7Hz), 5.15(2H, s), 4.94(1H, quint, J=8.7Hz), 3.61(3H, s), 3.40(3H, s), 2.41–1.42(8H, m)

Example 16

Production of ethyl 1-cyclohexyl-2-{4-[{4-(4-fluorophenyl)-2-methyl-5-thiazolyl}methoxy]phenyl}benzimidazole-5-carboxylate Step 1: Production of 4-(4-fluorophenyl)-5-hydroxymethyl-2-methylthiazole Ethyl 4-(4-fluorophenyl)-2-methyl-5-thiazolecarboxylate (59 g) prepared by a known method (Chem. Pharm. Bull., 43(6), 947, 1995) was dissolved in tetrahydrofuran (700 ml). Lithium aluminum hydride (13 g) was added under ice-cooling and the mixture was stirred for 30 min. Water (13 ml), 15% sodium hydroxide (13 ml) and water (39 ml) were added successively to the reaction mixture, and the precipitated insoluble materials were filtered off. The filtrate was concentrated under reduced pressure to give the title compound (37 g, yield 71%).

¹H-NMR (300MHz, CDCl₃): 7.60(2H, dd, J=8.7, 6.6Hz), 7.11(2H, t, J=8.7Hz), 4.80(2H, s), 2.70(3H, s)

Step 2: Production of 5-chloromethyl-4-(4-fluorophenyl)-2-methylthiazole 4-(4-Fluorophenyl)-5-hydroxymethyl-2-methylthiazole (37 g) obtained in the previous step was dissolved in chloroform (500 ml), and thionyl chloride (24 ml) and pyridine (2 ml) were added. The mixture was stirred for 3 hr at room temperature. The reaction mixture was poured into ice-cold water. The mixture was extracted with chloroform, and washed with water and saturated brine. The organic layer was dried over sodium sulfate, and concentrated under reduced pressure to give the title compound (29 g, yield 76%).

¹H-NMR (300MHz, CDCl₃): 7.67(2H, dd, J=8.8, 5.4Hz), 7.16(2H, t, J=8.7Hz), 4.79(2H, s), 2.73(3H, s)

Step 3: Production of ethyl 1-cyclohexyl-2-{4-[{4-(4-fluorophenyl)-2-methyl-5-thiazolyl}methoxy]phenyl}benzimidazole-5-carboxylate 5-Chloromethyl-4-(4-fluorophenyl)-2-methylthiazole (28 g) obtained in the previous step and ethyl 1-cyclohexyl-2-(4-hydroxyphenyl)benzimidazole-5-carboxylate (36 g) obtained in Example 3 were treated in the same manner as in Example 4 to give the title compound (61 g, yield 100%).

APCI-Ms: 570(MH+)

¹H-NMR (300MHz, DMSO-d₆): 8.25(1H, d, J=1.5Hz), 7.97(1H, d, J=8.7Hz), 7.86(1H, dd, J=8.6, 1.6Hz), 7.74(2H, dd, J=8.8, 5.5Hz), 7.62(2H, d, J=8.7Hz), 7.33(2H, t, J=8.9Hz), 7.22(2H, t, J=8.9Hz), 5.41(2H, s), 4.34(2H, q, J=7.1Hz), 4.31(1H, m), 2.71(3H, s), 2.40–2.15(2H, m), 2.05–1.75(4H, m), 1.55–1.15(3H, m), 1.36(3H, t, J=7.1Hz)

Example 17

Production of 1-cyclohexyl-2-{4-[{4-(4-fluorophenyl)-2-methyl-5-thiazolyl}methoxy]phenyl}benzimidazole-5-carboxylic acid Ethyl 1-cyclohexyl-2-{4-[{4-(4-fluorophenyl)-2-methyl-5-thiazolyl}methoxy]phenyl}benzimidazole-5-carboxylate (60 g) obtained in Example 16 was treated in the same manner as in Example 2 to give the title compound (39 g, yield 69%).

melting point: 196–198° C.
FAB-Ms: 542(MH+)

¹H-NMR (300MHz, DMSO-d₆): 13.1(1H, brs), 8.34(1H, s), 8.29(1H, d, J=8.8Hz), 8.06(1H, d, J=8.7Hz), 7.80–7.72 (4H, m), 7.36–7.31(4H, m), 5.46(2H, s), 4.38(1H, m), 2.72 (3H, s), 2.45–2.15(2H, m), 2.15–1.95(2H, m), 1.95–1.75 (2H, m), 1.75–1.55(1H, m), 1.55–1.20(3H, m)

Example 18

Production of ethyl 1-cyclohexyl-2-(2-fluoro-4-hydroxyphenyl)-benzimidazole-5-carboxylate In the same manner as in Example 3, the title compound (50 g) was obtained.

Example 19

Production of ethyl 2-{4-[bis(3-fluorophenyl)methoxy]-2-fluorophenyl}-1-cyclohexylbenzimidazole-5-carboxylate Step 1: Production of 3,3'-difluorobenzhydrol To a stirred solution of magnesium strip (35.4 g) in THF (200 ml), iodine strip was added and the mixture was heated with stirring under nitrogen stream until most of color of iodine was disappeared. A solution of 3-fluoro-bromobenzene (250.0 g) in THF (1000 ml) was added dropwise over 2.5 hr while the temperature of the solution was maintained at 60° C. After the completion of the addition of the solution, the resulting mixture was refluxed for 1 hr with heating. The resulting Grignard solution was ice-cooled and a solution of ethyl formate (63.2 g) in THF (200 ml) was added dropwise over 1 hr. After a stirring of the reaction solution for an additional 30 min, saturated aqueous ammonium chloride solution (700 ml) was added dropwise with ice-cooling and water (300 ml) was added. The mixture was stirred for 10 min. The organic layer and water layer were separated. Water layer was extracted with ethyl acetate, and the combined organic layer was washed with 2N hydrochloric acid, saturated aqueous sodium hydrogencarbonate and saturated brine. The organic layer was dried over anhydrous magnesium sulfate, filtered, and the solvent was evaporated off under reduced pressure to give the title compound (156.2 g, yield 99%).

¹H-NMR (300MHz, CDCl₃): 7.31(2H, td, J=7.9, 5.8Hz), 7.15–7.80(4H, m), 6.97–6.94(2H, m), 5.82(1H, d, J=3.3Hz), 2.30(1H, d, J=3.3Hz)

Step 2: Production of 3,3'-difluorobenzhydryl chloride

To a solution of 3,3'-difluorobenzhydrol (150.0 g) obtained in the previous step in toluene (400 ml), pyridine (539 mg) was added at room temperature. To the solution, thionyl chloride (89.1 g) was added dropwise over 1 hr at room temperature and the resulting solution was stirred for an additional 2 hr. The solution was heated so that the temperature of the solution was at 40° C., and then stirred for an additional 1.5 hr. Thionyl chloride (8.1 g) was added again and the mixture was stirred for 30 min. To the reaction mixture, water was added. The organic layer was separated, and washed with water, saturated aqueous sodium hydrogencarbonate and saturated brine. The organic layer was dried over anhydrous magnesium sulfate, filtered, the solvent was evaporated off under reduced pressure to give the title compound (158.2 g, yield 97%).

¹H-NMR (300MHz, CDCl₃): 7.32(2H, td, J=8.0, 5.9Hz), 7.18–7.10(4H, m), 7.01(2H, tdd, J=8.2, 2.5, 1.2Hz), 6.05 (1H, s)

Step 3: Production of ethyl 2-{4-[bis(3-fluorophenyl)methoxy]-2-fluorophenyl}-1-cyclohexylbenzimidazole-5-carboxylate Ethyl 1-cyclohexyl-2-(2-fluoro-4-hydroxyphenyl)-benzimidazole-5-carboxylate (50 g) obtained in Example 18 and 3,3'-difluorobenzhydryl chloride (34 g) obtained in the previous step were treated in the same manner as in Example 4 to give the title compound (76 g, yield 99%).

FAB-Ms: 585(MH+)

$^1$H-NMR (300MHz, DMSO-$d_6$): 8.24(1H, d, J=1.4Hz), 7.98(1H, d, J=8.7Hz), 7.88(1H, d, J=8.7Hz), 7.56(1H, t, J=8.6Hz), 7.50–1.40(6H, m), 6.82(1H, s), 4.34(2H, q, J=7.1Hz), 3.95(1H, m), 2.20–2.10(2H, m), 1.90–1.80(4H, m), 1.6(1H, m), 1.35(3H, t, J=7.2Hz), 1.30–1.20(3H, mz)

Example 20

Production of 2-{4-(bis[3-fluorophenyl]methoxy)-2-fluorophenyl}-1-cyclohexylbenzimidazole-5-carboxylic acid Ethyl 2-{4-[bis(3-fluorophenyl)methoxy]-2-fluorophenyl}-1-cyclohexylbenzimidazole-5-carboxylate (75 g) obtained in Example 19 was treated in the same manner as in Example 2 to give the title compound (48 g, yield 62%).

melting point: 242–243° C.

FAB-Ms: 557(MH+)

$^1$H-NMR (300MHz, DMSO-$d_6$): 8.29(1H, s), 8.16(1H, d, J=8.8Hz), 7.99(1H, d, J=8.7Hz), 7.66(1H, t, J=8.7Hz), 7.51–7.40(6H, m), 7.30(1H, d, J=12.1Hz), 7.20–7.14(3H, m), 6.88(1H, s), 4.07(1H, m), 2.40–2.10(2H, m), 2.00–1.75(4H, m), 1.70–1.55(1H, m), 1.50–1.15(3H, m)

Example 21

Production of ethyl 1-cyclopentyl-2-(4-nitrophenyl)benzimidazole-5-carboxylate

In the same manner as in Example 1, the title compound (12 g) was obtained.

Example 22

Production of ethyl 2-(4-aminophenyl)-1-cyclopentylbenzimidazole-5-carboxylate

Ethyl 1-cyclopentyl-2-(4-nitrophenyl)benzimidazole-5-carboxylate (12 g) obtained in Example 21 was dissolved in tetrahydrofuran (200 ml) and ethyl alcohol (50 ml), 7.5% palladium carbon (50% wet, 1 g) was added. The mixture was hydrogenated for 1 hr at atmospheric pressure. The catalyst was filtered off and the filtrate was concentrated under reduced pressure. Tetrahydrofuran was added to the residue to allow crystallization and the crystals were collected by filtration to give the title compound (11 g, yield 98%).

$^1$H-NMR (300MHz, CDCl$_3$): 8.49(1H, d, J=1.3Hz), 7.95 (1H, dd, J=8.5, 1.3Hz), 7.50–7.40(3H, m), 6.79(2H, d, J=4.6Hz), 4.97(1H, quint, J=8.9Hz), 4.40(2H, q, J=7.1Hz), 3.74(2H, brs), 2.40–1.60(8H, m), 1.41(3H, t, J=7.1Hz)

Example 23

Production of ethyl 2-(4-benzoylaminophenyl)-1-cyclopentylbenzimidazole-5-carboxylate Ethyl 1-cyclopentyl-2-(4-aminophenyl)benzimidazole-5-carboxylate (300 mg) obtained in Example 22 was dissolved in pyridine (3 ml) and chloroform (3 ml), and benzoyl chloride (127 mg) was added. The mixture was stirred for 30 min at room temperature. The reaction mixture was concentrated under reduced pressure and water was added to the residue to allow crystallization. The crystals were collected by filtration to give the title compound (403 mg, yield 100%).

$^1$H-NMR (300MHz, CDCl$_3$): 8.58(1H, s), 8.00(1H, d, J=9.0Hz), 7.84(2H, d, J=7.5Hz), 7.60–7.40(6H, m), 7.14 (2H, d, J=7.5Hz), 4.84(1H, quint, J=8.7Hz), 4.41(2H, q, J=7.5Hz), 2.20–1.30(8H, m), 1.41(3H, t, J=7.5Hz)

Example 24

Production of 2-(4-benzoylaminophenyl)-1-cyclopentylbenzimidazole-5-carboxylic acid Ethyl 2-(4-benzoylaminophenyl)-1-cyclopentylbenzimidazole-5-carboxylate (200 mg) obtained in Example 23 was treated in the same manner as in Example 2 to give the title compound (131 mg, yield 70%).

melting point: not lower than 300° C.

FAB-Ms: 426(MH+)

$^1$H-NMR (300MHz, DMSO-$d_6$): 10.75(1H, s), 8.35(1H, s), 8.15 and 7.85(4H, ABq, J=8.9Hz), 8.10–7.98(4H, m), 7.70–7.55(3H, m), 5.02(1H, quint, J=8.7Hz), 2.36–2.15(4H, m), 2.14–1.95(2H, m), 1.80–1.62(2H, m)

Example 25

Production of ethyl 2-{4-[3-(3-chlorophenyl)phenoxy]phenyl}-1-cyclohexylbenzimidazole-5-carboxylate Ethyl 2-(4-[3-bromophenoxy)phenyl]-1-cyclohexylbenzimidazole-5-carboxylate (65 g) obtained in Example 1 and 3-chlorophenylboronic acid (23 g) were treated in the same manner as in Example 5 to give the title compound (59 g, yield 85%).

$^1$H-NMR (300MHz, CDCl$_3$): 8.51(1H, d, J=1.8Hz), 7.99 (1H, dd, J=8.7, 1.8Hz), 7.71–7.55(4H, m), 7.51–7.43(2H, m), 7.43–7.27(4H, m), 7.19(1H, d, J=8.4Hz), 7.12(1H, m), 4.41(2H, q, J=7.2Hz), 4.39(1H, m), 2.42–2.22(2H, m), 2.03–1.87(4H, m), 1.79(1H, m), 1.42(3H, t, J=7.2Hz), 1.39–1.29(3H, m)

Example 26

Production of 2-{4-[3-(3-chlorophenyl)phenoxy]phenyl}-1-cyclohexylbenzimidazole-5-carboxylic acid Ethyl 2-{4-[3-(3-chlorophenyl)phenoxy]phenyl}-1-cyclohexylbenzimidazole-5-carboxylate (59 g) obtained in Example 25 was treated in the same manner as in Example 2 to give the title compound (43 g, yield 76%).

melting point: 253–254° C.

FAB-Ms: 523(MH+)

$^1$H-NMR (300MHz, DMSO-$d_6$): 12.82(1H, brs), 8.24(1H, d, J=1.3Hz), 7.98(1H, d, J=8.7Hz), 7.89(1H, dd, J=8.7, 1.3Hz), 7.78(1H, s), 7.72(2H, d, J=9.7Hz), 7.70(1H, m), 7.64–7.42(5H, m), 7.25(2H, d, J=8.7Hz), 7.20(1H, m), 4.33 (1H, m), 2.39–2.17(2H, m), 2.00–1.76(4H, m), 1.65(1H, m), 1.50–1.22(3H, m)

Example 27

Production of ethyl 2-[4-(3-acetoxyphenyloxy)phenyl]-1-cyclohexylbenzimidazole-5-carboxylate In the same manner as in Example 1, the title compound (87 g) was obtained.

Example 28

Production of ethyl 1-cyclohexyl-2-[4-(3-hydroxyphenyloxy)-phenyl]benzimidazole-5-carboxylate Ethyl 2-[4-(3-acetoxyphenyloxy)phenyl]-1-cyclohexylbenzimidazole-5-carboxylate (87 g) obtained in Example 27 was dissolved in methyl alcohol (250 ml) and tetrahydrofuran (250 ml), and potassium carbonate (31 g) was added. The mixture was stirred for 30 min at room temperature. The insoluble materials were filtered off and the filtrate was concentrated under reduced pressure. Water was added to the residue and the mixture was neutralized with 2N hydrochloric acid. The precipitated crystals were collected by filtration to give the title compound (78 g, yield 97%).

$^1$H-NMR (300MHz, DMSO-$d_6$): 9.71(1H, s), 7.98(1H, d, J=8.7Hz), 7.87(1H, d, J=8.7Hz), 7.68(2H, d, J=8.6Hz), 7.24(1H, t, J=8.1Hz), 7.18(2H, d, J=8.6Hz), 6.63(1H, d, J=8.1Hz), 6.57(1H, d, J=8.1Hz), 6.51(1H, s), 4.38–4.23(1H, m), 4.35(2H, q, J=6.9Hz), 2.36–2.18(2H, m), 1.99–1.78(4H, m), 1.71–1.59(1H, m), 1.45–1.20(3H, m), 1.36(3H, t, J=6.9Hz)

Example 29

Production of ethyl 1-cyclohexyl-2-{4-[3-(4-pyridylmethoxy)-phenyloxy]phenyl}benzimidazole-5-carboxylate Ethyl 1-cyclohexyl-2-[4-(3-hydroxyphenyloxy)phenyl]-benzimidazole-5-carboxylate (78 g) obtained in Example 28 was suspended in dimethylformamide (800 ml), and sodium hydride (60% oil, 14 g) was added under ice-cooling. The mixture was stirred for 1 hr at room temperature. After the reaction mixture was ice-cooled, 4-chloromethylpyridine hydrochloride (29 g) was added and the mixture was stirred for 30 min. The mixture was then stirred overnight at room temperature. Water was added to the reaction mixture and the precipitated crystals were collected by filtration. The resulting crystals were recrystallized from ethyl alcohol to give the title compound (77 g, yield 82%).

$^1$H-NMR (300MHz, CDCl$_3$): 8.63(2H, d, J=6.0Hz), 8.51 (1H, s), 7.99(1H, d, J=8.7Hz), 7.66(2H, d, J=8.7Hz), 7.62 (2H, d, J=8.7Hz), 7.36(2H, d, J=8.7Hz), 7.31(1H, t, J=8.2Hz), 7.26(1H, s), 7.16(2H, d, J=8.7Hz), 6.79–6.70(3H, m), 5.09(2H, s), 4.47–4.31(1H, m), 4.42(2H, q, J=7.0Hz), 2.42–2.22(2H, m), 2.04–1.71(5H, m), 1.45–1.25(3H, m), 1.42(3H, t, J=7.0Hz)

Example 30

Production of 1-cyclohexyl-2-{4-[3-(4-pyridylmethoxy)phenyloxy]-phenyl}benzimidazole-5-carboxylic acid Ethyl 1-cyclohexyl-2-{4-[3-(4-pyridylmethoxy) phenyloxy]-phenyl}benzimidazole-5-carboxylate (60 g) obtained in Example 29 was treated in the same manner as in Example 2 to give the title compound (54 g, yield 75%).

melting point: 235–237° C.

FAB-Ms: 520(MH+)

$^1$H-NMR (300MHz, DMSO-$d_6$): 8.58(2H, d, J=6.0Hz), 8.23(1H, s), 7.96 and 7.86(2H, ABq, J=8.7Hz), 7.68 and 7.17(4H, A'B'q, J=8.7Hz), 7.44(2H, d, J=8.7Hz), 7.39(1H, t, J=8.3Hz), 6.90(1H, d, J=8.1Hz), 6.84(1H, s), 6.75(1H, d, J=8.1Hz), 5.22(2H, s), 4.40–4.22(1H, m), 2.40–2.19(2H, m), 2.00–1.80(4H, m)

Example 241

Production of methyl 2-{4-[2-(4-chlorophenyl)-5-methoxybenzyloxylphenyl}-1-cyclohexylbenzimidazole-5-carboxylate Step 1: Production of 2-bromo-5-methoxybenzaldehyde 3-Methoxybenzaldehyde (15 g) was dissolved in acetic acid (75 ml), and a solution of bromine (5.7 ml) dissolved in acetic acid (15 ml) was added dropwise. The mixture was stirred overnight at room temperature and water (150 ml) was added to the reaction mixture. The precipitated crystals were collected by filtration, washed with water and dried under reduced pressure to give the title compound (21 g, yield 88%).

$^1$H-NMR (300MHz, CDCl$_3$): 10.31(1H, s), 7.52(1H, d, J=8.8Hz), 7.41(1H, d, J=3.3Hz), 7.03(1H, dd, J=8.8, 3.3Hz), 3.48(3H, s)

Step 2: Production of 2-(4-chlorophenyl)-5-methoxybenzaldehyde

2-Bromo-5-methoxybenzaldehyde (10 g) obtained in the previous step was treated in the same method as in Example 5 to give the title compound (11 g, yield 96%).

$^1$H-NMR (300MHz, CDCl$_3$): 9.92(1H, s), 7.50(1H, d, J=2.6Hz), 7.48–7.14(6H, m), 3.90(3H, s)

Step 3: Production of 2-(4-chlorophenyl)-5-methoxybenzyl alcohol 2-(4-Chlorophenyl)-5-methoxybenzaldehyde (10 g) obtained in the previous step was dissolved in tetrahydrofuran (30 ml). The solution was added dropwise to a suspension of sodium borohydride (620 mg) in isopropyl alcohol (50 ml) and the mixture was stirred for 1 hr. The solvent was evaporated under reduced pressure and water was added to the residue. The precipitated crystals were collected by filtration and dried under reduced pressure. The resulting crystals were recrystallized from a mixture of methanol and water to give the title compound (9.2 g, yield 91%).

$^1$H-NMR (300MHz, CDCl$_3$): 7.37(2H, d, J=8.6Hz), 7.27 (2H, d, J=8.6Hz), 7.17(1H, d, J=8.6Hz), 7.11(1H, d, J=2.6Hz), 6.89(1H, dd, J=8.6, 2.6Hz), 4.57(2H, s), 3.86(3H, s)

Step 4: Production of 2-(4-chlorophenyl)-5-methoxybenzyl chloride 2-(4-Chlorophenyl)-5-methoxybenzyl alcohol (20 g) obtained in the previous step was dissolved in ethyl acetate (100 ml) and pyridine (0.5 ml), and thionyl chloride (11 ml) was added dropwise. The mixture was stirred for 1 hr. Water was added to the reaction mixture and the mixture was extracted with ethyl acetate. The organic layer was washed with water, saturated aqueous sodium hydrogencarbonate, water and saturated brine, dried over anhydrous magnesium sulfate, and concentrated under reduced pressure. Isopropyl alcohol was added to the residue to allow crystallization. The resulting crystals were collected by filtration and dried under reduced pressure to give the title compound (16 g, yield 74%).

$^1$H-NMR (300MHz, CDCl$_3$): 7.43–7.29(4H, m), 7.17(1H, d, J=8.6Hz), 7.05(1H, d, J=2.6Hz), 6.96–6.89(1H, m), 4.46 (2H, s), 3.86(3H, s)

Step 5: Production of methyl 2-{4-[2-(4-chlorophenyl)-5-methoxybenzyloxy]phenyl}-1-cyclohexylbenzimidazole-5-carboxylate 2-(4-Chlorophenyl)-5-methoxybenzyl chloride (4.0 g) obtained in the previous step and methyl 1-cyclohexyl-2-

(4-hydroxyphenyl)-benzimidazole-5-carboxylate (5.0 g) obtained in the same manner as in Example 3 were treated in the same manner as in Example 4 to give the title compound (6.0 g, yield 72%).

$^1$H-NMR (300MHz, CDCl$_3$): 8.48(1H, s), 8.00–7.93(1H, m), 7.68–7.62(1H, m), 7.54(2H, d, J=9.0Hz), 7.41–7.16(6H, m), 7.04–6.93(3H, m), 4.97(2H, s), 4.36(1H, m), 3.94(3H, s), 3.87(3H, s), 2.39–2.21(2H, m), 2.02–1.88(4H, m), 1.85–1.45(4H, m)

Example 242

Production of 2-{4-[2-(4-chlorophenyl)-5-methoxybenzyloxy]phenyl}-1-cyclohexylbenzimidazole-5-carboxylic acid hydrochloride Methyl 2-{4-[2-(4-chlorophenyl)-5-methoxybenzyloxy]phenyl}-1-cyclohexylbenzimidazole-5-carboxylate (5.0 g) obtained in Example 241 was treated in the same manner as in Example 2 to give the title compound (5.1 g, yield 98%).

APCI-Ms: 568(MH+)

$^1$H-NMR (300MHz, DMSO-d$_6$): 8.30(1H, d, J=1.4Hz), 8.24(1H, d, J=8.7Hz), 8.03(1H, d, J=8.7Hz), 7.72(2H, d, J=8.7Hz), 7.51–7.39(4H, m), 7.34–7.18(4H, m), 7.11–7.03(1H, m), 5.08(2H, s), 4.35(1H, m), 3.83(3H, m), 2.40–2.18(2H, m), 2.10–1.96(2H, m), 1.93–1.78(2Hm), 1.72–1.18(4H, m)

Example 243

Production of ethyl 2-{4-[3-(4-chlorophenyl)pyridin-2-ylmethoxy]phenyl}-1-cyclohexylbenzimidazole-5-carboxylate Step 1: Production of methyl 3-hydroxypicolinate 3-Hydroxypicolinic acid (1.0 g) was suspended in methanol (10 ml) and concentrated sulfuric acid (1.0 ml) was added. The mixture was refluxed under heating for 5 hr. The reaction mixture was ice-cooled, neutralized with saturated aqueous sodium hydrogencarbonate, and extracted with chloroform. The organic layer was washed with water and saturated brine, and dried over anhydrous magnesium sulfate. The solvent was evaporated under reduced pressure to give the title compound (711 mg, yield 64%). $^1$H-NMR (300MHz, CDCl$_3$): 10.63(1H, s), 8.28(1H, dd, J=3.7, 1.8Hz), 7.47–7.35(2H, m), 4.06(3H, s)

Step 2: Production of methyl 3-(trifluoromethylsulfonyloxy)-pyridine-2-carboxylate Methyl 3-hydroxypicolinate (710 mg) obtained in the previous step and triethylamine (0.77 ml) were dissolved in dichloromethane (7 ml), and trifluoromethanesulfonic anhydride (0.86 ml) was added under ice-cooling. The reaction mixture was allowed to warm to room temperature and the mixture was stirred for 2 hr. Water was added to the reaction mixture and the mixture was extracted with ethyl acetate. The organic layer was washed with saturated brine and dried over anhydrous magnesium sulfate. The solvent was evaporated under reduced pressure to give the title compound (1.2 g, yield 90%).

$^1$H-NMR (300MHz, CDCl$_3$): 8.80–8.73(1H, m), 7.75–7.70(1H, m), 7.63(1H, dd, J=8.2, 4.5Hz), 4.05(3H, s)

Step 3: Production of methyl 3-(4-chlorophenyl)pyridine-2-carboxylate

Methyl 3-(trifluoromethylsulfonyloxy)pyridine-2-carboxylate (1.2 g) obtained in the previous step was treated in the same manner as in Example 5 to give the title compound (728 mg, yield 69%).

$^1$H-NMR (300MHz, CDCl$_3$): 8.73–8.66(1H, m), 7.77–7.68(1H, m), 7.49(1H, dd, J=7.8, 4.5Hz), 7.46–7.37 (2H, m), 7.32–7.23(2H, m), 3.80(3H, s)

Step 4: Production of (3-(4-chlorophenyl)pyridin-2-yl]methanol

Methyl 3-(4-chlorophenyl)pyridine-2-carboxylate (720 mg) obtained in the previous step was dissolved in tetrahydrofuran (10 ml) and the solution was ice-cooled. Lithium aluminum hydride (160 mg) was added to the solution and the mixture was stirred for 1 hr. To the reaction mixture were added successively water (1.6 ml), 15% sodium hydroxide (1.6 ml) and water (4.8 ml). The insoluble materials were filtered off and the filtrate was concentrated under reduced pressure. The residue was purified by silica gel flash chromatography (developing solvent, n-hexane:ethyl acetate= 1:1) to give the title compound (208 mg, yield 32%).

$^1$H-NMR (300MHz, CDCl$_3$): 8.60(1H, dd, J=4.8, 1.5Hz), 7.60–7.55(1H, m), 7.40–7.48(2H, m), 7.29–7.36(1H, m), 7.27–7.20(3H, m), 4.63(2H, s)

Step 5: Production of ethyl 2-{4-[3-(4-chlorophenyl)pyridin-2-ylmethoxy]phenyl}-1-cyclohexylbenzimidazole-5-carboxylate

[3-(4-Chlorophenyl)pyridin-2-yl]methanol (200 mg) obtained in the previous step was dissolved in chloroform (3 ml), and thionyl chloride (0.13 ml) and pyridine (catalytic amount) were added. The mixture was stirred for 1 hr at room temperature and concentrated under reduced pressure. The residue was dissolved in dimethylformamide (3 ml), and ethyl 1-cyclohexyl-2-(4-hydroxyphenyl)benzimidazole-5-carboxylate (232 mg) obtained in the same manner as in Example 3 and potassium carbonate (250 mg) were added. The mixture was stirred for 3 hr with heating at 80° C. The reaction mixture was then allowed to cool. Water was added and the mixture was extracted with ethyl acetate. The organic layer was washed with water and saturated brine, dried over anhydrous magnesium sulfate and concentrated under reduced pressure. The residue was purified by silica gel flash chromatography (developing solvent, n-hexane:ethyl acetate=1:2) to give the title compound (246 mg, yield 68%).

$^1$H-NMR (300MHz, CDCl$_3$): 8.71(1H, dd, J=4.7, 1.4Hz), 8.49(1H, d, J=2.1Hz), 7.96(1H, d, J=10.2Hz), 7.71–7.62(2H, m), 7.53(2H, d, J=8.7Hz), 7.45–7.34(5H, m), 7.04(2H, d, J=8.7Hz), 5.14(2H, s), 4.48–4.29(3H, m), 2.38–2.19(2H, m), 2.02–1.22(11H, m)

Example 244

Production of methyl 2-[4-(2-bromo-5-tert-butoxycarbonyl-benzyloxy)phenyl]-1-cyclohexylbenzimidazole-5-carboxylate Step 1: Production of tert-butyl 4-bromo-3-methylbenzoate 4-Bromo-3-methylbenzoic acid (25 g) was suspended in dichloromethane (200 ml), and oxalyl chloride (12 ml) and dimethylformamide (catalytic amount) were added. The mixture was stirred for 2 hr at room temperature and the solvent was evaporated under reduced pressure. The residue was dissolved in tetrahydrofuran (200 ml) and the solution was ice-cooled. To the solution was added dropwise a solution of potassium tert-butoxide dissolved in tetrahydrofuran (150 ml) and the mixture was stirred for 30 min. Water was added to the reaction mixture and the mixture was extracted with ethyl acetate. The organic layer was washed with water and saturated brine, and dried over anhydrous magnesium sulfate. The solvent was evaporated under reduced pressure to give the title compound (27 g, yield 85%).

¹H-NMR (300MHz, CDCl₃): 7.83(1H, d, J=2.2Hz), 7.67–7.53(2H, m), 2.43(3H, s), 1.58(9H, s)

Step 2: Production of methyl 2-[4-(2-bromo-5-tert-butoxycarbonylbenzyloxy)phenyl]-1-cyclohexylbenzimidazole-5-carboxylate tert-Butyl 4-bromo-3-methylbenzoate (7.0 q) obtained in the previous step and methyl 1-cyclohexyl-2-(4-hydroxyphenyl)-benzimidazole-5-carboxylate (6.3 g) obtained in the same manner as in Example 3 were treated in the same manner as in Example 4 to give the title compound (8.8 g, yield 77%).

¹H-NMR (300MHz, CDCl₃): 8.49(1H, d, J=1.5Hz), 8.21 (1H, d, J=2.1Hz), 7.97(1H, d, J=10.2Hz), 7.82(1H, d, J=10.2Hz), 7.71–7.58(4H, m), 7.16(2H, d, J=8.7Hz), 5.23 (2H, s), 4.38(1H, m), 3.95(3H, s), 2.40–2.23(2H, m), 2.04–1.90(4H, m), 1.84–1.73(1H, m), 1.59(9H, s), 1.44–1.27(3H, m)

Example 245

Production of methyl 2-4-[5-tert-butoxycarbonyl-2-(4-chlorophenyl)benzyloxy)phenyl]-1-cyclohexylbenzimidazole-5-carboxylate Methyl 2-[4-(2-bromo-5-tert-butoxycarbonylbenzyloxy) phenyl]-1-cyclohexylbenzimidazole-5-carboxylate (4.5 g) obtained in Example 244 was treated in the same manner as in Example 5 to give the title compound (3.6 g, yield 76%).

¹H-NMR (300MHz, CDCl₃): 8.48(1H, s), 8.27(1H, d, J=1.8Hz), 8.04(1H, dd, J=7.9, 1.5Hz), 7.96(1H, dd, J=7.0, 1.5Hz), 7.65(1H, d, J=8.6Hz), 7.55(2H, d, J=8.6Hz), 7.43–7.32(5H, m), 7.01(2H, d, J=8.6Hz), 4.99(2H, s), 4.43–4.29(1H, m), 3.95(3H, s), 2.41–2.21(2H, m), 2.02–1.89(4H, m), 1.82–1.73(1H, m), 1.62(9H, s), 1.46–1.28(3H, m)

Example 246

Production of methyl 2-{4-[5-carboxy-2-(4-chlorophenyl)-benzyloxylphenyl}-1-cyclohexylbenzimidazole-5-carboxylate hydrochloride Methyl 2-{4-(5-tert-butoxycarbonyl-2-(4-chlorophenyl)-benzyloxylphenyl}-1-cyclohexylbenzimidazole-5-carboxylate (3.5 g) obtained in Example 245 was dissolved in dichloromethane (35 ml), and trifluoroacetic acid (35 ml) was added. The mixture was stirred for 1 hr at room temperature and the reaction mixture was concentrated under reduced pressure. The residue was dissolved in ethyl acetate, and 4N hydrochloric acid-ethyl acetate was added. The precipitated crystals were collected by filtration and dried under reduced pressure to give the title compound (3.3 g, yield 97%).

¹H-NMR (300MHz, DMSO-d₆): 8.33(1H, d, J=1.5Hz), 8.29(1H, s), 8.24(1H, d, J=1.8Hz), 8.09–8.00(2H, m), 7.74 (2H, d, J=8.6Hz), 7.61–7.44(5H, m), 7.24(2H, d, J=8.6Hz), 5.19(2H, s), 4.36(1H, m), 3.93(3H, s), 2.37–1.21(10H, m)

Example 247

Production of methyl 2-{4-[2-(4-chlorophenyl)-5-methylcarbamoyl-benzyloxy]phenyl}-1-cyclohexylbenzimidazole-5-carboxylate Methyl 2-{4-[5-carboxy-2-(4-chlorophenyl)benzyloxy] phenyl}-1-cyclohexylbenzimidazole-5-carboxylate hydrochloride (400 mg) obtained in Example 246 was suspended in dichloromethane (5 ml), and oxalyl chloride (0.08 ml) and dimethylformamide (catalytic amount) were added. The mixture was stirred for 2 hr at room temperature. The reaction mixture was concentrated under reduced pressure and the residue was dissolved in dichloromethane (5 ml). The resulting solution was added dropwise to a mixed solution of 40% aqueous methylamine solution (5 ml) and tetrahydrofuran (5 ml) under ice-cooling. The reaction mixture was stirred for 1 hr and concentrated under reduced pressure. Water was added to the residue and the mixture was extracted with ethyl acetate. The organic layer was washed with water, saturated aqueous sodium hydrogencarbonate and saturated brine, and dried over anhydrous magnesium sulfate. The solvent was evaporated under reduced pressure and the residue was crystallized from ethyl acetate and diisopropyl ether. The crystals were collected by filtration and dried under reduced pressure to give the title compound (335 mg, yield 86%).

¹H-NMR (300MHz, CDCl₃): 8.47(1H, s), 8.06(1H, d, J=1.8Hz), 7.96(1H, dd, J=8.6, 1.5Hz), 7.82(1H, dd, J=8.2, 2.2Hz), 7.64(1H, d, J=8.6Hz), 7.54(2H, d, J=9.0Hz), 7.44–7.31(5H, m), 6.99(2H, d, J=9.0Hz), 6.35–6.26(1H, m), 5.00(2H, s), 4.35(1H, m), 3.95(3H, s), 3.05(3H, d, J=4.8Hz), 2.40–1.24(10H, m)

Example 248

Production of 2-{4-(2-(4-chlorophenyl)-5-methylcarbamoylbenzyloxy]phenyl}-1-cyclohexylbenzimidazole-5-carboxylate hydrochloride Methyl 2-{4-[2-(4-chlorophenyl)-5-methylcarbamoylbenzyloxy]-phenyl}-1-cyclohexylbenzimidazole-5-carboxylate (150 mg) obtained in Example 247 and tetrahydrofuran (2 ml) were treated in the same manner as in Example 2 to give the title compound (141 mg, yield 90%).

APCI-Ms: 594(MH+)

¹H-NMR (300MHz, DMSO-d₆): 8.65–8.58(1H, m), 8.27 (1H, d, J=1.5Hz), 8.21(1H, d, J=8.2Hz), 8.15(1H, d, J=1.5Hz), 8.05–7.90(2H, m), 7.70(2H, d, J=8.6Hz), 7.56–7.43(5H, m), 7.21(2H, d, J=8.6Hz), 5.14(2H, s), 4.34 (1H, m), 2.81(3H, d, J=4.5Hz), 2.39–1.19(10H, m)

Example 336

Production of methyl 2-[4-(2-bromo-5-nitrobenzyloxy)-2-fluorophenyl]-1-cyclohexylbenzimidazole-5-carboxylate Commercially available 2-bromo-5-nitrotoluene was dissolved in carbon tetrachloride (30 ml), and N-bromosuccinimide (2.9 g) and N,N'-azobisisobutyronitrile (228 mg) were added, which was followed by refluxing under heating overnight. The reaction mixture was allowed to cool, water was added and the mixture was extracted with chloroform. The organic layer was dried over magnesium sulfate and concentrated under reduced pressure. The residue was dissolved in dimethylformamide (30 ml) and methyl 2-(2-fluoro-4-hydroxyphenyl)-1-cyclohexylbenzimidazole-5-carboxylate (3.8 g) obtained in the same manner as in Example 3 and potassium carbonate (3.8 g) were added, which was followed by stirring at 80° C. for 1 hr. The reaction mixture was allowed to cool, water was added and the mixture was extracted with ethyl acetate. The organic layer was washed with water and saturated brine, dried over anhydrous magnesium sulfate and concentrated under reduced pressure. The residue was purified by silica gel flash chromatography (n-hexane:ethyl acetate=1:1) to give the title compound (3.7 g, yield 61%).

$^1$H-NMR (300MHz, CDCl$_3$): 8.55–8.45(2H, m), 8.15–8.05(1H, m), 7.99(1H, dd, J=8.6Hz, 1.5Hz), 7.70–7.55 (2H, m), 7.05–6.85(2H, m), 5.24(2H, s), 4.06(1H, m), 3.95 (3H, s), 2.35–2.15(2H, m), 2.05–1.85(4H, m), 1.80–1.70 (1H, m), 1.45–1.20(3H, m)

Example 337

Production of methyl 2-[4-{2-(4-chlorophenyl)-5-nitrobenzyloxy}-2-fluorophenyl]-1-cyclohexylbenzimidazole-5-carboxylate Methyl 2-[4-(2-bromo-5-nitrobenzyloxy)-2-fluorophenyl]-1-cyclohexylbenzimidazole-5-carboxylate (2.0 g) obtained in Example 336, 4-chlorophenylboronic acid (590 mg) and tetrakis(triphenylphosphine)palladium (396 mg) were suspended in dimethoxyethane (40 ml), and saturated aqueous sodium hydrogencarbonate solution (20 ml) was added, which was followed by refluxing under heating for 1 hr. The reaction mixture was allowed to cool, water was added and the mixture was extracted with chloroform. The organic layer was dried over anhydrous magnesium sulfate and concentrated under reduced pressure. The residue was purified by silica gel flash chromatography (n-hexane:ethyl acatate=2:1) to the title compound (1.9 g, yield 90%).

$^1$H-NMR (300MHz, CDCl$_3$): 8.55(1H, d, J=2.3Hz), 8.49 (1H, d, J=1.4Hz), 8.29(1H, dd, J=8.4Hz, 2.3Hz), 7.98(1H, dd, J=8.6Hz, 1.5Hz), 7.60–7.30(6H, m), 6.85–6.70(2H, m), 5.03(2H, s), 4.02(1H, m), 3.95(3H, s), 2.35–2.10(2H, m), 2.05–1.70(5H, m), 1.40–1.20(3H, m)

Example 338

Production of methyl 2-[4-{5-amino-2-(4-chlorophenyl)benzyloxy}-2-fluorophenyl]-1-cyclohexylbenzimidazole-5-carboxylate Methyl 2-[4-{2-(4-chlorophenyl)-5-nitrobenzyloxy}-2-fluorophenyl]-1-cyclohexylbenzimidazole-5-carboxylate (1.9 g) obtained in Example 337 was suspended in ethanol (40 ml), and tin(II) chloride dihydrate (3.5 g) was added, which was followed by refluxing under heating for 30 min. The reaction mixture was concentrated under reduced pressure, 4N sodium hydroxide was added and the mixture was extracted with chloroform. The organic layer was washed with 2N sodium hydroxide and water, dried over anhydrous magnesium sulfate and concentrated under reduced pressure. Diisopropyl ether was added to the residue, and the precipitated crystals were collected by filtration to give the title compound (1.5 g, yield 82%).

$^1$H-NMR (300MHz, CDCl$_3$): 8.49(1H, d, J=12Hz), 7.98 (1H, dd, J=9.0, 1.5Hz), 7.66(1H, d, J=8.7Hz), 7.49(1H, t, J=8.4Hz), 7.40–7.20(3H, m),7.13(1H, d, J=8.1Hz), 6.92(1H, d, J=2.7Hz), 6.85–6.65(4H, m), 4.92(2H, s), 4.03(1H, m), 3.95(3H, s), 3.82(2H, brs), 2.30–2.10(2H, m), 2.05–1.80 (4H, m), 1.80–1.70(1H, m), 1.40–1.10(3H, m)

Example 339

Production of methyl 2-[4-{2-(4-chlorophenyl)-5-(2-oxopyrrolidin-1-yl)benzyloxy}-2-fluorophenyl]-1-cyclohexylbenzimidazole-5-carboxylate Methyl 2-[4-{5-amino-2-(4-chlorophenyl)benzyloxy}-2-fluorophenyl]-1-cyclohexylbenzimidazole-5-carboxylate (500 mg) obtained in Example 338 and triethylamine (0.14 ml) were dissolved in chloroform (5 ml), and commercially available chlorobutyryl chloride (0.1 ml) was added under ice-cooling, which was followed by stirring at room temperature for 3 hr. Water was added to the reaction mixture and the mixture was extracted with ethyl acetate. The organic layer was washed with water and saturated brine, dried over anhydrous magnesium sulfate and concentrated under reduced pressure. The residue was dissolved in dimethylformamide (6 ml) and potassium carbonate (244 mg) was added, which was followed by stirring at 80° C. for 1 hr. The reaction mixture was allowed to cool, water was added and the precipitated crystals were collected by filtration to give the title compound (502 mg, yield 89%).

$^1$H-NMR (300MHz, CDCl$_3$): 4.89(1H, d, J=1.5Hz), 7.98 (1H, dd, J=8.6Hz, 1.6Hz), 7.72(1H, d, J=2.2Hz), 7.75–7.65 (2H, m), 7.49(1H, t, J=8.3Hz), 7.45–7.20(5H, m), 6.85–7.65 (2H, m), 4.99(2H, s), 4.10–3.85(6H, m), 2.66(2H, t, J=7.8Hz), 2.30–2.15(4H, m), 2.00–1.85(4H, m), 1.80–1.70 (1H, m), 1.45–1.20(3H, m)

Example 340

Production of 2-[4-{2-(4-chlorophenyl)-5-(2-oxopyrrolidin-1-yl)benzyloxy}-2-fluorophenyl]-1-cyclohexylbenzimidazole-5-carboxylic acid hydrochloride Methyl 2-[4-{2-(4-chlorophenyl)-5-(2-oxopyrrolidin-1-yl)benzyloxy}-2-fluorophenyl]-1-cyclohexylbenzimidazole-5-carboxylate (200 mg) obtained in Example 339 was treated in the same manner as in Example 2 to give the title compound (182 mg, yield 87%).

Ms: 638(M+1)

$^1$H-NMR (300MHz, CDCl$_3$): 8.28(1H, d, J=1.3Hz), 8.10 (1H, d, J=8.7Hz), 8.05–7.90(2H, m), 7.77(1H, dd, J=8.4Hz, 2.2Hz), 7.61(1H, t, J=8.5Hz), 7.55–7.35(5H, m), 7.00–7.20 (2H, m), 5.09(2H, s), 4.06(1H, in), 3.90(2H, t, J=6.9Hz), 2.60–2.45(2H, m), 2.30–2.00(4H, m), 1.95–1.75(4H, m), 1.70–1.55(1H, m), 1.45–1.15(3H, m)

Example 340-2

Step 1: Production of 4'-chloro-4-nitro-biphenyl-2-carbaldehyde

To a solution of 2-chloro-5-nitrobenzaldehyde (100 g) in 1,2-dimethoxyethane (1000 ml) were added 4-chlorophenylboronic acid (93 g), bistriphenylphosphine palladium(II) dichloride (380 mg), sodium hydrogencarbonate (68 g) and water (500 ml), and the mixture was refluxed for 1 hr. The reaction mixture was cooled to 50° C., ethyl acetate (1000 ml) was added thereto and the mixture was stirred. The aqueous layer was separated and the organic layer was washed with water (500 ml), 1N aqueous sodium hydroxide solution (500 ml), water (500 ml), 28% aqueous ammonia (500 ml), water (500 ml), 2N hydrochloric acid (500 ml) and saturated brine (500 ml), dried over anhydrous magnesium sulfate and concentrated under reduced pressure. The residue was suspended in diisopropyl ether (500 ml), filtrated and vacuum dried to give the title compound (120 g, yield 85%).

$^1$H-NMR (300MHz, DMSO-d$_6$): 9.92(1H, s), 8.61 (1H, d, J=2.5Hz), 8.53(1H, dd, J=2.6Hz, 8.5Hz), 7.82(1H, d, J=8.5Hz), 7.64(2H, d, J=8.7Hz), 7.59(2H, d, J=8.7Hz)

Step 2: Production of (4'-chloro-4-nitro-biphenyl-2-yl) methanol

A solution of 4'-chloro-4-nitro-biphenyl-2-carbaldehyde (120 g) obtained in the previous step in tetrahydrofuran (900 ml) was added dropwise to a suspension of sodium borohydride (47 g) in 2-propanol (600 ml), over 70 min under water-cooling. The reaction mixture was stirred at room temperature for 1 hr, and 2N hydrochloric acid (185 ml) was dropwise added thereto over 40 min under water-cooling. The mixture was stirred at room temperature for 30 min and concentrated under reduced pressure. The residue was suspended in 2-propanol (300 ml), and water (1000 ml) was added with stirring. After stirring the mixture for 30 min, the crystals were collected by filtration and vacuum dried to give the title compound (116 g, yield 96%).

$^1$H-NMR (300MHz, DMSO-$d_6$): 8.43(1H, d, J=2.5Hz), 8.19(1H, dd, J=2.6Hz, 8.4Hz), 7.57(2H, d, J=8.5Hz), 7.52 (1H, d, J=8.4Hz), 7.47(2H, d, J=8.6Hz), 5.59(1H, brs), 4.48(2H, s)

Step 3: Production of (4-amino-4'-chloro-biphenyl-2-yl) methanol

To a suspension of (4'-chloro-4-nitro-biphenyl-2-yl) methanol (1.0 g) obtained in the previous step and sodium hydrosulfite (2.0 g) in N,N-dimethylformamide (4 ml) and methanol (1 ml) was added water (0.3 ml, 50 μl each time in 6 portions) every 20 min at 100° C. Water (5 ml) was added threto at room temperature. Conc. hydrochloric acid (2.5 ml) was added threto at room temperature. The mixture was stirred at 55° C. for 2.5 hr, and a solution of sodium hydroxide (1.2 g) in water (3 ml) was added under ice-cooling. Water (5 ml) was added and the mixture was stirred at room temperature for 1 hr. The precipitate was filtrated and washed with water (3 ml). The crystals were vacuum dried to give the title compound (700 mg, yield 79%).

$^1$H-NMR (400MHz, DMSO-$d_6$): 7.39(2H, d, J=8.5Hz), 7.35(2H, d, J=8.5Hz), 6.90(1H, d, J=8.4Hz), 6.82(1H, s), 6.56(1H, d, J=8.4Hz), 5.20(2H, brs), 5.04(1H, t, J=5.4Hz), 4.29(2H, d, J=5.4Hz)

Step 4: Production of 4-chloro-N-(4'-chloro-2-hydroxymethyl-biphenyl-4-yl)butyramide To a solution of (4-amino-4'-chloro-biphenyl-2-yl)-methanol (1.0 g) obtained in the previous step in tetrahydrofuran (10 ml) were added sodium acetate (390 mg) and acetic acid (0.27 ml) at room temperature.

4-Chlorobutyryl chloride (0.48 ml) was gradually added dropwise under ice-cooling. After stirring the mixture at room temperature for 30 min, water (20 ml) and ethyl acetate (20 ml) were added to the reaction mixture and the organic layer was separated. The organic layer was washed with saturated aqueous sodium hydrogencarbonate (20 ml) and saturated brine (20 ml). The organic layer was dried over sodium sulfate, filtrated and the solvent was evaporated to give the title compound (1.44 g, yield 99%).

$^1$H-NMR (300MHz, CDCl$_3$): 7.68(1H, s), 7.55(1H, d, J=8.4Hz), 7.39(2H, d, J=8.5Hz), 7.28(2H, d, J=8.5Hz), 7.22(1H, d, J=8.3Hz), 4.58(2H, s), 3.69(2H, t, J=6.1Hz), 2.60(2H, t, J=7.0Hz), 2.22(2H, m)

Step 5: Production of 1-(4'-chloro-2-hydroxymethyl-biphenyl-4-yl)-2-pyrrolidinone To a solution of 4-chloro-N-(4'-chloro-2-hydroxymethyl-biphenyl-4-yl)butyramide (1.44 g) obtained in the previous step in N,N-dimethylformamide (15 ml) was added potassium carbonate (710 mg) at room temperature. After stirring the mixture at 100° C. for 90 min, 1N hydrochloric acid, (5 ml) and water (20 ml) were added at room temperature and the precipitated crystals were collected by filtration and washed with water (5 ml). The crystals were vacuum dried to give the title compound (970 mg, yield 76%).

$^1$H-NMR (300MHz, CDCl$_3$): 7.76(1H, d, J=2.3Hz), 7.62 (1H, dd, J=2.4Hz, 8.3Hz), 7.38(2H, d, J=8.5Hz), 7.29(2H, d, J=8.5Hz), 7.25(1H, d, J=8.3Hz), 4.61(2H, s), 3.91(2H, t, J=7.0Hz), 2.62(2H, t, J=7.8Hz), 2.18(2H, m)

Step 6: Production of 1-(4'-chloro-2-chloromethyl-biphenyl-4-yl)-2-pyrrolidinone To a mixed solution of 1-(4'-chloro-2-hydroxymethyl-biphenyl-4-yl)-2-pyrrolidinone (900 mg) obtained in the previous step in N,N-dimethylformamide (2 ml) and toluene (7 ml) was dropwise added thionyl chloride (0.26 ml) under ice-cooling. After stirring the mixture at room temperature for 3 hr, the reaction mixture was diluted with ethyl acetate (20 ml) and washed with water (20 ml), saturated aqueous sodium hydrogencarbonate (20 ml) and saturated brine (20 ml). The organic layer was dried over sodium sulfate, filtrated and the solvent was evaporated under reduced pressure to give the title compound (954 mg, yield 99%).

$^1$H-NMR (300MHz, CDCl$_3$): 7.77(1H, d, J=2.3Hz), 7.69 (1H, dd, J=2.4Hz, 8.5Hz),7.42(2H, d, J=8.6Hz), 7.34(2H, d, J=8.6Hz), 7.26(1H, d, J=8.4Hz), 4.50(2H, s), 3.92(2H, t, J=7.0Hz), 2.65(2H, t, J=7.8Hz), 2.20(2H, m)

Step 7: Production of methyl 2-[4-{2-(4-chlorophenyl)-5-(2-oxopyrrolidin-1-yl)benzyloxy}-2-fluorophenyl]-1-cyclohexylbenzimidazole-5-carboxylate To a suspension of methyl 1-cyclohexyl-2-(2-fluoro-4-hydroxyphenyl)benzimidazole-5-carboxylate (915 mg) obtained in Example 18 in N,N-dimethylformamide (6 ml) was added 1-(4'-chloro-2-chloromethyl-biphenyl-4-yl)-2-pyrrolidinone (954 mg) obtained in the previous step and potassium carbonate (415 mg) at room temperature. After stirring the mixture at 100° C. for 1 hr, 1N hydrochloric acid (3 ml) and water (8 ml) were added at room temperature and the precipitated crystals were collected by filtration and washed with water (5 ml). The crystals were vacuum dried to give the title compound (1.6 g, yield 100%).

$^1$H-NMR (300MHz, CDCl$_3$): 8.49(1H, d, J=1.5Hz), 7.98 (1H, dd, J=1.6Hz, 8.6Hz), 7.90(1H, d, J=2.2Hz), 7.72–7.65 (2H, m), 7.49(1H, t, J=8.3Hz), 7.40(2H, d, J=8.5Hz), 7.34 (1H, d, J=8.7Hz), 7.31(2H, d, J=8.6Hz), 6.80 (1H, d, J=8.6Hz), 6.71(1H, d, J=11.6Hz), 4.99(2H, s), 4.04(1H, m), 3.95(3H, s), 3.93(2H, t, J=7.1Hz), 2.66(2H, t, J=7.8Hz), 2.30–2.15(4H, m), 2.00–1.85(4H, m), 1.80–1.70(1H, m), 1.45–1.20(3H, m)

Step 8: Production of 2-[4-{2-(4-chlorophenyl)-5-(2-oxopyrrolidin-1-yl)benzyloxy}-2-fluorophenyl]-1-cyclohexylbenzimidazole-5-carboxylic acid Methyl 2-[4-{2-(4-chlorophenyl)-5-(2-oxopyrrolidin-1-yl)benzyloxy}-2-fluorophenyl]-1-cyclohexylbenzimidazole-5-carboxylate (2.0 g) obtained in the previous step was suspended in methanol (4.0 ml) and tetrahydrofuran (8.0 ml), and 2N aqueous sodium hydroxide solution (2.3 ml) was added. The mixture was heated under reflux for 3 hr. The reaction mixture was allowed to cool and tetrahydrofuran (1.0 ml) and water (5.0 ml) were added. 2N Hydrochloric acid (2.3 ml) was gradually added at room temperature. After stirring the mixture at room temperature for 2 hr, the precipitated crystals were collected by filtration and washed successively with methanol-water (1:1) mixed solution (6.0 ml), water (6.0 ml) and methanol-water (1:1) mixed solution (6.0 ml), and vacuum dried to give the title compound (1.84 g, yield 94%).

$^1$H-NMR (300MHz, DMSO-$d_6$): 12.75(1H, brs), 8.26(1H, s), 7.99(1H, s), 7.96(1H, d, J=9.0Hz), 7.89(1H, d, J=9.0Hz), 7.78(1H, dd, J=2.1Hz, 8.4Hz), 7.54(1H, t, J=9.0Hz), 7.49 (2H, d, J=8.7Hz), 7.45(2H, d, J=8.4Hz), 7.38(1H, d, J=8.4Hz), 7.08(1H, dd, J=2.1Hz, 12.0Hz), 6.96(1H, dd, J=2.1Hz, 8.7Hz), 5.09(2H, s), 3.99(1H, m), 3.91(2H, t, J=6.6Hz), 2.54(2H, t, J=7.8Hz), 2.30–2.00(4H, m), 1.95–1.50(5H, m), 1.45–1.20(3H, m)

Step 9: Production of 2-[4-{2-(4-chlorophenyl)-5-(2-oxopyrrolidine-1-yl)benzyloxy}-2-fluorophenyl]-1-cyclohexylbenzimidazole-5-carboxylic acid hydrochloride To 4N hydrochloric acid (50 ml) were successively added 2-[4-{2-(4-chlorophenyl)-5-(2-oxopyrrolidin-1-yl)benzyloxy}-2-fluorophenyl]-1-cyclohexylbenzimidazole-5-carboxylic acid (10.0 g) obtained in the previous step and acetone-methyl ethyl ketone (3:2) mixed solution (20 ml). The mixture was stirred at 60° C. for 3 hr and at room temperature for 1 hr. The crystals were collected by filtration, washed twice with acetone (10 ml) and vacuum dried to give the title compound (9.62 g, yield 91%).

melting point: 243–246° C.

Ms: 638(M+1)

$^1$H-NMR (300MHz, DMSO-$d_6$): 8.33(1H, d, J=1.1Hz), 8.21 (1H, d, J=8.8Hz), 8.02(1H, d, J=8.8Hz), 8.00(1H, d, J-2.2Hz), 7.77(1H, dd, J=2.2Hz, 8.4Hz), 7.68(1H, t, J=8.4Hz), 7.50(2H, d, J=8.4Hz), 7.45(2H, d, J=8.4Hz), 7.39(1H, d, J=8.4Hz), 7.20(1H, dd, J=2.2Hz, 12.1Hz), 7.06 (1H, dd, J=2.2Hz, 8.8Hz), 5.11(2H, s), 4.13(1H, m), 3.91 (2H, t, J=7.0Hz), 2.54(2H, t, J=8.1Hz), 2.40–2.05(4H, m), 2.00–1.75(4H, m), 1.70–1.55(1H, m), 1.50–1.20(3H, m)

In the same manner as in Examples 1–30, 241–248 and 336–340 and optionally using other conventional methods, where necessary, the compounds of Examples 31–240, 249–335, 341–471, 701–703 and 1001–1559 were obtained. The chemical structures and properties are shown in Table 1 to 177, 185 to 212, 219 to 221 and 225 to 269.

Example 501

Production of methyl 2-{4-(2-(4-chlorophenyl)-5-methoxybenzyloxylphenyl}-1-cyclohexyl-1H-indole-5-carboxylate Step 1: Production of methyl 3-bromo-4-cyclohexylaminobenzoate 3-Bromo-4-fluorobenzoic acid (2.0 g) was dissolved in methanol (20 ml) and concentrated sulfuric acid (2 ml) was added. The mixture was refluxed for 3 hr. The reaction mixture was poured into ice-cold water and extracted with ethyl acetate (50 ml). The organic layer was washed with water (30 ml) and saturated brine (30 ml), and dried over sodium sulfate. After filtration, the solvent was evaporated under reduced pressure. The residue was dissolved in dimethyl sulfoxide (20 ml) and cyclohexylamine (10.3 ml) was added. The mixture was stirred overnight at 120° C. The reaction mixture was poured into 10% aqueous citric acid solution (100 ml) and extracted with ethyl acetate (100 ml). The organic layer was washed with water (50 ml) and saturated brine (50 ml), and dried over sodium sulfate. After filtration, the solvent was evaporated under reduced pressure and the residue was purified by silica gel flash chromatography (developing solvent, n-hexane:ethyl acetate=10:1) to give the title compound (2.6 g, yield 92%).

$^1$H-NMR (300MHz, CDCl$_3$): 8.10(1H, d, J=1.9Hz), 7.83 (1H, dd, J=1.9Hz, 8.6Hz), 6.59(1H, d, J=8.7Hz), 4.73(1H, brd, J=7.3Hz), 3.85(3H, s), 3.38(1H, m), 2.10–2.00(2H, m), 1.90–1.20(8H, m)

Step 2: Production of 4'-chloro-2-(4-iodophenoxymethyl)-4-methoxybiphenyl

4-Iodophenol (5.0 g) was dissolved in acetone (50 ml), and potassium carbonate (4.7 g) and 4'-chloro-2-chloromethyl-4-methoxybiphenyl (6.0 g) obtained in Example 241, Step 4 were added. The mixture was refluxed for 10 hr. The reaction mixture was concentrated and 4N aqueous sodium hydroxide solution (50 ml) was added. The precipitated crystals were collected by filtration, washed with water, and dried under reduced pressure to give the title compound (10.0 g, yield 98%).

$^1$H-NMR (300MHz, CDCl$_3$): 7.52(2H, d, J=8.9Hz), 7.35 (2H, d, J=8.5Hz), 7.27–7.20(3H, m), 7.12(1H, s), 6.95(1H, d, J=8.5Hz), 6.62(2H, d, J=8.9Hz), 4.84(2H, s), 3.85(3H, s)

Step 3: Production of [4-(4'-chloro-4-methoxybiphenyl-2-ylmethoxy)phenylethynyl]trimethylsilane 4'-Chloro-2-(4-iodophenoxymethyl)-4-methoxybiphenyl (7.0 g) obtained in the previous step was dissolved in acetonitrile (50 ml), and trimethylsilylacetylene (2.3 g), tetrakis-(triphenylphosphine)palladium complex (1.8 g), copper(I) iodide (0.6 g) and triethylamine (50 ml) were added. The mixture was stirred overnight at room temperature and concentrated. Water (30 ml) was added and the mixture was extracted with ethyl acetate (50 ml). The organic layer was washed with water (30 ml) and saturated brine (30 ml) and dried over sodium sulfate. After filtration, the solvent was evaporated under reduced pressure and the residue was purified by silica gel flash chromatography (developing solvent, n-hexane:ethyl acetate=10:1) to give the title compound (5.1 g, yield 79%).

$^1$H-NMR (300MHz, CDCl$_3$): 7.37(2H, d, J=8.9Hz), 7.34 (2H, d, J=8.2Hz), 7.28–7.21(3H, m), 7.13(1H, s), 6.94(1H, d, J=8.2Hz), 6.75(2H, d, J=8.9Hz), 4.87(2H, s), 3.85(3H, s), 0.23(9H, s)

Step 4: Production of methyl 3-[4-(4'-chloro-4-methoxybiphenyl-2-ylmethoxy)phenylethynyl]-4-cyclohexylaminobenzoate

[4-(4'-Chloro-4-methoxybiphenyl-2-ylmethoxy)phenylethynyl]-trimethylsilane (5.1 g) obtained in the previous step was dissolved in methanol (50 ml) and chloroform (50 ml), and potassium carbonate (2.5 g) was added. The mixture was stirred for 3 hr at room temperature and concentrated. Water (30 ml) was added and the mixture was extracted with ethyl acetate (50 ml). The organic layer was washed with water (30 ml) and saturated brine (30 ml) and dried over sodium sulfate. After filtration, the solvent was evaporated under reduced pressure to give white crystals (3.8 g). The white crystals (2.3 g) were dissolved in acetonitrile (10 ml), and methyl 3-bromo-4-cyclohexylaminobenzoate (1.0 g) obtained in Step 1, tetrakis(triphenylphosphine)palladium complex (0.4 g), copper(I) iodide (0.1 g) and triethylamine (10 ml) were added. The mixture was stirred overnight at 100° C. and concentrated under reduced pressure. Water (30 ml) was added and the mixture was extracted with ethyl acetate (50 ml). The organic layer was washed with water (30 ml) and saturated brine (30 ml), and dried over sodium sulfate. After filtration, the solvent was evaporated under reduced pressure and the residue was purified by silica gel flash chromatography (developing solvent, n-hexane:ethyl acetate=8:1) to give the title compound (0.9 g, yield 49%).

$^1$H-NMR (300MHz, CDCl$_3$): 8.03(1H, s), 7.84(1H, d, J=8.7Hz), 7.42–7.22(7H, m), 7.15(1H, s), 6.95(1H, d, J=8.2Hz), 6.85(2H, d, J=8.8Hz), 6.59(1H, d, J=8.8Hz), 5.07(1H, brs), 4.91(2H, s), 3.86(3H, s), 3.85(3H, s), 3.42 (1H, m), 2.15–2.00(2H, m), 1.80–1.20(8H, m)

Step 5: Production of methyl 2-{4-[2-(4-chlorophenyl)-5-methoxybenzyloxy]phenyl}-1-cyclohexyl-1H-indole-5-carboxylate Methyl 3-[4-(4'-chloro-4-methoxybiphenyl-2-ylmethoxy)phenyl-ethynyl]-4-cyclohexylaminobenzoate (0.5 g) obtained in the previous step was dissolved in N,N-dimethylformamide (5 ml), and copper(I) iodide (0.17 g)

was added. The mixture was refluxed for 3 hr at 180° C. The insoluble materials were removed by filtration. Water (10 ml) was added and the mixture was extracted with ethyl acetate (30 ml). The organic layer was washed with water (10 ml) and saturated brine (10 ml), and dried over sodium sulfate. After filtration, the solvent was evaporated under reduced pressure and the residue was purified by silica gel flash chromatography (developing solvent, n-hexane:ethyl acetate=8:1) to give the title compound (0.27 g, yield 55%).

$^1$H-NMR (300MHz, CDCl$_3$): 8.34(1H, s), 7.85(1H, d, J=8.8Hz), 7.62(1H, d, J=8.8Hz), 7.40–7.18(8H, m), 7.00–6.94(3H, m), 6.48(1H, s), 4.95(2H, m), 4.18(1H, m), 3.93(3H, s), 3.88(3H, s), 2.45–2.25(2H, m), 1.95–1.20(8H, m)

Example 502

Production of 2-{4-[2-(4-chlorophenyl)-5-methoxybenzyloxy]phenyl}-1-cyclohexyl-1H-indole-5-carboxylic acid Methyl 2-{4-[2-(4-chlorophenyl)-5-methoxybenzyloxy]phenyl}-1-cyclohexyl-1H-indole-5-carboxylate (0.27 g) obtained in Example 501 was treated in the same manner as in Example 2 to give the title compound (0.19 g, yield 71%).

APCI-Ms: 566(MH+)

$^1$H-NMR (300MHz, DMSO-d$_6$): 12.43(1H, brs), 8.20(1H, s), 7.79(1H, d, J=9.3Hz), 7.72(1H, d, J=9.0Hz), 7.50–7.20 (8H, m), 7.07–7.03(3H, m), 6.53(1H, s), 5.01(2H, s), 4.13 (1H, m), 3.83(3H, m), 2.35–2.25(2H, m), 1.85–1.10(8H, m)

In the same manner as in Examples 501 and 502, and optionally using other conventional methods where necessary, the compound of Example 503 was obtained. The chemical structure and properties are shown in Table 207.

Example 601

Production of ethyl 2-(4-benzyloxyphenyl)-3-cyclohexylimidazo-[1,2-a]pyridine-7-carboxylate Step 1: Production of 4-benzyloxy-N-methoxy-N-methylbenzamide 4-Benzyloxybenzoic acid (5.0 g) and N,O-dimethylhydroxylamine hydrochloride (2.5 g) were suspended in dimethylformamide (50 ml), and 1-(3-dimethylaminopropyl)-3-ethylcarbodiimide hydrochloride (5.0 g), 1-hydroxybenzotriazole (3.5 g) and triethylamine (3.6 ml) were added. The mixture was stirred overnight at room temperature. Water was added to the reaction mixture and the mixture was extracted with ethyl acetate. The organic layer was washed successively with water, saturated aqueous sodium hydrogencarbonate, water and saturated brine, and dried over anhydrous magnesium sulfate. The solvent was evaporated under reduced pressure to give the title compound (5.6 g, yield 94%).

$^1$H-NMR (300MHz, CDCl$_3$): 7.22, 2H, d, J=8.8Hz), 7.28–7.46(5H, m), 6.97(2H, d, J=8.8Hz), 5.10(2H, s), 3.56 (3H, s), 3.35(3H, s)

Step 2: Production of 1-(4-benzyloxyphenyl)-2-cyclohexylethanone

Magnesium (470 mg) was suspended in tetrahydrofuran (2 ml) and cyclohexylmethyl bromide (3.4 g) was added dropwise at room temperature. After the addition, the reaction mixture was stirred for 30 min at 60° C. The reaction mixture was allowed to cool and diluted with tetrahydrofuran (5 ml). Separately, 4-benzyloxy-N-methoxy-N-methylbenzamide (3.4 g) obtained in the previous step was dissolved in tetrahydrofuran (10 ml) and the solution was added dropwise to the reaction mixture at room temperature. The mixture was stirred for 2 hr and saturated aqueous ammonium chloride solution was added to the reaction mixture. The mixture was extracted with diethyl ether. The organic layer was washed with saturated brine and dried over anhydrous magnesium sulfate, and the solvent was evaporated under reduced pressure. The residue was purified by silica gel flash chromatography (developing solvent, n-hexane:ethyl acetate=9:1) to give the title compound (3.8 g, yield 66%).

$^1$H-NMR (300MHz, CDCl$_3$): 7.93(2H, d, J=8.8Hz), 7.28–7.46(5H, m), 7.00(2H, d, J=8.8Hz), 5.13(2H, s), 2.76 (2H, d, J=6.8Hz), 1.95(1H, m), 0.78–1.82(10H, m)

Step 3: Production of 1-(4-benzyloxyphenyl)-2-bromo-2-cyclohexylethanone 1-(4-Benzyloxyphenyl)-2-cyclohexylethanone (1.0 g) obtained in the previous step was dissolved in 1,4-dioxane (10 ml) and bromine (0.17 ml) was added. The mixture was stirred for 10 min at room temperature. Saturated aqueous sodium hydrogencarbonate was added to the reaction mixture and the mixture was extracted with diethyl ether. The organic layer was washed with water and saturated brine and dried over anhydrous magnesium sulfate, and the solvent was evaporated under reduced pressure. The residue was purified by silica gel flash chromatography (developing solvent, n-hexane:ethyl acetate=9:1) to give the title compound (696 mg, yield 55%).

$^1$H-NMR (300MHz, CDCl$_3$): 7.98(2H, d, J=8.9Hz), 7.28–7.48(5H, m), 7.02(2H, d, J=8.9Hz), 5.14(2H, s), 4.89 (1H, d, J=9.3Hz), 0.86–3.30(11H, m)

Step 4: Production of ethyl 2-(4-benzyloxyphenyl)-3-cyclohexylimidazo[1,2-a]pyridine-7-carboxylate Ethyl 2-aminopyridine-4-carboxylate (214 mg) prepared according to JP-A-8-48651, 1-(4-benzyloxyphenyl)-2-bromo-2-cyclohexylethanone (500 mg) obtained in the previous step and potassium carbonate (356 mg) were stirred for 5 hr with heating at 140° C. The reaction mixture was allowed to cool and chloroform was added. The insoluble materials were filtered off and the filtrate was concentrated under reduced pressure. The residue was purified by silica gel flash chromatography (developing solvent, n-hexane:ethyl acetate=1:1) to give the title compound (95 mg, yield 16%).

APCI-MS: 455(MH+)

$^1$H-NMR (300MHz, CDCl$_3$): 8.33(1H, s), 8.21(1H, d, J=7.5Hz), 7.55(2H, d, J=8.7Hz), 7.25–7.50(6H, m), 5.13 (2H, s), 4.41(2H, q, J=7.1Hz), 3.25(1H, m), 1.41(3H, t, J=7.1Hz), 1.15–2.00(10H, m)

Example 602

Production of 2-(4-benzyloxyphenyl)-3-cyclohexylimidazo[1,2-a]pyridine-7-carboxylic acid Ethyl 2-(4-benzyloxyphenyl)-3-cyclohexylimidazo[1,2-a]pyridine-7-carboxylate (95 mg) obtained in the previous step was treated in the same manner as in Example 2 to give the title compound (33 mg, 37%).

APCI-MS: 427(MH+)

$^1$H-NMR (300MHz, DMSO-d$_6$): 8.67(1H, d, J=7.3Hz), 8.08(1H, s), 7.25–7.58(8H, m), 7.13(2H, d, J=8.7Hz), 5.17 (2H, s), 3.23(1H, m), 1.25–2.10(10H, m)

The compounds shown in Tables 213 to 218 can be further obtained in the same manner as in Examples 1 to 703 or by other conventional method employed as necessary.

The evaluation of the HCV polymerase inhibitory activity of the compound of the present invention is explained in the following. This polymerase is an enzyme coded for by the non-structural protein region called NS5B on the RNA gene of HCV (EMBO J., 15:12–22, 1996).

Experimental Example [I]

i) Preparation of enzyme (HCV polymerase)

Using, as a template, a cDNA clone corresponding to the full length RNA gene of HCV BK strain obtained from the blood of a patient with hepatitis C, a region encoding NS5B (591 amino acids; J Virol 1991 Mar, 65(3), 1105–13) was amplified by PCR. The objective gene was prepared by adding a 6 His tag {base pair encoding 6 continuous histidine (His)} to the 5' end thereof and transformed to *Escherichia coli*. The *Escherichia coli* capable of producing the objective protein was cultured. The obtained cells were suspended in a buffer solution containing a surfactant and crushed in a microfluidizer. The supernatant was obtained by centrifugation and applied to various column chromatographys {poly[U]-Sepharose, Sephacryl S-200, mono-S (Pharmacia)}, inclusive of metal chelate chromatography, to give a standard enzyme product.

ii) Synthesis of substrate RNA

Using a synthetic primer designed based on the sequence of HCV genomic 3' untranslated region, a DNA fragment (148 bp) containing polyU and 3'X sequence was entirely synthesized and cloned into plasmid pBluescript SK II(+) (Stratagene). The cDNA encoding full length NS5B, which was prepared in i) above, was digested with restriction enzyme KpnI to give a cDNA fragment containing the nucleotide sequence of from the restriction enzyme cleavage site to the termination codon. This cDNA fragment was inserted into the upstream of 3' untranslated region of the DNA in pBluescript SK II(+) and ligated. The about 450 bp inserted DNA sequence was used as a template in the preparation of substrate RNA. This plasmid was cleaved immediately after the 3'X sequence, linearized and purified by phenol-chloroform treatment and ethanol precipitation to give DNA.

RNA was synthesized (37° C., 3 hr) by run-off method using this purified DNA as a template, a promoter of pBluescript SK II(+), MEGAscript RNA synthesis kit (Ambion) and T7 RNA polymerase. DNaseI was added and the mixture was incubated for 1 hr. The template DNA was removed by decomposition to give a crude RNA product. This product was treated with phenol-chloroform and purified by ethanol precipitation to give the objective substrate RNA.

This RNA was applied to formaldehyde denaturation agarose gel electrophoresis to confirm the quality thereof and preserved at −80° C.

iii) Assay of enzyme (HCV polymerase) inhibitory activity

A test substance (compound of the present invention) and a reaction mixture (30 μl) having the following composition were reacted at 25° C. for 90 min.

10% Trichloroacetic acid at 4° C. and 1% sodium pyrophosphate solution (150 μl) were added to this reaction mixture to stop the reaction. The reaction mixture was left standing in ice for 15 min to insolubilize RNA. This RNA was trapped on a glass filter (Whatman GF/C and the like) upon filtration by suction. This filter was washed with a solution containing 1% trichloroacetic acid and 0.1% sodium pyrophosphate, washed with 90% ethanol and is dried. A liquid scintillation cocktail (Packard) was added and the radioactivity of RNA synthesized by the enzyme reaction was measured on a liquid scintillation counter.

The HCV polymerase inhibitory activity ($IC_{50}$) of the compound of the present invention was calculated from the values of radioactivity of the enzyme reaction with and without the test substance.

The results are shown in Tables 178–184 and 222–224.

Reaction mixture : HCV polymerase (5 μg/ml) obtained in i), substrate RNA (10 μg/ml) obtained in ii), ATP (50 μM), GTP (50 μM), CTP (50 μM), UTP (2 μM), [5,6-$^3$H]UTP (46 Ci/mmol (Amersham), 1.5 CCi) 20 mM Tris-HCl (pH 7.5), EDTA (1 mM), $MgCl_2$ (5 mM), NaCl (50 mM), DTT (1 mM), BSA (0.01%)

Formulation Example is given in the following. This example is merely for the purpose of exemplification and does not limit the invention.

| Formulation Example | |
|---|---|
| (a) compound of Example 1 | 10 g |
| (b) lactose | 50 g |
| (c) corn starch | 15 g |
| (d) sodium carboxymethylcellulose | 44 g |
| (e) magnesium stearate | 1 g |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

TABLE 1

Example No. 31

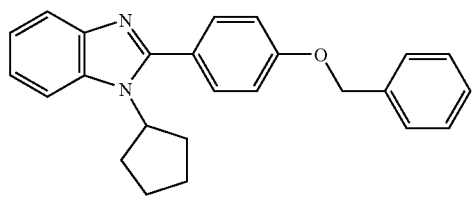

1H NMR(δ)ppm

300MHz, CDCl3 7.81(2H, d, J=6.6Hz), 7.60(2H, d, J=8.8Hz), 7.51–7.21(8H, m), 7.11(2H, d, J=8.8Hz), 5.15(2H, s), 4.93(1H, quint, J=8.8Hz), 2.36–2.32(2H, m), 2.09–2.04(3H, m), 1.75–1.68(3H, m).

Purity >90%(NMR)
MS 369(M+1)

TABLE 1-continued

| Example No. 32 | 1H NMR(δ)ppm |
|---|---|
| 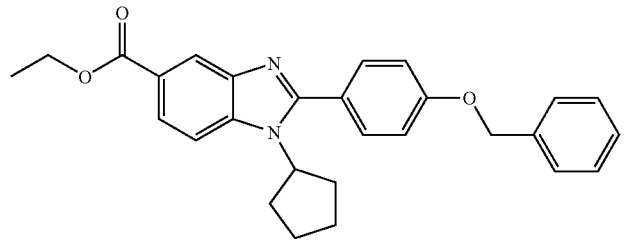 | 300MHz, CDCl3 8.51(1H, d, J=1.5Hz), 7.98(1H, d, J=8.4Hz), 7.61(2H, d, J=8.7Hz), 7.56–7.10(6H, m), 7.12(2H, d, J=8.7Hz), 5.15(2H, s), 4.94(1H, quint, J=9.3Hz), 4.41(2H, q, J=7.5Hz), 2.40–1.50(8H, m), 1.41(3H, t, J=7.5Hz) |

Purity >90%(NMR)

MS 441(M+1)

| Example No.33 | 1H NMR(δ)ppm |
|---|---|
| 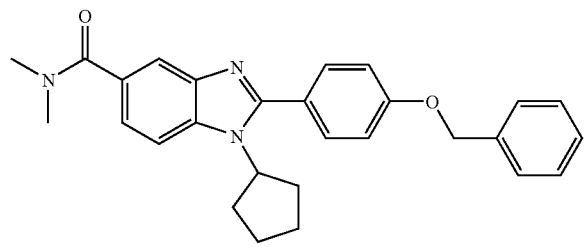 | 300MHz, CDCl3 7.84(1H, s), 7.61(2H, d, J=9.0Hz), 7.58–7.30(7H, m), 7.12(2H, d, J=9.0Hz), 5.15(2H, s), 4.94(1H, quint, J=8.7Hz), 3.10(6H, brs), 2.40–1.50(8H, m) |

Purity >90%(NMR)

MS 440(M+1)

TABLE 2

| Example No. 34 | 1H NMR(δ)ppm |
|---|---|
| 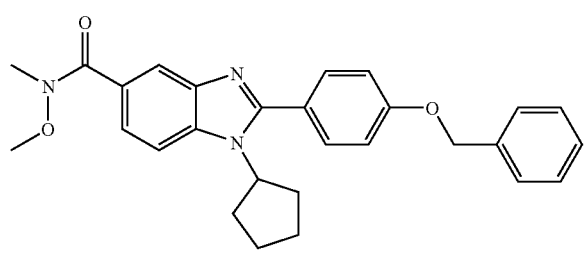 | 300MHz, CDCl3 8.20(1H, s), 7.50–7.31(9H, m), 7.12(2H, d, J=8.7Hz), 5.15(2H, s), 4.94(1H, quint, J=8.7Hz), 3.61(3H, s), 3.40(3H, s), 2.41–1.42(8H, m) |

Purity >90%(NMR)
MS 456(M+1)

| Example No. 35 | 1H NMR(δ)ppm |
|---|---|
| 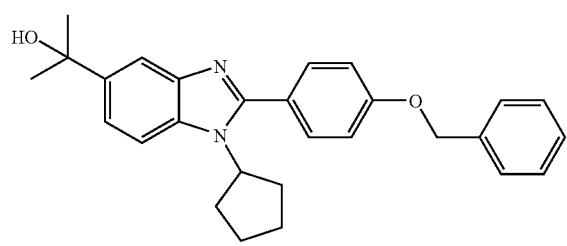 | 300MHz, CDCl3 7.91(1H, s), 7.59(2H, d, J=8.7Hz), 7.49–7.30(7H, m), 7.11(2H, d, J=8.8Hz), 5.15(2H, s), 4.19(1H, quint, J=8.8Hz), 2.41–2.22(2H, m), 2.13–1.49(14H, m) |

Purity >90%(NMR)
MS 427(M+1)

TABLE 2-continued

Example No. 36

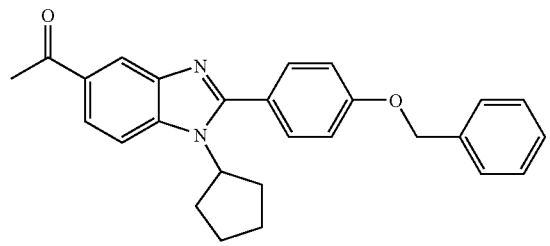

1H NMR(δ)ppm

300MHz, CDCl3 8.40(1H, d, J=1.4Hz), 7.95(1H, dd, J=8.6, 1.4Hz), 7.61(2H, d, J=8.7Hz), 7.57–7.30(6H, m), 7.13(2H, d, J=8.7Hz), 5.16(2H, s), 4.95(1H, quint, J=8.8Hz), 2.64(3H, s), 2.40–1.54(8H, m)

Purity >90%(NMR)
MS 411(M+1)

TABLE 3

Example No. 37

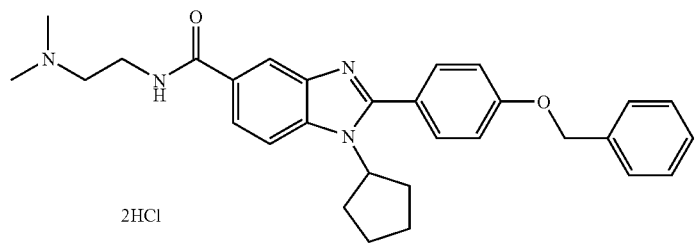

2HCl

1H NMR(δ)ppm

300MHz, DMSO-d6 10.47(1H, brs,), 9.15(1H, brs), 8.40(1H, s), 8.07(1H, d, J=9.0Hz), 7.93(1H, d, J=8.7Hz), 7.77(2H, d, J=8.7Hz), 7.55–7.29(7H, m), 5.26(2H, s), 4.93(1H, quint, J=9.0Hz), 3.77–3.63(2H, m), 3.39–3.23(2H, m), 2.84(6H, d, J=4.8Hz), 2.32–1.60(8H, m)

Purity >90%(NMR)
MS 483(M+1)

Example No. 38

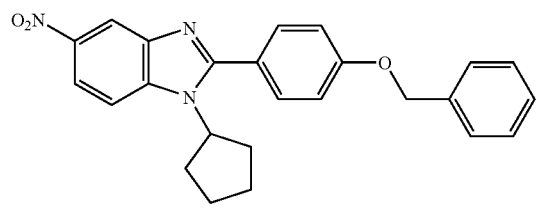

1H NMR(δ)ppm

300MHz, CDCl3 8.69(1H, s), 8.19(1H, d, J=9.0Hz), 7.62(2H, d, J=8.7Hz), 7.54(1H, d J=9.0Hz), 7.48–7.36(5H, m), 7.15(2H, d, J=8.7Hz), 5.17(2H, s), 4.98(1H, quint, J=9.0Hz), 2.27–2.07(6H, m), 1.82–1.78(2H, m)

Purity >90%(NMR)
MS 414(M+1)

Example No. 39

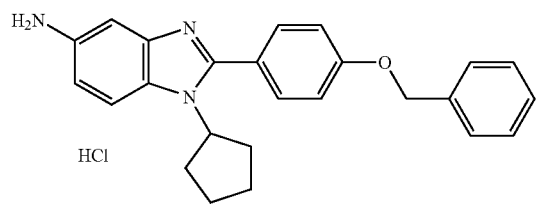

HCl

1H NMR(δ)ppm

300MHz, DMSO-d6 7.84(1H, d, J=9.0Hz), 7.79(2H, d, J=8.7Hz), 7.52–7.33(8H, m), 7.26(1H, d, J=9.0Hz), 5.27(2H, s), 4.92(1H, quint, J=9.3Hz), 2.19–1.70(8H, m).

Purity >90%(NMR)
MS 384(M+1)

TABLE 4

| Example No. 40 | 1H NMR(δ)ppm |
|---|---|
| 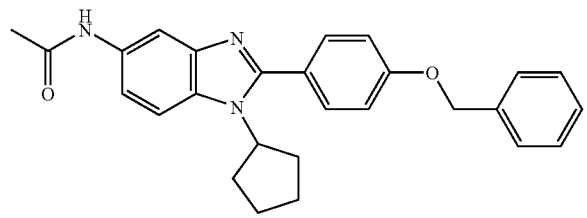 | 300MHz, CDCl3 7.72(1H, s), 7.60–7.35(10H, m), 7.10(2H, d, J=8.7Hz), 5.14(2H, s), 4.90(1H, quint, J=8.8Hz), 2.29–2.19(2H, m), 2.19(3H, s), 2.19–1.74(6H, m). |

Purity >90%(NMR)
MS 426(M+1)

| Example No. 41 | 1H NMR(δ)ppm |
|---|---|
| 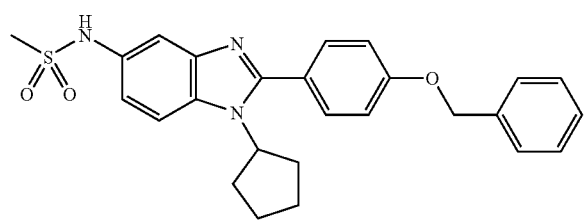 | 300MHz, CDCl3 7.66(1H, s), 7.61(2H, d, J=8.8Hz), 7.50–7.28(7H, m), 7.12(2H, d, J=8.8Hz), 6.86(1H, brs), 5.15(2H, s), 4.94(1H, quint, J=8.8Hz), 2.97(3H, s), 2.29–1.76(8H, m). |

Purity >90%(NMR)
MS 462(M+1)

| Example No. 42 | 1H NMR(δ)ppm |
|---|---|
| 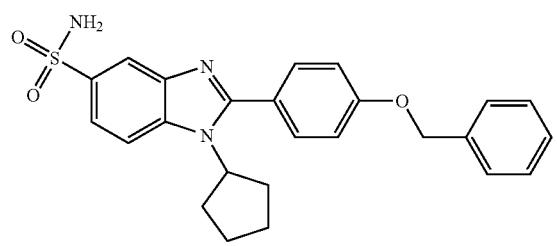 | 300MHz, DMSO 8.11(1H, s), 7.81(1H, d, J=8.4Hz), 7.72(1H, d, J=8.4Hz), 7.65(2H, d, J=8.4Hz), 7.51(2H, m), 7.43(2H, m), 7.37(1H, m), 7.29(2H, s), 7.23(2H, d, J=8.4Hz), 5.22(2H, s), 4.89(1H, quintet, J=9.2Hz), 2.2–2.0(6H, m), 1.7(2H, m). |

Purity >90%(NMR)
MS 448 (M+)

TABLE 5

| Example No. 43 | 1H NMR(δ)ppm |
|---|---|
| 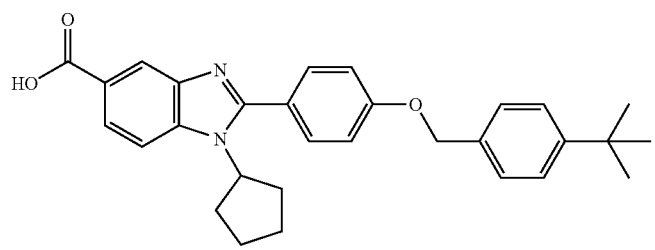 | 300MHz, DMSO-d6 8.33(1H, s), 8.08(1H, d, J=9.0Hz), 7.99(1H, d, J=9.0Hz), 7.47–7.41(4H, m), 7.33(2H, d, J=8.4Hz), 5.22(2H, s), 4.96(1H, quint, J=9.0Hz), 2.25–1.60(8H, m), 1.30(9H, s). |

Purity >90%(NMR)
MS 469(M+1)

TABLE 5-continued

Example No. 44

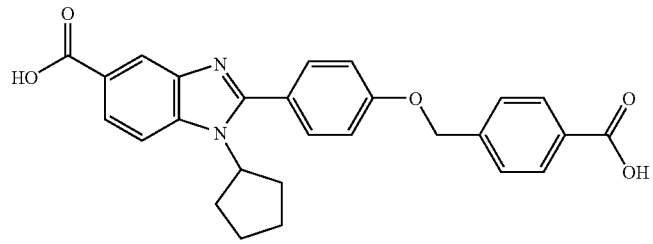

Purity >90%(NMR)
MS 457(M+1)

1H NMR(δ)ppm

300MHz, DMSO-d6 12.9(2H, brs), 8.25(1H, s), 8.00(2H, d, J=7.8Hz), 7.90(1H, d, J=8.4Hz), 7.74(1H, d, J=8.7Hz), 7.67(2H, d, J=9.0Hz), 7.62(2H, d, J=8.1Hz), 7.24(2H, d, J=8.4Hz), 5.32(2H, s), 4.88(1H, quint, J=9.0Hz, 2.25–1.60(8H, m).

Example No. 45

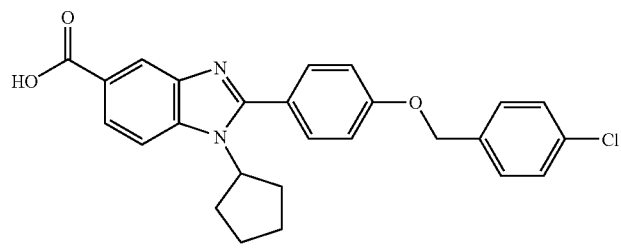

Purity >90%(NMR)
MS 447(M+1)

1H NMR(δ)ppm

300MHz, DMSO-d6 13.4(1H, brs), 8.32(1H, s), 8.06(1H, d, J=8.7Hz), 7.97(1H, d, J=8.7Hz), 7.79(2H, d, J=8.8Hz), 7.56–7.48(4H, m), 7.33(2H, d, J=8.8Hz), 5.27(2H, s), 4.95(1H, quint, J=8.9Hz), 2.30–1.60(8H, m).

TABLE 6

Example No. 46

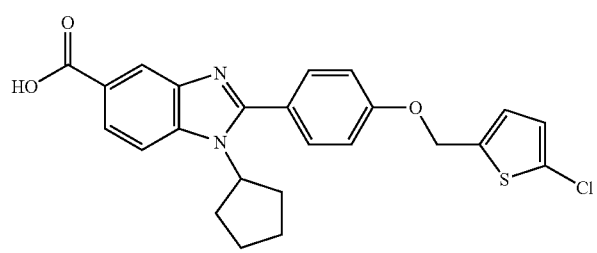

Purity >90%(NMR)
MS 453 (M+1)

1H NMR(δ)ppm

300MHz, DMSO-d6 8.33(1H, s), 8.07(1H, d, J=8.7Hz), 7.98(1H, d, J=8.7Hz), 7.80.(2H, d, J=8.4Hz), 7.34(2H, d, 8.4Hz), 7.19(1H, d, J=3.6Hz), 7.09(1H, d, J=3.6Hz), 5.41(2H, s), 4.95(1H, quint, J=8.7Hz), 2.30–1.60(8H, m).

Example No. 47

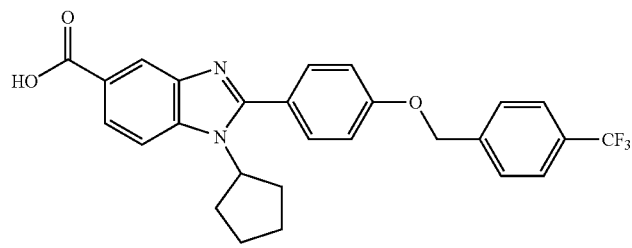

Purity >90%(NMR)
MS 481 (M+1)

1H NMR(δ)ppm

300MHz, DMSO-d6 8.33(1H, s), 8.07(1H, d, J=8.4Hz), 7.98(1H, d, J=9.0Hz), 7.82–7.72(6H, m), 7.35(2H, d, J=9.0Hz), 5.40(2H, s), 4.95(1H, quint, J=8.7Hz), 2.35–1.60(8H, m).

TABLE 6-continued

Example No. 48

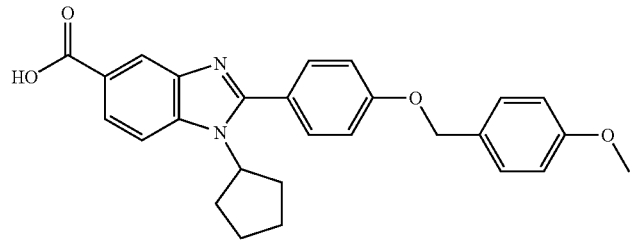

Purity >90%(NMR)
MS 443 (M+1)

1H NMR(δ)ppm

300MHz, DMSO-d6 8.23(1H, s), 7.88(1H, d, J=8.4Hz), 7.70(1H, d, J=8.4Hz), 7.64(2H, d, J=8.4Hz), 7.43(2H, d, J=8.4Hz), 7.20(2H, d, J=8.4Hz), 6.98(2H, d, J=8.4Hz), 5.13(2H, s), 4.88(1H, quint, J=8.7Hz), 3.77(3H, s), 2.35–1.60(8H, m).

TABLE 7

Example No. 49

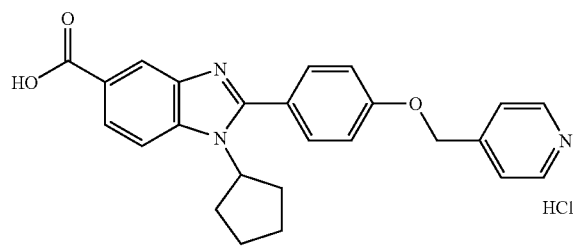

Purity >90%(NMR)
MS 414 (M+1)

1H NMR(δ)ppm

300MHz, DMSO-d6 8.93(2H, d, J=6.6Hz), 8.35(1H, s), 8.06–8.04(3H, m), 7.97(1H, d, J=8.7Hz), 7.83(2H, d, J=8.7Hz), 7.38(2H, d, J=8.7Hz), 5.61(2H, s), 4.94(1H, quint, J=8.7Hz), 2.40–1.60(8H, m).

Example No. 50

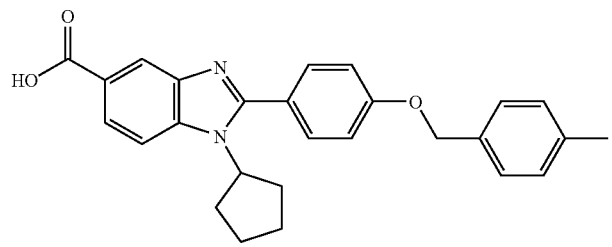

Purity >90%(NMR)
MS 427 (M+1)

1H NMR(δ)ppm

300MHz, DMSO-d6 8.33(1H, s), 8.08(1H, d, J=8.7Hz), 7.99(1H, d, J=9.0Hz), 7.78(2H, d, J=8.4Hz), 7.39(2H, d, J=8.1Hz), 7.32(2H, d, J=8.7Hz), 7.23(2H, d, J=7.8Hz), 5.22(2H, s), 4.96(1H, quint, J=9.0Hz), 2.32(3H, s), 2.30–1.60(8H, m).

Example No. 51

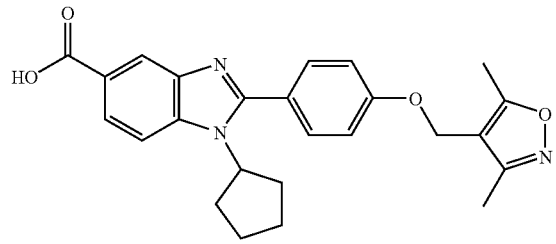

Purity >90%(NMR)
MS 432 (M+1)

1H NMR(δ)ppm

300MHz, DMSO-d6 8.31(1H, s), 8.03(1H, d, J=9.0Hz), 7.93(1H, d, J=9.0Hz), 7.77(2H, d, J=8.4Hz), 7.31(2H, d, J=8.7Hz), 5.07(2H, s), 4.94(1H, quint, J=8.7Hz), 2.45(3H, s), 2.26(3H, s), 2.26–1.60(8H, m).

TABLE 8

| Example No. 52 | 1H NMR(δ) ppm |
|---|---|
| 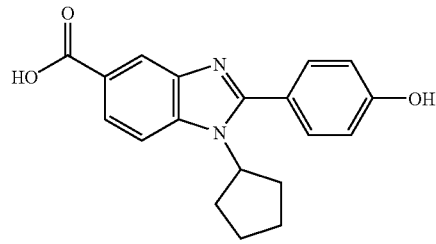 | 300 MHz, DMSO-d6 12.7(1H, brs), 10.0(1H, s), 8.22(1H, s), 7.87(1H, d, J=8.6Hz), 7.69(1H, d, J=8.6Hz), 7.53(2H, d, J=8.6Hz), 6.96(2H, d, J=8.6Hz), 4.89(1H, quint, J=9.0Hz), 2.30–1.60(8H, m). |
| Purity >90%(NMR)<br>MS 323 (M+1) | |
| Example No. 53 | 1H NMR(δ) ppm |
| (structure) | 300 MHz, DMSO-d6 9.18(1H, t, J=5.6Hz), 8.34(1H, s), 8.04(1H, d, J=9.6Hz), 7.98(1H, d, J=8.7Hz), 7.80(2H, d, J=8.7Hz), 7.52–7.32(7H, m), 5.27(2H, s), 4.95(1H, quint, J=9.0Hz), 3.99(2H, d, J=5.7Hz), 2.04–1.60(8H, m). |
| Purity >90%(NMR)<br>MS 470 (M+1) | |
| Example No. 54 | 1H NMR(δ) ppm |
| (structure) | 300 MHz, DMSO-d6 8.32(1H, s), 8.05(1H, d, J=8.7Hz), 7.95(1H, d, J=8.7Hz), 7.80(2H, d, J=8.4Hz), 7.67(1H, t, J=4.5Hz), 7.56(1H, t, J=4.5Hz), 7.45–7.42(2H, m), 7.35(2H, d, J=8.4Hz), 5.31(2H, s), 4.96(1H, quint, J=9.0Hz), 2.30–1.60(8H, m). |
| Purity >90%(NMR)<br>MS 447 (M+1) | |

TABLE 9

| Example No. 55 | 1H NMR(δ) ppm |
|---|---|
| 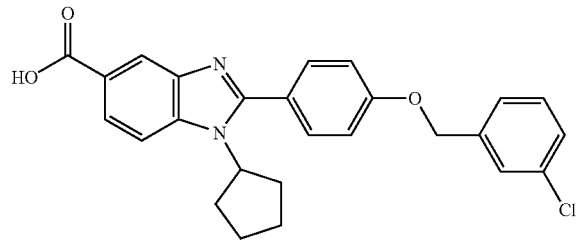 | 300 MHz, DMSO-d6 12.78(1H, brs), 8.24(1H, s), 7.88 and 7.72(2H, ABq, J=8.6Hz), 7.66 and 7.23(4H, A'B'q, J=8.6Hz), 7.58(1H, s), 7.48–7.42(3H, m), 5.24(1H, s), 4.88(1H, quint, J=8.8Hz), 2.30–1.91(6H, m), 1.78–1.60(2H, m) |
| Purity >90%(NMR)<br>MS 447 (M+1) | |

TABLE 9-continued

| Example No. 56 | 1H NMR(δ) ppm |
|---|---|
| 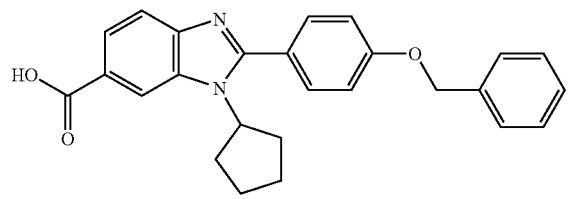 | 300 MHz, DMSO-d6 12.89(1H, broad), 8.18(1H, s), 7.87(1H, d, J=8.4Hz), 7.74(1H, d, J=9.2Hz), 7.67(2H, d, J=8.8Hz), 7.52(2H, m), 7.45(2H, m), 7.38(1H, m), 7.23(2H, d, J=8.8Hz), 5.22(2H, s), 4.94(1H, quintet, J=8.9Hz), 2.16(4H, m), 1.98(2H, m), 1.73(2H, m). |
| Purity >90%(NMR) | |
| MS 413 (M+1) | |
| Example No. 57 | 1H NMR(δ) ppm |
| 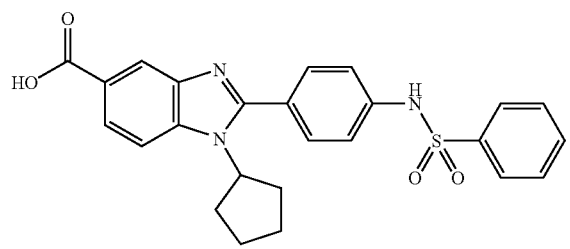 | 300 MHz, DMSO-d6 10.99(1H, s), 8.26(1H, s), 8.01–7.86(4H, m), 7.69–7.59(5H, m), 7.38(2H, d, J=8.7Hz), 4.86(1H, quint, J=8.7Hz), 2.12–1.90(6H, m), 1.72–1.59(2H, m). |
| Purity >90%(NMR) | |
| MS 462 (M+1) | |

TABLE 10

| Example No. 58 | 1H NMR(δ)ppm |
|---|---|
| 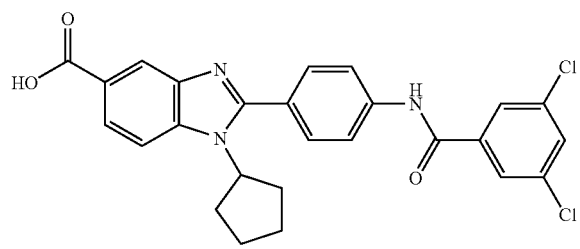 | 300MHz, DMSO-d6 12.78(1H, s), 10.69(1H, s), 8.26–7.72(9H, m), 4.92(1H, quint, J=9.0Hz), 2.34–1.70(6H, m), 1.75–1.61(2H, m) |
| Purity >90%(NMR) | |
| MS 494 (M+1) | |
| Example No. 59 | 1H NMR(δ)ppm |
| 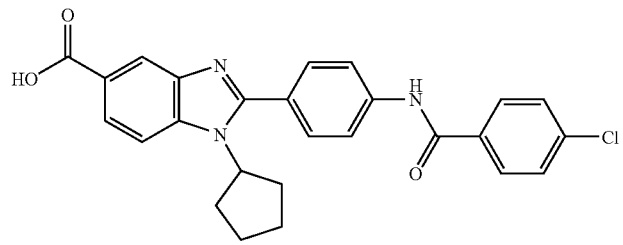 | 300MHz, DMSO-d6 10.82(1H, s), 8.34(1H, s), 8.14 and 7.84(4H, ABq, J=8.4Hz), 8.06 and 7.66(4H, A'B'q, J=8.6Hz), 8.06–7.98(4H, m), 5.01(1H, quint, J=9.3Hz), 2.35–2.15(4H, m), 2.11–1.96(2H, m), 1.80–1.62(2H, m) |
| Purity >90%(NMR) | |
| MS 460 (M+1) | |

TABLE 10-continued

| Example No. 60 | 1H NMR(δ)ppm |
|---|---|
| 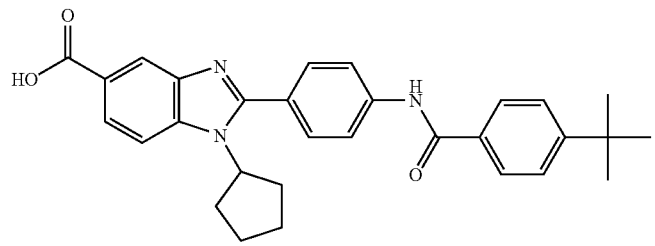 | 300MHz, DMSO-d6 10.61(1H, s), 8.32(1H, s), 8.12 and 7.81(4H, ABq, J=8.9Hz), 8.03 and 7.93(2H, A'B'q, J=8.7Hz), 7.95 and 7.59(4H, A"B"q, J=8.4Hz), 4.99(1H, quint, J=9.0Hz), 2.33–2.12(4H, m), 2.10–1.93(2H, m), 1.80–1.63(2H, m), 1.34(9H, m) |

Purity >90%(NMR)
MS 482 (M+1)

TABLE 11

| Example No. 61 | 1H NMR(δ)ppm |
|---|---|
| 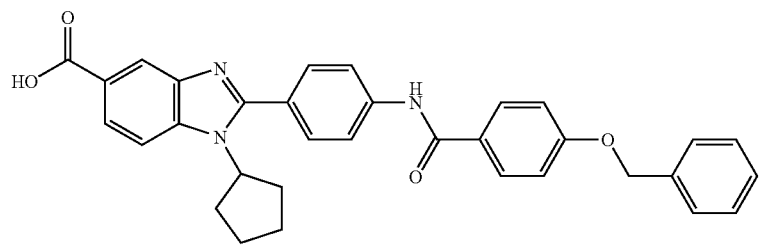 | 300MHz, DMSO-d6 10.6(1H, s), 8.34(1H, s), 8.13(2H, d, J=8.7Hz), 8.09–7.98(4H, m), 7.82(2H, d, J=8.7Hz), 7.50–7.35(5H, m), 7.20–7.17(2H, d, J=9.0Hz), 5.24(2H, s), 5.01(1H, quint, J=9.3Hz), 2.40–1.60(8H, m). |

Purity >90%(NMR)
MS 532 (M+1)

| Example No. 62 | 1H NMR(δ)ppm |
|---|---|
| 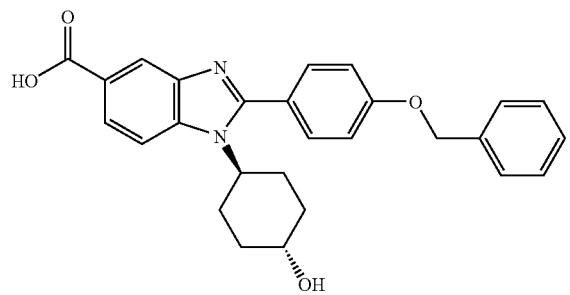 | 300MHz, DMSO-d6 8.32(1H, s), 8.26(1H, d, J=8.7Hz), 8.04(1H, d, J=8.7Hz), 7.77(2H, d, J=8.4Hz), 7.52(2H, d, J=6.9Hz), 7.46–7.39(5H, m), 5.28(2H, s), 4.38(1H, m), 3.71(1H, m), 2.60–2.15(2H, m), 2.04–1.96(4H, m), 1.30–1.20(2H, m). |

Purity >90%(NMR)
MS 443 (m+1)

| Example No. 63 | 1H NMR(δ)ppm |
|---|---|
| 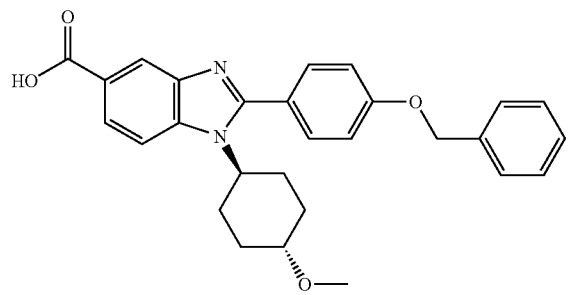 | 300MHz, DMSO-d6 8.27(1H, s), 8.14(1H, d, J=8.7Hz), 7.96(1H, d, J=8.4Hz), 7.71(2H, d, J=9.0Hz), 7.51(2H, d, J=6.9Hz), 7.46–7.37(3H, m), 7.30(2H, d, J=8.4Hz), 5.25(3H, s), 4.39(1H m), 3.44(1H, m), 3.27(3H, s), 2.60–1.95(6H, m), 1.25–1.05(2H, m). |

Purity >90%(NMR)
MS 457 (M+1)

TABLE 12

Example No. 64

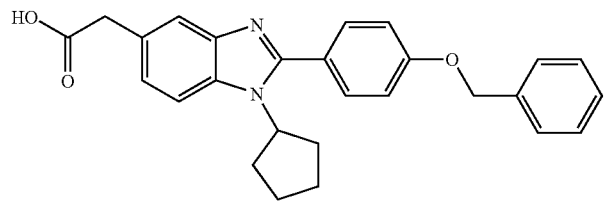

Purity >90%(NMR)
MS 427 (M+1)

1H NMR(δ)ppm

300MHz, DMSO-d6 12.25(1H, brs), 7.70–7.30(9H, m), 7.20(2H, d, J=8.7Hz), 7.14(1H, d, J=8.4Hz), 5.20(2H, s), 4.84(1H, quint, J=6.0Hz), 3.66(2H, s), 2.30–1.51(8H, m)

Example No. 65

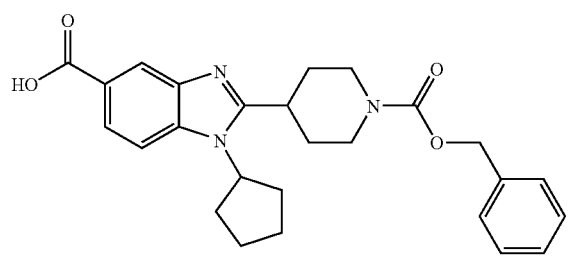

Purity >90%(NMR)
MS 448 (M+1)

1H NMR(δ)ppm

300MHz, DMSO-d6 12.64(1H, brs), 8.13(1H, s), 7.80(1H, d, J=7.2Hz), 7.59(1H, d J=8.7Hz), 7.48–7.30(5H, m), 5.11(2H, s), 5.03(1H, quint, J=8.7Hz), 4.20–4.05(2H, m), 3.45–3.90(3H, m), 2.15–1.60(12H, m)

Example No. 66

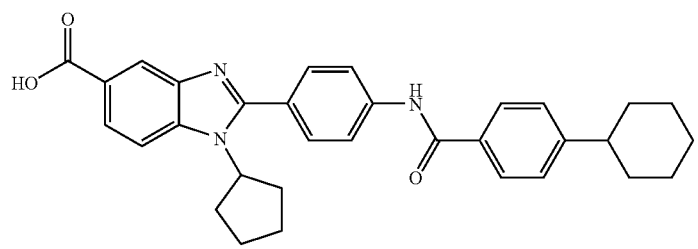

Purity >90%(NMR)
MS 508 (M+1)

1H NMR(δ)ppm

300MHz, DMSO-d6 10.59(1H, s), 8.31(1H, s), 8.10(2H, d, J=8.6Hz), 8.03(1H, d, J=8.7Hz), 8.00–7.85(3H, m), 7.80(2H, d, J=8.6Hz), 7.41(2H, d, J=8.2Hz), 4.98(1H, quint, J=8.8Hz), 2.71–1.10(19H, m)

TABLE 13

Example No. 67

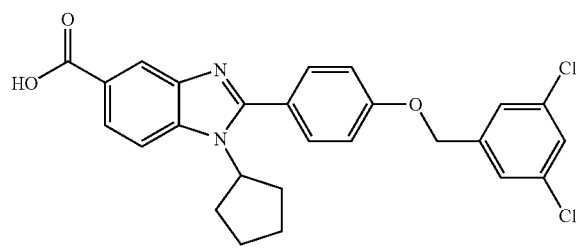

Purity >90% (NMR)
MS 481 (M+1)

1H NMR(δ)ppm

300MHz, DMSO-d6 12.81(1H, brs), 8.42(1H, s), 7.90(1H, d, J=8.5Hz), 7.80–7.52(6H, m), 7.44(2H, d, J=8.6Hz), 5.25(2H, s), 4.88(1H, quint, J=8.8Hz), 2.30–1.52(8H, m)

TABLE 13-continued

| Example No. 68 | 1H NMR(δ)ppm |
|---|---|
| 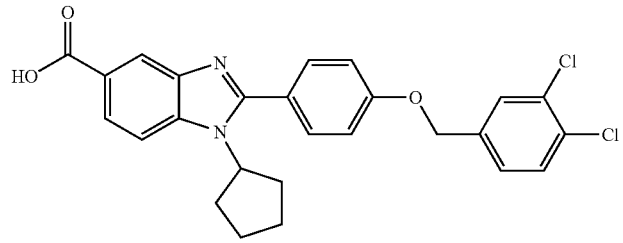 | 300MHz, DMSO-d6 8.31(1H, d, J=1.4Hz), 8.05(1H, d, J=8.6Hz), 7.96(1H, d, J=8.6Hz), 8.86–8.61(4H, m), 7.51(1H, d, J=6.3Hz), 7.33(2H, d, J=8.8Hz), 5.28(2H, s), 4.94(1H, quint, J=8.8Hz), 2.31–1.60(8H, m) |

Purity >90% (NMR)
MS 481 (M+1)

| Example No. 69 | 1H NMR(δ)ppm |
|---|---|
| 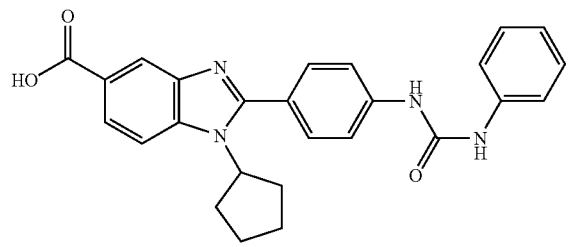 | 300MHz, DMSO-d6 9.88(1H, s), 9.42(1H, s), 8.32(1H, s), 8.09 and 8.02(2H, ABq, J=9.0Hz), 7.81 and 7.78(4H, A'B'q, J=9.2Hz), 7.50(2H, d, J=7.8Hz), 7.31(2H, t, J=7.8Hz), 7.00(1H, t, J=7.8Hz), 5.03(1H, quint, J=8.7Hz), 2.34–2.17(4H, m), 2.13–1.96(2H, m), 1.83–1.64(2H, m) |

Purity >90% (NMR)
MS 441 (M+1)

TABLE 14

| Example No. 70 | 1H NMR(δ)ppm |
|---|---|
| 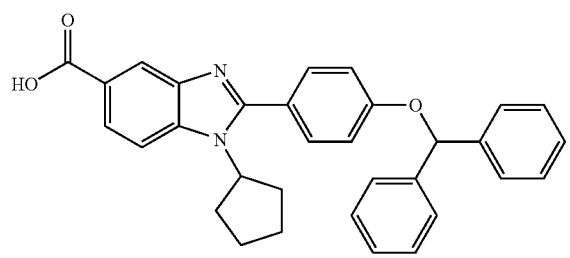 | 300MHz, DMSO-d6 8.27(1H, d, J=1.2Hz), 8.04(1H, d, J=8.7Hz), 7.94(1H, d, J=8.7Hz), 7.72(2H, d, J=8.7Hz), 7.60–7.20(12H, m) 6.74(1H, s), 4.92(1H, quint, J=8.9Hz), 2.30–1.58(8H, m) |

Purity >90% (NMR)
MS 489 (M+1)

| Example No. 71 | 1H NMR(δ)ppm |
|---|---|
| 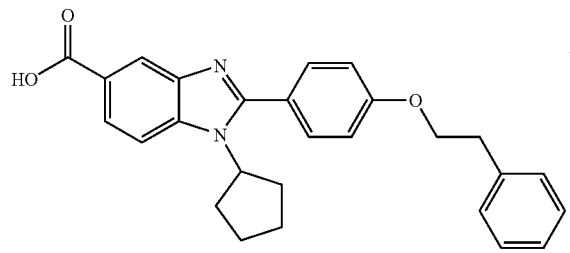 | 300MHz, DMSO-d6 8.31(1H, s), 8.05(1H, d, J=8.7Hz), 7.97(1H, d, J=8.7Hz), 7.76(2H, d, J=8.6Hz), 7.44–7.19(7H, m), 4.94(1H, quint, J=8.8Hz), 4.35(2H, t, J=6.7Hz), 3.10(2H, t, J=6.7Hz), 2.32–1.60(8H, m) |

Purity >90% (NMR)
MS 427 (M+1)

TABLE 14-continued

| Example No. 72 | 1H NMR(δ)ppm |
|---|---|
| 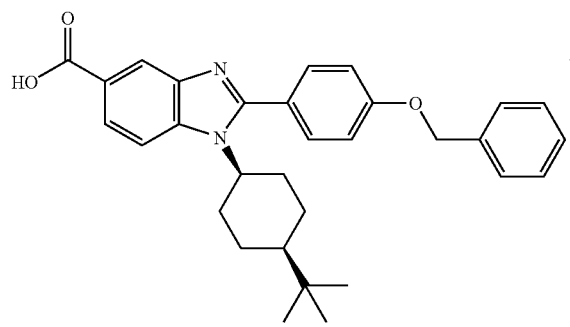 | 300MHz, DMSO-d6 8.30(1H, s), 8.25(1H, d, J=8.7Hz), 8.03(1H, d, J=9.0Hz), 7.75(2H, d, J=8.7Hz), 7.51(2H, d, J=7.2Hz), 7.46–7.33(5H, m), 5.27(2H, s), 4.36(1H, m), 2.50–2.25(2H, m), 2.15–2.00(2H, m), 1.95–1.85(2H, m), 1.35(1H, m), 1.20–1.10(2H, m), 0.87(9H, s). |

Purity >90% (NMR)
MS 483 (M+1)

TABLE 15

| Example No.73 | 1H NMR(δ)ppm |
|---|---|
| 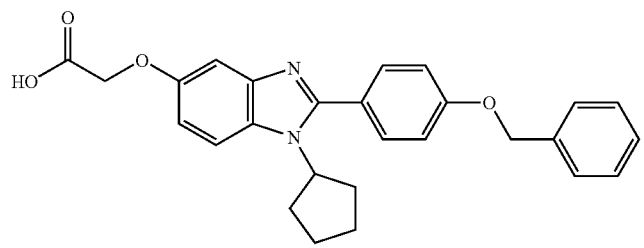 | 300MHz, DMSO-d6 7.59(2H, d, J=8.4Hz), 7.52–7.35(6H, m), 7.20(2H, d, J=8.7Hz), 7.14(1H, d, J=2.1Hz), 6.90(1H, dd, J=9.0, 2.4Hz), 5.21(2H, s), 4.83(1H, quint, J=8.7Hz), 4.70(2H, s), 2.30–1.90(6H, m), 1.75–1.55(2H, m). |

Purity >90% (NMR)
MS 443 (M+1)

| Example No. 74 | 1H NMR(δ)ppm |
|---|---|
| 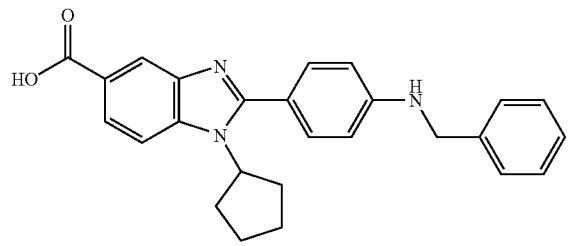 | 300MHz, DMSO-d6 8.27(1H, s), 8.06 and 7.97(2H, ABq, J=8.7Hz), 7.57 and 6.86(4H, A'B'q, J=8.9Hz), 7.42–7.26(5H, m), 5.04(1H, quint, J=9.0Hz), 4.42(2H, s), 2.32–1.94(6H, m), 1.80–1.62(2H, m) |

Purity >90% (NMR)
MS 412 (M+1)

| Example No. 75 | 1H NMR(δ)ppm |
|---|---|
| 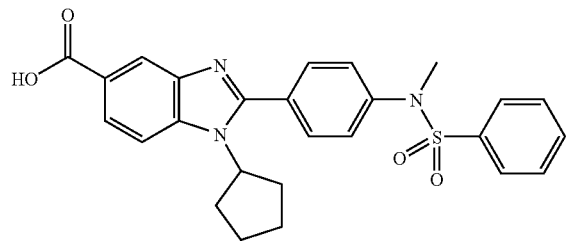 | 300MHz, DMSO-d6 12.80(1H, s), 8.26(1H, s), 7.90(1H, d, J=9.2Hz), 7.76–7.60(8H, m), 7.35(2H, d, J=8.4Hz), 4.84(1H, quint, J=8.8Hz), 3.23(3H, s), 2.32–1.90(6H, m), 1.78–1.61(2H, m) |

Purity >90% (NMR)
MS 476 (M+1)

TABLE 16

| Example No. 76 | 1H NMR(δ)ppm |
|---|---|
| 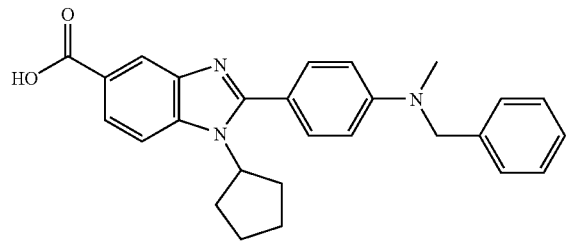 | 300MHz, DMSO-d6 8.29(1H, s), 8.07 and 7.49(2H, ABq, J=8.7Hz), 7.66 and 7.00(4H, A'B'q, J=7.7Hz), 7.39–7.24(5H, m), 5.05(1H, quint, J=8.8Hz), 4.76(2H, s), 3.21(3H, s), 2.35–1.92(6H, m), 1.81–1.62(2H, m) |
| Purity >90% (NMR) MS 426 (M+1) | |
| Example No. 77 | 1H NMR(δ)ppm |
| 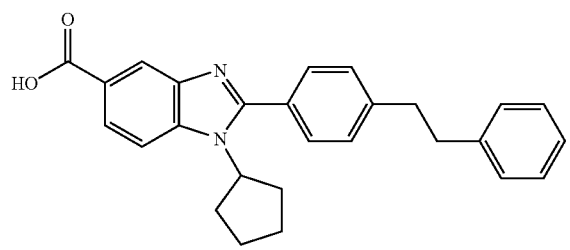 | 300MHz, DMSO-d6 8.21(1H, s), 7.87(1H, s), 7.56 and 7.43(4H, ABq, J=8.1Hz), 7.34–7.16(5H, m), 4.25(1h, brt, J=12.5Hz), 3.06–2.92(4H, m), 2.41–2.17(2H, m), 1.96–1.77(4H, m), 1.72–1.58(1H, m), 1.48–1.15(3H, m) |
| Purity >90% (NMR) MS 425 (M+1) | |
| Example No. 78 | 1H NMR(δ)ppm |
| 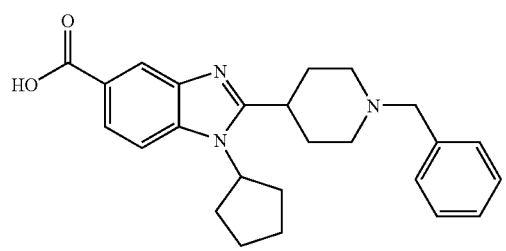 | 300MHz, DMSO-d6 8.14(1H, s), 7.79(1H, d, J=9.0Hz), 7.57(1H, d, J=8.7Hz), 7.40–7.20(5H, m), 4.89(1H, quint, J=8.7Hz), 3.54(2H, s), 3.19–2.90(3H, m), 2.23–1.69(14H, m) |
| Purity >90% (NMR) MS 404 (M+1) | |

TABLE 17

| Example No. 79 | 1H NMR(δ)ppm |
|---|---|
| 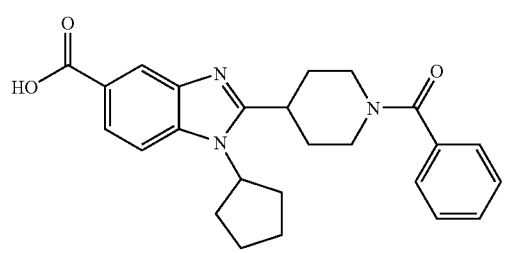 | 300MHz, DMSO-d6 8.15(1H, s), 7.81(1H, d, J=8.4Hz), 7.59(1H, d, J=9.0Hz), 7.50–7.38(5H, m), 5.05(1H, quint, J=9.0Hz), 3.85–2.95(3H, m), 2.20–1.65(14H, m) |
| Purity >90% (NMR) MS 418 (M+1) | |

TABLE 17-continued

| Example No. 80 | 1H NMR(δ)ppm |
|---|---|
| 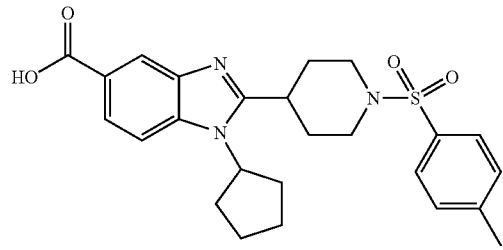 | 300MHz, DMSO-d6 8.17(1H, m), 7.84(1H, d, J=8.4Hz), 7.78–7.62(3H, m), 7.49(2H, d, J=8.1Hz), 5.05–4.91(1H, m), 3.80–3.70(2H, m), 3.30–3.12(1H, m), 2.48–2.31(5H, m), 2.15–1.60(12H, m) |

Purity >90% (NMR)
MS 468 (M+1)

| Example No. 81 | 1H NMR(δ)ppm |
|---|---|
| 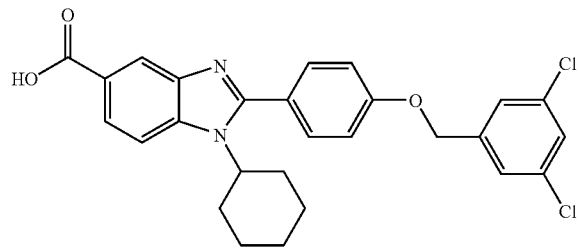 | 300MHz, DMSO-d6 12.75(1H, brs), 8.21(1H, d, J=1.4Hz), 7.49(1H, d, J=8.6Hz), 7.85(1H, dd, J=8.6, 1.4Hz), 7.70–7.55(5H, m), 7.23(2H, d, J=8.7Hz), 5.25(2H, s), 4.36–4.15(1H, m), 2.39–2.18(2H, m), 2.00–1.78(4H, m), 1.70–1.57(1H, m), 1.48–1.15(3H, m) |

Purity >90% (NMR)
MS 495 (M+1)

TABLE 18

| Example No. 82 | 1H NMR(δ)ppm |
|---|---|
| 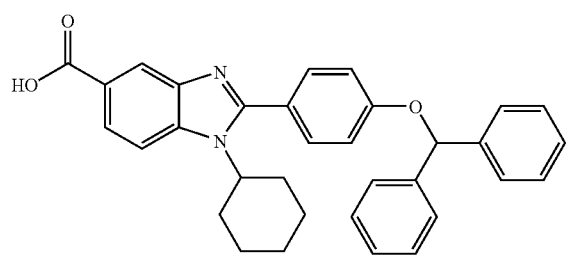 | 300MHz, DMSO-d6 8.27(1H, s), 8.22(1H, d, J=8.7Hz), 8.02(1H, d, J=8.7Hz), 7.69(2H, d, J=8.7Hz), 7.60–7.50(4H, m), 7.45–7.25(8H, m), 6.75(1H, s), 4.21–4.23(1H, m), 2.39–2.18(2H, m), 2.10–1.78(4H, m), 1.70–1.15(4H, m) |

Purity >90%(NMR)
MS 503(M+1)

| Example No. 83 | 1H NMR(δ)ppm |
|---|---|
| 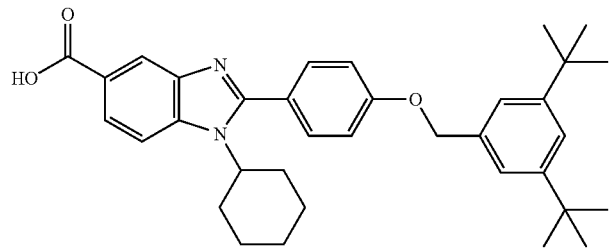 | 300MHz, DMSO-d6 13.2(1H, brs), 8.30(1H, s), 8.23(1H, d, J=8.8Hz), 8.02(1H, d, J=8.7Hz), 7.74(2H, d, J=8.6Hz), 7.40–7.33(5H, m), 5.22(2H, s), 4.36(1H, m), 2.50–1.40(10H, m), 1.31(18H, s). |

Purity >90%(NMR)
MS 539(M+1)

TABLE 18-continued

| Example No. 84 | 1H NMR(δ)ppm |
|---|---|
| 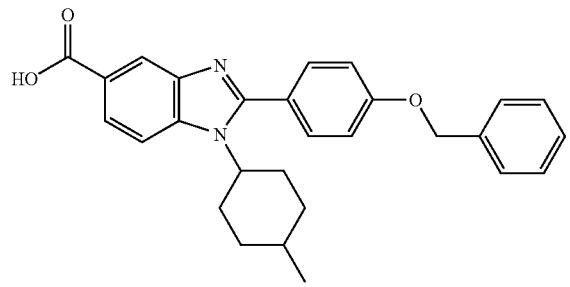 | mixture of isomers (cis:trans=3:1) 300MHz, DMSO-d6 8.30(1H, s), 8.20–7.95(2H, m), 7.72(2H, d, J=8.4Hz), 7.52–7.29(7H, m), 5.25(2H, s), 4.34, 3.40(1H, m), 2.50–2.20(2H, m), 2.05–1.50(6H, m), 1.14, 0.90(3H, d, J=6.9, 6.3Hz), 1.09(1H, m). |

Purity >90%(NMR)
MS 441(M+1)

TABLE 19

| Example No. 85 | 1H NMR(δ)ppm |
|---|---|
| 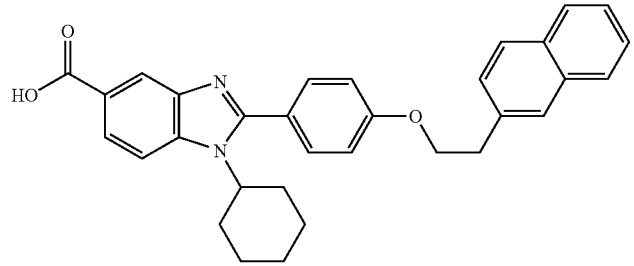 | 300MHz, DMSO-d6 8.25(1H, s), 8.14–7.83(6H, m), 7.77–7.44(5H, m), 7.21(2H, d, J=7.8Hz), 4.44(2H, brt), 4.31(1H, brt), 3.56(2H, brt), 2.20–2.16(2H, m), 2.00–1.74(4H, m), 1.70–1.55(1H, m), 1.45–1.14(3H, m) |

Purity >90%(NMR)
MS 491(M+1)

| Example No. 86 | 1H NMR(δ)ppm |
|---|---|
| 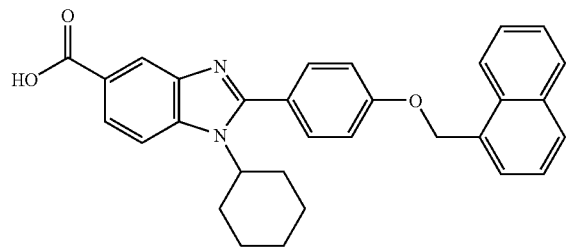 | 300MHz, DMSO-d6 12.75(1H, s), 8.23(1H, s), 8.15(1H, d, J=7.6Hz), 8.02–7.53(10H, m), 7.32(2H, d, J=8.7Hz), 5.68(2H, s), 4.32(1H, brt, J=12.2Hz), 2.41–2.20(2H, m), 2.01–1.78(4H, m), 1.71–1.56(1H, m), 1.50–1.16(3H, m) |

Purity >90%(NMR)
MS 477(M+1)

| Example No. 87 | 1H NMR(δ)ppm |
|---|---|
| 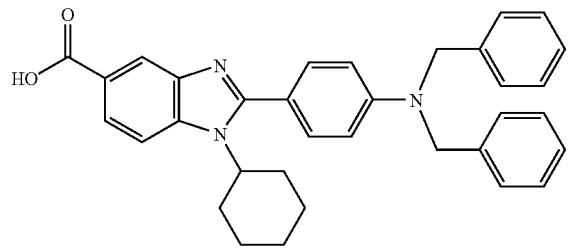 | 300MHz, DMSO-d6 12.75(1H, brs), 8.16(1H, s), 7.91 and 7.82(2H, ABq, J=8.5Hz), 7.44 and 6.86(4H, A'B'q, J=8.6Hz), 7.39–7.26(10H, m), 4.82(2H, s), 4.35(1H, brt, J=12.2Hz), 2.35–2.16(2H, m), 1.97–1.75(4H, m), 1.69–1.56(1H, m), 1.45–1.16(3H, m) |

Purity >90%(NMR)
MS 516(M+1)

TABLE 20
| Example No. 88 | 1H NMR(δ) ppm |
|---|---|
| 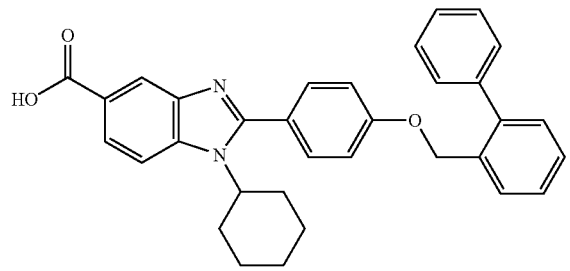 | 300 MHz, DMSO-d6 8.31(1H, s), 8.26 and 8.06(2H, ABq, J=8.9Hz), 7.73 and 7.22(4H, A'B'q, J=8.7hz), 7.50–7.36(8H, m), 5.10(2h, s), 4.37(1h, brt, J=12.2Hz), 2.38–2.28(2H, m), 2.10–1.80(4H, m), 1.70–1.56(1H, m), 1.50–1.20(3H, m) |
| Purity >90%(NMR) MS 503(M+1) | |
| Example No. 89 | 1H NMR(δ) ppm |
| 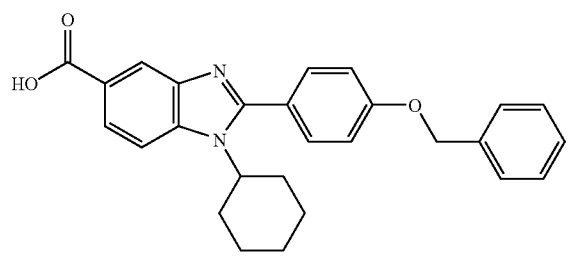 | |
| Purity 91%(HPLC) MS 427(M+1) | |
| Example No. 90 | 1H NMR(δ) ppm |
| | 300 MHz, DMSO-d6 8.40–8.20(2H, m), 8.04(1H, d, J=8.4Hz), 7.65(2H, d, J=8.4Hz), 7.50–7.10(12H, m), 5.08(1H, m), 4.33(1H, m), 3.00(4H, m), 2.50–1.10(10H, m) |
| Purity >90%(NMR) MS 531(M+1) | |
TABLE 21
| Example No. 91 | 1H NMR(δ)ppm |
|---|---|
| 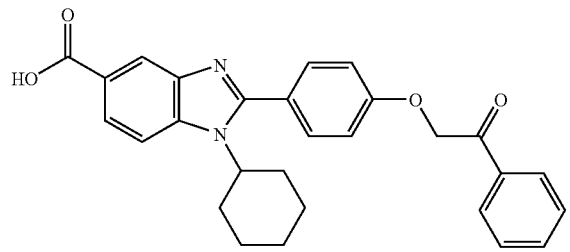 | 300MHz, DMSO-d6 8.31(1H, s), 8.27(1H, d, J=8.7Hz), 8.08–8.03(3H, m), 7.77–7.58(5H, m), 7.31(2H, d, J=8.7Hz), 5.81(2H, s), 4.40(1H, m), 2.50–1.20(10H, m). |
| Purity about 90%(NMR) MS 455(M+1) | |

TABLE 21-continued

Example No. 92

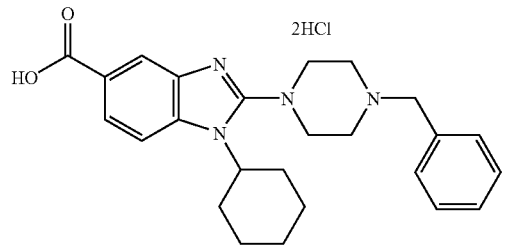

Purity >90%(NMR)
MS 419(M+1)

1H NMR(δ)ppm

300MHz, DMSO-d6 11.8(1H, brs), 8.07(1H, s), 7.89(1H, d, J=8.7Hz), 7.84(1H, d, J=8.4Hz), 7.69(2H, m), 7.48(3H, m), 4.42(2H, s), 4.11(1H, m), 3.73(4H, m), 3.40(4H, m), 2.40–1.40(10H, m)

Example No. 93

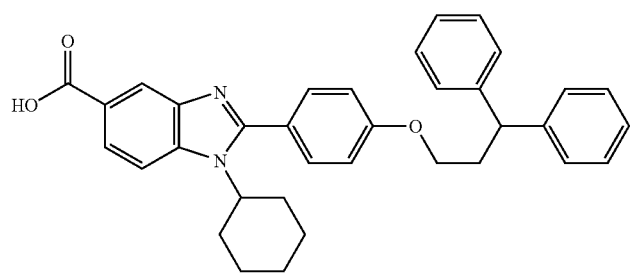

Purity >90%(NMR)
MS 531(M+1)

1H NMR(δ)ppm

300MHz, DMSO-d6 8.32(1H, s), 8.28(1H, d, J=8.9Hz), 8.05(1H, d, J=8.7Hz), 7.72(2H, d, J=8.7Hz), 7.38(4H, d, J=7.2Hz), 7.31(4H, t, J=7.3Hz), 7.21–7.17(4H, m), 4.37(1H, m), 4.26(1H, t, J=7.9Hz), 4.01(2H, t, J=6.2Hz), 2.57(2H, m), 2.50–2.20(2H, m), 2.10–2.00(2H, m), 2.00–1.75(2H, m), 1.75–1.55(1H, m), 1.55–1.20(3H, m).

TABLE 22

Example No. 94

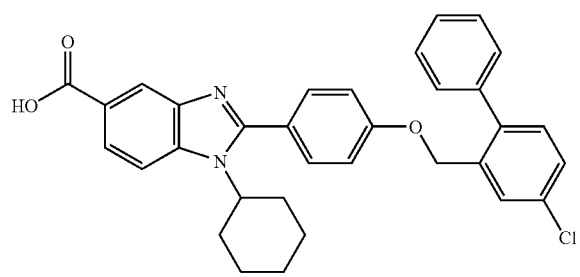

Purity >90%(NMR)
MS 537(M+1)

1H NMR(δ)ppm

300MHz, DMSO-d6 8.32(1H, s), 8.27(1H, d, J=9.0Hz), 8.05(1H, d, J=8.7Hz), 7.75–7.70(3H, m), 7.56(1H, d, J=8.4Hz), 7.55–7.35(6H, m), 7.22(2H, d, J=8.7Hz), 5.11(2H, s), 4.36(1H, m), 2.40–2.15(2H, m), 2.15–1.95(2H, m), 1.95–1.75(2H, m), 1.75–1.55(1H, m), 1.55–1.20(3H, m).

Example No. 95

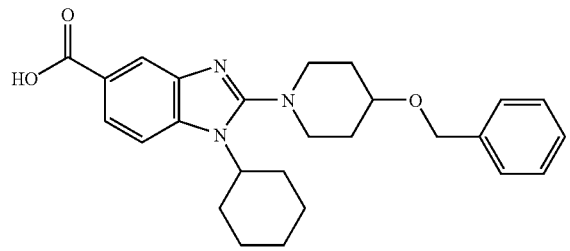

Purity >90%(NMR)
MS 434(M+1)

1H NMR(δ)ppm

300Hz, DMSO-d6 12.9(1H, brs), 8.02(1H, s), 7.82(2H, m), 7.40–7.25(5H, m), 4.58(2H, s), 4.09(1H, m), 3.71(1H, m), 3.49(2H, m), 3.21(2H, m), 2.35–1.30(14H, m).

TABLE 22-continued

| Example No. 96 | 1H NMR(δ)ppm |
|---|---|
| 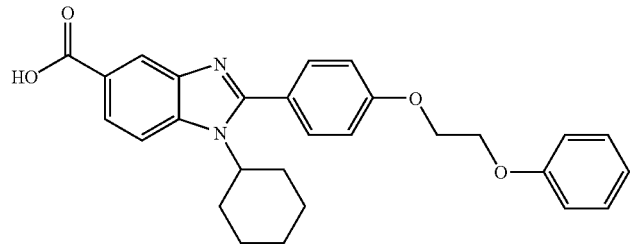 | 300MHz, DMSO-d6 8.31(1H, d, J=1.3Hz), 8.27(1H, d, J=8.8Hz), 8.05(1H, d, J=8.8Hz), 7.76(2H, d, J=8.7Hz), 7.40–7.25(4H, m), 7.06–6.90(3H, m), 4.53–4.26(5H, m), 2.40–2.18(2H, m), 2.12–1.56(5H, m), 1.50–1.19(3H, m) |

Purity >90%(NMR)

MS 457(M+1)

TABLE 23

| Example No. 97 | 1H NMR(δ)ppm |
|---|---|
| 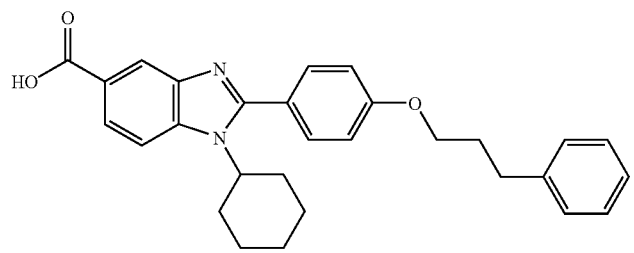 | 300 MHz, DMSO-d6 8.32(1H, d, J=1.3Hz), 8.29(1H, d, J=8.8Hz,), 8.05(1H, dd, J=8.8, 1.3Hz), 8.42(2H, d, J=8.8Hz), 7.37–7.16 (7H, m), 4.48–4.30(1H, m), 4.12(2H, t, J=6.2Hz), 2.83–2.70(2H, m), 2.40–1.50(9H, m), 1.59–1.19(3H, m) |

Purity >90%(NMR)
MS 455(M+1)

| Example No. 98 | 1H NMR(δ) ppm |
|---|---|
| 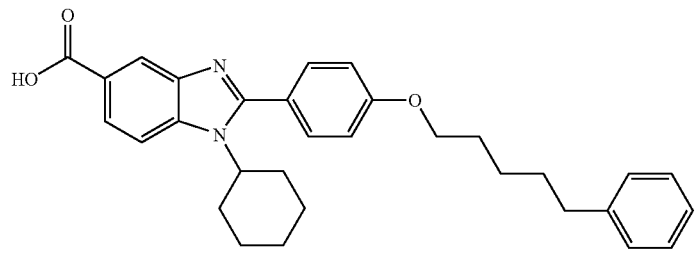 | 300 MHz, DMSO-d6 8.28(1H, d, J=1.3Hz), 8.21(1H, d, J=8.8Hz), 8.01(1H, d, J=10.1Hz), 7.70(2H, d, J=8.7Hz), 7.33–7.12(7H, m), 4.44–4.28(1H, m), 4.10(2H, t, J=6.3Hz), 2.62(2H, t, J=7.4Hz), 2.39–2.15(2H, m), 2.10–1.18(14H, m) |

Purity >90%(NMR)
MS 483(M+1)

| Example No. 99 | 1H NMR(δ) ppm |
|---|---|
| 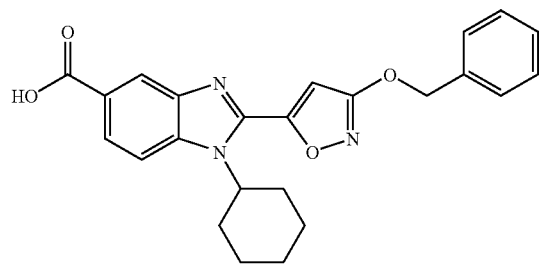 | 300 MHz, DMSO-d6 12.93(1H, brs), 8.30(1H, d, J=1.4Hz), 8.04(1H, d, J=8.7Hz), 7.92(1H, dd, J=8.7, 1.4Hz), 7.59–7.34(5H, m), 7.07 (1H, s), 5.38(2H, s), 4.78–4.60 (1H, m), 2.32–2.14(2H, m), 2.03–1.28 (8H, m) |

Purity >90%(NMR)
MS 418(M+1)

TABLE 24

| Example No. 100 | 1H NMR(δ)ppm |
|---|---|
| 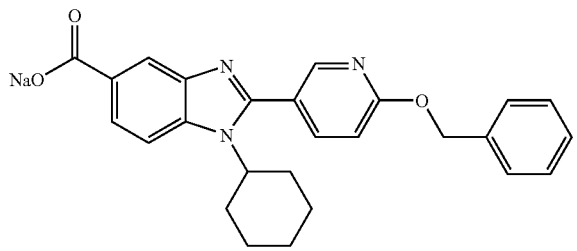<br>Purity >90%(NMR)<br>MS 427(M+1) | 300MHz, DMSO-d6 8.46(1H, d, J=2.1Hz), 8.16(1H, s), 8.00(1H, dd, J=8.5, 2.1Hz), 7.87(1H, d, J=8.5Hz), 7.68(1H, d, J=8.5Hz), 7.55–7.30(5H, m), 7.08(1H, d, J=8.5Hz), 5.45(2H, s), 4.25–4.08(1H, m), 2.39–2.18(2H, m), 2.00–1.75(4H, m), 1.70–1.55(1H, m), 1.45–1.19(3H, m) |
| Example No. 101 | 1H NMR(δ)ppm |
| 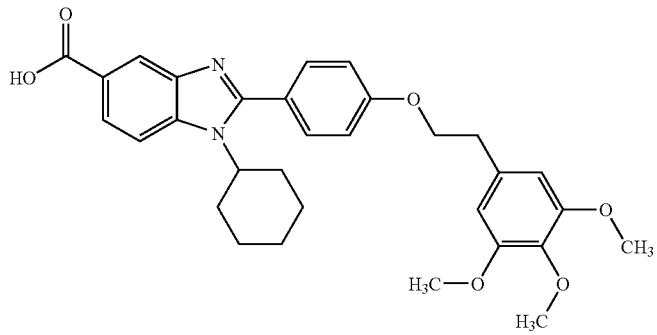<br>Purity >90%(NMR)<br>MS 531(M+1) | 300MHz, DMSO-d6 8.33(1H, s), 8.31(1H, d, J=6.9Hz), 8.06(1H, d, J=8.4Hz), 7.76 and 7.29(4H, ABq, J=8.9Hz), 6.68(2H, s), 4.37(1H, m), 4.35(2H, t, J=7.0Hz), 3.79(6H, s), 3.63(3H, s), 3.04(2H, t, J=6.9Hz), 2.30(2H, m), 2.04(2H, m), 1.86(2H, m), 1.65(1H, m), 1.50–1.15(3H, m) |
| Example No. 102 | 1H NMR(δ)ppm |
| 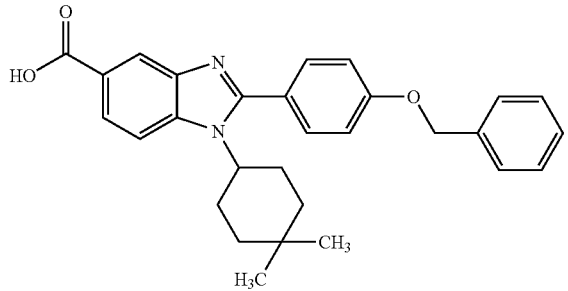<br>Purity >90%(NMR)<br>MS 455(M+1) | 300MHz, DMSO-d6 12.88(1H, s), 8.34(1H, s), 7.86(1H, d, J=8.5Hz), 7.73(1H, d, J=8.5Hz), 7.63 and 7.23 (4H, ABq, J=8.7Hz), 7.52–7.35(5H, m), 5.22(2H, s), 4.31(1H, m), 2.39(2H, m), 1.79(2H, m), 1.53(2H, m), 1.31(2H, m), 1.11(3H, s), 0.95(3H, s) |

TABLE 25

| Example No. 103 | 1H NMR(δ)ppm |
|---|---|
| 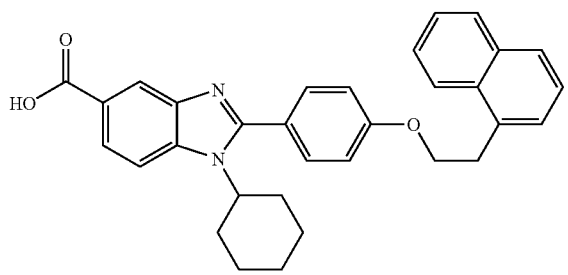<br>Purity >90%(NMR)<br>MS 491 (M+1) | 300MHz, DMSO-d6 12.79(1H, brs), 8.22(2H, s), 8.02–7.78(4H, m), 7.63–7.42(6H, m), 7.20–7.09(2H, m), 4.43(2H, s), 4.27(1H, brt, J=12.2Hz), 3.59(2H, s), 2.39–2.15(2H, m), 1.98–1.72(4H, m), 1.68–1.59(1H, m), 1.43–1.12(3H, m) |

TABLE 25-continued

Example No. 104

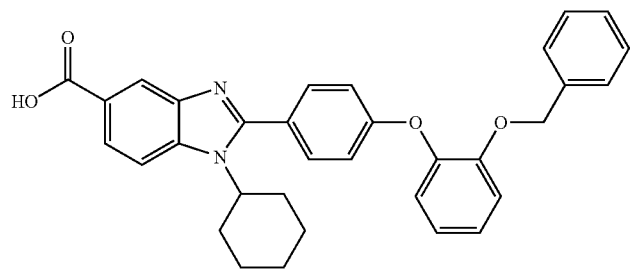

Purity >90%(NMR)
MS 519 (M+1)

1H NMR(δ)ppm

300MHz, DMSO-d6 12.75(1H, s), 8.23(1H, s), 7.94 and 7.86(2H, ABq, J=8.6Hz), 7.64 and 7.05(4H, A'B'q, J=8.7Hz), 7.32–7.09(9H, m), 5.13(2H, s), 4.28(1H, brt, J=12.2Hz), 2.36–2.19(2H, m), 1.95–1.77(4H, m), 1.66–1.56(1H, m), 1.46–1.10(3H, m)

Example No. 105

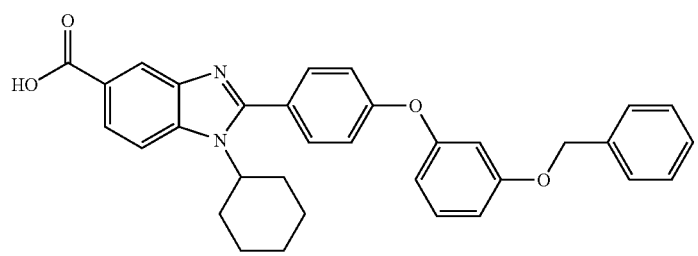

Purity >90%(NMR)
MS 519 (M+1)

1H NMR(δ)ppm

300MHz, DMSO-d6 8.23(1H, s), 7.94 and 7.87(2H, ABq, J=8.6Hz), 7.68 and 7.17(4H, A'B'q, J=8.7Hz), 7.46–7.33(6H, m), 6.93 and 6.75(2H, A"B"q, J=8.2Hz), 6.82(1H, s), 5.13(2H, s), 4.30(1H, brt, J=12.2Hz), 2.39–2.18(2H, m), 1.98–1.77(4H, m), 1.71–1.59(1H, m), 1.48–1.20(3H, m)

TABLE 26

Example No. 106

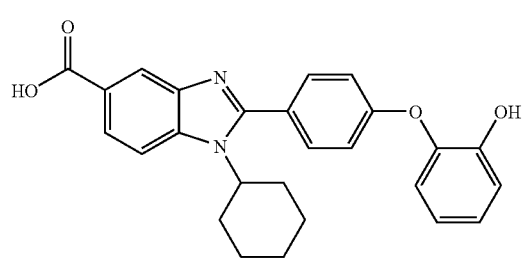

Purity >90%(NMR)
MS 429 (M+1)

1H NMR(δ)ppm

300MHz, DMSO-d6 12.89(1H, brs), 9.73(1H, s), 8.24(1H, s), 8.03 and 7.91(2H, ABq, J=8.7Hz), 7.66 and 7.04(4H, A'B'q, J=8.7Hz), 7.16–7.03(3H, m), 6.89(2H, t, J=9.2Hz), 4.33(1H, brt, J=12.2Hz), 2.40–2.18(2H, m), 2.00–1.78(4H, m), 1.70–1.58(1H, m), 1.50–1.20(3H, m)

Example No. 107

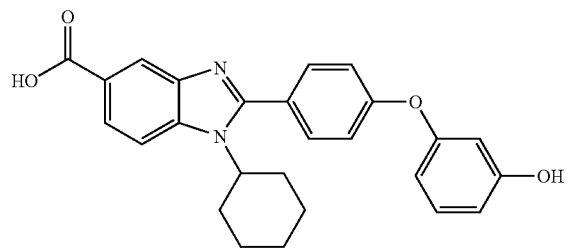

Purity >90%(NMR)
MS 429 (M+1)

1H NMR(δ)ppm

300MHz, DMSO-d6 12.98(1H, brs), 9.82(1H, brs), 8.27(1H, s), 8.09 and 7.94(2H, ABq, J=8.7Hz), 7.74 and 7.22(4H, A'B'q, J=8.7Hz), 7.28–7.22(1H, m), 6.67–6.54(3H, m), 4.35(1H, brt, J=12.2Hz), 2.40–2.20(2H, m), 2.05–1.80(4H, m), 1.72–1.59(1H, m), 1.50–1.21(3H, m)

TABLE 26-continued

| Example No. 108 | 1H NMR(δ)ppm |
|---|---|
| 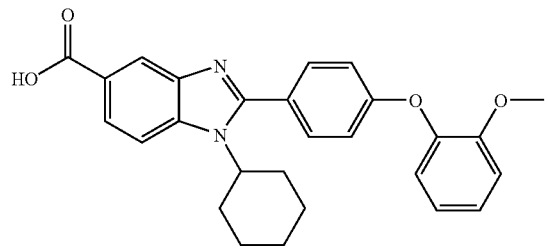 | 300MHz, DMSO-d6 8.24(1H, s), 8.01 and 7.90(2H, ABq, J=8.7Hz), 7.65 and 7.03(4H, A'B'q, J=8.7Hz), 7.32–7.20(3H, m), 7.08–7.03(1H, m), 4.32(1H, brt, J=12.2Hz), 3.77(3H, s), 2.36–2.20(2H, m), 2.00–1.78(4H, m), 1.71–1.59(1H, m), 1.44–1.11(3H, m) |

Purity >90%(NMR)

MS 443 (M+1)

TABLE 27

| Example No. 109 | 1H NMR(δ)ppm |
|---|---|
| 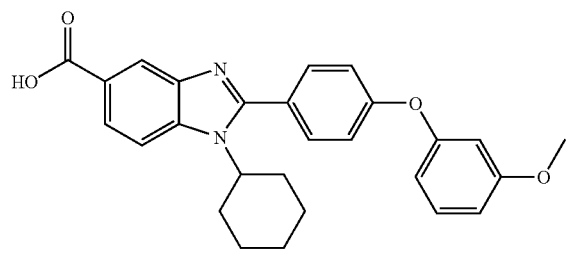 | 300MHz, DMSO-d6 12.75(1H, s), 8.24(1H, s), 7.96 and 7.87(2H, ABq, J=9.0Hz), 7.69 and 7.19(4H, A'B'q, J=8.6Hz), 7.37(1H, t, J=7.1Hz), 6.84–6.70(3H, m), 4.31(1H, brt, J=12.2Hz), 3.78(3H, s), 2.39–2.20(2H, m), 1.98–1.78(4H, m), 1.76–1.60(1H, m), 1.48–1.13(3H, m) |

Purity >90%(NMR)
MS 443 (M+1)

| Example No. 110 | 1H NMR(δ)ppm |
|---|---|
| 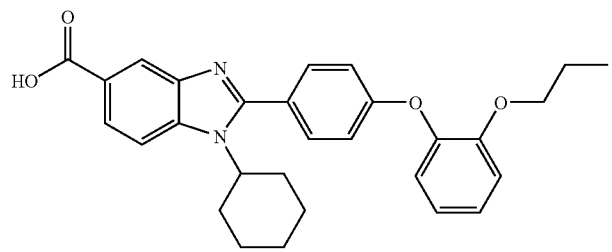 | 300MHz, DMSO-d6 8.31(1H, s), 8.26 and 8.04(2H, ABq, J=8.8Hz), 7.75 and 7.71(4H, A'B'q, J=8.8Hz), 7.32–7.03(4H, m), 4.34(1H, brt, J=12.2Hz), 3.94(2H, t, J=6.3Hz), 2.40–2.19(2H, m), 2.11–1.81(4H, m), 1.72–1.16(6H, m), 0.71(3H, t, J=7.3Hz) |

Purity >90%(NMR)
MS 471 (M+1)

| Example No. 111 | 1H NMR(δ)ppm |
|---|---|
| 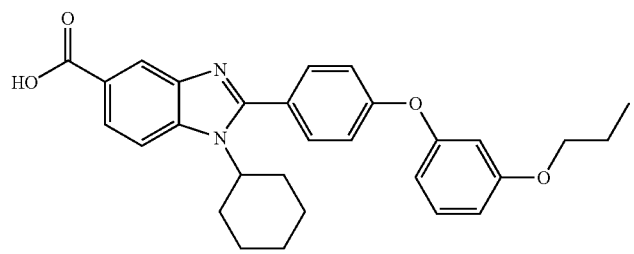 | 300MHz, DMSO-d6 8.22(1H, s), 7.91 and 7.87(2H, ABq, J=8.7Hz), 7.68 and 7.18(4H, A'B'q, J=8.7Hz), 7.35(1H, t, J=8.5Hz), 6.80(1H, d, J=9.0Hz), 6.72–6.68(2H, m), 4.30(1H, brt, J=12.2Hz), 3.94(2H, t, J=6.5Hz), 2.39–2.18(2H, m), 1.97–1.58(7H, m), 1.45–1.20(3H, m), 0.97(3H, t, J=7.4Hz) |

Purity >90%(NMR)
MS 471 (M+1)

TABLE 28

| Example No. 112 | 1H NMR(δ)ppm |
|---|---|
| 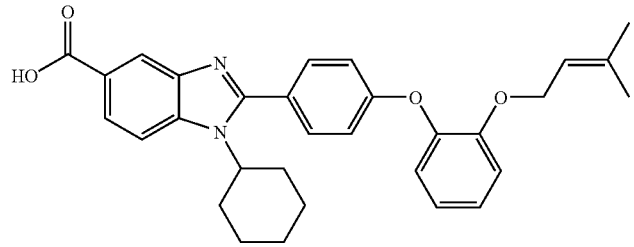 Purity >90%(NMR)<br>MS 497 (M+1) | 300MHz, DMSO-d6 12.73(1H, s), 8.22(1H, s), 7.94 and 7.85(2H, ABq, J=9.3Hz), 7.61 and 7.01(4H, A'B'q, J=8.6Hz), 7.25–7.00(4H, m), 5.25(2H, brs), 4.55(2H, d, J=6.6Hz), 4.29(1H, brt, J=12.2Hz), 2.38–2.18(2H, m), 1.96–1.78(4H, m), 1.70–1.56(1H, m), 1.67(3H, s), 1.60(3H, s), 1.48–1.15(3H, m) |
| Example No. 113 | 1H NMR(δ)ppm |
| 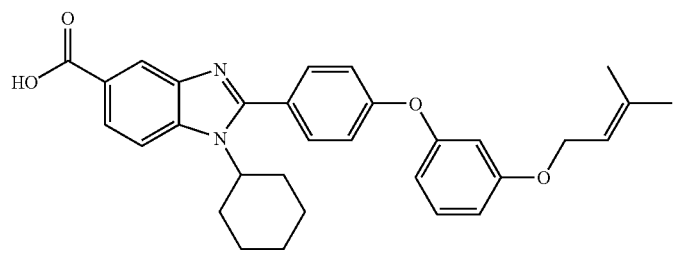 Purity >90%(NMR)<br>MS 497 (M+1) | 300MHz, DMSO-d6 12.75(1H, s), 8.23(1H, s), 7.95 and 7.86(2H, ABq, J=8.9Hz), 7.69 and 7.18(4H, A'B'q, J=8.9Hz), 7.35(1H, t, J=8.3Hz), 6.81–6.69(3H, m), 5.41(2H, brs), 4.54(2H, d, J=6.6Hz), 4.31(1H, brt, J=12.2Hz), 2.41–2.18(2H, m), 1.98–1.76(4H, m), 1.73(3H, s), 1.70–1.58(1H, m), 1.68(3H, s), 1.45–1.17(3H, m) |
| Example No. 114 | 1H NMR(δ)ppm |
| 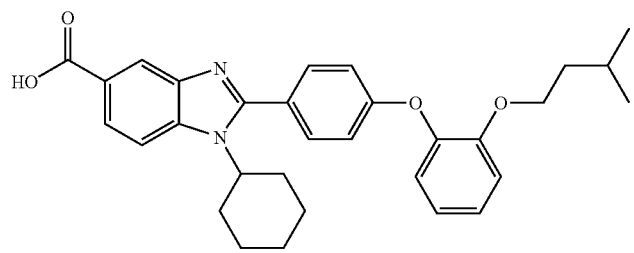 Purity >90%(NMR)<br>MS 499 (M+1) | 300MHz, DMSO-d6 12.73(1H, s), 8.22(1H, s), 7.94 and 7.85(2H, ABq, J=8.4Hz), 7.60 and 6.99(4H, A'B'q, J=8.6Hz), 7.29–7.00(4H, m), 4.29(1H, brt, J=12.2Hz), 3.99(2H, t, J=6.3Hz), 2.41–2.20(2H, m), 1.95–1.76(4H, m), 1.70–1.14(7H, m), 0.76(3H, d, J=6.6Hz) |

TABLE 29

| Example No. 115 | 1H NMR(δ)ppm |
|---|---|
| 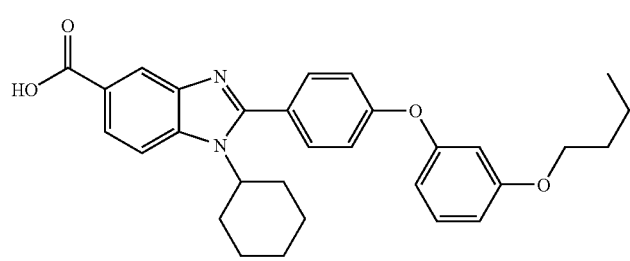 Purity >90%(NMR)<br>MS 499 (M+1) | 300MHz, DMSO-d6 8.23(1H, s), 7.93 and 7.87(2H, ABq, J=8.6Hz), 7.69 and 7.19(4H, A'B'q, J=8.6Hz), 7.35(1H, t, J=7.8Hz), 6.82–6.69(3H, m), 4.30(1H, brt, J=12.2Hz), 4.00(2H, t, J=6.9Hz), 2.38–2.20(2H, m), 1.97–1.54(8H, m), 1.47–1.20(3H, m), 0.93(6H, d, J=6.6Hz) |

TABLE 29-continued

| Example No. 116 | 1H NMR(δ)ppm |
|---|---|
| 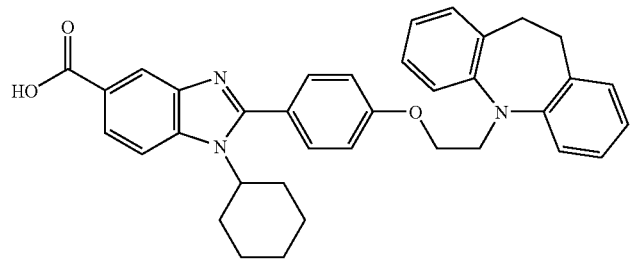 | 300MHz, DMSO-d6 8.30(1H, s), 8.25(1H, d, J=8.9Hz), 8.03(1H, d, J=8.8Hz), 7.68(2H, d, J=8.8Hz), 7.24(2H, d, J=7.2Hz), 7.19–7.10(6H, m), 6.94(2H, t, J=7.2Hz), 4.34(1H, m), 4.19(4H, brs), 3.10(4H, brs), 2.40–2.15(2H, m), 2.10–1.95(2H, m), 1.95–1.75(2H, m), 1.75–1.55(1H, m), 1.55–1.20(3H, m). |

Purity >90%(NMR)
MS 557 (M+1)

| Example No. 117 | 1H NMR(δ)ppm |
|---|---|
| 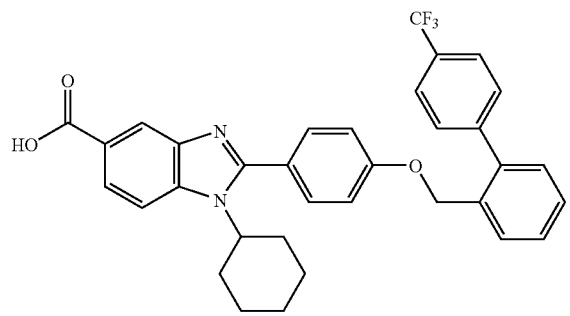 | 300MHz, DMSO-d6 12.8(1H, brs), 8.22(1H, s), 7.98(1H, d, J=8.7Hz), 7.87(1H, d, J=8.6Hz), 7.80(2H, d, J=8.2Hz), 7.72–7.67(3H, m), 7.59(2H, d, J=8.7Hz), 7.54–7.51(2H, m), 7.42–7.41(1H, m), 7.11(2H, d, J=8.8Hz), 5.09(2H, s), 4.27(1H, m), 2.40–2.15(2H, m), 2.00–1.75(4H, m), 1.75–1.55(1H, m), 1.55–1.15(3H, m). |

Purity >90%(NMR)
MS 571 (M+1)

TABLE 30

| Example No. 118 | 1H NMR(δ)ppm |
|---|---|
| 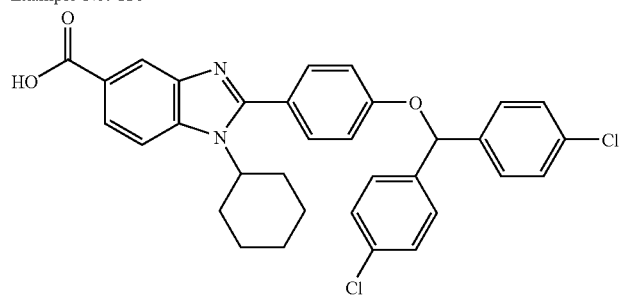 | 300MHz, DMSO-d6 13.3(1H, brs), 8.30(1H, s), 8.25(1H, d, J=8.9Hz), 8.04(1H, d, J=8.7Hz), 7.72(2H, d, J=8.8Hz), 7.57(4H, d, J=8.6Hz), 7.47(4H, d, J=8.6Hz), 7.33(2H, d, J=8.9Hz), 6.84(1H, s), 4.33(1H, m), 2.45–2.10(2H, m), 2.10–1.95(2H, m), 1.95–1.70(2H, m), 1.70–1.55(1H, m), 1.55–1.15(3H, m). |

Purity >90% (NMR)
MS 571(M+1)

| Example No. 119 | 1H NMR(δ)ppm |
|---|---|
| 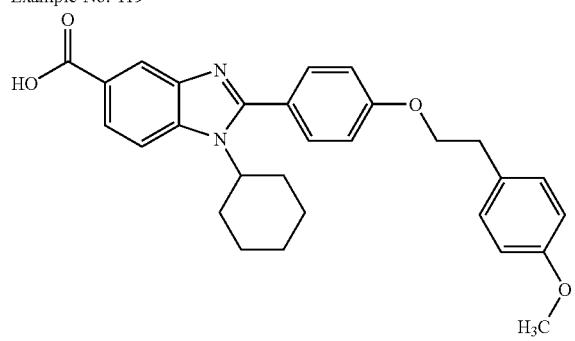 | 300MHz, DMSO-d6 8.32–8.30(2H, m), 8.07–8.03(1H, m), 7.74 and 6.90(4H, ABq, J=8.7Hz), 4.37(1H, m), 4.31(2H, t, J=6.8Hz,), 3.74(3H, s), 3.04(2H, t, J=6.7Hz), 2.30(2H, m), 2.02(2H, m), 1.86(2H, m), 1.63(1H, m), 1.55–1.15(3H, m) |

Purity >90% (NMR)
MS 471(M+1)

TABLE 30-continued

| Example No. 120 | 1H NMR(δ)ppm |
|---|---|
| 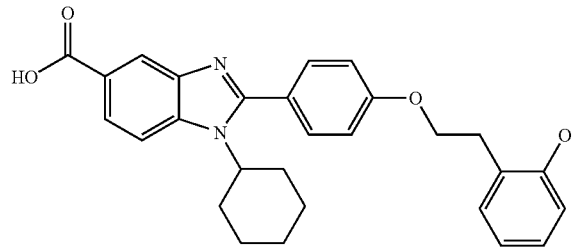 | 300MHz, DMSO-d6<br>8.23(1H, s), 7.99(1H, d, J=8.7Hz), 7.88(1H, d, J=8.4Hz), 7.61 and 7.16(4H, ABq, J=8.6Hz), 7.30–7.22(2H, m), 7.01 (2H, d, J=8.1Hz), 6.92(1H, t, J=7.5Hz), 4.28(1H, m), 4.25(2H, t, J=7.2Hz), 3.83(3H, s), 3.07(2H, t, J=7.1Hz), 2.28(2H, m)2.00–1.75(4H, m), 1.70–1.55(1H, m), 1.50–1.15(3H, m) |
| Purity >90% (NMR) | |
| MS 471(M+1) | |

TABLE 31

| Example No. 121 | 1H NMR(δ)ppm |
|---|---|
| 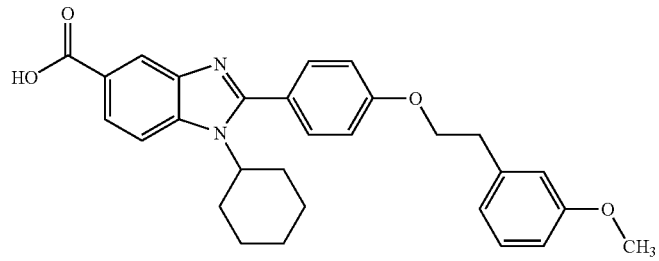 | 300MHz, DMSO-d6<br>12.85(1H, brs), 8.24(1H, s), 8.01(1H, d, J=8.7Hz), 7.90 (1H, d, J=8.6Hz), 7.62 and 7.17(4H, Abq, J=8.7Hz), 7.24 (1H, m), 6.94(2H, m), 6.82 (1H, m), 4.32(2H, t, J=6.7Hz), 3.76(3H, s), 3.07(2H, t, J=6.7Hz), 2.29(2H, m), 2.00–1.75(4H, m), 1.70–1.55(1H, m), 1.50–1.15(3H, m) |
| Purity >90% (NMR) | |
| MS 471(M+1) | |

| Example No. 122 | 1H NMR(δ)ppm |
|---|---|
| 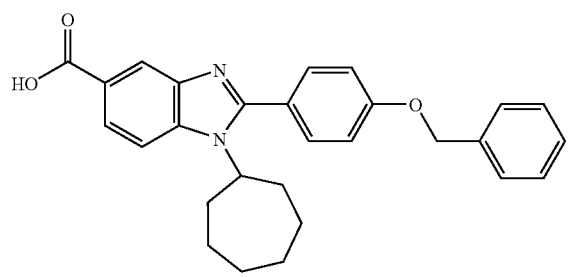 | 300MHz, DMSO-d6<br>12.8(1H, brs), 8.22(1H, s), 7.87(2H, m), 7.62(2H, d, J=8.1Hz), 7.60–7.20(7H, m), 5.23(2H, s), 4.46(1H, m), 2.50–2.30(2H, m), 1.70–1.40 (10H, m). |
| Purity >90% (NMR) | |
| MS 441(M+1) | |

| Example 123 | 1H NMR(δ)ppm |
|---|---|
| 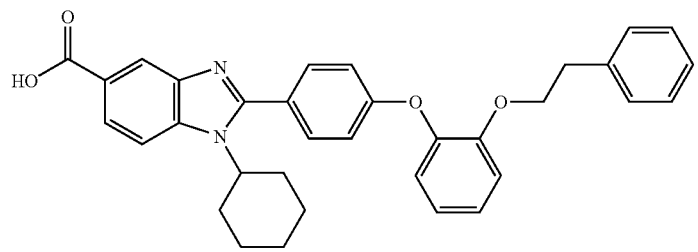 | 300MHz, DMSO-d6<br>8.24(1H, s), 7.97(1H, d, J=9.0Hz), 7.87(1H, d, J=8.4Hz), 7.65(2H, d, J=8.7Hz), 7.40–7.05(9H, m), 7.03(2H, d, J=8.4Hz), 4.31(1H, m), 4.18 (2H, t, J=6.6Hz), 2.81(2H, t, J=6.3Hz), 2.40–2.20(2H, m), 2.00–1.70(4H, m), 1.70–1.50(1H, m), 1.50–1.05(3H, m). |
| Purity >90% (NMR) | |
| MS 533(M+1) | |

TABLE 32

Example No. 124

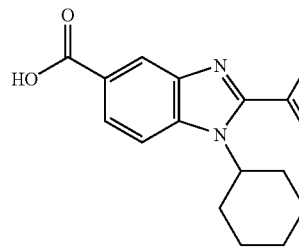

Purity >90% (NMR)
MS 533(M+1)

1H NMR(δ)ppm
300MHz, DMSO-d6
13.1(1H, brs), 8.29(1H, s),
8.17(1H, d, J=8.7Hz), 7.99
(1H, d, J=8.7Hz), 7.77(2H, d,
J=8.7Hz), 7.40–7.20(8H, m),
6.84(1H, d, J=9.3Hz), 6.75–
6.72(2H, m), 4.36(1H, m),
4.22(2H, t, J=6.8Hz), 3.04
(2H, t, J=6.7Hz), 2.40–2.15
(2H, m), 2.15–1.95(2H, m), 1.95–
1.75(2H, m),1.75–1.55
(1H, m), 1.55–1.15(3H, m).

Example No. 125

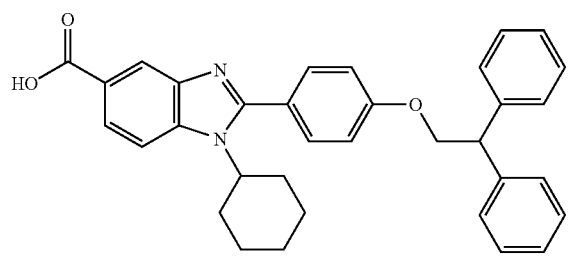

Purity >90% (NMR)
MS 517(M+1)

1H NMR(δ)ppm
300MHz, DMSO-d6
8.32(1H, s), 8.28(1H, d, J=
8.7Hz), 8.05(1H, d, J=9.0Hz),
7.73(2H, d, J=9.0Hz), 7.43
(4H, d, J=7.2Hz), 7.36–7.20
(8H, m), 4.74(2H, d, J=7.5Hz),
4.57(1H, t, J=7.5Hz), 4.38
(1H, m), 2.40–2.15(2H, m),
2.15–1.95(2H, m), 1.95–1.85
(2H, m), 1.85–1.55(1H, m),
1.55–1.20(3H, m).

Example No. 126

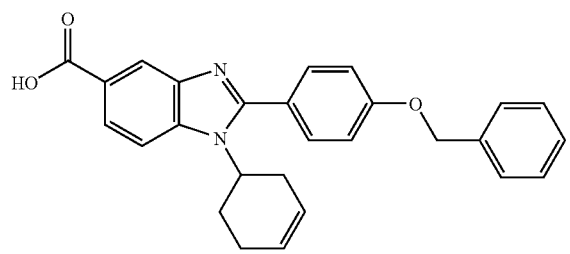

Purity >90% (NMR)
MS 425(M+1)

1H NMR(δ)ppm
300MHz, DMSO-d6
8.32(1H, s), 8.14(1H, d, J=
8.7Hz), 8.03(1H, d, J=8.7Hz),
7.77(2H, d, J=9.0Hz), 7.52–
7.31(7H, m), 5.74(2H, m),
5.26(2H, s), 4.61(1H, m), 2.96
(1H, m), 2.60–2.10(5H, m).

TABLE 33

Example No. 127

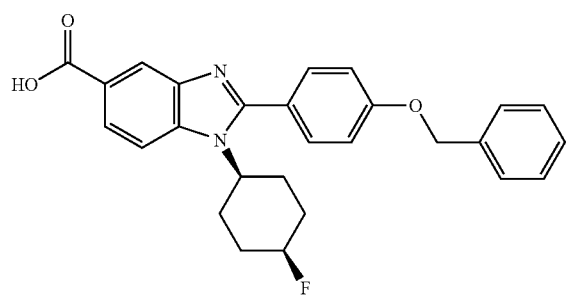

Purity >90% (NMR)
MS 445(M+1)

1H NMR(δ)ppm
300MHz, DMSO-d6
13.2(1H, brs), 8.33(1H, s),
8.12(1H, d, J=8.7Hz), 7.96
(1H, d, J=8.8Hz), 7.79(2H, d,
J=8.7Hz), 7.52–7.32(7H, m),
5.26(2H, s), 4.92(1H, d, J=
49.4Hz), 4.57(1H, m), 2.65–
2.35(2H, m), 2.25–1.50(6H, m).

TABLE 33-continued

Example No. 128

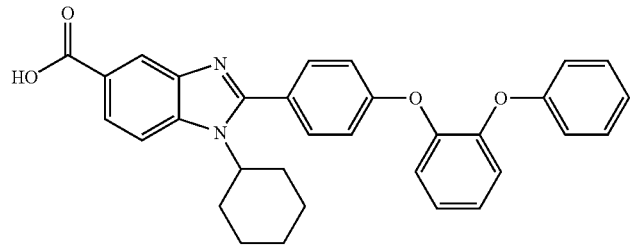

Purity >90% (NMR)
MS 505(M+1)

1H NMR(δ)ppm
300MHz, DMSO-d6
8.21(1H, s), 7.92 and 7.85 (2H, ABq, J=8.6Hz), 7.61 and 7.06(4H, A'B'q, J=8.6Hz), 7.36–6.91(9H, m), 4.24(1H, brt, J=12.2Hz), 2.35–2.15(2H, m), 1.95–1.75(4H, m), 1.70–1.58(1H, m), 1.48–1.14(3H, m)

Example No. 129

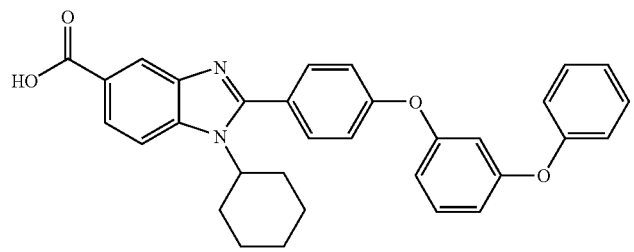

Purity >90% (NMR)
MS 505(M+1)

1H NMR(δ)ppm
300MHz, DMSO-d6
8.21(1H, s), 7.92 and 7.86 (2H, ABq, J=8.6Hz), 7.69 and 7.22(4H, A'B'q, J=8.6Hz), 7.52–7.39(1H, m), 7.47 and 7.41 (2H, A"B"q, J=8.1Hz), 6.91 (1H, d, J=8.0Hz), 6.89(1H, d, J=8.2Hz), 6.75(1H, s), 4.36–4.18(1H, m), 2.38–2.17(2H, m), 1.95–1.76(4H, m), 1.70–1.59(1H, m), 1.44–1.19(3H, m)

TABLE 34

Example No. 130

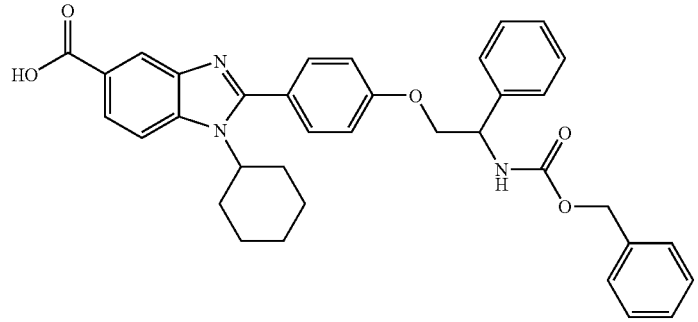

Purity >90% (NMR)
MS 590(M+1)

1H NMR(δ)ppm
300MHz, DMSO-d6
8.27(1H, s), 7.69(2H, d, J=8.6Hz), 7.49–7.21(11H, m), 5.08 and 5.03(2H, ABq, J=12.6Hz), 5.07–4.99(1H, m), 4.26 (2H, d, J=6.6Hz), 2.40–2.18 (2H, m), 2.04–1.77(4H, m), 1.70–1.58(1H, m), 1.48–1.15 (3H, m)

Example No. 131

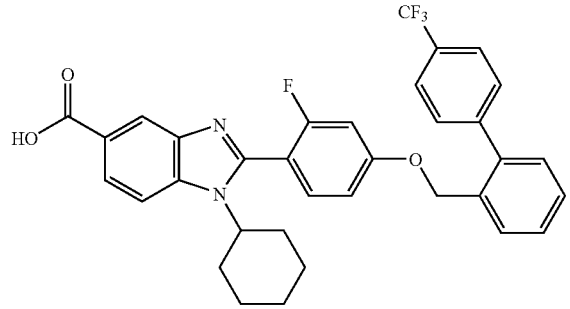

Purity >90% (NMR)
MS 589(M+1)

1H NMR(δ)ppm
300MHz, DMSO-d6
8.29(1H, s), 8.11(1H, d, J=9.0Hz), 7.96(1H, d, J=8.4Hz), 7.80(2H, d, J=8.1Hz), 7.72–7.41(7H, m), 7.12(1H, d, J=12.6Hz), 7.01(1H, d, J=8.4Hz), 5.12(2H, s), 4.06(1H, m), 2.35–2.10(2H, m), 2.00–1.75 (4H, m), 1.75–1.55(1H, m), 1.60–1.20(3H, m).

TABLE 34-continued

| Example No. 132 | 1H NMR(δ)ppm |
|---|---|
| 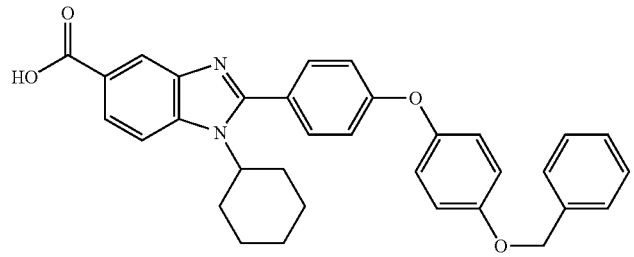 | 300MHz, DMSO-d6<br>12.8(1H, brs), 8.23(1H, s), 7.97(1H, d, J=8.7Hz), 7.87 (1H, d, J=8.6Hz), 7.66(2H, d, J=8.6Hz), 7.49–7.33(5H, m), 7.17–7.05(6H, m), 5.12(2H, s), 4.31(1H, m), 2.40–2.15 (2H, m), 2.05–1.20(8H, m). |
| Purity >90% (NMR)<br>MS 519(M+1) | |

TABLE 35

| Example No. 133 | 1H NMR(δ)ppm |
|---|---|
| 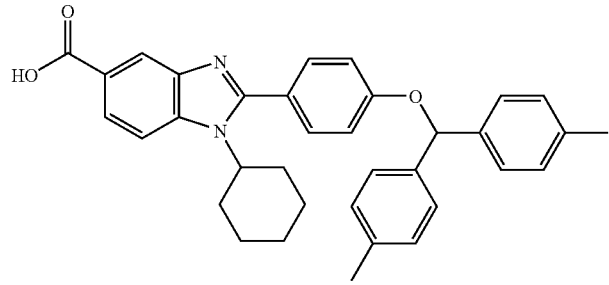 | 300MHz, DMSO-d6<br>8.57(1H, s), 8.01(1H, d, J=8.7Hz), 7.66(1H, d, J=8.7Hz), 7.51(2H, d, J=8.7Hz), 7.31 (4H, d, J=8.0Hz), 7.16(4H, d, J=8.0Hz), 7.09(2H, d, J=8.7Hz), 6.26(1H, s), 4.37(1H, m), 2.41–2.28(2H, m), 2.33 (6H, s), 2.03–1.84(4H, m), 1.77(1H, m), 1.45–1.20(3H, m). |
| Purity >90%(NMR)<br>MS 531(M+1) | |

| Example No. 134 | 1H NMR(δ)ppm |
|---|---|
| 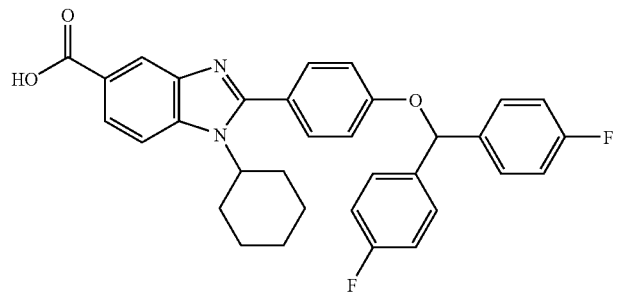 | 8.59(1H, d, J=1.5Hz), 8.02 (1H, dd, J=8.7, 1.5Hz), 7.68 (1H, d, J=8.7Hz), 7.54(2H, d, J=8.8Hz), 7.39(4H, dd, J=8.7, 5.3Hz), 7.08(4H, d, J=8.7Hz), 7.05(2H, d, J=8.8Hz), 6.29(1H, s), 4.36(1H, m), 2.43–2.19(2H, m), 2.04–1.85 (4H, m), 1.78(1H, m), 1.45–1.23 (3H, m). |
| Purity >90%(NMR)<br>MS 539(M+1) | |

| Example No. 135 | 1H NMR(δ)ppm |
|---|---|
| 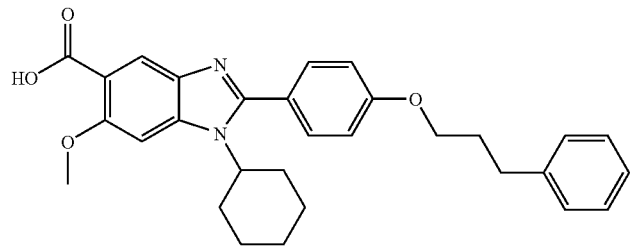 | 300MHz, DMSO-d6<br>12.34(1H, brs), 7.39(1H, s), 7.55(1H, d, J=8.6Hz), 7.33–7.15(6H, m), 7.11(2H, d, J=8.6Hz), 4.30–4.20(1H, m), 4.07(2H, t, J=6.3Hz), 3.93 (3H, s), 2.78(2H, t, J=7.4Hz), 2.35–2.19(2H, m), 2.12–2.00 (2H, m), 1.91–1.79(4H, m), 1.69–1.60(1H, m), 1.47–1.20 (3H, m) |
| Purity >90%(NMR)<br>MS 485(M+1) | |

TABLE 36
Example No. 136
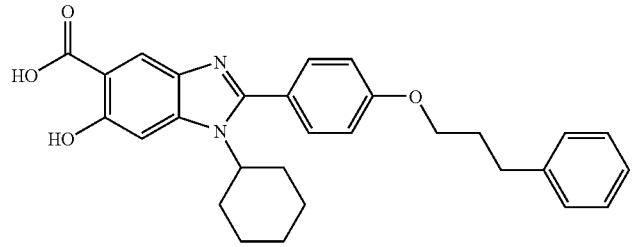
Purity >90%(NMR)
MS 471(M+1)
1H NMR(δ)ppm
300MHz, DMSO-d6
8.13(1H, s), 7.65(2H, d, J=
8.7Hz), 7.63(1H, s), 7.35–7.12
(7H, m), 4.35–4.20(1H, m),
4.10(1H, t, J=6.3Hz), 2.78
(2H, t, J=7.5Hz), 2.33–1.78
(8H, m), 1.70–1.16(4H, m)
Example No. 137
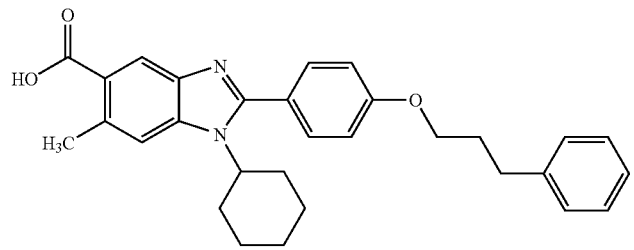
Purity >90%(NMR)
MS 469(M+1)
1H NMR(δ)ppm
300MHz, DMSO-d6
8.24(1H, s), 8.11(1H, s),
7.76(2H, d, J=9.0Hz), 7.37–
7.16(7H, m), 4.43–4.30(1H, m),
4.13(2H, t, J=6.3Hz), 2.84–
2.68(5H, m), 2.42–2.22(2H,
m), 2.18–1.80(6H, m), 1.70–
1.20(4H, m)
Example No. 138
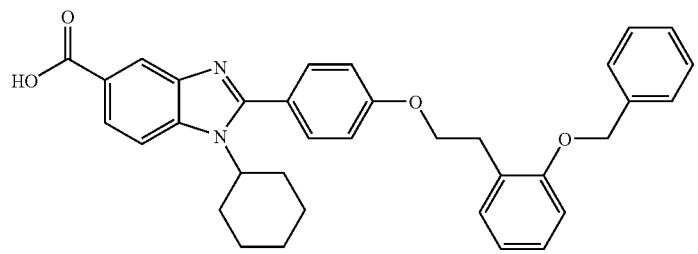
Purity >90%(NMR)
MS 547(M+1)
1H NMR(δ)ppm
300MHz, DMSO-d6
12.73(1H, brs), 8.22(1H, s),
7.76(1H, d, J=8.7Hz), 7.85
(1H, d, J=8.7Hz), 7.54–7.49
(4H, m), 7.42–7.21(5H, m),
7.11–7.09(3H, m), 6.93(1H, m),
5.17(2H, s), 4.29(3H, m),
3.11(2H, m), 2.40–2.20(2H,
m), 1.99–1.23(8H, m)
TABLE 37
Example No. 139
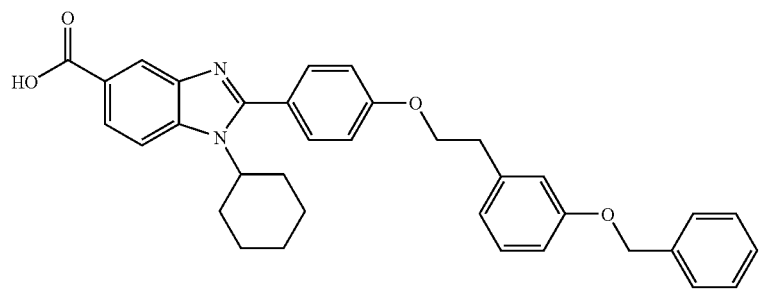
Purity >90%(NMR)
MS 547(M+1)
1H NMR(δ)ppm
300MHz, DMSO-d6
12.73(1H, brs), 8.22(1H, s),
7.93(1H, d, J=8.7Hz), 7.73
(1H, m), 7.60–7.57(2H, m),
7.47–6.90(1H, m), 5.11(2H, s),
4.33–4.28(3H, m), 3.09–
3.04(2H, t, J=6.7Hz), 2.35–
2.20(2H, m), 1.95–1.10(8H, m)

TABLE 37-continued

Example No. 140

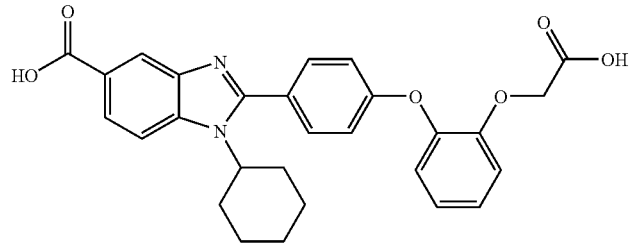

Purity >90%(NMR)
MS 487(M+1)

1H NMR(δ)ppm
300MHz, DMSO-d6
12.83(2H, brs), 8.22(1H, s),
7.94(1H, d, J=8.7Hz), 7.85
(1H, d, J=8.4Hz), 7.63–7.60
(2H, m), 7.26–7.03(6H, m),
4.73(2H, s), 4.30(1H, m), 2.40–
2.15(2H, m), 2.00–1.20(8H, m)

Example No. 141

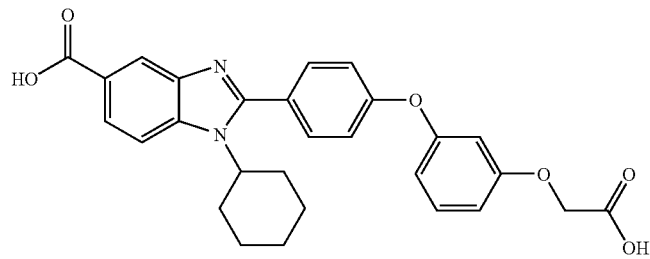

Purity >90%(NMR)
MS 487(M+1)

1H NMR(δ)ppm
300MHz, DMSO-d6
12.87(1H, brs), 8.24(1H, s),
7.97(1H, d, J=9.0Hz), 7.87
(1H, d, J=8.7Hz), 7.69 and
7.19(4H, ABq, J=8.7Hz), 7.36
(1H, t, J=8.7Hz), 6.80–6.72
(3H, m), 4.71(2H, s), 4.32(1H,
m), 2.29(2H, m), 1.95–1.25
(8H, m)

TABLE 38

Example No. 142

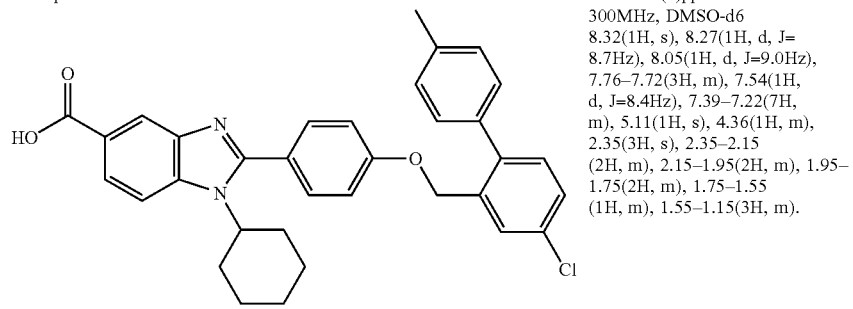

Purity >90%(NMR)
MS 551(M+1)

1H NMR(δ)ppm
300MHz, DMSO-d6
8.32(1H, s), 8.27(1H, d, J=
8.7Hz), 8.05(1H, d, J=9.0Hz),
7.76–7.72(3H, m), 7.54(1H,
d, J=8.4Hz), 7.39–7.22(7H,
m), 5.11(1H, s), 4.36(1H, m),
2.35(3H, s), 2.35–2.15
(2H, m), 2.15–1.95(2H, m), 1.95–
1.75(2H, m), 1.75–1.55
(1H, m), 1.55–1.15(3H, m).

Example No. 143

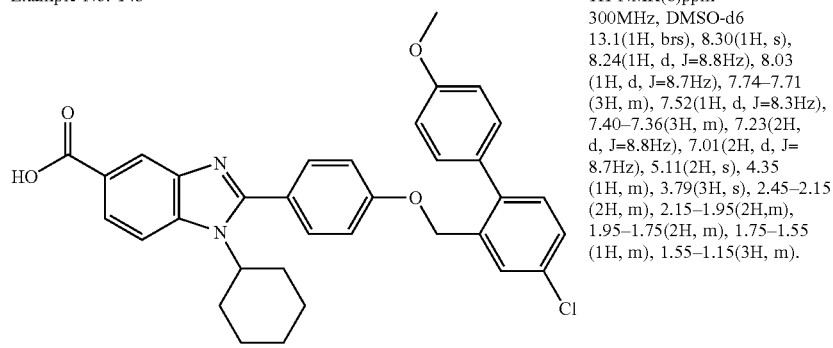

Purity >90%(NMR)
MS 567(M+1)

1H NMR(δ)ppm
300MHz, DMSO-d6
13.1(1H, brs), 8.30(1H, s),
8.24(1H, d, J=8.8Hz), 8.03
(1H, d, J=8.7Hz), 7.74–7.71
(3H, m), 7.52(1H, d, J=8.3Hz),
7.40–7.36(3H, m), 7.23(2H,
d, J=8.8Hz), 7.01(2H, d, J=
8.7Hz), 5.11(2H, s), 4.35
(1H, m), 3.79(3H, s), 2.45–2.15
(2H, m), 2.15–1.95(2H,m),
1.95–1.75(2H, m), 1.75–1.55
(1H, m), 1.55–1.15(3H, m).

TABLE 38-continued

| Example No. 144 | 1H NMR(δ)ppm 300MHz, DMSO-d6 13.0(1H, brs), 8.31(1H, s), 8.23(1H, d, J=8.7Hz), 8.04 (1H, d, J=8.7Hz), 7.80(2H, d, J=8.3Hz), 7.70–7.66(3H, m), 7.55–7.40(4H, m), 7.03– 6.95(2H, m), 5.08(2H, s), 4.03 (1H, m), 2.40–2.15(2H, m), 2.18(3H, s), 2.05–1.70(4H, m), 1.70–1.50(1H, m), 1.50– 1.10(3H, m). |
|---|---|
| 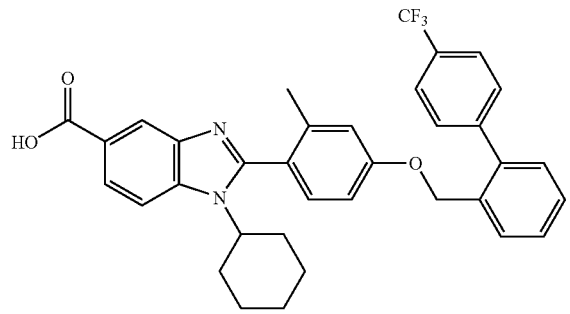 Purity >90%(NMR) MS 585(M+1) | |

TABLE 39

| Example No. 145 | 1H NMR(δ)ppm 300MHz, DMSO-d6 8.31(1H, s), 8.23(1H, d, J= 8.8Hz), 8.02(1H, d, J=8.7Hz), 7.73–7.71(3H, m), 7.54(1H, d, J=8.3Hz), 7.48(2H, d, J= 8.4Hz), 7.41–7.37(3H, m), 7.22(2H, d, J=8.7Hz), 5.13 (2H, s), 4.34(1H, m), 2.40–2.20 (2H, m), 2.15–1.95(2H, m), 1.95–1.75(2H, m), 1.70– 1.55(1H, m), 1.50–1.15(3H, m), 1.31(9H, s). |
|---|---|
| 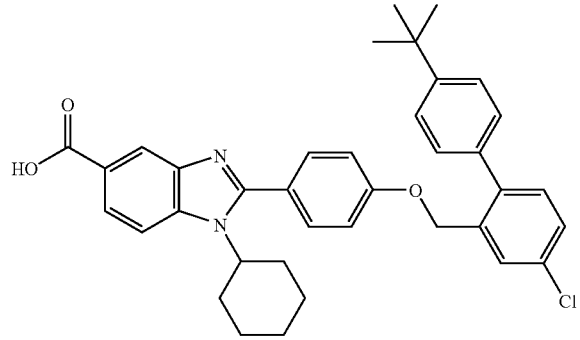 Purity >90%(NMR) MS 593(M+1) | |
| Example No. 146 | 1H NMR(δ)ppm 300MHz, DMSO-d6 8.29(1H, s), 8.13(1H, d, J= 8.7Hz), 7.97(1H, d, J=8.6Hz), 7.76(1H, d, J=2.1Hz), 7.63 (1H, t, J=8.5Hz), 7.57(1H, dd, J=8.2, 2.2Hz), 7.55–7.35 (6H, m), 7.15(1H, d, J=12.1Hz), 7.02(1H, d, J=8.6Hz), 5.10(2H, s), 4.07(1H, m), 2.35– 2.10(2H, m), 2.00–1.70(4H, m), 1.70–1.55(1H, m), 1.50– 1.15(3H, m). |
| 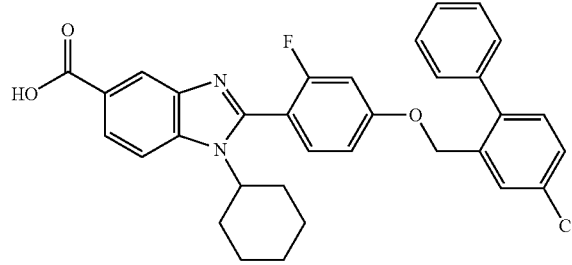 Purity >90%(NMR) MS 555(M+1) | |
| Example No. 147 | 1H NMR(δ)ppm 300MHz, CDCl3 8.61(1H, s), 8.04(1H, d, J= 8.7Hz), 7.69(1H, d, J=8.7Hz), 7.66(1H, d, J=2.4Hz), 7.59 (2H, d, J=8.7Hz), 7.42(1H, dd, J=8.0, 2.4Hz), 7.38(1H, t, J=1.8Hz), 7.28(2H, d, J= 1.8Hz), 7.26(1H, d, J=8.0Hz), 7.03(2H, d, J=8.7Hz), 4.94 (2H, s), 4.37(1H, m), 2.43– 2.21(2H, m), 2.17–1.86(4H,m), 1.79(1H, m), 1.43–1.26(3H, m). |
| 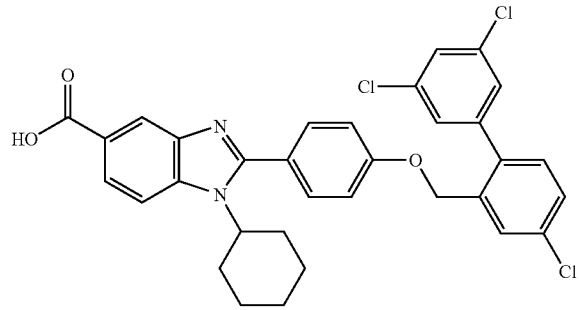 Purity >90%(NMR) MS 605(M+1) | |

TABLE 40

Example No. 148

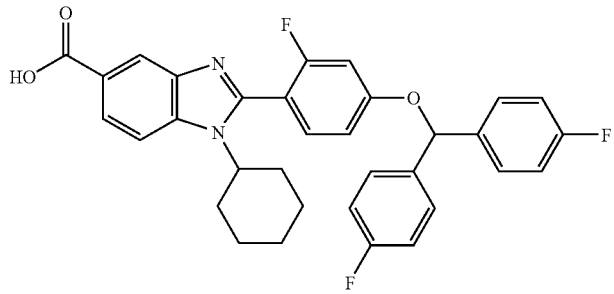

Purity >90%(NMR)
MS 557(M+1)

1H NMR(δ)ppm
300MHz, DMSO-d6
8.21(s, 1H), 7.89(1H, d, J=8.7Hz), 7.87(1H, d, J=8.7Hz), 7.63–7.46(5H, m), 7.30–7.12(5H, m), 7.08(1H, d, J=11.0Hz), 6.81(1H, s), 3.92(1H, m), 2.15–2.06(2H, m), 1.89–172(4H, m), 1.61(1H, m), 1.42–1.09(3H, m).

Example No. 149

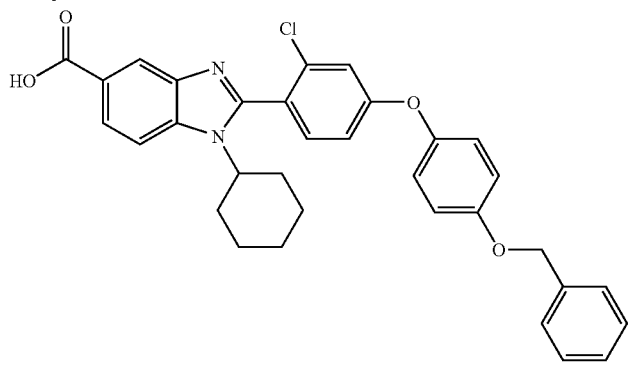

Purity >90%(NMR)
MS 553(M+1)

1H NMR(δ)ppm
300MHz, DMSO-d6
8.24(1H, d, J=1.5Hz), 7.96(1H, d, J=9.0Hz), 7.88(1H, dd, J=9.0, 1.5Hz), 7.58(1H, d, J=8.7Hz), 7.50–7.30(5H, m), 7.22–7.00(6H, m), 5.13(2H, s), 3.98–3.80(1H, s), 2.36–1.10(10H, m)

Example No. 150

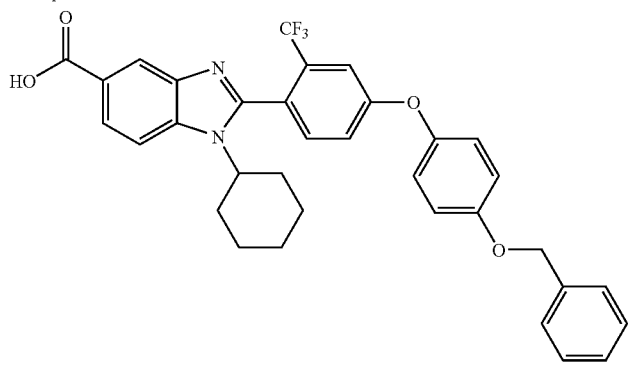

Purity >90%(NMR)
MS 587(M+1)

1H NMR(δ)ppm
300MHz, DMSO-d6
8.23(1H, s), 8.95(1H, d, J=8.4Hz), 7.88(1H, d, J=8.7Hz), 7.66(1H, d, J=8.4Hz), 7.52–7.28(7H, m), 7.23(2H, d, J=9.3Hz), 7.14(2H, d, J=8.7Hz), 5.14(2H, s), 3.90–3.72(1H, m), 2.20–1.10(10H, m)

TABLE 41

Example No. 151

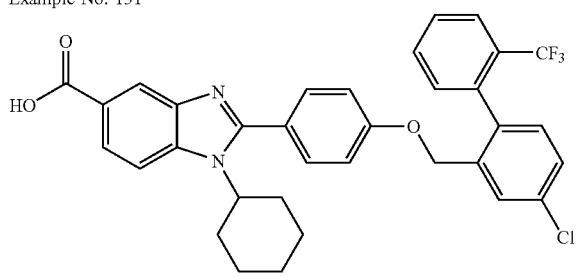

Purity >90%(NMR)
MS 605(M+1)

1H NMR(δ)ppm
300MHz, DMSO-d6
8.18(1H, s), 7.92–7.78(3H, m), 7.78–7.58(3H, m), 7.58–7.44(4H, m), 7.29(1H, d, J=8.2Hz), 7.01(2H, d, J=8.7Hz), 4.88(1H, d, J=11.8Hz), 4.80(1H, d, J=11.8Hz), 4.22(1H, m), 2.37–2.16(2H, m), 1.95–1.75(4H, m), 1.64(1H, m), 1.48–1.14(3H, m).

TABLE 41-continued

Example No. 152

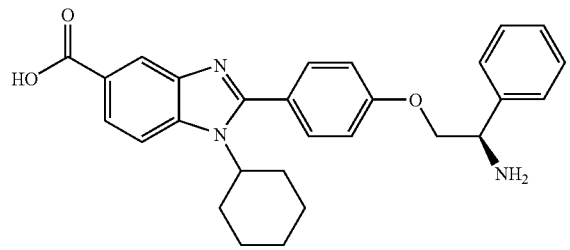

Purity >90%(NMR)

MS 456(M+1)

1H NMR(δ)ppm

300MHz, DMSO-d6
8.21(2H, m), 7.99–7.80(2H, m), 7.63–7.08(9H, m), 4.20–3.98(4H, m), 2.20–2.15(2H, m), 1.95–1.74(4H, m), 1.70–1.54(1H, m), 1.44–1.14(3H, m)

Example No. 153

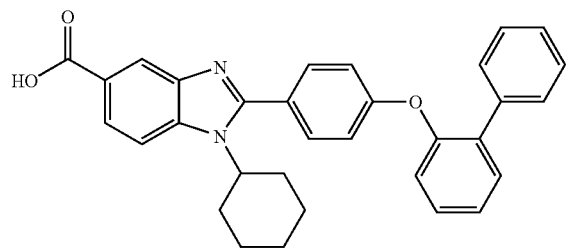

Purity >90%(NMR)

MS 489(M+1)

1H NMR(δ)ppm

300MHz, DMSO-d6
8.20(1H, s), 8.93 and 7.83 (2H, ABq, J=8.7Hz), 7.86–7.21 (11H, m), 7.03(2H, d, J=8.7Hz), 4.20(1H, brt, J=12.2Hz), 2.32–2.13(2H, m), 1.92–1.74(4H, m), 1.69–1.58(1H, m) 1.45–1.15(3H, m)

TABLE 42

Example No. 154

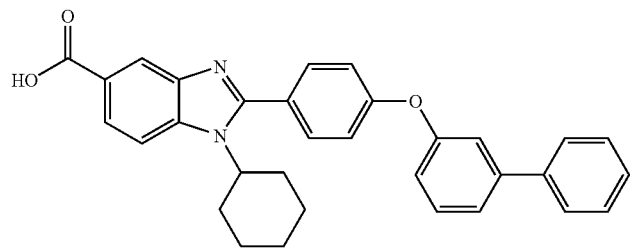

Purity >90%(NMR)

MS 489(M+1)

1H NMR(δ)ppm

300MHz, DMSO-d6
8.23(1H, s), 7.94 and 7.86 (2H, ABq, J=8.6Hz), 7.72–7.16 (13H, m), 5.25(2H, brs), 4.55 (2H, d, J=6.6Hz), 4.31(1H, brt, J=12.2Hz), 2.37–2.18 (2H, m), 1.98–1.77(4H, m), 1.70–1.58(1H, m), 1.48–1.20 (3H, m)

Example No. 155

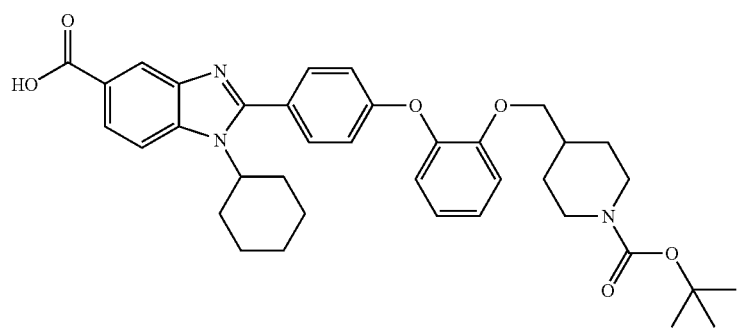

Purity >90%(NMR)

MS 626(M+1)

1H NMR(δ)ppm

300MHz, DMSO-d6
8.21(1H, s), 7.85 and 7.61 (2H, ABq, J=8.7Hz), 7.61 and 6.99(4H, A'B'q, J=8.7Hz), 7.28–7.18(1H, m), 7.25(2H, d, J= 7.5Hz), 7.07–6.99(1Hm), 4.30(1H, brt, J=12.2Hz), 3.83 (2H, d, J=6.0Hz), 3.82–3.72 (1H, m), 2.68–2.49(2H, m), 2.39–2.21(2H, m), 1.95–1.80 (4H, m),1.79–1.60(2H, m), 1.46–1.22(5H, m), 1.30(9H, s), 1.00–0.82(2H, m)

TABLE 42-continued

Example No. 156

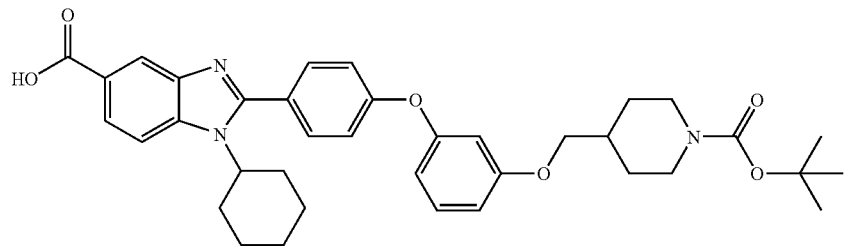

Purity >90%(NMR)
MS 626(M+1)

1H NMR(δ)ppm

300MHz, DMSO-d6
8.22(1H, s), 7.92 and 7.86 (2H, ABq, J=8.7Hz), 7.68 and 7.18(4H, A'B'q, J=8.7Hz), 7.35 (1H, t, J=8.5Hz), 6.80(1H, d, J=8.3Hz), 6.72–6.70(2H, m)4.30(1H, brt, J=12.2Hz), 3.99(2H, brd, J=12.0Hz), 3.85(2H, d, J=6.3Hz), 2.82–2.62(2H, m), 2.38–2.20(2H, m), 1.99–1.59(8H, m), 1.42–1.03(5H, m), 1.39(9H, s)

TABLE 43

Example No. 157

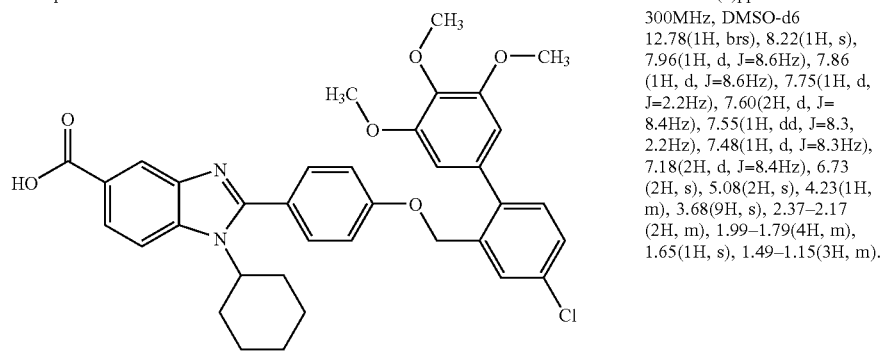

Purity >90%(NMR)
MS 627(M+1)

1H NMR(δ)ppm

300MHz, DMSO-d6
12.78(1H, brs), 8.22(1H, s), 7.96(1H, d, J=8.6Hz), 7.86 (1H, d, J=8.6Hz), 7.75(1H, d, J=2.2Hz), 7.60(2H, d, J=8.4Hz), 7.55(1H, dd, J=8.3, 2.2Hz), 7.48(1H, d, J=8.3Hz), 7.18(2H, d, J=8.4Hz), 6.73 (2H, s), 5.08(2H, s), 4.23(1H, m), 3.68(9H, s), 2.37–2.17 (2H, m), 1.99–1.79(4H, m), 1.65(1H, s), 1.49–1.15(3H, m).

Example No. 158

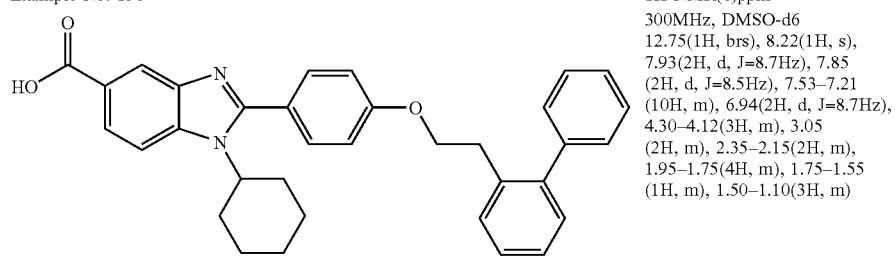

Purity >90%(NMR)
MS 517(M+1)

1H NMR(δ)ppm

300MHz, DMSO-d6
12.75(1H, brs), 8.22(1H, s), 7.93(2H, d, J=8.7Hz), 7.85 (2H, d, J=8.5Hz), 7.53–7.21 (10H, m), 6.94(2H, d, J=8.7Hz), 4.30–4.12(3H, m), 3.05 (2H, m), 2.35–2.15(2H, m), 1.95–1.75(4H, m), 1.75–1.55 (1H, m), 1.50–1.10(3H, m)

Example No. 159

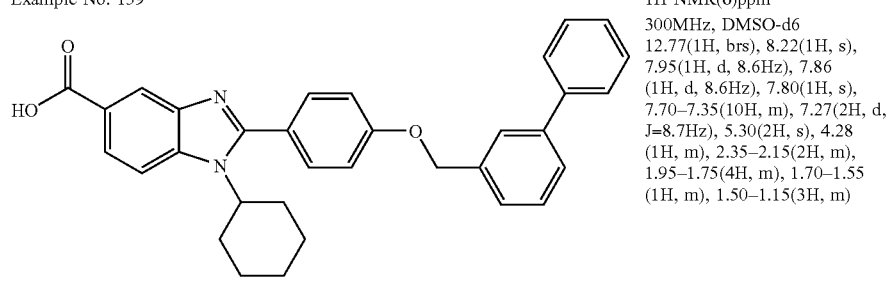

Purity >90%(NMR)
MS 503(M+1)

1H NMR(δ)ppm

300MHz, DMSO-d6
12.77(1H, brs), 8.22(1H, s), 7.95(1H, d, 8.6Hz), 7.86 (1H, d, 8.6Hz), 7.80(1H, s), 7.70–7.35(10H, m), 7.27(2H, d, J=8.7Hz), 5.30(2H, s), 4.28 (1H, m), 2.35–2.15(2H, m), 1.95–1.75(4H, m), 1.70–1.55 (1H, m), 1.50–1.15(3H, m)

TABLE 44

Example No. 160

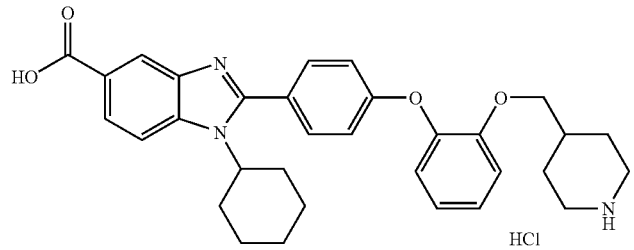

Purity >90%(NMR)
MS 526(M+1)

1H NMR(δ)ppm

300MHz, DMSO-d6
8.90(1H, brs), 8.59(1h, brs), 8.33(1H, s), 8.18 and 8.00 (2H, ABq, J=8.5Hz), 7.73 and 7.10(4H, A'B'q, J=8.5Hz), 7.32–7.05(4H, m), 4.35(1H, brt, J=12.2Hz), 3.86(2H, d, J=6.3Hz), 3.25–3.08(2H, m), 2.85–2.66(2H, m), 2.40–2.28 (2H, m), 2.07–1.14(15H, m)

Example No. 161

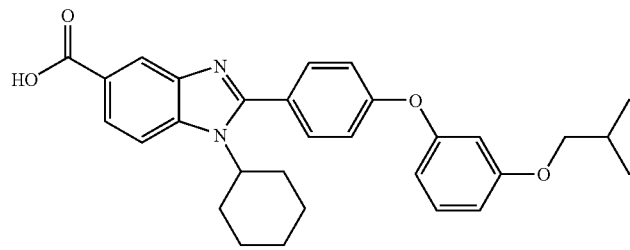

Purity >90%(NMR)
MS 526(M+1)

1H NMR(δ)ppm

300MHz, DMSO-d6
9.05(1H, brs), 8.76(1h, brs), 8.31(1H, s), 8.19 and 8.00 (2H, ABq, J=8.3Hz), 7.79 and 7.25(4H, A'B'q, J=8.3Hz), 7.39(1H, brs), 6.86–6.74(4H, m), 4.37(1H, brt, J=12.2Hz), 3.89(2H, d, J=5.0Hz), 3.35–3.18(2H, m), 2.98–2.75(2H, m), 2.38–2.17(2H, m), 2.16–1.15(15H, m)

Example No. 162

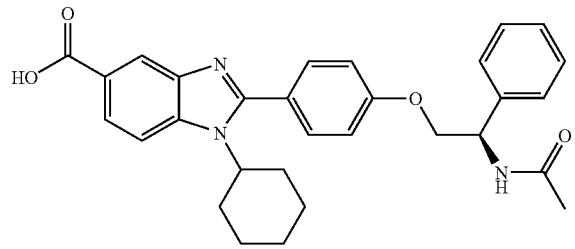

Purity >90%(NMR)
MS 498(M+1)

1H NMR(δ)ppm

300MHz, DMSO-d6
12.87(1H, brs), 8.58(1H, d, J=6.0Hz), 8.23(1H, s), 7.99 and 7.80(2H, ABq, J=8.6Hz), 7.61 and 7.18(4H, A'B'q, J=8.0Hz), 7.45–7.30(5H, m), 5.29(1H, brs), 4.26(1H, brt, J=12.2Hz), 2.37–2.11(2H, m), 2.00–1.71(4H, m), 1.92(3H, s), 1.70–1.52(1H, m), 1.45–1.11(3H, m)

TABLE 45

Example No. 163

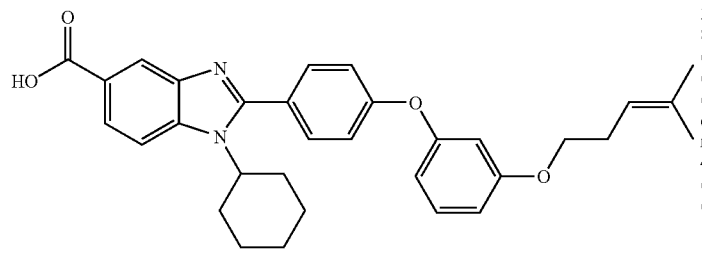

Purity >90%(NMR)
MS 511(M+1)

1H NMR(δ)ppm

300MHz, DMSO-d6
8.23(1H, s), 7.95 and 7.86 (2H, ABq, J=8.6Hz), 7.69 and 7.18 (4H, A'B'q, J=8.6Hz), 7.35 (1H, t, J=8.6Hz), 6.80(1H, d, J=7.5Hz), 6.72–6.69(2H, m), 5.20(1H, t, J=3.7Hz), 4.31(1H, brt, J=12.2Hz), 3.95 (2H, t, J=6.8Hz), 2.49–2.19 (4H, m), 1.97–1.76(4H, m), 1.68(3H, s), 1.67–1.54(1H, m), 1.61(3H, s), 1.45–1.20 (3H, m)

TABLE 45-continued

Example No. 164

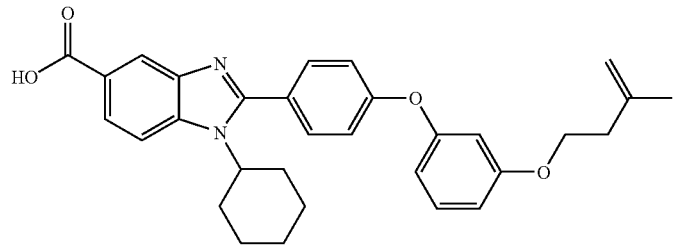

Purity >90%(NMR)
MS 497(M+1)

1H NMR(δ)ppm
300MHz, DMSO-d6
8.20(1H, s), 7.87(2H, s),
7.68 and 7.18(4H, ABq, J=8.7Hz),
7.35(1H, t, J=7.9Hz), 6.81
(1H, d, J=9.4Hz), 6.72(1Hs),
6.71(1H, d, J=6.8Hz), 4.80
(2H, s), 4.29(1H, brt, J=
12.2Hz), 4.10(1H, t, J=6.7Hz),
2.43(1H, t, J=6.7Hz), 2.39–
2.19(2H, m), 1.97–1.78(4H,
m), 1.76(3H, s), 1.70–1.56
(1H, m), 1.43–1.19(3H, m)

Example No. 165

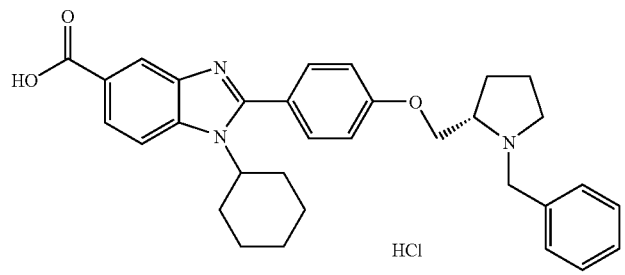

Purity >90%(NMR)
MS

1H NMR(δ)ppm
300MHz, DMSO-d6
11.21(1H, brs), 8.33(1H, s),
8.25(1H, d, J=8.6Hz), 8.04
(1H, d, J=8.6Hz), 7.78(2H, d,
J=8.7Hz), 7.70–7.67(2H, m),
7.55–7.42(3H, m), 7.27
(2H, d, J=8.7Hz), 4.73–4.30
(5H, m), 4.20–3.97(1H, m),
3.42–3.10(2H, m), 2.45–1.23
(14H, m)

TABLE 46

Example No. 166

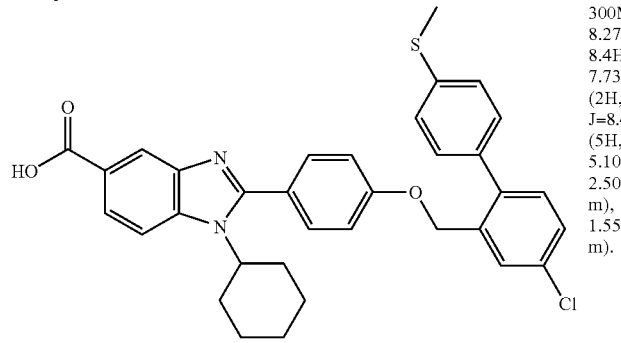

Purity >90%(NMR)
MS 583(M+1)

1H NMR(δ)ppm
300MHz, DMSO-d6
8.27(1H, s), 8.13(1H, d, J=
8.4Hz), 7.97(1H, d, J=9.0Hz),
7.73(1H, d, J=1.8Hz), 7.68
(2H, d, J=8.4Hz), 7.54(1H, dd,
J=8.4, 2.1Hz), 7.41–7.31
(5H, m), 7.19(2H, d, J=8.4Hz),
5.10(2H, s), 4.32(1H, m),
2.50(3H, s), 2.40–2.15(2H,
m), 2.10–1.75(4H, m), 1.75–
1.55(1H, m), 1.55–1.10(3H,
m).

Example No. 167

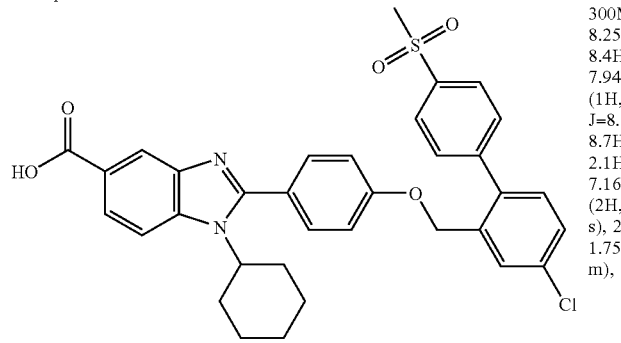

Purity >90%(NMR)
MS 615(M+1)

1H NMR(δ)ppm
300MHz, DMSO-d6
8.25(1H, s), 8.09(1H, d, J=
8.4Hz), 8.00(2H, d, J=8.4Hz),
7.94(1H, d, J=8.7Hz), 7.80
(1H, d, J=2.1Hz), 7.73(2H, d,
J=8.1Hz), 7.65(2H, d, J=
8.7Hz), 7.60(1H, dd, J=8.1,
2.1Hz), 7.44(1H, d, J=8.1Hz),
7.16(2H, d, J=8.7Hz), 5.13
(2H, s), 4.30(1H, m), 3.26(3H,
s), 2.40–1.15(2H, m), 2.05–
1.75(4H, m), 1.75–1.55(1H,
m), 1.55–1.15(3H, m).

TABLE 46-continued

Example No. 168

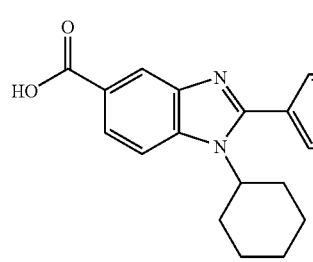

Purity >90%(NMR)

MS 543(M+1)

1H NMR(δ)ppm
300MHz, DMSO-d6
13.1(1H, brs), 8.32(1H, s),
8.28(1H, d, J=8.8Hz), 8.05
(1H, d, J=8.7Hz), 7.80–7.75
(3H, m), 7.69(1H, d, J=4.1Hz),
7.57(2H, m), 7.34–7.29(3H,
m), 7.20–7.15(1H, m), 5.24
(2H, s), 4.39(1H, m), 2.45–
2.20(2H, m), 2.20–1.95(2H, m),
1.95–1.75(2H, m), 1.75–
1.55(1H, m), 1.55–1.15(3H, m).

TABLE 47

Example No. 169

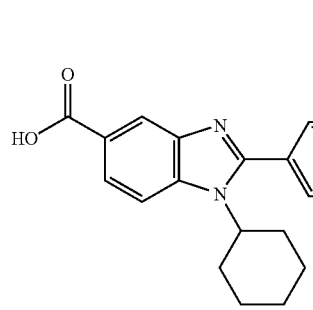

Purity >90%(NMR)
MS 571(M+1)

1H NMR(δ)ppm
300MHz, DMSO-d6
8.31(1H, s), 8.26(1H, d, J=
8.7Hz), 8.05(1H, d, J=8.7Hz),
7.78–7.71(3H, m), 7.59–
7.41(6H, m), 7.23(2H, d, J=9.0Hz),
5.11(2H, s), 4.35(1H, m),
2.40–2.15(2H, m), 2.15–
1.95(2H, m), 1.95–1.75(2H, m),
1.75–1.55(1H, m), 1.55–
1.15(3H, m).

Example No. 170

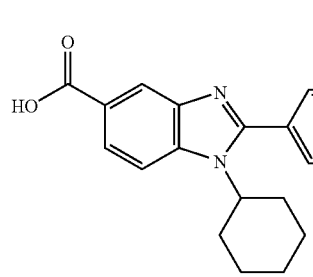

Purity >90%(NMR)
MS 538(M+1)

1H NMR(δ)ppm
300MHz, DMSO-d6
12.7(1H, brs), 8.66(1H, s),
8.61(1H, m), 8.21(1H, s),
7.92–7.79(4H, m), 7.61–7.56
(3H, m), 7.50–7.43(2H, m),
7.10(2H, d, J=8.7Hz), 5.09(2H,
s), 4.26(1H, m), 2.40–2.15
(2H, m), 2.00–1.75(4H, m),
1.75–1.55(1H, m), 1.50–1.15
(3H, m).

Example No. 171

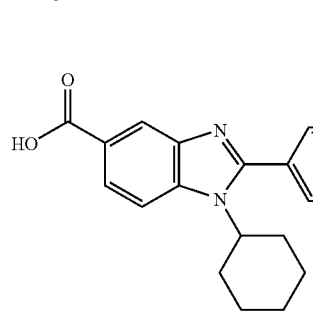

Purity >90%(NMR)
MS 555(M+1)

1H NMR(δ)ppm
300MHz, DMSO-d6
8.31(1H, s), 8.25(1H, d, J=
8.7Hz), 8.04(1H, d, J=8.7Hz),
7.74–7.71(3H, m), 7.57–
7.46(3H, m), 7.39(1H, d, J=8.1Hz),
7.31–7.21(4H, m), 5.11
(2H, s), 4.35(1H, m), 2.40–
2.15(2H, m), 2.15–1.95(2H, m),
1.95–1.75(2H, m), 1.75–
1.55(1H, m), 1.55–1.15(3H, m).

TABLE 48

Example No. 172

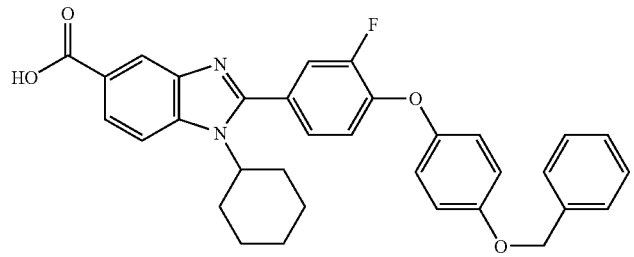

Purity >90%(NMR)
MS 537(M+1)

1H NMR(δ)ppm
300MHz, DMSO-d6
8.24(1H, s), 7.99(1H, d, J=8.7Hz), 7.88(1H, d, J=10.5Hz), 7.70(1H, dd, J=11.4, 1.8Hz), 7.48–7.32(6H, m), 7.17–7.09(5H, m), 5.12(2H, s), 4.30(1H, m), 2.40–2.15(2H, m), 2.05–1.75(4H, m), 1.75–1.55(1H, m), 1.55–1.20(3H, m).

Example No. 173

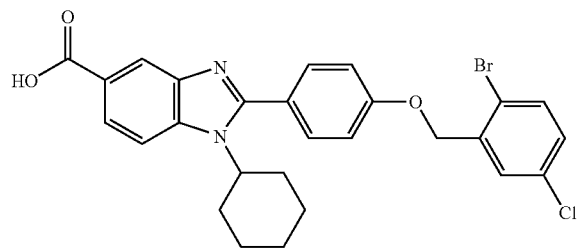

Purity >90%(NMR)
MS 540(M+1)

1H NMR(δ)ppm
300MHz, DMSO-d6
8.33(1H, s), 8.29(1H, d, J=8.7Hz), 8.06(1H, d, J=8.7Hz), 7.82–7.74(4H, m), 7.45(1H, dd, J=8.4, 3.0Hz), 7.39(2H, d, J=8.7Hz), 5.28(2H, s), 4.40(1H, m), 2.40–2.15(2H, m), 2.15–1.95(2H, m), 1.95–1.75(2H, m), 1.75–1.55(1H, m), 1.55–1.15(3H, m).

Example No. 174

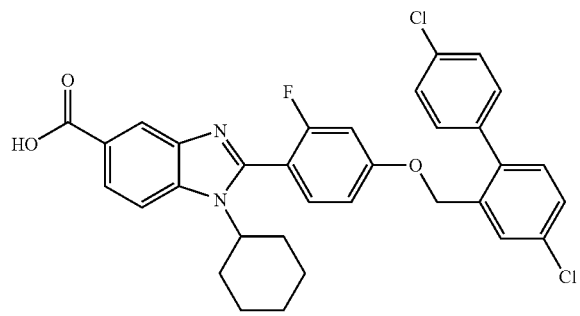

Purity >90%(NMR)
MS 590(M+1)

1H NMR(δ)ppm
300MHz, DMSO-d6
12.80(1H, brs), 8.26(1H, s), 8.01(1H, d, J=8.7Hz), 7.85(1H, d, J=8.7Hz), 7.80–7.70(1H, m), 7.60–7.36(7H, m), 7.18–6.91(2H, m), 5.09(2H, s), 4.11–3.90(1H, m), 2.32–1.18(14H, m)

TABLE 49

Example No. 175

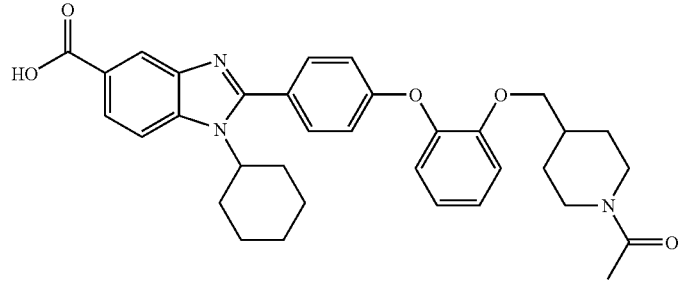

Purity >90%(NMR)
MS 568(M+1)

1H NMR(δ)ppm
300MHz, DMSO-d6
12.75(1H, s), 8.21(1H, s), 7.94 and 7.85(2H, ABq, J=8.7Hz), 7.61 and 7.00(4H, A'B'q, J=8.5Hz), 7.31–6.91(2H, m), 7.25(2H, d, J=7.7Hz), 5.41(2H, brs), 4.54(2H, d, J=6.6Hz), 4.35–4.14(2H, m), 2.49–2.15(3H, m), 1.95–1.55(5H, m), 1.50–1.13(5H, m), 1.10–0.77(2H, m)

TABLE 49-continued

Example No. 176

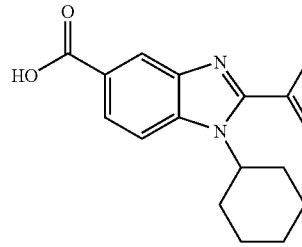

Purity >90%(NMR)
MS 568(M+1)

1H NMR(δ)ppm

300MHz, DMSO-d6
8.24(1H, s), 7.97 and 7.87
(2H, ABq, J=8.6Hz), 7.69 and
7.19(4H, A'B'q, J=8,6Hz), 7.35
(1H, t, J=8.1Hz), 6.81(1H,
d, J=9.2Hz), 6.72(1H, s),
6.71(1H, d, J=6.5Hz), 4.48–
4.20(2H, m), 3.95–3.75(3H, m),
3.03(1H, t, J=12.3Hz), 2.60–
2.40(1H, m), 2.39–2.15
(2H, m), 2.07–1.58(6H, m), 1.99
(3H, s), 1.50–1.00(5H, m)

Example No. 177

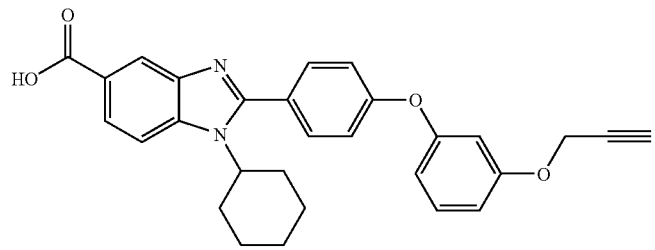

Purity >90%(NMR)
MS 467(M+1)

1H NMR(δ)ppm

300MHz, DMSO-d6
12.76(1H, s), 8.23(1H, s),
7.96 and 7.86(2H, ABq, J=8.6Hz),
7.69 and 7.20(4H, A'B'q,
J=8.6Hz), 7.39(1H, t, J=8.2Hz),
6.86(1H, d, J=8.3Hz),
6.81(1H, s), 6.76(1h, d, J=8.0Hz),
4.83(2H, s), 4.31(1H,
brt, J=12.2Hz), 2.39–2.19
(2H, m), 1.99–1.79(4H, m),
1.70–1.58(1H, m), 1.48–1.20
(3H, m)

TABLE 50

Example No. 178

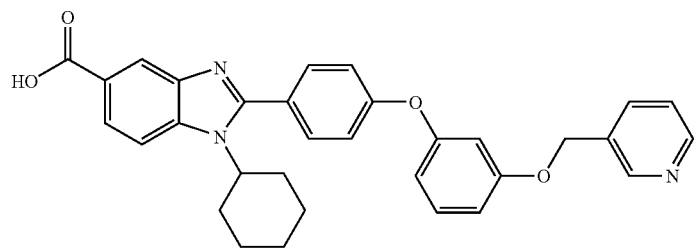

Purity >90%(NMR)
MS 520(M+1)

1H NMR(δ)ppm

300MHz, DMSO-d6 12.85(1H, s), 8.75(1H, s), 8.63(2H, d,
J=3.8Hz), 8.25(1H, s), 8.04–8.01(2H, m), 8.02 and 7.90(2H,
ABq, J=8.6Hz), 7.72 and 7.20(4H, A'B'q, J=8.6Hz), 7.57(2H,
dd, J=7.8, 5.0Hz), 7.40(1H, t, J=8.2Hz), 6.93(1H, d, J=
8.2Hz), 6.87(1H, s), 6.77(1H, d, J=8.2Hz), 5.23(2H, s),
4.33(1H, brt, J=12.2Hz), 2.40–2.18(2H, m), 2.00–1.55(5H,
m), 1.50–1.15(3H, m)

Example No. 179

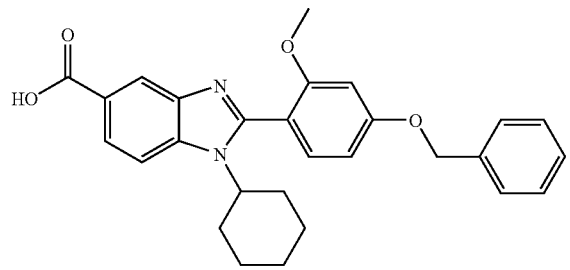

Purity >90%(NMR)
MS 457(M+1)

1H NMR(δ)ppm

300MHz, DMSO-d6 8.32(1H, s), 8.29(1H, d, J=9.0Hz),
8.06(1H, d, J=8.7Hz), 7.61(1H, d, J=8.4Hz), 7.58–7.32(5H,
m), 6.98(1H, d, J=2.1Hz), 6.93(1H, dd, J=8.7, 2.1Hz),
5.27(2H, s), 4.16–4.00(1H, m), 3.87(3H, s), 2.20–2.12(2H,
m), 2.02–1.98(4H, m), 1.70–1.60(1H, m), 1.52–1.10(3H, m)

TABLE 50-continued

| Example No. 180 | 1H NMR(δ)ppm |
|---|---|
| 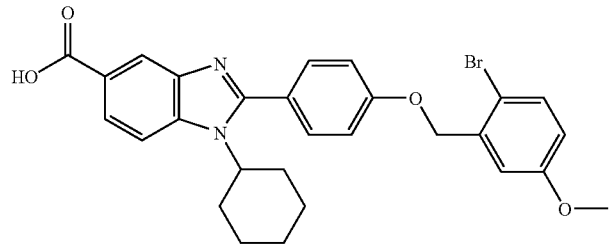<br>Purity >90%(NMR)<br>MS 536(M+1) | 300MHz, DMSO-d6 8.21(1H, s), 7.91(1H, d, J=8.6Hz), 7.85(1H, d, J=8.6Hz), 7.63(2H, d, J=8.4Hz), 7.60(1H, d, J=9.0Hz), 7.25(2H, d, J=8.4Hz), 7.23(1H, d, J=3.0Hz), 6.95(1H, dd, J=9.0, 3.0Hz), 5.19(2H, s), 4.30(1H, m), 3.78(3H, s), 2.40–2.19(2H, m), 2.00–1.87(4H, m), 1.66(1H, m), 1.49–1.18(3H, m). |

TABLE 51

| Example No. 181 | 1H NMR(δ)ppm |
|---|---|
| 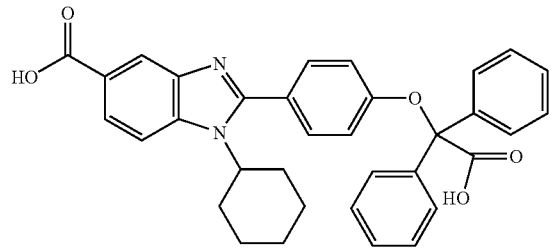<br>Purity >90%(NMR)<br>MS 547(M+1) | 300MHz, DMSO-d6 8.19(1H, s), 7.95(1H, d, J=8.7Hz), 7.86(1H, d, J=8.7Hz), 7.65(4H, d, J=7.4Hz), 7.47(2H, d, J=8.7Hz), 7.44–7.27(6H, m), 6.99(2H, d, J=8.7Hz), 4.20(1H, m), 2.34–2.12(2H, m), 1.98–1.75(4H, m), 1.64(1H, m), 1.46–1.13(3H, m). |
| Example No. 182 | 1H NMR(δ)ppm |
| 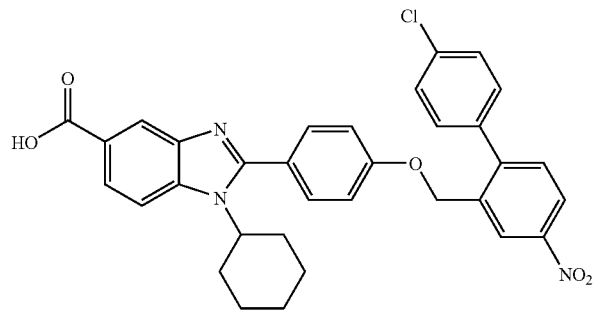<br>Purity >90%(NMR)<br>MS 582 (M+) | 300MHz, DMSO-d6 8.55(1H, d, J=2.1Hz), 8.32(1H, m), 8.21(1H, s), 7.95(1H, d, J=8.4Hz), 7.86(1H, d, J=7.8Hz), 7.68–7.56(7H, m), 7.14(2H, d, J=8.7Hz), 5.21(1H, s), 4.26(1H, m), 2.35–2.15(2H, m), 2.00–1.75(4H, m), 1.74–1.55(1H, m), 1.50–1.15(3H, m) |
| Example No. 183 | 1H NMR(δ)ppm |
| 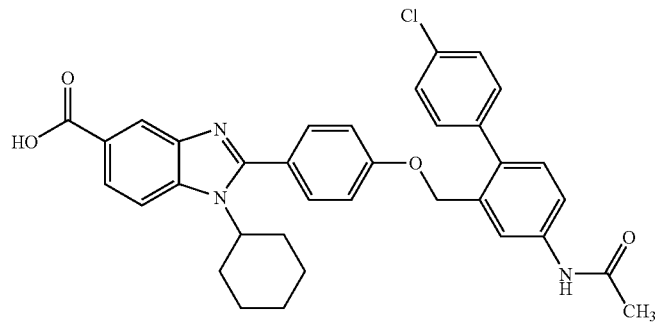<br>Purity >90%(NMR)<br>MS 594 (M+) | 300MHz, DMSO-d6 10.16(1H, s), 8.25(1H, s), 8.07(1H, d, J=8.7Hz), 7.94–7.87(2H, m), 7.71–7.62(3H, m), 7.50–7.42(4H, m), 7.30(1H, d, J=8.4Hz), 7.14(2H, d, J=8.4Hz), 5.06(2H, s), 4.31(1H, m), 2.35–2.15(2H, m), 2.05–1.75(4H, m), 1.75–1.55(1H, m), 1.50–1.15(3H, m) |

TABLE 52

Example No. 184

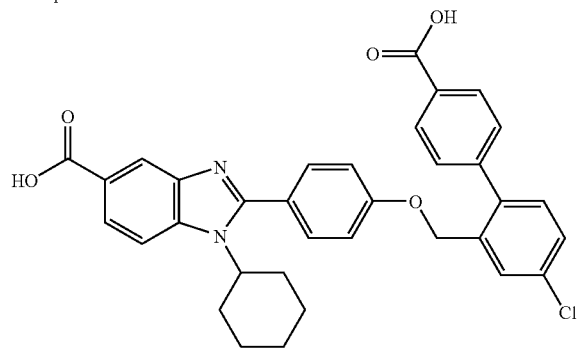

Purity >90%(NMR)
MS 581(M+1)

1H NMR(δ)ppm
300MHz, DMSO-d6 13.2(2H, brs), 8.30(1H, s), 8.26(LH, d, J=8.8Hz), 8.04(1H, d, J=8.8Hz), 8.00(2H, d, J=8.2Hz), 7.79(1H, s), 7.73(2H, d, J=8.7Hz), 7.61–7.56(3H, m), 7.44(1H, d, J=8.3Hz), 7.23(2H, d, J=8.8Hz), 5.13(2H, s), 4.35(1H, m), 2.45–2.15(2H, m), 2.15–1.95(2H, m), 1.95–1.75(1H, m), 1.75–1.15(3H, m).

Example No. 185

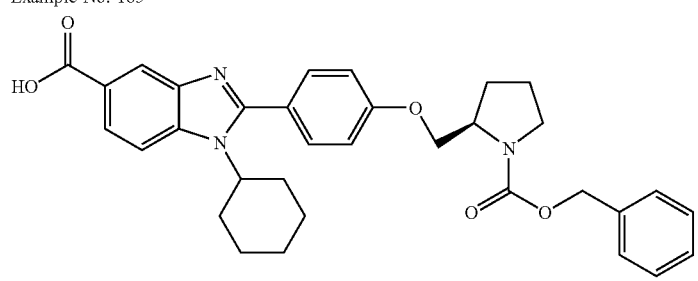

Purity >90%(NMR)
MS 554(M+1)

1H NMR(δ)ppm
300MHz, DMSO-d6 8.30(1H, m), 8.24(1H, d, J=9.0Hz), 8.03(1H, d, J=9.0Hz), 7.79–7.10(9H, m), 5.20–5.07(2H, m), 4.43–4.04(4H, m), 3.50–3.36(2H, m), 2.40–1.19(14H, m)

Example No. 186

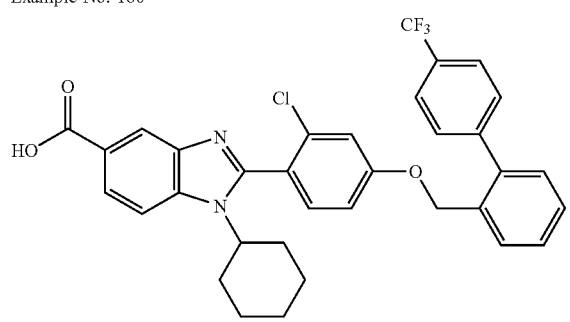

Purity >90%(NMR)
MS 605(M+1)

1H NMR(δ)ppm
(DMSO-d6) δ:8.29(1H, brs), 8.10(1H, d, J=8.4Hz), 7.97(1H, d, J=8.4Hz), 7.79(2H, d, J=8.4Hz), 7.74–7.67(1H, m), 7.68(2H, d, J=8.4Hz), 7.61(1H, d, J=8.4Hz), 7.57–7.50(2H, m), 7.46–7.39(1H, m), 7.29(1H, d, J=2.4Hz), 7.11(1H, dd, J=2.4, 8.4Hz), 5.12(2H, s), 3.99–3.84(1H, m), 2.35–1.72(6H, m), 1.68–1.55(1H, m), 1.42–1.10(3H, m)

TABLE 53

Example No. 187

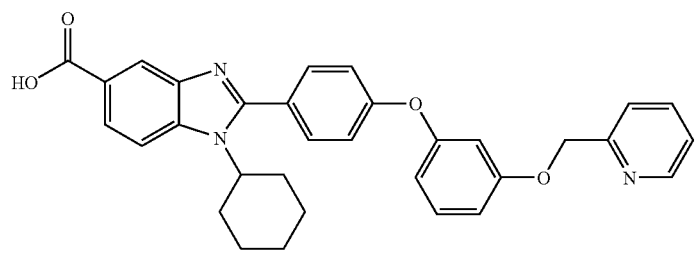

Purity >90%(NMR)
MS 520(M+1)

1H NMR(δ)ppm

300MHz, DMSO-d6 12.76(1H, s), 8.57(1H, d, J=4.4Hz), 8.23(1H, s), 7.96 and 7.86(2H, ABq, J=8.2Hz), 7.87–7.82(1H, m), 7.68 and 7.12(4H, A'B'q, J=8.6Hz), 7.53(2H, d, J=7.8Hz), 7.37(1H, t, J=8.3Hz), 7.36–7.33(1H, m), 6.90(1H, d, J=8.3Hz), 6.83(1H, s), 6.74(1H, d, J=8.0Hz), 5.20(2H, s), 4.31(1H, brt, J=12.2Hz), 2.35–2.19(2H, m), 1.99–1.57(5H, m), 1.45–1.20(3H, m)

TABLE 53-continued

Example No. 188

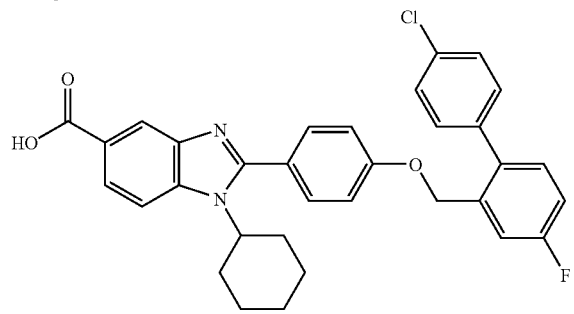

Purity >90%(NMR)
MS 555(M+1)

1H NMR(δ)ppm
300MHz, DMSO-d6 12.77(1H, brs), 8.21(1H, d, J=1, 4Hz), 7.92(1H, d, J=8.7Hz), 7.88(1H, dd, J=8.7, 1.4Hz), 7.57(2H, d, J=8.7Hz), 7.57–7.27(7H, m), 7.11(2H, d, J=8.7Hz), 5.07(2H, s), 4.26(1H, m), 2.36–2.16(2H, m), 1.98–1.75(4H, m), 1.64(1H, m), 1.49–1.17(3H, m).

Example No. 189

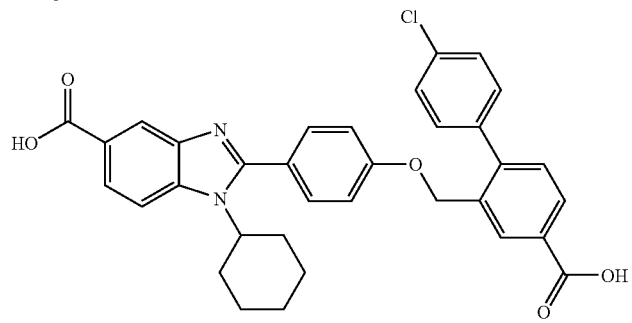

Purity >90%(NMR)
MS 581(M+1)

1H NMR(δ)ppm
300MHz, DMSO-d6 8.32(1H, s), 8.30–8.20(2H, m), 8.10–7.98(2H, m), 7.74(2H, d, J=9.0Hz), 7.60–7.46(5H, m), 7.24(2H, d, J=9.0Hz), 5.19(2H, s), 4.44–4.30(1H, m), 2.40–2.20(2H, m), 2.12–1.78(4H, m), 1.72–1.58(4H, m)

TABLE 54

Example No. 190

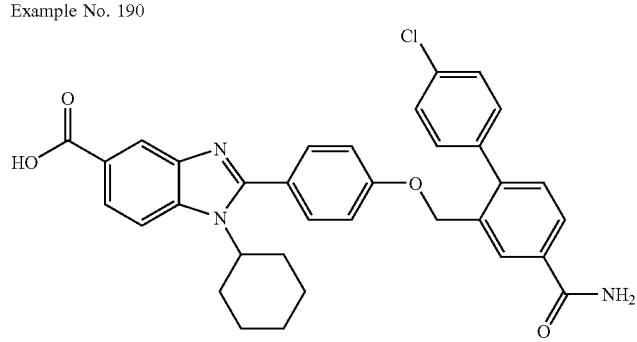

Purity >90%(NMR)
MS 580(M+1)

1H NMR(δ)ppm
300MHz, DMSO-d6 8.36–7.90(5H, m), 7.74(2H, d, J=8.6Hz), 7.60–7.40(5H, m), 7.25(2H, d, J=8.7Hz), 5.14(2H, s), 4.45–4.28(1H, m), 2.40–2.15(4H, m), 1.75–1.55(1H, m), 1.55–1.20(3H, m)

Example No. 191

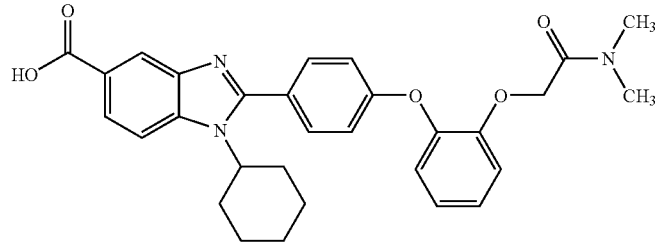

Purity >90%(NMR)
MS 514(M+1)

1H NMR(δ)ppm
300MHz, DMSO-d6 8.22(1H, s), 7.94(1H, d, J=8.4Hz), 7.85(1H, d, J=8.7Hz), 7.61(2H, d, J=8.7Hz), 7.25–7.00(6H, m), 4.86(2H, s), 4.30(1H, m), 2.89(3H, s), 2.80(3H, s), 2.29(2H, m), 2.00–1.75(4H, m), 1.70–1.55(1H, m), 1.50–1.15(3H, m)

| TABLE 54-continued | |
|---|---|
| Example No. 192 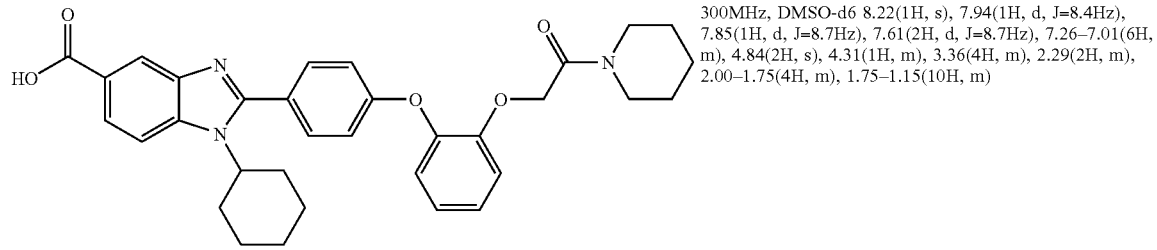 Purity >90%(NMR) MS 554(M+1) | 1H NMR(δ)ppm 300MHz, DMSO-d6 8.22(1H, s), 7.94(1H, d, J=8.4Hz), 7.85(1H, d, J=8.7Hz), 7.61(2H, d, J=8.7Hz), 7.26–7.01(6H, m), 4.84(2H, s), 4.31(1H, m), 3.36(4H, m), 2.29(2H, m), 2.00–1.75(4H, m), 1.75–1.15(10H, m) |

| TABLE 55 | |
|---|---|
| Example No. 193 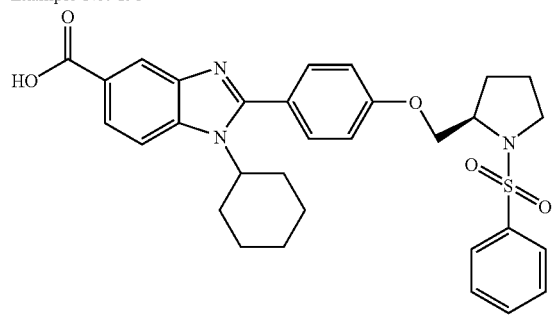 Purity >90%(NMR) MS 560 (M+1) | 1H NMR(δ)ppm 300MHz, DMSO-d6 13.00(1H, brs), 8.29(1H, d, J=1.4Hz), 8.15(1H, d, J=8.8Hz), 7.97(1H, dd, J=1.4Hz, 8.8Hz), 7.89(2H, d, J=8.8Hz), 7.80–7.60(5H, m) 7.25(2H, d, J=8.8Hz), 4.47–3.90(4H, m), 3.20–3.10(2H, m), 2.41–1.22(14H, m) |
| Example No. 194 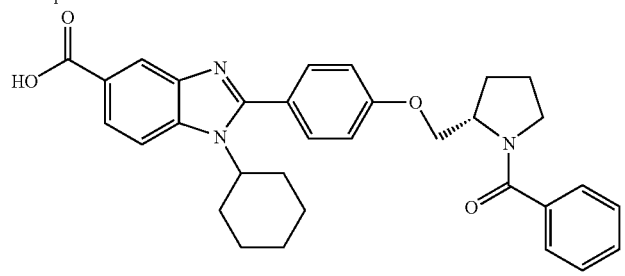 Purity >90%(NMR) MS 524 (M+1) | 1H NMR(δ)ppm 300MHz, DMSO-d6 12.80(1H, brs), 8.23(1H, s), 7.97(1H, d, J=8.5Hz), 7.87(1H, d, J=8.5Hz), 7.70–7.17(9H, m), 4.60–4.13(4H, m), 3.72–3.40(2H, m), 2.40–1.15(14H, m) |
| Example No. 195 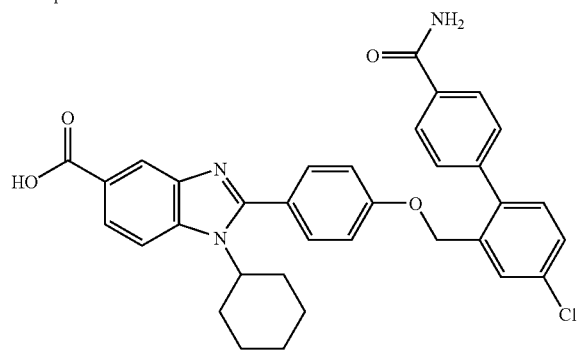 Purity >90%(NMR) MS 580 (M+1) | 1H NMR(δ)ppm 300MHz, DMSO-d6 8.25(1H, s), 8.09–7.92(5H, m), 7.77(1H, s), 7.65(2H, d, J=8.4Hz), 7.59–7.51(3H, m), 7.43(2H, d, J=8.4Hz), 7.17(2H, d, J=8.7Hz), 5.10(2H, s), 4.30(1H, m), 2.40–2.15(2H, m), 2.10–1.75(4H, m), 1.75–1.55(1H, m), 1.55–1.10(3H, m). |

TABLE 56

Example No. 196

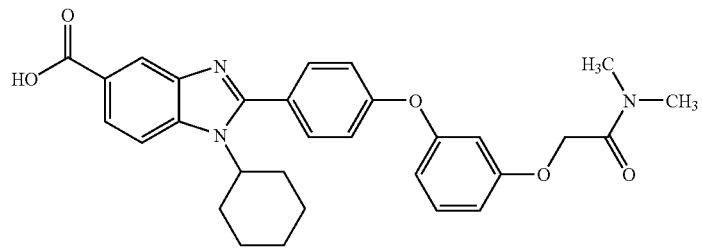

Purity >90%(NMR)
MS 514 (M+1)

1H NMR(δ)ppm

300MHz, DMSO-d6 8.22(1H, s), 7.95(1H, d, J=8.4Hz), 7.86(1H, d, J=8.4Hz), 7.69 and 7.18(4H, ABq, J=8.7Hz), 7.34(1H, t, J=8.0Hz), 6.80–6.69(3H, m), 4.83(2H, s), 4.31(1H, m), 2.98(3H, s), 2.84(3H, s), 2.29(2H, m), 2.00–1.75(4H, m), 1.70–1.55(1H, m), 1.50–1.15(3H, m)

Example No. 197

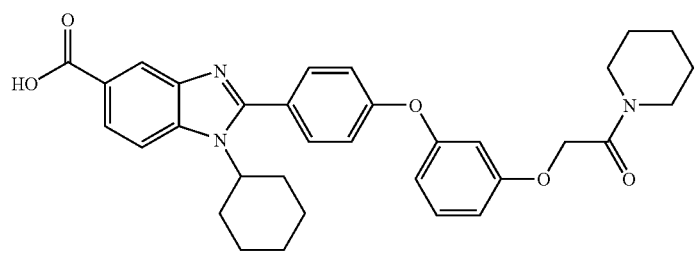

Purity >90%(NMR)
MS 554 (M+1)

1H NMR(δ)ppm

300MHz, DMSO-d6 8.23(1H, s), 7.95(1H, d, J=8.4Hz), 7.86(1H, d, J=8.7Hz), 7.69 and 7.18(4H, ABq, J=8.7Hz), 7.35(1H, t, J=8.4Hz), 6.80–6.70(3H, m), 4.82(2H, s), 4.31(1H, m), 3.40(4H, m), 2.29(2H, m), 2.00–1.75(4H, m), 1.70–1.15(10H, m)

Example No. 198

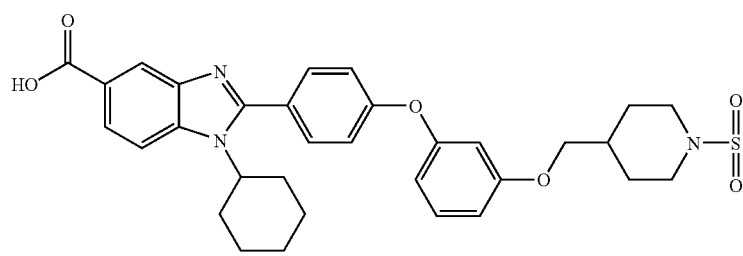

Purity >90%(NMR)
MS 604 (M+1)

1H NMR(δ)ppm

300MHz, DMSO-d6 12.75(1H, s), 8.23(1H, d, J=4.4Hz), 7.95 and 7.86(2H, ABq, J=8.6Hz), 7.69 and 7.19(4H, A'B'q, J=8.6Hz), 7.36(1H, t, J=7.8Hz) , 6.82(1H, d, J=9.3Hz), 6.73(1H, s), 6.71(1H, d, J=7.2Hz), 4.30(1H, brt, J=12.2Hz), 3.89(2H, d, J=6.0Hz), 3.59(2H, d, J=11.7Hz), 2.85(3H, s) 2.73(2H, t, J=10.5Hz), 2.41–2.20(2H, m),1.98–1.59(8H, m), 1.46–1.18(5H, m)

TABLE 57

Example No. 199

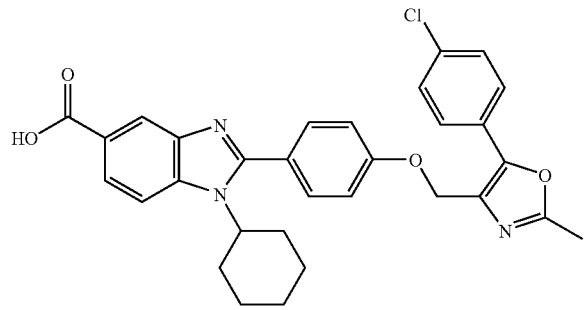

Purity >90%(NMR)
MS 542 (M+1)

1H NMR(δ)ppm

300MHz, DMSO-d6 8.33(1H, s), 8.30(1H, d, J=8.9Hz), 8.06(1H, d, J=8.7Hz), 7.79(2H, d, J=8.7Hz), 7.70(2H, d, J=8.7Hz), 7.61(2H, d, J=8.7Hz), 7.39(2H, d, J=8.8Hz), 5.28(2H, s), 4.39(1H, m), 2.50–2.15(2H, m), 2.15–1.95(2H, m), 1.95–1.75(2H, m), 1.75–1.55(1H, m), 1.55–1.15(3H, m).

TABLE 57-continued

Example No. 200

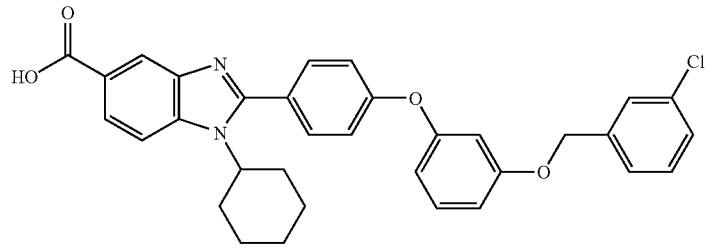

Purity >90%(NMR)
MS 553 (M+1)

1H NMR(δ)ppm (DMSO-d6) δ:8.23(1H, s), 7.96(1H, d, J=8.6Hz), 7.86(1H, d, J=8.6Hz), 7.69(2H, d, J=8.4Hz), 7.52(1H, s), 7.50–7.30(4H, m), 7.18(2H, d, J=8.4Hz), 6.90(1H, d, J=8.3Hz), 6.84(1H, s), 6.74(1H, d, J=8.3Hz), 5.15(2H, s), 4.39–4.21(1H, m), 2.39–2.18(2H, m), 1.99–1.80(4H, m), 1.71–1.59(1H, m), 1.50–1.20(3H, m)

Example No. 201

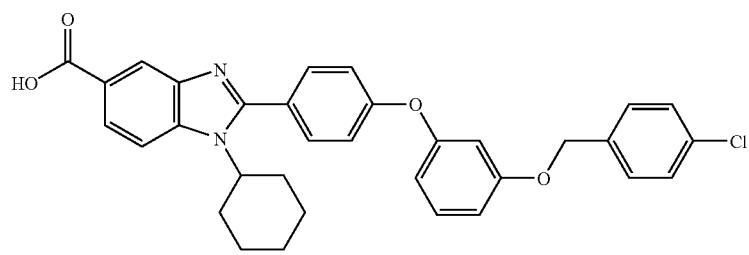

Purity >90%(NMR)
MS 553 (M+1)

1H NMR(δ)ppm (DMSO-d6) δ:8.26(1H, s), 8.06(1H, d, J=8.7Hz), 7.92(1H, d, J=8.7Hz), 7.72(2H, d, J=8.7Hz), 7.47(4H, s), 7.38(1H, t, J=8.2Hz), 7.20(2H, d, J=8.7Hz), 6.90(1H, d, J=8.2Hz), 6.83(1H, s), 6.74(1H, d, J=8.2Hz), 5.14(2H, s), 2.40–2.19(2H, m), 2.04–1.78(4H, m), 1.71–1.60(1H, m), 1.50–1.21(3H, m)

TABLE 58

Example No. 202

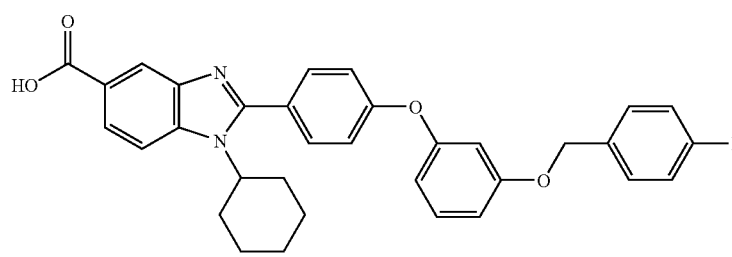

Purity >90%(NMR)
MS 537 (M+1)

1H NMR(δ)ppm (DMSO-d6) δ:12.81(1H, brs), 8.24(1H, s), 7.99(1H, d, J=8.7Hz), 7.87(1H, d, J=8.7Hz), 7.69(2H, d, J=8.6Hz), 7.53–7.47(2H, m), 7.38(1H, t, J=8.2Hz), 7.26–7.16(4H, m), 6.89(1H, d, J=8.2Hz), 6.82(1H, s), 6.73(1H, d, J=8.2Hz), 5.11(2H, s), 4.40–4.21(1H, m), 2.40–2.17(2H, m), 2.01–1.77(4H, m), 1.71–1.59(1H, m), 1.50–1.20(3H, m)

Example No. 203

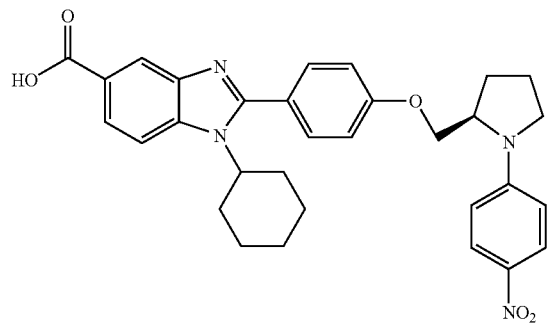

Purity >90%(NMR)
MS 541 (M+1)

1H NMR(δ)ppm

300MHz, DMSO-d6 12.74(1H, brs), 8.21(1H, s), 8.08(2H, d, J=9.0Hz), 7.93(1H, d, J=8.7Hz), 7.85(2h, d, J=8.7Hz), 7.58(2H, d, J=8.7Hz), 7.13(2H, d, J=8.7Hz), 6.83(2H, d, J=9.0Hz), 4.50–4.08(4H, m), 3.68–3.30(2H, m), 2.40–1.23(14H, m)

TABLE 58-continued
| Example No. 204 | 1H NMR(δ)ppm |
|---|---|
| 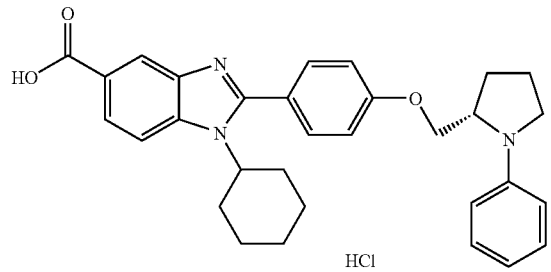 | 300MHz, DMSO-d6 8.39–8.28(2H, m), 8.08(1H, d, J=8.8Hz), 7.76(2H, d, J=8.7Hz), 7.29(2H, d, J=8.7Hz), 7.25–7.13(2H, m), 6.80–6.60(3H, m), 4.46–3.98(4H, m), 3.51–3.42(1H, m), 3.20–3.04(1H, m), 2.39–1.20(14H, m) |
Purity >90%(NMR)
MS
TABLE 59
| Example No. 205 | 1H NMR(δ)ppm |
|---|---|
| 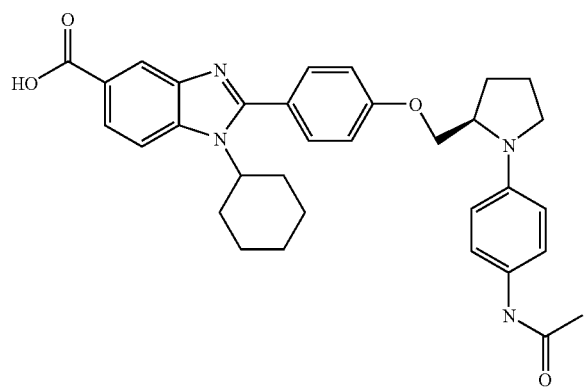 | 300MHz, DMSO-d6 9.59(1H, brs), 8.23(1H, s), 8.04(1H, d, J=8.4Hz), 7.90(1H, d, J=8.4Hz), 7.62(2H, d, J=8.7Hz), 7.39(2H, 2H, d, J=8.7Hz) 7.18(2H, d, J=8.7Hz), 6.63(2H, d, J=8.7Hz), 3.95–3.37(4H, m), 3.51–3.40(1H, m), 3.17–3.02(1H, m), 2.39–1.18(17H, m) |
Purity >90%(NMR)
MS 553 (M+1)
| Example No. 206 | 1H NMR(δ)ppm |
|---|---|
| 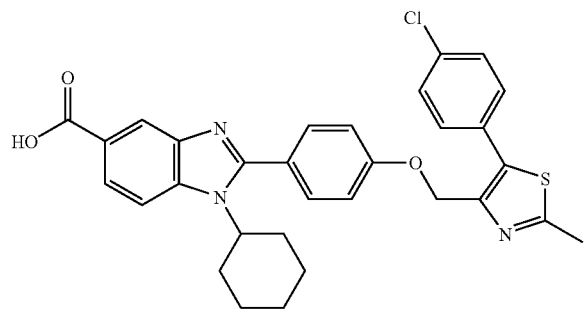 | 300MHz, DMSO-d6 13.1(1H, brs), 8.33(1H, s), 8.29(1H, d, J=8.8Hz), 8.06(1H, d, J=8.7Hz), 7.77(2H, d, J=8.7Hz), 7.59–7.52(4H, m), 7.35(2H, d, J=8.8Hz), 5.19(2H, s), 4.39(1H, m), 2.71(3H, s), 2.45–2.20(2H, m), 2.20–1.95(2H, m), 1.95–1.75(2H, m), 1.75–1.55(1H, m), 1.55–1.15(3H, m). |
Purity >90%(NMR)
MS 558 (M+1)

TABLE 59-continued

| Example No. 207 | 1H NMR(δ)ppm |
|---|---|
| 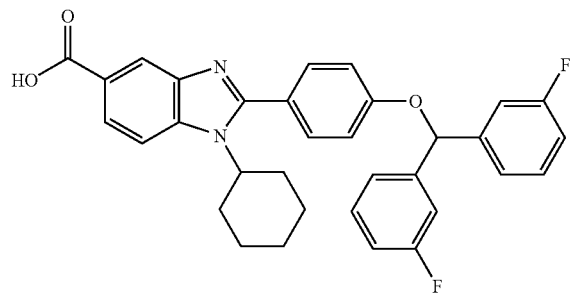 Purity >90%(NMR)<br>MS 539 (M+1) | 300MHz, DMSO-d6 8.29(1H, s), 8.26(1H, d, J=8.8Hz), 8.04(1H, d, J= 8.7Hz), 7.73(2H, d, J=8.8Hz), 7.50–7.41(6H, m), 7.36(2H, d, J=8.8Hz), 7.18–7.13(2H, m), 6.84(1H, s), 4.33(1H, m), 2.40–2.15(2H, m), 2.15– 1.95(2H, m), 1.95–1.75(2H, m), 1.75–1.55(1H, m), 1.55–1.15(3H, m). |

TABLE 60

| Example No. 208 | 1H NMR(δ)ppm |
|---|---|
| 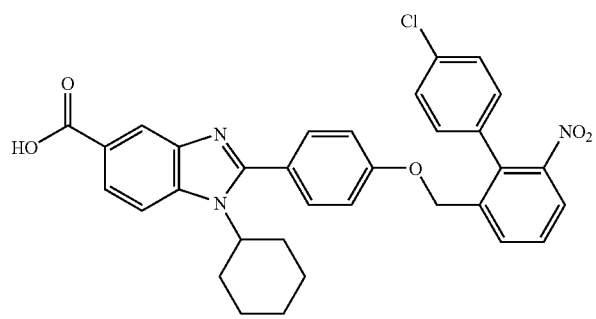 Purity >90% (NMR)<br>MS 582 (M+1) | 300MHz, DMSO-d6 8.32(1H, s), 8.27(1H, d, J= 9.0Hz), 8.07–8.00(3H, m), 7.79–7.70(3H, m), 7.51(2H, d, J=8.1Hz), 7.40(2H, d, J=8.4Hz), 7.18(2H, d, J=8.7Hz), 4.99(2H, s), 4.34(1H, m), 2.40–2.15(2H, m), 2.15–1.95(2H, m), 1.95– 1.75(2H, m), 1.75–1.55(1H, m), 1.55–1.15(3H, m). |
| Example No. 209 | 1H NMR(δ)ppm |
| 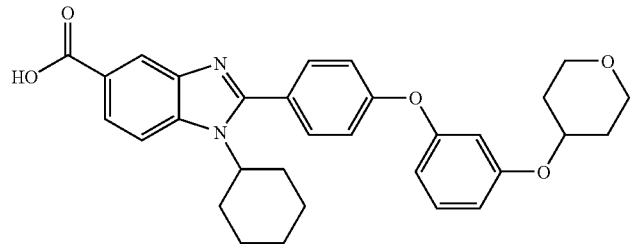 Purity >90% (NMR)<br>MS 513 (M+1) | 300MHz, DMSO-d6 8.24(1H, d, J=4.4Hz), 7.98 and 7.88(2H, ABq, J=8.6Hz), 7.70 and 7.19(4H, A'B'q, J=8.4Hz), 7.35(1H, t, J=8.4Hz), 6.86(1H, d, J= 8.1Hz), 6.79(1H, s), 6.71(1H, d, J=8.1Hz), 4.65– 4.53(1H, m), 4.31(1H, brt, J=12.2Hz), 3.88– 3.78(2H, m), 3.48(2H, t, J=9.0Hz), 2.39–2.19(2H, m), 1.02–1.71(6H, m), 1.70–1.50(3H, m), 1.46–1.19(3H, m) |
| Example No. 210 | 1H NMR(δ)ppm |
| 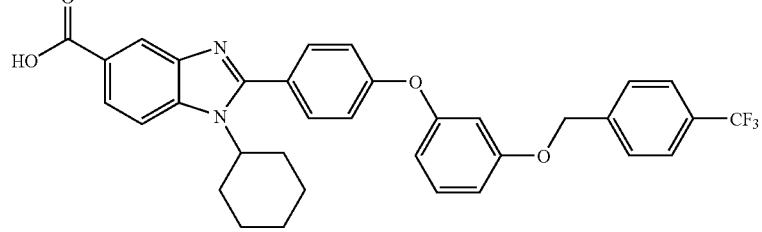 Purity >90% (NMR)<br>MS 587 (M+1) | 300MHz, DMSO-d6 12.75(1H, s), 8.23(1H, s), 7.96 and 7.87(2H, ABq, J=8.7Hz), 7.84–7.66(6H, m), 7.38(1H, t, J=8.4Hz), 7.18(2H, d, J=8.4Hz), 6.91(1H, d, J=9.0Hz), 6.84(1H, s), 6.74(1H, d, J= 8.1Hz), 5.26(2H, s), 4.31(1H, brt, J=12.2Hz), 2.40– 2.20(2H, m), 1.99–1.76(4H, m), 1.69–1.58(1H, m), 1.45–1.20(3H, m) |

TABLE 61

| Example No. 211 | 1H NMR(δ)ppm |
|---|---|
| 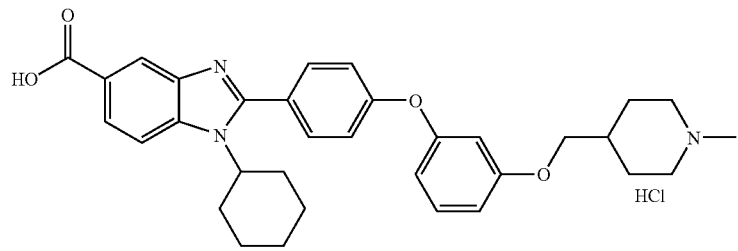 | 300MHz, DMSO-d6 8.29(1H, s), 8.15 and 7.47(2H, ABq, J=9.0Hz), 7.77 and 7.24(4H, ABq, J=8.9Hz), 7.39(1H, t, J=7.8Hz), 6.84(1H, d, J=9.3Hz), 6.76(1H, s), 6.75(1H, d, J=9.5Hz), 4.36(1H, brt, J=12.2Hz), 3.89(2H, d, J=6.0Hz), 3.42(2H, d, J=10.8Hz), 3.04–2.88(2H, m), 2.78–2.60(1H, m), 2.71(2H, d, J=4.8Hz), 2.38–2.20(2H, m), 2.07–1.80(7H, m), 1.70–1.20(5H, m) |

Purity >90% (NMR)
MS 540 (M+1)

| Example No. 212 | 1H NMR(δ)ppm |
|---|---|
| 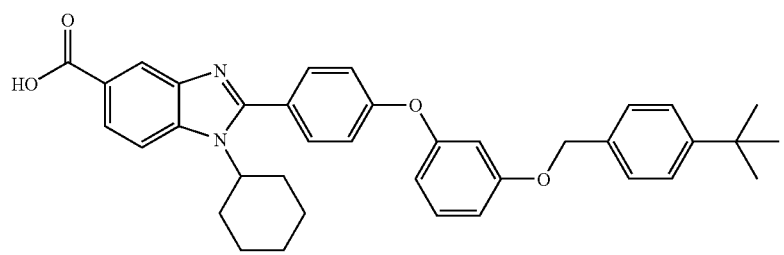 | 300MHz, DMSO-d6 8.22(1H, s), 7.93 and 7.87(2H, ABq, J=8.6Hz), 7.68 and 7.17(4H, A'B'q, J=8.7Hz), 7.43–7.33(5H, m), 6.87(1H, d, J=8.1Hz), 7.18(2H, d, J=8.4Hz), 6.91(1H, d, J=9.0Hz), 6.81(1H, s), 6.72(1H, d, J=8.0Hz), 5.08(2H, s), 4.36(1H, brt, J=12.2Hz), 2.37–2.20(2H, m), 1.98–1.78(4H, m), 1.69–1.60(1H, m), 1.41–1.21(3H, m), 1.28(9H, s) |

Purity >90% (NMR)
MS 575 (M+1)

| Example No. 213 | 1H NMR(δ)ppm |
|---|---|
| 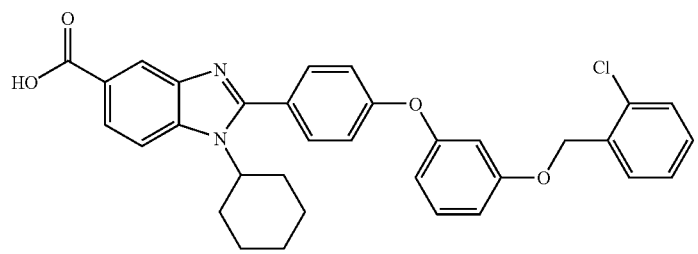 | 300MHz, DMSO-d6 8.23(1H, s), 7.95 and 7.86(2H, ABq, J=8.4Hz), 7.69 and 7.19(4H, A'B'q, J=8.7Hz), 7.62–7.36(5H, m), 6.90(1H, d, J=8.1Hz), 6.84(1H, s), 6.76(1H, d, J=8.1Hz), 5.19(2H, s), 4.31(1H, brt, J=12.2Hz), 2.40–2.19(2H, m), 1.99–1.76(4H, m), 1.68–1.55(1H, m), 1.50–1.18(3H, m) |

Purity >90% (NMR)
MS 553 (M+1)

TABLE 62

| Example No. 214 | 1H NMR(δ)ppm |
|---|---|
| 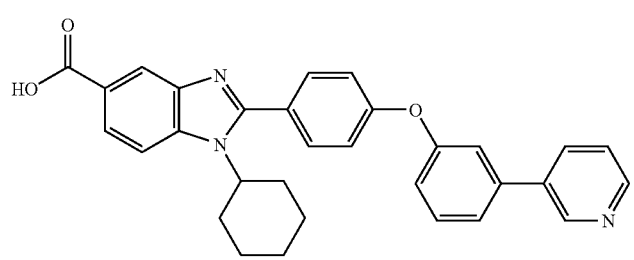 | 300MHz, DMSO-d6 8.94(1H, d, J=2.1Hz), 8.60(1H, dd, J=4.8, 1.5Hz), 8.23(1H, d, J=1.5Hz), 8.12(1H, dt, J=8.1, 2.1Hz), 7.93(1H, d, J=8.7Hz), 7.87(1H, dd, J=8.7, 1.5Hz), 7.70(1H, d, J=8.7Hz), 7.67–7.54(3H, m), 7.50(1H, dd, J=8.1, 4.8Hz), 7.25(2H, d, J=8.7Hz), 7.21(1H, m), 4.31(1H, m), 2.38–2.19(2H, m), 2.00–1.78(4H, m), 1.65(1H, m), 1.48–1.22(3H, m). |

Purity >90% (NMR)
MS 490 (M+1)

TABLE 62-continued

| Example No. 215 | 1H NMR(δ)ppm |
|---|---|
| 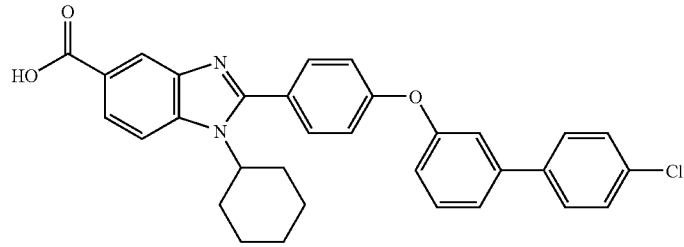 | 300MHz, DMSO-d6 12.75(1H, brs), 8.23(1H, s), 7.95(1H, d, J=8.7Hz), 7.86(1H, d, J=8.7Hz), 7.73(2H, d, J=8.4Hz), 7.71(2H, d, J=8.4Hz), 7.63–7.39(2H, m), 7.52(2H, d, J=8.4Hz), 7.24(2H, d, J=8.4Hz), 7.18(1H, m), 4.31(1H, m), 2.39–2.20(2H, m), 2.00–1.76(4H, m), 1.65(1H, m), 1.49–1.18(3H, m). |
| Purity >90% (NMR) MS 523 (M+1) | |
| Example No. 216 | 1H NMR(δ)ppm |
| 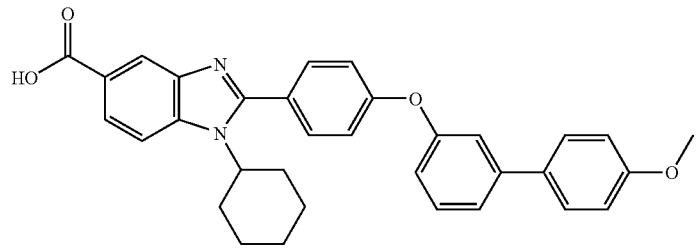 | 300MHz, DMSO-d6 12.77(1H, s), 8.23(1H, d, J=1.4Hz), 7.95(1H, d, J=8.6Hz), 7.86(1H, dd, J=8.6, 1.4Hz), 7.70(2H, d, J=8.7Hz), 7.64(2H, d, J=8.8Hz), 7.56–7.48(2H, m), 7.40(1H, s), 7.23(2H, d, J=8.7Hz), 7.10(1H, m), 7.03(2H, d, J=8.8Hz), 4.31(1H, m), 3.80(3H, s), 2.48–2.20(2H, m), 2.00–1.88(4H, m), 1.66(1H, m), 1.50–1.21(3H, m). |
| Purity >90% (NMR) MS 519 (M+1) | |

TABLE 63

| Example No. 217 | 1H NMR(δ)ppm |
|---|---|
| 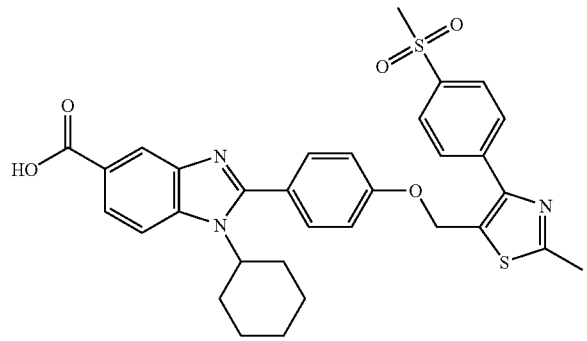 | (DMSO-d6) δ:12.80(1H, brs), 8.23(1H, s), 8.04(1H, d, J=8.6Hz), 7.96(3H, d, J=8.6Hz), 7.86(1H, d, J=8.7Hz), 7.63(2H, d, J=8.6Hz), 7.25(2H, d, J=8.6Hz), 5.50(2H, s), 4.36–4.21(1H, m), 3.27(3H, s), 2.74(3H, s), 2.40–2.19(2H, m), 1.99–1.79(4H, m), 1.71–1.60(1H, m), 1.49–1.19(3H, m) |
| Purity >90% (NMR) MS 602 (M+1) | |
| Example No. 218 | 1H NMR(δ)ppm |
| 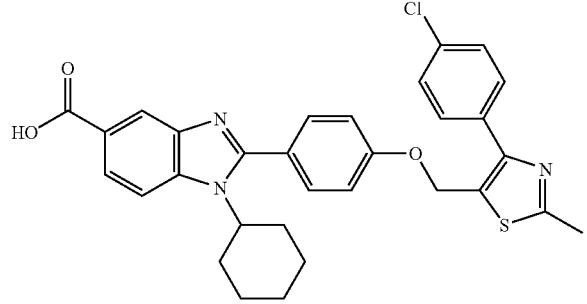 | 300MHz, DMSO-d6 12.9(1H, brs), 8.25(1H, s), 8.04(1H, d, J=8.7Hz), 7.91(1H, d, J=8.6Hz), 7.72(2H, d, J=8.5Hz), 7.67(2H, d, J=8.7Hz), 7.56(2H, d, J=8.5Hz), 7.26(2H, d, J=8.7Hz), 5.45(2H, s), 4.31(1H, m), 2.71(3H, s), 2.40–2.15(2H, m), 2.05–1.80(4H, m), 1.75–1.55(1H, m), 1.55–1.15(3H, m). |
| Purity >90% (NMR) MS 558 (M+1) | |

TABLE 63-continued

Example No. 219

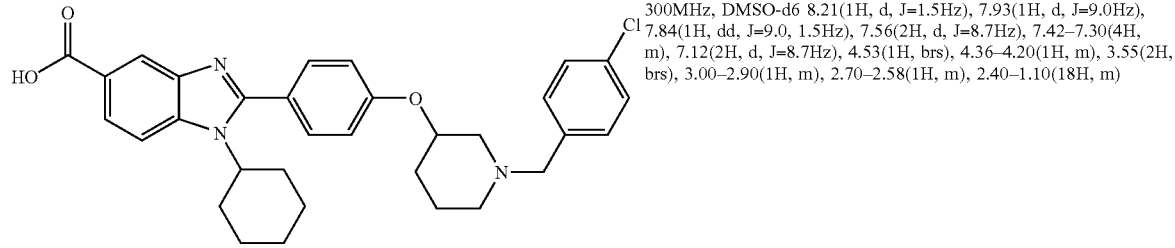

1H NMR(δ)ppm

300MHz, DMSO-d6 8.21(1H, d, J=1.5Hz), 7.93(1H, d, J=9.0Hz), 7.84(1H, dd, J=9.0, 1.5Hz), 7.56(2H, d, J=8.7Hz), 7.42–7.30(4H, m), 7.12(2H, d, J=8.7Hz), 4.53(1H, brs), 4.36–4.20(1H, m), 3.55(2H, brs), 3.00–2.90(1H, m), 2.70–2.58(1H, m), 2.40–1.10(18H, m)

Purity >90% (NMR)
MS 544 (M+1)

TABLE 64

Example No. 220

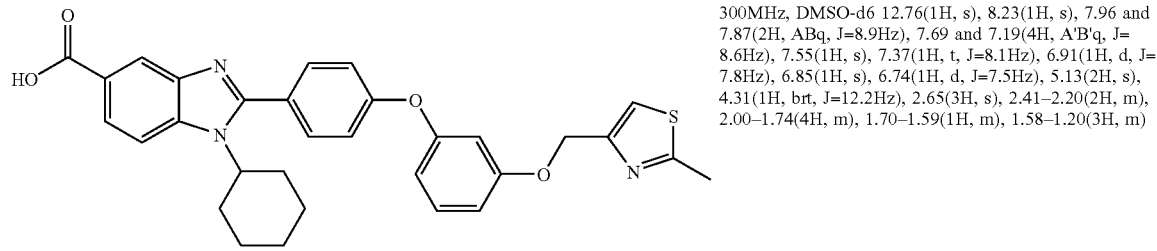

1H NMR(δ)ppm

300MHz, DMSO-d6 12.76(1H, s), 8.23(1H, s), 7.96 and 7.87(2H, ABq, J=8.9Hz), 7.69 and 7.19(4H, A'B'q, J= 8.6Hz), 7.55(1H, s), 7.37(1H, t, J=8.1Hz), 6.91(1H, d, J= 7.8Hz), 6.85(1H, s), 6.74(1H, d, J=7.5Hz), 5.13(2H, s), 4.31(1H, brt, J=12.2Hz), 2.65(3H, s), 2.41–2.20(2H, m), 2.00–1.74(4H, m), 1.70–1.59(1H, m), 1.58–1.20(3H, m)

Purity >90% (NMR)
MS 540 (M+1)

Example No. 221

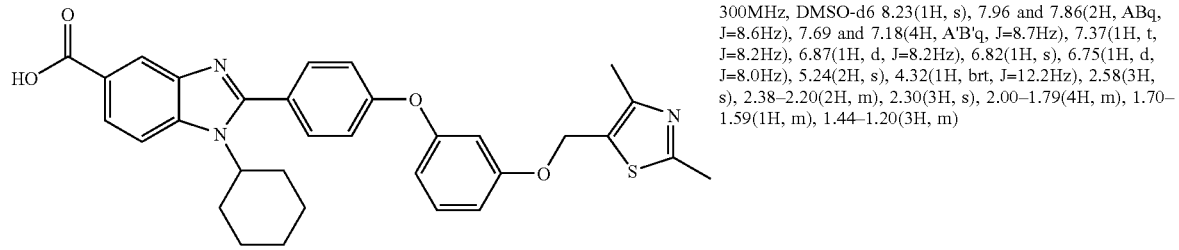

1H NMR(δ)ppm

300MHz, DMSO-d6 8.23(1H, s), 7.96 and 7.86(2H, ABq, J=8.6Hz), 7.69 and 7.18(4H, A'B'q, J=8.7Hz), 7.37(1H, t, J=8.2Hz), 6.87(1H, d, J=8.2Hz), 6.82(1H, s), 6.75(1H, d, J=8.0Hz), 5.24(2H, s), 4.32(1H, brt, J=12.2Hz), 2.58(3H, s), 2.38–2.20(2H, m), 2.30(3H, s), 2.00–1.79(4H, m), 1.70–1.59(1H, m), 1.44–1.20(3H, m)

Purity >90% (NMR)
MS 554 (M+1)

Example No. 222

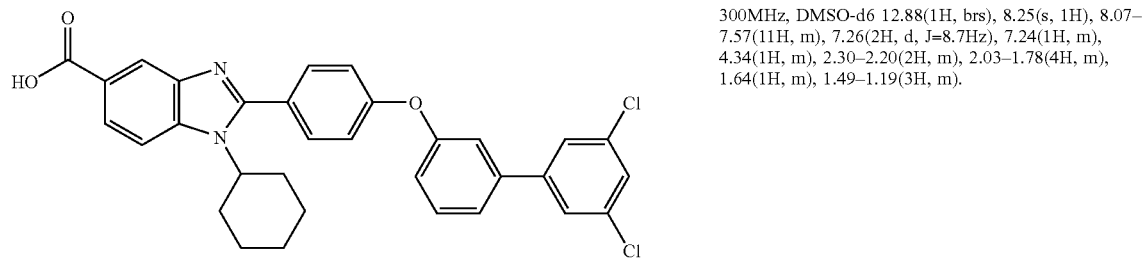

1H NMR(δ)ppm

300MHz, DMSO-d6 12.88(1H, brs), 8.25(s, 1H), 8.07–7.57(11H, m), 7.26(2H, d, J=8.7Hz), 7.24(1H, m), 4.34(1H, m), 2.30–2.20(2H, m), 2.03–1.78(4H, m), 1.64(1H, m), 1.49–1.19(3H, m).

Purity >90% (NMR)
MS 557 (M+1)

TABLE 65

Example No. 223

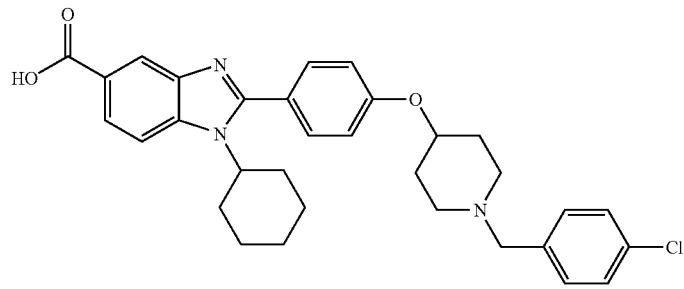

Purity >90%(NMR)
MS 544(M+1)

1H NMR(δ)ppm

300MHz, DMSO-d6 10.96(1H, brs), 8.21(1H, d, J=1.4Hz), 7.93(1H, d, J=8.7Hz), 7.84(1H, dd, J=8.7, 1.4Hz), 7.76–7.40(7H, m), 7.18(2H, d, J=8.0Hz), 4.24–4.16(2H, m), 2.40–1.12(18H, m)

Example No. 224

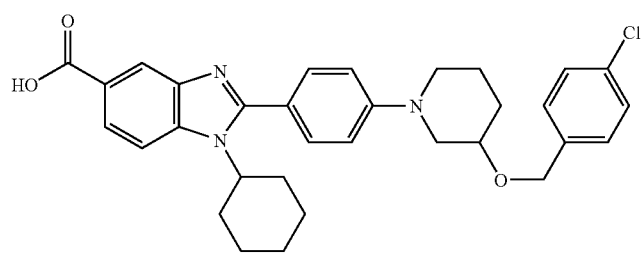

Purity >90%(NMR)
MS 544(M+1)

1H NMR(δ)ppm (DMSO-d6) δ:8.22(1H, s), 8.07(1H, d, J=8.4Hz), 7.92(1H, d, J=8.4Hz), 7.54(2H, d, J=8.7Hz), 7.40(2H, d, J=8.4Hz), 7.30(2H, d, J=8.4Hz), 7.14(2H, d, J=8.7Hz), 4.61(2H, s), 4.48–4.32(1H, m), 3.82(1H, brd, J=12.3Hz), 3.65–3.47(2H, m), 3.10(brdd, J=8.4, 12.3Hz), 2.40–2.20(2H, m), 2.09–1.76(6H, m), 1.71–1.16(6H, m)

Example No. 225

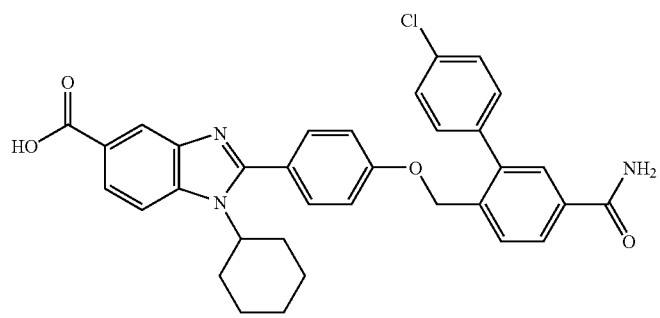

Purity >90%(NMR)
MS 580(M+1)

1H NMR(δ)ppm (DMSO-d6) δ:12.83(1H, brs), 8.21(1H, s), 8.10(1H, brs), 7.01–7.91(2H, m), 7.89–7.82(2H, m), 7.75(1H, d, J=8.0Hz), 7.59(2H, d, J=8.7Hz), 7.53(4H, s), 7.46(1H, brs), 7.12(2H, d, J=8.7Hz), 7.23(2H, s), 4.35–4.17(1H, m), 2.38–2.20(2H, m), 1.99–1.79(4H, m), 1.71–1.59(1H, m), 1.48–1.18(3H, m)

TABLE 66

Example No. 226

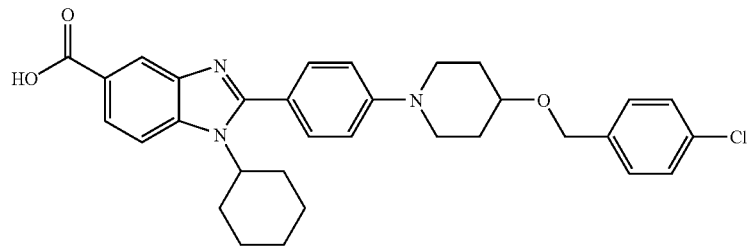

Purity >90%(NMR)
MS 544(M+1)

1H NMR(δ)ppm

300MHz, DMSO-d6 8.33 and 8.08(2H, ABq, J=8.7Hz), 8.31(1H, m), 7.66 and 7.26(4H, A'B'q, J=9.2Hz), 7.42 and 7.39(4H, A''B''q, J=8.7Hz), 4.57(2H, s), 4.50(1H, brt, J=12.2Hz), 3.85–3.62(3H, m), 3.28–3.16(2H, m), 2.42–2.23(2H, m), 2.14–1.81(6H, m), 1.72–1.25(6H, m)

TABLE 66-continued

Example No. 227

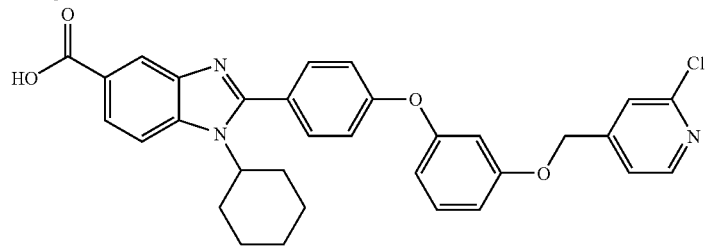

Purity >90%(NMR)
MS 554(M+1)

1H NMR(δ)ppm
300MHz, DMSO-d6 8.43(1H, d, J=5.0Hz), 8.23(1H, s), 7.96 and 7.86(2H, ABq, J=8.6Hz), 7.69 and 7.18(4H, A'B'q, J=8.6Hz), 7.57(1H, s), 7.47(1H, d, J=5.0Hz), 7.40(2H, t, J=8.2Hz), 6.91(1H, d, J=8.3Hz), 6.85(1H, s), 6.77(1H, d, J=7.9Hz), 5.25(2H, s), 4.31(1H, brt, J=12.2Hz), 2.40–2.19(2H, m), 1.99–1.75(4H, m), 1.73–1.57(1H, m), 1.49–1.19(3H, m)

Example No. 228

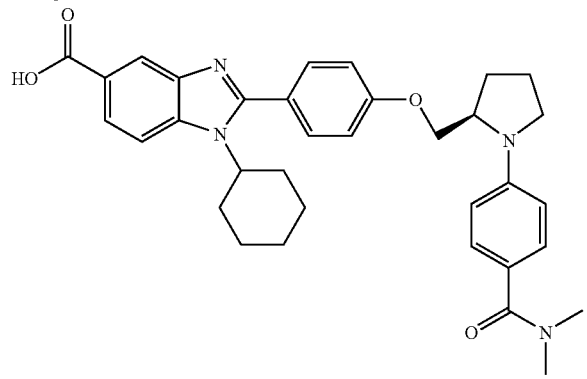

Purity >90%(NMR)
MS 567(M+1)

1H NMR(δ)ppm
300MHz, DMSO-d6 12.80(1H, brs), 8.22(1H, s), 7.94(1H, d, J=8.6Hz), 7.87(1H, d, J=8.6Hz), 7.60(2H, d, J=8.7Hz), 7.32(2H, d, J=8.7Hz)7.17(2H, d, J=8.7Hz), 6.70(2H, d, J=8.7Hz), 4.35–3.97(4H, m), 3.62–3.11(2H, m), 2.96(6H, s), 2.39–1.12(14H, m)

TABLE 67

Example No. 229

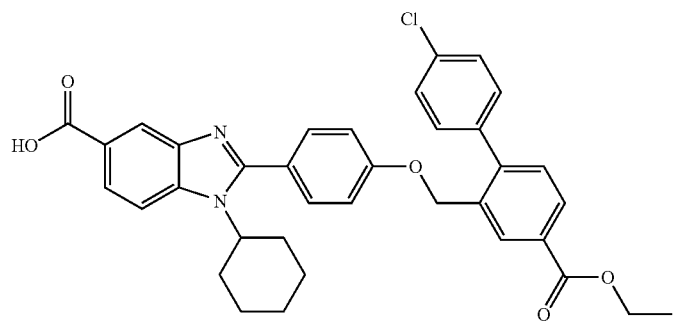

Purity >90%(NMR)
MS 608(M+1)

1H NMR(δ)ppm

300MHz, DMSO-d6 8.25(1H, s), 8.20(1H, s), 8.04(1H, dd, J=8.1, 1.8Hz), 7.92(1H, d, J=8.1Hz), 7.84(1H, d, J=9.9Hz), 7.62–7.50(7H, m), 7.12(2H, d, J=8.7Hz), 5.14(2H, s), 4.36(2H, q, J=6.9Hz), 4.30–4.20(1H, m), 2.38–2.18(2H, m), 1.98–1.18(8H, m), 1.35(3H, t, J=6.9Hz)

Example No. 230

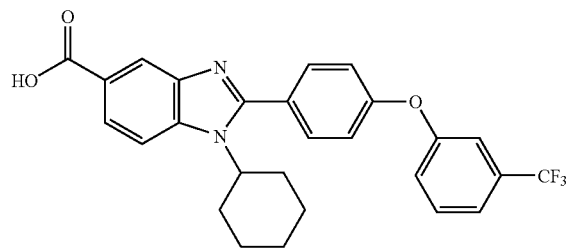

Purity about 90%(NMR)
MS 481(M+1)

1H NMR(δ)ppm

300MHz, DMSO-d6 8.35(1H, s), 8.27(1H, d, J=8.7Hz), 8.05(1H, d, J=9.0Hz), 7.87(2H, d, J=8.7Hz), 7.74(1H, t, J=8.1Hz), 7.64(1H, d, J=7.8Hz), 7.59–7.50(2H, m), 7.36(2H, d, J=8.7Hz), 4.39(1H, m), 2.40–2.15(2H, m), 2.15–1.95(2H, m), 1.95–1.75(2H, m), 1.75–1.55(1H, m), 1.55–1.20(3H, m).

TABLE 67-continued

| Example No. 231 | 1H NMR(δ)ppm |

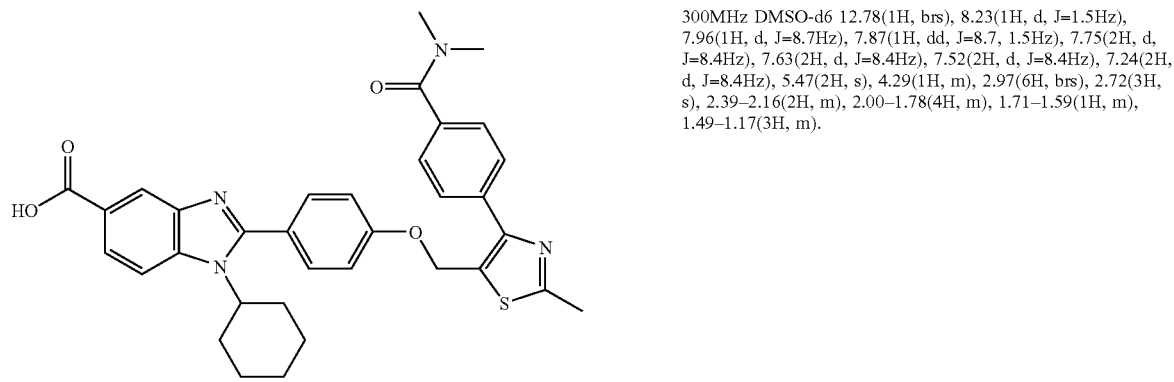

300MHz DMSO-d6 12.78(1H, brs), 8.23(1H, d, J=1.5Hz), 7.96(1H, d, J=8.7Hz), 7.87(1H, dd, J=8.7, 1.5Hz), 7.75(2H, d, J=8.4Hz), 7.63(2H, d, J=8.4Hz), 7.52(2H, d, J=8.4Hz), 7.24(2H, d, J=8.4Hz), 5.47(2H, s), 4.29(1H, m), 2.97(6H, brs), 2.72(3H, s), 2.39–2.16(2H, m), 2.00–1.78(4H, m), 1.71–1.59(1H, m), 1.49–1.17(3H, m).

Purity about 90%(NMR)
MS 595(M+1)

TABLE 68

| Example No. 232 | 1H NMR(δ)ppm |

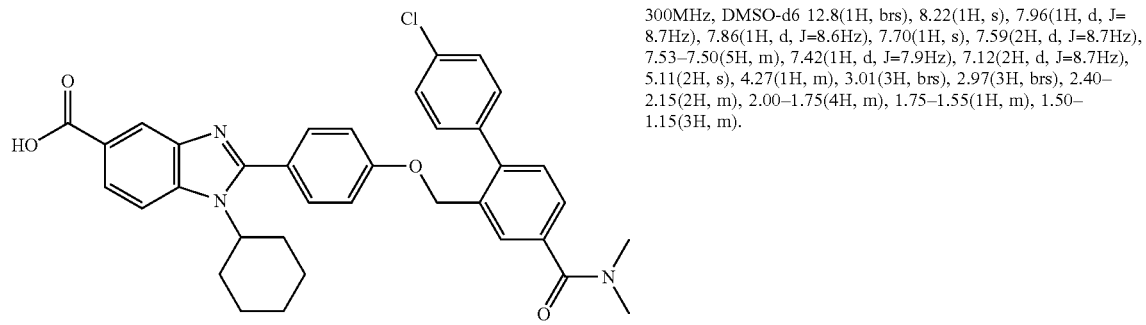

300MHz, DMSO-d6 12.8(1H, brs), 8.22(1H, s), 7.96(1H, d, J=8.7Hz), 7.86(1H, d, J=8.6Hz), 7.70(1H, s), 7.59(2H, d, J=8.7Hz), 7.53–7.50(5H, m), 7.42(1H, d, J=7.9Hz), 7.12(2H, d, J=8.7Hz), 5.11(2H, s), 4.27(1H, m), 3.01(3H, brs), 2.97(3H, brs), 2.40–2.15(2H, m), 2.00–1.75(4H, m), 1.75–1.55(1H, m), 1.50–1.15(3H, m).

Purity >90%(NMR)
MS 608(M+1)

| Example No. 233 | 1H NMR(δ)ppm |

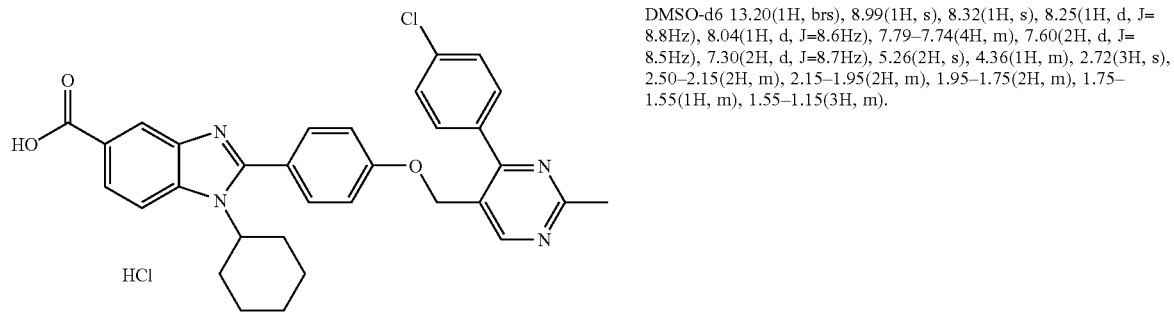

DMSO-d6 13.20(1H, brs), 8.99(1H, s), 8.32(1H, s), 8.25(1H, d, J=8.8Hz), 8.04(1H, d, J=8.6Hz), 7.79–7.74(4H, m), 7.60(2H, d, J=8.5Hz), 7.30(2H, d, J=8.7Hz), 5.26(2H, s), 4.36(1H, m), 2.72(3H, s), 2.50–2.15(2H, m), 2.15–1.95(2H, m), 1.95–1.75(2H, m), 1.75–1.55(1H, m), 1.55–1.15(3H, m).

Purity >90%(NMR)
MS 553(M+1 − HCl)

TABLE 68-continued
| Example No. 234 | 1H NMR(δ)ppm |
|---|---|
| 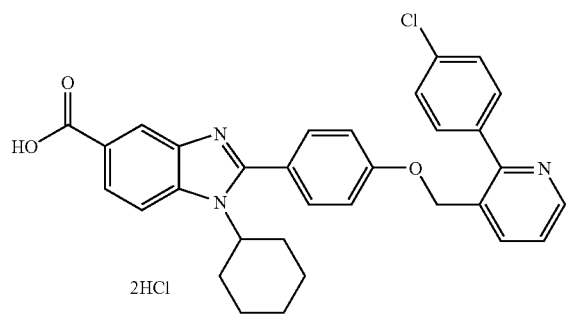<br>2HCl | DMSO-d6 8.77(1H, d, J=3.6Hz), 8.36–8.26(3H, m), 8.08(1H, d, J=8.8Hz), 7.79(2H, d, J=8.7Hz), 7.72–7.64(3H, m), 7.58(2H, d, J=8.4Hz), 7.30(2H, d, J=8.7Hz), 5.26(2H, s), 4.38(1H, m), 2.50–2.15(2H, m), 2.15–1.95(2H, m), 1.95–1.75(2H, m), 1.75–1.55(1H, m), 1.55–1.15(3H, m). |
Purity >90%(NMR)
MS 538(M+1−2HCl)
TABLE 69
| Example No. 235 | 1H NMR(δ)ppm |
|---|---|
| 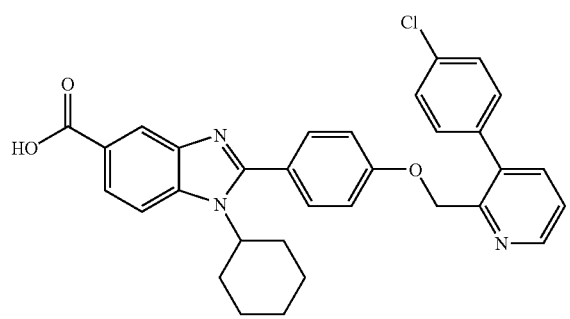 | 300MHz, DMSO-d6 12.74(1H, brs), 8.67(1H, dd, J=3.1, 1.6Hz), 8.21(1H, d, J=1.6Hz), 7.93(1H, dJ=8.6Hz), 7.90–7.80(2H, m), 7.60–7.50(7H, m), 7.09(2H, d, J=8.7Hz), 5.16(2H, s), 4.26(1H, m), 2.40–2.20(2H, m), 2.00–1.60(5H, m), 1.50–1.20(3H, m) |
Purity >90%(NMR)
MS APCI-Ms 538(M+1)
| Example No. 236 | 1H NMR(δ)ppm |
|---|---|
| 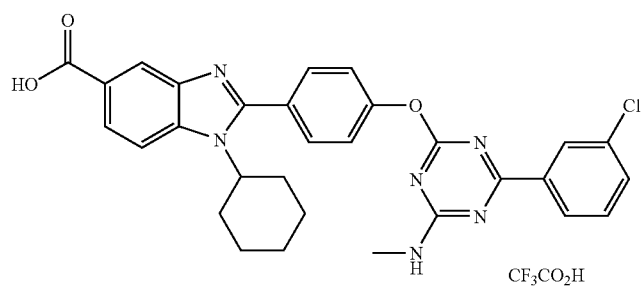 | 300MHz, DMSO-d-6 8.40–7.40(11H, m), 2.95, 2.81(3H, each d, J=4.7Hz), 2.40–2.20(2H, m), 2.10–1.80(4H, m), 1.70–1.60(1H, m), 1.50–1.20(3H, m) |
Purity >90%(NMR)
MS APCI-Ms 555(M+1)

TABLE 69-continued

| Example No. 237 | 1H NMR(δ)ppm |
|---|---|
| 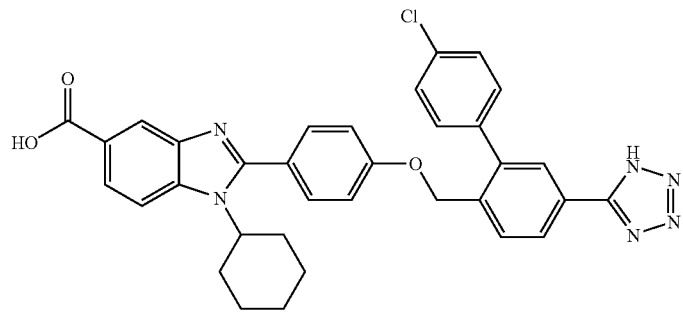<br>Purity >90%(NMR)<br>MS FAB-Ms 605(M+1) | 300MHz, DMSO-d6 8.21(1H, s), 8.15(1H, d, J=9.5Hz), 8.02(1H, s), 8.00–7.80(3H, m), 7.70–7.50(6H, m), 7.12(2H, d, J=8.7Hz), 5.16(2H, s), 4.28(1H, m), 2.40–2.20(2H, m), 2.00–1.80(4H, m), 1.65(1H, m), 1.50–1.20(3H, m) |

TABLE 70

| Example No. 238 | 1H NMR(δ)ppm |
|---|---|
| 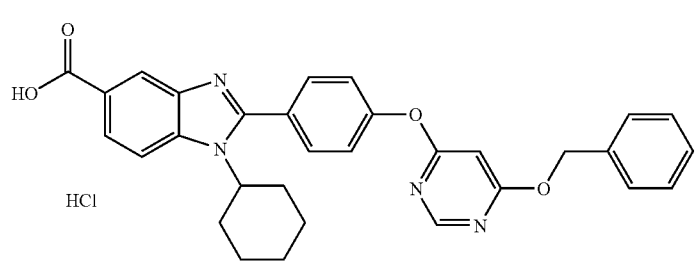<br>Purity >90%(NMR)<br>MS APCI-Ms 521 (M+1) | 300MHz, DMSO-d6 12.80(1H, brs), 8.54(1H, s), 8.25(1H, s), 7.98 and 7.88(2H, Abq, J=8.6Hz), 7.76(2H, d, J=8.6Hz), 7.53–7.31(3H, m), 6.61(1H, s), 5.46(2H, s), 4.32(1H, brt), 2.40–2.20(2H, m), 2.02–1.79(4H, m), 1.69–1.59(1H, m), 1.48–1.19(3H, m) |
| Example No. 239 | 1H NMR(δ)ppm |
| 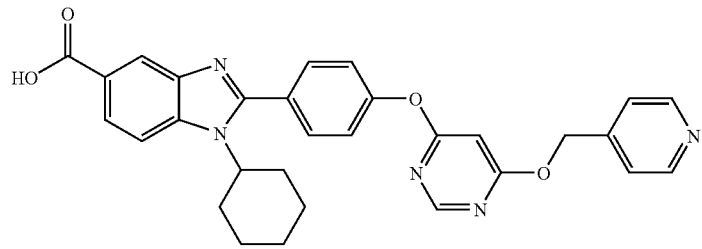<br>Purity >90%(NMR)<br>MS APCI-Ms 522 (M+1) | 300MHz, DMSO-d6 12.79(1H, brs), 8.60(2H, d, J=1.5Hz), 8.53(1H, s), 8.25(1H, s), 7.98 and 7.85(2H, ABq, J=9.4Hz), 7.76(2H, d, J=9.0Hz), 7.44(4H, d, J=6.5Hz), 6.69(1H, s), 5.53(2H, s), 4.32(1H, brt), 2.40–2.19(2H, m), 2.03–1.82(4H, m), 1.72–1.61(1H, m), 1.42–1.22(3H, m) |
| Example No. 240 | 1H NMR(δ)ppm |
| 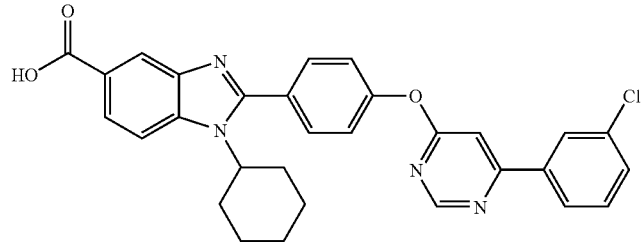<br>Purity >90%(NMR)<br>MS APCI-Ms 525 (M+1) | 300MHz, DMSO-d6 8.90(1H, s), 8.32(1H, s), 8.28(1H, s), 8.25(1H, d, J=8.3Hz), 8.05(1H, d, J=8.8Hz), 7.96(1H, s), 7.93(1H, d, J=8.8Hz), 7.83(1H, d, J=8.4Hz), 7.68–7.59(2H, m), 7.54(2H, d, J=8.8Hz), 4.37(1H, brt), 2.30(2H, m), 2.00(2H, m), 1.88(2H, m), 1.67(1H, m), 1.5–1.2(3H, m) |

TABLE 71

| Ex. No. | Formula | MS |
|---|---|---|
| 1001 | benzimidazole-5-carboxamide, 1-cyclopentyl, 2-(4-methoxycarbonylphenyl) | 364 (M+H) |
| 1002 | benzimidazole-5-carboxamide, 1-cyclopentyl, 2-[3-(4-tert-butylphenoxy)phenyl] | 454 (M+H) |
| 1003 | benzimidazole-5-carboxamide, 1-cyclopentyl, 2-(4-phenoxyphenyl) | 398 (M+H) |
| 1004 | benzimidazole-5-carboxamide, 1-cyclopentyl, 2-(quinolin-3-yl) | 357 (M+H) |
| 1005 | benzimidazole-5-carboxamide, 1-cyclopentyl, 2-(4-hydroxyphenyl) | 322 (M+H) |
| 1006 | benzimidazole-5-carboxamide, 1-cyclopentyl, 2-(4-chloro-3-nitrophenyl) | 385 (M+H) |

TABLE 72

| Ex. No. | Formula | MS |
|---|---|---|
| 1007 | | 357 (M+H) |
| 1008 | | 416 (M+H) |
| 1009 | | 310 (M+H) |
| 1010 | | 390 (M+H) |
| 1011 | | 395 (M+H) |
| 1012 | | 366 (M+H) |

TABLE 73

| Ex. No. | Formula | MS |
|---|---|---|
| 1013 | 1-cyclopentyl-2-[3-(trifluoromethyl)phenyl]-1H-benzimidazole-5-carboxamide | 374 (M+H) |
| 1014 | 2-(biphenyl-4-yl)-1-cyclopentyl-1H-benzimidazole-5-carboxamide | 382 (M+H) |
| 1015 | 3-(5-carbamoyl-1-cyclopentyl-1H-benzimidazol-2-yl)benzoic acid | 350 (M+H) |
| 1016 | 2-(5-bromo-2-fluorophenyl)-1-cyclopentyl-1H-benzimidazole-5-carboxamide | 402 (M+H) |
| 1017 | 2-(3-bromo-4-methoxyphenyl)-1-cyclopentyl-1H-benzimidazole-5-carboxamide | 414 (M+H) |
| 1018 | 2-(3-chlorophenyl)-1-cyclopentyl-1H-benzimidazole-5-carboxamide | 340 (M+H) |

TABLE 74

| Ex. No. | Formula | MS |
|---|---|---|
| 1019 | benzimidazole-5-carboxamide, 1-cyclopentyl, 2-(2-ethoxyphenyl) | 350 (M+H) |
| 1020 | benzimidazole-5-carboxamide, 1-cyclopentyl, 2-[4-(carboxymethoxy)phenyl] | 380 (M+H) |
| 1021 | benzimidazole-5-carboxamide, 1-cyclopentyl, 2-[2-(2-hydroxyethoxy)phenyl] | 366 (M+H) |
| 1022 | benzimidazole-5-carboxamide, 1-cyclopentyl, 2-(4-butoxyphenyl) | 378 (M+H) |
| 1023 | benzimidazole-5-carboxamide, 1-cyclopentyl, 2-(3-bromo-4-fluorophenyl) | 402 (M+H) |

TABLE 75

| Ex. No. | Formula | MS |
|---|---|---|
| 1024 | | 518(M+H) |
| 1025 | | 408(M+H) |
| 1026 | | 336(M+H) |
| 1027 | | 408(M+H) |
| 1028 | | 366(M+H) |

TABLE 75-continued
| Ex. No. | Formula | MS |
|---------|---------|-----|
| 1029 | 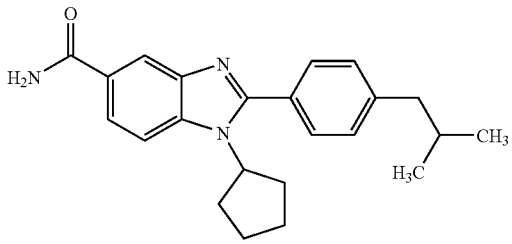 | 362(M+H) |
TABLE 76
| Ex. No. | Formula | MS |
|---------|---------|-----|
| 1030 | 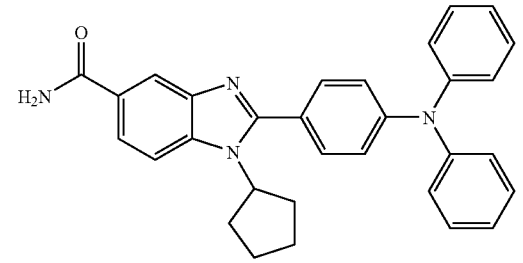 | 473(M+H) |
| 1031 | 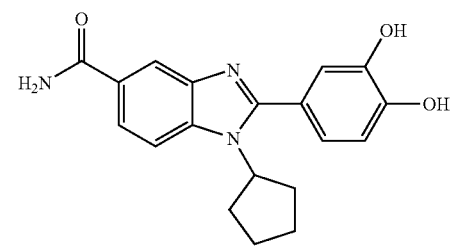 | 338(M+H) |
| 1032 | 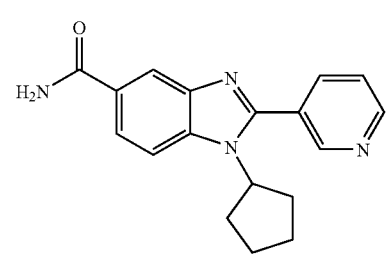 | 307(M+H) |
| 1033 | 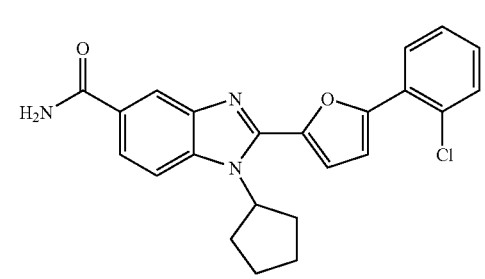 | 406(M+H) |

TABLE 76-continued

| Ex. No. | Formula | MS |
| --- | --- | --- |
| 1034 | | 466(M+H) |
| 1035 | | 412(M+H) |

TABLE 77

| Ex. No. | Formula | MS |
| --- | --- | --- |
| 1036 | | 412(M+H) |
| 1037 | | 428(M+H) |
| 1038 | | 466(M+H) |

TABLE 77-continued

| Ex. No. | Formula | MS |
|---|---|---|
| 1039 | benzimidazole-5-carboxamide, 1-cyclopentyl, 2-[5-(3-chlorophenyl)furan-2-yl] | 406(M+H) |
| 1040 | benzimidazole-5-carboxamide, 1-cyclopentyl, 2-[5-(3-nitrophenyl)furan-2-yl] | 417(M+H) |
| 1041 | benzimidazole-5-carboxamide, 1-cyclopentyl, 2-[5-(2-trifluoromethylphenyl)furan-2-yl] | 440(M+H) |

TABLE 78

| Ex. No. | Formula | MS |
|---|---|---|
| 1042 | benzimidazole-5-carboxamide, 1-cyclopentyl, 2-[5-(2-nitrophenyl)furan-2-yl] | 417(M+H) |
| 1043 | benzimidazole-5-carboxamide, 1-cyclopentyl, 2-[5-(3-trifluoromethylphenyl)furan-2-yl] | 440(M+H) |

TABLE 78-continued

| Ex. No. | Formula | MS |
|---|---|---|
| 1044 | | 312(M+H) |
| 1045 | | 423(M+H) |
| 1046 | | 352(M+H) |
| 1047 | | 307(M+H) |

TABLE 79

| Ex. No. | Formula | MS |
|---|---|---|
| 1048 | | 374(M+H) |

TABLE 79-continued

| Ex. No. | Formula | MS |
|---|---|---|
| 1049 | | 398(M+H) |
| 1050 | | 326(M+H) |
| 1051 | | 442(M+H) |
| 1052 | | 518(M+H) |

TABLE 80

| Ex. No. | Formula | MS |
|---|---|---|
| 1053 | | 442(M+H) |
| 1054 | | 376(M+H) |
| 1055 | | 442(M+H) |
| 1056 | | 352(M+H) |
| 1057 | | 367(M+H) |

TABLE 80-continued

| Ex. No. | Formula | MS |
|---|---|---|
| 1058 | | 367(M+H) |

TABLE 81

| Ex. No. | Formula | MS |
|---|---|---|
| 1059 | | 364(M+H) |
| 1060 | | 324(M+H) |
| 1061 | | 352(M+H) |
| 1062 | | 357(M+H) |

TABLE 81-continued
| Ex. No. | Formula | MS |
|---|---|---|
| 1063 | 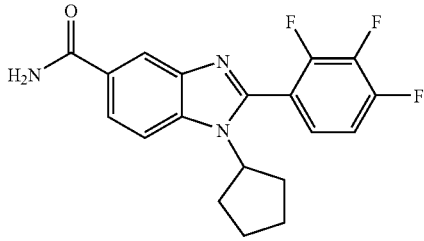 | 360(M+H) |
| 1064 | 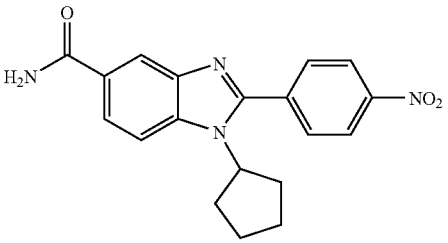 | 351(M+H) |
TABLE 82
| Ex. No. | Formula | MS |
|---|---|---|
| 1065 | 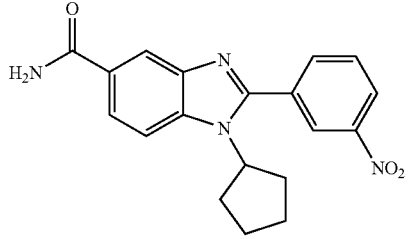 | 351(M+H) |
| 1066 | 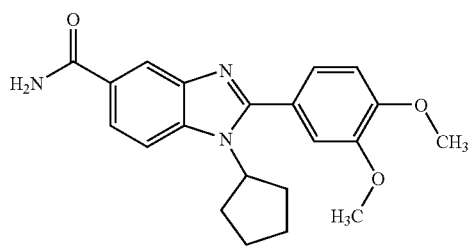 | 366(M+H) |
| 1067 | 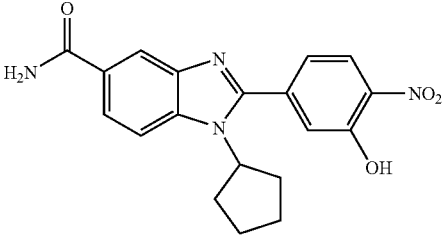 | 367(M+H) |

TABLE 82-continued

| Ex. No. | Formula | MS |
|---|---|---|
| 1068 | | 364(M+H) |
| 1069 | | 350(M+H) |
| 1070 | | 306(M+H) |

TABLE 83

| Ex. No. | Formula | MS |
|---|---|---|
| 1071 | | 365(M+H) |
| 1072 | | 455(M+H) |

TABLE 83-continued
| Ex. No. | Formula | MS |
|---|---|---|
| 1073 | 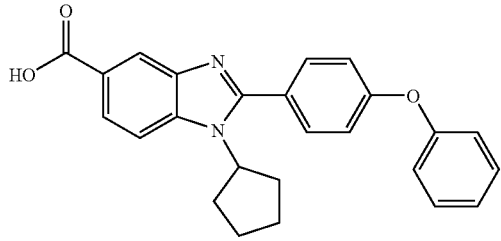 | 399(M+H) |
| 1074 | 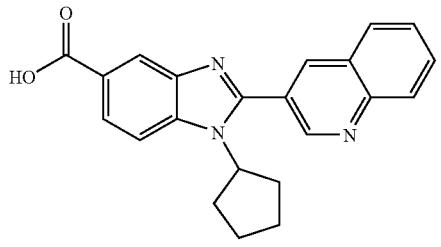 | 358(M+H) |
| 1075 | 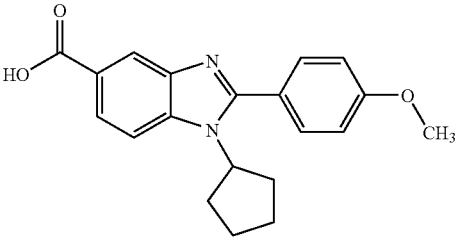 | 337(M+H) |
| 1076 | 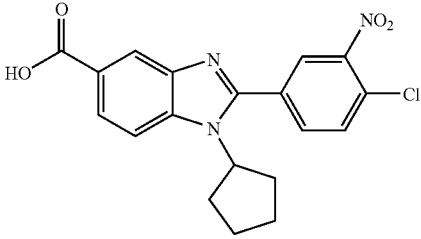 | 386(M+H) |
TABLE 84
| Ex. No. | Formula | MS |
|---|---|---|
| 1077 | 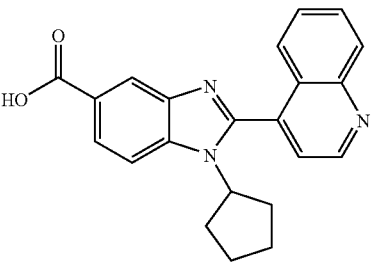 | 358(M+H) |

TABLE 84-continued
| Ex. No. | Formula | MS |
|---|---|---|
| 1078 | 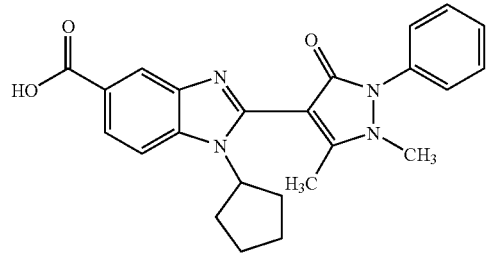 | 417(M+H) |
| 1079 | 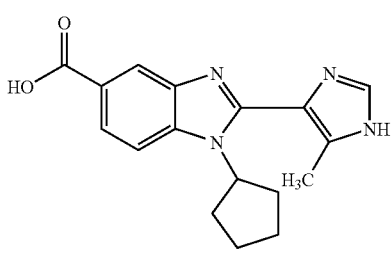 | 311(M+H) |
| 1080 | 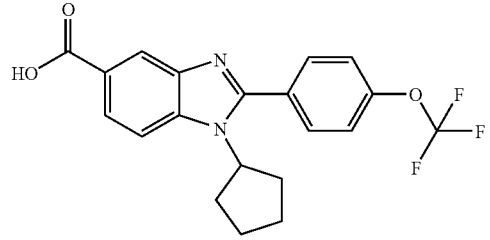 | 391(M+H) |
| 1081 |  | 396(M+H) |
| 1082 | 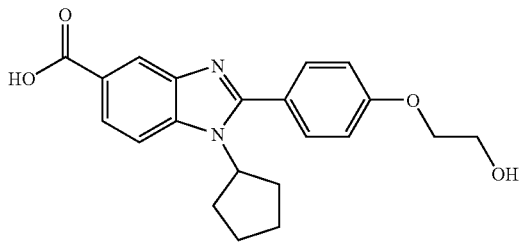 | 367(M+H) |

TABLE 85
| Ex. No. | Formula | MS |
|---|---|---|
| 1083 | 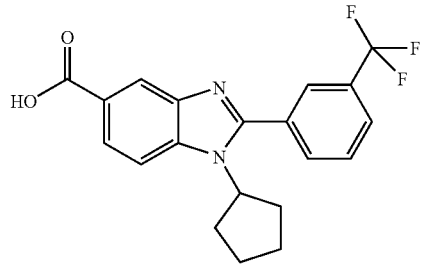 | 375(M+H) |
| 1084 | 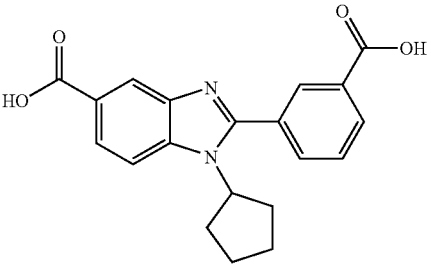 | 351(M+H) |
| 1085 | 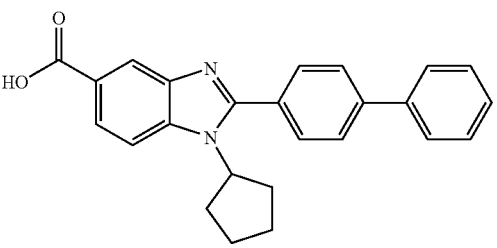 | 383(M+H) |
| 1086 | 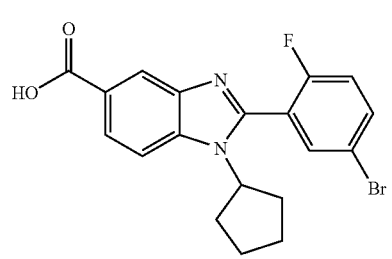 | 403(M+H) |
| 1087 | 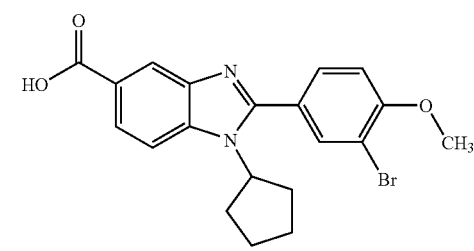 | 415(M+H) |
| 1088 | 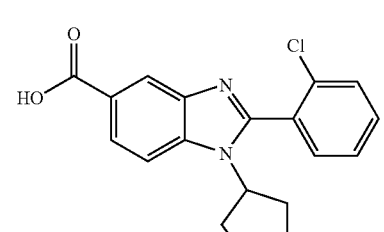 | 341(M+H) |

TABLE 86

| Ex. No. | Formula | MS |
|---|---|---|
| 1089 | | 351(M+H) |
| 1090 | | 381(M+H) |
| 1091 | | 367(M+H) |
| 1092 | | 379(M+H) |
| 1093 | | 403(M+H) |

TABLE 87
| Ex. No. | Formula | MS |
|---|---|---|
| 1094 | 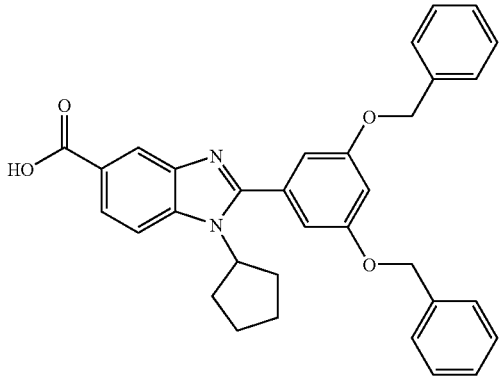 | 519(M+H) |
| 1095 | 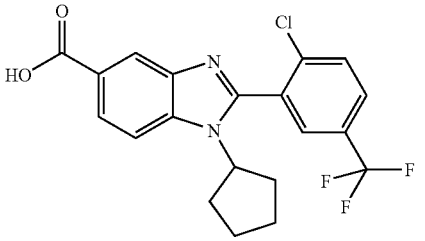 | 409(M+H) |
| 1096 | 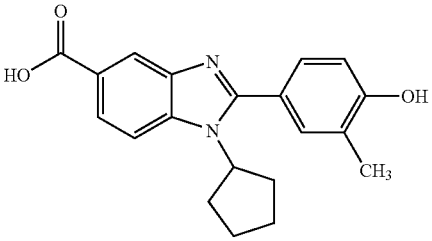 | 337(M+H) |
| 1097 | 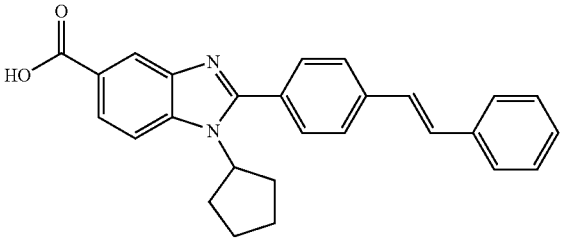 | 409(M+H) |
| 1098 | 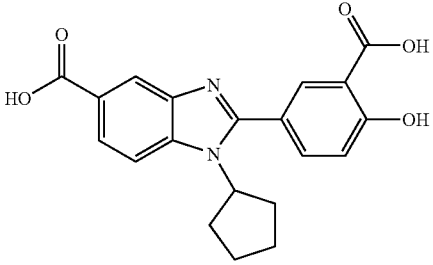 | 367(M+H) |

TABLE 87-continued
| Ex. No. | Formula | MS |
| --- | --- | --- |
| 1099 | 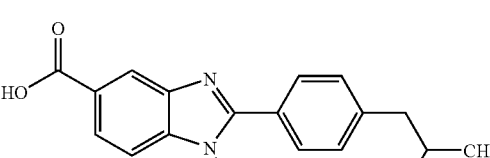 | 363(M+H) |
TABLE 88
| Ex. No. | Formula | MS |
| --- | --- | --- |
| 1100 | | 474(M+H) |
| 1101 | | 339(M+H) |
| 1102 | | 308(M+H) |
| 1103 | | 467(M+H) |

TABLE 88-continued
| Ex. No. | Formula | MS |
| --- | --- | --- |
| 1104 | 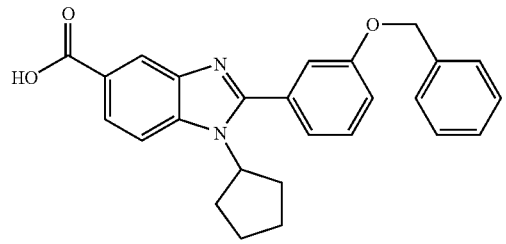 | 413(M+H) |
| 1105 | 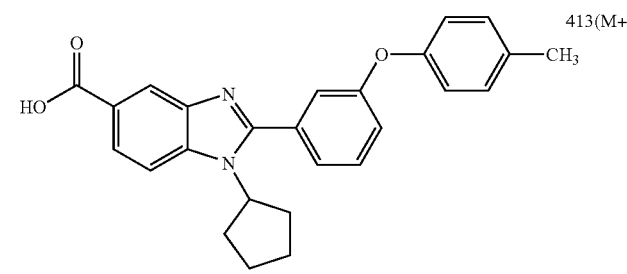 | 413(M+H) |
TABLE 89
| Ex. No. | Formula | MS |
| --- | --- | --- |
| 1106 | 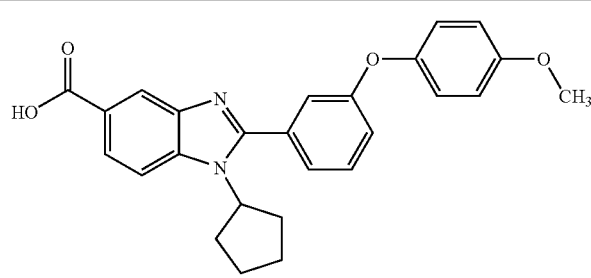 | 429(M+H) |
| 1107 | 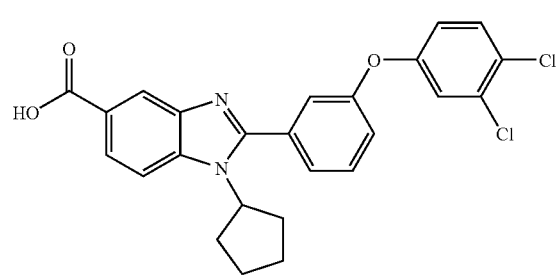 | 467(M+H) |
| 1108 | 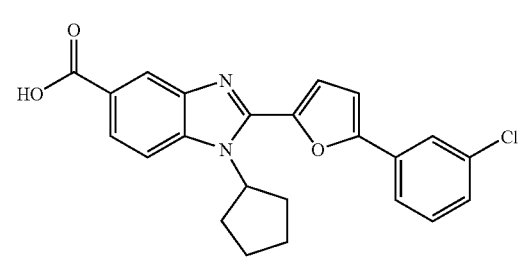 | |

TABLE 89-continued

| Ex. No. | Formula | MS |
|---|---|---|
| 1109 | | |
| 1110 | | 441(M+H) |
| 1111 | | 418(M+H) |

TABLE 90

| Ex. No. | Formula | MS |
|---|---|---|
| 1112 | | 313(M+H) |
| 1113 | | 308(M+H) |

TABLE 90-continued

| Ex. No. | Formula | MS |
|---------|---------|-----|
| 1114 | | 375(M+H) |
| 1115 | | 399(M+H) |
| 1116 | | 327(M+H) |
| 1117 | | 443(M+H) |

TABLE 91

| Ex. No. | Formula | MS |
|---|---|---|
| 1118 | | 519(M+H) |
| 1119 | | 443(M+H) |
| 1120 | | 377(M+H) |
| 1121 | | 443(M+H) |
| 1122 | | 353(M+H) |

TABLE 92

| Ex. No. | Formula | MS |
|---|---|---|
| 1123 | | 368(M+H) |
| 1124 | | 368(M+H) |
| 1125 | | 365(M+H) |
| 1126 | | 325(M+H) |
| 1127 | | 353(M+H) |
| 1128 | | 358(M+H) |

TABLE 93

| Ex. No. | Formula | MS |
|---|---|---|
| 1129 | | 361(M+H) |
| 1130 | | 352(M+H) |
| 1131 | | 352(M+H) |
| 1132 | | 367(M+H) |
| 1133 | | 368(M+H) |
| 1134 | | 365(M+H) |

TABLE 94

| Ex. No. | Formula | MS |
|---|---|---|
| 1135 | | 351(M+H) |
| 1136 | | 307(M+H) |
| 1137 | | 385(M+H) |
| 1138 | | 365(M+H) |
| 1139 | | 467(M+H) |

TABLE 94-continued
| Ex. No. | Formula | MS |
|---|---|---|
| 1140 | 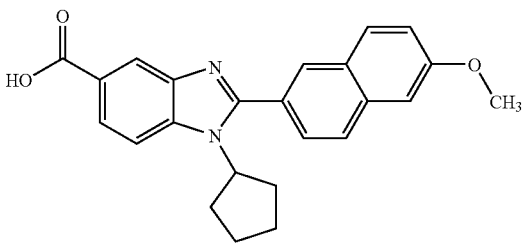 | 387(M+H) |
TABLE 95
| Ex. No. | Formula | MS |
|---|---|---|
| 1141 | 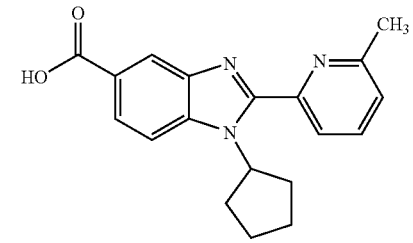 | 322(M+H) |
| 1142 | 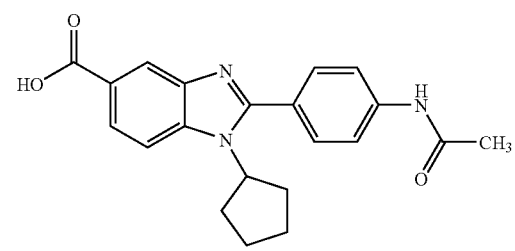 | 364(M+H) |
| 1143 | 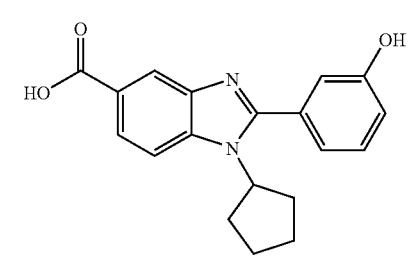 | 323(M+H) |
| 1144 | 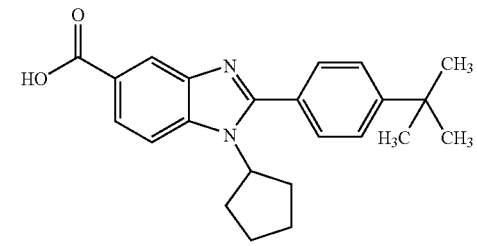 | 363(M+H) |

TABLE 95-continued

| Ex. No. | Formula | MS |
|---|---|---|
| 1145 | | 484(M+H) |
| 1146 | | 385(M+H) |

TABLE 96

| Ex. No. | Formula | MS |
|---|---|---|
| 1147 | | 427(M+H) |
| 1148 | | 420(M+H) |
| 1149 | | 508(M+H) |

TABLE 96-continued

| Ex. No. | Formula | MS |
|---|---|---|
| 1150 | | 458(M+H) |
| 1151 | | 458(M+H) |

TABLE 97

| Ex. No. | Formula | MS |
|---|---|---|
| 1152 | | 474(M+H) |
| 1153 | | 458(M+H) |

TABLE 97-continued

| Ex. No. | Formula | MS |
|---|---|---|
| 1154 | | 508(M+H) |
| 1155 | | 454(M+H) |

TABLE 98

| Ex. No. | Formula | MS |
|---|---|---|
| 1156 | | 470(M+H) |
| 1157 | | 496(M+H) |

TABLE 98-continued

| Ex. No. | Formula | MS |
|---|---|---|
| 1158 | | 482(M+H) |
| 1159 | | 448(M+H) |
| 1160 | | 488(M+H) |

TABLE 99

| Ex. No. | Formula | MS |
|---|---|---|
| 1161 | | 468(M+H) |

TABLE 99-continued

| Ex. No. | Formula | MS |
| --- | --- | --- |
| 1162 | | 447(M+H) |
| 1163 | | 466(M+H) |
| 1164 | | 526(M+H) |
| 1165 | | 420(M+H) |

TABLE 100

| Ex. No. | Formula | MS |
|---|---|---|
| 1166 | | 490(M+H) |
| 1167 | | 435(M+H) |
| 1168 | | 436(M+H) |
| 1169 | | 436(M+H) |
| 1170 | | 404(M+H) |

TABLE 100-continued

| Ex. No. | Formula | MS |
|---|---|---|
| 1171 | | 406(M+H) |

TABLE 101

| Ex. No. | Formula | MS |
|---|---|---|
| 1172 | | 392(M+H) |
| 1173 | | 420(M+H) |
| 1174 | | 406(M+H) |
| 1175 | | 420(M+H) |

TABLE 101-continued
| Ex. No. | Formula | MS |
|---|---|---|
| 1176 | 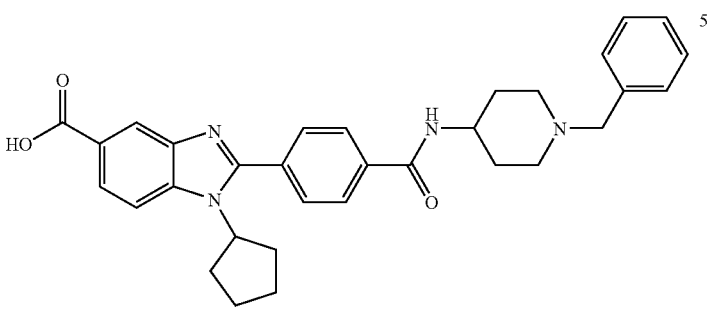 | 523(M+H) |
| 1177 | 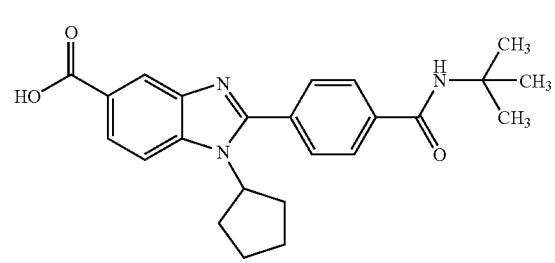 | 406(M+H) |
TABLE 102
| Ex. No. | Formula | MS |
|---|---|---|
| 1178 | 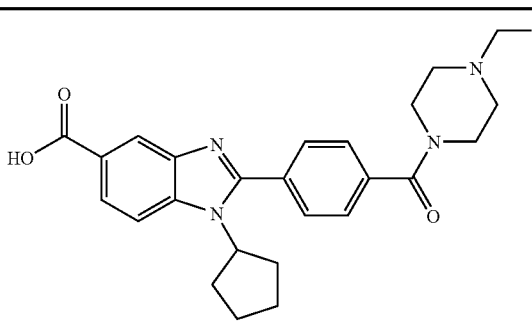 | 447(M+H) |
| 1179 | 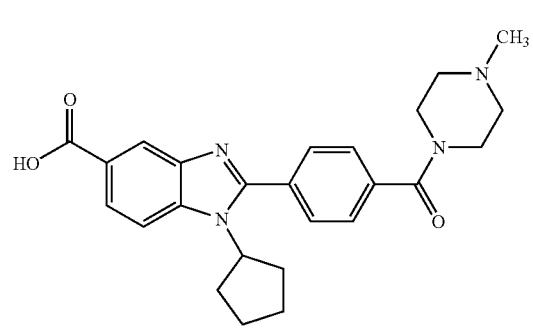 | 433(M+H) |

TABLE 102-continued

| Ex. No. | Formula | MS |
|---|---|---|
| 1180 | | 509(M+H) |
| 1181 | | 513(M+H) |

TABLE 103

| Ex. No. | Formula | MS |
|---|---|---|
| 1182 | | 497(M+H) |

TABLE 103-continued
| Ex. No. | Formula | MS |
|---|---|---|
| 1183 | 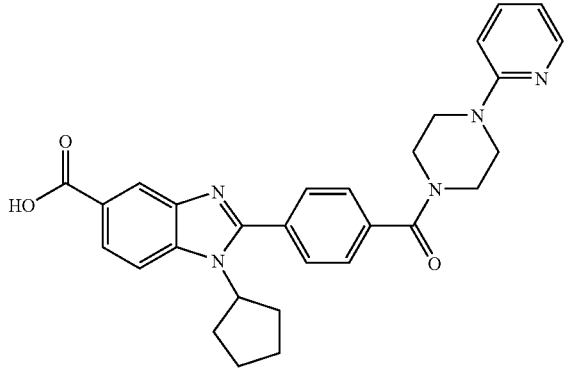 | 496(M+H) |
| 1184 | 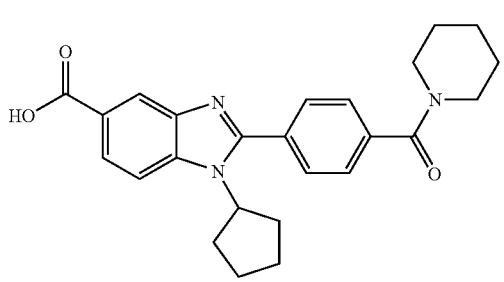 | 418(M+H) |
| 1185 | 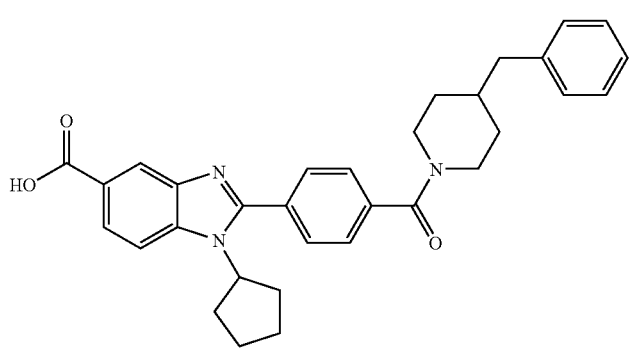 | 508(M+H) |
| 1186 | 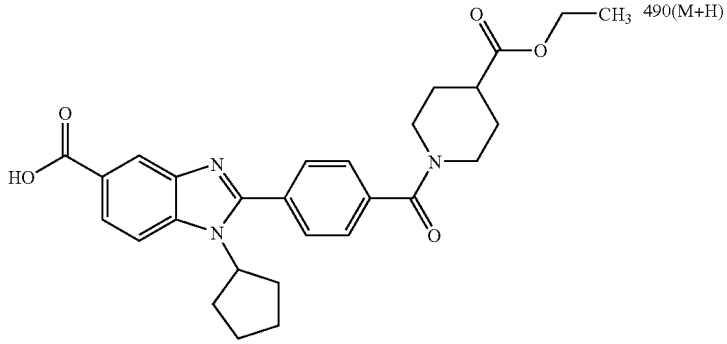 | 490(M+H) |

TABLE 104

| Ex. No. | Formula | MS |
|---|---|---|
| 1187 | | 441(M+H) |
| 1188 | | 455(M+H) |
| 1189 | | 455(M+H) |
| 1190 | | 513(M+H) |
| 1191 | | 504(M+H) |

TABLE 104-continued

| Ex. No. | Formula | MS |
|---|---|---|
| 1192 | | 494(M+H) |

TABLE 105

| Ex. No. | Formula | MS |
|---|---|---|
| 1193 | | 512(M+H) |
| 1194 | | 504(M+H) |
| 1195 | | 516(M+H) |
| 1196 | | 497(M+H) |

TABLE 105-continued

| Ex. No. | Formula | MS |
|---|---|---|
| 1197 | | 456(M+H) |
| 1198 | | 509(M+H) |

TABLE 106

| Ex. No. | Formula | MS |
|---|---|---|
| 1199 | | 483 (M+H) |
| 1200 | | 427 (M+H) |
| 1201 | | 427 (M+H) |

TABLE 106-continued

| Ex. No. | Formula | MS |
|---|---|---|
| 1202 | | 477 (M+H) |
| 1203 | | 519 (M+H) |
| 1204 | | 440 (M+H) |

TABLE 107

| Ex. No. | Formula | MS |
|---|---|---|
| 1205 | | 454 (M+H) |
| 1206 | | 325 (M+H) |

TABLE 107-continued

| Ex. No. | Formula | MS |
|---|---|---|
| 1207 | 2-(4-chlorophenyl)-1-cyclopentyl-benzimidazole-5-carboxylic acid | 341 (M+H) |
| 1208 | 2-(4-bromophenyl)-1-cyclopentyl-benzimidazole-5-carboxylic acid | 385 (M+H) |
| 1209 | 2-(4-butylphenyl)-1-cyclopentyl-benzimidazole-5-carboxylic acid | 363 (M+H) |
| 1210 | 2-(4-cyanophenyl)-1-cyclopentyl-benzimidazole-5-carboxylic acid | 332 (M+H) |

TABLE 108

| Ex. No. | Formula | MS |
|---|---|---|
| 1211 | 1-cyclopentyl-2-(4-ethoxyphenyl)-benzimidazole-5-carboxylic acid | 351 (M+H) |

TABLE 108-continued

| Ex. No. | Formula | MS |
|---|---|---|
| 1212 | | 335 (M+H) |
| 1213 | | 349 (M+H) |
| 1214 | | 321 (M+H) |
| 1215 | | 375 (M+H) |
| 1216 | | 367 (M+H) |

TABLE 109

| Ex. No. | Formula | MS |
|---|---|---|
| 1217 | | 433 (M+H) |
| 1218 | | 391 (M+H) |
| 1219 | | 337 (M+H) |
| 1220 | | 385 (M+H) |
| 1221 | | 341 (M+H) |
| 1222 | | 332 (M+H) |

TABLE 110

| Ex. No. | Formula | MS |
|---|---|---|
| 1223 | | 395 (M+H) |
| 1224 | | 375 (M+H) |
| 1225 | | 351 (M+H) |
| 1226 | | 321 (M+H) |
| 1227 | | 426 (M+H) |
| 1228 | | 460 (M+H) |

TABLE 111

| Ex. No. | Formula | MS |
|---|---|---|
| 1229 | | 442 (M+H) |
| 1230 | | 468 (M+H) |
| 1231 | | 456 (M+H) |
| 1232 | | 494 (M+H) |
| 1233 | | 451 (M+H) |

TABLE 111-continued
| Ex. No. | Formula | MS |
|---|---|---|
| 1234 | 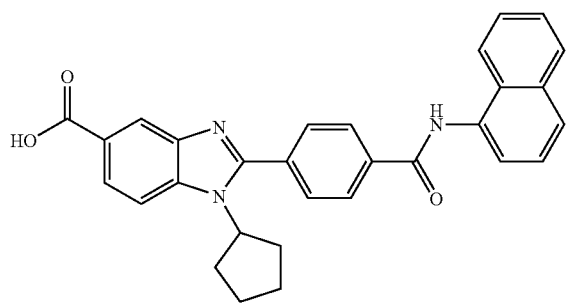 | 468 (M+H) |
TABLE 112
| Ex. No. | Formula | MS |
|---|---|---|
| 1235 | 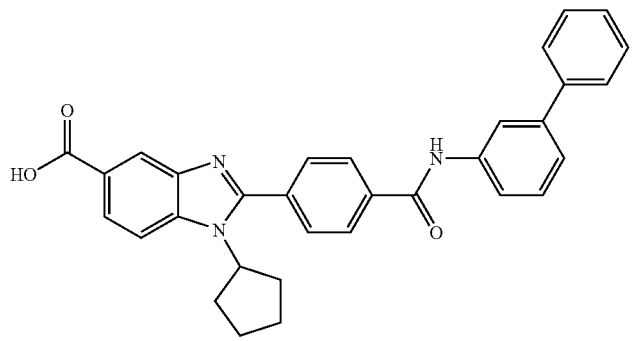 | 498 (M+H) |
| 1236 | | 476 (M+H) |
| 1237 | | 502 (M+H) |

TABLE 112-continued

| Ex. No. | Formula | MS |
| --- | --- | --- |
| 1238 | | 505 (M+H) |
| 1239 | | 469 (M+H) |

TABLE 113

| Ex. No. | Formula | MS |
| --- | --- | --- |
| 1240 | | 483 (M+H) |
| 1241 | | 408 (M+H) |
| 1242 | | 460 (M+H) |

TABLE 113-continued
| Ex. No. | Formula | MS |
|---|---|---|
| 1243 | 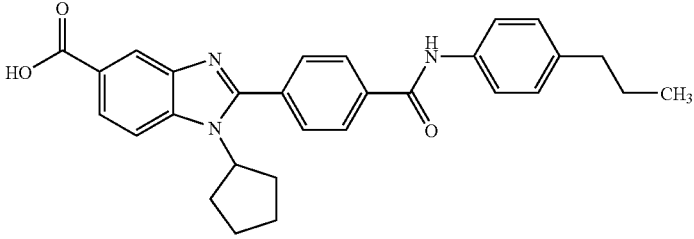 | 468 (M+H) |
| 1244 | 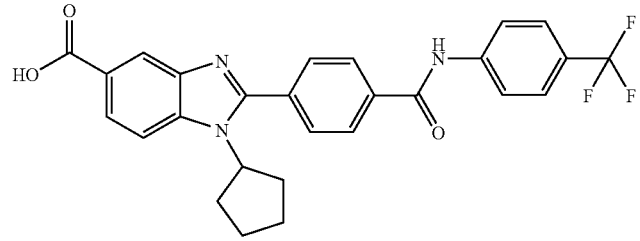 | 494 (M+H) |
| 1245 | 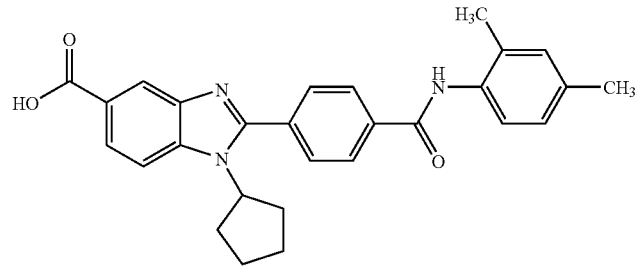 | 454 (M+H) |
TABLE 114
| Ex. No. | Formula | MS |
|---|---|---|
| 1246 | 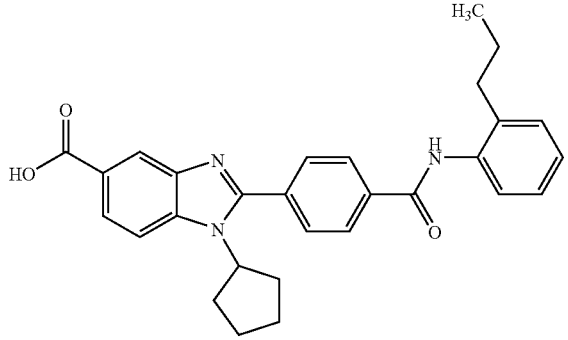 | 468 (M+H) |
| 1247 | 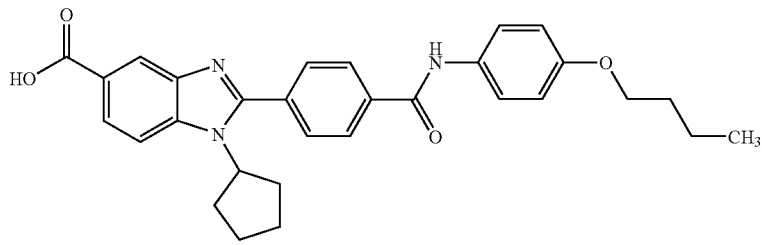 | 498 (M+H) |

TABLE 114-continued

| Ex. No. | Formula | MS |
|---|---|---|
| 1248 | | 482 (M+H) |
| 1249 | | 468 (M+H) |
| 1250 | | 460 (M+H) |

TABLE 115

| Ex. No. | Formula | MS |
|---|---|---|
| 1251 | | 442 (M+H) |

TABLE 115-continued

| Ex. No. | Formula | MS |
|---|---|---|
| 1252 | | 468 (M+H) |
| 1253 | | 456 (M+H) |
| 1254 | | 494 (M+H) |

TABLE 116

| Ex. No. | Formula | MS |
|---|---|---|
| 1255 | | 451 (M+H) |
| 1256 | | 468 (M+H) |
| 1257 | | 498 (M+H) |
| 1258 | | 470 (M+H) |

TABLE 117

| Ex. No. | Formula | MS |
|---|---|---|
| 1259 | | 476 (M+H) |
| 1260 | | 502 (M+H) |
| 1261 | | 505 (M+H) |
| 1262 | | 469 (M+H) |

TABLE 118

| Ex. No. | Formula | MS |
| --- | --- | --- |
| 1263 | | 483 (M+H) |
| 1264 | | 408 (M+H) |
| 1265 | | 460 (M+H) |
| 1266 | | 468 (M+H) |

TABLE 119

| Ex. No. | Formula | MS |
|---|---|---|
| 1267 | | 494 (M+H) |
| 1268 | | 454 (M+H) |
| 1269 | | 468 (M+H) |

TABLE 119-continued

| Ex. No. | Formula | MS |
|---|---|---|
| 1270 | | 498 (M+H) |

TABLE 120

| Ex. No. | Formula | MS |
|---|---|---|
| 1271 | | 482 (M+H) |
| 1272 | | 468 (M+H) |

TABLE 120-continued

| Ex. No. | Formula | MS |
|---------|---------|-----|
| 1273 | | 494 (M+H) |
| 1274 | | 484 (M+H) |

TABLE 121

| Ex. No. | Formula | MS |
|---------|---------|-----|
| 1275 | | 519 (M+H) |
| 1276 | | 427 (M+H) |

TABLE 121-continued
| Ex. No. | Formula | MS |
|---|---|---|
| 1277 | 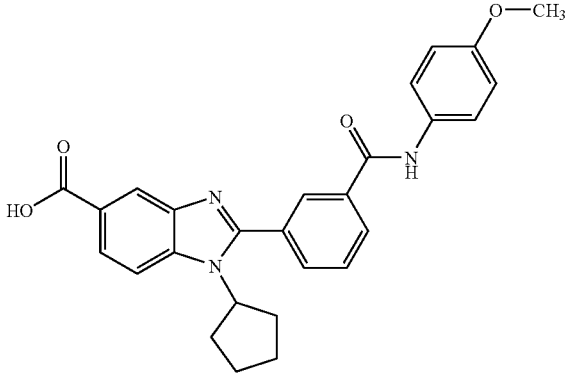 | 456 (M+H) |
| 1278 | 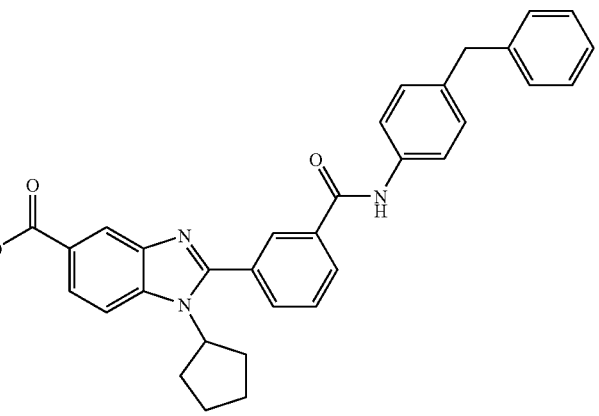 | 516 (M+H) |
TABLE 122
| Ex. No. | Formula | MS |
|---|---|---|
| 1279 | 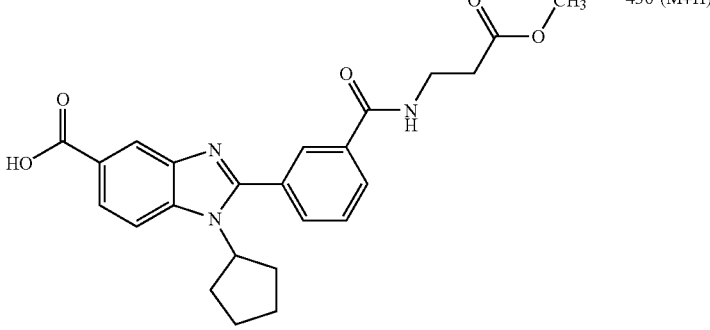 | 436 (M+H) |

TABLE 122-continued

| Ex. No. | Formula | MS |
|---|---|---|
| 1280 | | 426 (M+H) |
| 1281 | | 440 (M+H) |
| 1282 | | 454 (M+H) |
| 1283 | | 468 (M+H) |

TABLE 123

| Ex. No. | Formula | MS |
|---|---|---|
| 1284 | | 482 (M+H) |
| 1285 | | 406 (M+H) |
| 1286 | | 420 (M+H) |
| 1287 | | 508 (M+H) |

TABLE 123-continued
| Ex. No. | Formula | MS |
|---|---|---|
| 1288 | 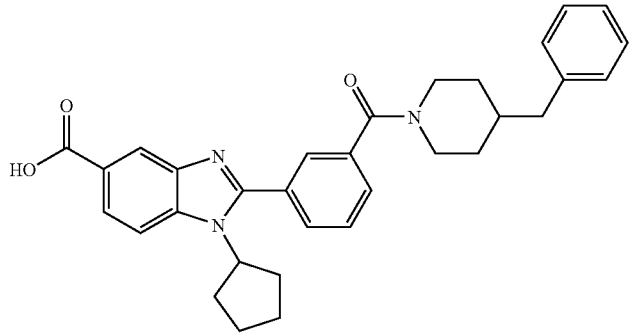 | 508 (M+H) |
TABLE 124
| Ex. No. | Formula | MS |
|---|---|---|
| 1289 | 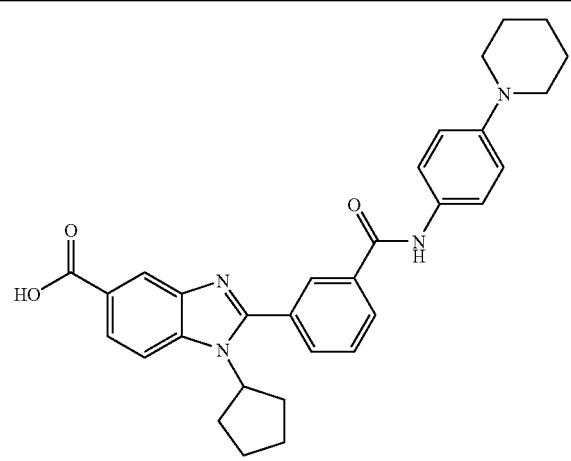 | 509 (M+H) |
| 1290 | 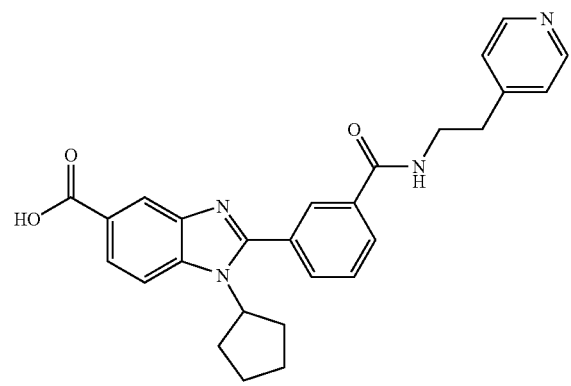 | 455 (M+H) |

TABLE 124-continued

| Ex. No. | Formula | MS |
|---|---|---|
| 1291 | | 494 (M+H) |
| 1292 | | 418 (M+H) |

TABLE 125

| Ex. No. | Formula | MS |
|---|---|---|
| 1293 | | 490 (M+H) |
| 1294 | | 496 (M+H) |

TABLE 125-continued

| Ex. No. | Formula | MS |
|---|---|---|
| 1295 | | 477 (M+H) |
| 1296 | | 508 (M+H) |
| 1297 | | 470 (M+H) |

TABLE 126

| Ex. No. | Formula | MS |
|---|---|---|
| 1298 | | 435 (M+H) |

TABLE 126-continued

| Ex. No. | Formula | MS |
|---|---|---|
| 1299 | | 488 (M+H) |
| 1300 | | 454 (M+H) |
| 1301 | | 504 (M+H) |

TABLE 127
| Ex. No. | Formula | MS |
|---|---|---|
| 1302 | 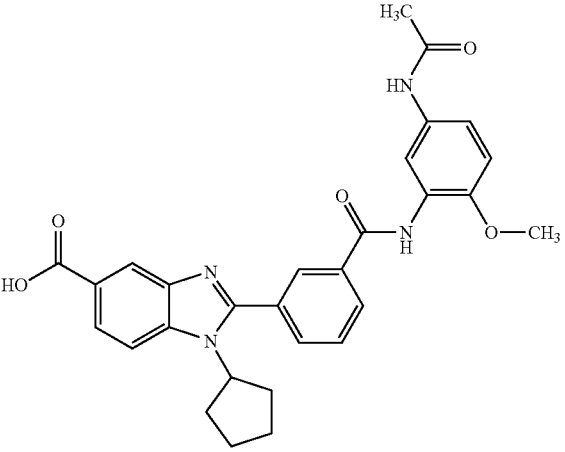 | 513 (M+H) |
| 1303 | 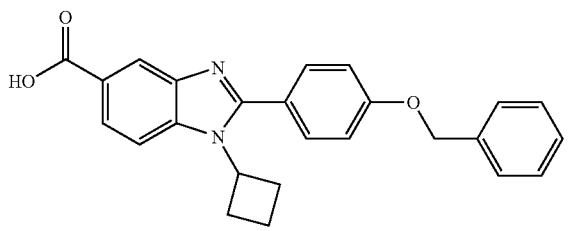 | 399 (M+H) |
| 1304 | 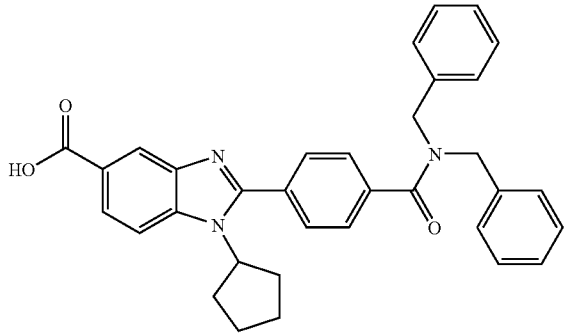 | 530 (M+H) |
| 1305 | 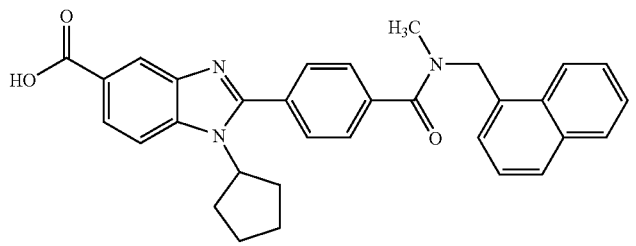 | 504 (M+H) |
| 1306 | 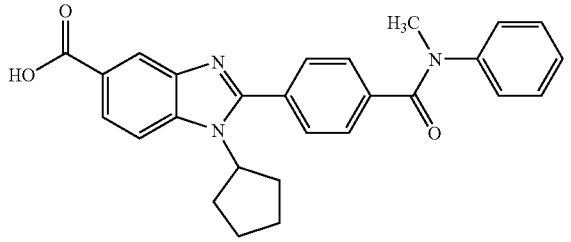 | 440 (M+H) |

TABLE 128

| Ex. No. | Formula | MS |
|---|---|---|
| 1307 | | 494 (M+H) |
| 1308 | | 508 (M+H) |
| 1309 | | 518 (M+H) |
| 1310 | | 532 (M+H) |
| 1311 | | 522 (M+H) |

TABLE 129
| Ex. No. | Formula | MS |
|---|---|---|
| 1312 | 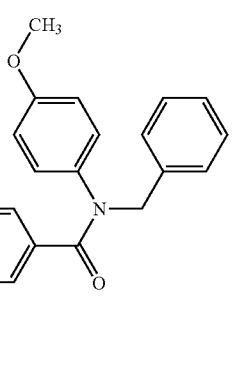 | 546 (M+H) |
| 1313 | 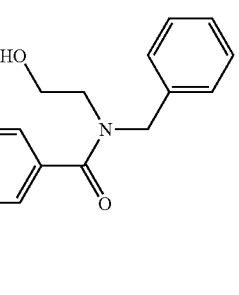 | 484 (M+H) |
| 1314 | 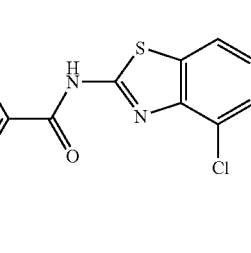 | 517 (M+H) |
| 1315 | 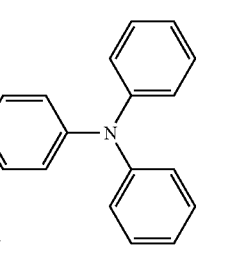 | 488 (M+H) |
| 1316 | 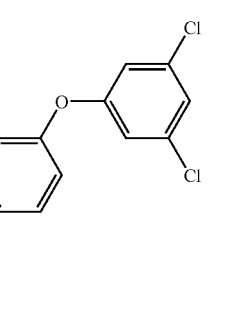 | 481 (M+H) |

TABLE 130

| Ex. No. | Formula | MS |
|---|---|---|
| 1317 | | 413 (M+H) |
| 1318 | | 423 (M+H) |
| 1319 | | 504 (M+H) |
| 1320 | | 510 (M+H) |
| 1321 | | 522 (M+H) |

TABLE 130-continued

| Ex. No. | Formula | MS |
|---|---|---|
| 1322 | | 522 (M+H) |

TABLE 131

| Ex. No. | Formula | MS |
|---|---|---|
| 1323 | | 484 (M+H) |
| 1324 | | 449 (M+H) |
| 1325 | | 502 (M+H) |
| 1326 | | 491 (M+H) |

TABLE 131-continued

| Ex. No. | Formula | MS |
|---|---|---|
| 1327 | | 496 (M+H) |

TABLE 132

| Ex. No. | Formula | MS |
|---|---|---|
| 1328 | | 497 (M+H) |
| 1329 | | 470 (M+H) |
| 1330 | | 530 (M+H) |

TABLE 132-continued

| Ex. No. | Formula | MS |
|---|---|---|
| 1331 | | 502 (M+H) |
| 1332 | | 522 (M+H) |

TABLE 133

| Ex. No. | Formula | MS |
|---|---|---|
| 1333 | | 491 (M+H) |
| 1334 | | 536 (M+H) |

TABLE 133-continued

| Ex. No. | Formula | MS |
|---|---|---|
| 1335 | | 547 (M+H) |
| 1336 | | 484 (M+H) |
| 1337 | | 484 (M+H) |
| 1338 | | 498 (M+H) |

TABLE 134

| Ex. No. | Formula | MS |
|---|---|---|
| 1339 | | 528 (M+H) |

TABLE 134-continued

| Ex. No. | Formula | MS |
|---|---|---|
| 1340 | | 498 (M+H) |
| 1341 | | 514 (M+H) |
| 1342 | | 513 (M+H) |
| 1343 | | 488 (M+H) |
| 1344 | | 502 (M+H) |

TABLE 135

| Ex. No. | Formula | MS |
|---|---|---|
| 1345 | | 488 (M+H) |
| 1346 | | 502 (M+H) |
| 1347 | | 499 (M+H) |
| 1348 | | 480 (M+H) |
| 1349 | | 522 (M+H) |
| 1350 | | 546 (M+H) |

TABLE 136

| Ex. No. | Formula | MS |
|---|---|---|
| 1351 | | 482 (M+H) |
| 1352 | | 484 (M+H) |
| 1353 | | 609 (M+H) |
| 1354 | | 532 (M+H) |
| 1355 | | 480 (M+H) |

TABLE 136-continued
| Ex. No. | Formula | MS |
|---|---|---|
| 1356 | 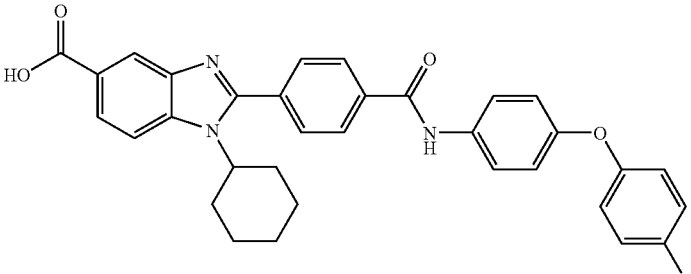 | 566 (M+H) |
TABLE 137
| Ex. No. | Formula | MS |
|---|---|---|
| 1357 | | 602 (M+H) |
| 1358 | | 596 (M+H) |
| 1359 | | 491 (M+H) |
| 1360 | | 491 (M+H) |

TABLE 137-continued

| Ex. No. | Formula | MS |
|---|---|---|
| 1361 | | 491 (M+H) |
| 1362 | | 496 (M+H) |

TABLE 138

| Ex. No. | Formula | MS |
|---|---|---|
| 1363 | | 512 (M+H) |
| 1364 | | 494 (M+H) |
| 1365 | | 488 (M+H) |

TABLE 138-continued

| Ex. No. | Formula | MS |
| --- | --- | --- |
| 1366 | | 481 (M+H) |
| 1367 | | 524 (M+H) |
| 1368 | | 497 (M+H) |

TABLE 139

| Ex. No. | Formula | MS |
| --- | --- | --- |
| 1369 | | 472 (M+H) |
| 1370 | | 469 (M+H) |

TABLE 139-continued

| Ex. No. | Formula | MS |
|---------|---------|-----|
| 1371 | | 470 (M+H) |
| 1372 | | 469 (M+H) |
| 1373 | | 494 (M+H) |
| 1374 | | 458 (M+H) |

TABLE 140

| Ex. No. | Formula | MS |
|---------|---------|-----|
| 1375 | | 612 (M+H) |

TABLE 140-continued

| Ex. No. | Formula | MS |
|---|---|---|
| 1376 | | 554 (M+H) |
| 1377 | | 542 (M+H) |
| 1378 | | 526 (M+H) |
| 1379 | | 496 (M+H) |
| 1380 | | 510 (M+H) |

TABLE 141

| Ex. No. | Formula | MS |
|---|---|---|
| 1381 | | 540 (M+H) |
| 1382 | | 525 (M+H) |
| 1383 | | 558 (M+H) |
| 1384 | | 523 (M+H) |
| 1385 | | 539 (M+H) |

TABLE 142

| Ex. No. | Formula | MS |
|---|---|---|
| 1386 | | 533 (M+H) |
| 1387 | | 500 (M+H) |
| 1388 | | 485 (M+H) |
| 1389 | | 523 (M+H) |
| 1390 | | 512 (M+H) |

TABLE 143
| Ex. No. | Formula | MS |
|---|---|---|
| 1391 | 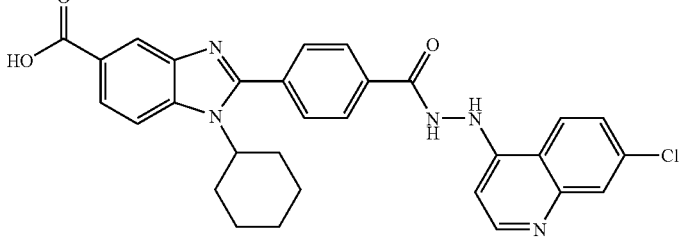 | 540 (M+H) |
| 1392 | 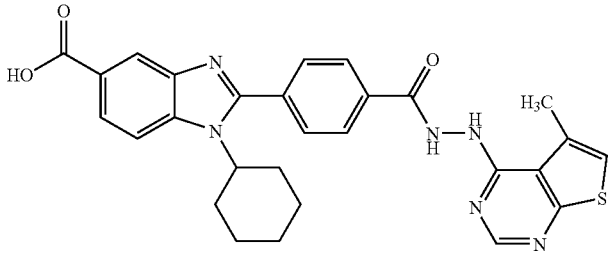 | 527 (M+H) |
| 1393 | 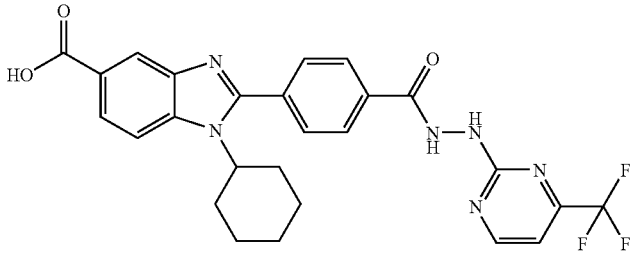 | 525 (M+H) |
| 1394 | 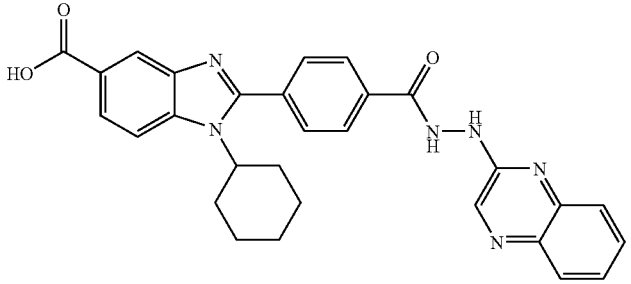 | 507 (M+H) |
| 1395 | 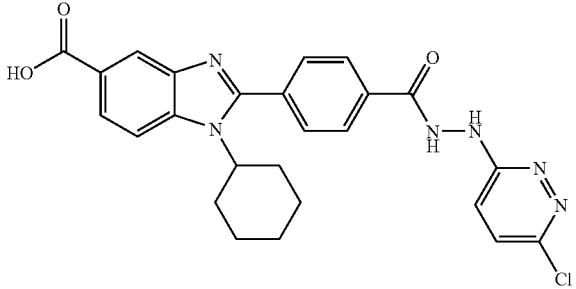 | 491 (M+H) |

TABLE 143-continued

| Ex. No. | Formula | MS |
|---|---|---|
| 1396 | | 506 (M+H) |

TABLE 144

| Ex. No. | Formula | MS |
|---|---|---|
| 1397 | | 522 (M+H) |
| 1398 | | 538 (M+H) |
| 1399 | | 522 (M+H) |

TABLE 144-continued

| Ex. No. | Formula | MS |
|---|---|---|
| 1400 | | 530 (M+H) |
| 1401 | | 600 (M+H) |
| 1402 | | 504 (M+H) |

TABLE 145

| Ex. No. | Formula | MS |
|---|---|---|
| 1403 | | 534 (M+H) |
| 1404 | | 475 (M+H) |

TABLE 145-continued

| Ex. No. | Formula | MS |
|---|---|---|
| 1405 | | 472 (M+H) |
| 1406 | | 455 (M+H) |
| 1407 | | 469 (M+H) |
| 1408 | | 547 (M+H) |

TABLE 146

| Ex. No. | Formula | MS |
|---|---|---|
| 1409 | | 529 (M+H) |

TABLE 146-continued

| Ex. No. | Formula | MS |
|---|---|---|
| 1410 | | 435 (M+H) |
| 1411 | | 504 (M+H) |
| 1412 | | 469 (M+H) |
| 1413 | | 522 (M+H) |
| 1414 | | 488 (M+H) |

TABLE 147

| Ex. No. | Formula | MS |
|---|---|---|
| 1415 | | 502 (M+H) |
| 1416 | | 488 (M+H) |
| 1417 | | 502 (M+H) |
| 1418 | | 455 (M+H) |
| 1419 | | 455 (M+H) |

TABLE 147-continued

| Ex. No. | Formula | MS |
|---|---|---|
| 1420 | | 522 (M+H) |

TABLE 148

| Ex. No. | Formula | MS |
|---|---|---|
| 1421 | | 469 (M+H) |
| 1422 | | 536 (M+H) |
| 1423 | | 510 (M+H) |
| 1424 | | 494 (M+H) |

TABLE 148-continued

| Ex. No. | Formula | MS |
|---|---|---|
| 1425 | | 458 (M+H) |

TABLE 149

| Ex. No. | Formula | MS |
|---|---|---|
| 1426 | | 612 (M+H) |
| 1427 | | 526 (M+H) |
| 1428 | | 480 (M+H) |

TABLE 149-continued

| Ex. No. | Formula | MS |
|---|---|---|
| 1429 | | 441 (M+H) |
| 1430 | | 511 (M+H) |

TABLE 150

| Ex. No. | Formula | MS |
|---|---|---|
| 1431 | | 530 (M+H) |
| 1432 | | 497 (M+H) |
| 1433 | | 441 (M+H) |

TABLE 150-continued
| Ex. No. | Formula | MS |
|---|---|---|
| 1434 | 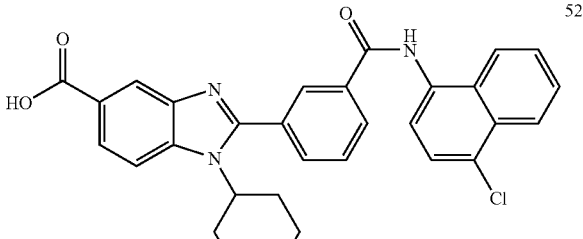 | 491 (M+H) |
| 1435 | | 491 (M+H) |
| 1436 | | 491 (M+H) |
TABLE 151
| Ex. No. | Formula | MS |
|---|---|---|
| 1437 | 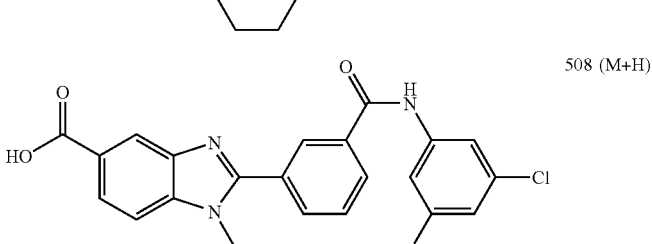 | 524 (M+H) |
| 1438 | | 508 (M+H) |

TABLE 151-continued

| Ex. No. | Formula | MS |
|---|---|---|
| 1439 | | 474 (M+H) |
| 1440 | | 490 (M+H) |
| 1441 | | 508 (M+H) |
| 1442 | | 474 (M+H) |

TABLE 152

| Ex. No. | Formula | MS |
|---|---|---|
| 1443 | | 516 (M+H) |

TABLE 152-continued

| Ex. No. | Formula | MS |
|---|---|---|
| 1444 | | 600 (M+H) |
| 1445 | | 504 (M+H) |
| 1446 | | 534 (M+H) |
| 1447 | | 475 (M+H) |

TABLE 153

| Ex. No. | Formula | MS |
|---|---|---|
| 1448 | | 530 (M+H) |
| 1449 | | 440 (M+H) |
| 1450 | | 490 (M+H) |
| 1451 | | 474 (M+H) |
| 1452 | | 441 (M+H) |

TABLE 153-continued

| Ex. No. | Formula | MS |
|---|---|---|
| 1453 | (benzimidazole-COOH, N-cyclohexyl, 2-(4-((3,4-dichlorobenzyl)aminomethyl)phenyl)) | 508 (M+H) |

TABLE 154

| Ex. No. | Formula | MS |
|---|---|---|
| 1454 | (benzimidazole-COOH, N-cyclohexyl, 2-(4-((2-(pyridin-3-yl)ethyl)aminomethyl)phenyl)) | 455 (M+H) |
| 1455 | (benzimidazole-COOH, N-cyclohexyl, 2-(4-((2-(2,4-dichlorophenyl)ethyl)aminomethyl)phenyl)) | 522 (M+H) |
| 1456 | (benzimidazole-COOH, N-cyclohexyl, 2-(4-((4-tert-butylbenzyl)aminomethyl)phenyl)) | 496 (M+H) |
| 1457 | (benzimidazole-COOH, N-cyclohexyl, 2-(4-((diphenylmethyl)aminomethyl)phenyl)) | 516 (M+H) |

TABLE 154-continued

| Ex. No. | Formula | MS |
|---|---|---|
| 1458 | | 426 (M+H) |
| 1459 | | 482 (M+H) |

TABLE 155

| Ex. No. | Formula | MS |
|---|---|---|
| 1460 | | 486 (M+H) |
| 1461 | | 516 (M+H) |
| 1462 | | 427 (M+H) |

TABLE 155-continued

| Ex. No. | Formula | MS |
|---|---|---|
| 1463 | | 476 (M+H) |
| 1464 | | 460 (M+H) |
| 1465 | | 502 (M+H) |

TABLE 156

| Ex. No. | Formula | MS |
|---|---|---|
| 1466 | | 586 (M + H) |
| 1467 | | 518 (M + H) |

TABLE 156-continued

| Ex. No. | Formula | MS |
|---|---|---|
| 1468 | | 530 (M + H) |
| 1469 | | 598 (M + H) |
| 1470 | | 512 (M + H) |
| 1471 | | 544 (M + H) |

TABLE 157

| Ex. No. | Formula | MS |
|---|---|---|
| 1472 | | 440 (M + H) |

TABLE 157-continued

| Ex. No. | Formula | MS |
|---|---|---|
| 1473 | | 490 (M + H) |
| 1474 | | 474 (M + H) |
| 1475 | | 441 (M + H) |
| 1476 | | 508 (M + H) |
| 1477 | | 455 (M + H) |

TABLE 158

| Ex. No. | Formula | MS |
|---|---|---|
| 1478 | | 522 (M + H) |
| 1479 | | 496 (M + H) |
| 1480 | | 516 (M + H) |
| 1481 | | 426 (M + H) |

TABLE 158-continued
| Ex. No. | Formula | MS |
|---|---|---|
| 1482 | 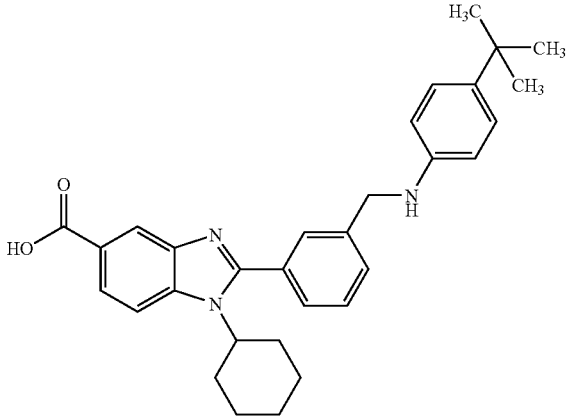 | 482 (M + H) |
TABLE 159
| Ex. No. | Formula | MS |
|---|---|---|
| 1483 | 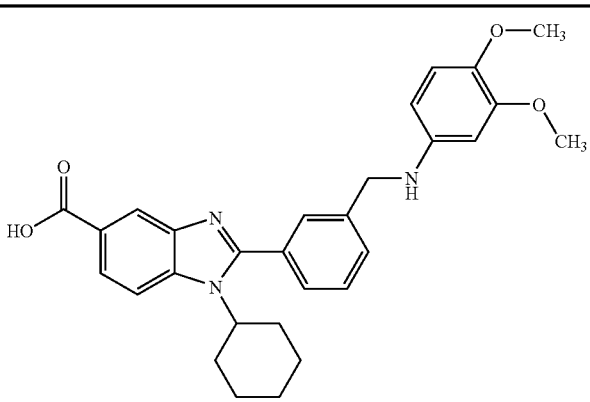 | 486 (M + H) |
| 1484 | 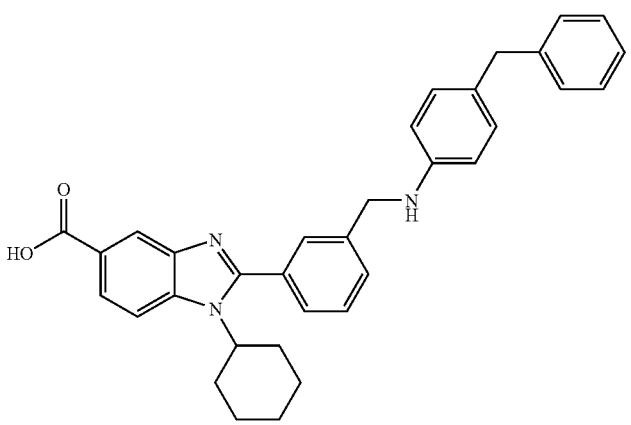 | 516 (M + H) |

TABLE 159-continued

| Ex. No. | Formula | MS |
|---|---|---|
| 1485 | | 427 (M + H) |
| 1486 | | 476 (M + H) |

TABLE 160

| Ex. No. | Formula | MS |
|---|---|---|
| 1487 | | 460 (M + H) |
| 1488 | | 502 (M + H) |

TABLE 160-continued

| Ex. No. | Formula | MS |
|---|---|---|
| 1489 | | 586 (M + H) |
| 1490 | | 518 (M + H) |

TABLE 161

| Ex. No. | Formula | MS |
|---|---|---|
| 1491 | | 530 (M + H) |
| 1492 | | 598 (M + H) |

TABLE 161-continued
| Ex. No. | Formula | MS |
|---|---|---|
| 1493 | 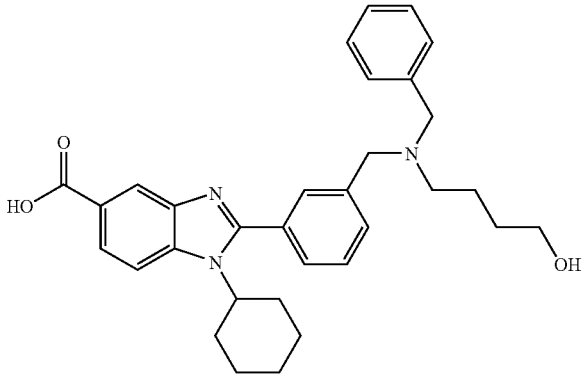 | 512 (M + H) |
| 1494 | 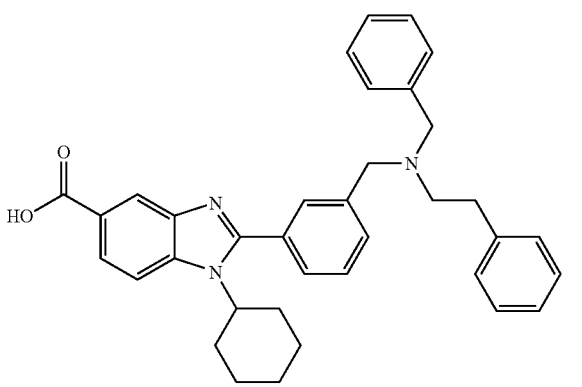 | 544 (M + H) |
TABLE 162
| Ex. No. | Formula | MS |
|---|---|---|
| 1495 | 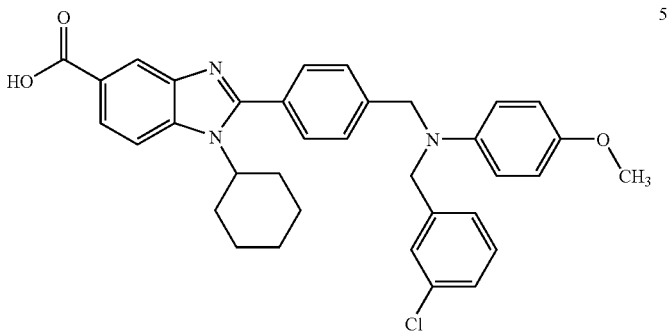 | 580 (M + H) |
| 1496 | 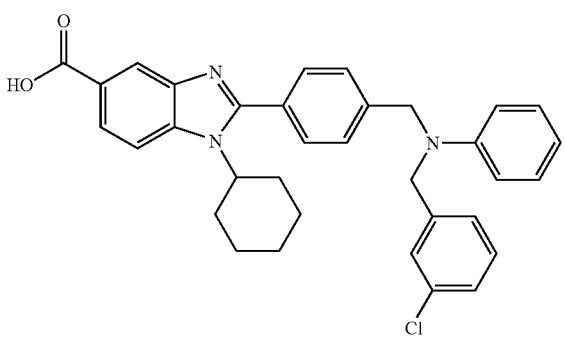 | 550 (M + H) |

TABLE 162-continued

| Ex. No. | Formula | MS |
|---|---|---|
| 1497 | | 606 (M + H) |
| 1498 | | 580 (M + H) |
| 1499 | | 550 (M + H) |

TABLE 163

| Ex. No. | Formula | MS |
|---|---|---|
| 1500 | | 606 (M + H) |
| 1501 | | 630 (M + H) |
| 1502 | | 600 (M + H) |
| 1503 | | 656 (M + H) |

TABLE 164
| Ex. No. | Formula | MS |
|---|---|---|
| 1504 | 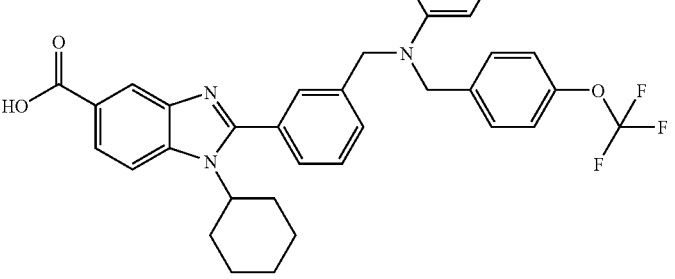 | 630 (M + H) |
| 1505 | 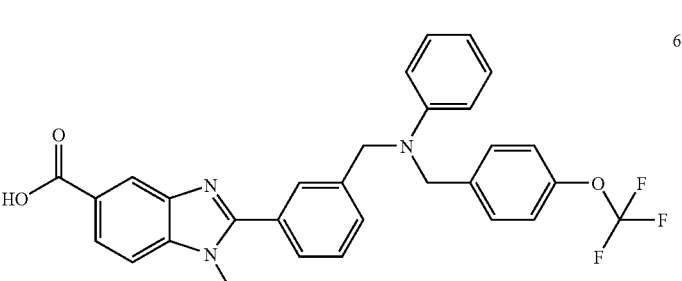 | 600 (M + H) |
| 1506 | 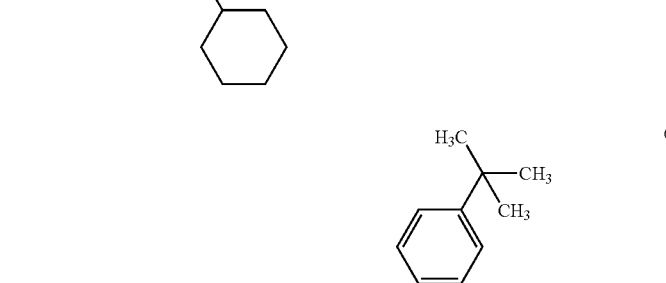 | 656 (M + H) |
| 1507 | 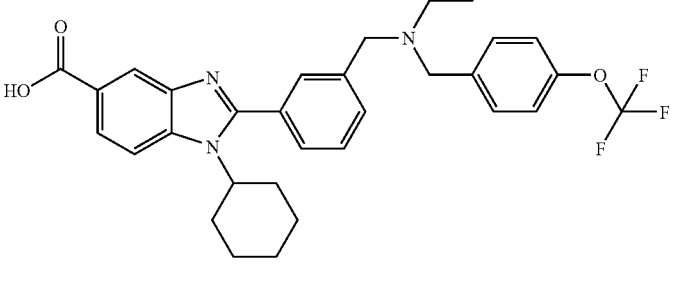 | 580 (M + H) |

TABLE 165

| Ex. No. | Formula | MS |
|---|---|---|
| 1508 | | 550 (M + H) |
| 1509 | | 606 (M + H) |
| 1510 | | 580 (M + H) |
| 1511 | | 550 (M + H) |

TABLE 165-continued
| Ex. No. | Formula | MS |
|---|---|---|
| 1512 | 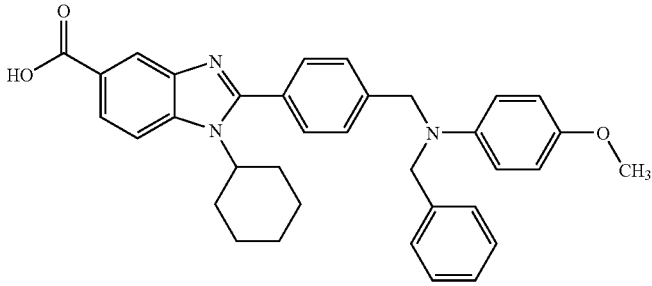 | 546 (M + H) |
TABLE 166
| Ex. No. | Formula | MS |
|---|---|---|
| 1513 | 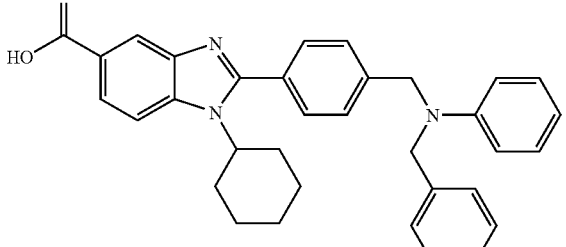 | 516 (M + H) |
| 1514 | 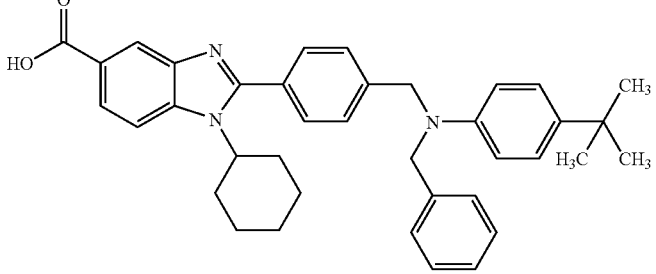 | 572 (M + H) |
| 1515 | 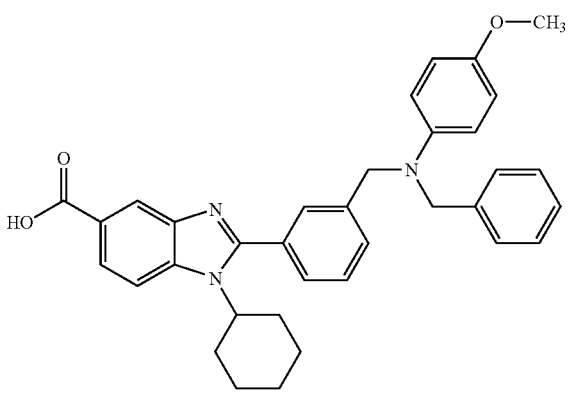 | 546 (M + H) |

TABLE 166-continued
| Ex. No. | Formula | MS |
|---|---|---|
| 1516 | 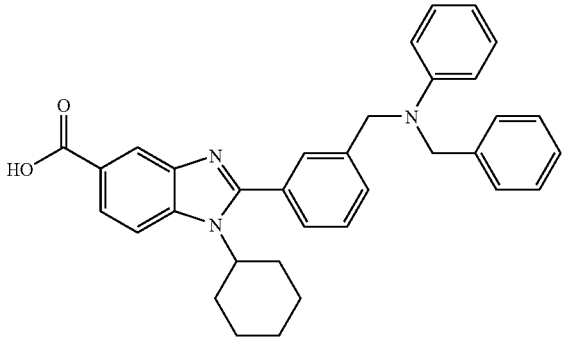 | 516 (M + H) |
| 1517 | 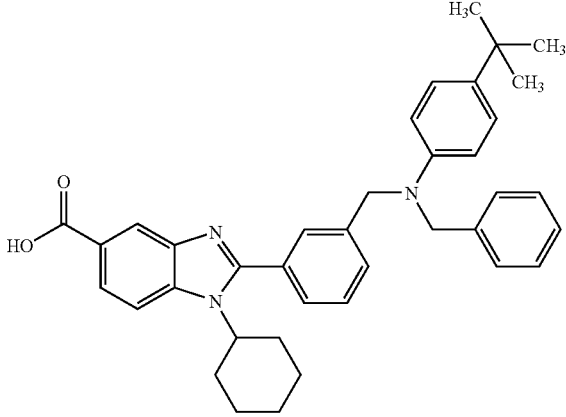 | 572 (M + H) |
TABLE 167
| Ex. No. | Formula | MS |
|---|---|---|
| 1518 | 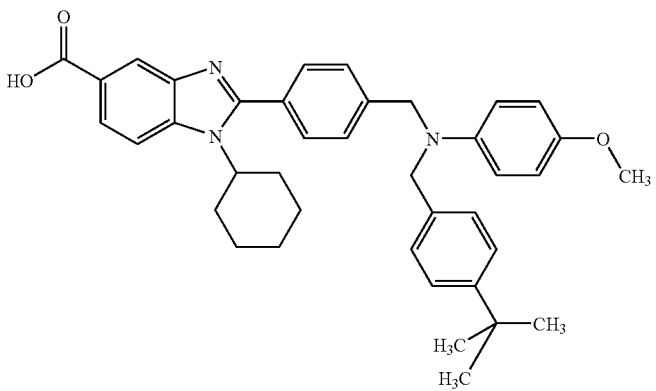 | 602 (M + H) |

TABLE 167-continued

| Ex. No. | Formula | MS |
|---|---|---|
| 1519 | | 572 (M + H) |
| 1520 | | 628 (M + H) |
| 1521 | | 606 (M + H) |

TABLE 168
| Ex. No. | Formula | MS |
|---|---|---|
| 1522 | 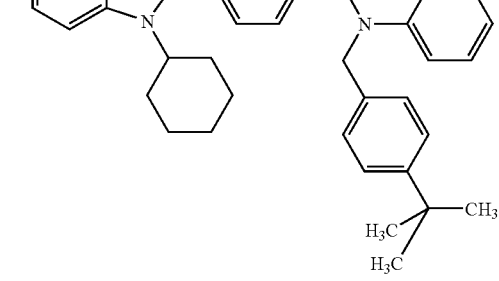 | 573 (M + H) |
| 1523 | 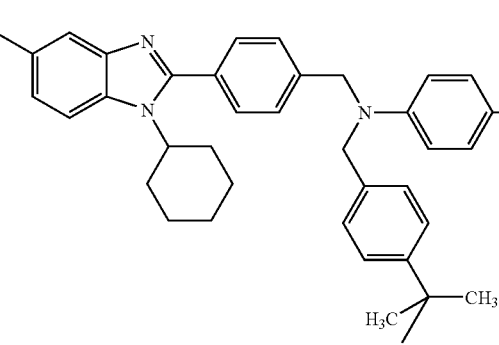 | 606 (M + H) |
| 1524 | 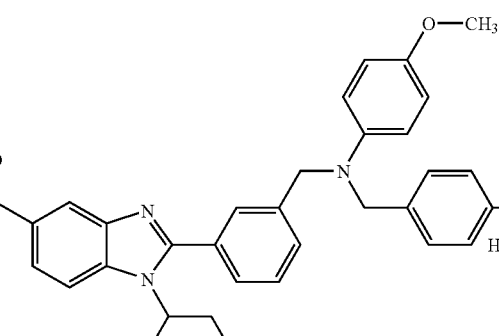 | 602 (M + H) |
| 1525 | 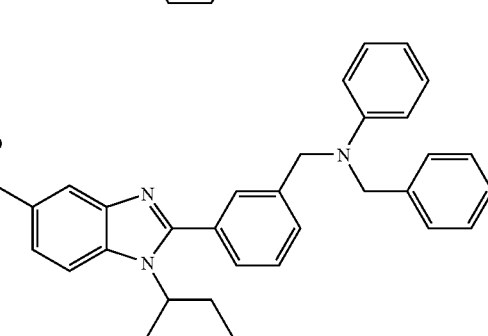 | 572 (M + H) |

TABLE 169

| Ex. No. | Formula | MS |
|---|---|---|
| 1526 | | 628 (M + H) |
| 1527 | | 606 (M + H) |
| 1528 | | 606 (M + H) |
| 1529 | | 614 (M + H) |

TABLE 170
| Ex. No. | Formula | MS |
|---|---|---|
| 1530 | 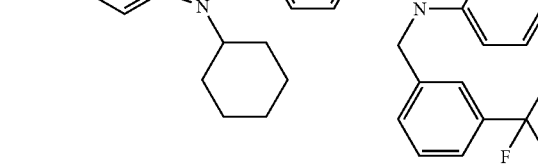 | 584 (M + H) |
| 1531 | 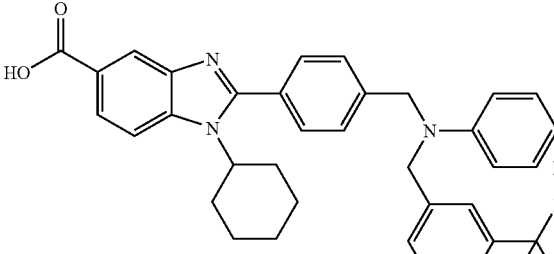 | 640 (M + H) |
| 1532 | 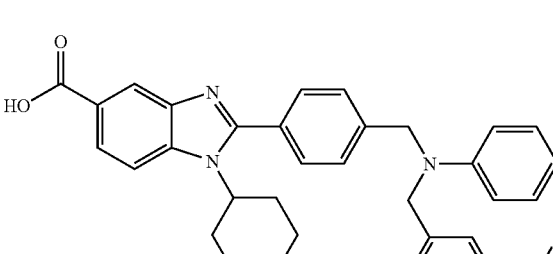 | 618 (M + H) |
| 1533 |  | 614 (M + H) |

TABLE 170-continued

| Ex. No. | Formula | MS |
|---|---|---|
| 1534 | | 584 (M + H) |

TABLE 171

| Ex. No. | Formula | MS |
|---|---|---|
| 1535 | | 640 (M + H) |
| 1536 | | 627 (M + H) |

TABLE 171-continued

| Ex. No. | Formula | MS |
|---|---|---|
| 1537 | | 627 (M + H) |

TABLE 172

| Ex. No. | Formula | MS |
|---|---|---|
| 1538 | | 560 (M + H) |
| 1539 | | 634 (M + H) |

TABLE 172-continued
| Ex. No. | Formula | MS |
| --- | --- | --- |
| 1540 | 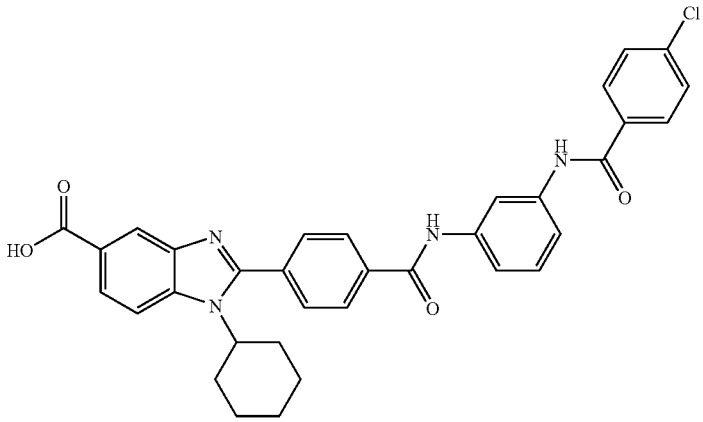 | 593 (M + H) |
| 1541 | 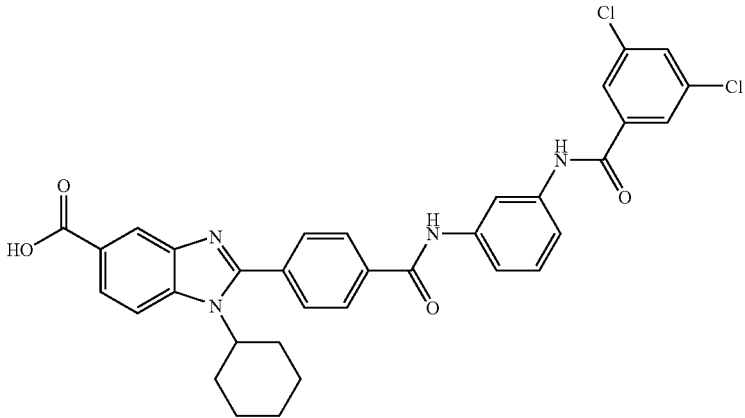 | 627 (M + H) |
TABLE 173
| Ex. No. | Formula | MS |
| --- | --- | --- |
| 1542 | 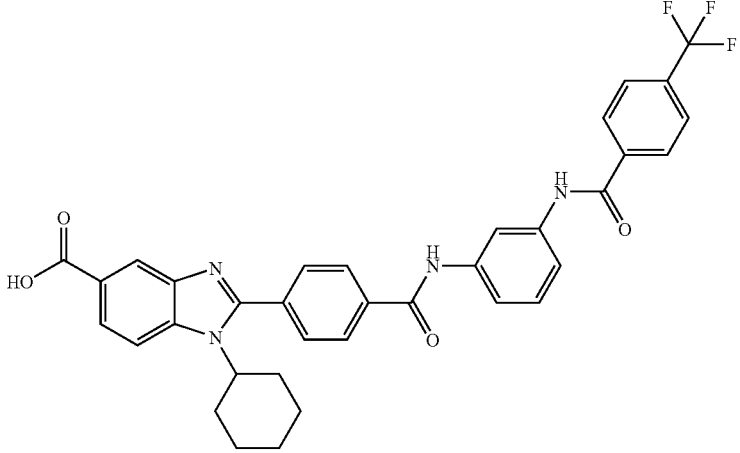 | 627 (M + H) |

TABLE 173-continued
| Ex. No. | Formula | MS |
|---|---|---|
| 1543 | 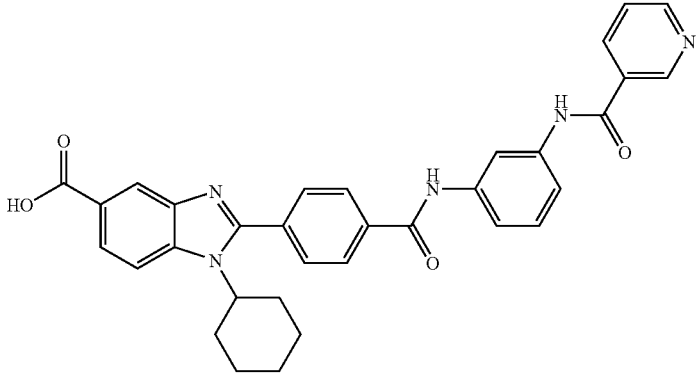 | 560 (M + H) |
| 1544 | 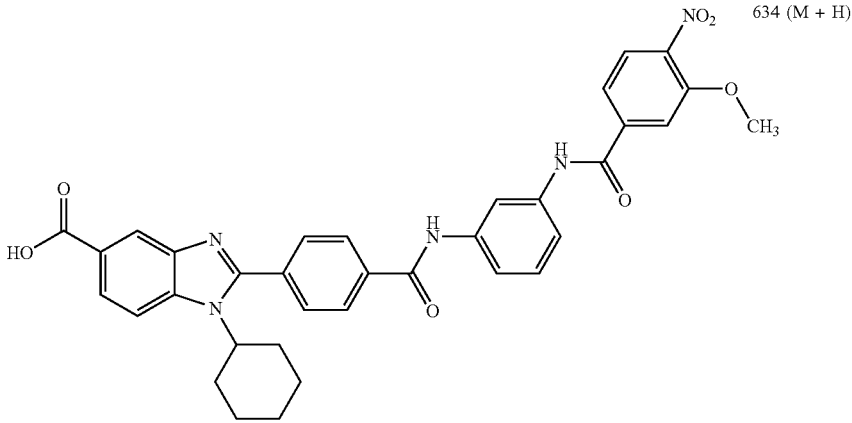 | 634 (M + H) |
| 1545 | 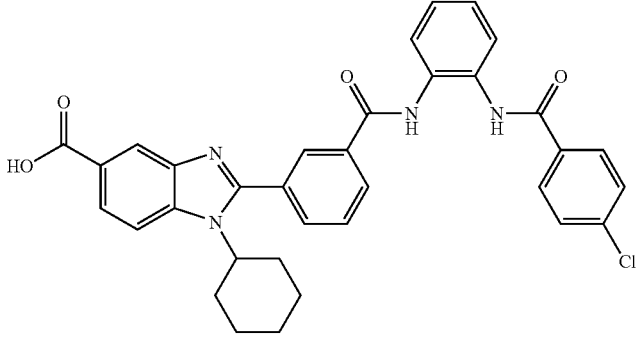 | 593 (M + H) |

TABLE 174

| Ex. No. | Formula | MS |
|---|---|---|
| 1546 | | 627 (M + H) |
| 1547 | | 627 (M + H) |
| 1548 | | 560 (M + H) |
| 1549 | | 634 (M + H) |

TABLE 175

| Ex. No. | Formula | MS |
|---|---|---|
| 1550 | | 627 (M + H) |
| 1551 | | 560 (M + H) |
| 1552 | | 532 (M + H) |
| 1553 | | 565 (M + H) |

TABLE 176
| Ex. No. | Formula | MS |
|---|---|---|
| 1554 | 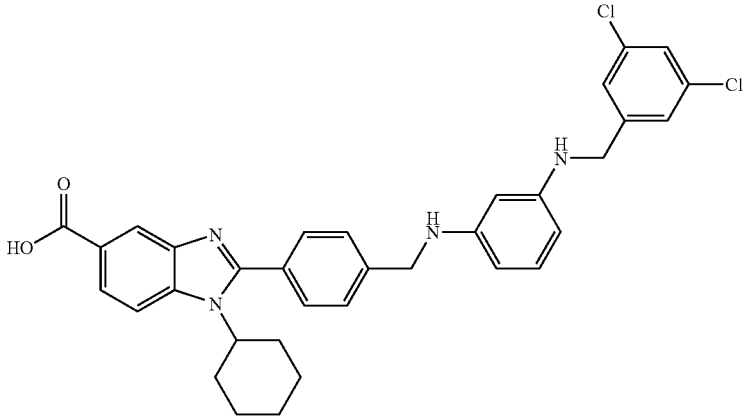 | 599 (M+H) |
| 1555 | 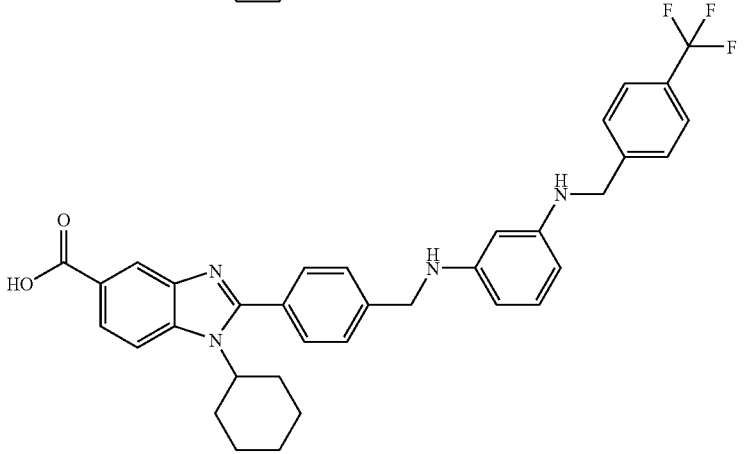 | 599 (M+H) |
| 1556 | 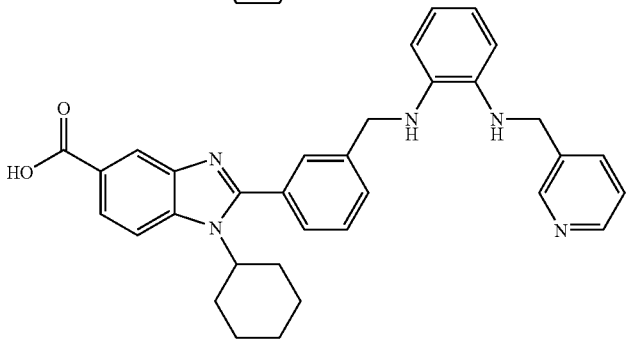 | 532 (M+H) |
| 1557 | 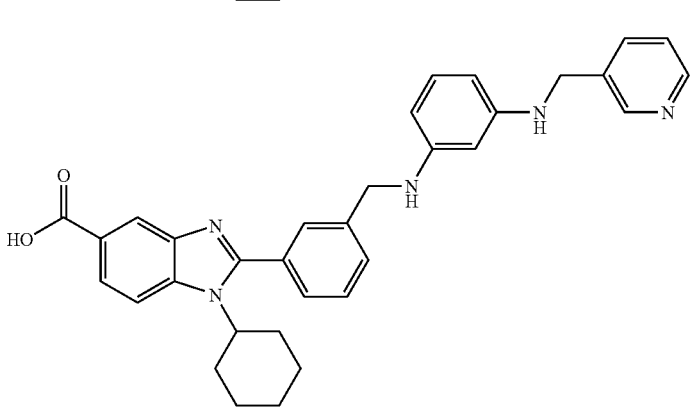 | 532 (M+H) |

TABLE 177

| Ex. No. | Formula | MS |
|---|---|---|
| 1558 | | 584 (M+H) |
| 1559 | | 570 (M+H) |

TABLE 178

| Ex. No. | HCV polymerase inhibitory activity IC$_{50}$ [μM] |
|---|---|
| 2 | 0.079 |
| 6 | 0.034 |
| 9 | 0.019 |
| 11 | 0.53 |
| 12 | 0.60 |
| 17 | 0.047 |
| 20 | 0.042 |
| 26 | 0.033 |
| 30 | 0.052 |
| 43 | 0.58 |
| 44 | 0.95 |
| 45 | 0.40 |
| 46 | 0.47 |
| 47 | 0.54 |
| 48 | 0.44 |
| 49 | 0.94 |
| 50 | 0.54 |
| 51 | 1.0 |
| 54 | 0.56 |
| 55 | 0.36 |
| 67 | 0.26 |
| 68 | 0.28 |
| 70 | 0.19 |
| 71 | 0.62 |
| 77 | 0.51 |
| 81 | 0.18 |
| 82 | 0.097 |
| 83 | 0.52 |
| 85 | 0.17 |
| 86 | 0.13 |
| 87 | 0.80 |
| 88 | 0.092 |
| 89 | 0.34 |

TABLE 178-continued

| Ex. No. | HCV polymerase inhibitory activity IC$_{50}$ [μM] |
|---|---|
| 90 | 0.20 |
| 91 | 0.53 |
| 93 | 0.16 |
| 94 | 0.084 |
| 96 | 0.25 |
| 97 | 0.16 |
| 98 | 0.30 |

TABLE 179

| Ex. No. | HCV polymerase inhibitory activity IC$_{50}$ [μM] |
|---|---|
| 99 | 0.53 |
| 100 | 0.78 |
| 101 | 0.14 |
| 103 | 0.17 |
| 104 | 0.073 |
| 105 | 0.076 |
| 106 | 0.40 |
| 107 | 0.11 |
| 108 | 0.21 |
| 109 | 0.11 |
| 110 | 0.24 |
| 111 | 0.14 |
| 112 | 0.11 |
| 113 | 0.071 |
| 114 | 0.56 |
| 115 | 0.17 |

TABLE 179-continued

| Ex. No. | HCV polymerase inhibitory activity IC$_{50}$ [μM] |
|---|---|
| 116 | 0.37 |
| 117 | 0.075 |
| 118 | 0.14 |
| 119 | 0.13 |
| 120 | 0.16 |
| 121 | 0.19 |
| 122 | 0.51 |
| 123 | 0.10 |
| 124 | 0.091 |
| 125 | 0.12 |
| 128 | 0.14 |
| 129 | 0.12 |
| 130 | 0.16 |
| 131 | 0.046 |
| 132 | 0.055 |
| 133 | 0.12 |
| 134 | 0.071 |
| 139 | 0.26 |
| 140 | 0.11 |
| 141 | 0.43 |
| 142 | 0.055 |
| 143 | 0.053 |
| 144 | 0.19 |
| 145 | 0.088 |

TABLE 180

| Ex. No. | HCV polymerase inhibitory activity IC$_{50}$ [μM] |
|---|---|
| 146 | 0.043 |
| 147 | 0.31 |
| 148 | 0.038 |
| 149 | 0.15 |
| 150 | 0.24 |
| 151 | 0.20 |
| 153 | 0.19 |
| 154 | 0.076 |
| 155 | 0.53 |
| 156 | 0.23 |
| 157 | 0.16 |
| 158 | 0.11 |
| 159 | 0.13 |
| 160 | 0.24 |
| 161 | 0.062 |
| 162 | 0.43 |
| 163 | 0.15 |
| 164 | 0.16 |
| 165 | 0.58 |
| 166 | 0.055 |
| 167 | 0.033 |
| 168 | 0.078 |
| 169 | 0.15 |
| 170 | 0.048 |
| 171 | 0.050 |
| 172 | 0.10 |
| 173 | 0.14 |
| 174 | 0.030 |
| 175 | 0.29 |
| 176 | 0.053 |
| 177 | 0.077 |
| 178 | 0.052 |
| 179 | 0.63 |
| 180 | 0.11 |
| 181 | 0.71 |
| 182 | 0.021 |
| 183 | 0.017 |
| 184 | 0.018 |
| 185 | 0.11 |
| 186 | 0.37 |

TABLE 181

| Ex. No. | HCV polymerase inhibitory activity IC$_{50}$ [μM] |
|---|---|
| 187 | 0.056 |
| 188 | 0.038 |
| 189 | 0.017 |
| 190 | 0.020 |
| 191 | 0.43 |
| 192 | 0.22 |
| 193 | 0.13 |
| 194 | 0.52 |
| 195 | 0.023 |
| 196 | 0.20 |
| 197 | 0.11 |
| 198 | 0.044 |
| 199 | 0.11 |
| 200 | 0.10 |
| 201 | 0.14 |
| 202 | 0.095 |
| 203 | 0.063 |
| 204 | 0.16 |
| 205 | 0.077 |
| 206 | 0.05 |
| 207 | 0.081 |
| 208 | 0.039 |
| 209 | 0.12 |
| 210 | 0.31 |
| 211 | 0.059 |
| 212 | 0.23 |
| 213 | 0.10 |
| 214 | 0.059 |
| 215 | 0.078 |
| 216 | 0.084 |
| 217 | 0.058 |
| 218 | 0.033 |
| 219 | 0.13 |
| 220 | 0.073 |
| 221 | 0.058 |
| 222 | 0.041 |
| 223 | 0.21 |
| 225 | 0.014 |
| 227 | 0.045 |
| 228 | 0.18 |

TABLE 182

| Ex. No. | HCV polymerase inhibitory activity IC$_{50}$ [μM] |
|---|---|
| 229 | 0.022 |
| 230 | 0.17 |
| 231 | 0.073 |
| 232 | 0.015 |
| 233 | 0.028 |
| 234 | 0.022 |
| 235 | 0.036 |
| 236 | 0.075 |
| 237 | 0.015 |
| 238 | 0.19 |
| 239 | 0.17 |
| 240 | 0.055 |
| 248 | 0.012 |
| 249 | 0.022 |
| 250 | 0.018 |
| 252 | 0.32 |
| 253 | 0.65 |
| 254 | 0.038 |
| 255 | 0.038 |
| 256 | 0.079 |
| 257 | 0.074 |
| 259 | 0.10 |
| 260 | 0.27 |
| 262 | 0.013 |
| 263 | 0.035 |

TABLE 182-continued
| Ex. No. | HCV polymerase inhibitory activity IC$_{50}$ [μM] |
|---|---|
| 264 | <0.01 |
| 265 | 0.014 |
| 266 | 0.018 |
| 267 | 0.014 |
| 268 | 0.012 |
| 269 | 0.013 |
| 270 | 0.012 |
| 271 | 0.024 |
| 272 | 0.066 |
| 273 | 0.041 |
| 276 | 0.023 |
| 279 | 0.017 |
| 280 | 0.016 |
| 281 | 0.052 |
| 282 | 0.019 |
TABLE 183
| Ex. No. | HCV polymerase inhibitory activity IC$_{50}$ [μM] |
|---|---|
| 283 | 0.014 |
| 284 | 0.014 |
| 285 | 0.012 |
| 286 | 0.014 |
| 287 | 0.012 |
| 288 | 0.013 |
| 289 | <0.01 |
| 290 | 0.012 |
| 291 | 0.016 |
| 292 | 0.015 |
| 293 | 0.034 |
| 294 | 0.032 |
| 295 | 0.045 |
| 296 | 0.034 |
| 297 | 0.022 |
| 298 | 0.011 |
| 299 | 0.018 |
| 300 | 0.045 |
| 301 | 0.017 |
TABLE 183-continued
| Ex. No. | HCV polymerase inhibitory activity IC$_{50}$ [μM] |
|---|---|
| 303 | 0.10 |
| 304 | 0.017 |
| 305 | 0.01 |
| 306 | 0.013 |
| 307 | 0.022 |
| 308 | 0.023 |
| 311 | 0.16 |
| 312 | 0.023 |
| 313 | 0.025 |
| 314 | 0.097 |
| 315 | 0.028 |
| 316 | 0.022 |
| 317 | 0.032 |
| 318 | 0.012 |
| 319 | 0.030 |
TABLE 184
| Ex. No. | HCV polymerase inhibitory activity IC$_{50}$ [μM] |
|---|---|
| 320 | 0.036 |
| 321 | 0.015 |
| 322 | 0.016 |
| 323 | 0.018 |
| 324 | 0.027 |
| 325 | 0.019 |
| 326 | 0.018 |
| 327 | 0.019 |
| 328 | 0.015 |
| 329 | 0.047 |
| 330 | 0.011 |
| 331 | 0.017 |
| 332 | 0.023 |
| 333 | 0.016 |
| 334 | 0.016 |
| 335 | 0.013 |
TABLE 185
| Example No. 249 | 1H NMR(δ)ppm |
|---|---|
| 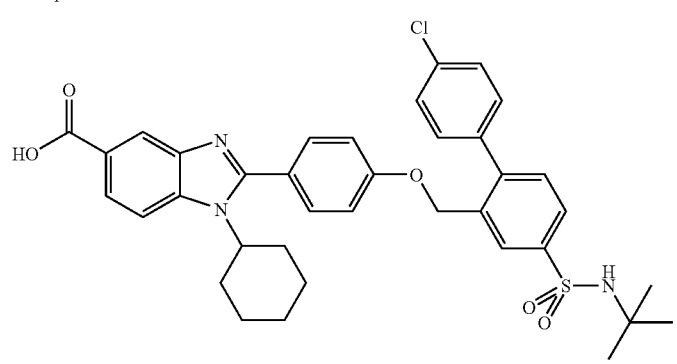 | 300MHz, DMSO-d6<br>8.02(1H, d, J=1.5Hz), 8.11(1H, d, J=1.8Hz), 7.96–7.81(3H, m), 7.67(1H, s), 7.61–7.49(6H, m), 7.08(2H, d, J=8.6Hz), 5.19(2H, s), 4.25(1H, m), 2.38–2.17(2H, m), 1.96–1.78(4H, m), 1.70–1.56(1H, m), 1.46–1.16(3H, m), 1.11(9H, s) |
| Purity | >90% (NMR) |
| MS | 672(M+1) |

TABLE 185-continued

Example No. 250

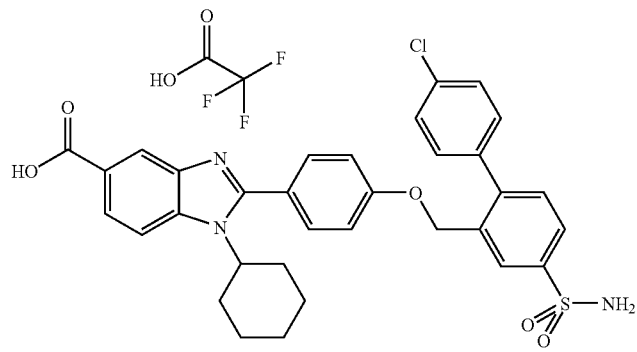

Purity >90% (NMR)
MS 616 (M+1)

1H NMR(δ)ppm
300MHz, DMSO-d6
8.25(1H, d, J=1.5Hz), 8.16–8.08(2H, m), 7.99–7.88(2H, m), 7.66(2H, d, J=8.6Hz), 7.60–7.48(5H, m), 7.19(2H, d, J=8.6Hz), 5.17(2H, s), 4.31(1H, m), 2.39–2.20(2H, m), 2.04–1.79(4H, m), 1.72–1.60(1H, m), 1.50–1.18(3H, m)

Example No. 251

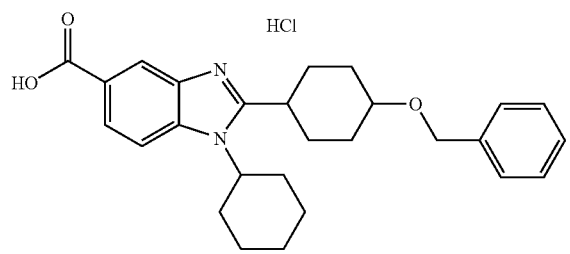

Purity >90% (NMR)
MS 433 (M+1)

1H NMR(δ)ppm
300MHz, DMSO-d6
cis and trans mixture 8.13 and 8.11 (total 1H, each s), 7.90–7.42 (2H, m), 7.42–7.22(5H, m), 4.56 and 4.52(total 2H, each s), 4.42(1H, brs), 3.78–3.06(2H, m)2.33–1.33(18H, m)

TABLE 186

Example No. 252

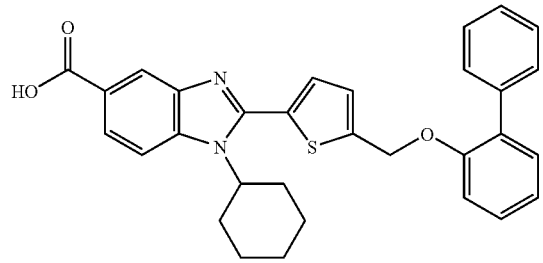

Purity >90% (NMR)
MS 509 (M+1)

1H NMR(δ)ppm
300MHz, DMSO-d6
8.20(1H, d, J=1.5Hz), 7.96(1H, d, J=8.6Hz), 7.84(1H, dd, J=8.6, 1.5Hz), 7.54(2H, d, J=6.9Hz), 7.48–7.26(8H, m), 7.09(1H, t, J=7.3Hz), 5.43(2H, s), 4.06(1H, m), 2.40–2.20(2H, m), 2.01–1.80(4H, m), 1.75–1.64(1H, m), 1.51–1.28(3H, m)

Example No. 253

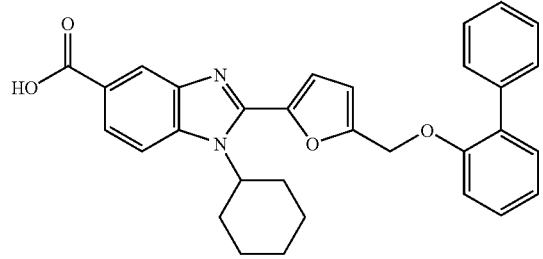

Purity >90% (NMR)
MS 493 (M+1)

1H NMR(δ)ppm
300MHz, DMSO-d6
8.21(1H, d, J=1.5Hz), 7.93(1H, d, J=8.7Hz), 7.85(1H, dd, J=8.4, 1.5Hz), 7.54–7.47(2H, m), 7.40–7.24(6H, m), 7.15(1H, d, J=3.6Hz), 7.11–7.05(1H, m), 6.81(1H, d, J=3.6Hz), 5.26(2H, s), 4.96(1H, m), 2.32–2.13(2H, m), 1.95–1.72(4H, m), 1.68–1.55(1H, m), 1.43–1.18(3H, m)

TABLE 186-continued

| Example No. 254 | 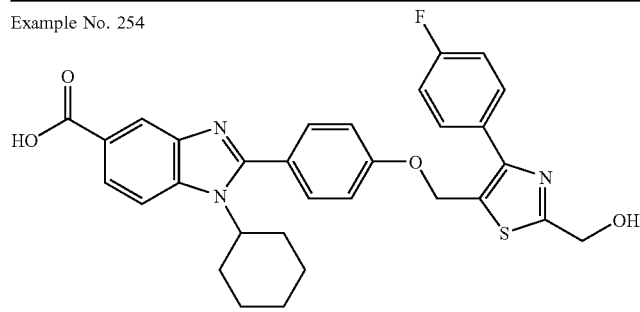 | 1H NMR(δ)ppm<br>300MHz, DMSO-d6<br>8.25(1H, s), 8.02(1H, d, J=8.7Hz), 7.90(1H, dd, J=8.4, 1.4Hz), 7.80–7.71(2H, m), 7.67(2H, d, J=8.7Hz), 7.33(2H, t, J=8.7Hz), 7.26(2H, d, J=8.7Hz), 5.46(2H, s), 4.78(2H, s), 4.31(1H, m), 2.39–2.19(2H, m), 2.03–1.79(4H, m), 1.71–1.59(1H, m), 1.50–1.17(3H, m) |
|---|---|---|
| Purity | >90% (NMR) | |
| MS | 558 (M+1) | |

TABLE 187

| Example No. 255 | 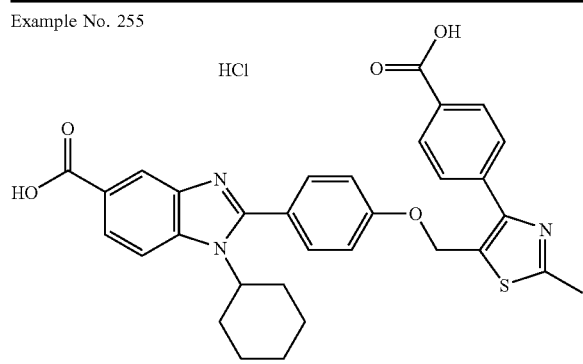 | 1H NMR(δ)ppm<br>300MHz, DMSO-d6<br>8.34(1H, s), 8.32(1H, d, J=8.8Hz), 8.09–8.03(3H, m), 7.83(2H, d, J=8.3Hz), 7.79(2H, d, J=8.8Hz), 7.36(2H, d, J=8.8Hz), 5.54(2H, s), 4.38(1H, m), 2.74(3H, s), 2.40–2.18(2H, m), 2.13–1.96(2H, m), 1.93–1.78(2H, m), 1.73–1.57(1H, m), 1.55–1.15(3H, m) |
|---|---|---|
| Purity | >90% (NMR) | |
| MS | 568 (M+1) | |
| Example No. 256 | 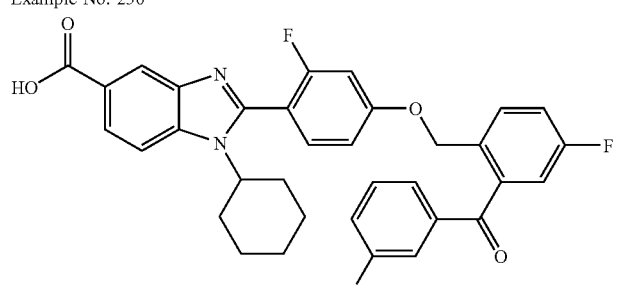 | 1H NMR(δ)ppm<br>300MHz, DMSO-d6<br>12.67(1H, brs), 8.23(1H, s), 7.94 and 7.87(2H, ABq, J=8.6Hz), 7.79(1H, dd, J=8.7, 5.4Hz), 7.62–7.41(7H, m), 6.80(1H, dd, J=11.9, 2.3Hz), 6.69(1H, dd, J=8.1, 2.1Hz), 5.20(2H, s), 3.93(1H, brt, J=15.3Hz), 2.30–2.11(2H, brm)1.88–1.74(4H, brm), 1.64–1.58(1H, brm), 1.41–1.14(3H, brm) |
| Purity | >90% (NMR) | |
| MS | 585 (M+1) | |
| Example No. 257 | 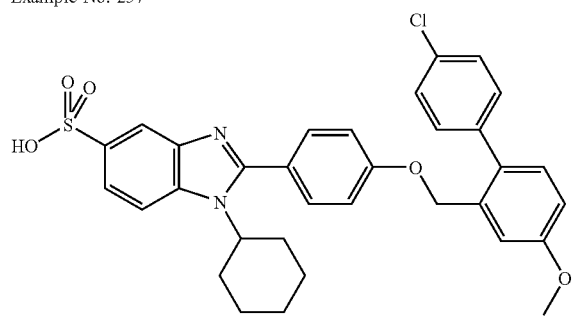 | 1H NMR(δ)ppm<br>300MHz, DMSO-d6<br>8.19(1H, d, J=8.7Hz), 7.93(1H, s), 7.83–7.71(3H, m), 7.50–7.39(4H, m), 7.34–7.10(4H, m), 7.06(1H, dd, J=8.4, 2.9Hz), 5.09(2H, s), 4.34(1H, m), 3.82(3H, s), 2.39–2.19(2H, m), 2.11–1.98(2H, m), 1.94–1.79(2H, m), 1.74–1.58(1H, m), 1.52–1.21(3H, m) |
| Purity | >90% (NMR) | |
| MS | 603 (M+1) | |

TABLE 188

Example No. 258

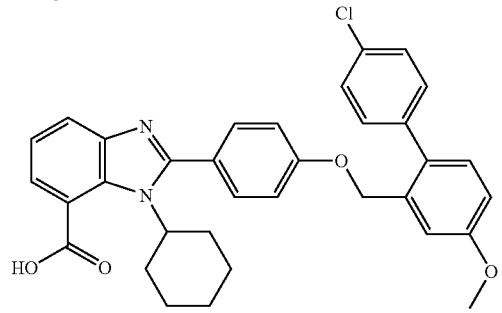

Purity >90% (NMR)
MS 567 (M+1)

1H NMR(δ)ppm
300MHz, DMSO-d6
7.79(1H, d, J=6.7Hz), 7.56(1H, d, J=7.5Hz), 7.49(2H, d, J=8.6Hz), 7.42(4H, s), 7.32–7.23(3H, m), 7.09–7.03(3H, m), 5.02(2H, s), 4.46(1H, m), 3.82(3H, s), 1.95–1.83(2H, m), 1.75–1.44(5H, m), 1.30–1.10(2H, m), 0.89–0.71(1H, m)

Example No. 259

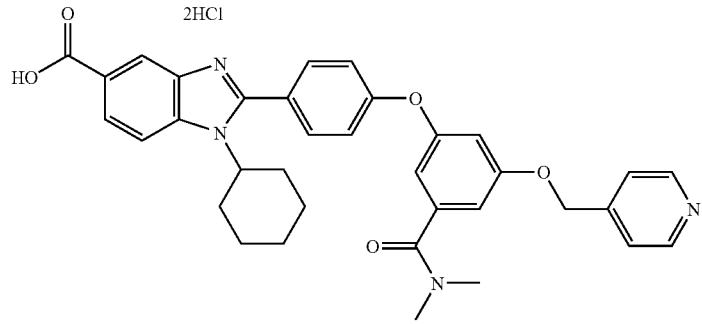

Purity >90% (NMR)
MS 591 (M+1)

1H NMR(δ)ppm
300MHz, DMSO-d6
8.93(2H, d, J=6.6Hz), 8.36(1H, s), 8.28(1H, d, J=8.7Hz), 8.10–8.03(3H, m), 7.85(2H, d, J=8.7Hz), 7.33(2H, d, J=8.7Hz), 7.23(1H, s), 7.23(1H, s), 6.81(1H, s), 5.56(2H, s), 4.39(1H, m), 2.97, 2.92(6H, s), 2.40–2.18(2H, m), 2.16–1.95(2H, m), 1.90–1.75(2H, m), 1.70–1.55(1H, m), 1.50–1.15(3H, m)

Example No. 260

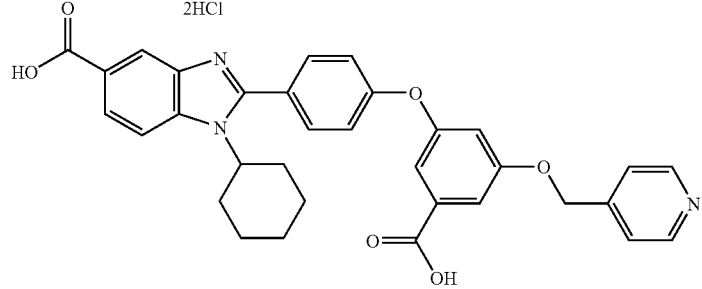

Purity >90% (NMR)
MS 564 (M+1)

1H NMR(δ)ppm
300MHz, DMSO-d6
8.93(2H, d, J=6.3Hz), 8.35(1H, s), 8.26(1H, d, J=8.7Hz), 8.09–8.02(3H, m), 7.86(2H, d, J=8.7Hz), 7.50(1H, s), 7.35(2H, d, J=8.4Hz), 7.24(2H, d, J=7.8Hz), 5.60(2H, s), 4.39(1H, m), 2.50–2.18(2H, m), 2.15–1.95(2H, m), 1.90–1.75(2H, m), 1.70–1.55(1H, m), 1.50–1.10(3H, m)

TABLE 189

Example No. 261

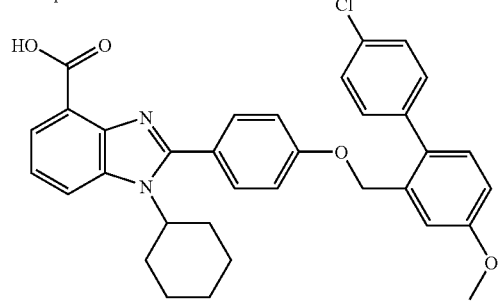

Purity >90% (NMR)
MS 567 (M+1)

1H NMR(δ)ppm
300MHz, DMSO-d6
8.22(1H, d, J=7.8Hz), 7.85(1H, d, J=6.7Hz), 7.63(2H, d, J=9.0H), 7.51–7.38(5H, m), 7.29(1H, d, J=8.3Hz), 7.23(1H, d, J=3.0Hz), 7.06(2H, d, J=9.0Hz), 7.06(1H, dd, J=8.6, 3.0Hz), 5.05(2H, s), 4.41–4.25(1H, m), 3.83(3H, s), 2.40–2.20(2H, m), 2.03–1.78(4H, m), 1.72–1.57(1H, m), 1.50–1.18(3H, m)

TABLE 189-continued

Example No. 262

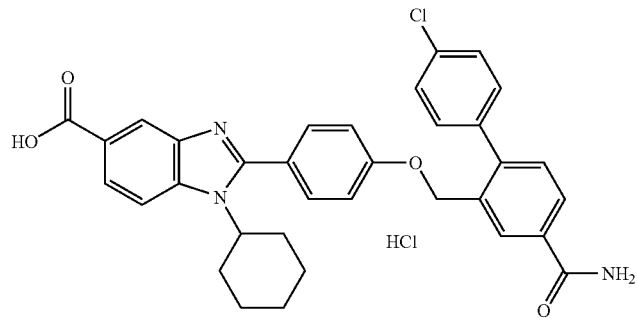

Purity >90% (NMR)
MS 580 (M+1)

1H NMR(δ)ppm
300MHz, DMSO-d6
8.29(1H, d, J=1.5Hz), 8.26(1H, d, J=9.0Hz), 8.19(1H, d, J=1.8Hz), 8.13(1H, brs), 8.08–7.96(2H, m), 7.73(2H, d, J=9.0Hz), 7.57–7.43 (6H, m), 7.24(2H, d, J=9.0Hz), 5.14(2H, s), 4.36(1H, m), 2.38–2.18(2H, m), 2.12–1.97(2H, m), 1.93–1.80(2H, m), 1.73–1.58(1H, m), 1.52–1.20(3H, m)

Example No. 263

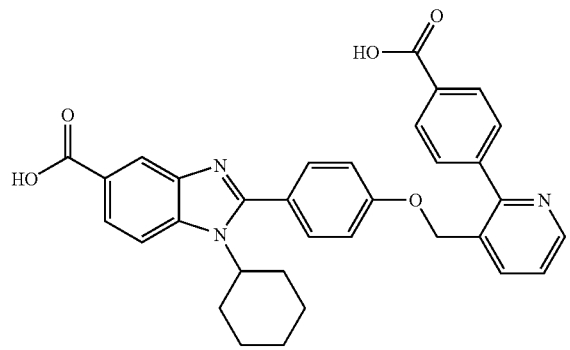

Purity >90% (NMR)
MS 548 (M+1)

1H NMR(δ)ppm
300MHz, DMSO-d6
12.85(1H, brs), 8.72(1H, d, J=4.8Hz), 8.22(1H, s), 8.14(1H, d, J=6.3Hz), 8.03 and 7.76(4H, ABq, J=8.6Hz), 7.93 and 7.85(2H, A'B'q, J=8.6Hz), 7.60 and 7.15(4H, A"B"q, J=8.7Hz), 7.55(1H, dd, J=6.3, 4.8Hz), 5.19(2H, s), 4.26(1H, brt, J=12.6Hz), 2.35–2.18 (2H, brm), 1.95–1.77(4H, brm), 1.70–1.60(1H, brm), 1.45–1.15(3H, brm)

TABLE 190

Example No. 264

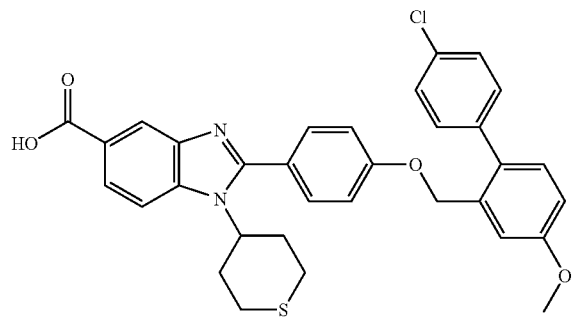

Purity >90% (NMR)
MS 586, 588 (M+1)

1H NMR(δ)ppm
300MHz, DMSO-d6
8.23(1H, d, J=1.0Hz), 7.92(1H, dd, J=8.7, 1.0Hz), 7.87(1H, d, J=8.7Hz), 7.60(2H, d, J=8.6Hz), 7.47(2H, d, J=8.7Hz), 7.30(1H, d, J=8.3Hz), 7.23(1H, d, J=2.6Hz), 7.11(2H, d, J=8.7Hz), 7.06(1H, dd, J=8.7, 2.6Hz), 5.04(2H, s), 4.36(1H, m), 3.83(3H, s), 2.80–2.70(4H, m), 2.60–2.40(2H, m), 2.30–2.20(2H, m)

TABLE 190-continued

| Example No. 265 | 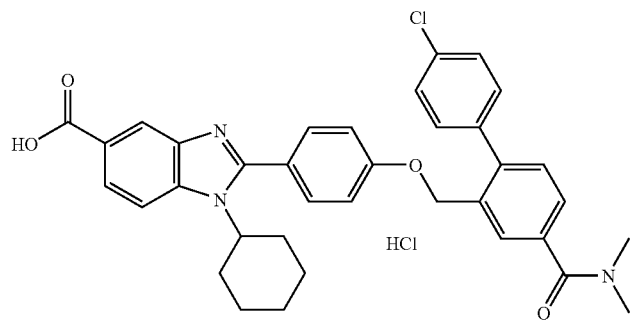 | 1H NMR(δ)ppm<br>300MHz, DMSO-d6<br>8.30(1H, d, J=1.5Hz), 8.25(1H, d, J=9.1Hz), 8.03(1H, dd, J=8.7, 1.5Hz), 7.76–7.96(3H, m), 7.55–7.49(5H, m), 7.42(1H, d, J=7.6Hz), 7.23(2H, d, J=8.7Hz), 5.15(2H, s), 4.35(1H, m), 3.01(3H, s), 2.97 (3H, s), 2.37–2.20(2H, m), 2.09–1.97(2H, m), 1.94–1.81(2H, m), 1.72–1.60(1H, m), 1.50–1.21(3H, m) |
|---|---|---|
| Purity | >90% (NMR) | |
| MS | 608 (M+1) | |
| Example No. 266 | 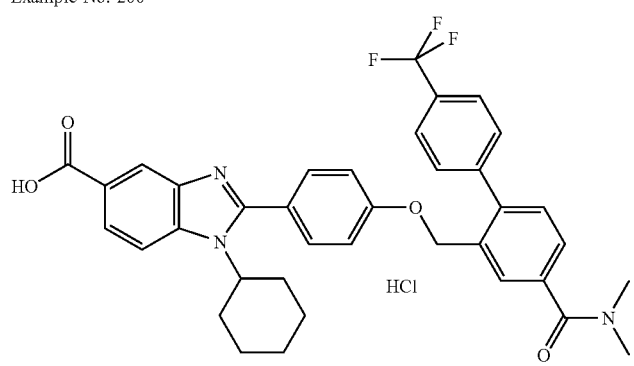 | 1H NMR(δ)ppm<br>300MHz, DMSO-d6<br>8.27(1H, d, J=1.5Hz), 8.20(1H, d, J=9.0Hz), 8.00(1H, dd, J=8.6, 1.5Hz), 7.82(2H, d, J=8.2Hz), 7.76–7.65(5H, m), 7.56(1H, dd, J=7.9, 1.8Hz), 7.47(1H, d, J=7.5Hz), 7.20(2H, d, J=8.6Hz), 5.16(2H, s), 4.32(1H, m), 3.02(3H, s), 2.98(3H, s), 2.38–2.19(2H, m), 2.07–1.95 (2H, m), 1.93–1.80(2H, m), 1.72–1.58(1H, m), 1.52–1.18(3H, m) |
| Purity | >90% (NMR) | |
| MS | 642 (M+1) | |

TABLE 191

| Example No. 267 | 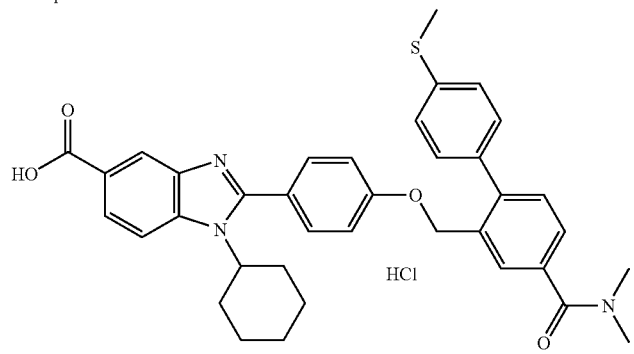 | 1H NMR(δ)ppm<br>300MHz, DMSO-d6<br>8.34(2H, m), 8.03(1H, d, J=8.3Hz) 7.77–7.68(3H, m), 7.54–7.40(4H, m), 7.33(2H, d, J=8.6Hz), 7.24(2H, d, J=9.0Hz), 5.16(2H, s), 4.36 (1H, m), 3.01(3H, s), 2.97(3H, s), 2.40–2.20(2H, m), 2.11–1.97(2H, m), 1.93–1.81(2H, m), 1.71–1.60(1H, m), 1.50–1.21(3H, m) |
|---|---|---|
| Purity | >90% (NMR) | |
| MS | 620 (M+1) | |

TABLE 191-continued
| Example No. 268 | 1H NMR(δ)ppm |
|---|---|
| 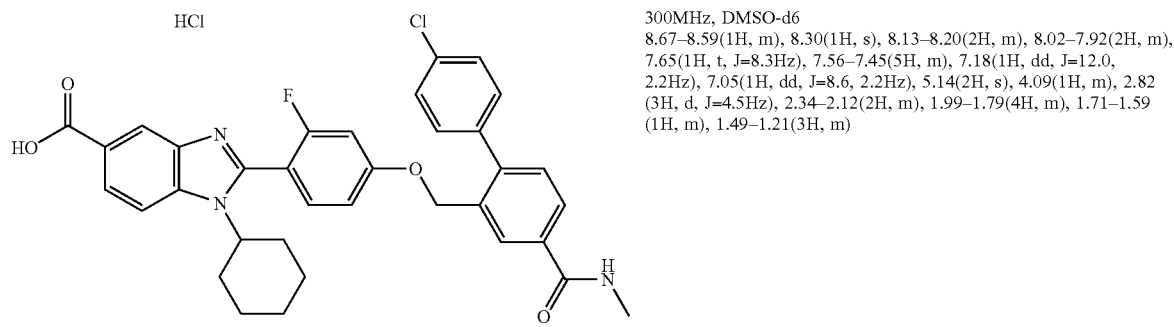 | 300MHz, DMSO-d6<br>8.67–8.59(1H, m), 8.30(1H, s), 8.13–8.20(2H, m), 8.02–7.92(2H, m), 7.65(1H, t, J=8.3Hz), 7.56–7.45(5H, m), 7.18(1H, dd, J=12.0, 2.2Hz), 7.05(1H, dd, J=8.6, 2.2Hz), 5.14(2H, s), 4.09(1H, m), 2.82 (3H, d, J=4.5Hz), 2.34–2.12(2H, m), 1.99–1.79(4H, m), 1.71–1.59 (1H, m), 1.49–1.21(3H, m) |
| Purity >90% (NMR) | |
| MS 612 (M+1) | |
| Example No. 269 | 1H NMR(δ)ppm |
| 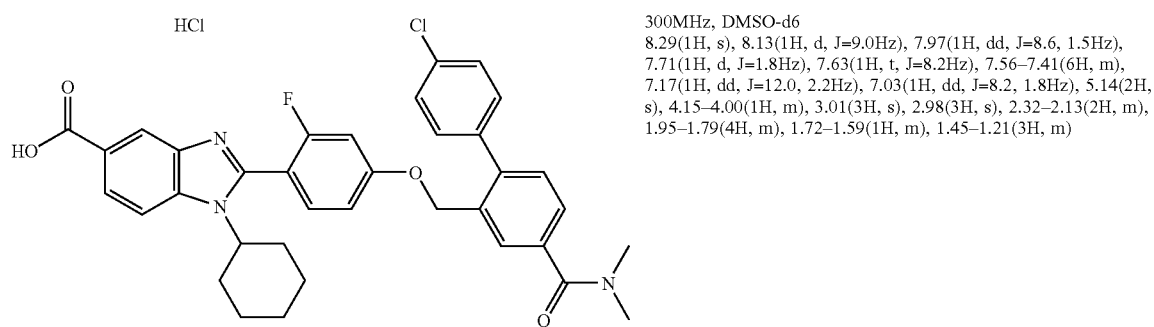 | 300MHz, DMSO-d6<br>8.29(1H, s), 8.13(1H, d, J=9.0Hz), 7.97(1H, dd, J=8.6, 1.5Hz), 7.71(1H, d, J=1.8Hz), 7.63(1H, t, J=8.2Hz), 7.56–7.41(6H, m), 7.17(1H, dd, J=12.0, 2.2Hz), 7.03(1H, dd, J=8.2, 1.8Hz), 5.14(2H, s), 4.15–4.00(1H, m), 3.01(3H, s), 2.98(3H, s), 2.32–2.13(2H, m), 1.95–1.79(4H, m), 1.72–1.59(1H, m), 1.45–1.21(3H, m) |
| Purity >90% (NMR) | |
| MS 626 (M+1) | |
TABLE 192
| Example No. 270 | 1H NMR(δ)ppm |
|---|---|
| 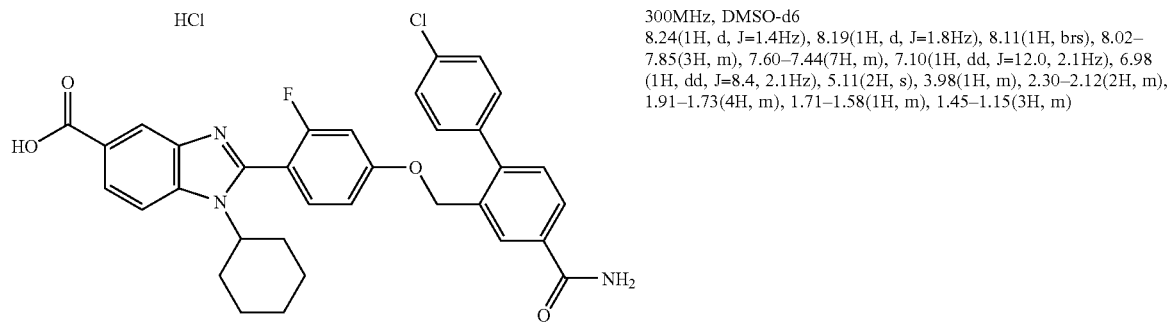 | 300MHz, DMSO-d6<br>8.24(1H, d, J=1.4Hz), 8.19(1H, d, J=1.8Hz), 8.11(1H, brs), 8.02–7.85(3H, m), 7.60–7.44(7H, m), 7.10(1H, dd, J=12.0, 2.1Hz), 6.98 (1H, dd, J=8.4, 2.1Hz), 5.11(2H, s), 3.98(1H, m), 2.30–2.12(2H, m), 1.91–1.73(4H, m), 1.71–1.58(1H, m), 1.45–1.15(3H, m) |
| Purity >90% (NMR) | |
| MS 598 (M+1) | |

TABLE 192-continued

| Example No. 271 | 1H NMR(δ)ppm |
|---|---|
| 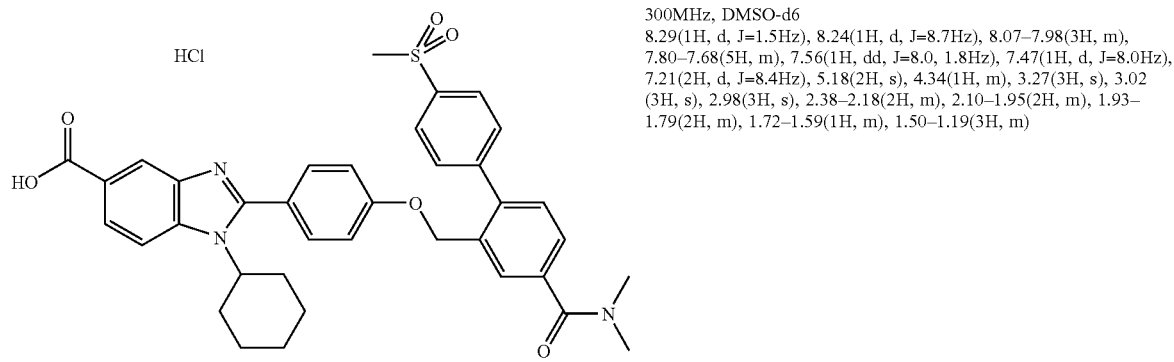 | 300MHz, DMSO-d6<br>8.29(1H, d, J=1.5Hz), 8.24(1H, d, J=8.7Hz), 8.07–7.98(3H, m), 7.80–7.68(5H, m), 7.56(1H, dd, J=8.0, 1.8Hz), 7.47(1H, d, J=8.0Hz), 7.21(2H, d, J=8.4Hz), 5.18(2H, s), 4.34(1H, m), 3.27(3H, s), 3.02 (3H, s), 2.98(3H, s), 2.38–2.18(2H, m), 2.10–1.95(2H, m), 1.93–1.79(2H, m), 1.72–1.59(1H, m), 1.50–1.19(3H, m) |

Purity >90% (NMR)
MS 652 (M+1)

| Example No. 272 | 1H NMR(δ)ppm |
|---|---|
| 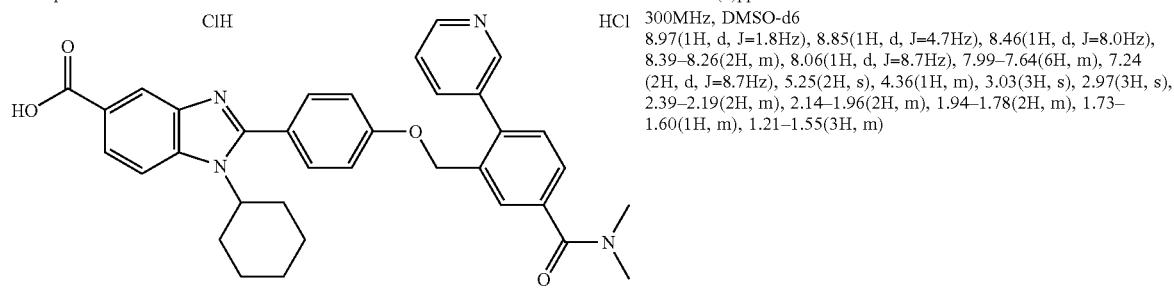 | 300MHz, DMSO-d6<br>8.97(1H, d, J=1.8Hz), 8.85(1H, d, J=4.7Hz), 8.46(1H, d, J=8.0Hz), 8.39–8.26(2H, m), 8.06(1H, d, J=8.7Hz), 7.99–7.64(6H, m), 7.24 (2H, d, J=8.7Hz), 5.25(2H, s), 4.36(1H, m), 3.03(3H, s), 2.97(3H, s), 2.39–2.19(2H, m), 2.14–1.96(2H, m), 1.94–1.78(2H, m), 1.73–1.60(1H, m), 1.21–1.55(3H, m) |

Purity >90% (NMR)
MS 575 (M+1)

TABLE 193

| Example No. 273 | 1H NMR(δ)ppm |
|---|---|
| 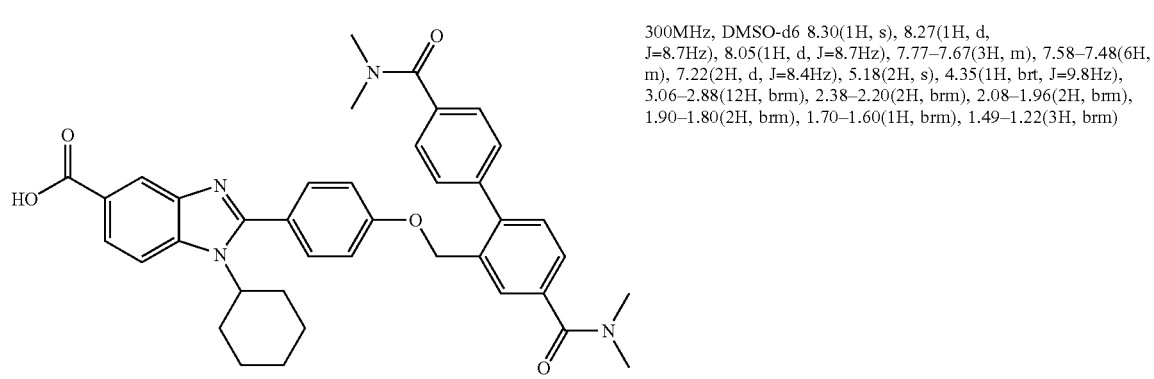 | 300MHz, DMSO-d6 8.30(1H, s), 8.27(1H, d, J=8.7Hz), 8.05(1H, d, J=8.7Hz), 7.77–7.67(3H, m), 7.58–7.48(6H, m), 7.22(2H, d, J=8.4Hz), 5.18(2H, s), 4.35(1H, brt, J=9.8Hz), 3.06–2.88(12H, brm), 2.38–2.20(2H, brm), 2.08–1.96(2H, brm), 1.90–1.80(2H, brm), 1.70–1.60(1H, brm), 1.49–1.22(3H, brm) |

Purity >90%(NMR)
MS 645 (M+1)

TABLE 193-continued

| Example No. 274 | 1H NMR(δ)ppm |
|---|---|
| 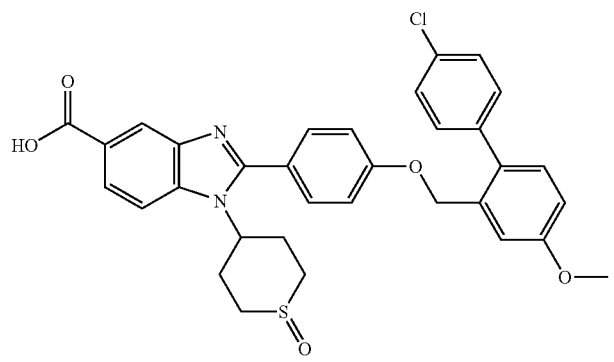 | 300MHz, DMSO-d6 mixture of cis and trans 8.35, 8.34(1H, s), 8.15–8.10(2H, m), 7.79–7.70(3H, m), 7.49(2H, d, J=8.7Hz), 7.44(2H, d, J=8.7Hz), 7.31(1H, d, J=8.4Hz), 7.25–7.19(2H, m), 7.07(1H, d, J=8.5Hz), 5.08(2H, s), 4.75(1H, m), 3.83(3H, s), 3.70–1.90(8H, m) |

Purity about 80%(NMR)

MS 601 (M+1)

| Example No. 275 | 1H NMR(δ)ppm |
|---|---|
| 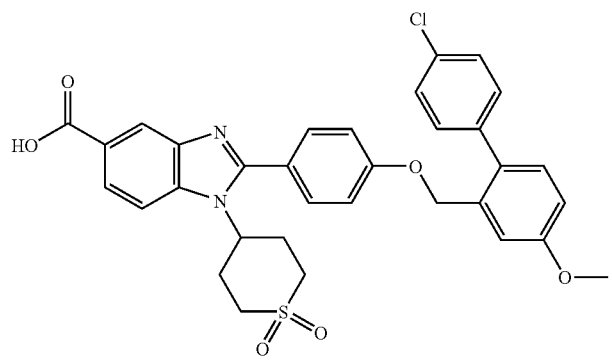 | 300MHz, DMSO-d6 8.33(1H, s), 8.13(1H, d, J=7.5Hz), 7.93(1H, d, J=8.8Hz), 7.74(2H, d, J=8.7Hz), 7.49(2H, d, J=8.6Hz), 7.44(2H, d, J=8.6Hz), 7.31(1H, d, J=8.5Hz), 7.25–7.15(3H, m), 7.07(1H, d, J=8.5Hz), 5.08(2H, s), 4.98(1H, m), 3.83(3H, s), 3.65–3.45(2H, m), 3.30–3.10(2H, m), 3.00–2.75(2H, m), 2.60–2.30(2H, m) |

Purity >90%(NMR)

MS 617 (M+1)

TABLE 194

| Example No. 276 | 1H NMR(δ)ppm |
|---|---|
| 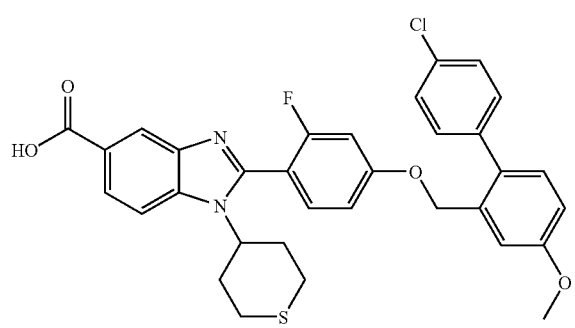 | 300MHz, DMSO-d6 8.25(1H, s), 7.93 and 7.87(2H, ABq, J=9.1Hz), 7.55(1H, t, J=8.6Hz), 7.48 and 7.42(4H, A'B'q, J=8.6Hz), 7.31(1H, d, J=8.5Hz), 7.24(1H, d, J=2.6Hz), 7.09–6.95(3H, m), 5.05(2H, s), 4.11(1H, brt, J=14.0Hz), 3.84(3H, s), 2.83–2.67(4H, brm), 2.50–2.32(2H, brm), 2.21–2.10(2H, brm) |

Purity >90%(NMR)

MS 603 (M+1)

TABLE 194-continued

| Example No. 277 | 1H NMR(δ)ppm |
|---|---|
| 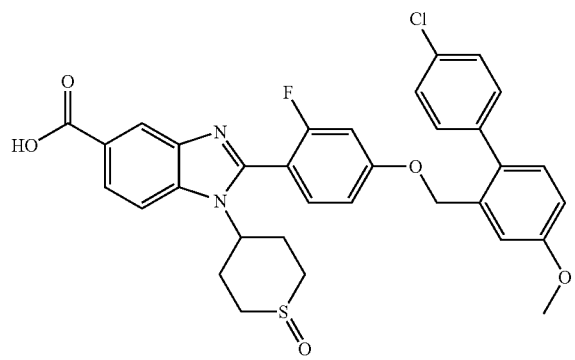 | 300MHz, DMSO-d6 cis and trans mixture 8.28 and 8.24(total 1H, each s), 7.94–7.87(1H, m), 7.60–7.41(5H, m), 7.31(1H, d, J=8.5Hz), 7.23–7.21(1H, m), 7.12–7.05(2H, m), 7.00–6.95(1H, m), 5.06 and 5.05(total 2H, each s), 4.47 and 4.34 (total 1H, each brs), 3.83(3H, s), 3.12–1.76(8H, m) |

Purity >90%(NMR)
MS 619 (M+1)

| Example No. 278 | 1H NMR(δ)ppm |
|---|---|
| 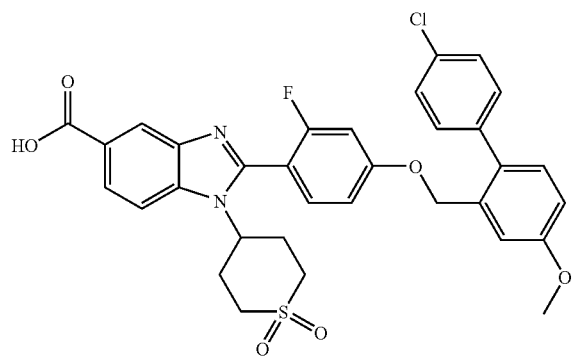 | 300MHz, DMSO-d6 12.9(1H, brs), 8.27(1H, s), 7.97 and 7.74(2H, ABq, J=8.6Hz), 7.58(1H, t, J=8.6Hz), 7.49 and 7.43(4H, A'B'q, J=8.5Hz), 7.31(1H, d, J=8.5Hz), 7.22(1H, d, J=2.6Hz), 7.13–6.92(3H, m), 5.05(2H, s), 4.67(1H, brt, J=14.2Hz), 3.57–3.40(2H, brm), 3.20–3.05(2H, brm), 2.91–2.70(2H, brm), 2.28–2.11(2H, brm) |

Purity >90%(NMR)
MS 635 (M+1)

TABLE 195

| Example No. 279 | 1H NMR(δ)ppm |
|---|---|
| 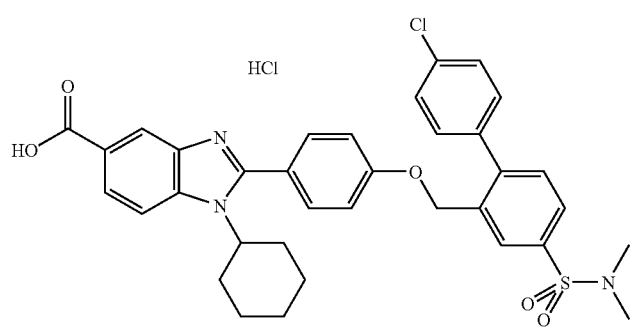 | 300MHz, DMSO-d6 8.30(1H, s), 8.23(1H, d, J=8.7Hz), 8.06–8.00(2H, m), 7.83(1H, dd, J=8.0, 1.8Hz), 7.71(2H, d, J=8.4Hz), 7.64(1H, d, J=8.0Hz), 7.59–7.54(4H, m), 7.22(2H, d, J=8.4Hz), 5.25(2H, s), 4.33(1H, m), 2.66(3H, s), 2.66(3H, s), 2.37–2.19(2H, m), 1.93–1.80(2H, m), 1.70–1.59(1H, m), 1.47–1.21(3H, m) |

Purity >90%(NMR)
MS 644 (M+1)

TABLE 195-continued
| Example No. 280 | 1H NMR(δ)ppm |
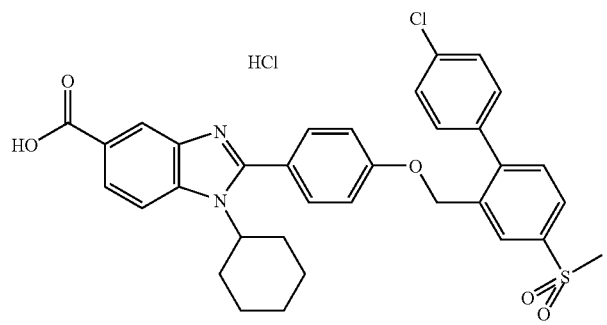
300MHz, DMSO-d6 8.32–8.23(3H, m), 8.08–8.01(2H, m), 7.73(2H, d, J=8.6Hz), 7.65(1H, d, J=8.2Hz), 7.59–7.51(4H, m), 7.25(2H, d, J=8.6Hz), 5.21(2H, s), 4.34(1H, m), 3.32(3H, s), 2.37–2.19(2H, m), 2.10–1.98(2H, m), 1.93–1.80(2H, m), 1.71–1.60(1H, m), 1.51–1.21(3H, m)
Purity >90%(NMR)
MS 615 (M+1)
| Example No. 281 | 1H NMR(δ)ppm |
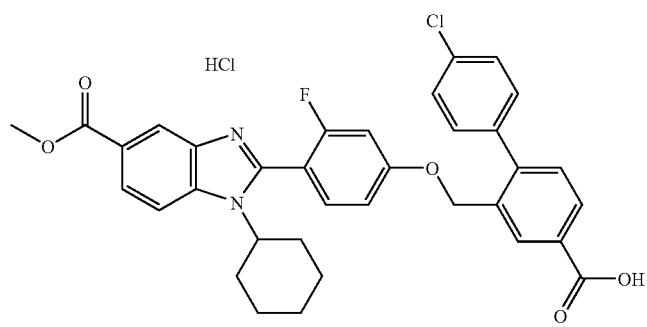
300MHz, DMSO-d6 8.30(1H, d, J=1.5Hz), 8.24(1H, s), 8.14(1H, d, J=8.6Hz), 8.07–7.95(2H, m), 7.63(1H, t, J=8.6Hz), 7.57–7.47(5H, m), 7.16(1H, dd, J=12.0, 2.2Hz), 7.03(1H, dd, J=8.6, 2.2Hz), 5.17(2H, s), 4.06(1H, m), 3.90(3H, s), 2.31–2.11(2H, m), 1.97–1.78(4H, m), 1.71–1.59(1H, m), 1.43–1.22(3H, m)
Purity >90%(NMR)
MS 315
TABLE 196
| Example No. 282 | 1H NMR(δ)ppm |
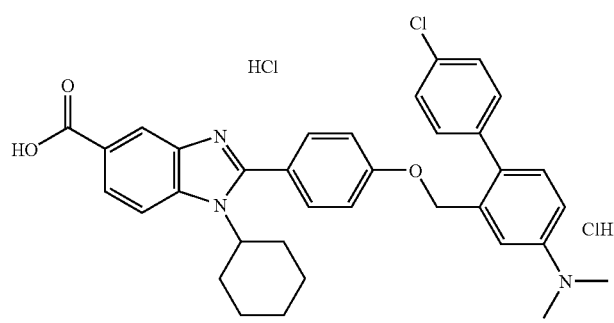
300MHz, DMSO-d6 8.36(1H, s), 8.35(1H, d, J=9.3Hz), 8.09(1H, d, J=9.3Hz), 7.78(2H, d, J=8.7Hz), 7.48–7.25(9H, m), 5.09(2H, s), 4.39(1H, m), 3.04(6H, s), 2.40–2.15(2H, m), 2.10–1.95(2H, m), 1.90–1.75(2H, m), 1.70–1.55(1H, m), 1.50–1.20(3H, m)
Purity >90%(NMR)
MS 580 (M+1)

TABLE 196-continued
Example No. 283
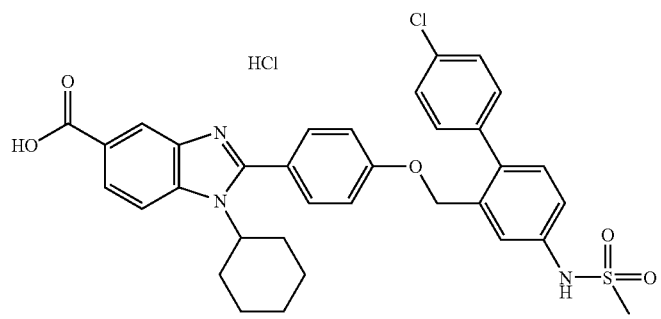
Purity >90%(NMR)
MS 630 (M+1)
1H NMR(δ)ppm
300MHz, DMSO-d6 10.03(1H, s), 8.33(1H, s), 8.29(1H, d, J=8.7Hz), 8.06(1H, d, J=9.0Hz), 7.74(2H, d, J=9.0Hz), 7.51–7.42(5H, m), 7.37–7.30(2H, m), 7.22(2H, d, J=8.7Hz), 5.10(2H, s), 4.37(1H, m), 3.06(3H, s), 2.40–2.18(2H, m), 2.15–1.95(2H, m), 1.90–1.80(2H, m), 1.75–1.55(1H, m), 1.50–1.20(3H, m)
Example No. 284
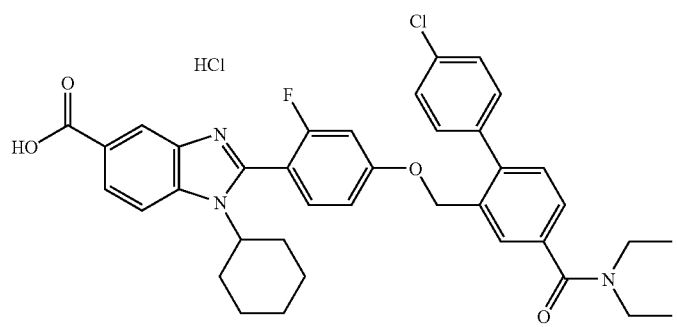
Purity >90%(NMR)
MS 654 (M+1)
1H NMR(δ)ppm
300MHz, DMSO-d6 8.30(1H, s), 8.14(1H, d, J=8.7Hz), 7.97(1H, d, J=8.7Hz), 7.96–7.81(8H, m), 7.16(1H, dd, J=12.4, 2.2Hz), 7.03(1H, dd, J=8.4, 2.2Hz), 5.15(2H, s), 4.15(1H, m), 3.54–3.16(4H, m), 2.33–2.13(2H, m), 1.97–1.79(4H, m), 1.70–1.02(9H, m)
TABLE 197
Example No. 285
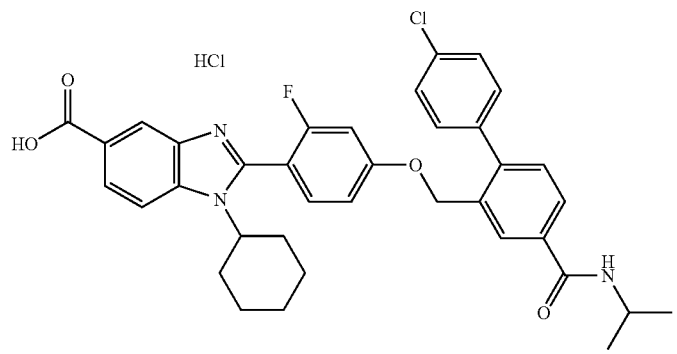
Purity >90%(NMR)
MS 640 (M+1)
1H NMR(δ)ppm
300MHz, DMSO-d6 8.37(1H, d, J=7.3Hz), 8.30(1H, s), 8.19–8.12(2H, m), 8.02–7.95(2H, m), 7.65(1H, t, J=8.4Hz), 7.56–7.43(5H, m), 7.18(1H, dd, J=12.0, 1.8Hz), 7.06(1H, dd, J=8.4, 2.1Hz), 5.13(2H, s), 4.22–4.03(2H, m), 2.34–2.13(2H, m), 1.99–1.78(4H, m), 1.72–1.57(1H, m), 1.44–1.14(3H, m), 1.20, 1.18(6H, each s)

TABLE 197-continued
| Example No. 286 | 1H NMR(δ)ppm |
|---|---|
| 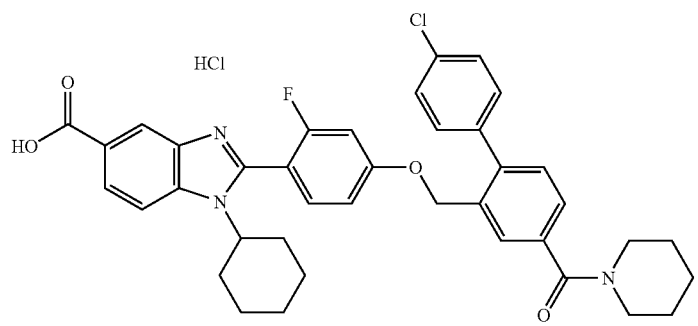 | 300MHz, DMSO-d6 8.29(1H, s), 8.13(1H, d, J=8.7Hz), 7.97(1H, dd, J=8.7, 1.4Hz), 7.69–7.40(8H, m), 7.16(1H, dd, J=12.0, 2.2Hz), 7.02(1H, dd, J=8.4, 2.2Hz), 5.15(2H, s), 4.07(1H, m), 3.71–3.23(2H, m), 1.98–1.71(4H, m), 1.71–1.18(10H, m) |
Purity >90%(NMR)
MS 666 (M+1)
| Example No. 287 | 1H NMR(δ)ppm |
|---|---|
| 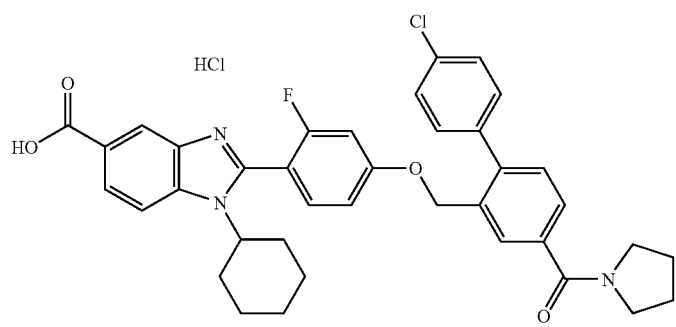 | 300MHz, DMSO-d6 8.29(1H, s), 8.13(1H, d, J=8.0Hz), 7.97(1H, d, J=8.4Hz), 7.83(1H, s), 7.68–7.41(7H, m), 7.17(1H, d, J=12.0Hz), 7.03(1H, d, J=8.4Hz), 5.15(2H, s), 4.07(1H, m), 3.58–3.41(4H, m), 2.34–2.13(2H, m), 1.97–1.77(8H, m), 1.71–1.58(1H, m), 1.49–1.18(3H, m) |
Purity >90%(NMR)
MS 652 (M+1)
TABLE 198
| Example No. 288 | 1H NMR(δ)ppm |
|---|---|
| 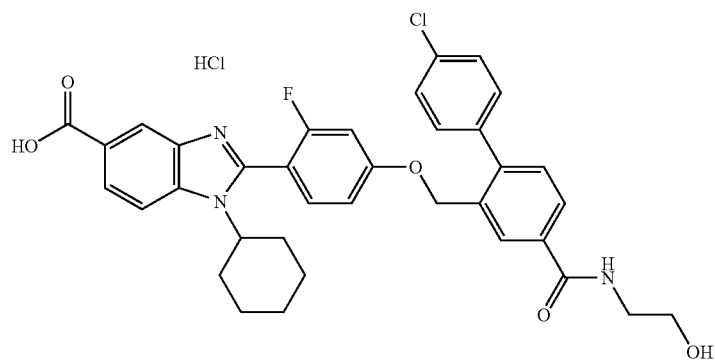 | 300MHz, DMSO-d6 8.62(1N, m), 8.31(1H, s), 8.22–8.14(2H, m), 8.99(2H, d, J=8.7Hz), 7.66(1H, t, J=7.7Hz), 7.58–7.44(5H, m), 7.19(1H, dd, J=8.7, 2.2Hz), 5.14(2H, s), 4.11(1H, m), 3.67–3.49(2H, m), 3.45–3.30(2H, m), 2.37–2.12(2H, m), 2.00–1.76(4H, m), 1.70–1.58(1H, m), 1.48–1.17(3H, m) |
Purity >90%(NMR)
MS 642 (M+1)

TABLE 198-continued
| Example No. 289 | 1H NMR(δ)ppm |
|---|---|
| 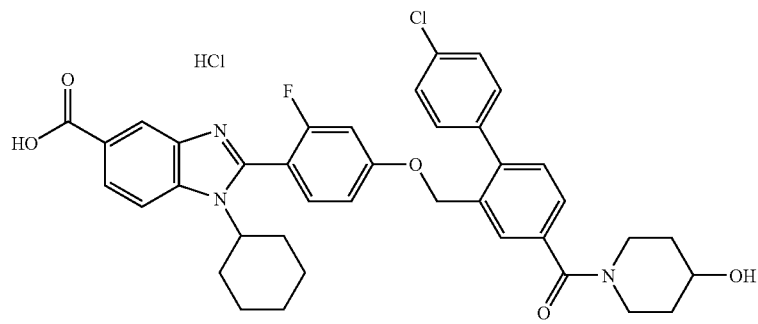 | 400MHz, DMSO-d6 8.28(1H, s), 8.11(1H, d, J= 8.9Hz), 7.96(1H, d, J=8.9Hz), 7.68(1H, s), 7.62(1H, t, J=8.2Hz), 7.55–7.41(6H, m), 7.15(1H, d, J= 11.7Hz), 7.02(1H, d, J=8.4Hz), 5.14(2H, s), 4.12– 3.13(6H, m), 2.30–1.19(13H, m) |
Purity >90%(NMR)
MS 682 (M+1)
| Example No. 290 | 1H NMR(δ)ppm |
|---|---|
| 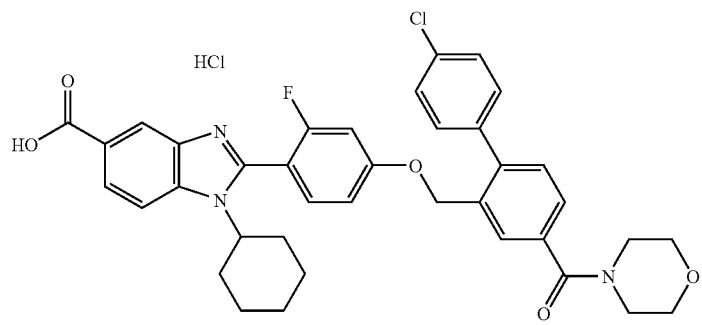 | 400MHz, DMSO-d6 8.29(1H, s), 8.15(1H, d, J= 8.6Hz), 7.98(1H, d, J=8.8Hz), 7.72(1H, s), 7.64(1H, t, J=8.8Hz), 7.57–7.43(6H, m), 7.18(1H, dd, J=12.1, 2.1Hz), 7.03(1H, d, J=10.7Hz), 5.12(2H, s), 4.15– 4.01(1H, m), 3.75–3.33(8H, m), 2.31–2.14(2H, m), 1.96–1.78(4H, m), 1.70–1.58(1H, m), 1.47– 1.21(3H, m) |
Purity >90%(NMR)
MS 668 (M+1)
TABLE 199
| Example No. 291 | 1H NMR(δ)ppm |
|---|---|
| 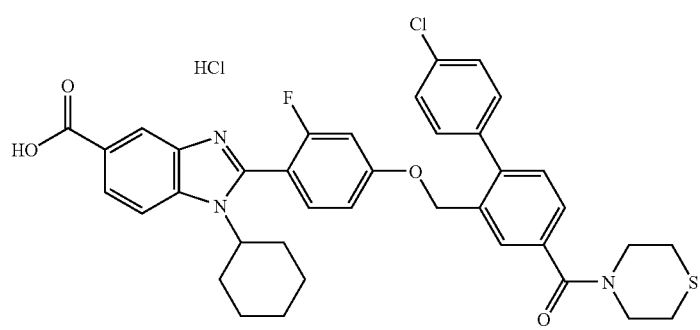 | 400MHz, DMSO-d6 8.29(1H, s), 8.14(1H, d, J=8.9Hz), 7.97(1H, d, J=8.6Hz), 7.71(1H, s), 7.63(1H, t, J=8.2Hz), 7.56–7.42(6H, m), 7.17(1H, d, J=12.3Hz), 7.03(1H, d, J=10.7Hz), 5.14(2H, s), 4.07(1H, m), 3.96–3.52(4H, m), 2.79–2.56(4H, m), 2.32–2.14(2H, m), 1.97–1.79(4H, m), 1.71–1.58(1H, m), 1.51–1.19(3H, m) |
Purity >90%(NMR)
MS 684 (M+1)

TABLE 199-continued

Example No. 292

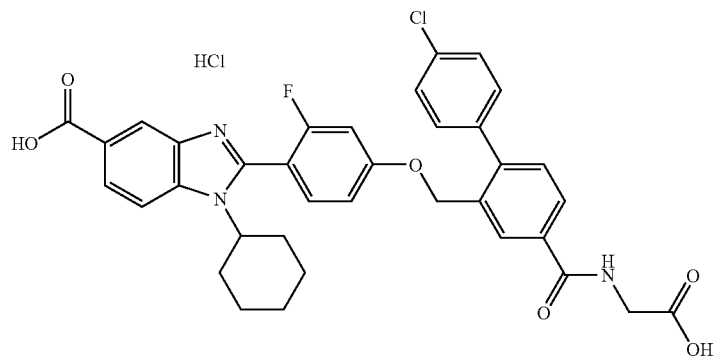

Purity >90%(NMR)
MS 656 (M+1)

1H NMR(δ)ppm

300MHz, DMSO-d6 9.07–8.99(1H, m), 8.30(1H, s), 8.23–8.12(2H, m), 8.04–7.95(2H, m), 7.65(1H, t, J=8.2Hz), 7.60–7.45(5H, m), 7.19(1H, dd, J=12.0, 2.6Hz), 7.06(1H, dd, J=8.6, 2.2Hz), 5.16(2H, s), 4.18–4.02(1H, m), 3.97(2H, d, J=6.0Hz), 2.33–2.14(2H, m), 1.99–1.79(4H, m), 1.72–1.59(1H, m), 1.45–1.19(3H, m)

Example No. 293

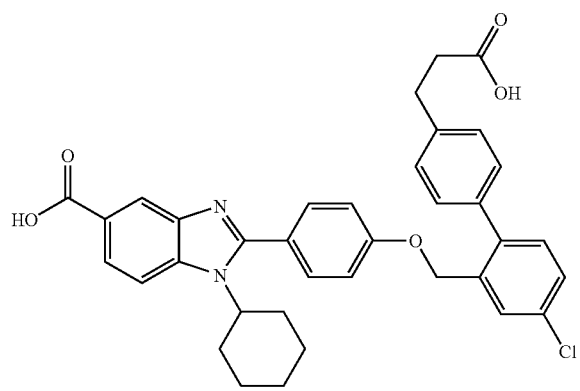

Purity >90%(NMR)
MS 637 (M+1)

1H NMR(δ)ppm

300MHz, DMSO-d6:8.21(1H, s), 7.94 and 7.86(2H, ABq, J=8.6Hz), 7.72(1H, d, J=2.4Hz), 7.59 and 7.11(4H, A'B'q, J=8.9Hz), 7.53(1H, dd, J=8.4, 2.4Hz), 7.38(1H, d, J=8.4Hz), 7.36 and 7.32(4H, A"B"q, J=8.1Hz), 5.07(2H, s), 4.27(1H, brt, J=13.8Hz), 2.87(2H, t, J=7.8Hz), 2.57(2H, t, J=7.8Hz), 2.35–2.20(2H, brm), 1.96–1.79(4H, brm), 1.68–1.59(1H, brm), 1.47–1.18(3H, brm)

TABLE 200

Example No. 294

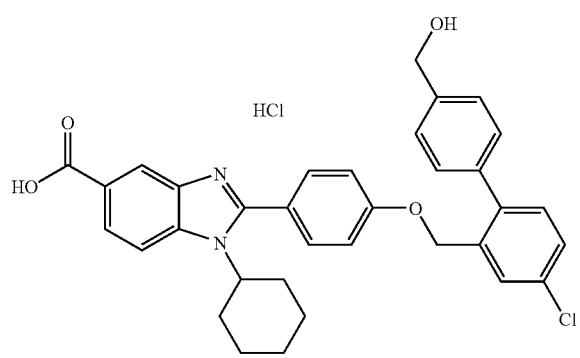

Purity >90%(NMR)
MS 567 (M+1)

1H NMR(δ)ppm

300MHz, DMSO-d6 8.30(1H, s), 8.25 and 8.03(2H, ABq, J=8.9Hz), 7.73(1H, s), 7.73(2H, d, J=8.6Hz), 7.55(1H, dd, J=8.0, 2.3Hz), 7.40(4H, s), 7.39(1H, d, J=8.0Hz), 7.23(2H, d, J=8.6Hz), 5.11(2H, s), 4.55(2H, s), 4.36(1H, brt, J=14.8Hz), 2.37–2.19(2H, brm), 2.09–1.96(2H, brm), 1.91–1.79(2H, brm), 1.71–1.59(1H, brm), 1.50–1.20(3H, brm)

TABLE 200-continued

Example No. 295

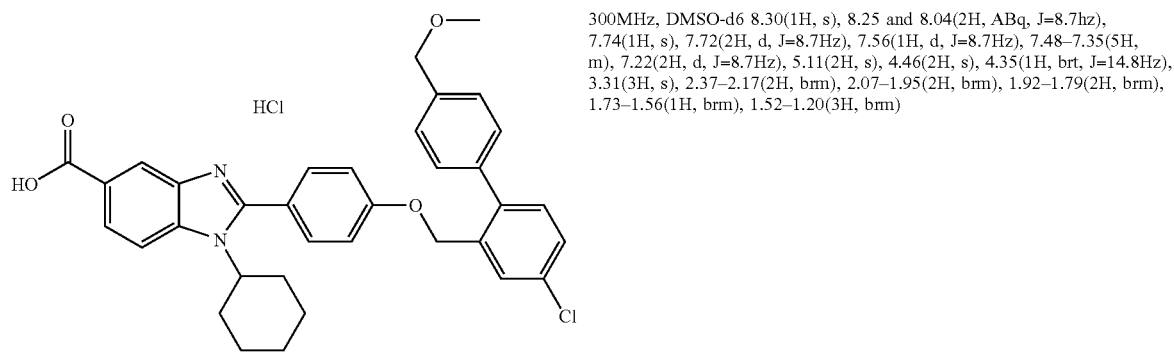

1H NMR(δ)ppm

300MHz, DMSO-d6 8.30(1H, s), 8.25 and 8.04(2H, ABq, J=8.7hz), 7.74(1H, s), 7.72(2H, d, J=8.7Hz), 7.56(1H, d, J=8.7Hz), 7.48–7.35(5H, m), 7.22(2H, d, J=8.7Hz), 5.11(2H, s), 4.46(2H, s), 4.35(1H, brt, J=14.8Hz), 3.31(3H, s), 2.37–2.17(2H, brm), 2.07–1.95(2H, brm), 1.92–1.79(2H, brm), 1.73–1.56(1H, brm), 1.52–1.20(3H, brm)

Purity >90%(NMR)
MS 581 (M+1)

Example No. 296

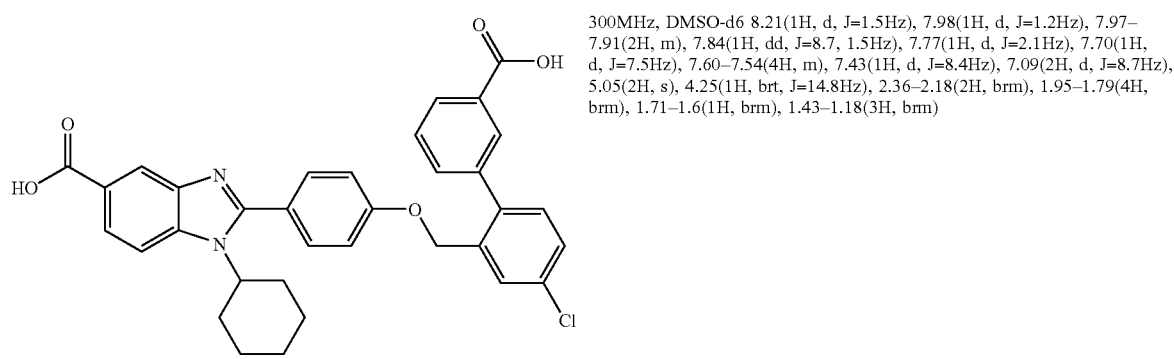

1H NMR(δ)ppm

300MHz, DMSO-d6 8.21(1H, d, J=1.5Hz), 7.98(1H, d, J=1.2Hz), 7.97–7.91(2H, m), 7.84(1H, dd, J=8.7, 1.5Hz), 7.77(1H, d, J=2.1Hz), 7.70(1H, d, J=7.5Hz), 7.60–7.54(4H, m), 7.43(1H, d, J=8.4Hz), 7.09(2H, d, J=8.7Hz), 5.05(2H, s), 4.25(1H, brt, J=14.8Hz), 2.36–2.18(2H, brm), 1.95–1.79(4H, brm), 1.71–1.6(1H, brm), 1.43–1.18(3H, brm)

Purity >90%(NMR)
MS 581 (M+1)

TABLE 201

Example No. 297

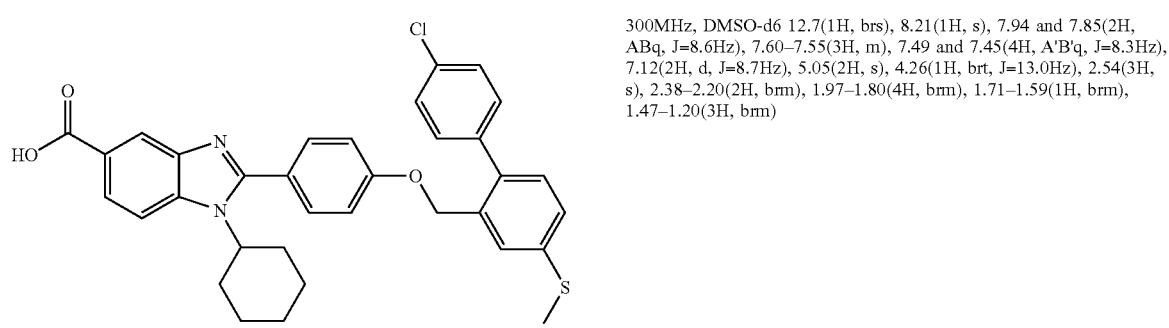

1H NMR(δ)ppm

300MHz, DMSO-d6 12.7(1H, brs), 8.21(1H, s), 7.94 and 7.85(2H, ABq, J=8.6Hz), 7.60–7.55(3H, m), 7.49 and 7.45(4H, A'B'q, J=8.3Hz), 7.12(2H, d, J=8.7Hz), 5.05(2H, s), 4.26(1H, brt, J=13.0Hz), 2.54(3H, s), 2.38–2.20(2H, brm), 1.97–1.80(4H, brm), 1.71–1.59(1H, brm), 1.47–1.20(3H, brm)

Purity >90%(NMR)
MS 583 (M+1)

TABLE 201-continued

Example No. 298

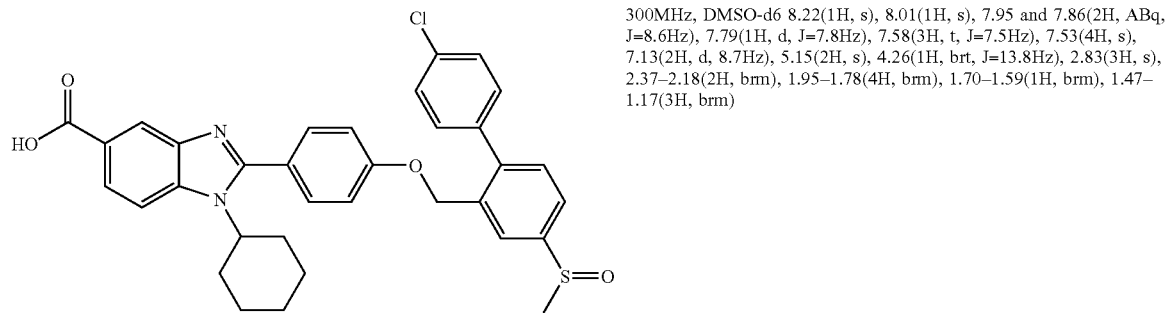

Purity >90%(NMR)
MS 599 (M+1)

1H NMR(δ)ppm

300MHz, DMSO-d6 8.22(1H, s), 8.01(1H, s), 7.95 and 7.86(2H, ABq, J=8.6Hz), 7.79(1H, d, J=7.8Hz), 7.58(3H, t, J=7.5Hz), 7.53(4H, s), 7.13(2H, d, 8.7Hz), 5.15(2H, s), 4.26(1H, brt, J=13.8Hz), 2.83(3H, s), 2.37–2.18(2H, brm), 1.95–1.78(4H, brm), 1.70–1.59(1H, brm), 1.47–1.17(3H, brm)

Example No. 299

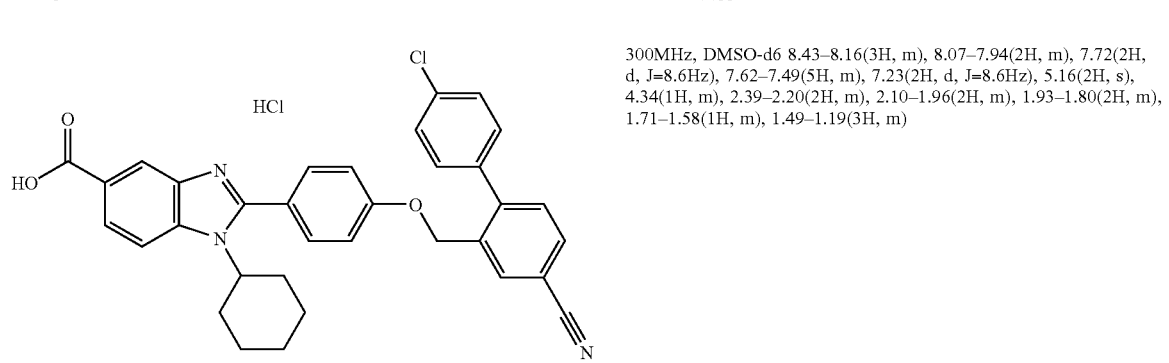

Purity >90%(NMR)
MS 562 (M+1)

1H NMR(δ)ppm

300MHz, DMSO-d6 8.43–8.16(3H, m), 8.07–7.94(2H, m), 7.72(2H, d, J=8.6Hz), 7.62–7.49(5H, m), 7.23(2H, d, J=8.6Hz), 5.16(2H, s), 4.34(1H, m), 2.39–2.20(2H, m), 2.10–1.96(2H, m), 1.93–1.80(2H, m), 1.71–1.58(1H, m), 1.49–1.19(3H, m)

TABLE 202

Example No. 300

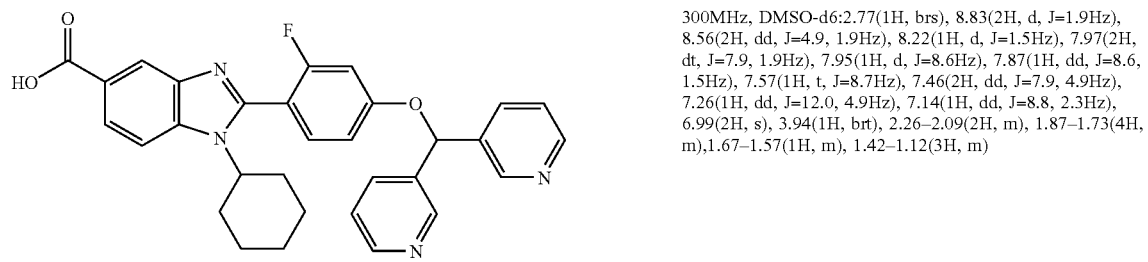

Purity >90%(NMR)
MS 523 (M+1)

1H NMR(δ)ppm

300MHz, DMSO-d6:2.77(1H, brs), 8.83(2H, d, J=1.9Hz), 8.56(2H, dd, J=4.9, 1.9Hz), 8.22(1H, d, J=1.5Hz), 7.97(2H, dt, J=7.9, 1.9Hz), 7.95(1H, d, J=8.6Hz), 7.87(1H, dd, J=8.6, 1.5Hz), 7.57(1H, t, J=8.7Hz), 7.46(2H, dd, J=7.9, 4.9Hz), 7.26(1H, dd, J=12.0, 4.9Hz), 7.14(1H, dd, J=8.8, 2.3Hz), 6.99(2H, s), 3.94(1H, brt), 2.26–2.09(2H, m), 1.87–1.73(4H, m),1.67–1.57(1H, m), 1.42–1.12(3H, m)

TABLE 202-continued
| Example No. 301 | 1H NMR(δ)ppm |
|---|---|
| 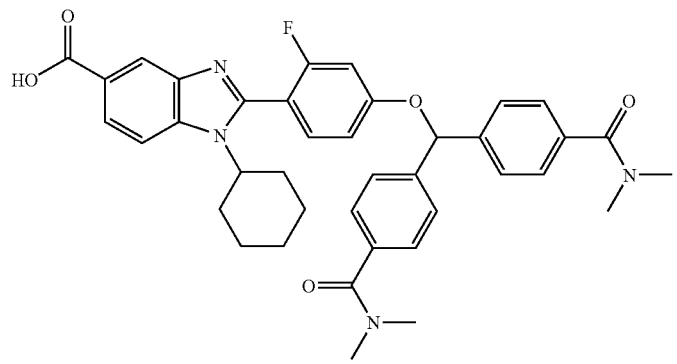 | 300MHz, DMSO-d6 8.22(1H, s), 7.95(1H, d, J=8.7Hz), 7.87(1H, dd, J=1.5Hz, 9.0Hz), 7.62(4H, d, J=8.4Hz), 7.55(1H, t, J=9.0Hz), 7.44(4H, d, J=8.1Hz), 7.20(1H, dd, J=2.1Hz, 12.0Hz), 7.11(1H, dd, J=2.1Hz, 8.7Hz), 6.86(1H, s), 3.94(1H, m), 2.96, 2.88(12H, s), 2.35–2.00(2H, m), 1.95–1.70(4H, m), 1.65–1.50(1H, m), 1.45–1.10(3H, m) |
| Purity >90%(NMR) MS 663 (M+1) | |
| Example No. 302 | 1H NMR(δ)ppm |
| 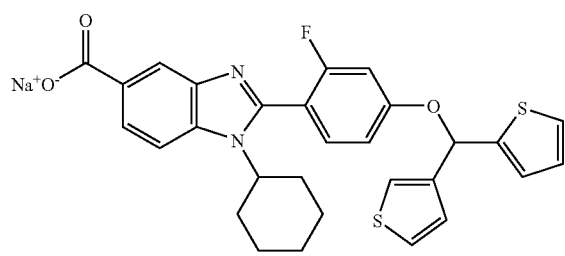 | 300MHz, DMSO-d6 8.14(1H, s), 7.88(1H, d, J=8.4Hz), 7.68(1H, d, J=8.7Hz), 7.64–7.55(3H, m), 7.50(1H, t, J=8.7Hz), 7.22–7.17(3H, m), 7.11(1H, s), 7.08–7.00(2H, m), 3.90(1H, m), 2.15–2.00(2H, m), 1.95–1.50(5H, m), 1.45–1.00(3H, m) |
| Purity >90%(NMR) MS 532 (M+1) | |
TABLE 203
| Example No. 303 | 1H NMR(δ)ppm |
|---|---|
| 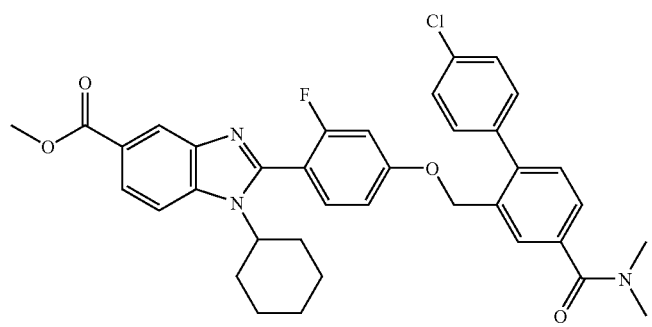 | 300MHz, CDCl3 8.49(1H, s), 7.98(1H, dd, J=8.6, 1.5Hz), 7.71(1H, d, J=1.8Hz), 7.66(1H, d, J=8.6Hz), 7.55–7.29(7H, m), 6.80(1H, dd, J=8.2, 2.2Hz), 6.69(1H, dd, J=11.2, 2.2Hz), 4.99(2H, s), 4.10–3.92(1H, m), 3.95(3H, s), 3.15(3H, s), 3.06(3H, s), 2.31–2.14(2H, m), 2.04–1.86(4H, m), 1.81–1.71(1H, m), 1.41–1.21(3H, m) |
| Purity >90%(NMR) MS 640 (M+1) | |

TABLE 203-continued
| Example No. 304 | 1H NMR(δ)ppm |
|---|---|
| 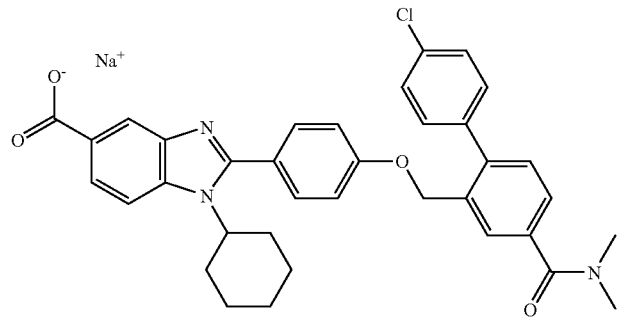 | 300MHz, DMSO-d6 8.21(1H, s), 7.94(1H, d, J=8.7Hz), 7.84(1H, d, J=9.1Hz), 7.70(1H, s), 7.26–7.39(9H, m), 7.11(2H, d, J=8.4Hz), 5.11(2H, s), 4.26(1H, m), 3.01(3H, s), 2.97(3H, s), 2.38–2.19(2H, m), 1.97–1.78(4H, m), 1.72–1.57(1H, m), 1.48–1.17(3H, m) |
Purity >90%(NMR)
MS 608 (M+1)
| Example No. 305 | 1H NMR(δ)ppm |
|---|---|
| 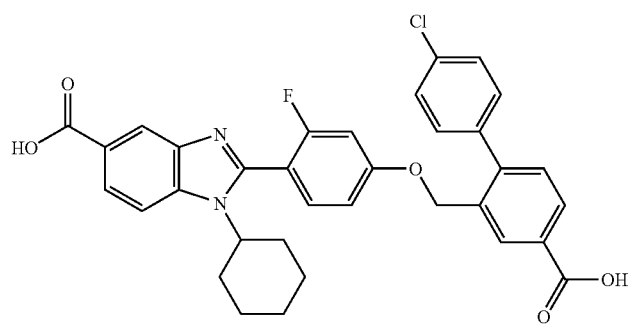 | 300MHz, DMSO-d6 8.24(2H, s), 8.03(1H, d, J=8.0Hz), 7.96(1H, d, J=8.8Hz), 7.87(1H, d, J=9.1Hz), 7.60–7.46(6H, m), 7.09(1H, dd, J=12.0, 1.8Hz), 6.97(1H, dd, J=8.4, 1.8Hz), 5.16(2H, s), 3.97(1H, m), 2.31–2.11(2H, m), 1.92–1.73(4H, m), 1.70–1.57(1H, m), 1.46–1.13(3H, m) |
Purity >90%(NMR)
MS 599 (M+1)
TABLE 204
| Example No. 306 | 1H NMR(δ)ppm |
|---|---|
| 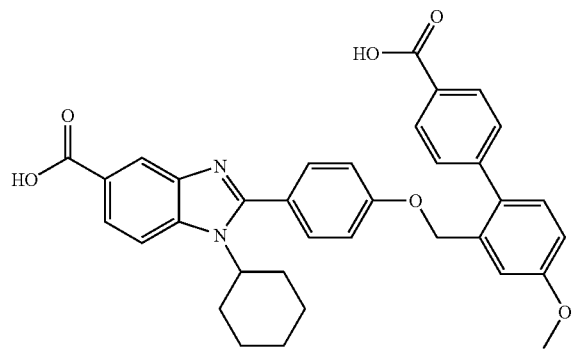 | 300MHz, DMSO-d6 12.84(1H, brs), 8.21(1H, s), 7.98–7.84(5H, m), 7.58(2H, d, J=8.7Hz), 7.54(2H, d, J=7.8Hz), 7.34(1H, d, J=8.7Hz), 7.26(1H, d, J=2.4Hz), 7.13–7.06(3H, m), 5.06(2H, s), 4.26(1H, brt, J=12.7Hz), 3.84(3H, s), 2.36–2.17(2H, brm), 1.99–1.80(4H, brm), 1.73–1.59(1H, brm), 1.47–1.17(3H, brm) |
Purity >90%(NMR)
MS 577 (M+1)

TABLE 204-continued

Example No. 307

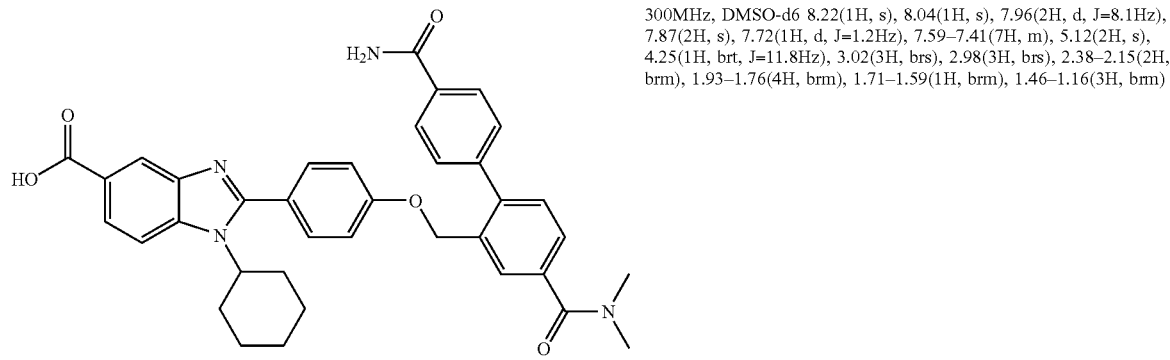

Purity >90%(NMR)
MS 617 (M+1)

1H NMR(δ)ppm

300MHz, DMSO-d6 8.22(1H, s), 8.04(1H, s), 7.96(2H, d, J=8.1Hz), 7.87(2H, s), 7.72(1H, d, J=1.2Hz), 7.59–7.41(7H, m), 5.12(2H, s), 4.25(1H, brt, J=11.8Hz), 3.02(3H, brs), 2.98(3H, brs), 2.38–2.15(2H, brm), 1.93–1.76(4H, brm), 1.71–1.59(1H, brm), 1.46–1.16(3H, brm)

Example No. 308

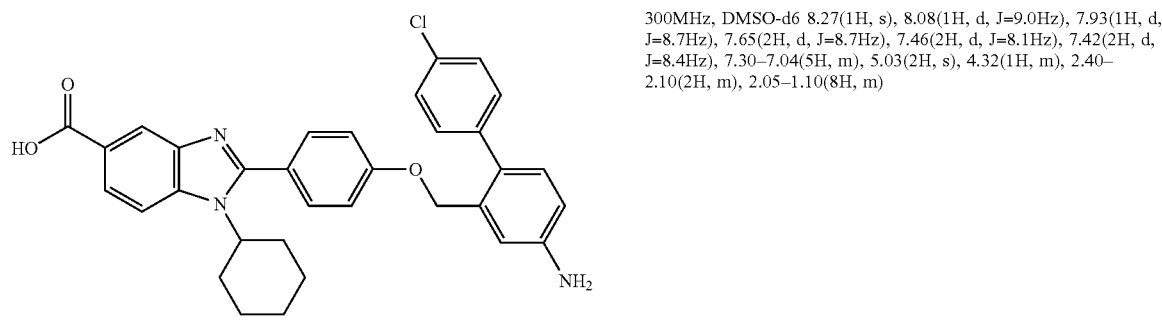

Purity >90%(NMR)
MS 552 (M+1)

1H NMR(δ)ppm

300MHz, DMSO-d6 8.27(1H, s), 8.08(1H, d, J=9.0Hz), 7.93(1H, d, J=8.7Hz), 7.65(2H, d, J=8.7Hz), 7.46(2H, d, J=8.1Hz), 7.42(2H, d, J=8.4Hz), 7.30–7.04(5H, m), 5.03(2H, s), 4.32(1H, m), 2.40–2.10(2H, m), 2.05–1.10(8H, m)

TABLE 205

Example No. 309

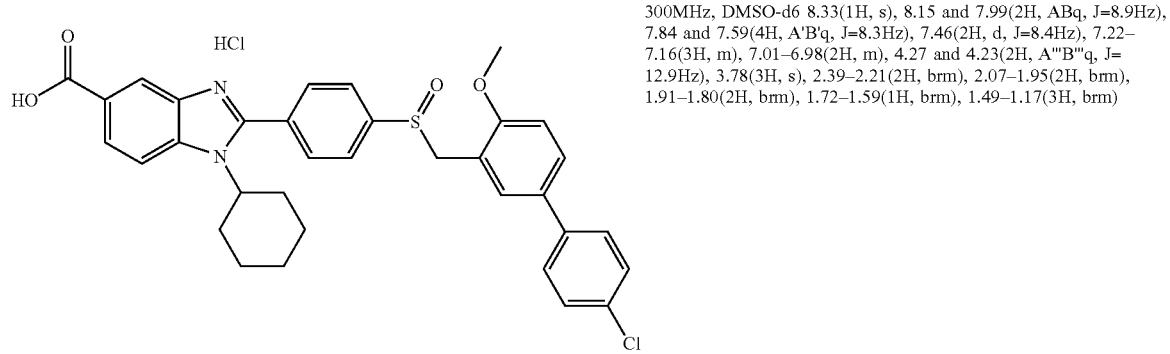

Purity >90%(NMR)
MS

1H NMR(δ)ppm

300MHz, DMSO-d6 8.33(1H, s), 8.15 and 7.99(2H, ABq, J=8.9Hz), 7.84 and 7.59(4H, A'B'q, J=8.3Hz), 7.46(2H, d, J=8.4Hz), 7.22–7.16(3H, m), 7.01–6.98(2H, m), 4.27 and 4.23(2H, A'''B'''q, J=12.9Hz), 3.78(3H, s), 2.39–2.21(2H, brm), 2.07–1.95(2H, brm), 1.91–1.80(2H, brm), 1.72–1.59(1H, brm), 1.49–1.17(3H, brm)

TABLE 205-continued

Example No. 310

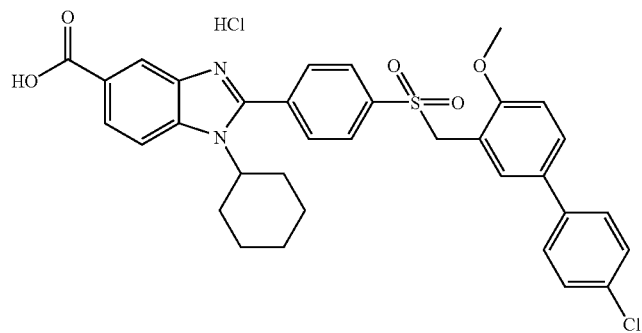

Purity >90%(NMR)
MS 615 (M+1)

1H NMR(δ)ppm

300MHz, DMSO-d6 8.33(1H, s), 8.09 and 7.95(2H, ABq, J=8.7Hz), 7.87 and 7.71(4H, A'B'q, J=8.0Hz), 7.43(2H, d, J=7.8Hz), 7.15(1H, d, J=8.7Hz), 7.07–7.02(4H, m), 4.66(2H, s), 4.23(1H, brt, J=11.8Hz), 3.76(3H, s), 2.38–2.20(2H, brm), 2.04–1.93(2H, brm), 1.89–1.79(2H, brm), 1.70–1.59(1H, brm), 1.49–1.18(3H, brm)

Example No. 311

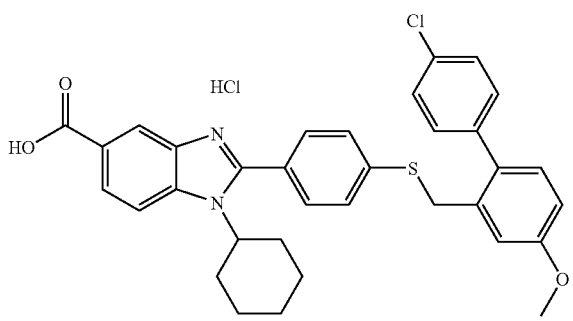

Purity >90%(NMR)
MS 583 (M+1)

1H NMR(δ)ppm

300MHz, DMSO-d6 8.30(1H, s), 8.21 and 8.01(2H, ABq, J=8.7Hz), 7.65(2H, d, J=8.4Hz), 7.52–7.41(6H, m), 7.20(1H, d, J=8.4Hz), 7.14(1H, d, J=2.7Hz), 6.97(1H, dd, J=8.4, 2.4Hz), 4.31(1H, brt, J=9.8Hz), 4.28(2H, s), 3.78(3H, s), 2.37–2.20(2H, brm), 2.07–1.95(2H, brm), 1.92–1.80(2H, brm), 1.71–1.60(1H, brm), 1.50–1.19(3H, brm)

TABLE 206

Example No. 312

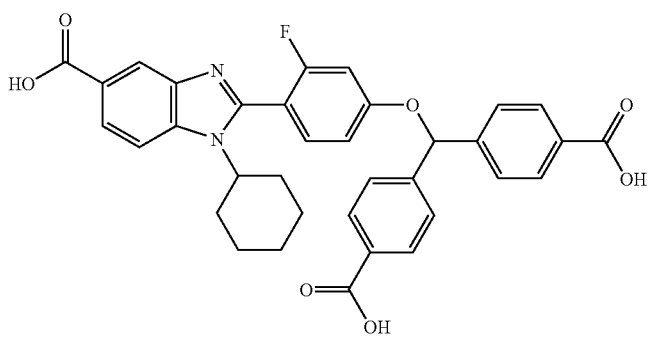

Purity >90%(NMR)
MS 609 (M+1)

1H NMR(δ)ppm

300MHz DMSO-d6 8.22(1H, s), 8.12(1H, d, J=8.4Hz), 8.00–7.84(5H, m), 7.70(4H, d, J=8.4Hz), 7.56(1H, t, J=8.6Hz), 7.23(1H, d, J=12.0Hz), 7.13(1H, d, J=8.6Hz), 6.97(1H, s), 3.92(1H, m), 2.35–2.00(2H, m), 1.95–1.70(4H, m), 1.65–1.55(1H, m), 1.50–1.05(3H, m)

TABLE 206-continued

| Example No. 313 | 1H NMR(δ)ppm |
|---|---|
| 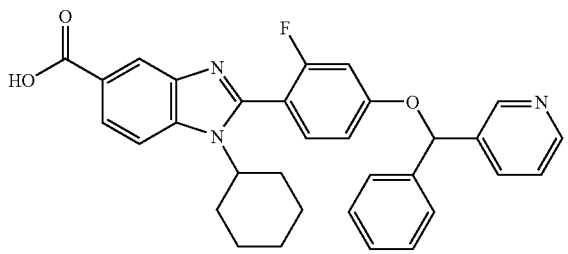<br>Purity >90%(NMR)<br>MS 522 (M+1) | 300MHz, DMSO-d6 8.89(1H, brs), 8.63(1H, brs), 8.24(1H, s), 8.11(1H, d, J=7.8Hz), 7.99(1H, d, J=8.8Hz), 7.89(1H, d, J=9.9Hz), 7.61–7.55(4H, m), 7.43(2H, t, J=7.7Hz), 7.34(1H, t, J=7.2Hz), 7.24(1H, d, J=12.0Hz), 7.14(1H, d, J=8.6Hz), 6.95(1H, s), 3.96(1H, m), 2.35–2.05(2H, m), 2.00–1.50(5H, m), 1.45–1.10(3H, m) |
| Example No. 314 | 1H NMR(δ)ppm |
| 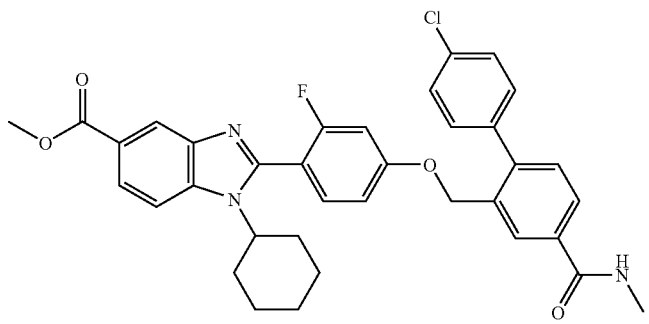<br>Purity >90%(NMR)<br>MS 626 (M+1) | 300MHz, CDCl3 8.48(1H, d, J=1.4Hz), 8.05(1H, d, J=1.8Hz), 8.98(1H, d, J=8.6Hz), 7.82(1H, d, J=7.9Hz), 7.66(1H, d, J=8.6Hz), 7.55–7.24(6H, m), 6.78(1H, dd, J=8.6, 2.6Hz), 6.69(1H, dd, J=11.6Hz), 2.2Hz), 6.40–6.30(1H, m), 4.99(2H, s), 4.02(1H, m), 3.95(3H, s), 3.05(3H, d, J=4.8Hz), 2.32–2.13(2H, m), 2.03–1.87(4H, m), 1.81–1.71(1H, m), 1.46–1.23(3H, m) |

TABLE 207

| Example No. 503 | 1H NMR(δ) ppm |
|---|---|
| 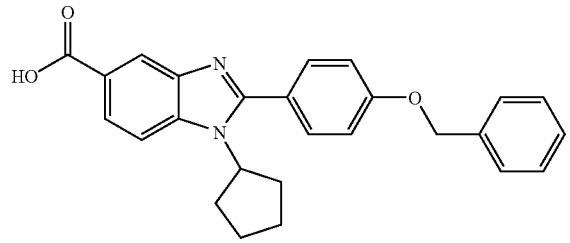<br>Purity >90%(NMR)<br>MS 412(M+1) | 300 MHz, DMSO-d6 8.23(1H, s), 7.76(1H, d, J=8.7Hz), 7.58(1H, d, J=8.8Hz), 7.51–7.32(7H, m), 7.17(2H, d, J=8.7Hz), 6.55(1H, s), 5.18 (2H, s), 4.75(1H, m), 2.35–2.12(2H, m), 2.10–1.85(4H, m), 1.80–1.50(2H, m) |
| Example No. 701 | 1H NMR(δ) ppm |
| 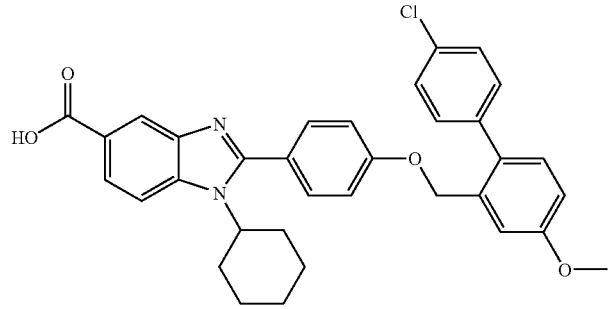<br>Purity >90%(NMR)<br>MS 568(M+1) | 300 MHz, DMSO-d6 8.96(1H, s), 8.50(1H, s), 7.77 (2H, d, J=8.7Hz), 7.50–7.40 (4H, m), 7.30(1H, d, J=8.4 Hz), 7.24(1H, d, J=2.4Hz), 7.16(2H, d, J=8.4Hz), 7.06(1H, dd, J=2.4Hz, 8.1Hz), 5.06 (2H, s), 4.31(1H, s), 3.83(3 H, s), 2.80–2.55(2H, m), 2.00–1.80(4H, m), 1.70–1.55(1H, m), 1.40–1.15(3H, m) |

TABLE 208

Example No. 315

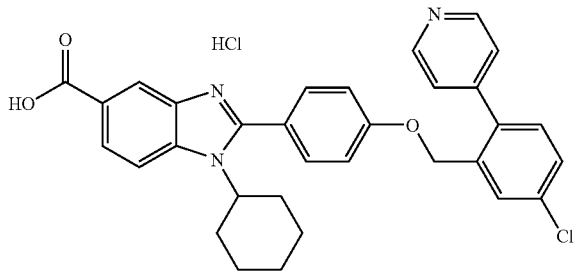

Purity >90%(NMR)
MS 538 (M+1)

1H NMR(δ)ppm

300MHz, DMSO-d6 8.84(2H, d, J=6.3Hz), 8.28(1H, s), 8.17 and 7.99(2H, ABq, J=8.7Hz), 7.87–7.85(3H, m), 7.70–7.50(3H, m), 7.52(1H, d, J=8.3Hz), 7.18(2H, d, J=8.7Hz), 5.22(2H, s) 4.31(1H, brt, J=12.5Hz), 2.36–2.18(2H, m), 2.03–1.78(4H, m), 1.70–1.58(1H, m), 1.50–1.23(3H, m)

Example No. 316

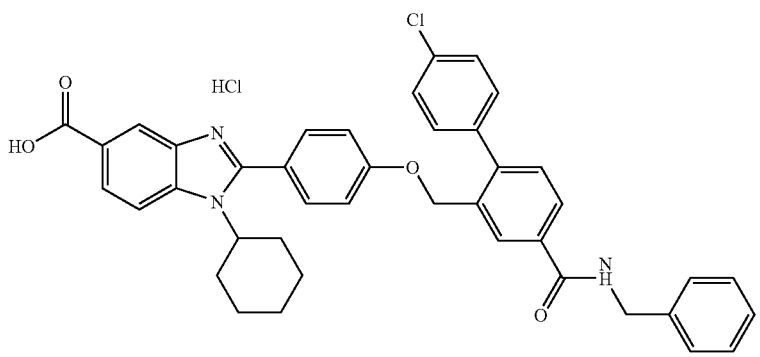

Purity >90%(NMR)
MS 670 (M+1)

1H NMR(δ)ppm

300MHz, DMSO-d6 9.23(1H, t, J=6.3Hz), 8.29(1H, s), 8.25–8.22(2H, m), 8.03(2H, d, J=7.9Hz), 7.55–7.48(5H, m) 7.34(4H, d, J=4.4Hz), 7.28–7.22,(3H, m), 5.15(2H, s), 4.52(2H, d, J=5.9Hz), 4.35(1H, brt, J=12.1Hz), 2.37–2.18(2H, m), 2.08–1.95(2H, m), 1.91–1.79(2H, m), 1.72–1.59(1H, m), 1.47–1.19(3H, m)

Example No. 317

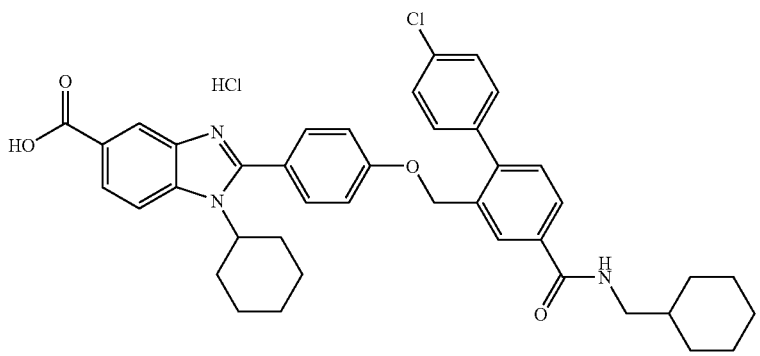

Purity >90%(NMR)
MS 676 (M+1)

1H NMR(δ)ppm

300MHz, DMSO-d6 8.59(1H, t, J=5.5Hz), 8.28(1H, s), 8.21 and 8.01(2H, ABq, J=8.8Hz), 8.16(1H, s), 7.97 and 7.46(2H, A'B'q, J=8.0Hz), 7.71 and 7.23(4H, A"B"q, J=8.7Hz), 7.53 and 7.49(4H, A'''B'''q, J=9.2Hz), 5.14(2H, s), 4.34(1H, brt, J=12.8Hz), 3.14(2H, t, J=6.3Hz), 2.38–2.18(2H, m), 2.07–1.78(4H, m), 1.78–1.47(7H, m), 1.47–1.07(6H, m), 1.03–0.83(2H, m)

TABLE 209

| Example No. 318 | 1H NMR(δ)ppm |
|---|---|
| 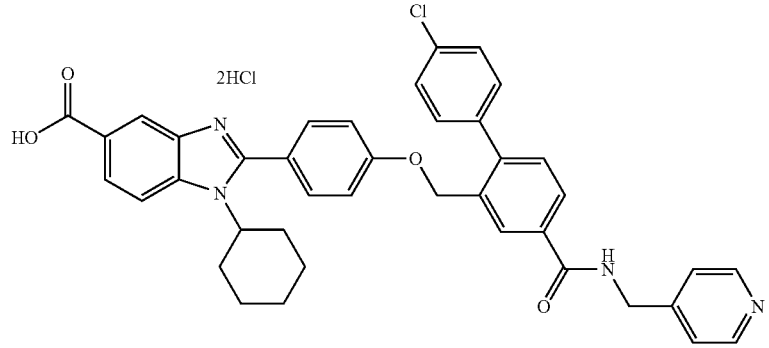<br>Purity >90%(NMR)<br>MS 671 (M+1) | 300MHz, DMSO-d6 9.63(1H, t, J=4.8Hz), 8.86 and 7.97(4H, ABq, J=6.6Hz), 8.30(1H, s), 8.27(1H, s), 8.23 and 8.03(2H, A'B'q, J=8.8Hz), 8.09 and 7.54(2H, A''B''q, J=8.1Hz), 7.73 and 7.24(4H, A'''B'''q, J=8.8Hz), 7.54 and 7.52(4H, A''''B''''q, J=8.8Hz), 5.16(2H, s) 4.78(2H, d, J=5.6Hz), 4.35(1H, brt, J=11.0Hz), 2.39–2.19(2H, m), 2.07–1.96(2H, m), 1.91–1.78(2H, m), 1.70–1.57(1H, m) 1.50–1.19(3H, m) |
| Example No. 319 | 1H NMR(δ)ppm |
| 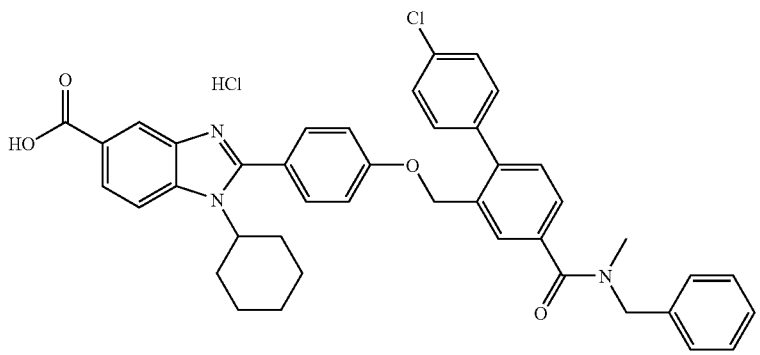<br>Purity >90%(NMR)<br>MS 684 (M+1) | 300MHz, DMSO-d6 8.28(1H, s), 8.24 and 8.03(2H, ABq, J=9.0Hz), 7.77(1H, s), 7.70(2H, d, J=8.4Hz), 7.64–7.10(13H, m), 5.16(2H, s), 4.74 and 4.57(total 2H, each brs), 4.34(1H, brt, J=11.7Hz), 2.90(3H, s), 2.35–2.17(2H, m), 2.07–1.93(2H, m), 1.93–1.78(2H, m), 1.71–1.57(1H, m), 1.51–1.19(3H, m) |
| Example No. 320 | 1H NMR(δ)ppm |
| 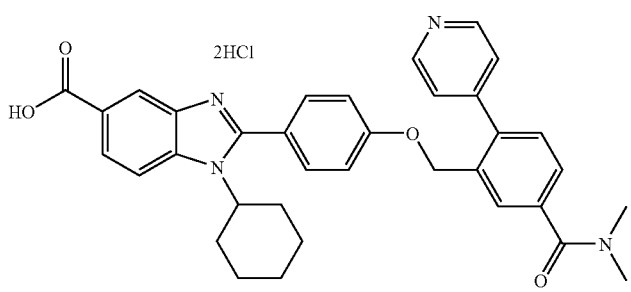<br>Purity >90%(NMR)<br>MS 575 (M+1) | 300MHz, DMSO-d6 8.94 and 8.06(4H, ABq, J=6.8Hz), 8.33(1H, s), 8.28 and 8.05(2H, A'B'q, J=8.7Hz), 7.80(1H, s), 7.73 and 7.22(4H, A''B''q, J=8.7Hz), 7.63 and 7.57(2H, A'''B'''q, J=7.9Hz), 5.30(2H, s), 4.34(1H, brt, J=12.1Hz), 3.04(3H, s), 2.97(3H, s), 2.38–2.18(2H, m), 2.10–1.96(2H, m), 1.93–1.80(2H, m), 1.72–1.58(1H, m), 1.52–1.08(3H, m) |

TABLE 210

Example No. 321

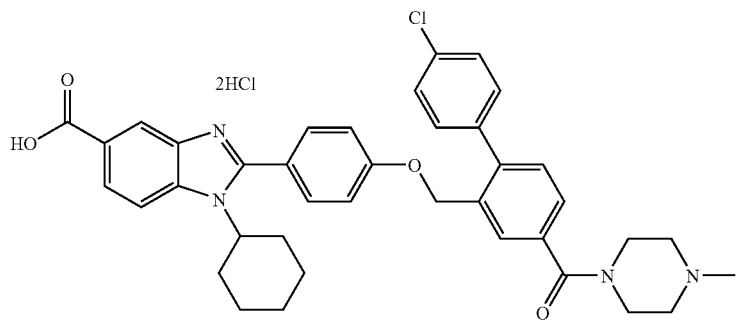

Purity >90%(NMR)
MS 663 (M+1)

1H NMR(δ)ppm

300MHz, DMSO-d6 11.19(1H, brs), 8.31(1H, s), 8.23 and 8.02(2H, ABq, J=9.0Hz), 7.77(1H, s), 7.72 and 7.23(4H, A'B'q, J=8.7Hz), 7.59 and 7.48(2H, A''B''q, J=7.9Hz), 7.53 and 7.51(4H, A'''B'''q, J=9.0Hz),
5.16(2H, s), 4.72–2.97(8H, br m), 4.34(1H, brt, J=12.1Hz), 2.79(3H, s), 2.38–2.17(2H, m), 2.07–1.93(2H, m), 1.93–1.78(2H, m), 1.69–1.58(1H, m), 1.50–1.10(3H, m)

Example No. 322

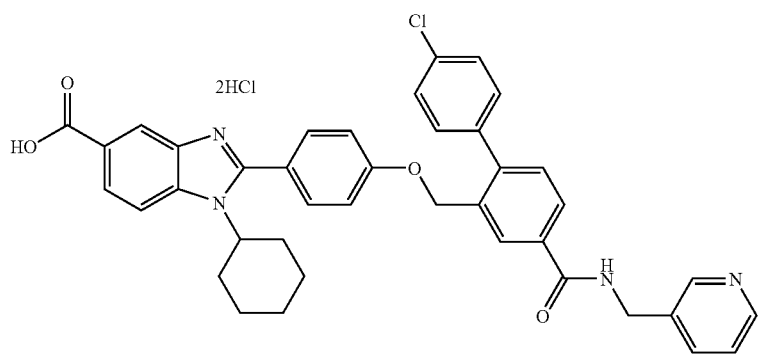

Purity >90%(NMR)
MS 671 (M+1)

1H NMR(δ)ppm

300MHz, DMSO-d6 9.54(1H, t, J=5.7Hz), 8.91(1H, s), 8.81(1H, d, J=4.9Hz), 8.48(1H, d, J=7.9Hz), 8.32(1H, s), 8.27(1H, d, J=9.0Hz), 8.25(1H, s), 8.07–7.97(3H, m), 7.74 and 7.25(4H, ABq, J=8.9Hz), 7.56–7.49(5H, m), 5.16(2H, s), 4.69(2H, d, J=5.6Hz), 4.36(1H, brt, J=12.4Hz), 2.37–2.20(2H, m), 2.09–1.97(2H, m), 1.91–1.78(2H, m), 1.70–1.57(1H, m), 1.50–1.17(3H, m)

Example No. 323

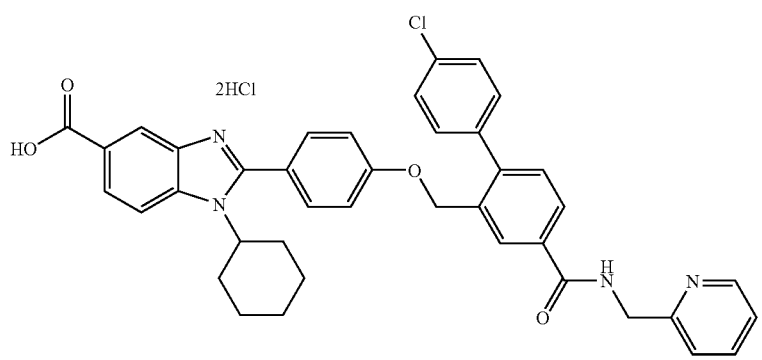

Purity >90%(NMR)
MS 671 (M+1)

1H NMR(δ)ppm

300MHz, DMSO-d6 9.52(1H, t, J=6.0Hz), 8.72(1H, d, J=5.3Hz), 8.30–8.19(4H, m), 8.08(1H, d, J=7.9Hz), 8.02(1H, d, J=7.6Hz), 7.77–7.64(4H, m), 7.57–7.49(5H, m), 7.24(2H, d, J=8.7Hz), 5.16(2H, s), 4.77(2H, d, J=5.6Hz), 4.34(1H, t, J=12.8Hz), 2.36–2.19(2H, m), 2.07–1.95(2H, m), 1.91–1.78(2H, m), 1.69–1.59(1H, m), 1.45–1.20(3H, m)

TABLE 211

Example No. 324

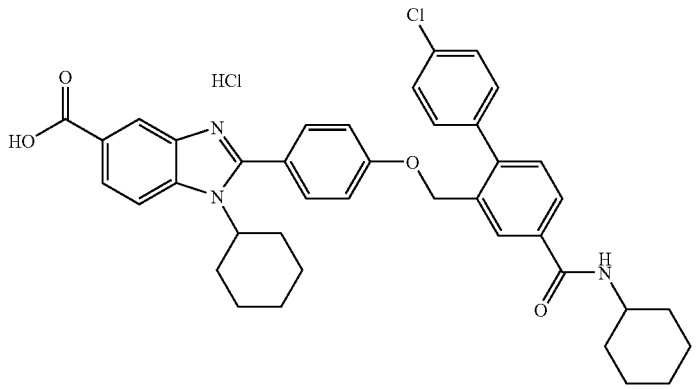

Purity >90%(NMR)
MS 662 (M+1)

1H NMR(δ)ppm

300MHz, DMSO-d6 8.36(1H, d, J=7.9Hz), 8.30(1H, s), 8.28 and 8.05(2H, ABq, J=8.8Hz), 8.16(1H, s), 7.79 and 7.46(2H, A'B'q, J=8.3Hz), 7.74 and 7.25(4H, A'''B'''q, J=8.9Hz), 7.52 and 7.50(4H, A'''B'''q, J=8.7Hz), 5.14(2H, s), 4.36(1H, brt, J=12.1Hz), 3.80(1H, brs), 2.39–2.18(2H, m), 2.10–1.98(2H, m), 1.93–1.57(8H, m), 1.49–1.04(8H, m)

Example No. 325

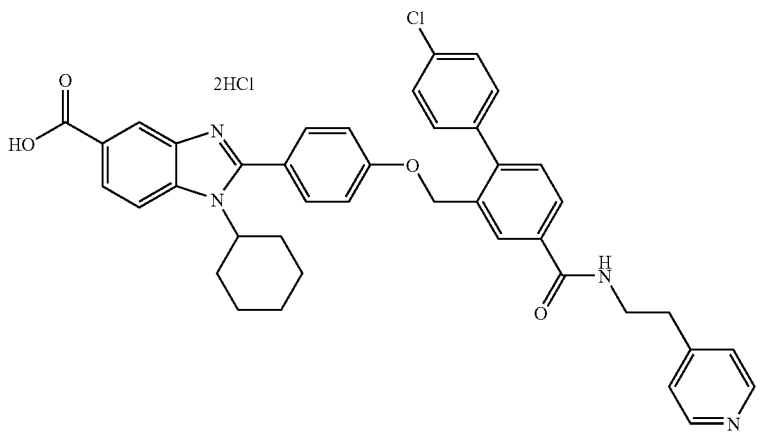

Purity >90%(NMR)
MS 685 (M+1)

1H NMR(δ)ppm

300MHz, DMSO-d6 8.86(1H, t, J=6.0Hz), 8.84 and 8.00(4H, ABq, J=6.6Hz), 8.33(1H, s), 8.27 and 8.04(2H, A'B'q, J=9.0Hz), 8.12(1H, s), 7.92 and 7.46(2H, A''B''q, J=7.9Hz), 7.74 and 7.23(4H, A'''B'''q, J=9.0Hz), 7.53 and 7.49(4H, A''''B''''q, J=9.1Hz), 5.13(2H, s), 4.36(1H, brt, J=12.8Hz), 3.70(2H, td, J=6.8, 6.0Hz), 3.21(2H, t, J=6.8Hz), 2.38–2.20(2H, m), 2.09–1.95(2H, m), 1.91–1.77(2H, m), 1.70–1.59(1H, m), 1.49–1.20(3H, m)

Example No. 326

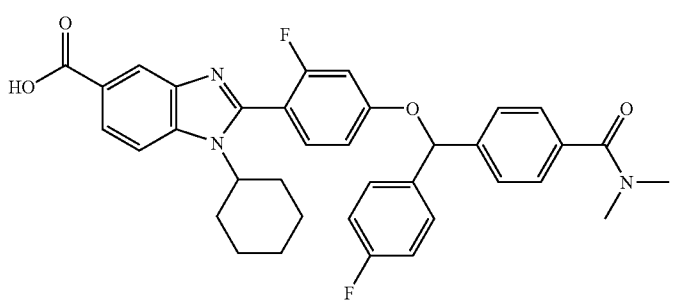

Purity >90%(NMR)
MS 610 (M+1)

1H NMR(δ)ppm

300MHz, DMSO-d6 12.80(1H, brs), 8.23(1H, s), 7.90(1H, d, J=8.7Hz), 7.83(1H, d, J=8.7Hz), 7.60–7.50(5H, m), 7.39(2H, d, J=7.8Hz), 7.23–7.10(3H, m), 7.05(1H, d, J=7.8Hz), 6.85(1H, s), 3.94(1H, s), 2.97, 2.88(6H, s), 2.30–2.10(2H, m), 1.90–1.50(5H, m), 1.40–1.00(3H, m)

TABLE 212
| Example No. 327 | 1H NMR(δ)ppm |
|---|---|
| 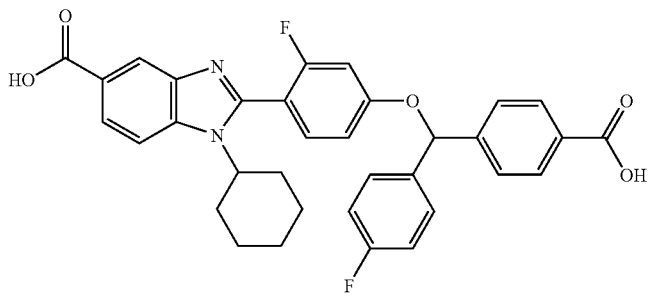 | 300MHz, DMSO-d6 13.20–12.60(2H, brs), 8.23(1H, s), 7.98(2H, d, J=6.6Hz), 7.95(1H, d, J=8.7Hz), 7.87(1H, d, J=8.7Hz), 7.70–7.50(5H, m), 7.27–7.20(3H, m), 7.08(1H, d, J=7.8Hz), 6.90(1H, s), 3.93(1H, s), 2.51–2.05(2H, m), 1.90–1.70(4H, m), 1.65–1.55(1H, m), 1.40–1.10(3H, m) |
Purity >90%(NMR)
MS 583 (M+1)
TABLE 213
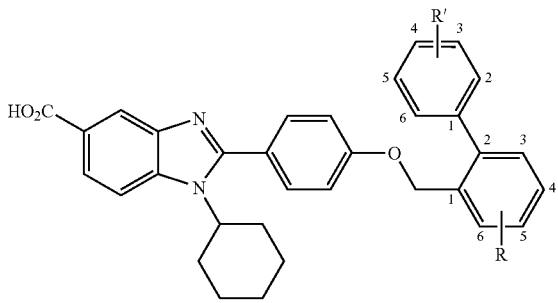
| Ex. No. | R | R' |
|---|---|---|
| 2001 | —H | 4-(—Me) |
| 2002 | —H | 3-(—CF₃) |
| 2003 | 5-(—F) | —H |
| 2004 | 3-(—F) | 2-(—F) |
| 2005 | 3-(—F) | 3-(—F) |
| 2006 | 3-(—F) | 4-(—F) |
| 2007 | 4-(—F) | 4-(—F) |
| 2008 | 5-(—F) | 4-(—F) |
| 2009 | 6-(—F) | 4-(—F) |
| 2010 | 4-(—F) | 4-(—Cl) |
| 2011 | 5-(—F) | 4-(—Me) |
| 2012 | 5-(—F) | 4-(—CF₃) |
| 2013 | 5-(—F) | 4-(—CO₂H) |
| 2014 | 5-(—F) | 4-(—CO₂Me) |
| 2015 | 5-(—F) | 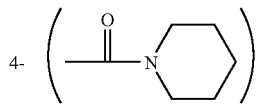 |
| 2016 | 5-(—F) | 4-(—CONH₂) |
| 2017 | 5-(—F) | 4-{—CON(Me)₂} |
| 2018 | 5-(—F) | 4-(—OMe) |
| 2019 | 5-(—F) | 4-(—SMe) |
| 2020 | 5-(—F) | 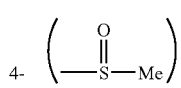 |
| 2021 | 5-(—F) | 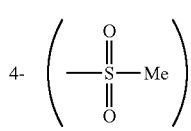 |

TABLE 213-continued
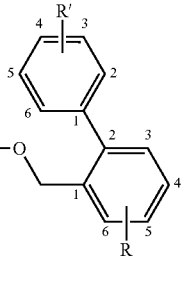
| Ex. No. | R | R' |
|---|---|---|
| 2022 | 4-(—Cl) | —H |
| 2023 | 4-(—Cl) | 4-(—F) |
| 2024 | 4-(—Cl) | 4-(—Cl) |
| 2025 | 4-(—Cl) | 4-(—Me) |
| 2026 | 5-(—Cl) | 4-(—CF$_3$) |
| 2027 | 4-(—Cl) | 4-(—CO$_2$H) |
| 2028 | 5-(—Cl) | 4-(—CO$_2$Me) |
| 2029 | 5-(—Cl) | 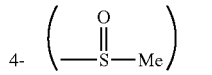 |
| 2030 | 4-(—Cl) | 4-(—CONH2) |
| 2031 | 5-(—Cl) | 4-{—CON(Me)$_2$} |
| 2032 | 5-(—Cl) | 3-(—OMe) |
| 2033 | 4-(—Cl) | 4-(—SMe) |
| 2034 | 5-(—Cl) | 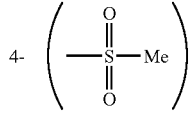 |
| 2035 | 4-(—Cl) | 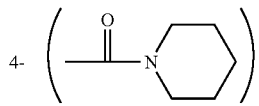 |
| 2036 | 5-(—CN) | 4-(—F) |
| 2037 | 4-(—CN) | 4-(—Cl) |
| 2038 | 5-(—NO$_2$) | 4-(—F) |
| 2039 | 4-(—NO$_2$) | 4-(—Cl) |
| 2040 | 5-(—Me) | 4-(—CO$_2$H) |
| 2041 | 5-(—Me) | 4-(—CO$_2$Me) |
| 2042 | 5-(—Me) | 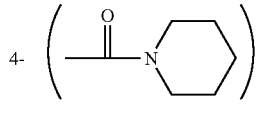 |
| 2043 | 5-(—CF$_3$) | 4-(—CO$_2$H) |
| 2044 | 5-(—CF$_3$) | 4-(—CO$_2$Me) |
| 2045 | 5-(—CF$_3$) | 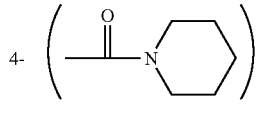 |
| 2046 | 5-(—CO$_2$H) | 4-(—F) |
| 2047 | 4-(—CO$_2$H) | 4-(—Cl) |
| 2048 | 5-(—CO$_2$Me) | 4-(—F) |
| 2049 | 5-(—CO$_2$Me) | 4-(—Cl) |
| 2050 | 5-(—Ac) | 4-(—F) |
| 2051 | 5-(—Ac) | 4-(—Cl) |

TABLE 213-continued

[Structure: benzimidazole with HO₂C- group, N-cyclohexyl, 2-(4-(benzyloxymethyl)phenyl) substituent, with biphenyl bearing R and R' substituents]

| Ex. No. | R | R' |
|---|---|---|
| 2052 | 5-(C(O)-N-piperidinyl) | —H |
| 2053 | 5-(C(O)-N-piperidinyl) | 4-(—F) |
| 2054 | 5-(C(O)-N-piperidinyl) | 4-(—Cl) |
| 2055 | 5-(C(O)-N-piperidinyl) | 4-(—CN) |
| 2056 | 5-(C(O)-N-piperidinyl) | 4-(—NO₂) |
| 2057 | 5-(C(O)-N-piperidinyl) | 4-(—Me) |
| 2058 | 5-(C(O)-N-piperidinyl) | 4-(—CF₃) |
| 2059 | 5-(C(O)-N-piperidinyl) | 4-(—Ac) |
| 2060 | 5-(C(O)-N-piperidinyl) | 4-(—CO₂H) |
| 2061 | 5-(C(O)-N-piperidinyl) | 4-(—CO₂Me) |

TABLE 213-continued
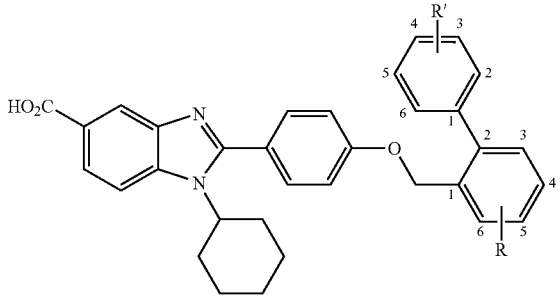
| Ex. No. | R | R' |
|---|---|---|
| 2062 | 5- 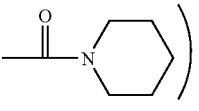 | 4-  |
| 2063 | 5- 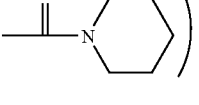 | 4-(—CONH$_2$) |
| 2064 | 5- 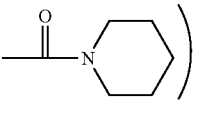 | 4-{—CON(Me)$_2$} |
| 2065 | 5- 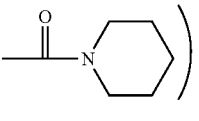 | 4-{—C(=NH)NH$_2$} |
| 2066 | 5- 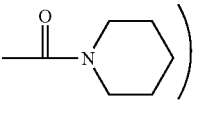 | 4-(—OMe) |
| 2067 | 5- 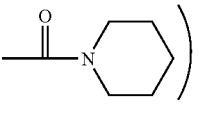 | 4- 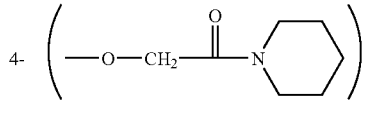 |
| 2068 | 5- 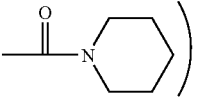 | 4-(—NHMe) |
| 2069 | 5- 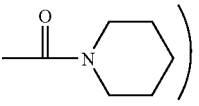 | 4-(—NHAc) |
| 2070 | 5- 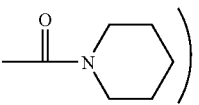 | 4- 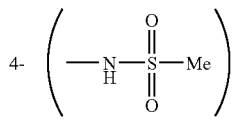 |
| 2071 | 5- 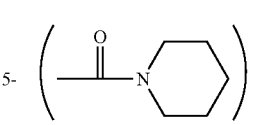 | 4-(—SMe) |

TABLE 213-continued
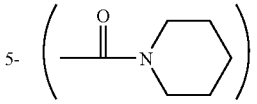
| Ex. No. | R | R' |
|---|---|---|
| 2072 | 5- 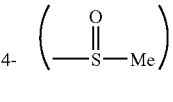 | 4- 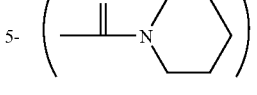 |
| 2073 | 5- 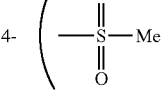 | 4- 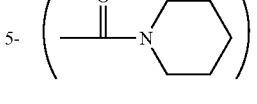 |
| 2074 | 5- 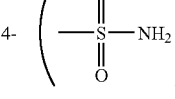 | 4- 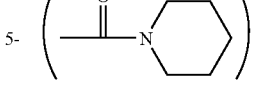 |
| 2075 | 5- 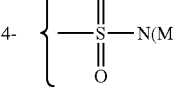 | 4- 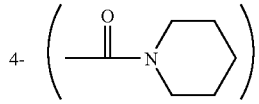 |
| 2076 | 5-(—CONH$_2$) | —H |
| 2077 | 5-(—CONH$_2$) | 4-(—F) |
| 2078 | 5-(—CONH$_2$) | 2,3,4,5,6-penta-(—F) |
| 2079 | 5-(—CONH$_2$) | 2-(—Cl) |
| 2080 | 5-(—CONH$_2$) | 3-(—Cl) |
| 2081 | 3-(—CONH$_2$) | 2-(—Cl) |
| 2082 | 3-(—CONH$_2$) | 3-(—Cl) |
| 2083 | 3-(—CONH$_2$) | 4-(—Cl) |
| 2084 | 4-(—CONH$_2$) | 2-(—Cl) |
| 2085 | 4-(—CONH$_2$) | 3-(—Cl) |
| 2086 | 4-(—CONH$_2$) | 4-(—Cl) |
| 2087 | 6-(—CONH$_2$) | 2-(—Cl) |
| 2088 | 6-(—CONH$_2$) | 3-(—Cl) |
| 2089 | 6-(—CONH$_2$) | 4-(—Cl) |
| 2090 | 5-(—CONH$_2$) | 3,5-di-(—Cl) |
| 2091 | 5-(—CCNH$_2$) | 4-(—CN) |
| 2092 | 5-(—CONH$_2$) | 4-(—NO$_2$) |
| 2093 | 5-(—CONH$_2$) | 4-(—Me) |
| 2094 | 5-(—CONH$_2$) | 2,6-di-(—Me) |
| 2095 | 5-(—CONH$_2$) | 4-(—CF$_3$) |
| 2096 | 5-(—CONH$_2$) | 4-(—Ac) |
| 2097 | 5-(—CONH$_2$) | 4-(—CO$_2$H) |
| 2098 | 5-(—CONH$_2$) | 4-(—CO$_2$Me) |
| 2099 | 5-(—CONH$_2$) | 4- 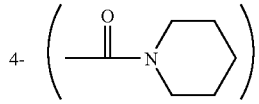 |
| 2100 | 5-(—CONH$_2$) | 4-(—CONH$_2$) |
| 2101 | 5-(—CONH$_2$) | 3,5-di-(—CONH$_2$) |
| 2102 | 5-(—CONH$_2$) | 4-{—CON(Me)$_2$} |
| 2103 | 5-(—CONH$_2$) | 4-{—C(=NH)NH$_2$} |

TABLE 213-continued
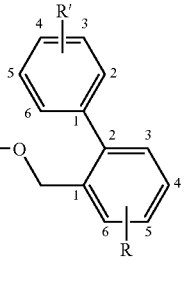
| Ex. No. | R | R' |
|---|---|---|
| 2104 | 5-(—CONH$_2$) | 4-(—OMe) |
| 2105 | 5-(—CONH$_2$) | 3,4,5-tri-(—OMe) |
| 2106 | 5-(—CONH$_2$) | 4-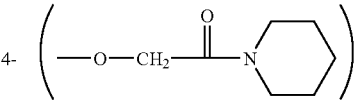 |
| 2107 | 5-(—CONH$_2$) | 4-(—NHMe) |
| 2108 | 5-(—CONH$_2$) | 4-(—NHAc) |
| 2109 | 5-(—CONH$_2$) | 4-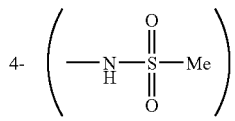 |
| 2110 | 5-(—CONH$_2$) | 4-(—SMe) |
| 2111 | 5-(—CONH$_2$) | 4-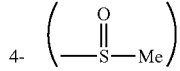 |
| 2112 | 5-(—CONH$_2$) | 4-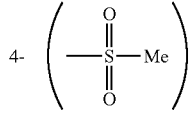 |
| 2113 | 5-(—CONH$_2$) | 4-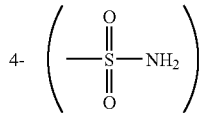 |
| 2114 | 5-(—CONH$_2$) | 4-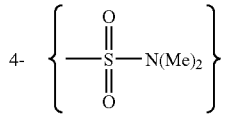 |
| 2115 | 5-{—CON(Me)$_2$} | —H |
| 2116 | 5-{—CON(Me)$_2$} | 4-(—F) |
| 2117 | 4-{—CON(Me)$_2$} | 4-(—Cl) |
| 2118 | 5-{—CON(Me)$_2$} | 4-(—CN) |
| 2119 | 5-{—CON(Me)$_2$} | 4-(—NO$_2$) |
| 2120 | 5-{—CON(Me)$_2$} | 4-(—Me) |
| 2121 | 4-{—CON(Me)$_2$} | 4-(—CF$_3$) |
| 2122 | 5-{—CON(Me)$_2$} | 4-(—Ac) |
| 2123 | 5-{—CON(Me)$_2$} | 4-(—CO$_2$H) |
| 2124 | 5-{—CON(Me)$_2$} | 4-(—CO$_2$Me) |

TABLE 213-continued
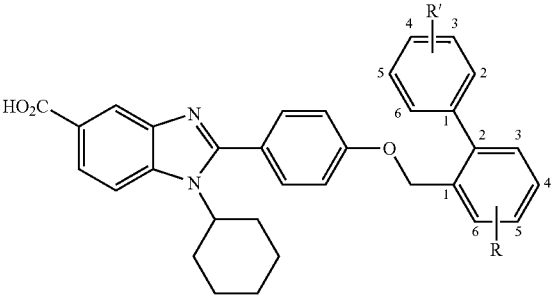
| Ex. No. | R | R' |
|---|---|---|
| 2125 | 5-{—CON(Me)₂} | 4- 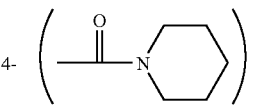 |
| 2126 | 5-{—CON(Me)₂} | 3-(—CONH₂) |
| 2127 | 4-{—CON(Me)₂} | 4-{—CON(Me)₂} |
| 2128 | 5-{—CON(Me)₂} | 4-{—C(=NH)NH₂} |
| 2129 | 5-{—CON(Me)₂} | 4-(—OMe) |
| 2130 | 5-{—CON(Me)₂} | 4- 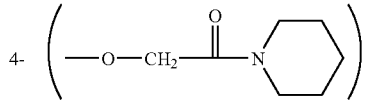 |
| 2131 | 5-{—CON(Me)₂} | 4-(—NHMe) |
| 2132 | 5-{—CON(Me)₂} | 4-(—NHAc) |
| 2133 | 5-{—CON(Me)₂} | 4- 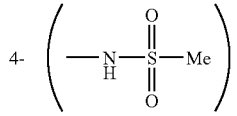 |
| 2134 | 4-{—CON(Me)₂} | 4-(—SMe) |
| 2135 | 5-{—CON(Me)₂} | 4- 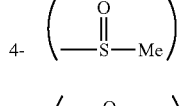 |
| 2136 | 4-{—CON(Me)₂} | 4- 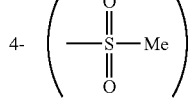 |
| 2137 | 5-{—CON(Me)₂} | 4- 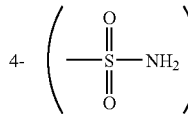 |
| 2138 | 5-{—CON(Me)₂} | 4- 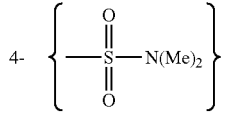 |
| 2139 | 5-(—OMe) | —H |
| 2140 | 5-(—OMe) | 4-(—F) |
| 2141 | 3-(—OMe) | 4-(—Cl) |
| 2142 | 4-(—OMe) | 4-(—Cl) |
| 2143 | 5-(—OMe) | 2-(—Cl) |
| 2144 | 5-(—OMe) | 3-(—Cl) |
| 2145 | 6-(—OMe) | 4-(—Cl) |

TABLE 213-continued
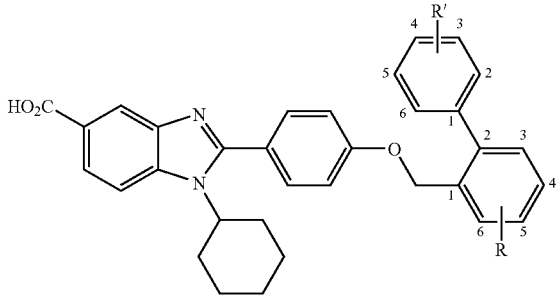
| Ex. No. | R | R' |
|---|---|---|
| 2146 | 5-(—OMe) | 4-(—CN) |
| 2147 | 5-(—OMe) | 4-(—NO₂) |
| 2148 | 5-(—OMe) | 4-(—Me) |
| 2149 | 5-(—OMe) | 4-(—CF₃) |
| 2150 | 5-(—CMe) | 4-(—Ac) |
| 2151 | 4-(—OMe) | 4-(—CO₂H) |
| 2152 | 4,5-di-(—OMe) | 4-(—CO₂H) |
| 2153 | 5-(—OMe) | 4-(—CO₂Me) |
| 2154 | 5-(—OMe) | 4- 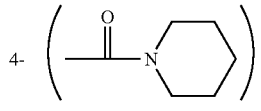 |
| 2155 | 5-(—OMe) | 4-(—CONH₂) |
| 2156 | 5-(—OMe) | 4-{—CON(Me)₂} |
| 2157 | 5-(—OMe) | 4-{—CON(=NH)NH₂} |
| 2158 | 5-(—OMe) | 4-(—OMe) |
| 2159 | 5-(—OMe) | 4- 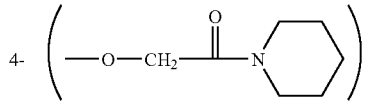 |
| 2160 | 5-(—OMe) | 4-(—NHMe) |
| 2161 | 5-(—OMe) | 4-(—NHAc) |
| 2162 | 5-(—OMe) | 4- 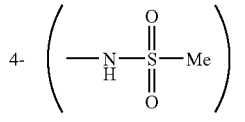 |
| 2163 | 5-(—OMe) | 4-(—SMe) |
| 2164 | 5-(—OMe) | 4- 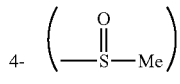 |
| 2165 | 5-(—OMe) | 4- 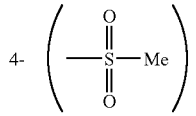 |
| 2166 | 5-(—OMe) | 4- 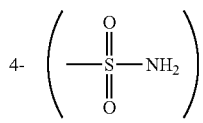 |

TABLE 213-continued
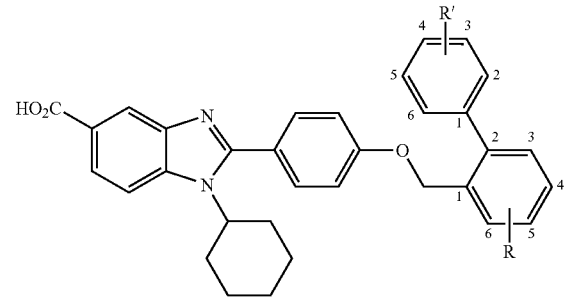
| Ex. No. | R | R' |
|---|---|---|
| 2167 | 5-(—OMe) | 4-{—S(O)₂—N(Me)₂} 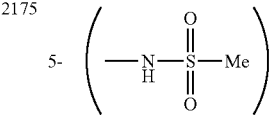 |
| 2168 | 5-(—NHMe) | 4-(—F) |
| 2169 | 5-(—NHMe) | 4-(—Cl) |
| 2170 | 5-(—NHAc) | 4-(—F) |
| 2171 | 5-(—NHAc) | 4-(—Cl) |
| 2172 | 5-(—NHAc) | 4-(—Ac) |
| 2173 | 5-(—NHAc) | 4-(—CONH₂) |
| 2174 | 5-(—NHAc) | 4-{—CON(Me)₂} |
| 2175 | 5-(—NHS(O)₂Me) 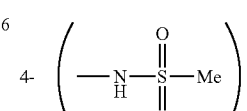 | 4-(—F) |
| 2176 | 4-(—NHS(O)₂Me) | 4-(—Cl) |
| 2177 | 5-(—NHS(O)₂Me) | 4-(—Me) |
| 2178 | 5-(—NHS(O)₂Me) | 4-(—CF₃) |
| 2179 | 5-(—NHS(O)₂Me) | 4-(—CO₂H) |
| 2180 | 5-(—NHS(O)₂Me) | 4-(—CO₂Me) |
| 2181 | 5-(—NHS(O)₂Me) | 4-{—C(O)-N-piperidine} 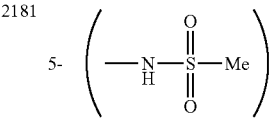 |

TABLE 213-continued

[Structure: benzimidazole with HO₂C- group, N-cyclohexyl, 2-(4-(phenylmethoxy))phenyl, with biphenyl group having R' on outer ring (positions 2-6) and R on inner ring (positions 3-6)]

| Ex. No. | R | R' |
|---|---|---|
| 2182 | 5-(—NH—S(=O)₂—Me) | 4-(—SMe) |
| 2183 | 5-(—NH—S(=O)₂—Me) | 4-(—S(=O)—Me) |
| 2184 | 5-(—NH—S(=O)₂—Me) | 4-(—S(=O)₂—Me) |
| 2185 | 5-(—SMe) | 4-(—F) |
| 2186 | 4-(—SMe) | 4-(—Cl) |
| 2187 | 5-(—SMe) | 4-(—Me) |
| 2188 | 5-(—SMe) | 4-(—CF₃) |
| 2189 | 5-(—SMe) | 4-(—Ac) |
| 2190 | 5-(—SMe) | 4-(—CONH₂) |
| 2191 | 5-(—SMe) | 4-{—CON(Me)₂} |
| 2192 | 5-(—S(=O)—Me) | 4-(—F) |
| 2193 | 4-(—S(=O)—Me) | 4-(—Cl) |
| 2194 | 5-(—S(=O)—Me) | 4-(—Me) |
| 2195 | 5-(—S(=O)—Me) | 4-(—CF₃) |
| 2196 | 5-(—S(=O)—Me) | 4-(—Ac) |
| 2197 | 5-(—S(=O)—Me) | 4-(—CONH₂) |
| 2198 | 5-(—S(=O)—Me) | 4-{—CON(Me)₂} |

TABLE 213-continued
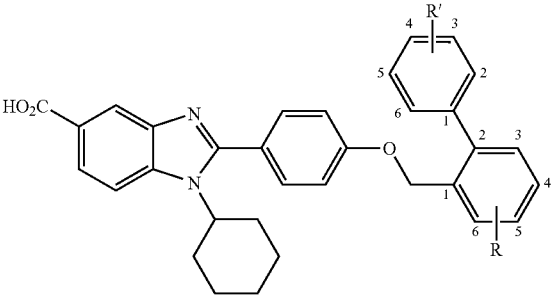
| Ex. No. | R | R' |
|---|---|---|
| 2199 | 5- (—S(O)₂—Me) | 4-(—F) |
| 2200 | 4- (—S(O)₂—Me) | 4-(—Cl) |
| 2201 | 5- (—S(O)₂—Me) | 4-(—Me) |
| 2202 | 5- (—S(O)₂—Me) | 4-(—CF₃) |
| 2203 | 5- (—S(O)₂—Me) | 4-(—Ac) |
| 2204 | 5- (—S(O)₂—Me) | 4-(—CONH₂) |
| 2205 | 5- (—S(O)₂—Me) | 4-{—CON(Me)₂} |
| 2206 | 5- (—S(O)₂—NH₂) | 4-(—F) |
| 2207 | 4- (—S(O)₂—NH₂) | 4-(—Cl) |

TABLE 213-continued
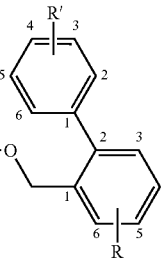
| Ex. No. | R | R' |
|---|---|---|
| 2208 | 4-(—S(O)$_2$—NH$_2$) | 2,4-di-(—Cl) |
| 2209 | 5-(—S(O)$_2$—NH$_2$) | 4-(—Me) |
| 2210 | 5-(—S(O)$_2$—NH$_2$) | 3-(—CF$_3$) |
| 2211 | 5-(—S(O)$_2$—NH$_2$) | 4-(—CF$_3$) |
| 2212 | 5-(—S(O)$_2$—NH$_2$) | 4-(—CONH$_2$) |
| 2213 | 5-(—S(O)$_2$—NH$_2$) | 4-{—CON(Me)$_2$} |
| 2214 | 5-(—S(O)$_2$—NH$_2$) | 4-(—SMe) |
| 2215 | 5-(—S(O)$_2$—NH$_2$) | 4-(—S(O)—Me) |
| 2216 | 5-(—S(O)$_2$—NH$_2$) | 4-(—S(O)$_2$—Me) |

TABLE 213-continued
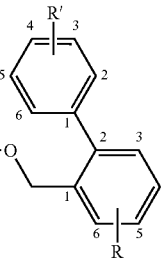
| Ex. No. | R | R' |
|---|---|---|
| 2217 | 5-{—S(O)₂—N(Me)₂} | 4-(—F) |
| 2218 | 4-{—S(O)₂—N(Me)₂} | 4-(—Cl) |
| 2219 | 5-{—S(O)₂—N(Me)₂} | 4-(—Me) |
| 2220 | 5-{—S(O)₂—N(Me)₂} | 4-(—CF₃) |
| 2221 | 5-{—S(O)₂—N(Me)₂} | 4-(—CONH₂) |
| 2222 | 5-{—S(O)₂—N(Me)₂} | 4-{—CON(Me)₂} |
| 2223 | 5-{—S(O)₂—N(Me)₂} | 4-(—SMe) |
| 2224 | 5-{—S(O)₂—N(Me)₂} | 4-(—S(O)—Me) |
| 2225 | 5-{—S(O)₂—N(Me)₂} | 4-(—S(O)₂—Me) |
| 2226 | 5-{—O—(CH₂)₂—OH} | 4-(—Cl) |

TABLE 213-continued
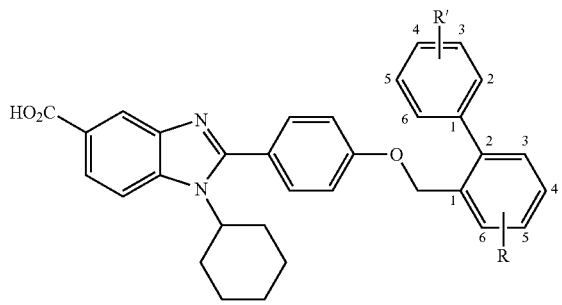
| Ex. No. | R | R' |
|---|---|---|
| 2227 | 5-{—O—(CH$_2$)$_3$—OH} | 4-(—Cl) |
| 2228 | 5- (—O—CH$_2$—cyclohexyl) | 4-(—Cl) |
| 2229 | 5- (—O—CH$_2$-(4-pyridyl)) | 4-(—Cl) |
| 2230 | 5- (—O—CH$_2$-(4-methylthiazol-2-yl)) | 4-(—Cl) |
| 2231 | 5- (—O—CH$_2$CH$_2$—N(4-hydroxypiperidinyl)) | 4-(—Cl) |
| 2232 | 5- (—O—CH$_2$—C(O)—N(4-hydroxypiperidinyl)) | 4-(—Cl) |
| 2233 | 5- (1-acetyl-3-hydroxypyrrolidinyl) | 4-(—Cl) |
| 2234 | 5- (1-acetyl-3-hydroxypiperidinyl) | 4-(—Cl) |
| 2235 | 5- (1-acetyl-3,4-dihydroxypiperidinyl) | 4-(—Cl) |

TABLE 213-continued

| Ex. No. | R | R' |
|---|---|---|
| 2236 | 5- (4-acetyl-piperidin-4-yl-methanol) | 4-(—Cl) |
| 2237 | 5- (1-acetyl-piperidine-4-carboxylic acid) | 4-(—Cl) |
| 2238 | 5- (1-acetyl-2,2,6,6-tetramethylpiperidine) | 4-(—Cl) |
| 2239 | 5- (1-acetyl-4-hydroxy-2,2,6,6-tetramethylpiperidine) | 4-(—Cl) |
| 2240 | 5- (1-acetyl-4-methoxypiperidine) | 4-(—Cl) |
| 2241 | 5- (1-acetylpiperidin-4-one) | 4-(—Cl) |
| 2242 | 5- (1-acetyl-2-oxopiperidine) | 4-(—Cl) |

TABLE 213-continued
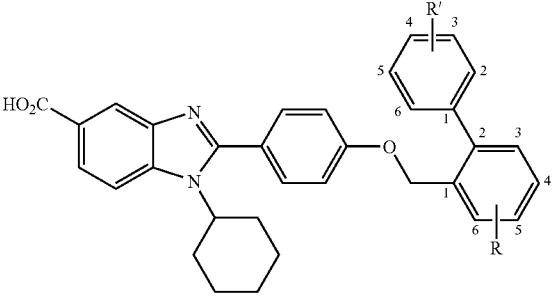
| Ex. No. | R | R' |
|---|---|---|
| 2243 | 5- 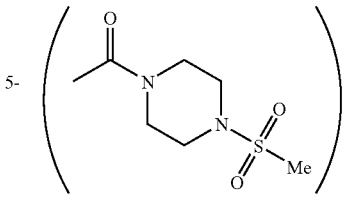 | 4-(—Cl) |
| 2244 | 5- 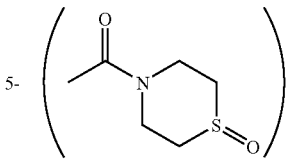 | 4-(—Cl) |
| 2245 | 5- 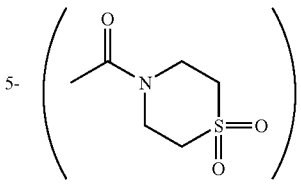 | 4-(—Cl) |
| 2246 | 5- 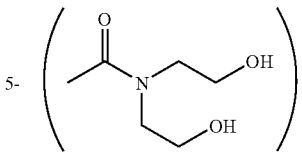 | 4-(—Cl) |
| 2247 | 5- 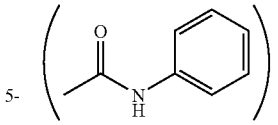 | 4-(—Cl) |

TABLE 213-continued
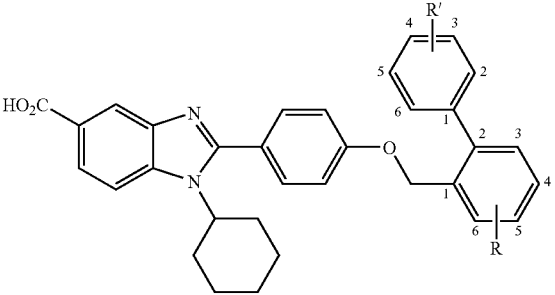
| Ex. No. | R | R' |
|---|---|---|
| 2248 | 4- 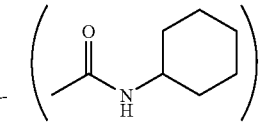 | 4-(—Cl) |
| 2249 | 5- 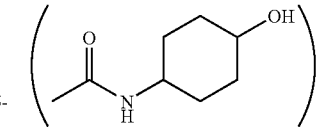 | 4-(—Cl) |
| 2250 | 5- 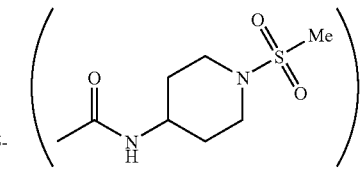 | 4-(—Cl) |
| 2251 | 4- 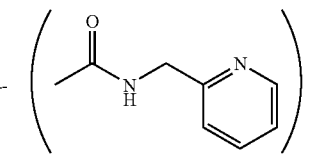 | 4-(—Cl) |
| 2252 | 4- 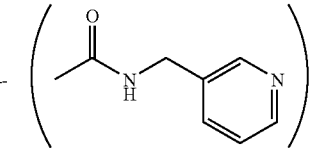 | 4-(—Cl) |
| 2253 | 5- 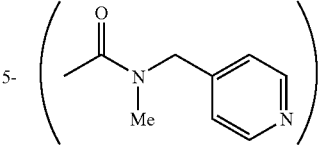 | 4-(—Cl) |
| 2254 | 5- 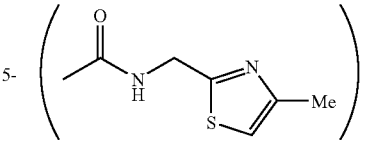 | 4-(—Cl) |

TABLE 214

[Structure: benzimidazole with HO2C group, N-cyclohexyl, 2-(2-fluoro-4-((biphenylmethyl)oxy)phenyl) substituent with R and R' on the biphenyl rings]

| Ex. No. | R | R' |
|---|---|---|
| 2255 | —H | —H |
| 2256 | —H | 4-(-Me) |
| 2257 | —H | 3-(-CF₃) |
| 2258 | 5-(-F) | —H |
| 2259 | 5-(-F) | 4-(-F) |
| 2260 | 5-(-F) | 4-(-Cl) |
| 2261 | 5-(-F) | 4-(-Me) |
| 2262 | 5-(-F) | 4-(-CF₃) |
| 2263 | 5-(-F) | 4-(-CO₂H) |
| 2264 | 5-(-F) | 4-(-CO₂Me) |
| 2265 | 5-(-F) | 4-(-C(O)-N-piperidinyl) |
| 2266 | 5-(-F) | 4-(-CONH₂) |
| 2267 | 5-(-F) | 4-{-CON(Me)₂} |
| 2268 | 5-(-F) | 4-(-OMe) |
| 2269 | 5-(-F) | 4-(-SMe) |
| 2270 | 5-(-F) | 4-(-S(O)Me) |
| 2271 | 5-(-F) | 4-(-SO₂Me) |
| 2272 | 4-(-Cl) | —H |
| 2273 | 5-(-Cl) | 4-(-F) |
| 2274 | 4-(-Cl) | 4-(-Cl) |
| 2275 | 5-(-Cl) | 4-(-Me) |
| 2276 | 5-(-Cl) | 4-(-CF₃) |
| 2277 | 5-(-Cl) | 4-(-CO₂H) |
| 2278 | 5-(-Cl) | 4-(-CO₂Me) |
| 2279 | 5-(-Cl) | 4-(-C(O)-N-piperidinyl) |
| 2280 | 5-(-Cl) | 4-(-CONH2) |
| 2281 | 5-(-Cl) | 4-{-CON(Me)₂} |
| 2282 | 5-(-Cl) | 4-(-OMe) |
| 2283 | 5-(-Cl) | 4-(-SMe) |
| 2284 | 5-(-Cl) | 4-(-S(O)Me) |

TABLE 214-continued
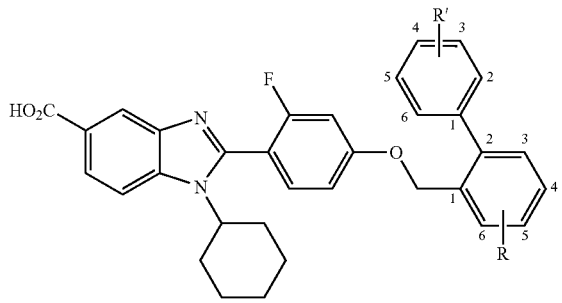
| Ex. No. | R | R' |
|---|---|---|
| 2285 | 5-(-Cl) | 4-  |
| 2286 | 5-(-CN) | 4-(-F) |
| 2287 | 5-(-CN) | 4-(-Cl) |
| 2288 | 5-(-NO$_2$) | 4-(-F) |
| 2289 | 5-(-NO$_2$) | 4-(-Cl) |
| 2290 | 5-(-Me) | 4-(-CO$_2$H) |
| 2291 | 5-(-Me) | 4-(-CO$_2$Me) |
| 2292 | 5-(-Me) | 4-  |
| 2293 | 5-(-CF$_3$) | 4-(-CO$_2$H) |
| 2294 | 5-(-CF$_3$) | 4-(-CO$_2$Me) |
| 2295 | 5-(-CF$_3$) | 4-  |
| 2296 | 5-(-CO$_2$H) | 4-(-F) |
| 2297 | 4-(-CO$_2$H) | 4-(-Cl) |
| 2298 | 5-(-CO$_2$Me) | 4-(-F) |
| 2299 | 5-(-CO$_2$Me) | 4-(-Cl) |
| 2300 | 5-(-Ac) | 4-(-F) |
| 2301 | 5-(-Ac) | 4-(-Cl) |
| 2302 | 5- 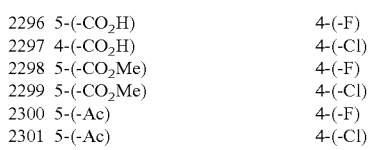 | —H |
| 2303 | 5- 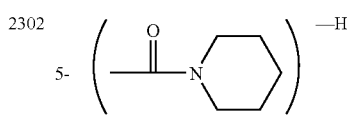 | 4-(-F) |
| 2304 | 5- 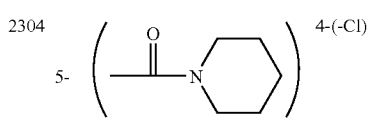 | 4-(-Cl) |
| 2305 | 5- 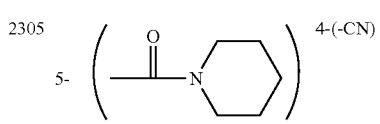 | 4-(-CN) |

TABLE 214-continued
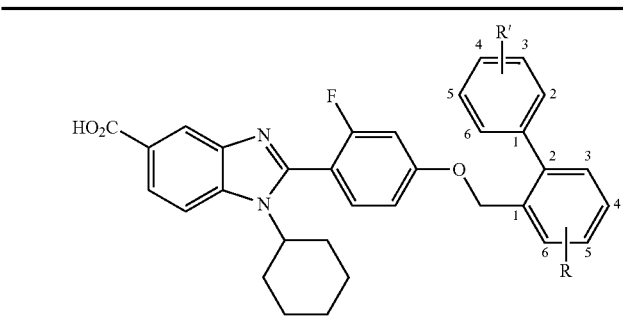
| Ex. No. | R | R' |
|---|---|---|
| 2306 | 5- ![piperidine amide] | 4-(-NO₂) |
| 2307 | 5- ![piperidine amide] | 4-(-Me) |
| 2308 | 5- ![piperidine amide] | 4-(-CF₃) |
| 2309 | 5- ![piperidine amide] | 4-(-Ac) |
| 2310 | 5- ![piperidine amide] | 4-(-CO₂H) |
| 2311 | 5- ![piperidine amide] | 4-(-CO₂Me) |
| 2312 | 5- ![piperidine amide] | 4- ![piperidine amide] |
| 2313 | 5- ![piperidine amide] | 4-(-CONH₂) |
| 2314 | 5- ![piperidine amide] | 4-{-CON(Me)₂} |
| 2315 | 5- ![piperidine amide] | 4-{-C(=NH)NH₂} |

TABLE 214-continued
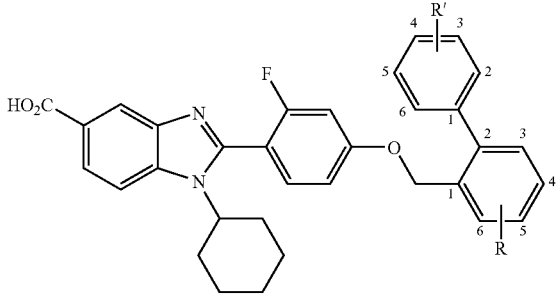
| Ex. No. | R | R' |
|---|---|---|
| 2316 | 5- 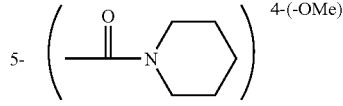 | 4-(-OMe) |
| 2317 | 5- 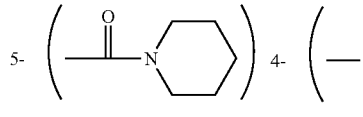 | 4- 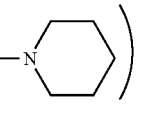 |
| 2318 | 5- 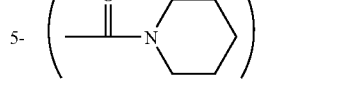 | 4-(-NHMe) |
| 2319 | 5- 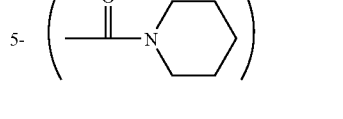 | 4-(-NHAc) |
| 2320 | 5- 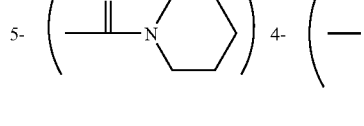 | 4-  |
| 2321 | 5- 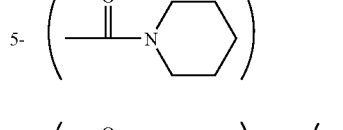 | 4-(-SMe) |
| 2322 | 5- 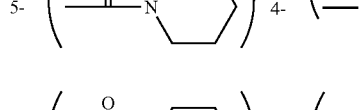 | 4-  |
| 2323 | 5- 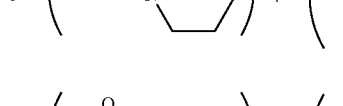 | 4-  |
| 2324 | 5- 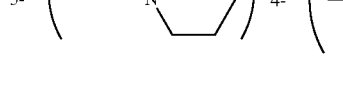 | 4-  |

TABLE 214-continued

[Structure diagram: benzimidazole core with HO2C- substituent, N-cyclohexyl group, 2-(2-fluoro-4-substituted phenyl), connected via OCH2 to a biphenyl system with positions labeled 1-6 on each ring, R on lower ring, R' on upper ring]

| Ex. No. | R | R' |
|---|---|---|
| 2325 | 5- (–C(O)–N-piperidinyl) | 4- {–S(O)₂–N(Me)₂} |
| 2326 | 5-(-CONH₂) | —H |
| 2327 | 5-(-CONH₂) | 4-(-F) |
| 2328 | 4-(-CONH₂) | 4-(-Cl) |
| 2329 | 5-(-CONH₂) | 4-(-CN) |
| 2330 | 5-(-CONH₂) | 4-(-NO₂) |
| 2331 | 5-(-CONH₂) | 4-(-Me) |
| 2332 | 5-(-CONH₂) | 4-(-CF₃) |
| 2333 | 5-(-CONH₂) | 4-(-Ac) |
| 2334 | 5-(-CONH₂) | 4-(-CO₂H) |
| 2335 | 5-(-CONH₂) | 4-(-CO₂Me) |
| 2336 | 5-(-CONH₂) | 4- (–C(O)–N-piperidinyl) |
| 2337 | 5-(-CONH₂) | 4-(-CONH₂) |
| 2338 | 5-(-CONH₂) | 4-{-CON(Me)₂} |
| 2339 | 5-(-CONH₂) | 4-{-C(=NH)NH₂} |
| 2340 | 5-(-CONH₂) | 4-(-OMe) |
| 2341 | 5-(-CONH₂) | 4- (–O–CH₂–C(O)–N-piperidinyl) |
| 2342 | 5-(-CONH₂) | 4-(-NHMe) |
| 2343 | 5-(-CONH₂) | 4-(-NHAc) |
| 2344 | 5-(-CONH₂) | 4- (–NH–S(O)₂–Me) |
| 2345 | 5-(-CONH₂) | 4-(-SMe) |
| 2346 | 5-(-CONH₂) | 4- (–S(O)–Me) |
| 2347 | 5-(-CONH₂) | 4- (–S(O)₂–Me) |

TABLE 214-continued

[Structure: benzimidazole with HO2C at 5-position, N-cyclohexyl, 2-(2-fluoro-4-(benzyloxy)phenyl) group, with biphenyl ether substituent bearing R and R']

| Ex. No. | R | R' |
|---|---|---|
| 2348 | 5-(-CONH₂) | 4- (—S(=O)₂—NH₂) |
| 2349 | 5-(-CONH₂) | 4- (—S(=O)₂—N(Me)₂) |
| 2350 | 5-{-CON(Me)₂} | —H |
| 2351 | 5-{-CON(Me)₂} | 4-(-F) |
| 2352 | 4-{-CON(Me)₂} | 4-(-Cl) |
| 2353 | 5-{-CON(Me)₂} | 4-(-CN) |
| 2354 | 5-{-CON(Me)₂} | 4-(-NO₂) |
| 2355 | 5-{-CON(Me)₂} | 4-(-Me) |
| 2356 | 5-{-CON(Me)₂} | 4-(-CF₃) |
| 2357 | 5-{-CON(Me)₂} | 4-(-Ac) |
| 2358 | 5-{-CON(Me)₂} | 4-(-CO₂H) |
| 2359 | 5-{-CON(Me)₂} | 4-(-CO₂Me) |
| 2360 | 5-{-CON(Me)₂} | 4- (—C(=O)—N-piperidinyl) |
| 2361 | 5-{-CON(Me)₂} | 4-(-CONH₂) |
| 2362 | 5-{-CON(Me)₂} | 4-{-CON(Me)₂} |
| 2363 | 5-{-CON(Me)₂} | 4-{-C(=NH)NH₂} |
| 2364 | 5-{-CON(Me)₂} | 4-(-OMe) |
| 2365 | 5-{-CON(Me)₂} | 4- (—O—CH₂—C(=O)—N-piperidinyl) |
| 2366 | 5-{-CON(Me)₂} | 4-(-NHMe) |
| 2367 | 5-{-CON(Me)₂} | 4-(-NHAc) |
| 2368 | 5-{-CON(Me)₂} | 4- (—NH—S(=O)₂—Me) |
| 2369 | 5-{-CON(Me)₂} | 4-(-SMe) |
| 2370 | 5-{-CON(Me)₂} | 4- (—S(=O)—Me) |

TABLE 214-continued
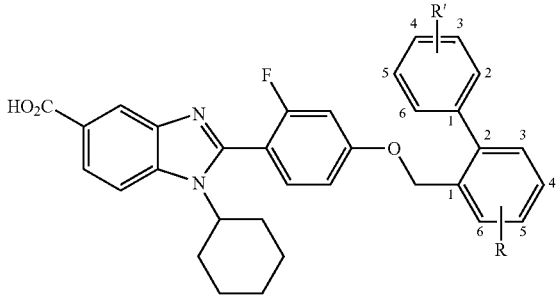
| Ex. No. | R | R' |
|---|---|---|
| 2371 | 5-{-CON(Me)₂} | 4- (—S(=O)₂—Me) |
| 2372 | 5-{-CON(Me)₂} | 4- (—S(=O)₂—NH₂) |
| 2373 | 5-{-CON(Me)₂} | 4- {—S(=O)₂—N(Me)₂} |
| 2374 | 5-(-OMe) | —H |
| 2375 | 5-(-OMe) | 4-(-F) |
| 2376 | 5-(-OMe) | 4-(-Cl) |
| 2377 | 5-(-OMe) | 4-(-CN) |
| 2378 | 5-(-OMe) | 4-(-NO₂) |
| 2379 | 5-(-OMe) | 4-(-Me) |
| 2380 | 5-(-OMe) | 4-(-CF₃) |
| 2381 | 5-(-OMe) | 4-(-Ac) |
| 2382 | 5-(-OMe) | 4-(-CO₂H) |
| 2383 | 5-(-OMe) | 4-(-CO₂Me) |
| 2384 | 5-(-OMe) | 4- (—C(=O)—N-piperidine) |
| 2385 | 5-(-OMe) | 4-(-CONH₂) |
| 2386 | 5-(-OMe) | 4-{-CON(Me)₂} |
| 2387 | 5-(-OMe) | 4-{-C(=NH)NH₂} |
| 2388 | 5-(-OMe) | 4-(-OMe) |
| 2389 | 5-(-OMe) | 4- (—O—CH₂—C(=O)—N-piperidine) |
| 2390 | 5-(-OMe) | 4-(-NHMe) |
| 2391 | 5-(-OMe) | 4-(-NHAc) |
| 2392 | 5-(-OMe) | 4- (—NH—S(=O)₂—Me) |
| 2393 | 5-(-OMe) | 4-(-SMe) |

TABLE 214-continued
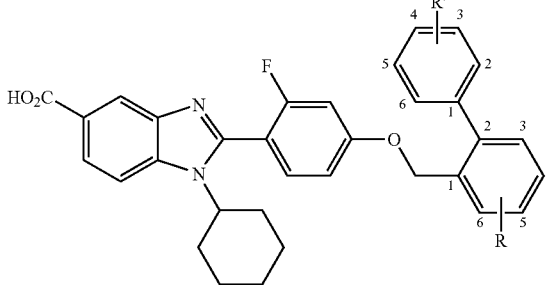
| Ex. No. | R | R' |
|---|---|---|
| 2394 | 5-(-OMe) | 4- (−S(=O)−Me) |
| 2395 | 5-(-OMe) | 4- (−S(=O)₂−Me) |
| 2396 | 5-(-OMe) | 4- (−S(=O)₂−NH₂) |
| 2397 | 5-(-OMe) | 4- {−S(=O)₂−N(Me)₂} |
| 2398 | 5-(-NHMe) | 4-(-F) |
| 2399 | 5-(-NHMe) | 4-(-Cl) |
| 2400 | 5-(-NHAc) | 4-(-F) |
| 2401 | 5-(-NHAc) | 4-(-Cl) |
| 2402 | 5-(-NHAc) | 4-(-Ac) |
| 2403 | 5-(-NHAc) | 4-(-CONH₂) |
| 2404 | 5-(-NHAc) | 4-{-CON(Me)₂} |
| 2405 | 5- (−NH−S(=O)₂−Me) | 4-(-F) |
| 2406 | 5- (−NH−S(=O)₂−Me) | 4-(-Cl) |
| 2407 | 5- (−NH−S(=O)₂−Me) | 4-(-Me) |
| 2408 | 5- (−NH−S(=O)₂−Me) | 4-(-CF₃) |

TABLE 214-continued

[Structure: benzimidazole with HO₂C at 5-position, N1-cyclohexyl, 2-position attached to fluorophenyl (F) bearing an -O-CH₂- linker to a biphenyl system; first ring labeled 1-6 with R at 5, second ring labeled 1-6 with R' at positions shown (4,3)]

| Ex. No. | R | R' |
|---|---|---|
| 2409 | 5-(-NH-S(O)₂-Me) | 4-(-CO₂H) |
| 2410 | 5-(-NH-S(O)₂-Me) | 4-(-CO₂Me) |
| 2411 | 5-(-NH-S(O)₂-Me) | 4-(-C(O)-N-piperidine) |
| 2412 | 5-(-NH-S(O)₂-Me) | 4-(-SMe) |
| 2413 | 5-(-NH-S(O)₂-Me) | 4-(-S(O)-Me) |
| 2414 | 5-(-NH-S(O)₂-Me) | 4-(-S(O)₂-Me) |
| 2415 | 5-(-SMe) | 4-(-F) |
| 2416 | 5-(-SMe) | 4-(-Cl) |
| 2417 | 5-(-SMe) | 4-(-Me) |
| 2418 | 5-(-SMe) | 4-(-CF₃) |
| 2419 | 5-(-SMe) | 4-(-Ac) |
| 2420 | 5-(-SMe) | 4-(-CONH₂) |
| 2421 | 5-(-SMe) | 4-{-CON(Me)₂} |
| 2422 | 5-(-S(O)-Me) | 4-(-F) |
| 2423 | 5-(-S(O)-Me) | 4-(-Cl) |
| 2424 | 5-(-S(O)-Me) | 4-(-Me) |

TABLE 214-continued
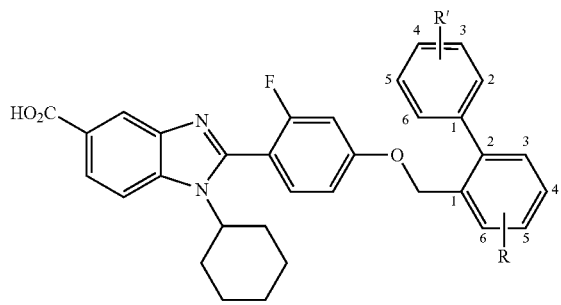
| Ex. No. | R | R' |
|---|---|---|
| 2425 | 5- (−S(O)−Me) | 4-(-CF₃) |
| 2426 | 5- (−S(O)−Me) | 4-(-Ac) |
| 2427 | 5- (−S(O)−Me) | 4-(-CONH₂) |
| 2428 | 5- (−S(O)−Me) | 4-{-CON(Me)₂} |
| 2429 | 5- (−S(O)₂−Me) | 4-(-F) |
| 2430 | 5- (−S(O)₂−Me) | 4-(-Cl) |
| 2431 | 5- (−S(O)₂−Me) | 4-(-Me) |
| 2432 | 5- (−S(O)₂−Me) | 4-(-CF₃) |
| 2433 | 5- (−S(O)₂−Me) | 4-(-Ac) |
| 2434 | 5- (−S(O)₂−Me) | 4-(-CONH₂) |

TABLE 214-continued
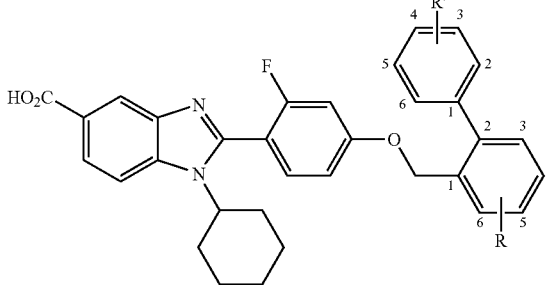
| Ex. No. | R | R' |
|---|---|---|
| 2435 | 5- (—S(O)₂—Me) | 4-{-CON(Me)₂} |
| 2436 | 5- (—S(O)₂—NH₂) | 4-(-F) |
| 2437 | 5- (—S(O)₂—NH₂) | 4-(-Cl) |
| 2438 | 5- (—S(O)₂—NH₂) | 4-(-Me) |
| 2439 | 5- (—S(O)₂—NH₂) | 4-(-CF₃) |
| 2440 | 5- (—S(O)₂—NH₂) | 4-(-CONH₂) |
| 2441 | 5- (—S(O)₂—NH₂) | 4-{-CON(Me)₂} |
| 2442 | 5- (—S(O)₂—NH₂) | 4-(-SMe) |
| 2443 | 5- (—S(O)₂—NH₂) | 4- (—S(O)—Me) |

TABLE 214-continued

[Structure: benzimidazole core with HO2C- substituent, N-cyclohexyl, linked to 2-F-phenyl-O-CH2-biphenyl system with positions labeled 1-6 on both phenyl rings, R on lower ring, R' on upper ring]

| Ex. No. | R | R' |
|---|---|---|
| 2444 | 5- (—S(O)₂—NH₂) | 4- (—S(O)₂—Me) |
| 2445 | 5- {—S(O)₂—N(Me)₂} | 4-(-F) |
| 2446 | 5- {—S(O)₂—N(Me)₂} | 4-(-Cl) |
| 2447 | 5- {—S(O)₂—N(Me)₂} | 4-(-Me) |
| 2448 | 5- {—S(O)₂—N(Me)₂} | 4-(-CF₃) |
| 2449 | 5- {—S(O)₂—N(Me)₂} | 4-(-CONH₂) |
| 2450 | 5- {—S(O)₂—N(Me)₂} | 4-{-CON(Me)₂} |
| 2451 | 5- {—S(O)₂—N(Me)₂} | 4-(-SMe) |
| 2452 | 5- {—S(O)₂—N(Me)₂} | 4- (—S(O)—Me) |

TABLE 214-continued
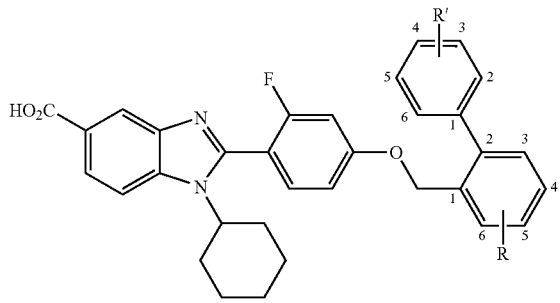
| Ex. No. | R | R' |
|---|---|---|
| 2453 | 5- {−S(O)₂−N(Me)₂} | 4- (−S(O)₂−Me) |
TABLE 215
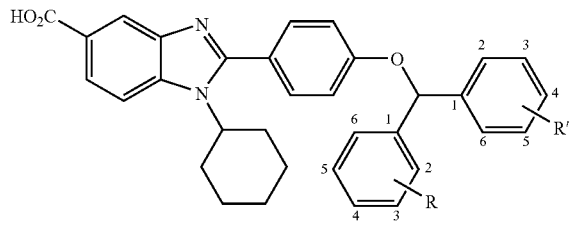
| Ex. No. | R | R' |
|---|---|---|
| 2454 | 2-(—F) | 2-(—F) |
| 2455 | 2-(—F) | 3-(—F) |
| 2456 | 2-(—F) | 4-(—F) |
| 2457 | 3-(—Cl) | 3-(—Cl) |
| 2458 | 3,5-di-(—Cl) | 3,5-di-(—Cl) |
| 2459 | 3-(—CN) | 3-(—CN) |
| 2460 | 3-(—NO₂) | 3-(—NO₂) |
| 2461 | 3-(—Me) | 3-(—Me) |
| 2462 | 3-(—CF₃) | 3-(—CF₃) |
| 2463 | 3-(—Ac) | 3-(—Ac) |
| 2464 | 3-(—CO₂H) | 3-(—CO₂H) |
| 2465 | 3-(—CO₂Me) | 3-(—CO₂Me) |
| 2466 | 3- (—C(O)-piperidinyl) | 3- (—C(O)-piperidinyl) |
| 2467 | 3-(—CONH₂) | 3-(—CONH₂) |
| 2468 | 3-(—CONH₂) | 3-(—F) |
| 2469 | 3-(—CONH₂) | 3-(—Cl) |
| 2470 | 3-{—CON(Me)₂} | 3-{—CON(Me)₂} |
| 2471 | 3-{—CON(Me)₂} | 3-(—F) |
| 2472 | 3-{—CON(Me)₂} | 3-(—Cl) |
| 2473 | 3-{—C(=NH)NH₂} | 3-{—C(=NH)NH₂} |
| 2474 | 3-(—OMe) | 3-(—OMe) |
| 2475 | 3- (—O—CH₂—C(O)-piperidinyl) | 3- (—O—CH₂—C(O)-piperidinyl) |
| 2476 | 3-(—NHMe) | 3-(—NHMe) |
| 2477 | 3-(—NHAc) | 3-(—NHAc) |

TABLE 215-continued
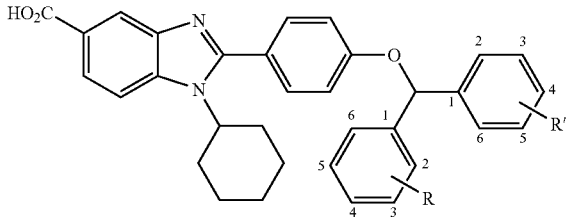
| Ex. No. | R | R' |
|---|---|---|
| 2478 | 3- (—NHSO₂Me) | 3- (—NHSO₂Me) |
| 2479 | 3-(—SMe) | 3-(—SMe) |
| 2480 | 3- (—S(O)Me) | 3- (—S(O)Me) |
| 2481 | 3- (—SO₂Me) | 3- (—SO₂Me) |
| 2482 | 3- (—SO₂NH₂) | 3- (—SO₂NH₂) |
| 2483 | 3- {—SO₂N(Me)₂} | 3- {—SO₂N(Me)₂} |
| 2484 | 3-(—F) | 4-(—F) |
| 2485 | 3-(—Cl) | 4-(—Cl) |
| 2486 | 4-(—CN) | 4-(—CN) |
| 2487 | 4-(—NO₂) | 4-(—NO₂) |
| 2488 | 3-(—Me) | 4-(—Me) |
| 2489 | 4-(—Me) | 2,6-di-(—Me) |
| 2490 | 4-(—CF₃) | 4-(—CF₃) |
| 2491 | 4-(—Ac) | 4-(—Ac) |
| 2492 | 4-(—CO₂H) | 4-(—CO₂H) |
| 2493 | 4-(—CO₂Me) | 4-(—CO₂Me) |
| 2494 | 4- (—C(O)-N-piperidine) | 4- (—C(O)-N-piperidine) |
| 2495 | 4-(—CONH₂) | 4-(—CONH₂) |
| 2496 | 4-(—CONH₂) | 4-(—F) |
| 2497 | 4-(—CONH₂) | 2,3,4,5,6-penta-(—F) |
| 2498 | 4-(—CONH₂) | 4-(—Cl) |
| 2499 | 4-{—CON(Me)₂} | 4-{—CON(Me)₂} |
| 2500 | 4-{—CON(Me)₂} | 4-(—F) |
| 2501 | 4-{—CON(Me)₂} | 4-(—Cl) |
| 2502 | 4-{—CON(Me)₂} | 3,5-di-(—Cl) |
| 2503 | 4-{—C(=NH)NH₂} | 4-{—C(=NH)NH₂} |
| 2504 | 4-(—OMe) | 4-(—OMe) |
| 2505 | 4-(—OMe) | 3,4,5-tri-(—OMe) |

TABLE 215-continued
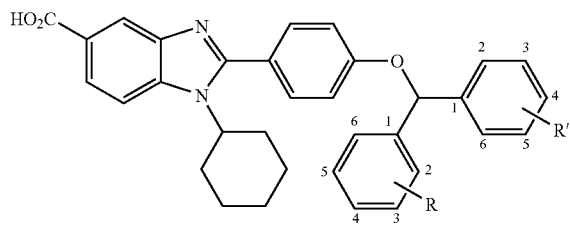
| Ex. No. | R | R' |
|---|---|---|
| 2506 | 4-(—O—CH₂—C(O)—N-piperidine) | 4-(—O—CH₂—C(O)—N-piperidine) |
| 2507 | 4-(—NHMe) | 4-(—NHMe) |
| 2508 | 4-(—NHAc) | 4-(—NHAc) |
| 2509 | 4-(—NH—SO₂—Me) | 4-(—NH—SO₂—Me) |
| 2510 | 4-(—SMe) | 4-(—SMe) |
| 2511 | 4-(—S(O)—Me) | 4-(—S(O)—Me) |
| 2512 | 4-(—SO₂—Me) | 4-(—SO₂—Me) |
| 2513 | 4-(—SO₂—NH₂) | 4-(—SO₂—NH₂) |
| 2514 | 4-(—SO₂—N(Me)₂) | 4-(—SO₂—N(Me)₂) |
TABLE 216
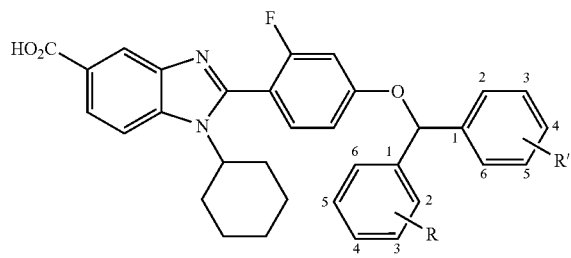
| Ex. No. | R | R' |
|---|---|---|
| 2515 | —H | —H |
| 2516 | 2-(—F) | 3-(—F) |

TABLE 216-continued

[Structure: benzimidazole with HO2C group, N-cyclohexyl, 2-(3-fluoro-4-oxyphenyl), O-CH(Ar-R)(Ar-R')]

| Ex. No. | R | R' |
|---|---|---|
| 2517 | 3-(—Cl) | 3-(—Cl) |
| 2518 | 3-(—CN) | 3-(—CN) |
| 2519 | 3-(—NO₂) | 3-(—NO₂) |
| 2520 | 3-(—Me) | 3-(—Me) |
| 2521 | 3-(—CF₃) | 3-(—CF₃) |
| 2522 | 3-(—Ac) | 3-(—Ac) |
| 2523 | 3-(—CO₂H) | 3-(—CO₂H) |
| 2524 | 3-(—CO₂Me) | 3-(—CO₂Me) |
| 2525 | 3-(—C(O)N-piperidine) | 3-(—C(O)N-piperidine) |
| 2526 | 3-(—CONH₂) | 3-(—CONH₂) |
| 2527 | 3-(—CONH₂) | 3-(—F) |
| 2528 | 3-(—CONH₂) | 3-(—Cl) |
| 2529 | 3-{—CON(Me)₂} | 3-{—CON(Me)₂} |
| 2530 | 3-{—CON(Me)₂} | 3-(—F) |
| 2531 | 3-{—CON(Me)₂} | 3-(—Cl) |
| 2532 | 3-{—C(=NH)NH₂} | 3-{—C(=NH)NH₂} |
| 2533 | 3-(—OMe) | 3-(—OMe) |
| 2534 | 3-(—O—CH₂—C(O)N-piperidine) | 3-(—O—CH₂—C(O)N-piperidine) |
| 2535 | 3-(—NHMe) | 3-(—NHMe) |
| 2536 | 3-(—NHAc) | 3-(—NHAc) |
| 2537 | 3-(—NHS(O)₂Me) | 3-(—NHS(O)₂Me) |
| 2538 | 3-(—SMe) | 3-(—SMe) |
| 2539 | 3-(—S(O)Me) | 3-(—S(O)Me) |
| 2540 | 3-(—S(O)₂Me) | 3-(—S(O)₂Me) |
| 2541 | 3-(—S(O)₂NH₂) | 3-(—S(O)₂NH₂) |

TABLE 216-continued
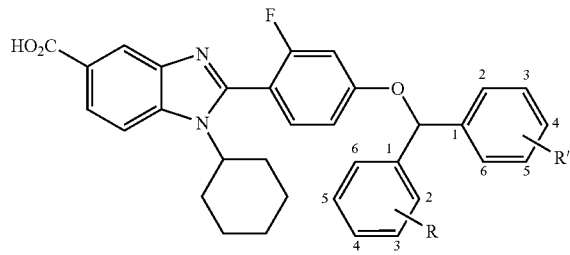
| Ex. No. | R | R' |
|---|---|---|
| 2542 | 3- {—S(O)₂—N(Me)₂} | 3- {—S(O)₂—N(Me)₂} |
| 2543 | 3-(—F) | 4-(—F) |
| 2544 | 4-(—Cl) | 4-(—Cl) |
| 2545 | 4-(—CN) | 4-(—CN) |
| 2546 | 4-(—NO₂) | 4-(—NO₂) |
| 2547 | 4-(—Me) | 4-(—Me) |
| 2548 | 4-(—CF₃) | 4-(—CF₃) |
| 2549 | 4-(—Ac) | 4-(—Ac) |
| 2550 | 3-(—CO₂H) | 4-(—CO₂H) |
| 2551 | 4-(—CO₂Me) | 4-(—CO₂Me) |
| 2552 | 4- (—C(O)—N-piperidine) | 4- (—C(O)—N-piperidine) |
| 2553 | 4-(—CONH₂) | 4-(—CONH₂) |
| 2554 | 4-(—CONH₂) | 4-(—F) |
| 2555 | 4-(—CONH₂) | 4-(—C#) |
| 2556 | 3-{—CON(Me)₂} | 4-{—CON(Me)₂} |
| 2557 | 3-{—CON(Me)₂} | 4-(—F) |
| 2558 | 4-{—CON(Me)₂} | 4-(—Cl) |
| 2559 | 4-{—C(=NH)NH₂} | 4-{—C(=NH)NH₂} |
| 2560 | 4-(—OMe) | 4-(—OMe) |
| 2561 | 4- (—O—CH₂—C(O)—N-piperidine) | 4- (—O—CH₂—C(O)—N-piperidine) |
| 2562 | 4-(—NHMe) | 4-(—NHMe) |
| 2563 | 4-(—N#IAc) | 4-(—NHAc) |
| 2564 | 4- (—NH—S(O)₂—Me) | 4- (—NH—S(O)₂—Me) |
| 2565 | 4-(—SMe) | 4-(—SMe) |
| 2566 | 4- (—S(O)—Me) | 4- (—S(O)—Me) |

TABLE 216-continued

[Structure: benzimidazole with HO2C, N-cyclohexyl, 2-(2-fluoro-4-(diphenylmethoxy)phenyl) substituent, with two phenyl rings labeled R and R']

| Ex. No. | R | R' |
|---|---|---|
| 2567 | 4-(—S(O)₂—Me) | 4-(—S(O)₂—Me) |
| 2568 | 4-(—S(O)₂—NH₂) | 4-(—S(O)₂—NH₂) |
| 2569 | 4-{—S(O)₂—N(Me)₂} | 4-{—S(O)₂—N(Me)₂} |

TABLE 217

[Structure: benzimidazole with HO2C, N-cyclohexyl, 2-(4-(pyridyl(phenyl)methoxy)phenyl) substituent]

Py : Pyridyl group

| Ex. No. | Py | R' |
|---|---|---|
| 2570 | 3-Py | —H |
| 2571 | 3-Py | 3-(—F) |
| 2572 | 3-Py | 3-(—Cl) |
| 2573 | 3-Py | 3-(—Me) |
| 2574 | 3-Py | 3-(—CF₃) |
| 2575 | 3-Py | 3-(—Ac) |
| 2576 | 3-Py | 3-(—CO₂H) |
| 2577 | 3-Py | 3-(—CO₂Me) |
| 2578 | 3-Py | 3-(—C(O)—N-piperidine) |
| 2579 | 3-Py | 3-(—CONH₂) |
| 2580 | 3-Py | 3-{—CON(Me)₂} |

TABLE 217-continued

[Structure: same as TABLE 217]

Py : Pyridyl group

| Ex. No. | Py | R' |
|---|---|---|
| 2581 | 3-Py | 4-(—F) |
| 2582 | 3-Py | 4-(—Cl) |
| 2583 | 3-Py | 4-(—Me) |
| 2584 | 3-Py | 4-(—CF₃) |
| 2585 | 3-Py | 4-(—Ac) |
| 2586 | 2-Py | 4-(—CO₂H) |
| 2587 | 3-Py | 4-(—CO₂Me) |
| 2588 | 3-Py | 4-(—C(O)—N-piperidine) |
| 2589 | 4-Py | 4-(—CONH₂) |
| 2590 | 3-Py | 4-{—CON(Me)₂} |

TABLE 218

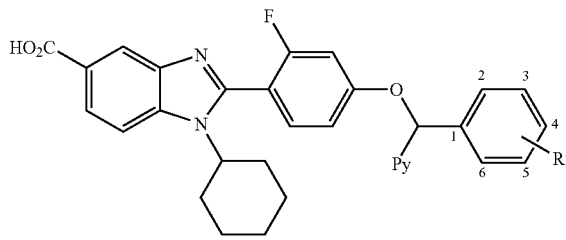

Py: Pyridyl group

| Ex. No. | Py | R' |
|---|---|---|
| 2591 | 3-Py | —H |
| 2592 | 3-Py | 3-(—F) |
| 2593 | 3-Py | 3-(—Cl) |
| 2594 | 3-Py | 3-(—Me) |
| 2595 | 3-Py | 3-(—CF₃) |
| 2596 | 3-Py | 3-(—Ac) |
| 2597 | 3-Py | 3-(—CO₂H) |
| 2598 | 3-Py | 3-(—CO₂Me) |
| 2599 | 3-Py | 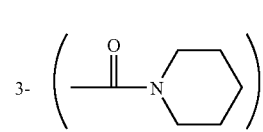 3- |
| 2600 | 3-Py | 3-(—CONH₂) |
| 2601 | 3-Py | 3-{—CON(Me)₂} |
| 2602 | 3-Py | 4-(—F) |

TABLE 218-continued

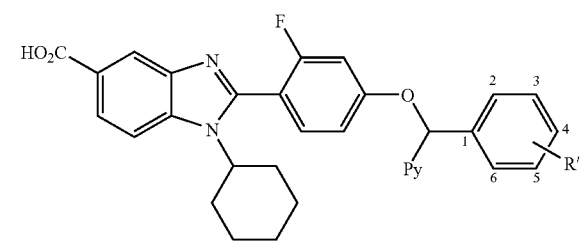

Py: Pyridyl group

| Ex. No. | Py | R' |
|---|---|---|
| 2603 | 3-Py | 4-(—Cl) |
| 2604 | 3-Py | 4-(—Me) |
| 2605 | 3-Py | 4-(—CF₃) |
| 2606 | 3-Py | 4-(—Ac) |
| 2607 | 3-Py | 4-(—CO₂H) |
| 2608 | 3-Py | 4-(—CO₂Me) |
| 2609 | 3-Py | 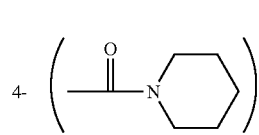 4- |
| 2610 | 3-Py | 4-(—CONH₂) |
| 2611 | 3-Py | 4-{—CON(Me)₂} |

TABLE 219

Example No. 328

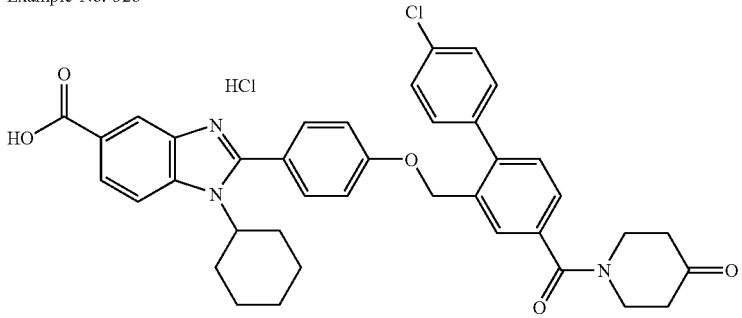

Purity > 90% (NMR)
MS 662 (M + 1)

1H NMR (δ) ppm

300MHz, DMSO-d6 8.29(1H, s), 8.23(1H, d, J= 9.0Hz), 8.02(1H, d, J=8.4Hz), 7.80(1H, s), 7.71(2H, d, J=8.4Hz), 7.61(1H, d, J=9.3Hz), 7.55–7.45(3H, m), 7.46(2H, d, J=8.1Hz), 7.22(2H, d, J=8.7Hz), 5.16(2H, s,), 4.34(1H, m), 4.20–3.40(4H, m), 2.60–2.15(6H, m), 2.10–1.90(2H, m), 1.85–1.70(2H, m), 1.65–1.55(1H, m), 1.50–1.10(3H, m)

Example No. 329

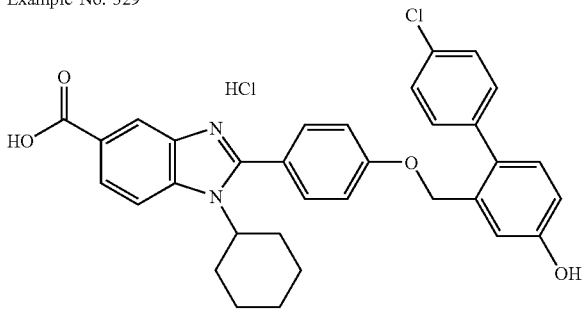

Purity > 90% (NMR)
MS 553 (M + 1)

1H NMR (δ) ppm

400MHz, DMSO-d6 9.80(1H, brs), 8.32(1H, s), 8.30(1H, d, J=8.8Hz), 8.06(1H, d, J=8.8Hz), 7.74(2H, d, J=8.6Hz), 7.48–7.37(4H, m), 7.22(1H, d, J=8.6Hz), 7.17(1H, d, J=8.2Hz), 7.05(1H, d, J=2.3Hz), 6.88(1H, dd, J=8.3, 2.5Hz), 5.04(2H, s), 4.37(1H, m), 2.37–2.22(2H, m), 2.11–1.98(2H, m), 1.93–1.81(2H, m), 1.70–1.58(1H, m), 1.56–1.22(3H, m)

TABLE 219-continued

Example No. 330

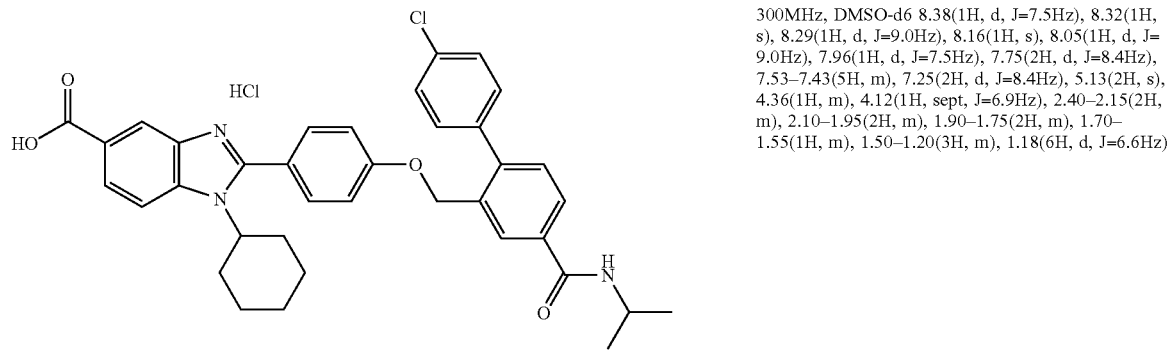

Purity > 90% (NMR)
MS 622 (M + 1)

1H NMR (p67) ppm

300MHz, DMSO-d6 8.38(1H, d, J=7.5Hz), 8.32(1H, s), 8.29(1H, d, J=9.0Hz), 8.16(1H, s), 8.05(1H, d, J=9.0Hz), 7.96(1H, d, J=7.5Hz), 7.75(2H, d, J=8.4Hz), 7.53–7.43(5H, m), 7.25(2H, d, J=8.4Hz), 5.13(2H, s), 4.36(1H, m), 4.12(1H, sept, J=6.9Hz), 2.40–2.15(2H, m), 2.10–1.95(2H, m), 1.90–1.75(2H, m), 1.70–1.55(1H, m), 1.50–1.20(3H, m), 1.18(6H, d, J=6.6Hz)

TABLE 220

Example No. 331

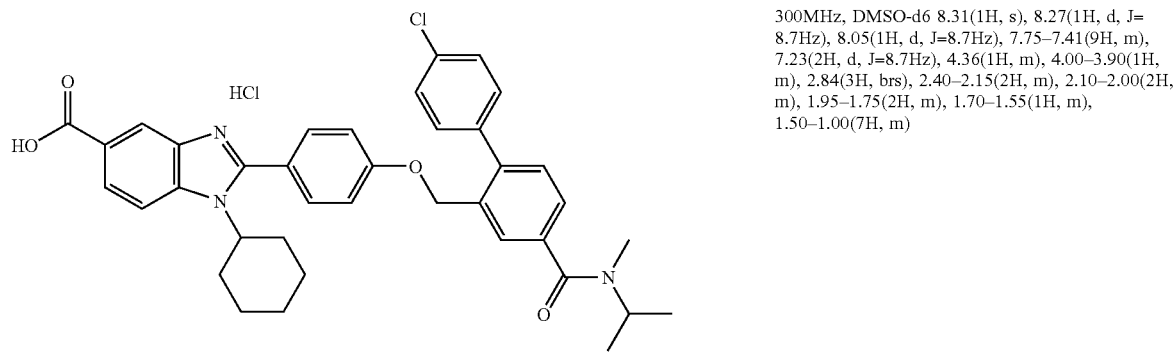

Purity > 90% (NMR)
MS 636 (M + 1)

1H NMR (δ) ppm

300MHz, DMSO-d6 8.31(1H, s), 8.27(1H, d, J=8.7Hz), 8.05(1H, d, J=8.7Hz), 7.75–7.41(9H, m), 7.23(2H, d, J=8.7Hz), 4.36(1H, m), 4.00–3.90(1H, m), 2.84(3H, brs), 2.40–2.15(2H, m), 2.10–2.00(2H, m), 1.95–1.75(2H, m), 1.70–1.55(1H, m), 1.50–1.00(7H, m)

Example No. 332

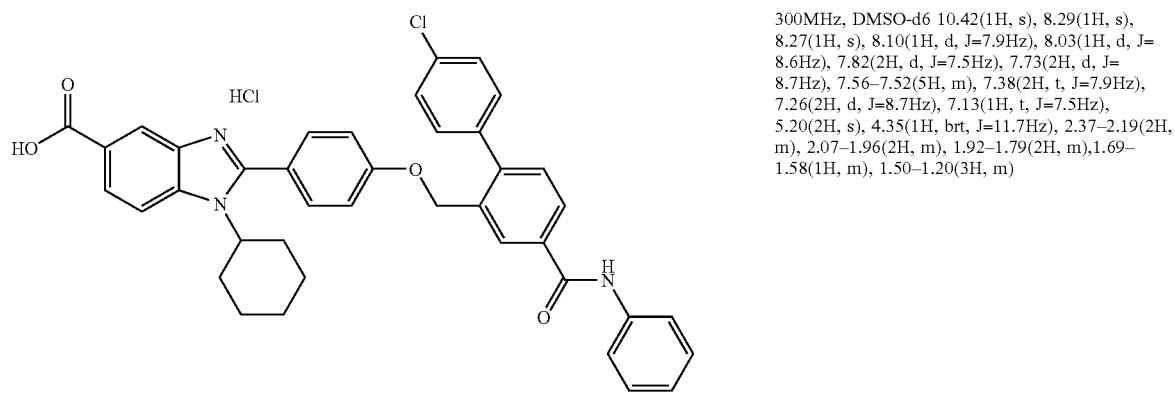

Purity > 90% (NMR)
MS 656 (M + 1)

1H NMR (δ) ppm

300MHz, DMSO-d6 10.42(1H, s), 8.29(1H, s), 8.27(1H, s), 8.10(1H, d, J=7.9Hz), 8.03(1H, d, J=8.6Hz), 7.82(2H, d, J=7.5Hz), 7.73(2H, d, J=8.7Hz), 7.56–7.52(5H, m), 7.38(2H, t, J=7.9Hz), 7.26(2H, d, J=8.7Hz), 7.13(1H, t, J=7.5Hz), 5.20(2H, s), 4.35(1H, brt, J=11.7Hz), 2.37–2.19(2H, m), 2.07–1.96(2H, m), 1.92–1.79(2H, m), 1.69–1.58(1H, m), 1.50–1.20(3H, m)

TABLE 220-continued

| Example No. 333 | 1H NMR (δ) ppm |
|---|---|
| 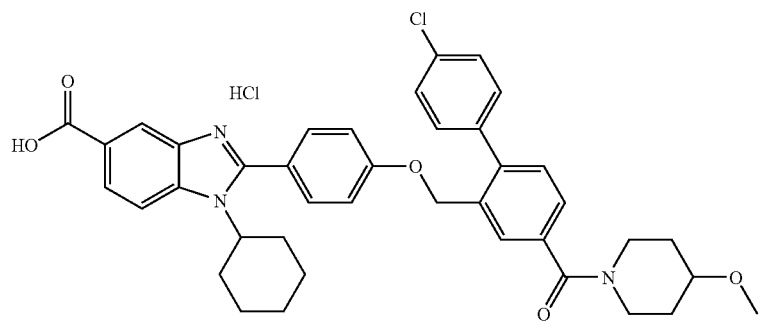 | 300MHz, DMSO-d6 8.30(1H, s), 8.24 and 8.03(2H, ABq, J=8.8Hz), 7.71 and 7.22(4H, A'B'q, J=8.8Hz), 7.69(1H, s), 7.52(4H, s), 7.50 and 7.43(2H, A"B"q, J=7.7Hz), 5.15(2H, s) 4.35(1H, brt, J=12.1Hz), 4.05–3.15(5H, brm), 3.27(3H, s), 2.39–2.20(2H, m), 2.07–1.75(6H, m), 1.70–1.58(1H, m) 1.55–1.20(5H, m) |

Purity > 90% (NMR)
MS 678 (M + 1)

TABLE 221

| Example No. 334 | 1H NMR (δ) ppm |
|---|---|
| 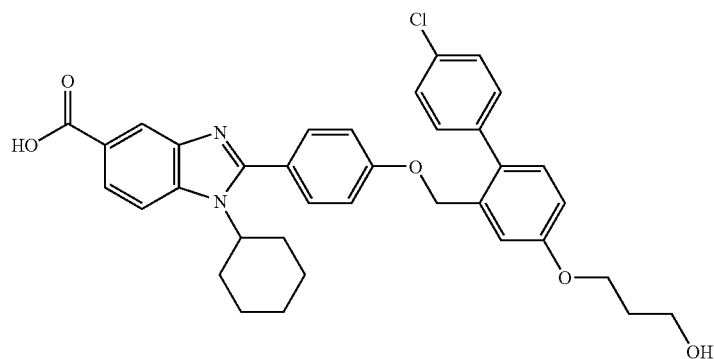 | 300MHz, DMSO-d6 8.22(1H, d, J=1.5Hz), 8.01(1H, d, J=9.0Hz), 7.89(1H, dd, J=8.6, 1.5Hz), 7.61(2H, d, J=8.6Hz), 7.50–7.39(4H, m), 7.27(1H, d, J=8.6Hz), 7.22(1H, d, J=2.6Hz), 7.13(2H, d, J=8.6Hz), 7.04(1H, dd, J=8.2, 2.6Hz), 5.04(2H, s), 4.28(1H, m), 4.11(2H, t, J=6.3Hz), 3.57(2H, t, J=6.3Hz), 2.38–2.17(2H, m), 2.00–1.79(6H, m), 1.70–1.59(1H, m), 1.52–1.16(3H, m) |

Purity > 90% (NMR)
MS 611 (M + 1)

| Example No. 335 | 1H NMR (δ) ppm |
|---|---|
| 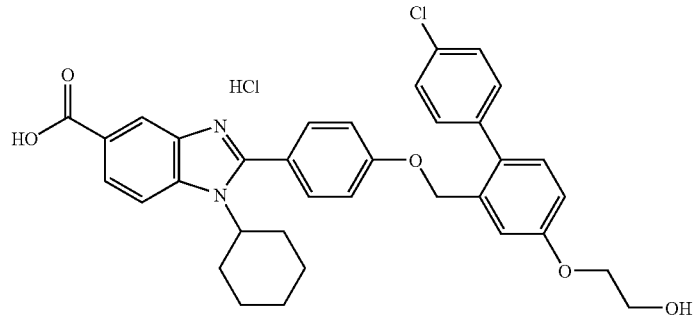 | 300MHz, DMSO-d6 8.30(1H, d, J=1.5Hz), 8.27(1H, d, J=9.0Hz), 8.04(1H, dd, J=8.6, 1.5Hz), 7.72(2H, d, J=9.0Hz), 7.60–7.40(4H, m), 7.32–7.19(4H, m), 7.06(1H, dd, J=8.6, 3.0Hz), 5.08(2H, s), 4.36(1H, m), 4.06(2H, t, J=4.8Hz), 3.74(2H, t, J=4.8Hz), 2.38–2.19(2H, m), 2.13–1.97(2H, m), 1.94–1.78(2H, m), 1.72–1.59(1H, m), 1.52–1.20(3H, m) |

Purity > 90% (NMR)
MS 597 (M + 1)

TABLE 222

| Ex. No. | HCV polymerase inhibitory activity IC$_{50}$ [μM] |
|---|---|
| 340 | 0.017 |
| 341 | 0.025 |
| 342 | 0.015 |
| 343 | 0.017 |
| 344 | 0.016 |
| 345 | 0.012 |
| 346 | 0.025 |
| 347 | 0.022 |
| 348 | 0.013 |
| 349 | 0.021 |
| 350 | 0.020 |
| 351 | 0.019 |
| 352 | 0.013 |
| 353 | 0.023 |
| 354 | 0.013 |
| 355 | 0.015 |
| 356 | 0.016 |
| 357 | 0.019 |
| 358 | 0.017 |
| 359 | 0.015 |
| 360 | 0.014 |
| 361 | 0.028 |
| 362 | 0.020 |
| 363 | 0.11 |
| 364 | 0.12 |
| 365 | 0.020 |
| 366 | 0.024 |
| 367 | 0.011 |
| 368 | 0.024 |
| 369 | 0.022 |
| 370 | 0.017 |
| 371 | 0.015 |
| 372 | 0.033 |
| 373 | 0.013 |
| 374 | 0.013 |
| 375 | 0.012 |
| 376 | 0.014 |
| 377 | 0.012 |
| 378 | 0.018 |
| 379 | 0.021 |

TABLE 223

| Ex. No. | HCV polymerase inhibitory activity IC$_{50}$ [μM] |
|---|---|
| 380 | 0.023 |
| 381 | 0.011 |
| 382 | 0.015 |
| 383 | 0.013 |
| 384 | 0.016 |
| 385 | 0.019 |
| 386 | 0.018 |
| 387 | 0.025 |
| 388 | 0.020 |
| 389 | 0.012 |
| 390 | 0.014 |
| 391 | 0.017 |
| 392 | 0.014 |
| 393 | 0.011 |
| 394 | 0.019 |
| 395 | 0.016 |
| 396 | 0.025 |
| 397 | 0.037 |
| 398 | 0.077 |
| 399 | 0.032 |
| 409 | 0.020 |
| 410 | 0.018 |
| 411 | 0.015 |
| 412 | 0.019 |
| 413 | 0.026 |

TABLE 223-continued

| Ex. No. | HCV polymerase inhibitory activity IC$_{50}$ [μM] |
|---|---|
| 414 | 0.024 |
| 415 | 0.019 |
| 416 | 0.024 |
| 417 | 0.029 |
| 418 | 0.016 |
| 419 | 0.021 |
| 420 | 0.015 |
| 421 | 0.017 |
| 422 | 0.017 |
| 423 | 0.017 |
| 424 | 0.020 |
| 425 | 0.026 |
| 426 | 0.053 |
| 427 | 0.020 |
| 428 | 0.026 |

TABEL 224

| Ex. No. | HCV polymerase inhibitory activity IC$_{50}$ [μM] |
|---|---|
| 429 | 0.017 |
| 430 | 0.017 |
| 431 | 0.015 |
| 432 | 0.022 |
| 433 | 0.014 |
| 434 | 0.011 |
| 435 | 0.012 |
| 436 | 0.026 |
| 440 | 0.070 |
| 442 | 0.024 |
| 443 | 0.030 |
| 445 | 0.33 |
| 446 | 0.016 |
| 447 | 0.12 |
| 448 | 0.20 |
| 449 | 0.025 |
| 450 | 0.040 |
| 451 | 0.031 |
| 452 | 0.028 |
| 454 | 0.013 |
| 455 | 0.015 |
| 456 | 0.017 |
| 457 | 0.015 |
| 458 | 0.015 |
| 459 | 0.014 |
| 460 | 0.017 |
| 461 | 0.021 |
| 462 | 0.028 |
| 463 | 0.026 |
| 464 | 0.030 |
| 465 | 0.033 |
| 466 | 0.023 |
| 467 | 0.032 |
| 468 | 0.028 |
| 469 | 0.024 |
| 502 | 0.024 |
| 503 | 0.196 |
| 601 | 0.32 |
| 701 | 0.052 |

TABLE 225

Example No. 341

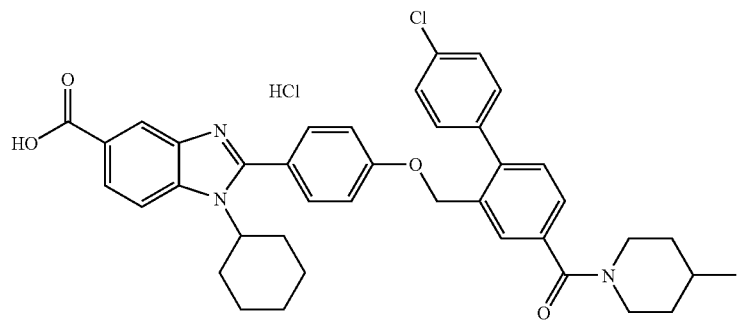

Purity > 90% (NMR)

MS 662 (M + 1)

1H NMR (δ) ppm

300MHz, DMSO-d6 8.29(1H, d, J=1.5Hz), 8.25(1H, d, J=8.7Hz), 8.03(1H, dd, J=8.7Hz), 7.72 and 7.22(4H, Abq, J=8.8Hz), 7.67(1H, d, J=1.5Hz), 7.52(4H, s), 7.49(1H, dd, J=7.9, 1.5Hz), 7.43(1H, d, J=7.9Hz), 4.46(1H, brs), 4.35(1H, brt, J=12.4Hz), 3.62(1H, brs), 3.06(1H, brs), 2.79(1H, brs), 2.38–2.20(2H, brm),2.08–1.81(4H, brm), 1.77–1.52(4H, brm), 1.46–1.20(3H, brm), 1.19–1.00(2H, brm), 0.94 and 0.92(total 3H, each s)

Example No. 342

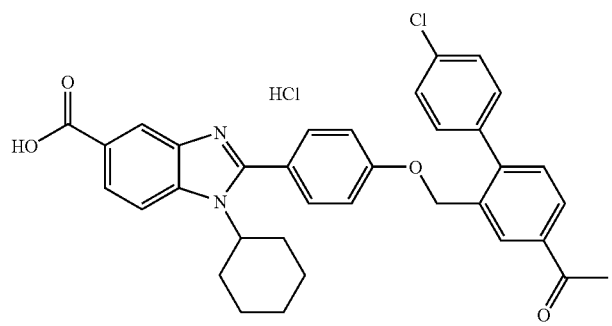

Purity > 90% (NMR)

MS 679 (M + 1)

1H NMR (δ) ppm

300Mz, DMSO-d6 8.28(1H, d, J=1.5Hz), 8.26(1H, d, J=1.8Hz), 8.19(1H, d, J=8.8Hz), 8.07(1H, dd, J=7.7, 1.8Hz), 8.00(1H, dd, J=8.8, 1.5Hz), 7.70 and 7.22(4H, Abq, J=8.8Hz), 7.56–7.50(1H, m), 7.56(4H, s), 5.17(2H, s), 4.33(1H, brt, J=12.5Hz), 2.05(3H, s), 2.37–2.20(2H, brm), 2.06–1.80(4H, brm), 1.70–1.60(1H, brm), 1.50–1.20(3H, brm)

Example No. 343

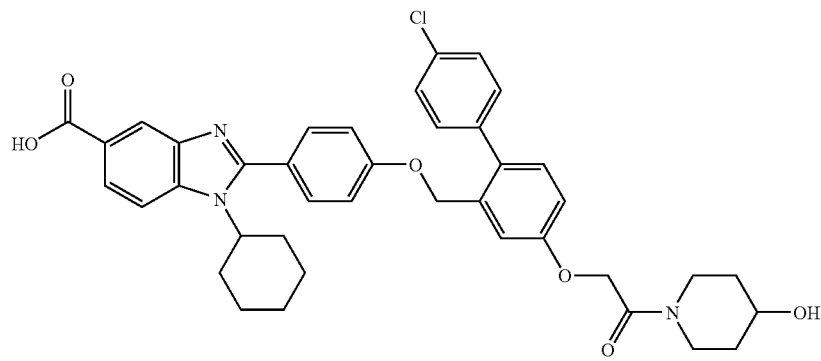

Purity > 90% (NMR)

MS 694 (M + 1)

1H NMR (δ) ppm

300MHz, DMSO-d6 8.20(1H, d, J=1.5Hz), 7.93(1H, d, J=8.6Hz), 7.84(1H, dd, J=8.3Hz, 1.5Hz), 7.57(2H, d, J=8.6Hz), 7.50–7.40(4H, m), 7.27(1H, d, J=8.2Hz), 7.22(1H, d, J=2.6Hz), 7.10(2H, d, J=8.6Hz) 7.01(1H, dd, J=8.6Hz, 2.6Hz), 5.02(2H, s), 4.89(2H, s), 4.78(1H, d, J=4.1Hz), 4.38–4.18(1H, m), 3.96–3.81(1H, m),3.78–3.62(2H, m), 3.27–2.99(2H, m), 2.35–1.15(14H, m)

TABLE 226

Example No. 344

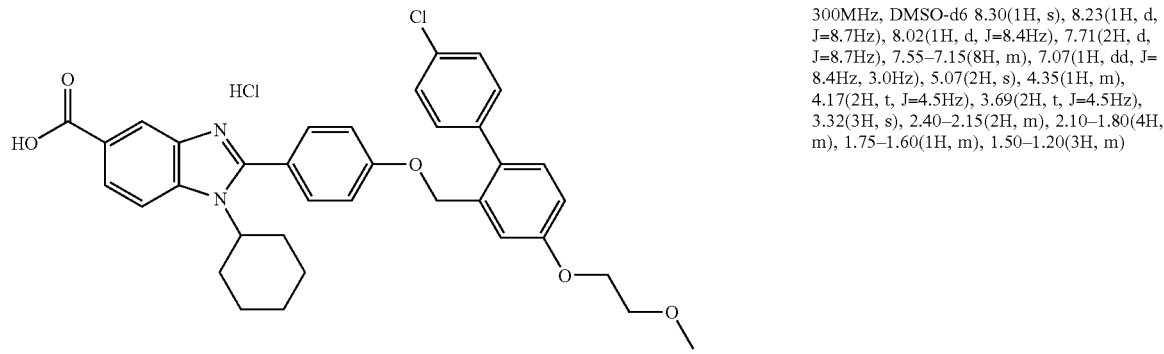

Purity > 90% (NMR)
MS 611 (M + 1)

1H NMR (δ) ppm

300MHz, DMSO-d6 8.30(1H, s), 8.23(1H, d, J=8.7Hz), 8.02(1H, d, J=8.4Hz), 7.71(2H, d, J=8.7Hz), 7.55–7.15(8H, m), 7.07(1H, dd, J=8.4Hz, 3.0Hz), 5.07(2H, s), 4.35(1H, m), 4.17(2H, t, J=4.5Hz), 3.69(2H, t, J=4.5Hz), 3.32(3H, s), 2.40–2.15(2H, m), 2.10–1.80(4H, m), 1.75–1.60(1H, m), 1.50–1.20(3H, m)

Example No. 345

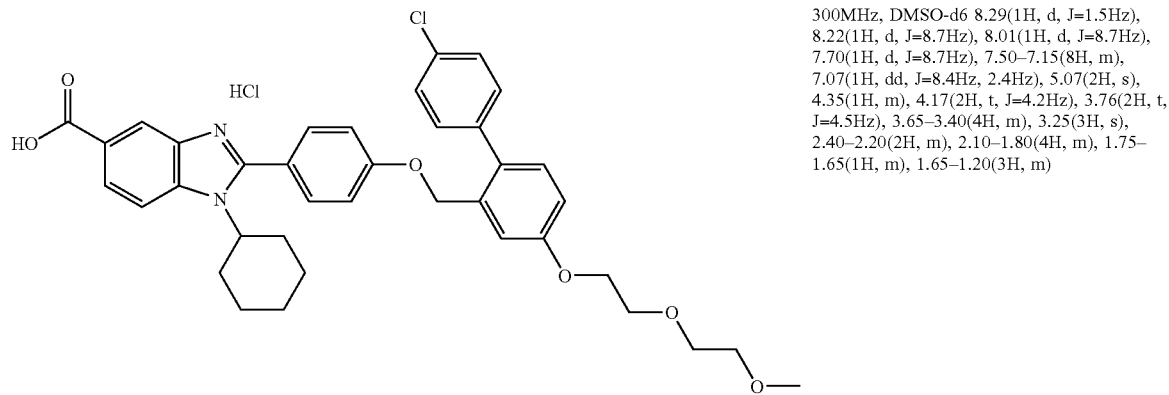

Purity > 90% (NMR)
MS 655 (M + 1)

1H NMR (δ) ppm

300MHz, DMSO-d6 8.29(1H, d, J=1.5Hz), 8.22(1H, d, J=8.7Hz), 8.01(1H, d, J=8.7Hz), 7.70(1H, d, J=8.7Hz), 7.50–7.15(8H, m), 7.07(1H, dd, J=8.4Hz, 2.4Hz), 5.07(2H, s), 4.35(1H, m), 4.17(2H, t, J=4.2Hz), 3.76(2H, t, J=4.5Hz), 3.65–3.40(4H, m), 3.25(3H, s), 2.40–2.20(2H, m), 2.10–1.80(4H, m), 1.75–1.65(1H, m), 1.65–1.20(3H, m)

Example No. 346

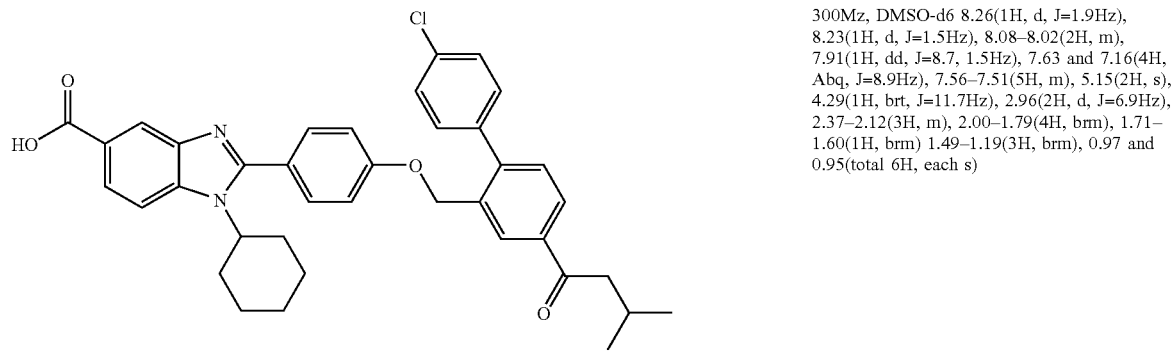

Purity > 90% (NMR)
MS 621 (M + 1)

1H NMR (δ) ppm

300Mz, DMSO-d6 8.26(1H, d, J=1.9Hz), 8.23(1H, d, J=1.5Hz), 8.08–8.02(2H, m), 7.91(1H, dd, J=8.7, 1.5Hz), 7.63 and 7.16(4H, Abq, J=8.9Hz), 7.56–7.51(5H, m), 5.15(2H, s), 4.29(1H, brt, J=11.7Hz), 2.96(2H, d, J=6.9Hz), 2.37–2.12(3H, m), 2.00–1.79(4H, brm), 1.71–1.60(1H, brm) 1.49–1.19(3H, brm), 0.97 and 0.95(total 6H, each s)

TABLE 227

Example No. 347

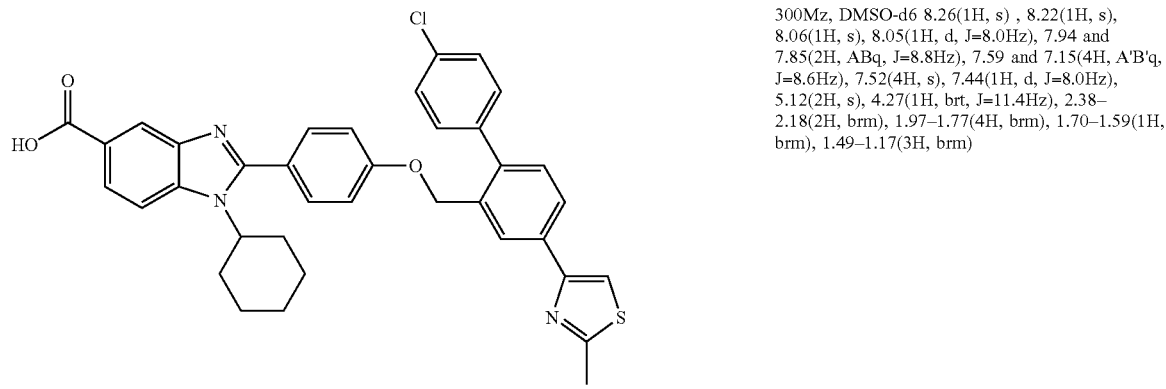

Purity > 90% (NMR)

MS 634 (M + 1)

1H NMR (δ) ppm

300Mz, DMSO-d6 8.26(1H, s) , 8.22(1H, s), 8.06(1H, s), 8.05(1H, d, J=8.0Hz), 7.94 and 7.85(2H, ABq, J=8.8Hz), 7.59 and 7.15(4H, A'B'q, J=8.6Hz), 7.52(4H, s), 7.44(1H, d, J=8.0Hz), 5.12(2H, s), 4.27(1H, brt, J=11.4Hz), 2.38–2.18(2H, brm), 1.97–1.77(4H, brm), 1.70–1.59(1H, brm), 1.49–1.17(3H, brm)

Example No. 348

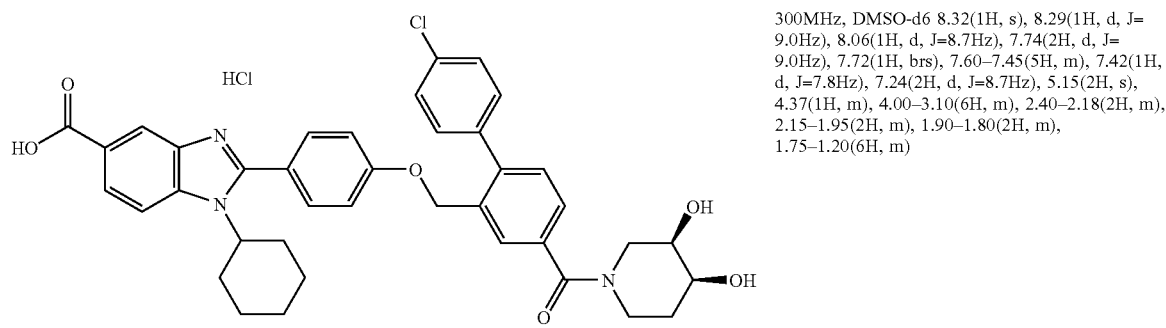

Purity > 90% (NMR)

MS 680 (M + 1)

1H NMR (δ) ppm

300MHz, DMSO-d6 8.32(1H, s), 8.29(1H, d, J=9.0Hz), 8.06(1H, d, J=8.7Hz), 7.74(2H, d, J=9.0Hz), 7.72(1H, brs), 7.60–7.45(5H, m), 7.42(1H, d, J=7.8Hz), 7.24(2H, d, J=8.7Hz), 5.15(2H, s), 4.37(1H, m), 4.00–3.10(6H, m), 2.40–2.18(2H, m), 2.15–1.95(2H, m), 1.90–1.80(2H, m), 1.75–1.20(6H, m)

Example No. 349

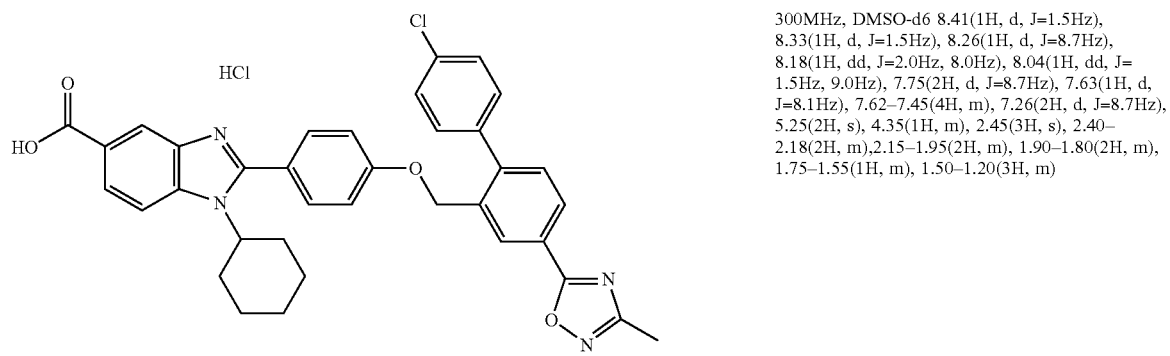

Purity > 90% (NMR)

MS 619 (M + 1)

1H NMR (δ) ppm

300MHz, DMSO-d6 8.41(1H, d, J=1.5Hz), 8.33(1H, d, J=1.5Hz), 8.26(1H, d, J=8.7Hz), 8.18(1H, dd, J=2.0Hz, 8.0Hz), 8.04(1H, dd, J=1.5Hz, 9.0Hz), 7.75(2H, d, J=8.7Hz), 7.63(1H, d, J=8.1Hz), 7.62–7.45(4H, m), 7.26(2H, d, J=8.7Hz), 5.25(2H, s), 4.35(1H, m), 2.45(3H, s), 2.40–2.18(2H, m), 2.15–1.95(2H, m), 1.90–1.80(2H, m), 1.75–1.55(1H, m), 1.50–1.20(3H, m)

TABLE 228
Example No. 350
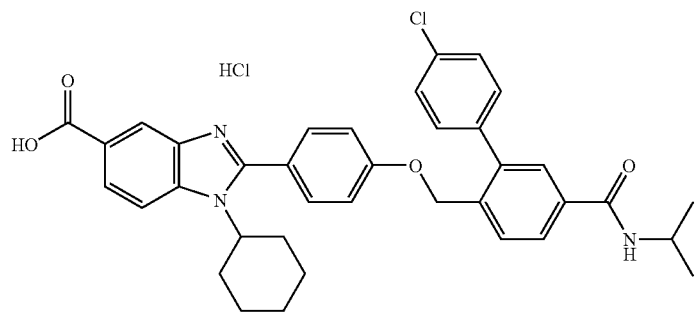
Purity > 90% (NMR)
MS 622 (M + 1)
1H NMR (δ) ppm
300MHz, DMSO-d6 8.36(1H, d, J=7.7Hz), 8.29(1H, s), 8.23(1H, d, J=8.8Hz), 8.02(1H, d, J=8.6Hz), 7.94(1H, d, J=7.9Hz), 7.84(1H, d, J=1.6Hz), 7.80–7.65(3H, m), 7.53(4H, s), 5.15(2H, s), 4.34(1H, m), 4.12(1H, m), 2.35–2.20(2H, m), 2.10–1.60(5H, m), 1.50–1.20(3H, m), 1.17(6H, d, J=6.5Hz)
Example No. 351
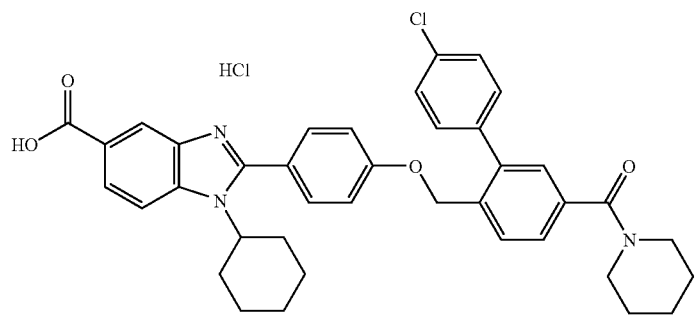
Purity > 90% (NMR)
MS 648 (M + 1)
1H NMR (δ) ppm
300MHz, DMSO-d6 8.29(1H, s), 8.24(1H, d, J=8.8Hz), 8.02(1H, d, J=8.6Hz), 7.80–7.65(3H, m), 7.55–7.45(5H, m), 7.32(1H, d, J=1.5Hz), 7.22(2H, d, J=8.8Hz), 5.13(2H, s), 4.35(1H, m), 3.60(2H, m), 3.33(2H, m), 2.40–2.15(2H, m), 2.10–1.15(14H, m)
Example No. 352
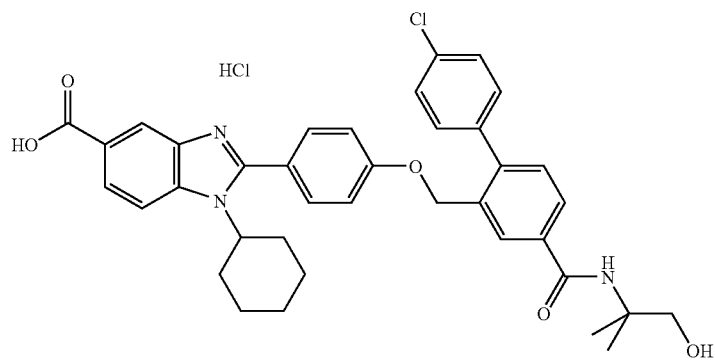
Purity > 90% (NMR)
MS 652 (M + 1)
1H NMR (δ) ppm
300MHz, DMSO-d6 13.20(1H, brs), 8.30–8.24(2H, m), 8.13(1H, s), 8.04(1H, d, J=8.7Hz), 7.94(1H, d, J=8.0Hz), 7.75–7.70(3H, m), 7.55–7.43(5H, m), 7.25(2H, d, J=8.7Hz), 5.13(2H, s), 4.36(1H, m), 3.53(2H, s), 2.40–2.18(2H, m), 2.15–1.95(2H, m), 1.90–1.80(2H, m), 1.75–1.55(1H, m), 1.50–1.20(9H, m)

TABLE 229

| Example No. 353 | 1H NMR(δ)ppm |
|---|---|
| 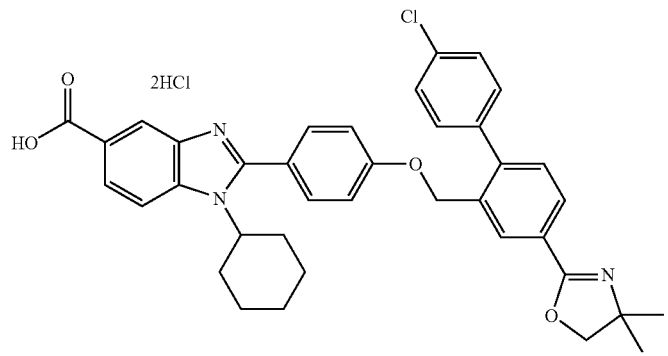<br>Purity about 90%(NMR)<br>MS 634 (M+1) | 300MHz, DMSO-d6 8.41(1H, s), B, 8.33–8.29(2H, m), 8.16(1H, d, J=8.2Hz), 8.07(1H, d, J=8.6Hz), 7.77(2H, d, J=8.7Hz), 7.62(1H, d, J=8.0Hz), 7.59–7.51(4H, m), 7.28(2H, d, J=8.8Hz), 5.21(2H, s), 4.56(2H, s), 4.37(1H, m), 2.40–2.18(2H, m), 2.15–1.95(2H,m), 1.90–1.80(2H, m), 1.75–1.55(1H, m), 1.50–1.20(9H, m) |
| Example No. 354 | 1H NMR(δ)ppm |
| 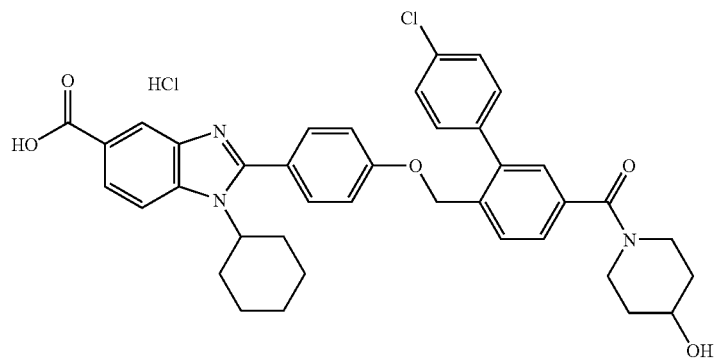<br>Purity >90%(NMR)<br>MS 664 (M+1) | 300MHz, DMSO-d6 8.31(1H, s), 8.25(1H, d, J=9.0Hz), 8.03(1H, d, J=8.7Hz), 7.76–7.71(3H, m), 7.51–7.47(5H, m), 7.33(1H, s), 7.23(2H, d, J=9.0Hz), 5.14(2H, s), 4.36(1H, m), 4.02(1H, m), 3.75(1H, m), 3.56(1H, m), 3.22(2H, m), 2.40–2.18(2H, m), 2.15–1.95(2H, m), 1.90–1.55(5H, m), 1.50–1.20(5H, m) |
| Example No. 355 | 1H NMR(δ)ppm |
| 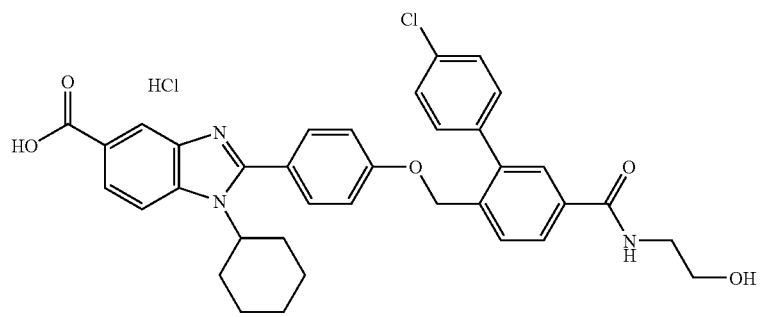<br>Purity >90%(NMR)<br>MS 624 (M+1) | 300MHz, DMSO-d6 8.62(1H, t, J=5.7Hz), 8.32–8.30(2H, m), 8.25(1H, d, J=8.7Hz), 8.03(1H, d, J=8.7Hz), 7.96(1H, d, J=8.1Hz), 7.86(1H, s), 7.75(1H, d, J=9.0Hz), 7.72(2H, d, J=9.0Hz), 7.55–7.50(4H, m), 7.22(2H, d, J=9.0Hz), 5.17(2H, s), 4.35(1H, m), 3.52(2H, t, J=6.0Hz), 3.36(2H, t, J=6.0Hz), 2.40–2.18(2H, m), 2.15–1.95(2H, m), 1.90–1.80(2H, m), 1.75–1.55(1H, m), 1.50–1.20(3H, m) |

TABLE 230

Example No. 356

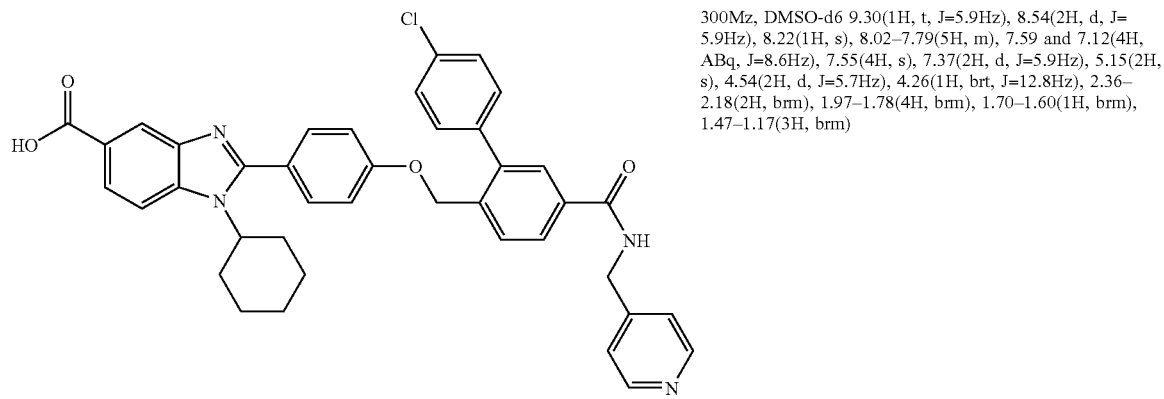

Purity >90%(NMR)
MS 671 (M+1)

1H NMR(δ)ppm

300Mz, DMSO-d6 9.30(1H, t, J=5.9Hz), 8.54(2H, d, J= 5.9Hz), 8.22(1H, s), 8.02–7.79(5H, m), 7.59 and 7.12(4H, ABq, J=8.6Hz), 7.55(4H, s), 7.37(2H, d, J=5.9Hz), 5.15(2H, s), 4.54(2H, d, J=5.7Hz), 4.26(1H, brt, J=12.8Hz), 2.36–2.18(2H, brm), 1.97–1.78(4H, brm), 1.70–1.60(1H, brm), 1.47–1.17(3H, brm)

Example No. 357

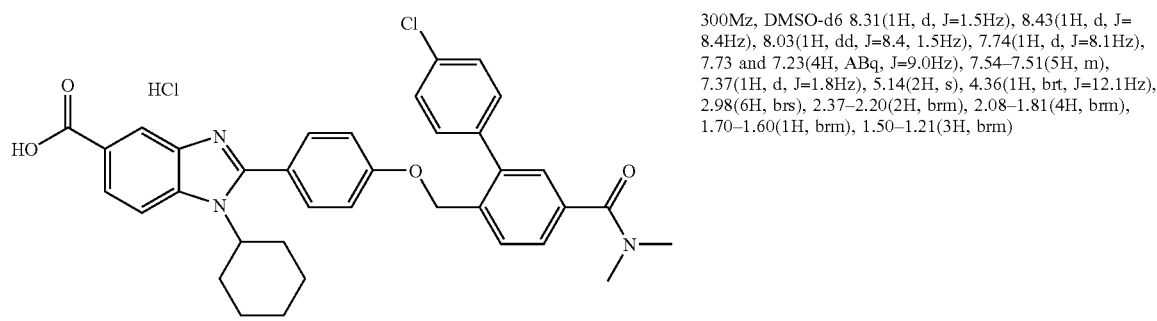

Purity >90%(NMR)
MS 608 (M+1)

1H NMR(δ)ppm

300Mz, DMSO-d6 8.31(1H, d, J=1.5Hz), 8.43(1H, d, J= 8.4Hz), 8.03(1H, dd, J=8.4, 1.5Hz), 7.74(1H, d, J=8.1Hz), 7.73 and 7.23(4H, ABq, J=9.0Hz), 7.54–7.51(5H, m), 7.37(1H, d, J=1.8Hz), 5.14(2H, s), 4.36(1H, brt, J=12.1Hz), 2.98(6H, brs), 2.37–2.20(2H, brm), 2.08–1.81(4H, brm), 1.70–1.60(1H, brm), 1.50–1.21(3H, brm)

Example No. 358

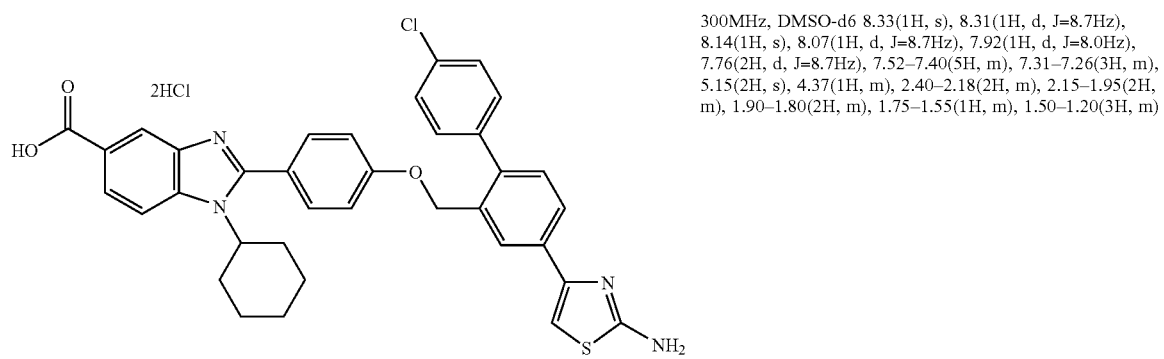

Purity about 90%(NMR)
MS 635 (M+1)

1H NMR(δ)ppm

300MHz, DMSO-d6 8.33(1H, s), 8.31(1H, d, J=8.7Hz), 8.14(1H, s), 8.07(1H, d, J=8.7Hz), 7.92(1H, d, J=8.0Hz), 7.76(2H, d, J=8.7Hz), 7.52–7.40(5H, m), 7.31–7.26(3H, m), 5.15(2H, s), 4.37(1H, m), 2.40–2.18(2H, m), 2.15–1.95(2H, m), 1.90–1.80(2H, m), 1.75–1.55(1H, m), 1.50–1.20(3H, m)

TABLE 231
| Example No. 359 | 1H NMR(δ)ppm |
|---|---|
| 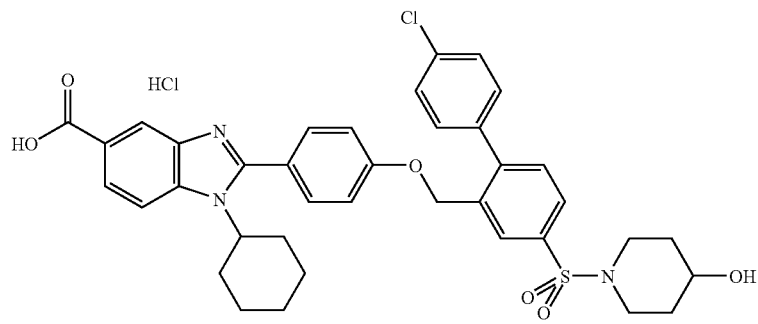<br>Purity >90%(NMR)<br>MS 700 (M+1) | 300MHz, DMSO-d6 8.31(1H, s), 8.25(1H, d, J= 8.7Hz), 8.10–7.90(2H, m), 7.82(1H, dd, J=7.8Hz, 1.8Hz), 7.72(2H, d, J=9.0Hz), 7.63(1H, d, J= 8.1Hz), 7.23(2H, d, J=9.0Hz), 5.25(2H, s), 4.34(1H, m), 3.65–3.50(1H, m), 3.20–3.05(2H, m), 2.90–2.75(2H, m), 2.40–2.15(2H, m), 2.10–1.10(12H, m) |
| Example No. 360 | 1H NMR(δ)ppm |
| 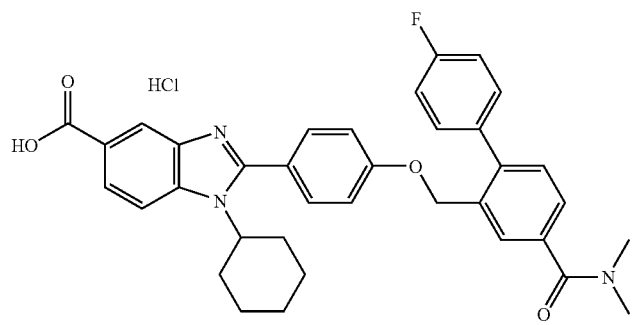<br>Purity >90%(NMR)<br>MS 592 (M+1) | 300MHz, DMSO-d6 8.33(1H, s), 8.30(1H, d, J= 8.5Hz), 8.06(1H, d, J=10.1Hz), 8.80–8.65(3H, m), 8.60–8.45(3H, m), 7.42(1H, d, J=7.8Hz), 7.35–7.15(4H, m), 5.15(2H, s), 4.36(1H, m), 3.01, 2.97(6H, s), 2.40–2.15(2H, m), 2.10–1.75(4H, m), 1.70–1.55(1H, m), 1.50–1.20(3H, m) |
| Example No. 361 | 1H NMR(δ)ppm |
| 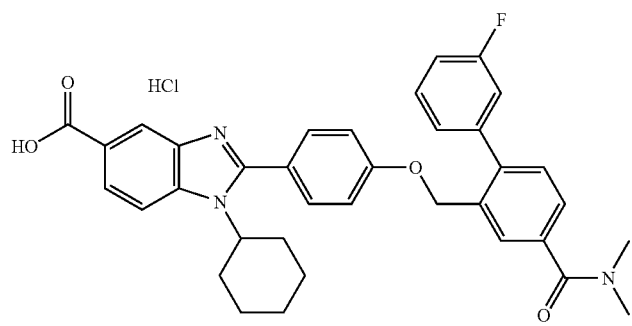<br>Purity >90%(NMR)<br>MS 592 (M+1) | 300MHz, DMSO-d6 8.35–8.20(2H, m), 8.05(1H, d, J=8.7Hz), 8.80–8.65(3H, m), 7.60–7.40(3H, m), 7.40–7.30(5H, m), 5.17(2H, s), 4.35(1H, m), 3.01, 2.97(6H, s), 2.40–2.15(2H, m), 2.10–1.80(4H, m), 1.70–1.20(4H, m) |

TABLE 232
| Example No. 362 | 1H NMR(δ)ppm |
|---|---|
| 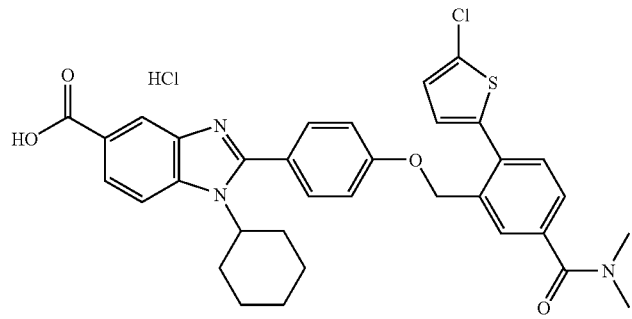<br>Purity >90%(NMR)<br>MS 614 (M+1) | 300MHz, DMSO-d6 8.33(1H, s), 8.29(1H, d, J=8.7Hz), 8.06(1H, d, J=8.7Hz), 7.79(2H, d, J=9.0Hz), 7.76(1H, d, J=9.0Hz), 7.60(1H, d, J=8.1Hz), 7.53(1H, dd, J=1.7Hz, 8.0Hz), 7.35(2H, d, J=8.7Hz), 6.85–6.80(2H, m), 5.29(2H, s), 4.38(1H, m), 3.01, 2.96(6H, s), 2.40–2.18(2H, m), 2.15–1.95(2H, m), 1.90–1.80(2H, m), 1.75–1.55(1H, m), 1.50–1.20(3H, m) |
| Example No. 363 | 1H NMR(δ)ppm |
| 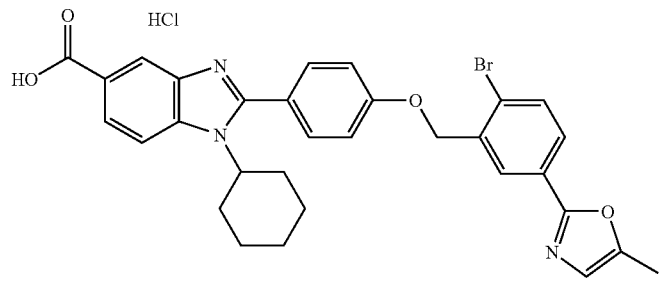<br>Purity >90%(NMR)<br>MS 586 (M+1) | 300MHz, DMSO-d6 8.28(1H, d, J=1.3Hz), 8.20–8.10(2H, m), 8.98(1H, d, J=8.6Hz), 7.90–7.80(2H, m), 7.75(2H, d, J=8.7Hz), 7.36(2H, d, J=8.7Hz), 7.04(1H, d, J=1.3Hz), 5.35(2H, s), 4.36(1H, m), 2.39(3H, s), 2.35–2.15(2H, m), 2.05–1.75(4H, m), 1.70–1.60(1H, m), 1.50–1.20(3H, m) |
| Example No. 364 | 1H NMR(δ)ppm |
| 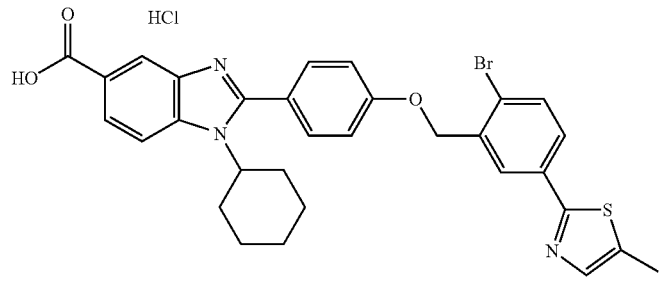<br>Purity >90%(NMR)<br>MS 604 (M+1) | 300MHz, DMSO-d6 8.31(1H, s), 8.26(1H, d, J=8.7Hz), 8.13(1H, s), 8.04(1H, d, J=9.0Hz), 7.90–7.70(4H, m), 7.65(1H, s), 7.39(2H, d, J=9.0Hz), 5.37(2H, s), 4.38(1H, m), 2.40–2.20(2H, m), 2.15–2.00(2H, m), 1.95–1.80(2H, m), 1.75–1.60(1H, m), 1.50–1.20(3H, m) |

TABLE 233
Example No. 365
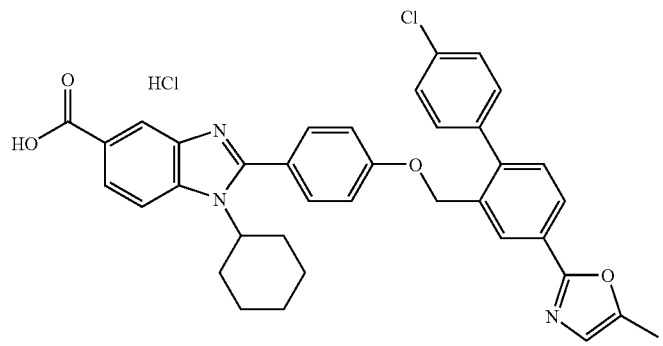
Purity >90%(NMR)
MS 618 (M+1)
1H NMR(δ)ppm
300MHz, DMSO-d6 8.28(1H, s), 8.23(1H, s), 8.17(1H, d, J= 8.7Hz), 8.00(2H, t, J=6.9Hz), 7.69(2H, d, J=8.4Hz), 7.60–7.45(5H, m), 7.21(2H, d, J=8.4Hz), 7.05(1H, s), 5.19(2H, s), 4.33(1H, m), 2.41(3H, s), 2.40–2.20(2H, m), 2.10–1.80(4H, m), 1.70–1.60(1H, m), 1.50–1.20(3H, m)
Example No. 366
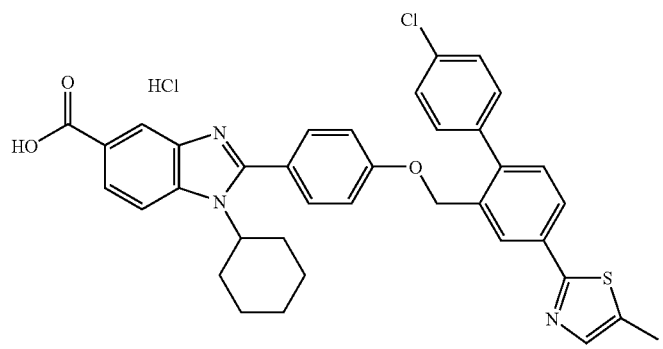
Purity >90%(NMR)
MS 634 (M+1)
1H NMR(δ)ppm
300MHz, DMSO-d6 8.26(1H, s), 8.17(1H, s), 8.11(1H, d, J= 8.7Hz), 7.95(2H, d, J=9.6Hz), 7.70–7.40(8H, m), 7.19(2H, d, J= 8.4Hz), 5.18(2H, s), 4.30(1H, m), 2.51(3H, s), 2.40–2.15(2H, m), 2.05–1.80(4H, m), 1.75–1.60(1H, m), 1.50–1.20(3H, m)
Example No. 367
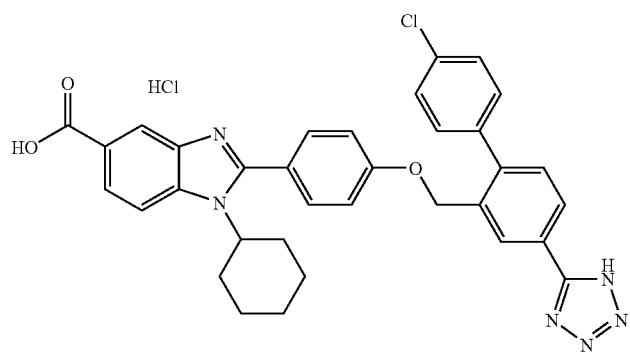
Purity >90%(NMR)
MS 605 (M+1)
1H NMR(δ)ppm
300Mz, DMSO-d6 8.42(1H, d, J=1.9Hz), 8.30(1H, J=1.5Hz), 8.27(1H, d, J=8.7Hz), 8.18(1H, dd, J=7.9, 1.9Hz), 8.04(1H, dd, J=8.7, 1.5Hz), 7.75 and 7.29(4H, ABq, J=8.9Hz) 7.63(1H, d, J= 7.9Hz), 5.23(2H, s), 4.36(1H, brt, J=12.3Hz) 2.37–2.20(2H, brm), 2.08–1.80(4H, brm), 1.71–1.60(1H, brm), 1.51–1.21(3H, brm)

TABLE 234

Example No. 368

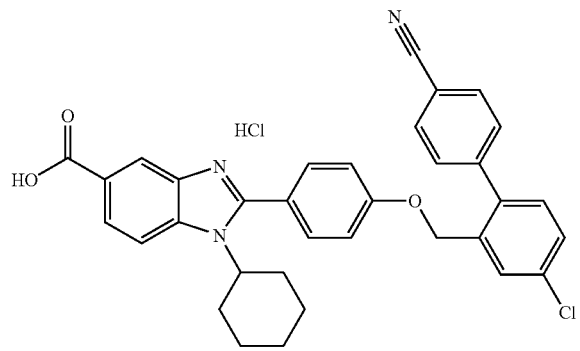

Purity >90%(NMR)
MS 562(M+1)

1H NMR(δ) ppm

300 MHz, DMSO-d6 8.30(1H, d, J=1.5Hz), 8.25(1H, d, J=8.6Hz), 8.04(1H, dd, J=8.6, 1.5Hz), 7.93 and 7.67(4H, ABq, J=8.1Hz), 7.80(1H, d, J=2.2Hz), 7.72 and 7.21(4H, A'B'q, J=8.6Hz), 7.60(1H, dd, J=8.1, 2.2Hz), 7.44(1H, d, J=8.1Hz), 5.13(2H, s), 4.34(1H, brt, J=11.7Hz), 2.37–2.19(2H, brm), 2.09–1.80(4H, brm), 1.72–1.60(1H, brm), 1.50–1.21(3H, brm)

Example No. 369

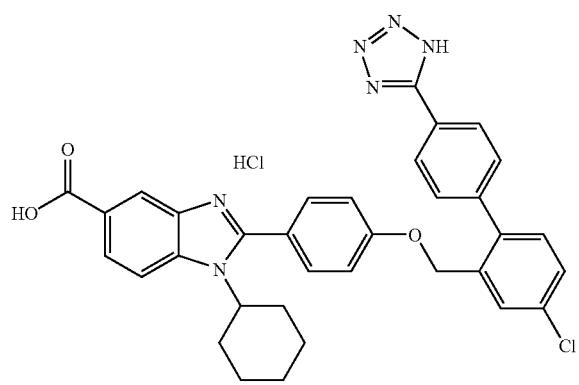

Purity >90%(NMR)
MS 605(M+1)

1H NMR(δ) ppm

300 MHz, DMSO-d6 8.30(1H, d, J=1.5Hz), 8.25(1H, d, J=8.6Hz), 8.16 and 7.72(4H, ABq, J=8.4Hz), 8.13(1H, dd, J=8.6, 1.5Hz), 7.80(1H, d, J=2.2Hz), 7.70 and 7.24(4H, A'B'q, J=8.8Hz), 7.61(1H, dd, J=8.1, 2.2Hz), 7.48(1H, d, J=8.1Hz), 5.17(2H, s), 4.33(1H, brt, J=12.1Hz), 2.36–2.18(2H, brm), 2.08–1.77(4H, brm), 1.69–1.57(1H, brm), 1.49–1.17(3H, brm)

Example No. 370

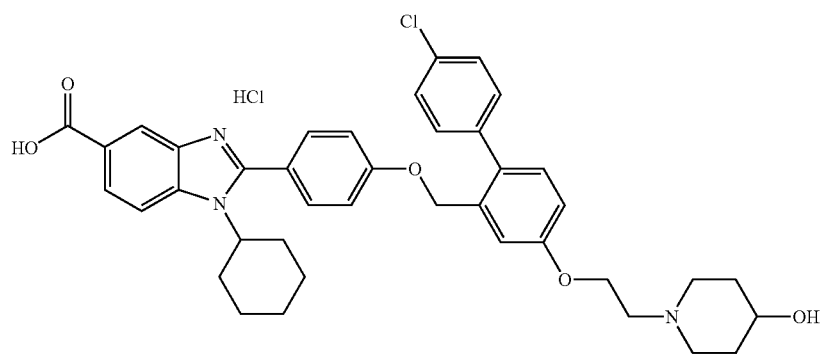

Purity >90%(NMR)
MS 680(M+1)

1H NMR(δ) ppm

300 MHz, DMSO-d6 10.94(1H, brs), 8.33(1H, s), 8.27 (1H, d, J=8.7Hz), 8.04(1H, d, J=8.7Hz), 7.74(2H, d, J=8.4Hz), 7.56–7.29(6H, m), 7.23(2H, d, J=8.7Hz), 7.13(1H, d, J=8.7Hz), 5.08(2H, s), 4.51(2H, brs), 4.36 (1H, m), 3.94(1H, brs), 3.75–3.00(6H, m), 3.20–1.20(14H, m)

TABLE 235

Example No. 371

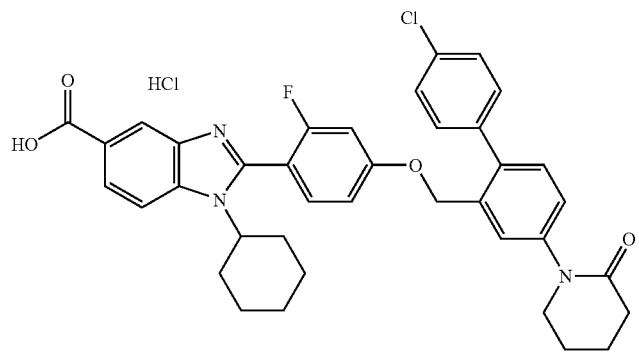

Purity >90%(NMR)

MS 652 (M+1)

1H NMR(δ)ppm

300MHz, DMSO-d6 8.31(1H, d, J=1.5Hz), 8.17(1H, d, J=9.0Hz) 7.99(1H, dd, J=8.7Hz, 1.4Hz), 7.70–7.55(2H, m), 7.50–7.30(6H, m), 7.19(1H, dd, J=12.0Hz, 2.2Hz), 7.06(1H, dd, J=8.6Hz, 2.2Hz), 5.08(2H, 4.10(1H, m), 3.68(2H, brt, J=5.2), 2.50(2H, brt, J=1.8Hz), 2.30–2.10(2H, m), 2.00–1.75(8H, m), 1.70–1.55(1H, m), 1.50–1.20(3H, m)

Example No. 372

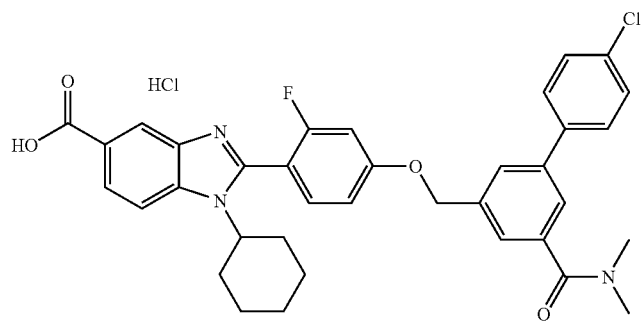

Purity >90%(NMR)

MS 626 (M+1)

1H NMR(δ)ppm

300Mz, DMSO-d6 8.29(1H, d, J=1.5Hz), 8.11(1H, d, J=8.6Hz), 7.96(1H, dd, J=8.6, 1.5Hz), 7.89(1H, s), 7.78 and 7.56(4H, ABq, J=8.4Hz), 7.69(1H, s), 7.66(1H, t, J=8.5Hz), 7.31(1H, dd, J=12.1, 2.2Hz), 7.18(1H, dd, J=8.8, 2.2Hz), 5.37(2H, s), 4.08(1H, brt, J=11.0Hz), 3.02(3H, s), 2.96(3H, s), 2.31–2.14(2H, brm), 1.95–1.77(4H, brm,) 1.69–1.59(31H, brm), 1.46–1.18(3H, brm)

Example No. 373

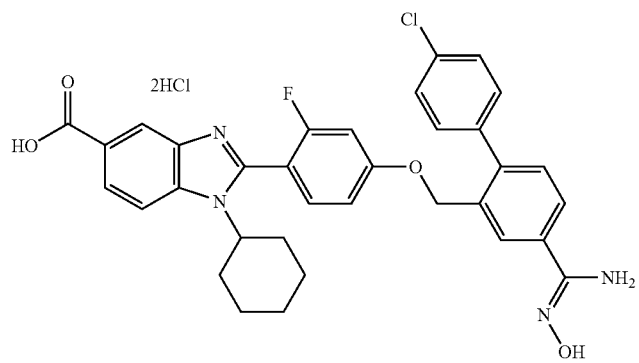

Purity >90%(NMR)

MS 613 (M+1)

1H NMR(δ)ppm

300MHz, DMSO-d6 11.40(1H, brs), 9.25(2H, brs), 8.29(1H, d, J=1.3Hz), 8.12–8.09(2H, m), 7.96(1H, d, J=8.7Hz), 7.88(1H, dd, J=1.8Hz, 8.1Hz), 7.67–7.63(2H, m), 7.56(2H, d, J=8.7Hz), 7.51(2H, d, J=8.7Hz), 7.17(1H, d, J=12.0Hz), 7.05(1H, d, J=8.6Hz), 5.16(2H, s), 4.05(1H, m), 2.40–2.10(2H, m), 2.00–1.75(4H, m), 1.70–1.55(1H, m), 1.50–1.20(3H, m)

TABLE 236

| Example No. 374 | 1H NMR(δ)ppm |

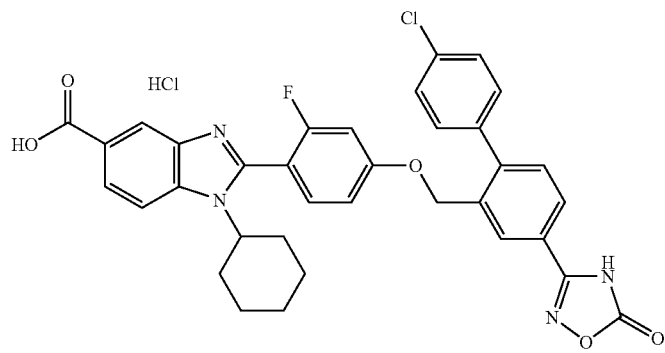

Purity >90%(NMR)
MS 639 (M+1)

300MHz, DMSO-d6 13.21(1H, brs), 8.31(1H, d, J=1.4Hz), 8.18–8.15(2H, m), 7.99(1H, d, J=8.7Hz), 7.94(1H, dd, J=1.8Hz, 8.0Hz), 7.70–7.53(6H, m), 7.17(1H, d, J=12.0Hz), 7.05(1H, d, J=8.6Hz), 5.20(2H, s), 4.09(1H, m), 2.40–2.10(2H, m), 2.00–1.75(4H, m), 1.70–1.55(1H, m), 1.50–1.20(3H, m)

| Example No. 375 | 1H NMR(δ)ppm |

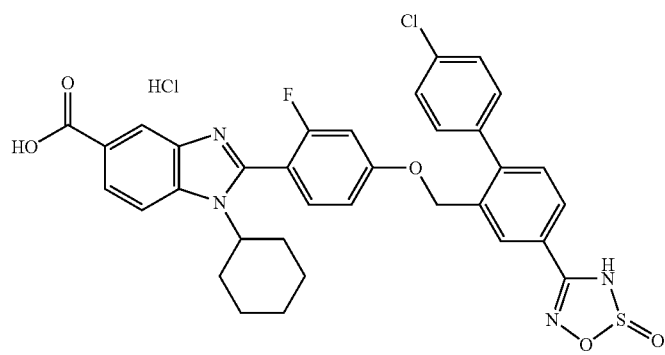

Purity >90 (NMR)
MS 658 (M+1)

300MHz, DMSO-d6 8.32(1H, d, J=1.5Hz), 8.23(1H, d, J=1.5Hz), 8.19(1H, d, J=9.0Hz), 8.03–7.98(2H, m), 7.68(1H, t, J=8.4Hz), 7.60(1H, d, J=8.1Hz), 7.56(2H, d, J=9.3Hz), 7.53(2H, d, J=9.0Hz), 7.22(1H, dd, J=2.1Hz, 12.0Hz), 7.09(1H, dd, J=2.1Hz, 8.4Hz), 5.21(2H, s), 4.12(1H, m), 2.40–2.10(2H, m), 2.00–1.75(4H, m), 1.70–1.55(1H, m), 1.50–1.20(3H, m)

| Example No. 376 | 1H NMR(δ)ppm |

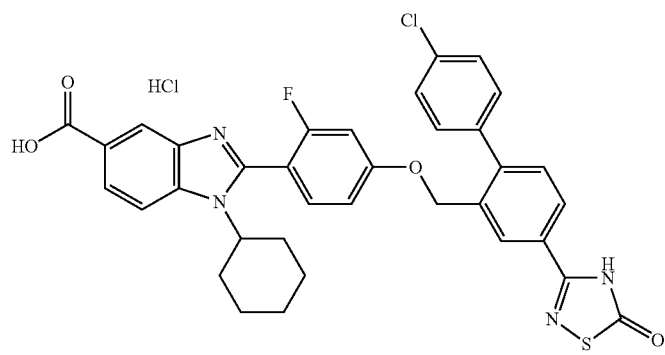

Purity >90%(NMR)
MS 655 (M+1)

300MHz, DMSO-d6 13.61(1H, brs), 8.34–8.30(2H, m), 8.21(1H, d, J=8.7Hz), 8.07(1H, dd, J=1.8Hz, 8.1Hz), 8.02(1H, dd, J=1.5Hz, 8.7Hz), 7.69(1H, t, J=8.4Hz), 7.57–7.49(5H, m), 7.22(1H, dd, J=2.7Hz, 12.0Hz), 7.09(1H, dd, J=2.4Hz, 9.0Hz), 5.19(2H, s), 4.12(1H, m), 2.40–2.10(2H, m), 2.00–1.75(4H, m), 1.70–1.55(1H, m), 1.50–1.20(3H, m)

TABLE 237

| Example No. 377 | 1H NMR(δ)ppm |
|---|---|
| 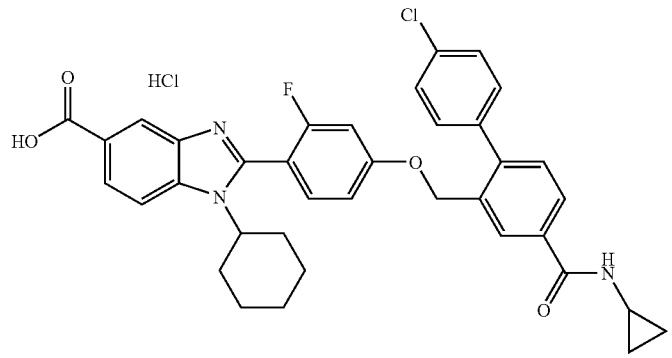<br>Purity >90%(NMR)<br>MS 638 (M+1) | 300Mz, DMSO-d6 8.60(1H, d, J=4.5Hz), 8.29(1H, d, J=1.5Hz), 8.14(1H, d, J=8.9Hz), 8.13(1H, d, J=1.5Hz), 7.98(1H, dd, J= 8.9, 1.5Hz), 7.94(1H, dd, J=8.1, 1.5Hz), 7.64(1H, t, J=8.7Hz), 7.52 and 7.49(4H, ABq, J=9.0Hz), 7.46(1H, d, J=8.1Hz), 7.18(1H, dd, J=12.1, 2.3Hz), 7.05(1H, dd, J=8.7, 2.3Hz), 5.13(2H, s), 4.08(1H, brt, J=12.1H), 2.95–2.84(1H, m), 2.31–2.14(2H, brm), 1.97–1.78(4H, brm), 1.72–1.59(1H, brm), 1.47–1.21(3H, brm), 0.76–0.58(4H, m) |
| Example No. 378 | 1H NMR(δ)ppm |
| 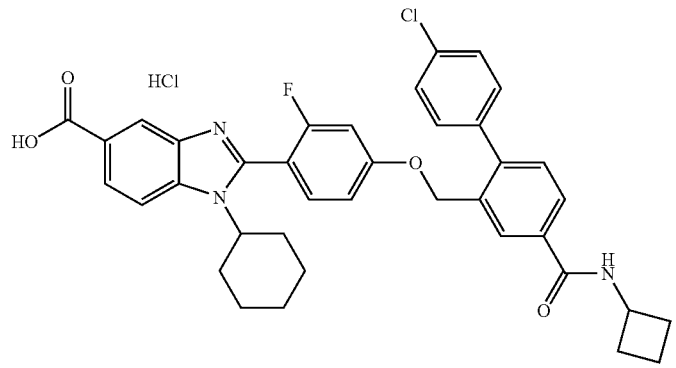<br>Purity >90%(NMR)<br>MS 652 (M+1) | 300Mz, DMSO-d6 8.77(1H, d, J=1.4Hz), 8.30(1H, d, J=1.4Hz), 8.16(1H, d, J=1.8Hz), 8.13(1H, d, J=8.4Hz), 7.98(2H, dd, J=8.4, 1.8Hz), 7.65(1H, t, J=8.4Hz), 7.53 and 7.49(4H, ABq, J= 8.8Hz), 7.47(1H, d, J=7.7Hz), 7.18(1H, dd, J=12.1, 2.2Hz), 7.05(1H, dd, J=8.4, 2.2Hz), 5.13(2H, s), 4.53–4.40(1H, m), 4.09(1H, brt, J=12.8Hz), 2.31–2.02(6H, brm,), 1.96–1.80(4H, brm), 1.78–1.60(3H, brm), 1.47–1.21(3H, brm) |
| Example No. 379 | 1H NMR(δ)ppm |
| 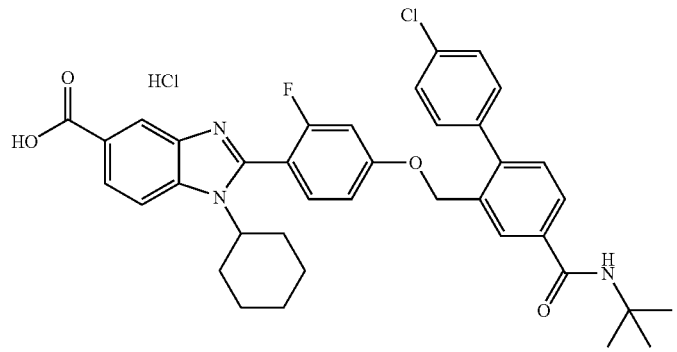<br>Purity >90%(NMR)<br>MS 654 (M+1) | 300Mz, DMSO-d6 8.29(1H, d, J=1.1Hz), 8.11(1H, d, J=1.5Hz), 8.11(1H, d, J=8.8Hz), 7.98–7.91(2H, m), 7.89(1H, s), 7.63(1H, t, J=8.8Hz), 7.52 and 7.48(4H, ABq, J=8.6Hz), 7.44(1H, d, J= 8.1Hz), 7.17(1H, dd, J=12.1, 2.2Hz), 7.04(1H, dd, J=8.8, 2.2Hz), 5.12(2H, s), 4.07(1H, brt, J=12.4Hz), 2.33–2.14(2H, brm), 1.96–1.79(4H, brm), 1.70–1.60(1H, brm), 1.48–1.21(3H, brm), 1.41(9H, s) |

TABLE 238

Example No. 380

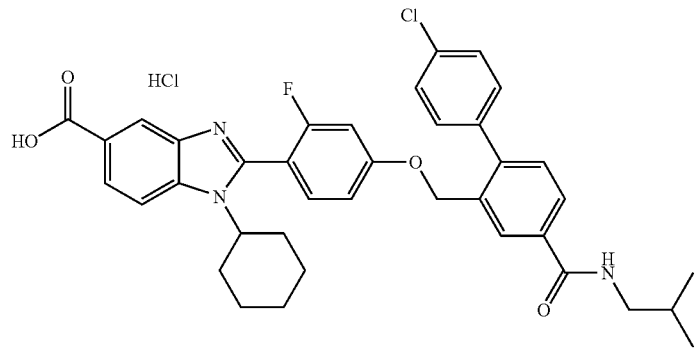

Purity >90%(NMR)
MS 654 (M+1)

1H NMR(δ)ppm

300Mz, DMSO-d6 8.62(1H, t, J=5.5Hz), 8.30(1H, d, J=1.5Hz), 8.17(1H, d, J=1.8Hz), 8.14(1H, d, J=8.8Hz), 7.98(1H, dd, J=8.1, 1.8Hz), 7.64(1H, t, J=8.8Hz), 7.52 and 7.50(4H, ABq, J=8.8Hz), 7.48(1H, d, J=8.1Hz), 7.18(1H, dd, J=12.1, 2.2Hz), 7.05(1H, dd, J=8.8, 2.2Hz), 5.14(2H, s), 4.08(1H, brt, J=12.1Hz), 3.13(1H, t, J=6.2Hz), 2.31–2.14(2H, brm), 1.97–1.78(5H, brm), 1.70–1.60(1H, brm), 1.47–1.21(3H, brm), 0.92(3H, s), 0.90(3H,s)

Example No. 381

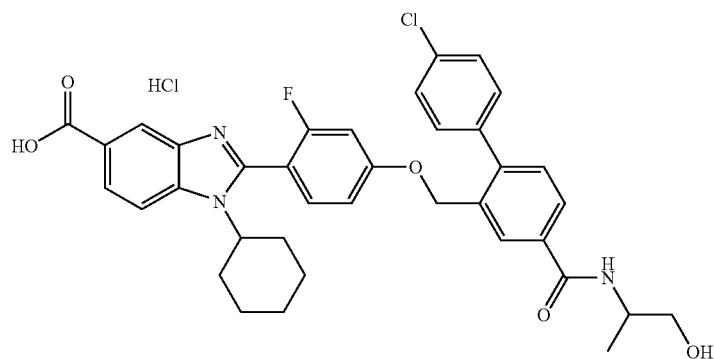

Purity >90%(NMR)
MS 656 (M+1)

1H NMR(δ)ppm

300Mz, DMSO-d6 8.29(1H, d, J=1.5Hz), 8.27(1H, d, J=8.3Hz), 8.18(1H, d, J=1.9Hz), 8.13(1H, d, J=8.7Hz), 8.01–7.96(2H, m), 7.64(1H, t, J=8.7Hz), 7.52 and 7.49(1H, ABq, J=8.8Hz), 7.49(1H, d, J=7.9Hz), 7.18(1H, dd, J=12.1, 2.3Hz), 7.05(1H, dd, J=8.7, 2.3Hz), 5.13(2H, s), 4.12–4.00(2H, m), 3.52–3.34(2H, m), 2.31–2.14(2H, brm), 1.97–1.79(4H, brm), 1.71–1.60(1H, brm), 1.48–1.21(3H, m), 1.17 and 1.15(total 3H, each s)

Example No. 382

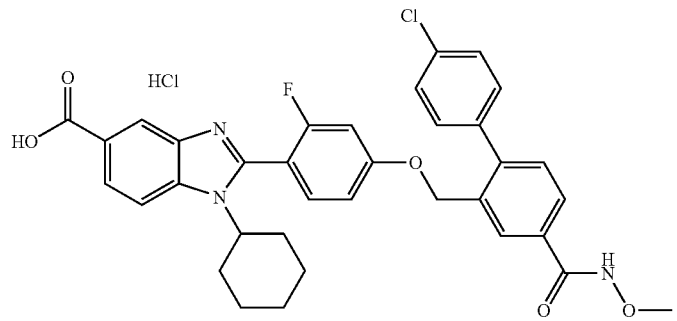

Purity >90%(NMR)
MS 628 (M+1)

1H NMR(δ)ppm

300Mz, DMSO-d6 8.30(1H, d, J=1.5Hz), 8.13(1H, d, J=8.8Hz), 8.09(1H, d, J=1.5Hz), 7.98(1H, dd, J=8.8, 1.5Hz), 7.86(1H, dd, J=8.1, 1.5Hz), 7.64(1H, J=8.8Hz), 7.55–7.47(5H, m), 7.17(1H, dd, J=12.1, 2.2Hz), 7.05(1H, dd, J=8.8, 2.2Hz), 5.14(2H, s), 4.08(1H, brt, J=12.8Hz), 3.75(3H, s), 2.32–2.14(2H, brm), 1.96–1.78(4H, brm), 1.70–1.59(1H, brm), 1.47–1.21(3H, brm)

TABLE 239

| Example No. 383 | 1H NMR(δ)ppm |

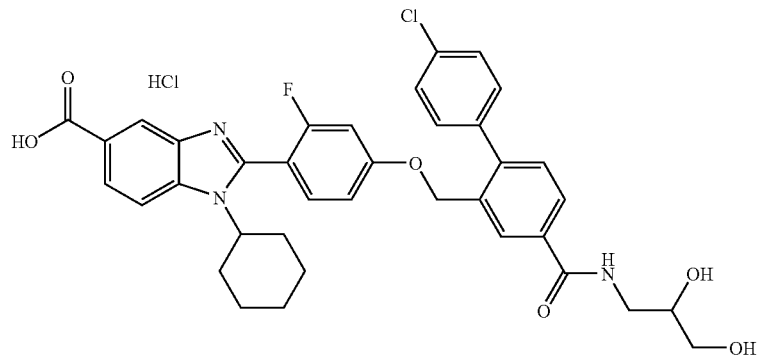

300Mz, DMSO-d6 8.57(1H, t, J=5.5Hz), 8.29(1H, d, J=1.4Hz), 8.19(1H, d, J=1.5Hz), 8.12(1H, d, J=9.2Hz), 8.01–7.95(2H, m), 7.64(1H, t, J=8.8Hz), 7.53 and 7.50(4H, ABq, J=8.8Hz), 7.48(1H, d, J=7.7Hz), 7.17(1H, dd, J=12.1, 2.2Hz), 7.04(1H, dd, J=8.8, 2.2Hz), 5.14(2H, s), 4.08(1H, brt, J=13.9Hz), 3.70–3.66(1H, m), 3.48–3.36(3H, m), 3.28–3.20(1H, m), 2.32–2.13(2H, brm), 1.96–1.79(4H, brm), 1.71–1.60(1H, brm), 1.47–1.19(3H, brm)

Purity >90%(NMR)
MS 672 (M+1)

Example No. 384 | 1H NMR(δ)ppm

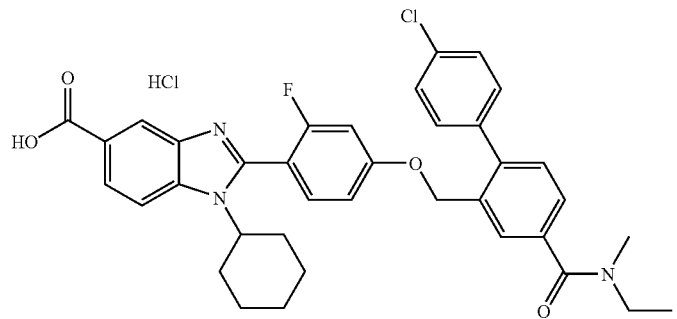

300Mz, DMSO-d6 8.30(1H, d, J=1.5Hz), 8.14(1H, d, J=8.4Hz), 7.98(1H, dd, J=8.4, 1.5Hz), 7.68(1H, brs), 7.63(1H, t, J=8.4Hz), 7.51(5H, s), 7.43(1H, d, J=8.1Hz), 7.17(1H, dd, J=12.5, 1.8Hz), 7.03(1H, dd, J=8.4, 1.8Hz), 4.08(1H, brt, J=11.4Hz), 3.50 and 3.30(total 2H, each brs), 2.97(3H, brs), 2.33–2.13(2H, brm), 1.96–1.79(4H, brm), 1.70–1.59(1H, brm), 1.47–1.03(6H, brm)

Purity >90%(NMR)
MS 640 (M+1)

Example No. 385 | 1H NMR(δ)ppm

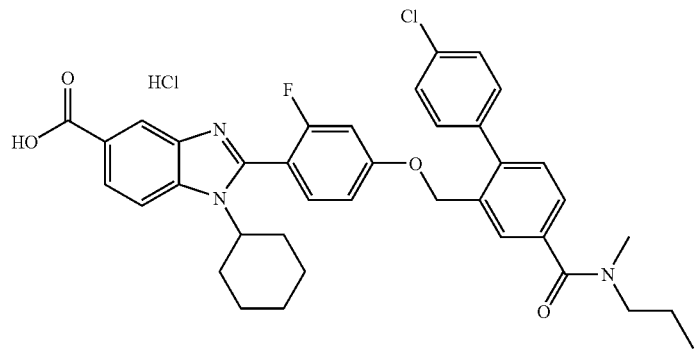

300Mz, DMSO-d6 8.29(1H, d, J=1.5Hz), 8.12(1H, d, J=8.8Hz), 7.97(1H, dd, J=8.8, 1.5Hz), 7.72–7.60(2H, m), 7.55–7.42(6H, m), 7.16(1H, d, J=11.7Hz), 7.03(1H, d, J=8.4Hz), 5.15(2H, s), 4.07(1H, brt, J=12.5Hz), 3.44 and 3.22(total 2H, each s), 2.97(3H, brs), 2.32–2.13(2H, brm), 1.72–1.50(3H, brm), 1.47–1.23(3H, brm), 0.93 and 0.72(total 3H, each brs)

Purity >90%(NMR)
MS 654 (M+1)

TABLE 240

Example No. 386

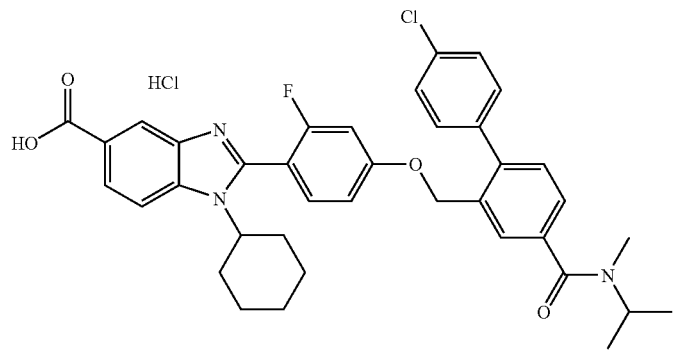

Purity >90%(NMR)
MS 654 (M+1)

1H NMR(δ)ppm

300Mz, DMSO-d6 8.29(1H, d, J=1.5Hz), 8.12(1H, d, J=8.7Hz), 7.97(1H, dd, J=8.7, 1.5Hz) 7.74–7.60(2H, m), 7.54–7.42(6H, m), 7.17(1H, dd, J=12.1, 2.2Hz), 7.02(1H, dd, J=8.3, 2.2Hz), 5.15(2H, s), 4.06(1H, brt, J=12.8Hz), 3.92(1H, brs), 2.85(3H, brs), 2.32–2.14(2H, brm), 1.96–1.79(4H, brm), 1.70–1.59(1H, brm), 1.46–1.07(3H, brm), 1.15(6H, brs)

Example No. 387

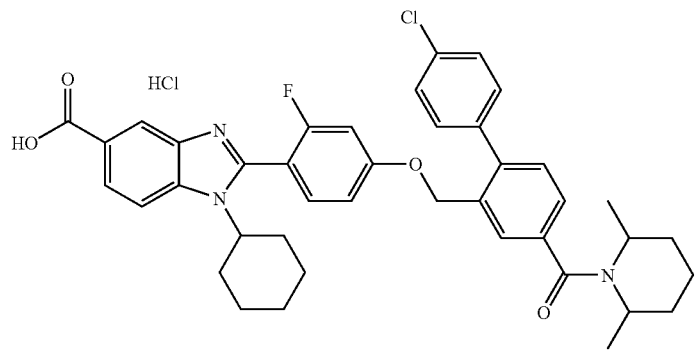

Purity >90%(NMR)
MS 694 (M+1)

1H NMR(δ)ppm

300Mz, DMSO-d6 8.29(1H, s), 8.14 and 7.97(2H, ABq, J=8.7Hz), 7.63(1H, s), 7.63(1H, t, J=8.7Hz), 7.51–7.41(6H, m), 7.16(1H, dd, J=12.1, 1.9Hz), 7.02(1H, dd, J=8.7, 1.9Hz), 5.16(2H, s), 4.26(2H, brs), 4.07(1H, brt, J=12.1Hz), 2.32–2.14(2H, brm), 1.97–1.78(5H, brm) 1.70–1.15(9H, brm), 1.24(3H, s), 1.21(3H, s)

Example No. 388

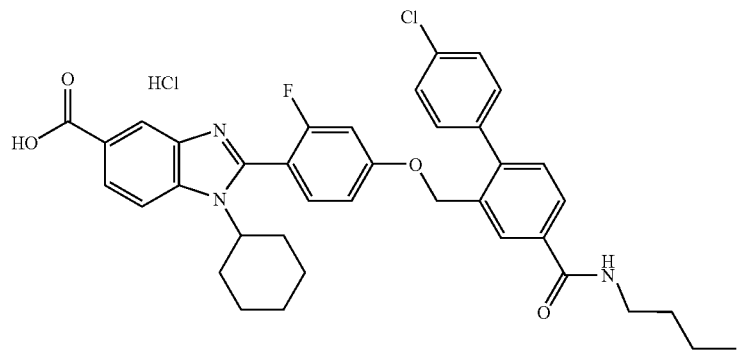

Purity >90%(NMR)
MS 654 (M+1)

1H NMR(δ)ppm

300MHz, DMSO-d6 8.58(1H, m), 8.29(1H, s), 8.20–8.10(2H, m), 8.05–7.90(2H, m), 7.64(1H<t, J=8.4Hz), 7.60–7.40(5H, m), 7.15(1H, d, J=12.3Hz), 7.04(1H, d, J=8.4Hz), 5.13(2H, s), 4.08(1H, m), 3.40–3.20(2H, m), 2.35–2.10(2H, m), 2.00–1.20(12H, m), 0.91(3H, t, J=6.9Hz)

TABLE 241

| Example No. 389 | 1H NMR(δ)ppm |
|---|---|
| 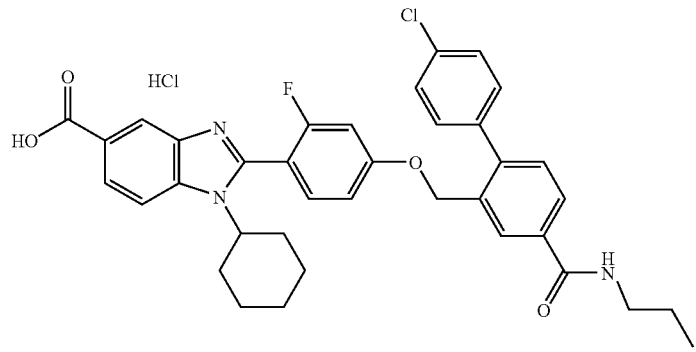<br>Purity >90%(NMR)<br>MS 640 (M+1) | 300MHz, DMSO-d6 8.60(1H, m), 8.29(1H, s), 8.20–7.90(4H, m), 7.64(1H, t, J=9.0Hz), 7.60–7.40(5H, m), 7.17(1H, d, J=12.0Hz), 7.04(1H, d, J=8.7Hz), 5.13(2H, s), 4.80(1H, m), 3.35–3.15(2H, m), 2.30–2.05(2H, m), 2.00–1.10(10H, m), 0.91(3H, t, J=7.5Hz) |
| Example No. 390 | 1H NMR(δ)ppm |
| 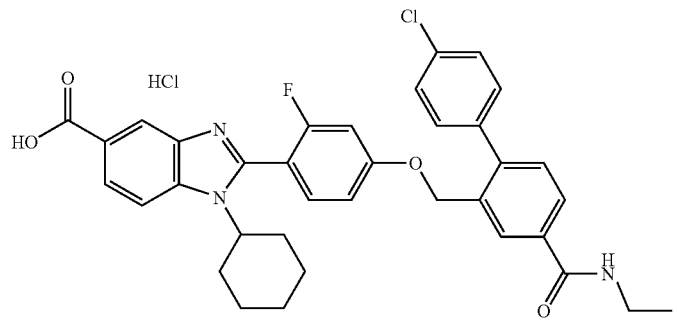<br>Purity >90%(NMR)<br>MS 626 (M+1) | 300MHz, DMSO-d6 8.62(1H, m), 8.30(1H, s), 8.20–8.10(2H, m), 8.05–7.90(2H, m), 7.65(1H, t, J=8.4Hz), 7.60–7.40(5H, m), 7.18(1H, d, J=12.0Hz), 7.05(1H, d, J=8.4Hz), 5.14(2H, s), 4.09(1H, m), 3.40–3.20(2H, m), 2.35–2.10(2H, m), 2.00–1.80(4H, m), 1.75–1.60(1H, m), 1.45–1.20(3H, m), 1.15(3H, t, J=7.2Hz) |
| Example No. 391 | 1H NMR(δ)ppm |
| 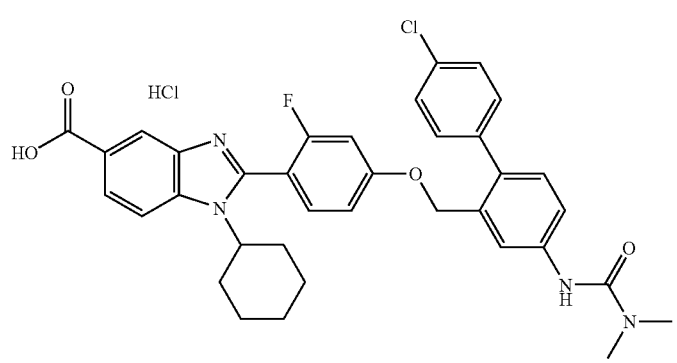<br>Purity >90%(NMR)<br>MS 641 (M+1) | 400NHz, DMSO-d6 8.54(1H, s), 8.31(1H, s), 8.19(1H, d, J=8.6Hz), 8.01(1H, d, J=8.6Hz), 7.81(1H, d, J=2.1Hz), 7.64(1H, t, J=8.4Hz), 7.61(1H, dd, J=2.3Hz, 8.4Hz), 7.47(2H, d, J=8.6Hz), 7.43(2H, d, J=8.8Hz), 7.25(1H, d, J=8.4Hz), 7.17(1H, dd, J=2.3Hz, 12.1Hz), 7.05(1H, dd, J=2.3Hz, 8.6Hz), 5.05(2H, s), 4.12(1H, m), 2.96(6H, s), 2.40–2.10(2H, m), 2.00–1.75(4H, m), 1.70–1.55(1H, m), 1.50–1.20(3H, m) |

TABLE 242

Example No. 392

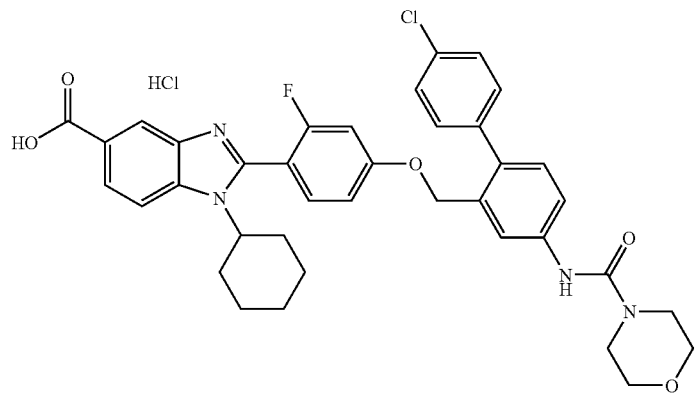

Purity >90%(NMR)
MS 683 (M+1)

1H NMR(δ)ppm

300Mz, DMSO-d6 8.79(1H, s), 8.29(1H, d, J=1.5Hz), 8.13(1H, d, J=8.8Hz), 7.98(1H, dd, J=8.8, 1.5Hz), 7.80(1H, d, J=2.2Hz), 7.63(1H, t, J=8.4Hz), 7.61(1H, dd, J=8.2, 2.2Hz), 7.47 and 7.43(4H, ABq, J=8.8Hz), 7.26(1H, d, J=8.2Hz), 7.14(1H, dd, J=12.1, 2.2Hz), 7.02(1H, dd, J=8.4, 2.2Hz), 5.05(2H, s), 4.08(1H, brt, J=12.1Hz), 3.64–3.61(2H, m), 3.48–3.45(2H, m), 2.32–2.13(2H, brm), 1.96–1.78(4H, brm), 1.70–1.66(1H, brm), 1.44–1.19(3H, brm)

Example No. 393

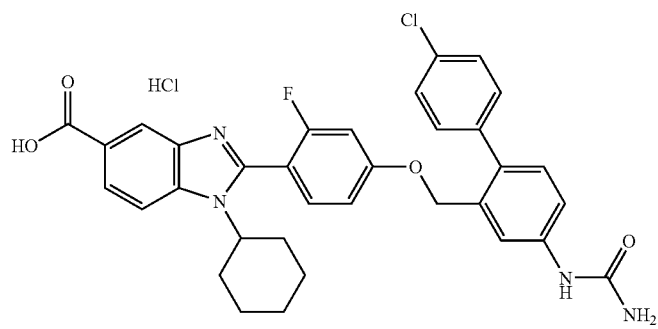

Purity >90%(NMR)
MS 613 (M+1)

1H NMR(δ)ppm

400MHz, DMSO-d6 8.94(1H, s), 8.31(1H, d, J=1.0Hz), 8.18(1H, d, J=8.6Hz), 8.00(1H, dd, J=1.4Hz, 8.8Hz), 7.71(1H, d, J=2.2Hz), 7.66(1H, t, J=8.6Hz), 7.52(1H, dd, J=2.4Hz, 8.6Hz), 7.46(2H, d, J=8.6Hz), 7.42(2H, d, J=8.2Hz), 7.24(1H, d, J=8.4Hz), 7.16(1H, d, J=12.1Hz), 7.04(1H, dd, J=2.4Hz, 8.8Hz), 5.05(2H, s), 4.13(1H, m), 2.40–2.10(2H, m), 2.00–1.75(4H, m), 1.70–1.55(1H, m), 1.50–1.20(3H, m)

Example No. 394

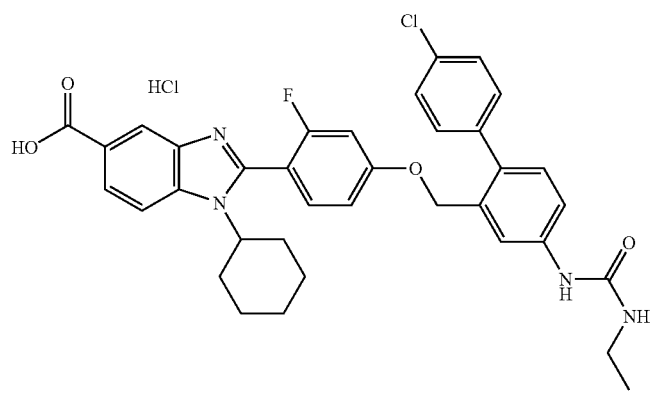

Purity >90%(NMR)
MS 641 (M+1)

1H NMR(δ)ppm

300MHz, DMSO-d6 8.93(1H, s), 8.31(1H, d, J=1.4Hz), 8.19(1H, d, J=8.8Hz), 8.01(1H, d, J=8.7Hz), 7.71(1H, d, J=2.2Hz), 7.66(1H, t, J=8.5Hz), 7.51(1H, dd, J=2.2Hz, 8.4Hz), 7.46(2H, d, J=8.6Hz), 7.41(2H, d, J=8.7Hz), 7.23(1H, d, J=8.4Hz), 7.16(1H, d, J=12.2Hz), 7.05(1H, d, J=8.7Hz), 5.05(2H, s), 4.13(1H, m), 3.12(2H, q, J=7.2Hz), 2.40–2.10(2H, m), 2.00–1.75(4H, m), 1.70–1.60(1H, m), 1.55–1.20(3H, m), 1.06(3H, t, J=7.2Hz)

TABLE 243

Example No. 395

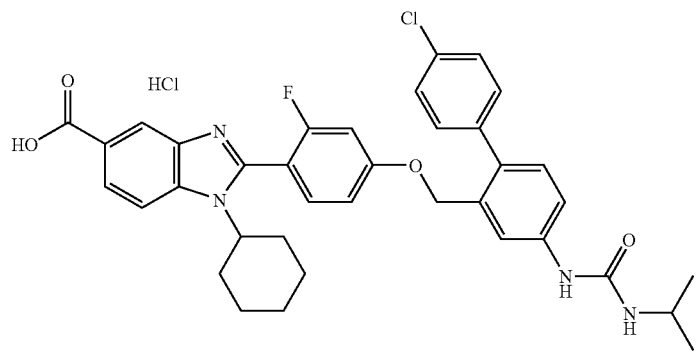

Purity >90%(NMR)

MS 655 (M+1)

1H NMR(δ)ppm

300MHz, DMSO-d6 8.83(1H, s), 8.32(1H, d, J=1.4Hz), 8.21(1H, d, J=8.8Hz), 8.02(1H, dd, J=1.4Hz, 8.7Hz), 7.71(1H, d, J=2.1Hz), 7.68(1H, t, J=8.6Hz), 7.49(1H, dd, J=2.2Hz, 8.4Hz), 7.46(2H, d, J=8.4Hz), 7.41(2H, d, J=8.6Hz), 7.23(1H, d, J=8.4Hz), 7.17(1H, d, J=12.2Hz), 7.06(1H, d, J=8.7Hz), 6.30(1H, brs), 5.05(2H, s), 4.14(1H, m), 3.77(1H, sept, J=6.5Hz), 2.40–2.10(2H, m), 2.00–1.75(4H, m), 1.70–1.55(1H, m), 1.50–1.20(3H, m), 1.11(6H, d, J=6.5Hz)

Example No. 396

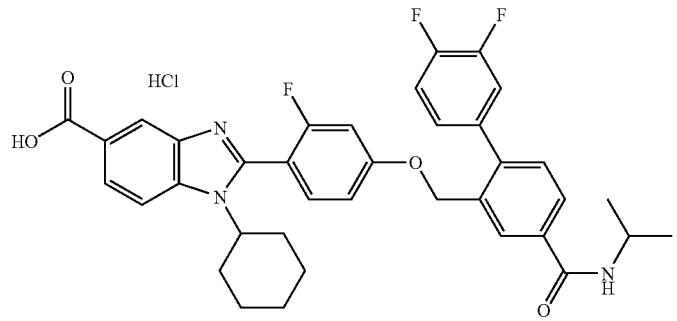

Purity >90%(NMR)

MS 642 (M+1)

1H NMR(δ)ppm

300MHz, DMSO-d6 8.37(1H, d, J=7.3Hz), 8.25(1H, s), 8.15(1H, s), 7.97(2H, d, J=8.8Hz), 7.88(1H, d, J=8.8Hz), 7.58–7.47(4H, m), 7.31(1H, m), 7.11(1H, dd, J=8.4, 2.2Hz), 6.98(1H, dd, J=8.4, 2.2), 5.13(2H, s), 4.13(1H, q, J=6.6Hz), 3.98(1H, m), 2.19(2H, m), 1.86(4H, m) 1.62(1H, m) 1.31(3H, m), 1.20(6H, d, J=6.6Hz)

Example No. 397

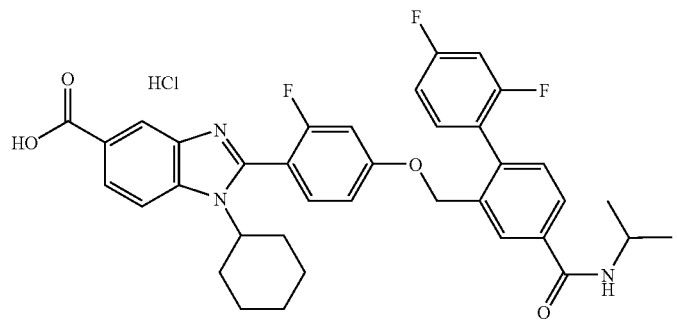

Purity >90%(NMR)

MS 642 (M+1)

1H NMR(δ)ppm

300MHz, DMSO-d6 8.40(1H, d, J=7.9Hz), 8.28(1H, d, J=1.9Hz), 8.15(1H, d, J=1.9Hz), 8.11(1H, d, J=8.7Hz), 7.96(2H, m), 7.56(1H, t, J=8.7Hz), 7.45(3H, m), 7.18(1H, m), 7.08(1H, dd, J=12.1, 1.9Hz), 6.96(1H, dd, J=8.3, 2.3Hz), 5.09(2H, s), 4.14(1H, m), 4.04(1H, m), 2.23(2H, m), 1.86(3H, m), 1.62(1H, m), 1.33(3H, m), 1.20(6H, d, J=6.4Hz)

TABLE 244

Example No. 398

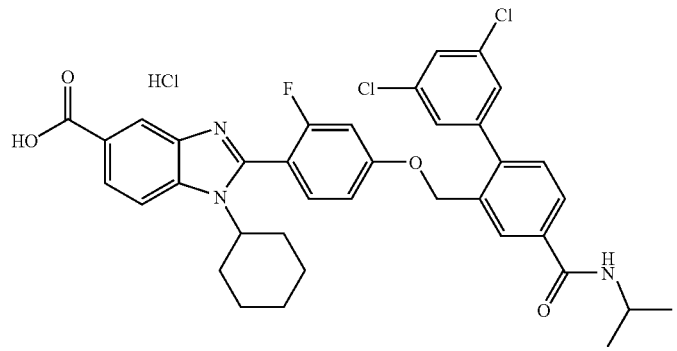

Purity >90%(NMR)
MS 674 (M+1)

1H NMR(δ)ppm 8.41(1H, d, J=8.1Hz), 8.29(1H, d, J=1.5Hz), 8.17(1H, d, J=1.8Hz), 8.12(1H, d, J=8.4Hz), 8.01–7.95(2H, m), 7.67–7.62(2H, m), 7.55–7.51(3H, m), 7.19(1H, dd, J=12.1, 2.2Hz), 7.05(1H, dd, J=8.8, 2.2Hz), 5.13(2H, s), 4.10–4.00(2H, m), 2.32–2.13(4H, m), 1.71–1.60(1H, m), 1.49–1.14(3H, m), 1.21(3H, s), 1.19(3H, s)

Example No. 399

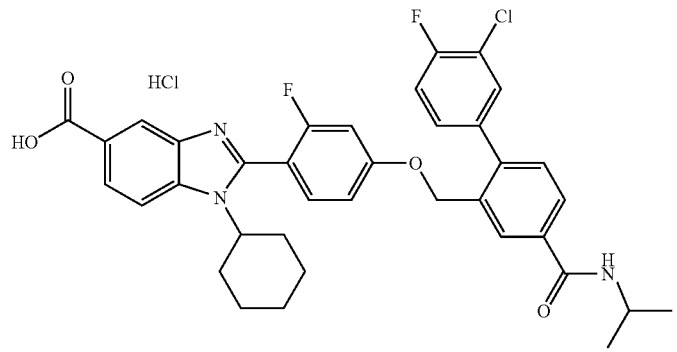

Purity >90%(NMR)
MS 658 (M+1)

1H NMR(δ)ppm

300Mz, DMSO-d6 8.39(1H, d, J=7.7Hz), 8.29(1H, d, J=1.5Hz), 8.16(1H, d, J=1.8Hz), 8.11(1H, d, J=8.8Hz), 8.00–7.95(2H, m), 7.69–7.61(2H, m), 7.54–7.46(3H, m), 7.18(1H, dd, J=12.1, 2.2Hz), 7.04(1H, dd, J=8.8, 2.2Hz), 5.13(2H, s), 4.20–4.02(2H, m), 2.33–2.13(2H, brm), 1.97–1.80(4H, m), 1.72–1.61(1H, m), 1.44–1.13(3H, m), 1.21(3H, s), 1.19(3H, s)

Example No. 400

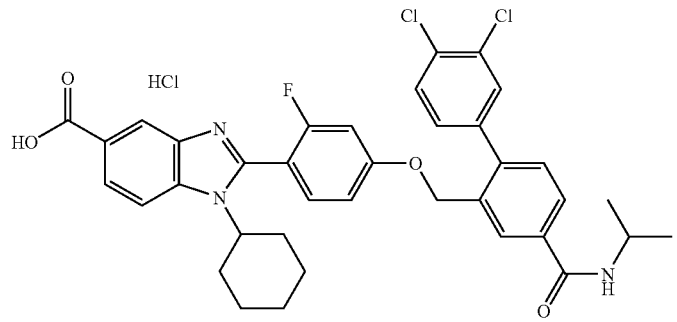

Purity >90%(NMR)
MS 642 (M+1)

1H NMR(δ)ppm

300MHz, DMSO-d6 8.39(1H, d, J=7.7Hz), 8.29(1H, s), 8.17(1H, d, J=1.5Hz), 8.11(1H, d, J=8.8Hz), 7.98(2H, m), 7.73(2H, m), 7.64(1H, t, J=8.4Hz), 7.52(1H, d, J=8.0Hz), 7.46(1H, dd, J=8.4, 1.8Hz), 7.18(1H, dd, J=11.9, 2.0Hz), 7.05(1H, dd, J=8.6, 2.4Hz), 5.14(2H, s), 4.13(2H, m), 2.22(2H, m), 1.88(4H, m) 1.64(1H, m), 1.34(3H, m), 1.20(6H, d, J=6.6Hz)

TABLE 245
Example No. 401
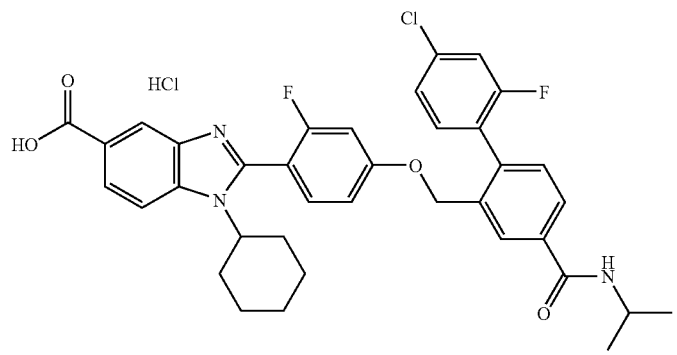
Purity >90%(NMR)
MS 658 (M+1)
1H NMR(δ)ppm
300MHz, DMSO-d6 8.38(1H, d, J=7.8Hz), 8.28(1H, s), 8.20–8.05(2H, m), 8.00–7.90(2H, m), 7.65–7.30(5H, m), 7.09(1H, d, J=12.3Hz), 6.97(1H, d, J=10.2Hz), 5.09(2H, s), 4.20–4.00(2H, m), 2.30–2.10(2H, m), 2.00–1.80(4H, m), 1.70–1.60(1H, m), 1.40–1.10(3H, m), 1.19(6H, d, J=6.6Hz)
Example No. 402
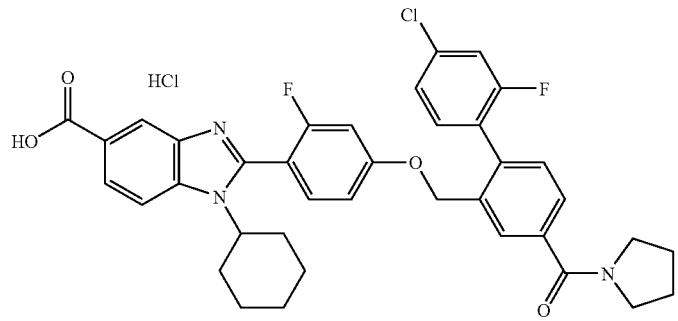
Purity >90%(NMR)
MS 670 (M+1)
1H NMR(δ)ppm
300MHz, DMSO-d6 8.25(1H, s), 8.03(1H, d, J=8.7Hz), 7.91(1H, d, J=8.7Hz), 7.83(1H, s), 7.70–7.35(6H, m), 7.04(1H, d, J=12.0Hz), 6.93(1H, d, J=8.4Hz), 5.09(2H, s), 4.00(1H, m), 3.60–3.40(4H, m), 2.30–2.10(2H, m), 1.45–1.15(3H, m)
Example No. 403
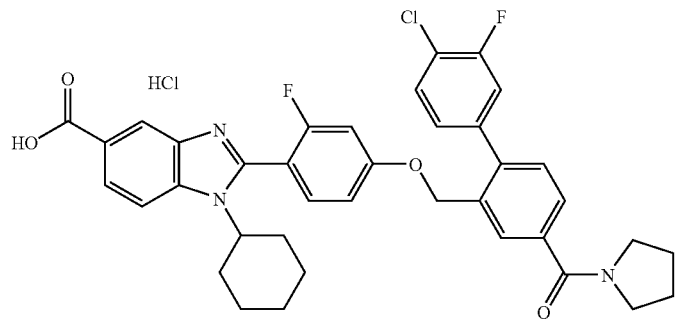
Purity >90%(NMR)
MS 670 (M+1)
1H NMR(δ)ppm
400MHz, DMSO-d6 8.25(1H, s), 8.08(1H, d, J=8.4Hz), 7.92(1H, d, J=9.2Hz), 7.79(1H, s), 7.66–7.49(4H, m), 7.42(1H, d, J=7.6Hz), 7.31–7.28(1H, m), 7.14(1H, d, J=11.3Hz), 6.99(1H, d, J=8.8Hz), 5.13(2H, s), 4.02(1H, m), 3.54–3.33(4H, m), 2.29–2.08(2H, m), 1.93–1.73(8H, m), 1.67–1.52(1H, m), 1.48–1.11(3H, m)

TABLE 246

Example No. 404

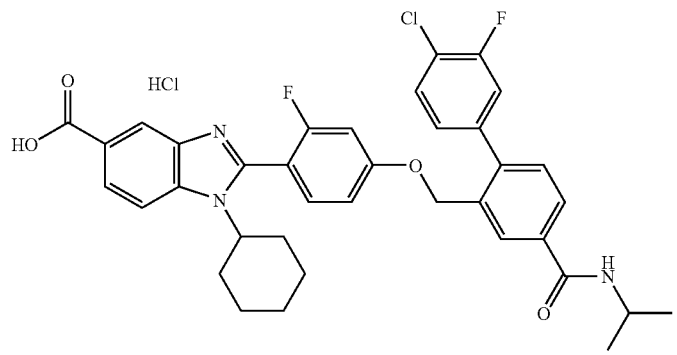

Purity >90%(NMR)
MS 658 (M+1)

1H NMR(δ)ppm

400MHz, DMSO-d6 8.41(1H, d, J=7.6Hz), 8.32(1H, d, J=1.5Hz), 8.20(1H, d, J=8.6Hz), 8.17(1H, d, J=1.7Hz), 8.00(1H, dt, J=8.8Hz, 1.5Hz), 7.71–7.64(2H, m), 7.54(1H, dd, J=10.3Hz, 1.9Hz), 7.32(1H, dd, J=8.2Hz, 1.9Hz), 7.22(1H, dd, J=12.1Hz, 2.3Hz), 7.08(1H, dd, J=8.6Hz), 2.3Hz), 5.17(2H, s), 4.15(1H, m), 2.31–2.14(2H, m), 1.99–1.70(4H, m), 1.70–1.60(1H, m), 1.46–1.20(3H, m), 1.19(6H, d, J=6.6Hz)

Example No. 405

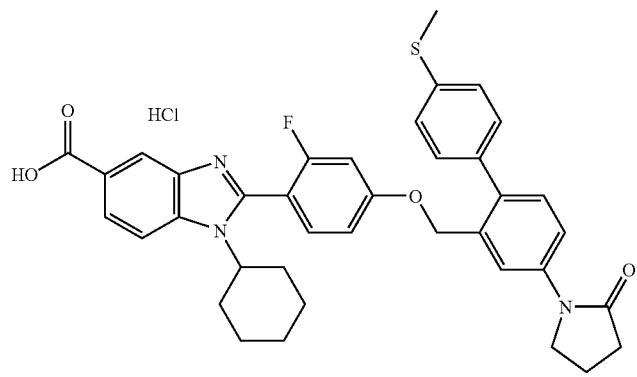

Purity >90%(NMR)
MS 650 (M+1)

1H NMR(δ)ppm

300MHz, DMSO-d6 8.32(1H, s), 8.19(1H, d, J=9.0Hz), 8.03–7.98(2H, m), 7.75(1H, dd, J=2.1Hz, 8.4Hz), 7.67(1H, t, J=8.6Hz), 7.40–7.36(3H, m), 7.32(2H, d, J=8.4Hz), 7.19(1H, dd, J=2.1Hz, 12.3Hz), 7.07(1H, dd, J=2.1Hz, 8.7Hz), 5.11(2H, s), 4.12(1H, m), 3.90(2H, t, J=6.9Hz), 2.54(2H, t, J=8.1Hz), 2.50(3H, s), 2.40–2.05(4H, m), 2.00–1.75(4H, m), 1.70–1.55(1H, m), 1.50–1.20(3H, m)

Example No. 406

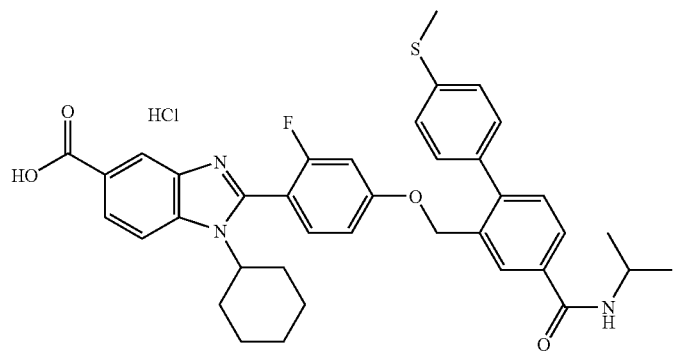

Purity >90%(NMR)
MS 652 (M+1)

1H NMR(δ)ppm

300MHz, DMSO-d6 8.34(1H, d, J=7.7Hz), 8.29(1H, s), 8.15(1H, s), 8.11(1H, d, J=8.8Hz), 7.97(2H, d, J=9.2Hz), 7.63(1H, t, J=8.8Hz), 7.47–7.31(5H, m), 7.18(1H, dd, J=12.4, 2.2Hz), 7.06(1H, dd, J=12.4, 2.2Hz), 5.13(2H, s), 4.13(2H, m), 1.96(2H, m), 1.87(4H, m), 1.62(1H, m), 1.34(3H, m), 1.20(6H, d, J=6.2Hz)

TABLE 247

| Example No. 407 | 1H NMR(δ)ppm |
|---|---|
| 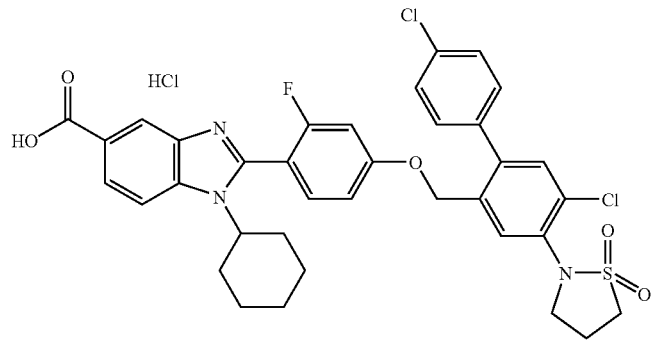 | 400MHz, DMSO-d6 8.32(1H, d, J=1.4Hz), 8.20(1H, d, J=8.8Hz), 8.01(1H, dd, J=1.6Hz, 8.8Hz), 7.90(1H, s), 7.67(1H, t, J=8.4Hz), 7.61(1H, s), 7.55–7.50(4H, m), 7.21(1H, dd, J=2.3Hz, 12.0Hz), 7.06(1H, dd, J=2.2Hz, 8.7Hz), 5.10(2H, s), 4.11(1H, m), 3.78(2H, t, J=6.7Hz), 3.47(2H, t, J=7.4Hz), 2.54–2.48(2H, m), 2.40–2.10(2H, m), 2.00–1.80(4H, m), 1.75–1.55(1H, m), 1.50–1.20(3H, m) |

Purity >90%(NMR)
MS 708 (M+1)

| Example No. 408 | 1H NMR(δ)ppm |
|---|---|
| 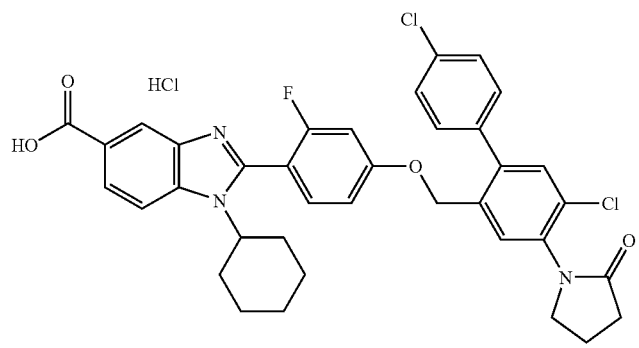 | 400MHz, DMSO-d6 8.32(1H, d, J=1.6Hz), 8.21(1H, d, J=8.8Hz), 8.02(1H, dd, J=1.6Hz, 8.8Hz), 7.76(1H, s), 7.68(1H, t, J=8.5Hz), 7.59(1H, s), 7.54–7.51(4H, m), 7.21(1H, dd, J=2.4Hz, 12.1Hz), 7.07(1H, dd, J=2.4Hz, 8.8Hz), 5.08(2H, s), 4.11(1H, m), 3.77(2H, t, J=6.9Hz), 2.47(2H, t, J=8.0Hz), 2.40–2.10(4H, m), 2.00–1.80(4H, m), 1.70–1.60(1H, m), 1.45–1.20(3H, m) |

Purity >90%(NMR)
MS 672 (M+1)

| Example No. 409 | 1H NMR(δ)ppm |
|---|---|
| 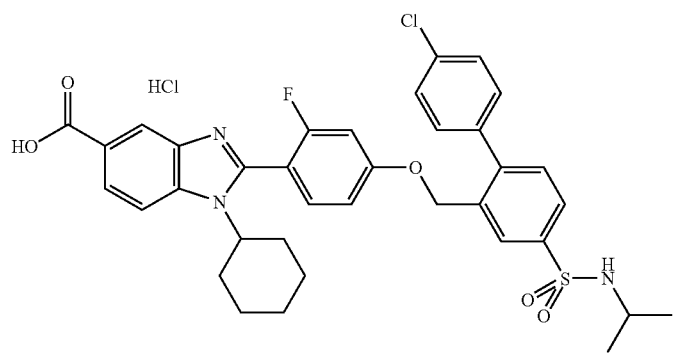 | 300MHz, DMSO-d6 8.28(1H, d, J=1.5Hz), 8.20–8.85(4H, m), 7.75(1H, d, J=6.9Hz), 7.70–7.45(6H, m), 7.13(1H, dd, J=12.0Hz, 2.1Hz), 7.00(1H, dd, J=8.7Hz, 2.1Hz), 5.22(2H s), 4.05(1H, m), 3.40–3.20(1H, m), 2.30–2.10(2H, m), 2.00–1.55(5H, m), 1.45–1.10(3H, m), 1.00(6H, d, J=6.6Hz) |

Purity >90%(NMR)
MS 676 (M+1)

TABLE 248

Example No. 410

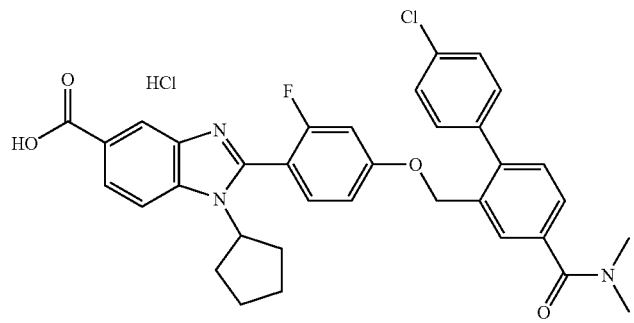

Purity >90%(NMR)

MS 612 (M+1)

1H NMR(δ)ppm

300MHz, DMSO-d6 8.31(1H, s), 8.00(1H, d, J=8.7Hz), 7.88(1H, d, J=8.7Hz), 7.70(1H, s), 7.65(1H, t, J=8.4Hz), 7.53(2H, d, J=8.4Hz), 7.49(2H, d, J=8.7Hz), 7.45–7.41(2H, m), 7.16(1H, d, J=12.0Hz), 7.04(1H, d, J=8.7Hz), 5.14(2H, s), 4.68(1H, quint, J=8.4Hz), 3.02, 2.98(6H, s), 2.30–1.85(6H, m), 1.80–1.50(2H, m)

Example No. 411

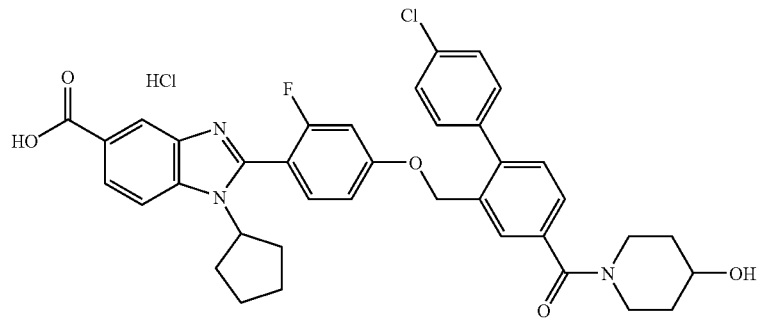

Purity >90%(NMR)

MS 668 (M+1)

1H NMR(δ)ppm

300MHz, DMSO-d6 8.30(1H, s), 7.99(1H, d, J=9.0Hz), 7.87(1H, d, J=8.7Hz), 7.67(1H, s), 7.64(1H, t, J=8.7Hz), 7.53(2H, d, J=8.7Hz), 7.49(2H, d, J=7.5Hz), 7.45–7.41(2H, m), 7.15(1H, d, J=12.3Hz), 7.02(1H, d, J=8.4Hz), 5.15(2H, s), 4.67(1H, quint, J=8.7Hz), 4.02(1H, m), 3.76(1H, m), 3.55(1H, m), 3.22(2H, m), 2.40–1.20(12H, m)

Example No. 412

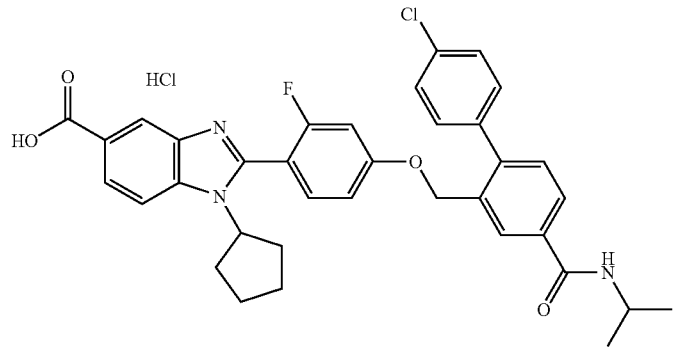

Purity >90%(NMR)

MS 626 (M+1)

1H NMR(δ)ppm

300MHz, DMSO-d6 8.38(1H, d, J=7.5Hz), 8.33(1H, s), 8.16(1H, s), 8.02(1H, d, J=8.7Hz), 7.98(1H, d, J=9.0Hz), 7.91(1H, d, J=8.4Hz), 7.67(1H, t, J=8.4Hz), 7.53(2H, d, J=8.7Hz), 7.48(2H, d, J=8.7Hz), 7.46(1H, d, J=8.1Hz), 7.18(1H, d, J=11.7Hz), 7.06(1H, d, J=8.7Hz), 5.13(2H, s), 4.70(1H, quint, J=8.4Hz), 4.13(1H, sept, J=6.6Hz), 2.30–1.85(6H, m), 1.80–1.50(2H, m), 1.16(6H, d, J=6.3Hz)

TABLE 249

| Example No. 413 | 1H NMR(δ)ppm |
|---|---|
| 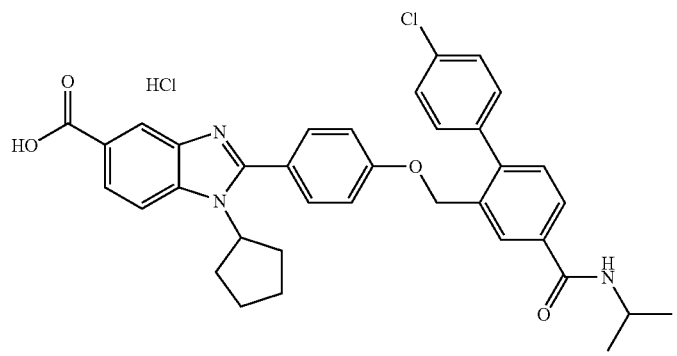<br>Purity >90%(NMR)<br>MS 608 (M+1) | 300Mz, DMSO-d6 8.39(1H, d, J=7.5Hz), 8.31(1H, d, J=1.5Hz), 8.16(1H, d, J=1.9Hz), 8.06(1H, dd, J=8.8, 1.5Hz), 7.99–7.95(2H, m), 7.76 and 7.24(4H, ABq, J=8.9Hz), 7.53 and 7.50(4H, A'B'q, J=9.1Hz), 7.46(1H, d, J=8.3Hz), 5.14(2H, s), 4.94(1H, quint, J=9.0Hz), 4.19–4.08(1H, m), 2.32–2.11(4H, brm), 2.10–1.95(2H, brm), 1.78–1.62(2H, brm), 1.26(3H, s), 1.18(3H, s) |
| Example No. 414 | 1H NMR(δ)ppm |
| 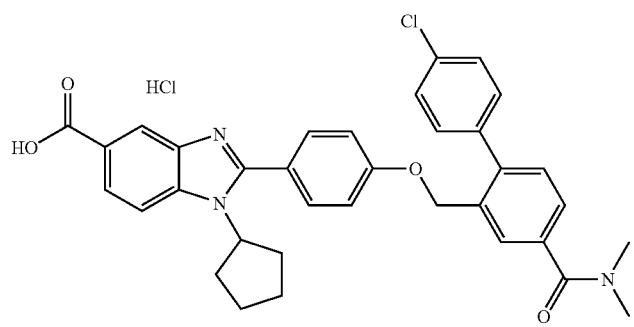<br>Purity >90%(NMR)<br>MS 594 (M+1) | 300Mz, DMSO-d6 8.31(1H, d, J=1.5Hz), 8.06(1H, dd, J=8.7, 1.5Hz), 7.97(1H, d, J=8.7Hz), 7.75 and 7.22(4H, ABq, J=8.9Hz), 7.70(1H, d, J=1.9Hz), 7.53(1H, dd, J=7.9, 1.9Hz), 7.52(4H, s), 7.43(1H, d, J=7.9Hz), 5.15(2H, s), 4.93(1H, quint, J=8.9Hz), 3.01(3H, s), 2.97(3H, s), 2.32–2.11(4H, brm), 2.09–1.94(2H, brm), 1.77–1.62(2H, brm) |
| Example No. 415 | 1H NMR(δ)ppm |
| 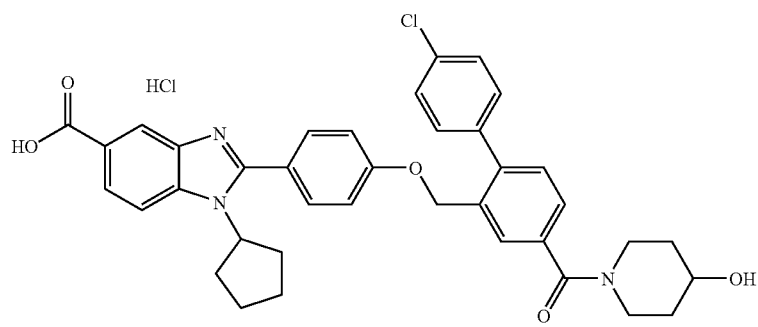<br>Purity >90%(NMR)<br>MS 650 (M+1) | 300Mz, DMSO-d6 8.31(1H, d, J=1.5Hz), 8.06(1H, dd, J=8.7, 1.5Hz), 7.98(1H, d, J=8.7Hz), 7.75 and 7.22(4H, ABq, J=8.9Hz), 7.67(1H, d, J=1.5Hz), 7.52(4H, s), 7.49(1H, dd, J=7.9, 1.5Hz), 7.43(1H, d, J=8.9Hz), 5.16(2H, s), 4.93(1H, quint, J=8.9Hz), 3.76(1H, brs), 3.55(2H, brs), 3.22(2H, brs), 2.31–2.11(4H, brm), 2.16–1.95(2H, brm), 1.88–1.62(4H, brm), 1.48–1.28(2H, brm) |

TABLE 250
| Example No. 416 | 1H NMR(δ)ppm |
|---|---|
| 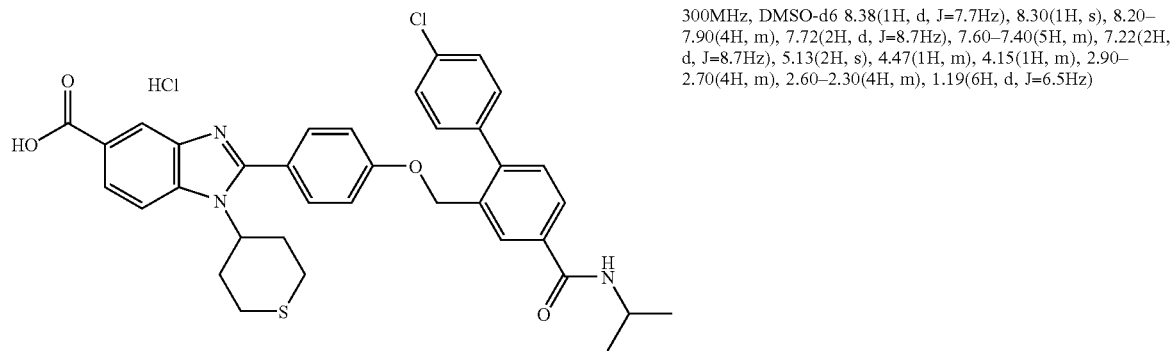 | 300MHz, DMSO-d6 8.38(1H, d, J=7.7Hz), 8.30(1H, s), 8.20–7.90(4H, m), 7.72(2H, d, J=8.7Hz), 7.60–7.40(5H, m), 7.22(2H, d, J=8.7Hz), 5.13(2H, s), 4.47(1H, m), 4.15(1H, m), 2.90–2.70(4H, m), 2.60–2.30(4H, m), 1.19(6H, d, J=6.5Hz) |
Purity >90%(NMR)
MS 640 (M+1)
| Example No. 417 | 1H NMR(δ)ppm |
|---|---|
| 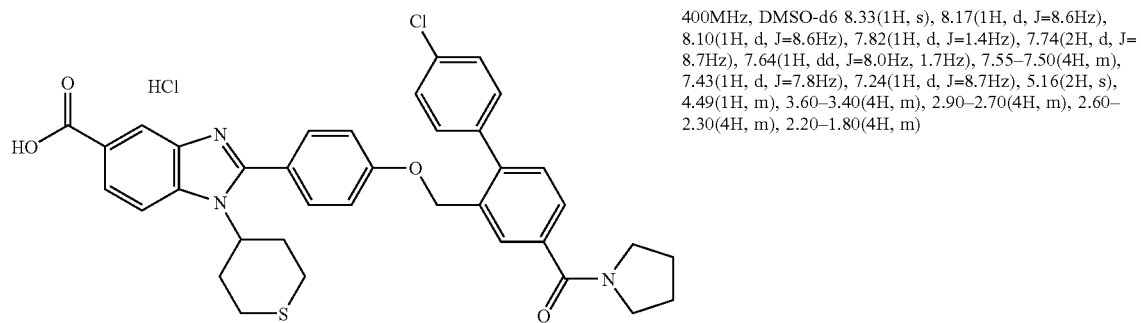 | 400MHz, DMSO-d6 8.33(1H, s), 8.17(1H, d, J=8.6Hz), 8.10(1H, d, J=8.6Hz), 7.82(1H, d, J=1.4Hz), 7.74(2H, d, J=8.7Hz), 7.64(1H, dd, J=8.0Hz, 1.7Hz), 7.55–7.50(4H, m), 7.43(1H, d, J=7.8Hz), 7.24(1H, d, J=8.7Hz), 5.16(2H, s), 4.49(1H, m), 3.60–3.40(4H, m), 2.90–2.70(4H, m), 2.60–2.30(4H, m), 2.20–1.80(4H, m) |
Purity >90%(NMR)
MS 652 (M+1)
| Example No. 418 | 1H NMR(δ)ppm |
|---|---|
| 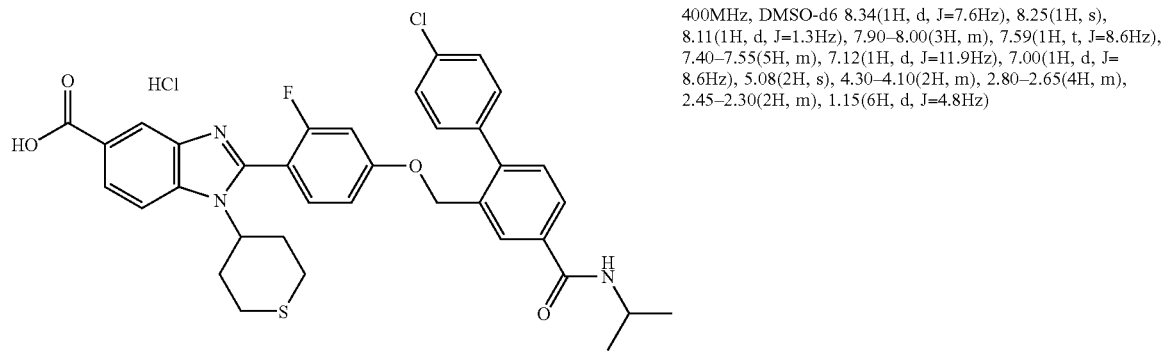 | 400MHz, DMSO-d6 8.34(1H, d, J=7.6Hz), 8.25(1H, s), 8.11(1H, d, J=1.3Hz), 7.90–8.00(3H, m), 7.59(1H, t, J=8.6Hz), 7.40–7.55(5H, m), 7.12(1H, d, J=11.9Hz), 7.00(1H, d, J=8.6Hz), 5.08(2H, s), 4.30–4.10(2H, m), 2.80–2.65(4H, m), 2.45–2.30(2H, m), 1.15(6H, d, J=4.8Hz) |
Purity >90%(NMR)
MS 658 (M+1)

TABLE 251

Example No. 419

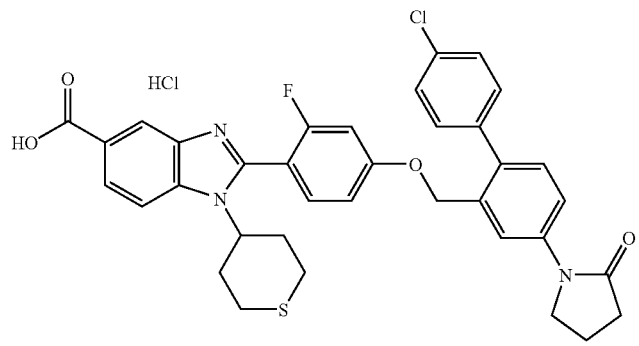

Purity >90%(NMR)
MS 656 (M+1)

1H NMR(δ)ppm

400MHz, DMSO-d6 8.30(1H, s), 8.05–7.95(3H, m), 7.80–7.75(1H, m), 7.63(1H, t, J=8.6Hz), 7.55–7.35(5H, m), 7.15(1H, dd, J=12.1Hz, 2.1Hz), 7.03(1H, dd, J=8.7Hz, 2.3Hz), 5.10(2H, s), 4.23(1H, m), 3.90(2H, t, J=7.0Hz), 2.95–2.70(4H, m), 2.60–2.35(4H, m), 2.30–2.00(4H, m)

Example No. 420

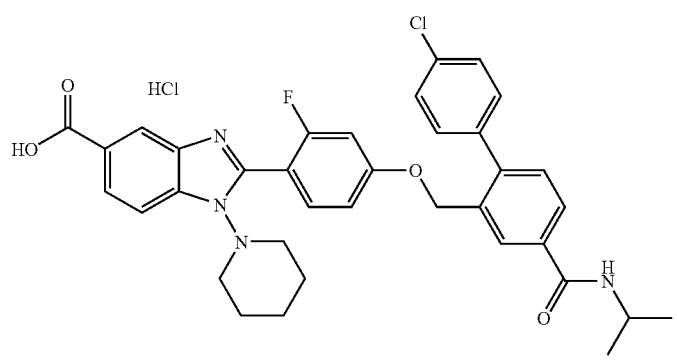

Purity >90%(NMR)
MS 641 (M+1)

1H NMR(δ)ppm

300Mz, DMSO-d6 8.37(1H, d, J=7.5Hz), 8.28(1H, d, J=1.5Hz), 8.17(1H, d, J=1.5Hz), 8.13(1H, d, J=8.7Hz), 7.97(1H, dd, J=8.1, 1.5Hz), 7.94(1H, dd, J=8.7, 1.5Hz), 7.61(1H, t, J=8.7Hz), 7.51 and 7.49(4H, ABq, J=8.9Hz), 7.46(1H, d, J=8.1Hz), 7.08(1H, dd, J=12.4, 2.3Hz), 6.97(1H, dd, J=8.7, 2.3Hz), 5.10(2H, s), 4.20–4.08(1H, m), 3.62–3.56(2H, brm), 3.13–3.10(2H, brm), 1.79–1.60(3H, brm), 1.54–1.34(3H, brm), 1.21(3H, s), 1.18(3H, s)

Example No. 421

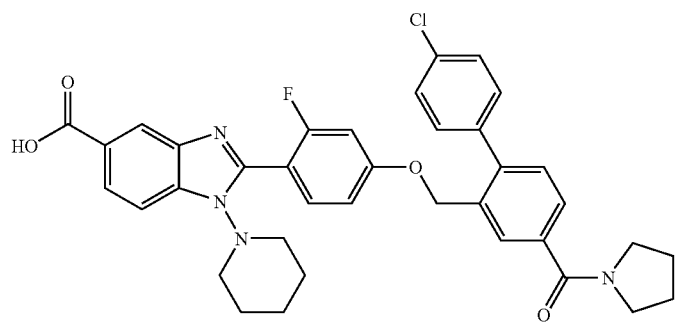

Purity >90%(NMR)
MS 653 (M+1)

1H NMR(δ)ppm

300Mz, DMSO-d6 8.24(1H, d, J=1.5Hz), 8.02(1H, d, J=8.7Hz), 7.88(1H, dd, J=8.7, 1.5Hz), 7.82(1H, d, J=1.9Hz), 7.63(1H, dd, J=7.9, 1.9Hz), 7.54(1H, t, J=8.7Hz), 7.50(4H, s), 7.42(1H, d, J=7.9Hz), 7.01(1H, dd, J=12.0, 2.3Hz), 6.91(1H, dd, J=8.7, 2.3Hz), 5.11(2H, s), 3.63–3.41(6H, m), 3.07–3.04(2H, brm), 1.95–1.79(4H, brm), 1.77–1.57(3H, brm), 1.50–1.32(3H, brm)

TABLE 252

Example No. 422

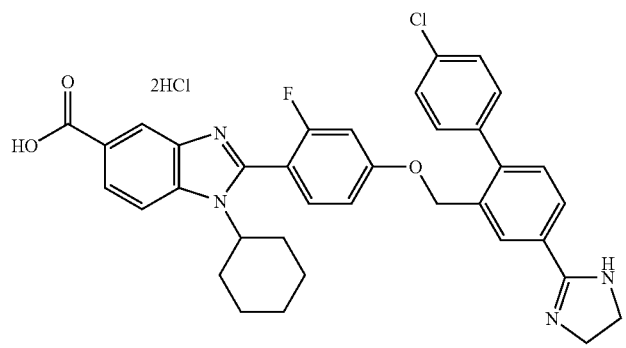

Purity >90%(NMR)
MS 623 (M+1)

1H NMR(δ)ppm

300MHz, DMSO-d6 10.99(2H, s), 8.44(1H, s), 8.30(1H, s), 8.18(1H, d, J=8.7Hz), 8.14(1H, d, J=8.7Hz), 7.98(1H, d, J=9.0Hz), 7.70–7.66(2H, m), 7.57(2H, d, J=8.7Hz), 7.54(2H, d, J=8.7Hz), 7.21(1H, d, J=12.0Hz), 7.09(1H, d, J=8.4Hz), 5.19(2H, s), 4.05(4H, s), 2.40–2.18(2H, m), 2.15–1.80(4H, m), 1.75–1.55(1H, m), 1.50–1.20(3H, m)

Example No. 423

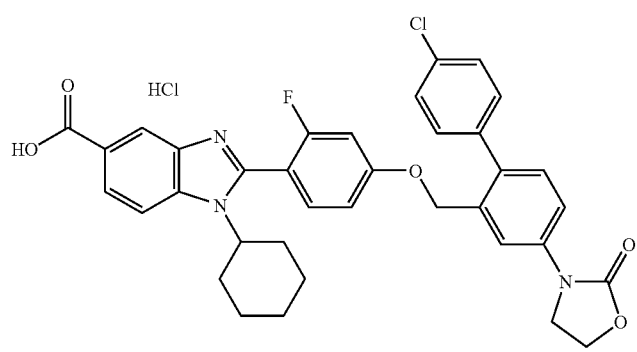

Purity >90%(NMR)
MS 640 (M+1)

1H NMR(δ)ppm

300MHz, DMSO-d6 8.27(1H, s), 8.05(1H, d, J=8.7Hz), 7.93(1H, d, J=8.7Hz), 7.90(1H, s), 7.70(1H, d, J=8.4Hz), 7.59(1H, t, J=8.4Hz), 7.50(2H, d, J=9.0Hz), 7.45(2H, d, J=8.7Hz), 7.41(1H, d, J=8.4Hz), 7.12(1H, d, J=12.0Hz), 7.00(1H, d, J=8.7Hz), 5.10(2H, s), 4.49(2H, t, J=7.8Hz), 4.14(2H, t, J=8.0Hz), 4.04(1H, m), 2.40–2.10(2H, m), 2.00–1.50(5H, m), 1.45–1.20(3H, m)

Example No. 424

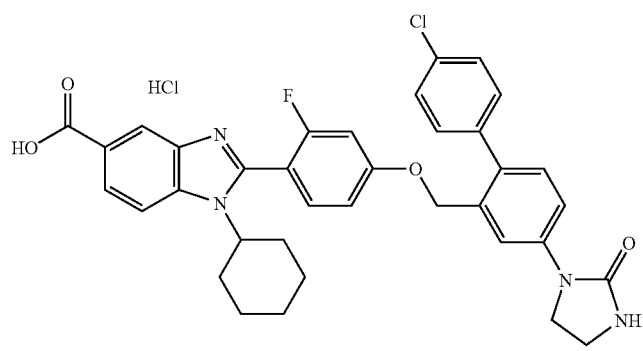

Purity >90%(NMR)
MS 639 (M+1)

1H NMR(δ)ppm

300MHz, DMSO-d6 8.30(1H, s), 8.14(1H, d, J=8.4Hz), 7.98(1H, d, J=9.3Hz), 7.89(1H, s), 7.68(1H, d, J=8.4Hz), 7.62(1H, d, J=9.0Hz), 7.48(2H, d, J=8.4Hz), 7.43(2H, d, J=8.4Hz), 7.33(1H, d, J=8.4Hz), 7.16(1H, d, J=12.0Hz), 7.04(1H, d, J=9.0Hz), 5.07(2H, s), 4.10(1H, m), 3.92(2H, t, J=8.0Hz), 3.45(2H, t, J=8.0Hz), 2.40–2.10(2H, m), 2.00–1.50(5H, m), 1.45–1.20(3H, m)

TABLE 253
Example No. 425
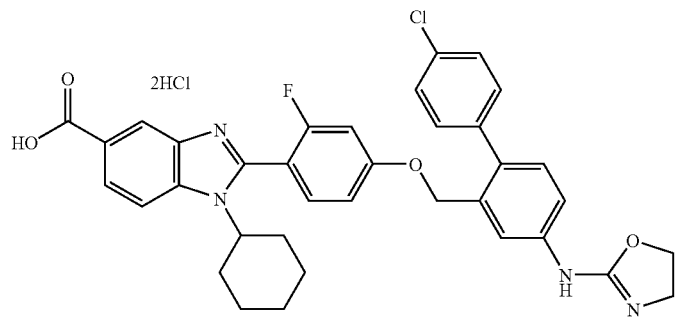
Purity >90%(NMR)
MS 639 (M+1)
1H NMR(δ)ppm
300MHz, DMSO-d6 9.05(1H, s), 8.30(1H, s), 8.16(1H, d, J=8.8Hz), 7.99(1H, d, J=8.6Hz), 7.72(1H, s), 7.64(1H, t, J=8.6Hz), 7.52(1H, d, J=8.4Hz), 7.47(2H, d, J=8.7Hz), 7.42(2H, d, J=8.6Hz), 7.25(1H, d, J=8.4Hz), 7.15(1H, d, J=12.2Hz), 7.04(1H, d, J=8.6Hz), 6.60(1H, brs), 5.05(2H, s), 4.10(1H, m), 3.68(2H, t, J=6.1Hz), 3.45(2H, t, J=6.1Hz), 2.40–2.10(2H, m), 2.00–1.55(5H, m), 1.50–1.20(3H, m)
Example No. 426
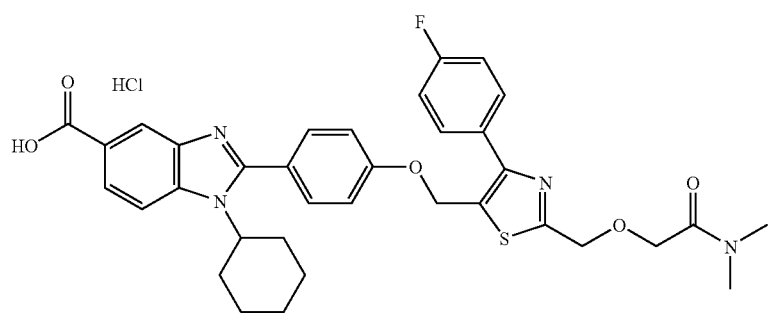
Purity >90%(NMR)
MS 643 (M+1)
1H NMR(δ)ppm
300MHz, DMSO-d6 8.32(1H, s), 8.24(1H, d, J=8.7Hz), 8.03(1H, d, J=8.7Hz), 7.78–7.73(4H, m), 7.38–7.32(4H, m), 5.52(2H, s), 4.88(2H, s), 4.40(2H, s), 4.37(1H, m), 2.92, 2.84(6H, s), 2.40–2.18(2H, m), 2.15–1.95(2H, m), 1.90–1.80(2H, m), 1.75–1.55(1H, m), 1.50–1.20(3H, m)
Example No. 427
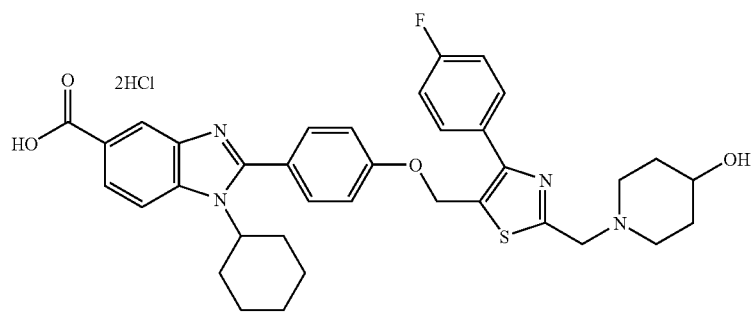
Purity >90%(NMR)
MS 641 (M+1)
1H NMR(δ)ppm
300MHz, DMSO-d6 11.26(1H, brs), 8.35(1H, s), 8.27(1H, d, J=9.0Hz), 8.05(1H, d, J=8.4Hz), 7.83–7.78(4H, m), 7.42–7.35(4H, m), 5.57(2H, s), 4.77, 4.73(2H, s), 4.37(1H, m), 3.95(1H, s), 3.70–3.00(4H, m), 2.40–1.00(14H, m)

TABLE 254
Example No. 428
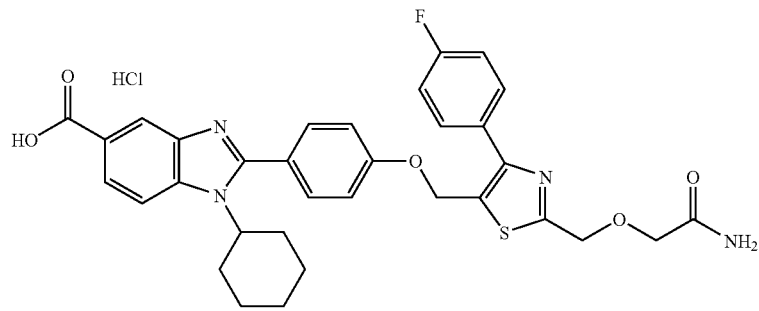
Purity >90%(NMR)
MS 615 (M+1)
1H NMR(δ)ppm
300MHz, DMSO-d6 8.31(1H, s), 8.26(1H, d, J=9.0Hz), 8.04(1H, d, J=8.7Hz), 7.79–7.73(4H, m), 7.38–7.31(6H, m), 5.53(2H, s), 4.90(2H, s), 4.37(1H, m), 4.05(2H, s), 2.40–2.18(2H, m), 2.15–1.95(2H, m), 1.90–1.80(2H, m), 1.75–1.55(1H, m), 1.50–1.20(3H, m)
Example No. 429
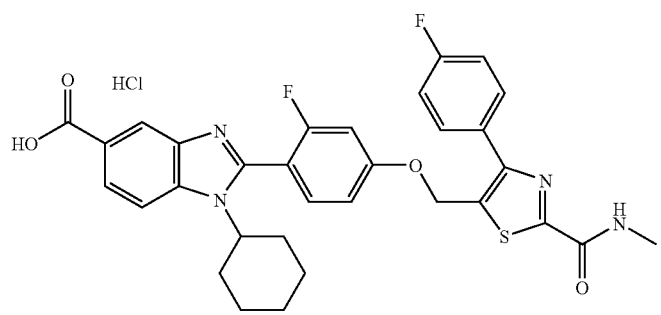
Purity >90%(NMR)
MS 603 (M+1)
1H NMR(δ)ppm
300MHz, DMSO-d6 8.88(1H, q, J=4.5Hz), 8.33(1H, d, J=1.5Hz), 8.18(1H, d, J=8.7Hz), 8.01(1H, dd, J=1.5Hz, 8.7Hz), 7.89–7.83(2H, m), 7.50–7.34(3H, m), 7.20(1H, dd, J=2.1Hz, 8.4Hz), 5.61(2H, s), 4.13(1H, m), 2.84(3H, d, J=4.8Hz), 2.40–2.10(2H, m), 2.00–1.75(4H, m), 1.70–1.55(1H, m), 1.50–1.20(3H, m)
Example No. 430
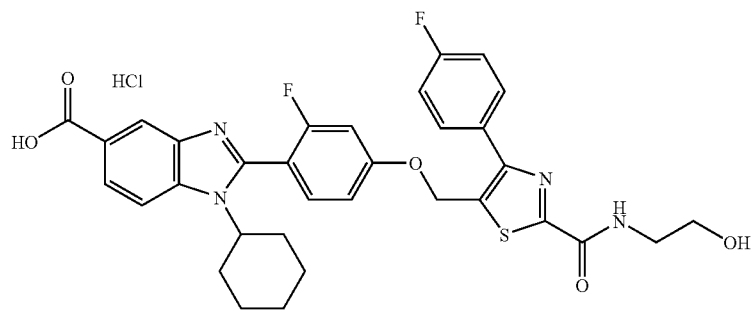
Purity >90%(NMR)
MS 633 (M+1)
1H NMR(δ)ppm
400MHz, DMSO-d6 8.79(1H, t, J=5.9Hz), 8.31(1H, s), 8.15(1H, d, J=8.7Hz), 7.99(1H, d, J=8.8Hz), 7.87(1H, d, J=8.1Hz), 7.85(1H, d, J=8.7Hz), 7.70(1H, t, J=8.4Hz), 7.42–7.33(3H, m), 7.18(1H, d, J=8.8Hz), 5.60(2H, s), 4.11(1H, m), 3.62–3.54(4H, m), 2.40–2.10(2H, m), 2.00–1.75(4H, m), 1.70–1.55(1H, m), 1.50–1.20(3H, m)

TABLE 255

Example No. 431

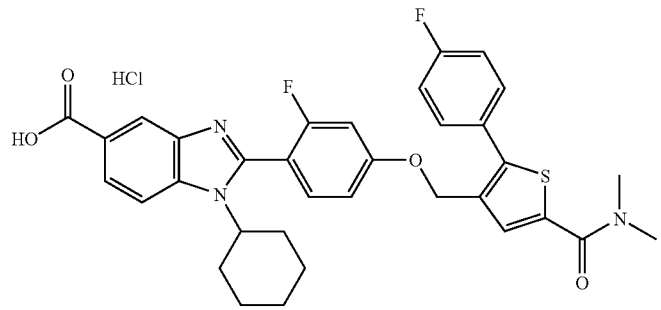

Purity >90%(NMR)
MS 616 (M+1)

1H NMR(δ)ppm

300MHz, DMSO-d6 8.31(1H, s), 8.16(1H, d, J=8.8Hz), 7.99(1H, d, J=8.7Hz), 7.74–7.60(4H, m), 7.37(2H, t, J=8.8Hz), 7.28(1H, dd, J=2.2Hz, 12.2Hz), 7.14(1H, dd, J=2.2Hz, 8.6Hz), 5.17(2H, s), 4.10(1H, m), 3.15(6H, brs), 2.40–2.10(2H, m), 2.00–1.75(4H, m), 1.70–1.55(1H, m), 1.50–1.15(3H, m)

Example No. 432

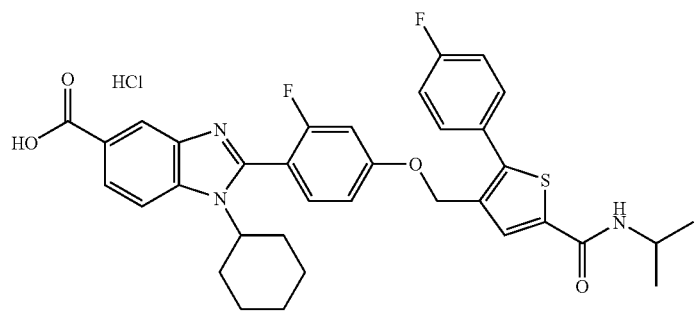

Purity >90%(NMR)
MS 630 (M+1)

1H NMR(δ)ppm

300MHz, DMSO-d6 8.45(1H, d, J=7.7Hz), 8.32(1H, s), 8 19(1H, d, J=8.8Hz), 8.02–7.99(2H, m), 7.70(1H, t, J=8.6Hz), 7.60(2H, dd, J=5.4Hz, 8.7Hz), 7.37(2H, t, J=8.8Hz), 7.27(1H, dd, J=2.3Hz, 12.2Hz), 7.14(1H, dd, J=2.2Hz, 8.7Hz), 5.16(2H, s), 4.20–4.00(2H, m), 2.40–2.10(2H, m), 2.00–1.75(4H, m), 1.70–1.55(1H, m), 1.50–1.20(3H, m), 1.18(6H, d, J=6.6Hz)

Example No. 433

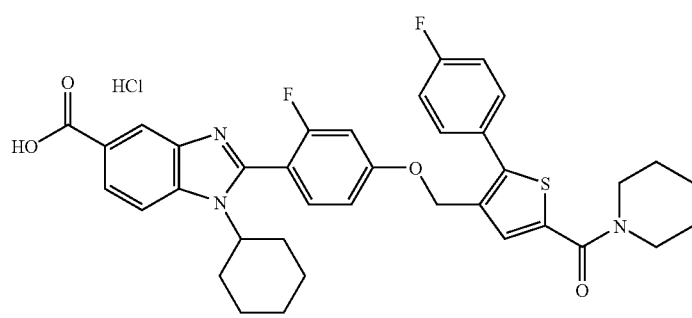

Purity >90%(NMR)
MS 672 (M+1)

1H NMR(δ)ppm

300MHz, DMSO-d6 8.31(1H, d, J=1.4Hz), 8.15(1H, d, J=8.8Hz), 7.98(1H, dd, J=1.4Hz, 8.7Hz), 7.68–7.60(4H, m), 7.36(2H, t, J=8.8Hz), 7.28(1H, dd, J=2.2Hz, 12.2Hz), 7.15(1H, dd, J=2.2Hz, 8.6Hz), 5.17(2H, s), 4.10(1H, m), 4.05–3.90(2H, m), 3.85–3.70(1H, m), 3.55–3.25(2H, m), 2.40–2.10(2H, m), 2.00–1.75(6H, m), 1.70–1.55(1H, m), 1.50–1.20(5H, m)

TABLE 256

Example No. 434

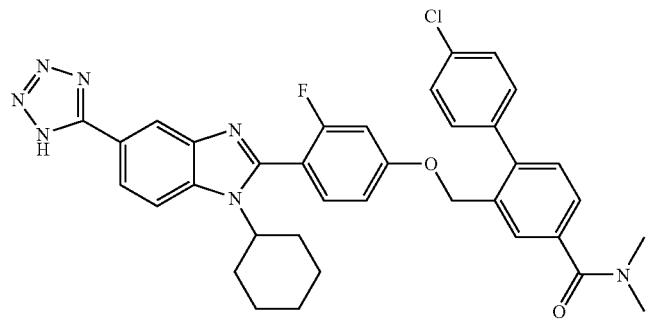

Purity >90%(NMR)
MS 650 (M+1)

1H NMR(δ)ppm

300Mz, DMSO-d6 8.45(1H, d, J=1.5Hz), 8.26(1H, d, J=8.8Hz), 8.10(1H, dd, J=8.8, 1.5Hz), 7.72(1H, d, J=1.5Hz), 7.64(1H, t, J=8.6Hz), 7.56–7.48(5H, m), 7.44(1H, d, J=J=7.7Hz), 7.18(1H, dd, J=12.3, 2.4Hz), 7.04(1H, dd, J=8.6, 2.4Hz), 5.15(2H, s), 4.08(1H, brt, J=11.7Hz), 3.02(3H, s), 2.99(3H, s), 2.34–2.17(2H, brm), 1.97–1.81(4H, brm), 1.70–1.60(1H, brm), 1.49–1.21(3H, brm)

Example No. 435

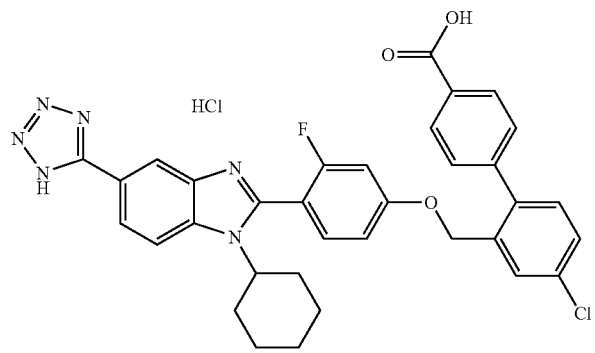

Purity >90%(NMR)
MS 623 (M+1)

1H NMR(δ)ppm

300Mz, DMSO-d6 8.42(1H, d, J=1.5Hz), 8.24(1H, d, J=8.8Hz), 8.08(1H, dd, J=8.8, 1.5Hz), 8.00(2H, d, J=8.8Hz), 7.79(1H, d, J=7.8Hz), 7.62(1H, t, J=8.4Hz), 7.61–7.55(3H, m), 7.44(1H, d, J=8.1Hz), 7.16(1H, dd, J=12.1, 2.6Hz), 7.02(1H, dd, J=8.4, 2.6Hz), 5.12(2H, s), 4.07(1H, brt, J=12.5Hz), 2.33(2H, brm), 1.96–1.79(4H, brm), 1.71–1.61(1H, brm), 1.49–1.21(3H, brm)

Example No. 436

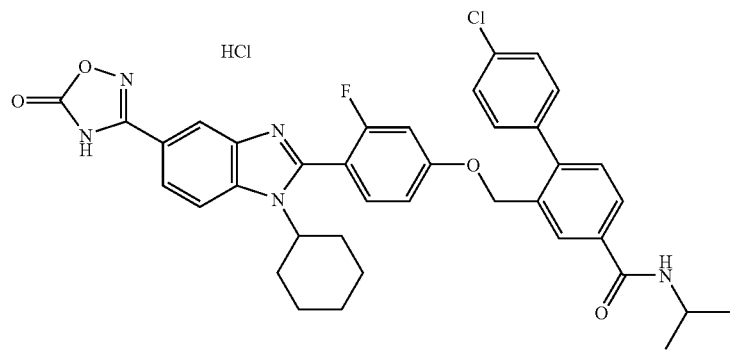

Purity >90%(NMR)
MS 680 (M+1)

1H NMR(δ)ppm

300MHz, DMSO-d6 8.41(1H, d, J=7.7Hz), 8.30–8.26(2H, m), 8.18(1H, d, J=1.4Hz), 7.99(1H, dd, J=1.7Hz, 8.0Hz), 7.89(1H, d, J=10.1Hz), 7.67(1H, t, J=8.8Hz), 7.55–7.45(5H, m), 7.20(1H, d, J=12.2Hz), 7.07(1H, dd, J=2.1Hz, 8.7Hz), 5.14(2H, s), 4.18–4.11(2H, m), 2.40–2.10(2H, m), 2.00–1.75(4H, m), 1.70–1.55(1H, m), 1.50–1.20(3H, m), 1.20(6H, d, J=6.6Hz)

TABLE 257
Example No. 437
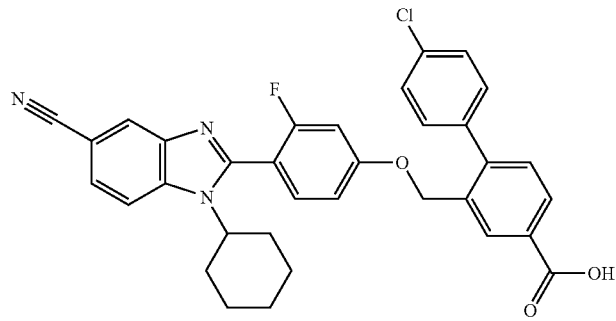
Purity >90%(NMR)
MS 580 (M+1)
1H NMR(δ)ppm
Example No. 438
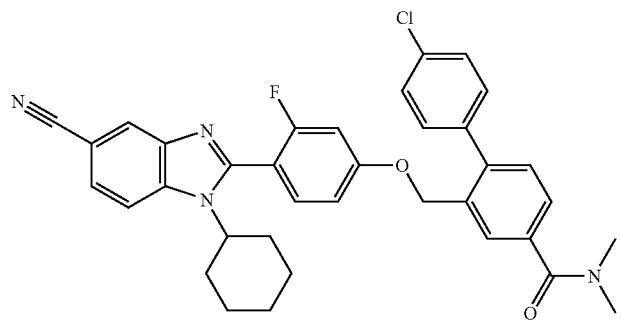
Purity >90%(NMR)
MS 607 (M+1)
1H NMR(δ)ppm
Example No. 439
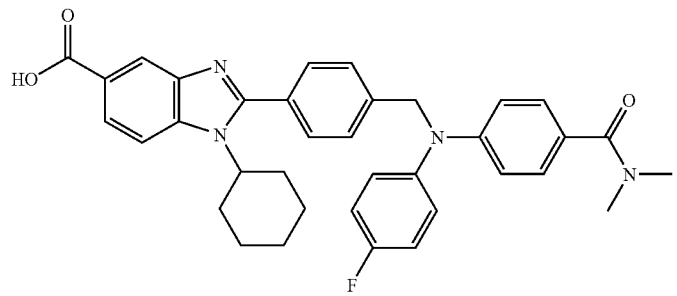
Purity >90%(NMR)
MS 591 (M+1)
1H NMR(δ)ppm
300MHz, CDCl3 8.60(1H, d, J=1.5Hz), 8.05(1H, dd, J=1.6Hz, 8.7Hz), 7.70(1H, d, J=8.7Hz), 7.62(2H, d, J=8.2Hz), 7.49(2H, d, J=8.2Hz), 7.31(2H, d, J=8.8Hz), 7.27–7.23(2H, m), 7.06(2H, t, J=8.6Hz), 6.80(2H, d, J=8.8Hz), 5.05(2H, s), 4.38(1H, m), 3.06(6H, s), 2.45–2.20(2H, m), 2.10–1.70(5H, m), 1.50–1.20(3H, m)

TABLE 258
| Example No. 440 | 1H NMR(δ)ppm |
|---|---|
| 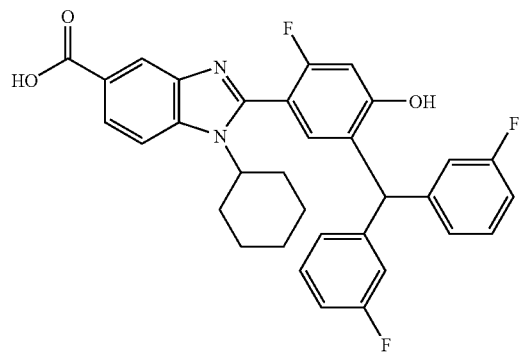  Purity >90%(NMR)  MS 557 (M+1) | 300MHz, DMSO-d6 8.20(1H, s), 7.86(2H, m), 7.39(1H, d, J=7.9Hz), 7.34(1H, d, J=7.9Hz), 7.07(2H, dt, J=2.3Hz, 8.6Hz), 6.98–6.88(5H, m), 6.83(1H, d, J=8.3Hz), 5.91(1H, s), 3.96(1H, m), 2.30–1.95(2H, m), 1.90–1.50(4H, m), 1.40–1.10(3H, m) |
| Example No. 441 | 1H NMR(δ)ppm |
| 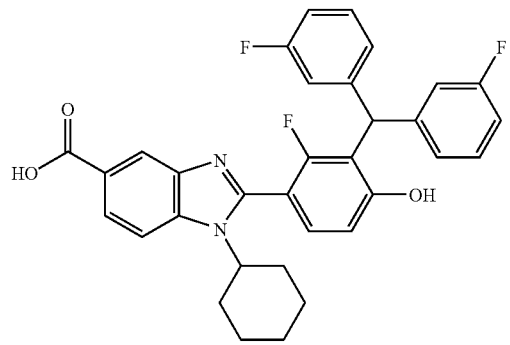  Purity >90%(NMR)  MS 557 (M+1) | 300MHz, DMSO-d6 8.24(1H, d, J=1.4Hz), 8.01(1H, d, J=8.8Hz), 7.91(1H, dd, J=1.4Hz, 8.7Hz), 7.47(1H, t, J=8.4Hz), 7.43–7.35(2H, m), 7.15–7.01(5H, m), 6.92(2H, d, J=10.4Hz), 6.11(1H, s), 3.90(1H, m), 2.30–1.95(2H, m), 1.90–1.50(4H, m), 1.40–1.10(3H, m) |
| Example No. 442 | 1H NMR(δ)ppm |
| 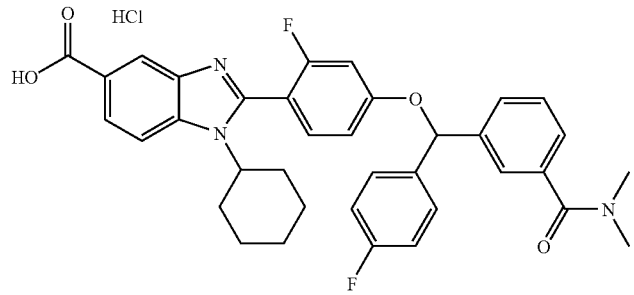  Purity >90%(NMR)  MS 610 (M+1) | 300Mz, DMSO-d6 8.26(1H, d, J=1.5Hz), 8.11(1H, d, J=8.9Hz), 7.96(1H, dd, J=8.9, 1.5Hz), 7.65–7.57(5H, m), 7.47(1H, t, J=7.7Hz), 7.35(1H, d, J=7.6Hz), 7.30–7.22(3H, m), 7.16(1H, dd, J=8.7, 2.3Hz), 6.88(1H, s), 4.04(1H, brt, J=11.3Hz), 2.98(3H, s) 2.84(3H, s), 2.30–2.10(2H, brm), 1.94–1.75(4H, brm), 1.68–1.57(1H, brm), 1.45–1.14(3H, brm) |

TABLE 259
| Example No. 443 | 1H NMR(δ)ppm |
|---|---|
| 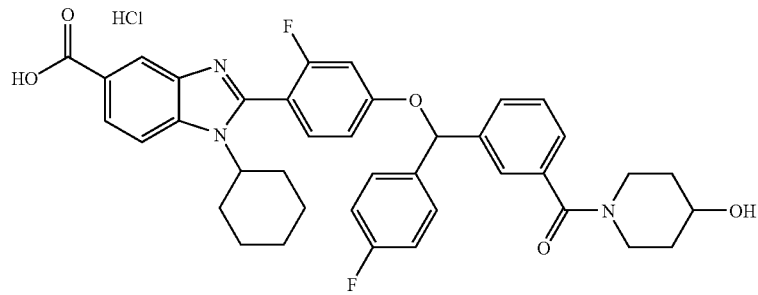 | 300Mz, DMSO-d6 8.23(1H, s), 7.98 and 7.89(2H, ABq, J=8.8Hz), 7.62–7.06(11H, m), 6.86(1H, s), 4.12–3.77(2H, brm), 3.72(1H, brs), 3.69(1H, brs), 3.18(1H, brs), 3.05(1H, brs), 2.31–2.08(2H, brm), 1.90–1.54(7H, brm), 1.48–1.13(5H, brm) |
Purity >90%(NMR)
MS 666 (M+1)
| Example No. 444 | 1H NMR(δ)ppm |
|---|---|
| 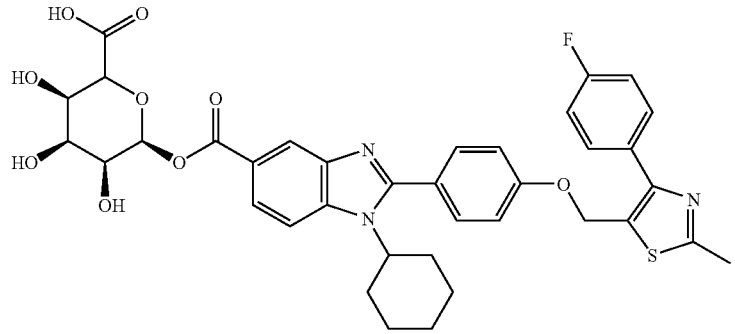 | 300MHz, DMSO-d6 8.36(1H, s), 8.00(1H, d, J= 8.7Hz), 7.90(1H, d, J=9.3Hz), 7.80–7.70(2H, m), 7.63(2H, d, J=8.4Hz), 7.32(2H, t, J=8.7Hz), 7.22(2H, d, J=8.4Hz), 5.62(1H, d, J=7.5Hz), 5.57(1H, brd, J=4.8Hz), 5.41(2H, s), 5.31(1H, m), 4.29(1H, m), 3.84(1H, d, J=9.0Hz), 3.50–3.20(3H, m), 2.71(3H, s), 2.40–2.20(2H, m), 1.75–1.60(1H, m), 1.50–1.20(3H, m) |
Purity >90%(NMR)
MS 718 (M+1)
| Example No. 445 | 1H NMR(δ)ppm |
|---|---|
| 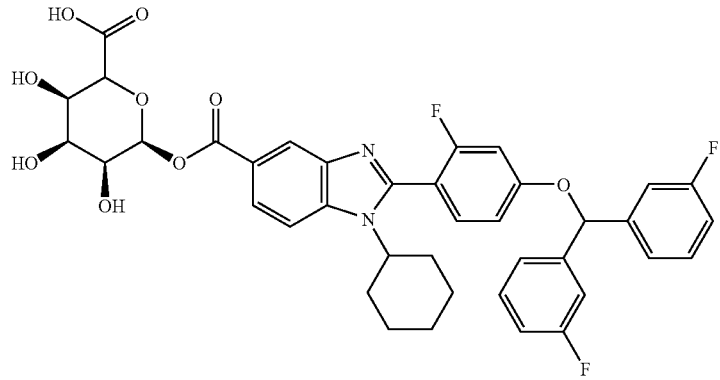 | 300MHz, DMSO-d6 8.36(1H, s), 8.00(1H, d, J= 8.7Hz), 7.92(1H, d, J=9.3Hz), 7.57(1H, t, J=8.4Hz), 7.50–7.35(6H, m), 7.25–7.05(4H, m), 6.82(1H, s), 5.62(1H, d, J=7.2Hz), 5.56(1H, m), 5.28(1H, brs), 3.95(1H, m), 3.82(1H, d, J=8.7Hz), 3.50–3.20(3H, m), 2.30–2.05(2H, m), 1.90–1.55(5H, m), 1.40–1.10(3H, m) |
Purity >90%(NMR)
MS 733 (M+1)

TABLE 260

Example No. 446

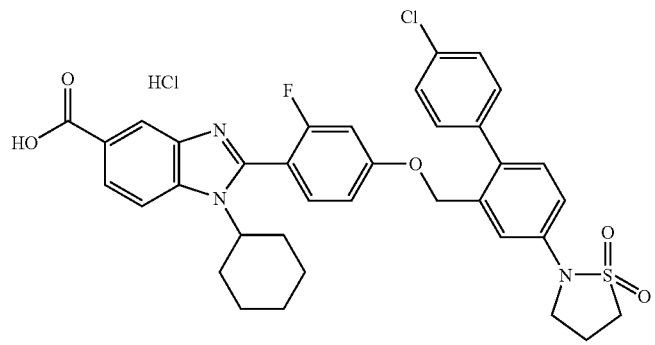

Purity >90%(NMR)
MS 674 (M+1)

1H NMR(δ)ppm

300MHz, DMSO-d6 8.29(1H, s), 8.13(1H, d, J=9.0Hz), 7.97(1H, d, J=9.0Hz), 7.63(1H, t, J=8.6Hz), 7.51–7.32(7H, m), 7.15 (1H, d, J=12.0Hz), 7.03(1H, d, J=9.0Hz), 5.10(2H, s), 4.09(1H, m), 3.82(2H, t, J=6.3Hz), 3.56(2H, t, J=7.4Hz), 2.45(2H, m), 2.40–2.10(2H, m), 2.00–1.55(5H, m), 1.50–1.20(3H, m)

Example No. 447

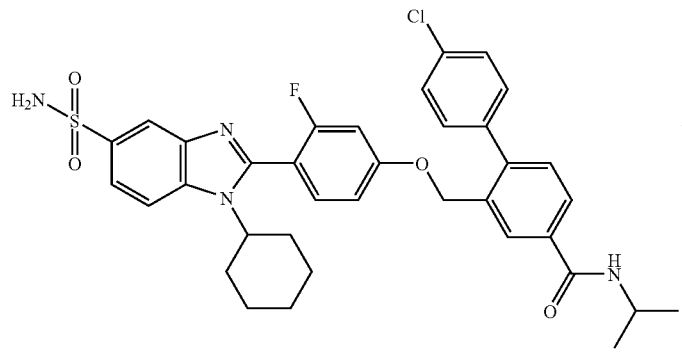

Purity >90%(NMR)
MS 675 (M+1)

1H NMR(δ)ppm

300MHz, DMSO-d6 8.36(1H, d, J=7.7Hz), 8.14(2H, d, J=12.1Hz), 8.08(1H, d, J=8.5Hz), 7.97(1H, dd, J=1.7Hz, 8.3Hz), 7.74(1H, dd, J=1.8Hz, 8.4Hz), 7.58–7.45(6H, m), 7.31(2H, s), 7.12(1H, dd, J=2.2Hz, 12.1Hz), 7.00(1H, dd, J=2.4Hz, 8.6Hz), 5.11(2H, s), 4.16(1H, m), 4.02(1H, m), 2.20(2H, m), 1.86(4H, m), 1.62(1H, m), 1.21(9H, m)

Example No. 448

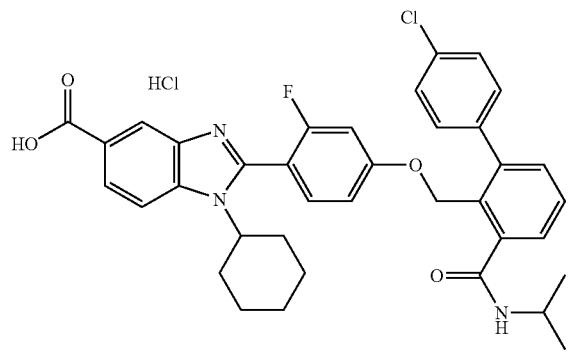

Purity >90%(NMR)
MS 640 (M+1)

1H NMR(δ)ppm

300MHz, DMSO-d6 8.29(2H, m), 8.04(1H, d, J=8.5Hz), 7.93(1H, dd, J=1.5Hz, 8.8Hz), 7.60–7.42(8H, m), 7.05(1H, dd, J=2.2Hz, 12.1Hz), 6.95(1H, dd, J=2.4Hz, 8.6Hz), 5.11(2H, s), 4.07–3.90(2H, m), 2.28–2.19(2H, m), 1.88–1.84(4H, m), 1.67–1.62(1H, m), 1.40–1.26(3H, m), 1.04(6H, d, J=6.6Hz)

TABLE 261
Example No. 449
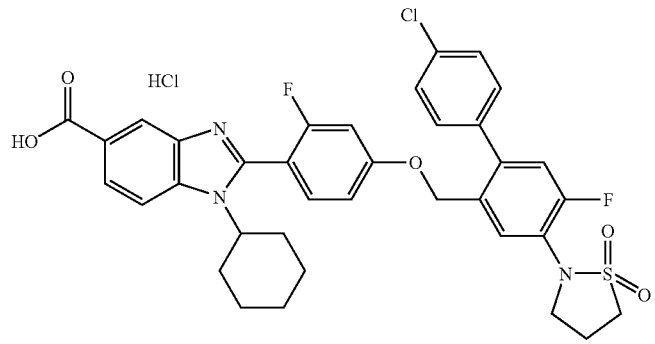
Purity >90 %(NMR)
MS 692 (M+1)
1H NMR(δ)ppm
300MHz, DMSO-d6 8.31(1H, s), 8.17(1H, d, J=8.7Hz), 8.00(1H, d, J=8.7Hz), 7.78(1H, d, J=8.1Hz), 7.66(1H, t, J=8.7Hz), 7.55–7.45(4H, m), 7.40(1H, d, J=11.7Hz), 7.19(1H, d, J=12.3Hz), 7.05(1H, d, J=8.7Hz), 5.07(2H, s), 4.10(1H, m), 3.85(2H, t, J=6.6Hz), 3.47(2H, t, J=7.5z) 2.60–2.50(2H, m), 2.40–2.10(2H, m), 2.00–1.80(4H, m), 1.75–1.55(1H, m), 1.50–1.20(3H, m)
Example No. 450
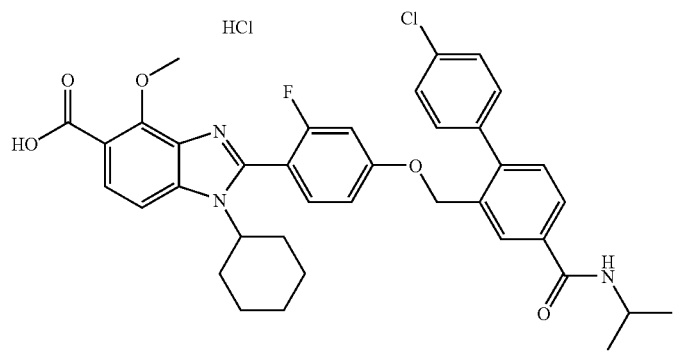
Purity >90%(NMR)
MS 670 (M+1)
1H NMR(δ)ppm
300MHz, DMSO-d6 8.37(1H, d, J=7.8Hz), 8.15(1H, s), 7.97(1H, d, J=9.8Hz), 7.64–7.45(8H, m), 7.12(1H, d, J=12.1Hz), 7.00(1H, d, J=8.6Hz), 5.11(2H, s), 4.21(3H, s), 4.18–4.05(1H, m), 4.04–3.89(1H, m), 2.29–2.08(2H, m), 1.90–1.74(4H, m), 1.68–1.58(1H, m), 1.40–1.17(3H, m), 1.20(6H, d, J=6.6Hz)
Example No. 451
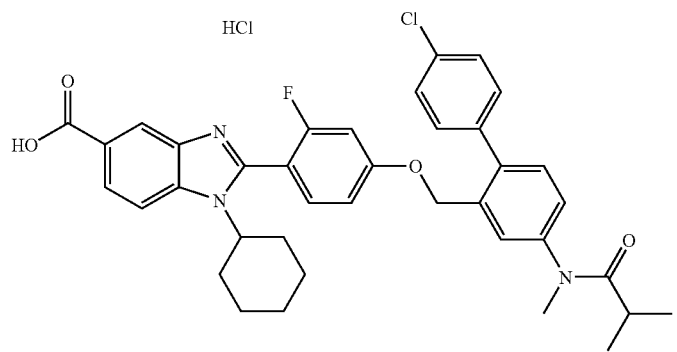
Purity >90%(NMR)
MS 654 (M+1)
1H NMR(δ)ppm
300MHz, DMSO-d6 8.29(1H, s), 8.12(1H, d, J=8.8Hz), 7.97(1H, d, J=10.2Hz), 7.65–7.59(2H, m), 7.51(4H, s), 7.46(2H, s), 7.15(1H, d, J=12.2Hz), 7.01(1H, d, J=8.6Hz), 5.15(2H, s), 4.13–3.98(1H, m), 3.21(3H, s), 2.56–2.42(1H, m), 2.30–2.15(2H, m), 1.95–1.77(4H, m), 1.69–1.59(1H, m), 1.45–1.17(3H, m), 0.96(6H, d, J=6.5Hz)

TABLE 262

Example No. 452

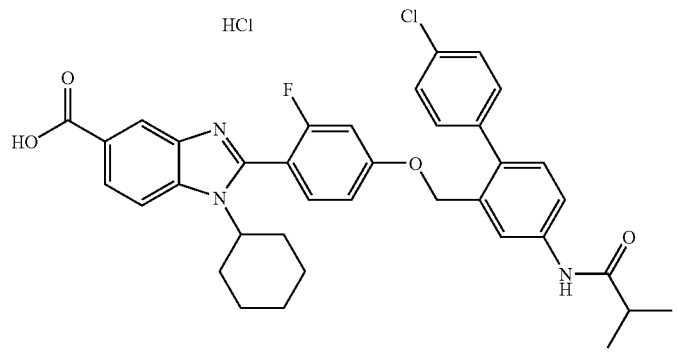

Purity >90%(NMR)
MS 640 (M+1)

1H NMR(δ)ppm

300MHz, DMSO-d6 10.1(1H, s), 8.28(1H, s), 8.11(1H, d, J=8.7Hz), 7.96(1H, d, J=11.4Hz), 7.95(1H, s), 7.72(1H, d, J=8.7Hz), 7.62(1H, t, J=9.0Hz), 7.48 and 7.43(4H, ABq, J=8.4Hz), 7.31(1H, d, J=8.4Hz), 7.13(1H, d, J=12.0Hz), 7.02(1H, d, J=9.0Hz), 5.07(2H, s), 4.14–4.00(1H, m), 2.69–2.59(1H, m), 2.30–2.12(2H, m), 1.95–1.77(4H, m), 1.71–1.57(1H, m), 1.45–1.20(3H, m), 1.12(6H, d, J=6.9Hz)

Example No. 453

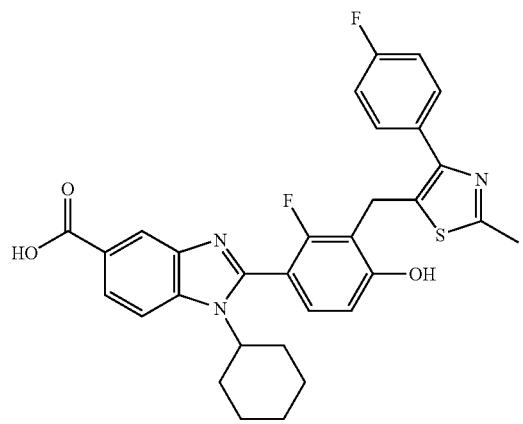

Purity >90%(NMR)
MS 542 (M+1)

1H NMR(δ)ppm

300MHz, DMSO-d6 11.1(1H, brs), 8.31(1H, d, J=9.4Hz), 8.29(1H, s), 8.07(1H, d, J=10.2Hz), 7.70–7.62(3H, m), 7.31–7.23(3H, m), 4.40–4.23(1H, m), 4.24(2H, s), 2.61(3H, s), 2.34–2.14(2H, m), 1.99–1.72(4H, m), 1.66–1.54(1H, m), 1.46–1.30(1H, m), 1.27–1.08(2H, m)

Example No. 454

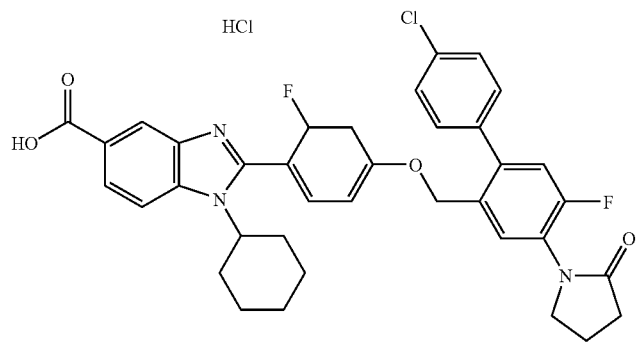

Purity >90%(NMR)
MS 656 (M+1)

1H NMR(δ)ppm

300MHz, DMSO-d6 8.27(1H, d, J=1.4Hz), 8.05(1H, d, J=8.7Hz), 7.92(1H, d, J=8.7Hz), 7.79(1H, d, J=7.8Hz), 7.59(1H, t, J=8.6Hz), 7.55–7.45(4H, m), 7.37(1H, d, J=11.4Hz), 7.14(1H, d, J=12.1Hz), 7.01(1H, d, J=8.6Hz), 5.04(2H, s), 4.10(1H, m), 3.84(2H, t, J=6.Hz), 2.55–2.45(2H, m), 2.40–2.10(4H, m), 2.00–1.80(4H, m), 1.75–1.55(1H, m), 1.50–1.20(3H, m)

TABLE 263

Example No. 455

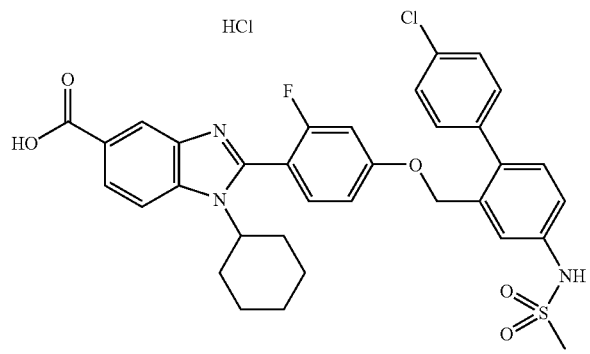

Purity >90%(NMR)
MS 648 (M+1)

1H NMR(δ)ppm

300MHz, DMSO-d6 10.05(1H, brs), 8.32(1H, d, J=1.3Hz), 8.19(1H, d, J=8.8Hz), 8.01(1H, d, J=8.7Hz), 7.67(1H, t, J=8.6Hz), 7.50–7.41(5H, m), 7.38–7.33(2H, m), 7.17(1H, dd, J=2.2Hz, 12.2Hz), 7.05(1H, dd, J=2.2Hz, 8.7Hz), 5.10(2H, s), 4.12(1H, m), 3.07(3H, s), 2.40–2.10(2H, m), 2.00–1.80(4H, m), 1.75–1.55(1H, m), 1.50–1.20(3H, m)

Example No. 456

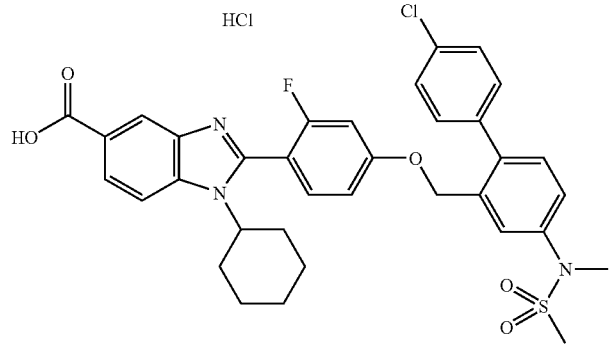

Purity >90%(NMR)
MS 662 (M+1)

1H NMR(δ)ppm

300MHz, DMSO-d6 8.31(1H, d, J=1.4Hz), 8.17(1H, d, J=8.8Hz), 8.00(1H, dd, J=1.5Hz, 8.7Hz), 7.73(1H, d, J=2.3Hz), 7.66(1H, t, J=8.6Hz), 7.56(1H, dd, J=2.3Hz, 8.3Hz), 7.50–7.47(4H, m), 7.42(1H, d, J=8.3Hz), 7.19(1H, d, J=12.2Hz), 7.06(1H, dd, J=2.2Hz, 8.6Hz), 5.11(2H, s), 4.10(1H, m), 3.31(3H, s), 3.03(3H, s), 2.40–2.10(2H, m), 2.00–1.80(1H, m), 1.75–1.55(1H, m), 1.50–1.20(3H, m)

Example No. 457

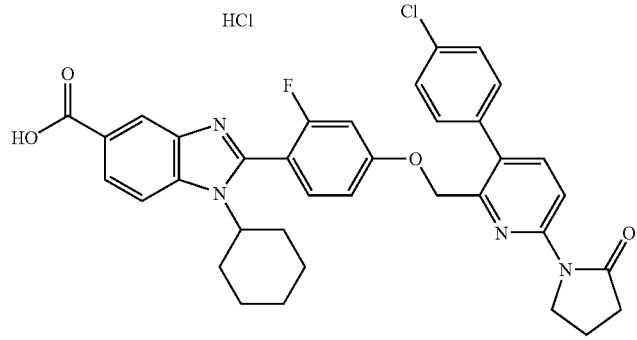

Purity >90%(NMR)
MS 639 (M+1)

1H NMR(δ)ppm

300MHz, DMSO-d6 8.41(1H, d, J=8.8Hz), 8.28(1H, s), 8.10(1H, d, J=9.2Hz), 7.96(1H, d, J=8.8Hz), 7.87(1H, d, J=8.8Hz), 7.61(1H, dd, J=8.5Hz, 8.5Hz), 7.56–7.49(4H, m), 7.19(1H, dd, J=2.4Hz, 12.2Hz), 7.05(1H, dd, J=2.4Hz, 8.7Hz), 5.18(2H, s), 4.06–3.97(4H, m), 2.62(2H, t, J=8.1Hz), 2.28–2.15(2H, m), 2.11–2.01(4H, m), 1.91–1.87(4H, m), 1.64(1H, m), 1.43–1.23(3H, m)

TABLE 264

Example No. 458

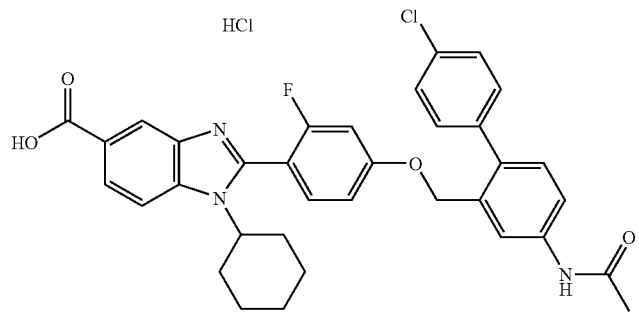

Purity >90%(NMR)
MS 612 (M+1)

1H NMR(δ)ppm (300MHz, DMSO-d6) 10.19(1H, s), 8.29(1H, s), 8.14(1H, d, J=8.8Hz), 7.98(1H, dd, J=1.7Hz, 8.7Hz), 7.90(1H, d, J=2.2Hz), 7.69(1H, dd, J=2.2Hz, 8.4Hz), 7.64(1H, dd, J=8.5Hz, 8.5Hz), 7.50–7.42(4H, m), 7.32(1H, d, J=8.4Hz), 7.14(1H, dd, J=2.5Hz, 12.1Hz), 7.02(1H, dd, J=2.4Hz, 8.6Hz), 5.08(2H, s), 4.17–4.02(1H, m), 2.30–2.18(2H, m), 2.08(3H, s), 1.87–1.79(4H, m), 1.68–1.59(1H, m), 1.35–1.23(3H, m)

Example No. 459

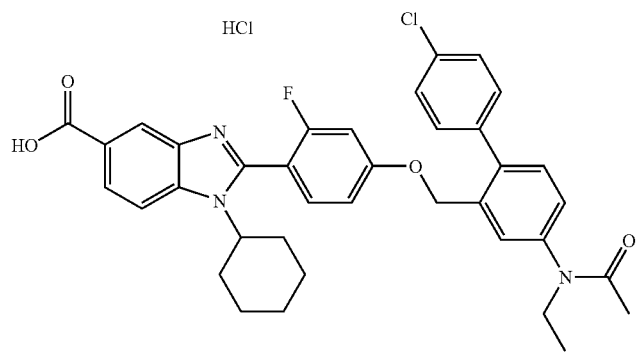

Purity >90%(NMR)
MS 640 (M+1)

1H NMR(δ)ppm

300MHz, DMSO-d6 8.29(1H, s), 8.11(1H, d, J=8.8Hz), 7.96(1H, d, J=8.6Hz), 7.64–7.58(2H, m), 7.51(4H, s), 7.44(2H, s), 7.15(1H, d, J=12.2Hz), 7.02(1H, d, J=8.5H), 5.14(2H, s), 4.12–3.95(1H, m), 3.70(2H, q, J=7.1 Hz), 2.50(3H, s) 2.31–2.12(2H, m), 1.92–1.82(4H, m), 1.69–1.57(1H, m), 1.43–1.16(3H, m), 1.05(3H, t, J=7.1Hz)

Example No. 460

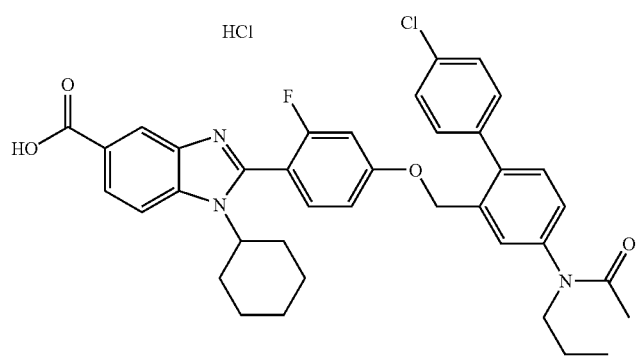

Purity >90%(NMR)
MS 654 (M+1)

1H NMR(δ)ppm

300MHz, DMSO-d6 8.28(1H, s), 8.09(1H, d, J=8.8Hz), 7.95(1H, d, J=10.1Hz), 7.64–7.56(2H, m), 7.51(4H, ws), 7.44(2H, s), 7.14(1H, d, J=12.2Hz), 7.01(1H, d, J=8.6Hz), 5.14(2H, s), 4.12–3.95(1H, m), 3.64(2H, t, J=7.2Hz). 2.50(3H, s), 2.31–2.12(2H, m), 1.93–1.84(4H, m), 1.69–1.59(1H, m), 1.52–1.17(5H, m), 0.84(3H, t, J=7.3Hz)

TABLE 265

Example No. 461

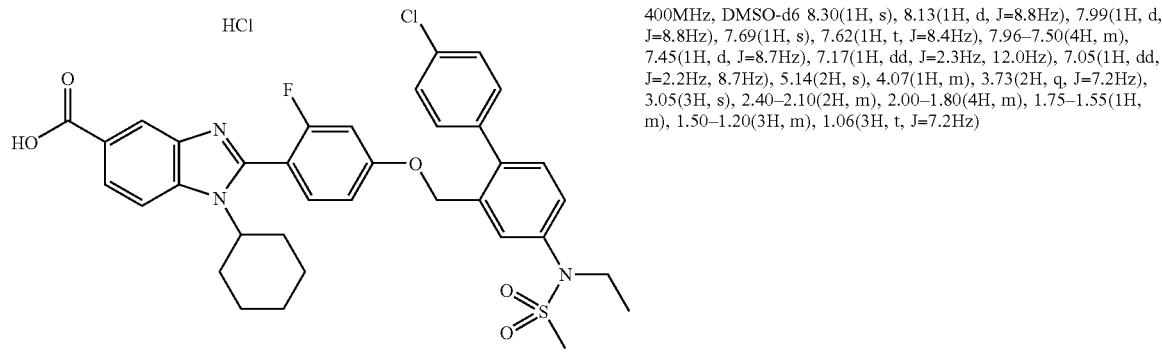

Purity >90%(NMR)
MS 676 (M+1)

1H NMR(δ)ppm

400MHz, DMSO-d6 8.30(1H, s), 8.13(1H, d, J=8.8Hz), 7.99(1H, d, J=8.8Hz), 7.69(1H, s), 7.62(1H, t, J=8.4Hz), 7.96–7.50(4H, m), 7.45(1H, d, J=8.7Hz), 7.17(1H, dd, J=2.3Hz, 12.0Hz), 7.05(1H, dd, J=2.2Hz, 8.7Hz), 5.14(2H, s), 4.07(1H, m), 3.73(2H, q, J=7.2Hz), 3.05(3H, s), 2.40–2.10(2H, m), 2.00–1.80(4H, m), 1.75–1.55(1H, m), 1.50–1.20(3H, m), 1.06(3H, t, J=7.2Hz)

Example No. 462

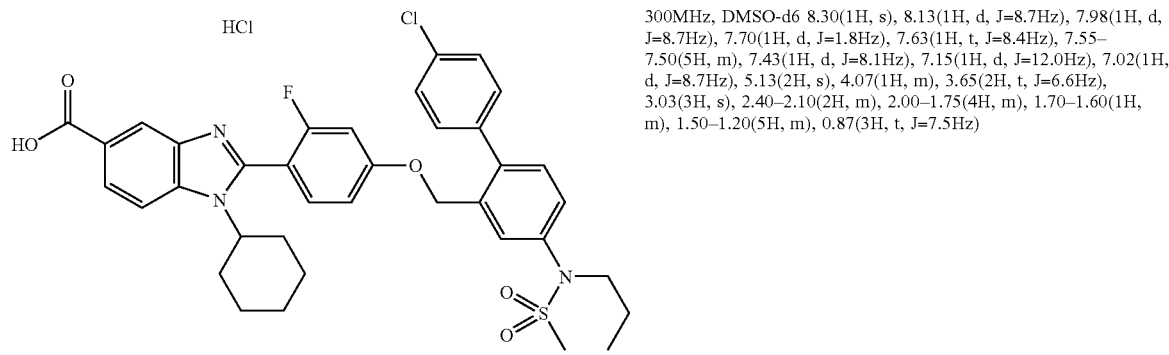

Purity >90%(NMR)
MS 690 (M+1)

1H NMR(δ)ppm

300MHz, DMSO-d6 8.30(1H, s), 8.13(1H, d, J=8.7Hz), 7.98(1H, d, J=8.7Hz), 7.70(1H, d, J=1.8Hz), 7.63(1H, t, J=8.4Hz), 7.55–7.50(5H, m), 7.43(1H, d, J=8.1Hz), 7.15(1H, d, J=12.0Hz), 7.02(1H, d, J=8.7Hz), 5.13(2H, s), 4.07(1H, m), 3.65(2H, t, J=6.6Hz), 3.03(3H, s), 2.40–2.10(2H, m), 2.00–1.75(4H, m), 1.70–1.60(1H, m), 1.50–1.20(5H, m), 0.87(3H, t, J=7.5Hz)

Example No. 463

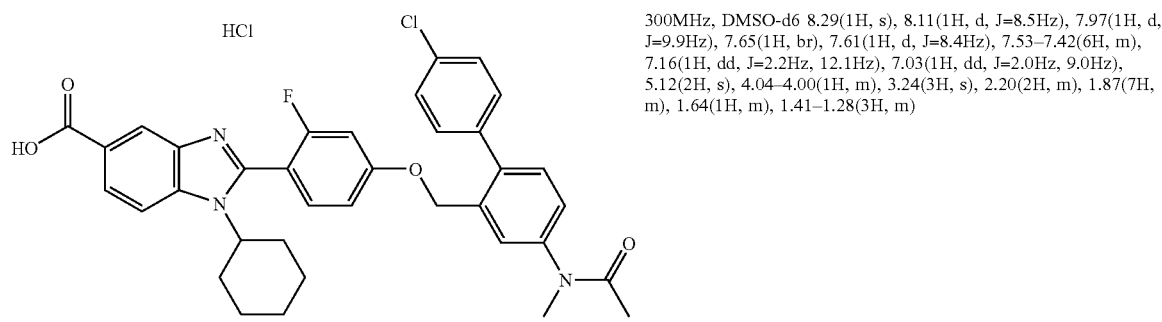

Purity >90%(NMR)
MS 626 (M+1)

1H NMR(δ)ppm

300MHz, DMSO-d6 8.29(1H, s), 8.11(1H, d, J=8.5Hz), 7.97(1H, d, J=9.9Hz), 7.65(1H, br), 7.61(1H, d, J=8.4Hz), 7.53–7.42(6H, m), 7.16(1H, dd, J=2.2Hz, 12.1Hz), 7.03(1H, dd, J=2.0Hz, 9.0Hz), 5.12(2H, s), 4.04–4.00(1H, m), 3.24(3H, s), 2.20(2H, m), 1.87(7H, m), 1.64(1H, m), 1.41–1.28(3H, m)

TABLE 266

Example No. 464

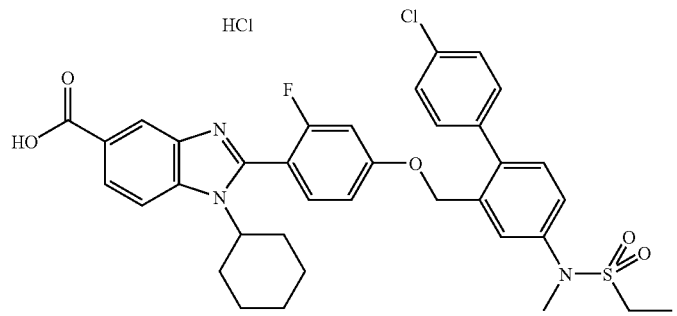

Purity >90%(NMR)
MS 676 (M+1)

1H NMR(δ)ppm

300MHz, DMSO-d6 8.28(1H, s), 8.09(1H, d, J=8.8Hz), 7.95(1H, d, J=8.8Hz), 7.73(1H, d, J=2.2Hz), 7.63–7.39(7H, m), 7.15(1H, dd, J=2.2Hz, 12.1Hz), 7.01(1H, dd, J=2.0Hz, 8.6Hz), 5.10(2H, s), 4.05–3.99(1H, m), 3.34(3H, s), 3.23(2H, q, J=7.2Hz), 2.20(2H, m), 1.87(4H, m), 1.62(1H, m), 1.33(3H, m), 1.24(3H, t, J=7.3Hz)

Example No. 465

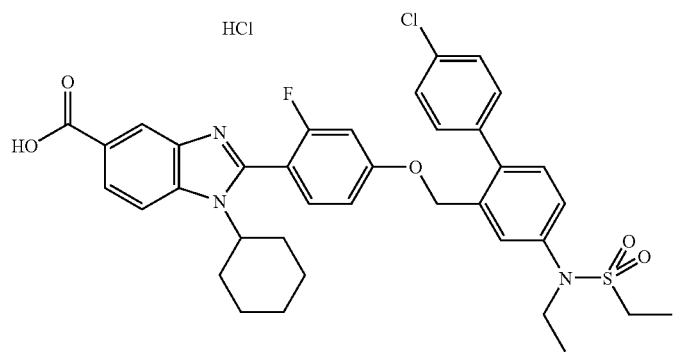

Purity >90%(NMR)
MS 690 (M+1)

1H NMR(δ)ppm

300MHz, DMSO-d6 8.29(1H, d, J=1.5Hz), 8.11(1H, d, J=8.8Hz), 7.98(1H, dd, J=1.4Hz, 8.4Hz), 7.69(1H, d, J=2.2Hz), 7.62(1H, dd, J=8.6Hz, 8.6Hz), 7.56–7.47(5H, m), 7.43(1H, d, J=8.1Hz), 7.16(1H, dd, J=2.2Hz, 12.1Hz), 7.02(1H, dd, J=2.4Hz, 8.7Hz), 5.13(2H, s), 4.09–4.02(1H, m), 3.77(2H, q, J=6.8Hz), 3.19(2H, q, J=7.4Hz), 2.25–2.21(2H, m), 1.90–1.87(4H, m), 1.63(1H, m), 1.39–1.33(3H, m), 1.27(3H, t, J=7.4Hz), 1.06(3H, t, J=6.9Hz)

Example No. 466

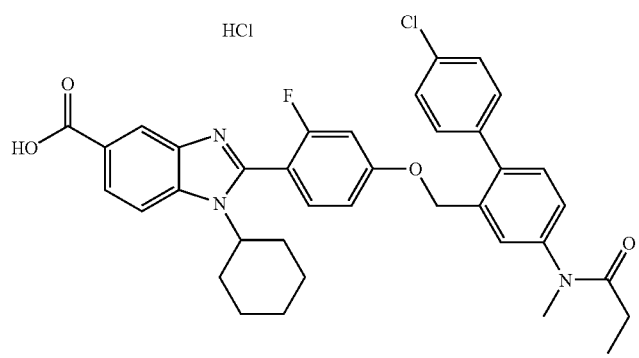

Purity >90%(NMR)
MS 640 (M+1)

1H NMR(δ)ppm

300MHz, DMSO-d6 8.28(1H, s), 8.10(1H, d, J=8.4Hz), 7.96(1H, d, J=8.4Hz), 7.64(1H, s), 7.61(1H, d, J=8.4Hz), 7.50(4H, s), 7.44(2H, s), 7.14(1H, d, J=12.0Hz), 7.02(1H, d, J=8.4Hz), 5.12(2H, s), 4.12–3.95(1H, m), 3.23(3H, s), 2.32–2.06(4H, m), 1.94–1.77(4H, m), 1.70–1.59(1H, m), 1.42–1.18(3H, m), 0.96(3H, t, J=7.2Hz)

TABLE 267

Example No. 467

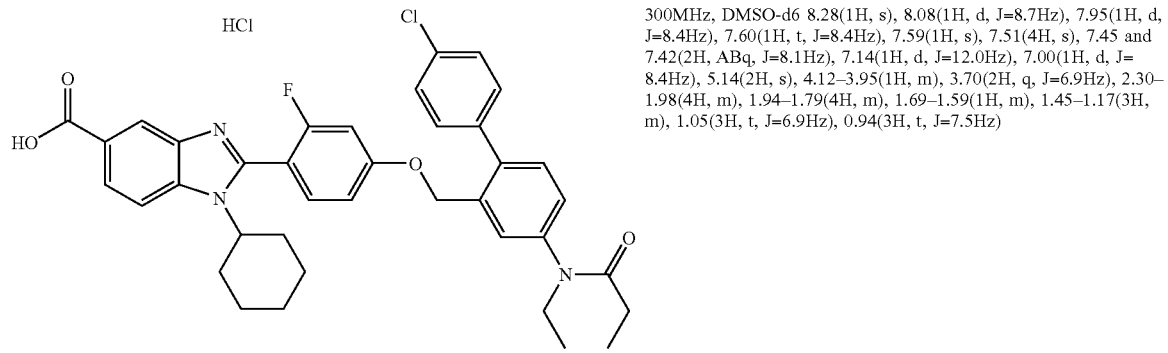

Purity >90%(NMR)
MS 654 (M+1)

1H NMR(δ)ppm

300MHz, DMSO-d6 8.28(1H, s), 8.08(1H, d, J=8.7Hz), 7.95(1H, d, J=8.4Hz), 7.60(1H, t, J=8.4Hz), 7.59(1H, s), 7.51(4H, s), 7.45 and 7.42(2H, ABq, J=8.1Hz), 7.14(1H, d, J=12.0Hz), 7.00(1H, d, J=8.4Hz), 5.14(2H, s), 4.12–3.95(1H, m), 3.70(2H, q, J=6.9Hz), 2.30–1.98(4H, m), 1.94–1.79(4H, m), 1.69–1.59(1H, m), 1.45–1.17(3H, m), 1.05(3H, t, J=6.9Hz), 0.94(3H, t, J=7.5Hz)

Example No. 468

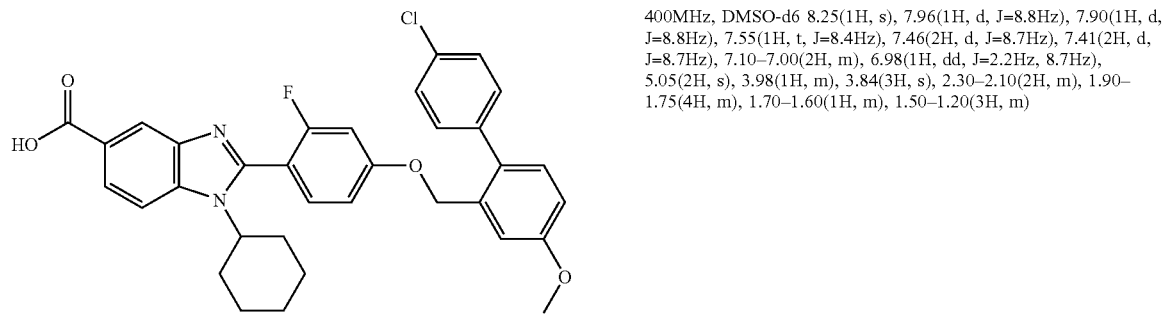

Purity >90%(NMR)
MS 585 (M+1)

1H NMR(δ)ppm

400MHz, DMSO-d6 8.25(1H, s), 7.96(1H, d, J=8.8Hz), 7.90(1H, d, J=8.8Hz), 7.55(1H, t, J=8.4Hz), 7.46(2H, d, J=8.7Hz), 7.41(2H, d, J=8.7Hz), 7.10–7.00(2H, m), 6.98(1H, dd, J=2.2Hz, 8.7Hz), 5.05(2H, s), 3.98(1H, m), 3.84(3H, s), 2.30–2.10(2H, m), 1.90–1.75(4H, m), 1.70–1.60(1H, m), 1.50–1.20(3H, m)

Example No. 469

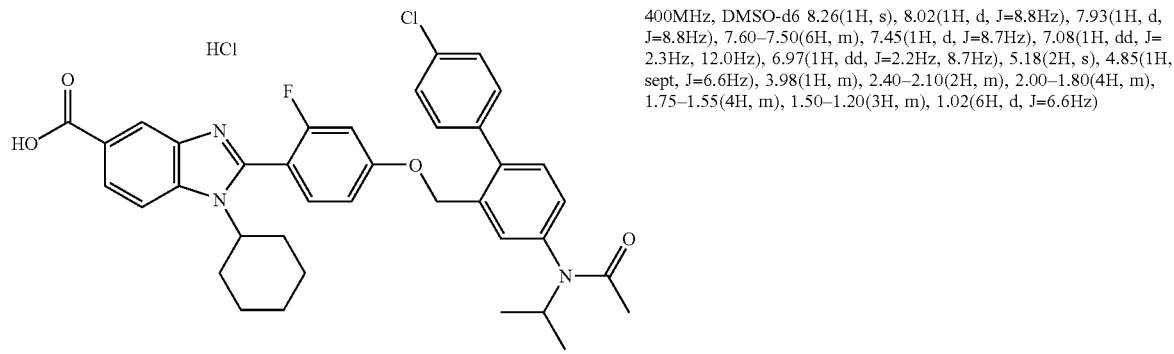

Purity >90%(NMR)
MS 654 (M+1)

1H NMR(δ)ppm

400MHz, DMSO-d6 8.26(1H, s), 8.02(1H, d, J=8.8Hz), 7.93(1H, d, J=8.8Hz), 7.60–7.50(6H, m), 7.45(1H, d, J=8.7Hz), 7.08(1H, dd, J=2.3Hz, 12.0Hz), 6.97(1H, dd, J=2.2Hz, 8.7Hz), 5.18(2H, s), 4.85(1H, sept, J=6.6Hz), 3.98(1H, m), 2.40–2.10(2H, m), 2.00–1.80(4H, m), 1.75–1.55(4H, m), 1.50–1.20(3H, m), 1.02(6H, d, J=6.6Hz)

TABLE 268

Example No. 470

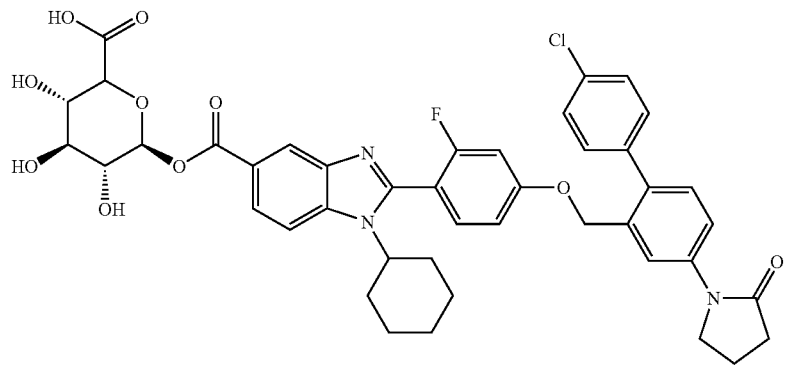

Purity >90%(NMR)

MS 814 (M+1)

1H NMR(δ)ppm

300MHz, DMSO-d6 8.39(1H, d, J=1.4Hz), 8.04(1H, J=8.8Hz), 7.98(1H, d, J=2.2Hz), 7.95(1H, d, J=8.8Hz), 7.78(1H, dd, J=2.3Hz, 8.5Hz), 7.57(1H, t, J=8.6Hz), 7.50(2H, d, J=8.8Hz), 7.45(2H, d, J=8.8Hz), 7.39(1H, d, J=8.4Hz), 7.10(1H, d, J=12.1Hz), 6.98(1H, d, J=8.6Hz), 5.65–5.60(2H, m), 5.35(1H, d, J=4.2Hz), 5.08(2H, s), 4.00(1H, m), 3.93–3.84(3H, m), 3.50–3.30(4H, m) 2.54(2H, t, J=7.8Hz), 2.40–2.00(4H, m), 1.95–1.75(4H, m), 1.70–1.55(1H, m), 1.45–1.15(3H, m)

Example No. 471

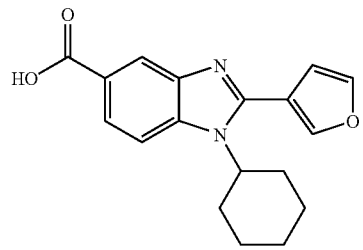

Purity >90%(NMR)

MS 311 (M+1)

1H NMR(δ)ppm

300MHz, DMSO-d6 12.78(1H, brs), 8.30(1H, dd, J=0.9Hz, 1.5Hz), 8.22(1H, d, J=1.5Hz), 7.95(1H, d, J=1.8Hz), 7.94(1H, d, J=8.4Hz), 7.85(1H, dd, J=1.2Hz, 8.4Hz), 6.96(1H, dd, J=0.9Hz, 1.8Hz), 4.46(1H, m), 2.40–2.10(2H, m), 2.00–1.20(8H, m)

TABLE 269

Example No. 702

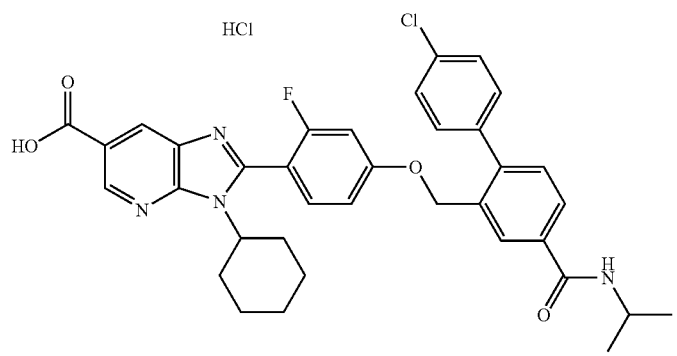

Purity >90%(NMR)

MS 641 (M+1)

1H NMR(δ)ppm

300MHz, DMSO-d6 8.97(1H, d, J=1.8Hz), 8.52(1H, d, J=2.4Hz), 8.36(1H, d, J=7.8Hz), 8.16(1H, s), 7.96(1H, d, J=8.1Hz), 7.55–7.40(5H, m), 7.14(1H, d, J=12.6Hz), 7.01(1H, dd, J=8.4Hz, 1.8Hz), 5.11(2H, s), 4.20–3.95(2H, m), 2.65–2.45(2H, m), 1.95–1.80(5H, m), 1.20–1.10(3H, m)

TABLE 269-continued

| Example No. 703 | 1H NMR(δ)ppm |
|---|---|
| 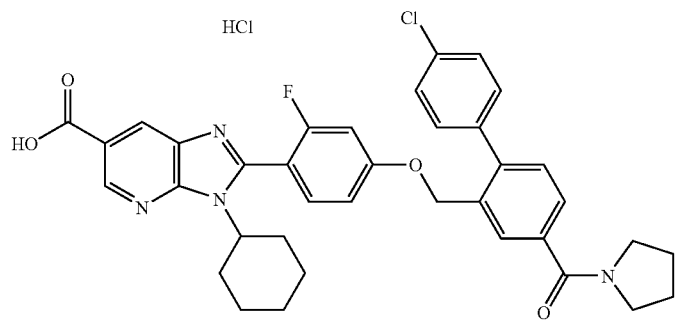 | 300MHz, DMSO-d6 8.97(1H, d, J=1.8Hz), 8.52(1H, d, J= 1.8Hz), 7.82(1H, s), 7.70–7.35(7H, m), 7.13(1H, d, J=12.3Hz), 7.00(1H, d, J=11.1Hz), 5.14(2H, s), 3.60–3.35(4H, m), 2.65–2.40(2H, m), 2.00–2.55(9H, m), 1.40–1.10(3H, m) |

Purity >90%(NMR)
MS 653 (M+1)

INDUSTRIAL APPLICABILITY

As is evident from the above-mentioned results, the compound of the present invention shows a high inhibitory activity against HCV polymerase.

Therefore, the compound of the present invention can provide a pharmaceutical agent effective for the prophylaxis or treatment of hepatitis C, based on the anti-HCV effect afforded by the HCV polymerase inhibitory activity. When used concurrently with a different anti-HCV agent, such as interferon, and/or an anti-inflammatory agent and the like, it can provide a pharmaceutical agent more effective for the prophylaxis or treatment of hepatitis C. Its high inhibitory activity specific to HCV polymerase suggests the possibility of the compound being a pharmaceutical agent with slight side effects, which can be used safely for humans.

This application is based on patent application Nos. 369008/1999, 391904/2000, 193786/2001 and 351537/2001 filed in Japan, international application No. PCT/JP00/09181 and U.S. patent application Ser. No. 09/939,374, the contents of which are hereby incorporated by reference.

What is claimed is:

1. A compound of the formula:

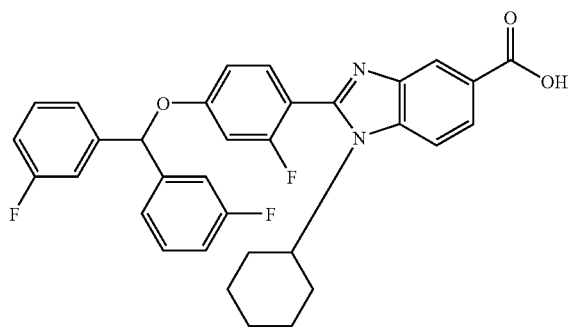

or a pharmaceutically acceptable salt, hydrate, or solvate thereof.

2. The compound of claim 1, wherein the compound is

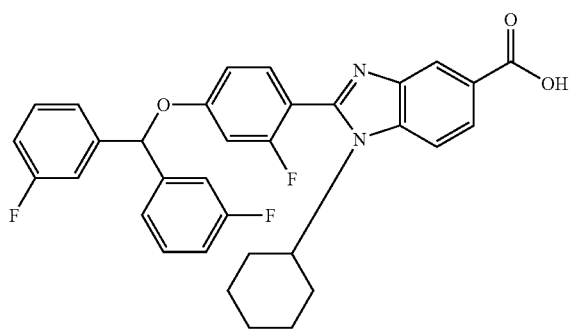

or a pharmaceutically acceptable salt.

3. The compound of claim 1, wherein the compound is a hydrate.

4. The compound of claim 1, wherein the compound is a solvate.

5. A composition comprising (i) a compound of the formula:

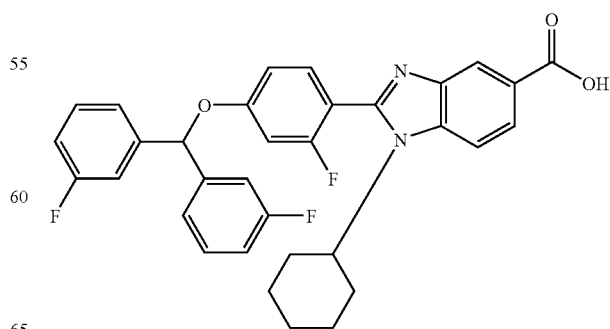

or a pharmaceutically acceptable salt, hydrate or solvate thereof, and (ii) a pharmaceutically acceptable carrier.

6. The composition of claim 5, wherein the compound is

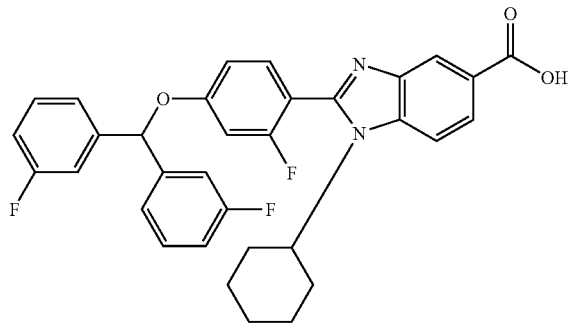

or a pharmaceutically acceptable salt.

7. The composition of claim 5, wherein the compound is a hydrate.

8. The composition of claim 5, wherein the compound is a solvate.

9. A method of treating hepatitis C in a patient, comprising administering to the patient an effective amount of a compound of the formula:

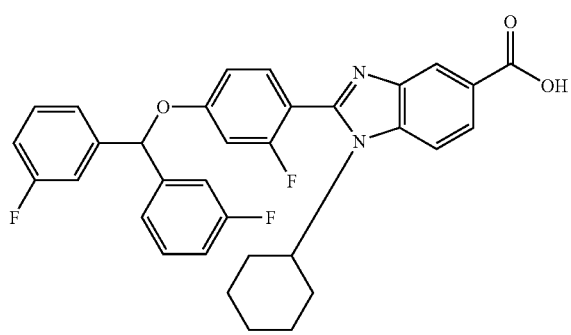

or a pharmaceutically acceptable salt hydrate, or solvate thereof, whereby hepatitis C is treated in the patient.

10. The method of claim 9, wherein the compound is

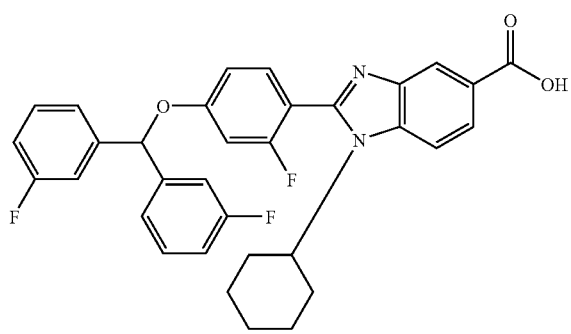

or a pharmaceutically acceptable salt.

11. The method of claim 9, wherein the compound is a hydrate.

12. The method of claim 9, wherein the compound is a solvate.

13. A method of inhibiting hepatitis C virus polymerase in a patient, comprising administering to the patient an effective amount of a compound of the formula:

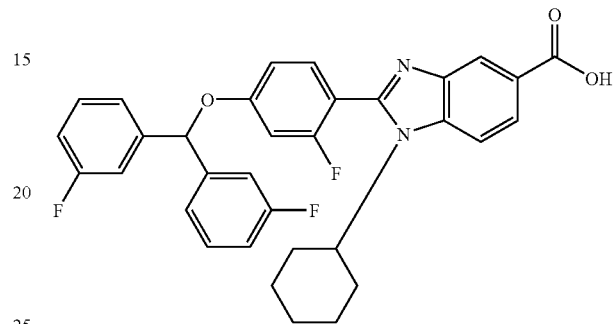

or a pharmaceutically acceptable salt, hydrate, or solvate thereof, whereby hepatitis C virus polymerase is inhibited in the patient.

14. The method of claim 13, wherein the compound is

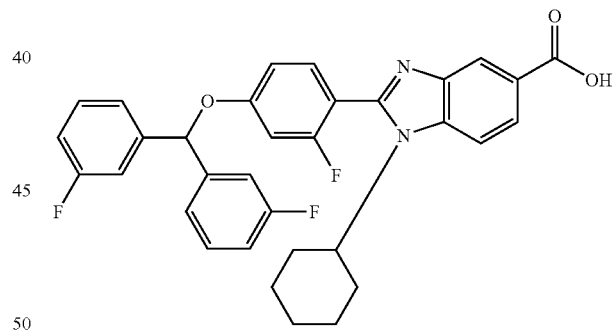

or a pharmaceutically acceptable salt.

15. The method of claim 13, wherein the compound is a hydrate.

16. The method of claim 13, wherein the compound is a solvate.

17. A method of inhibiting RNA-dependent RNA polymerase of hepatitis C virus in a patient, comprising administering to the patient an effective amount of a compound of the formula:

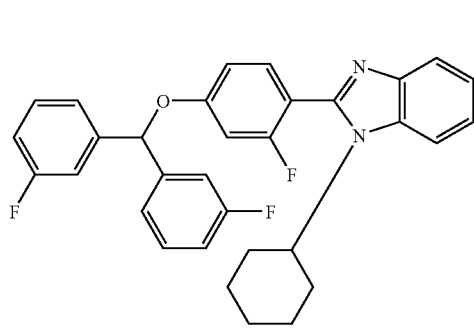
or a pharmaceutically acceptable salt, hydrate, or solvate thereof, whereby RNA-dependent RNA polymerase of hepatitis C virus is inhibited in the patient.
18. The method of claim 17, wherein the compound is
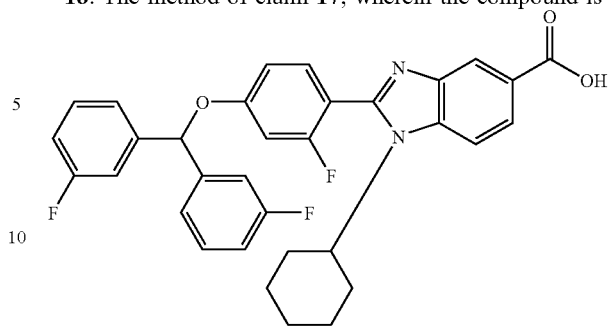
or a pharmaceutically acceptable salt.
19. The method of claim 17, wherein the compound is a hydrate.
20. The method of claim 17, wherein the compound is a solvate.
* * * * *